(12) United States Patent
Laurent et al.

(10) Patent No.: US 11,780,935 B2
(45) Date of Patent: Oct. 10, 2023

(54) MUTANT ANTIBODIES AND CONJUGATION THEREOF

(71) Applicant: Pfizer Healthcare Ireland, Dublin (IE)

(72) Inventors: Olivier Alexandre Laurent, San Diego, CA (US); Alice Lee, Poway, CA (US); Richard Ryan Preston, Escondido, CA (US); David Tumelty, San Diego, CA (US); Wei Hong Yu, San Diego, CA (US); Abhijit Suresh Bhat, Encinitas, CA (US); Anna Tempczyk-Russell, San Diego, CA (US)

(73) Assignee: Pfizer Healthcare Ireland, Dublin (IE)

( * ) Notice: Subject to any disclaimer, the term of this patent is extended or adjusted under 35 U.S.C. 154(b) by 496 days.

(21) Appl. No.: 16/896,930

(22) Filed: Jun. 9, 2020

(65) Prior Publication Data

US 2021/0147576 A1 May 20, 2021

Related U.S. Application Data

(63) Continuation of application No. 13/736,029, filed on Jan. 7, 2013, now abandoned.
(Continued)

(51) Int. Cl.
*C07K 16/46* (2006.01)
*A61K 39/395* (2006.01)
(Continued)

(52) U.S. Cl.
CPC ........ *C07K 16/46* (2013.01); *A61K 39/39558* (2013.01); *A61K 47/6811* (2017.08);
(Continued)

(58) Field of Classification Search
None
See application file for complete search history.

(56) References Cited

U.S. PATENT DOCUMENTS

2006/0205670 A1 9/2006 Bradshaw et al.
2009/0098130 A1 4/2009 Bradshaw et al.

FOREIGN PATENT DOCUMENTS

WO 2005016967 A2 2/2005
WO 2008056346 A2 5/2008
(Continued)

OTHER PUBLICATIONS

Bhat, A., et al., "CovX-Bodies." Fusion Protein Technologies for Biopharmaceuticals: Applications and Challenges. 1st Edition. Ed. Stefan R. Schmidt John Wiley & Sons, Inc., 2013. 571-582.
(Continued)

*Primary Examiner* — Karl J Puttlitz

(57) ABSTRACT

The present invention relates to a polypeptide comprising 7 β-strands A, B, C, D, E, F, and G sequentially connected together by connecting chains of amino acids, and a first α-helix sequentially located on the EF chain between β-strands E and F, wherein the β-strands are arranged so as to form a first β-sheet comprising β-strands A, B, D, and E, and a second β-sheet comprising β-strands C, F and G, said first and second β-sheets being covalently bonded together so as to form a first Ig domain; wherein the EF chain between β-strands E and F comprises the sequence $X^1$-$X^2$-$X^3$-$X^4$-$K^5H^6$ (SEQ ID NO:98), and $X^1$, $X^3$ and $X^4$ are each independently any amino acid residue, characterized in that $X^2$ is selected from the group consisting of A, G, I, V, L, R, S, T, Q, P, N, M, H, W, and pharmaceutically acceptable salts, stereoisomers, tautomers, solvates, and prodrugs thereof.

16 Claims, 50 Drawing Sheets

Figure 1A:
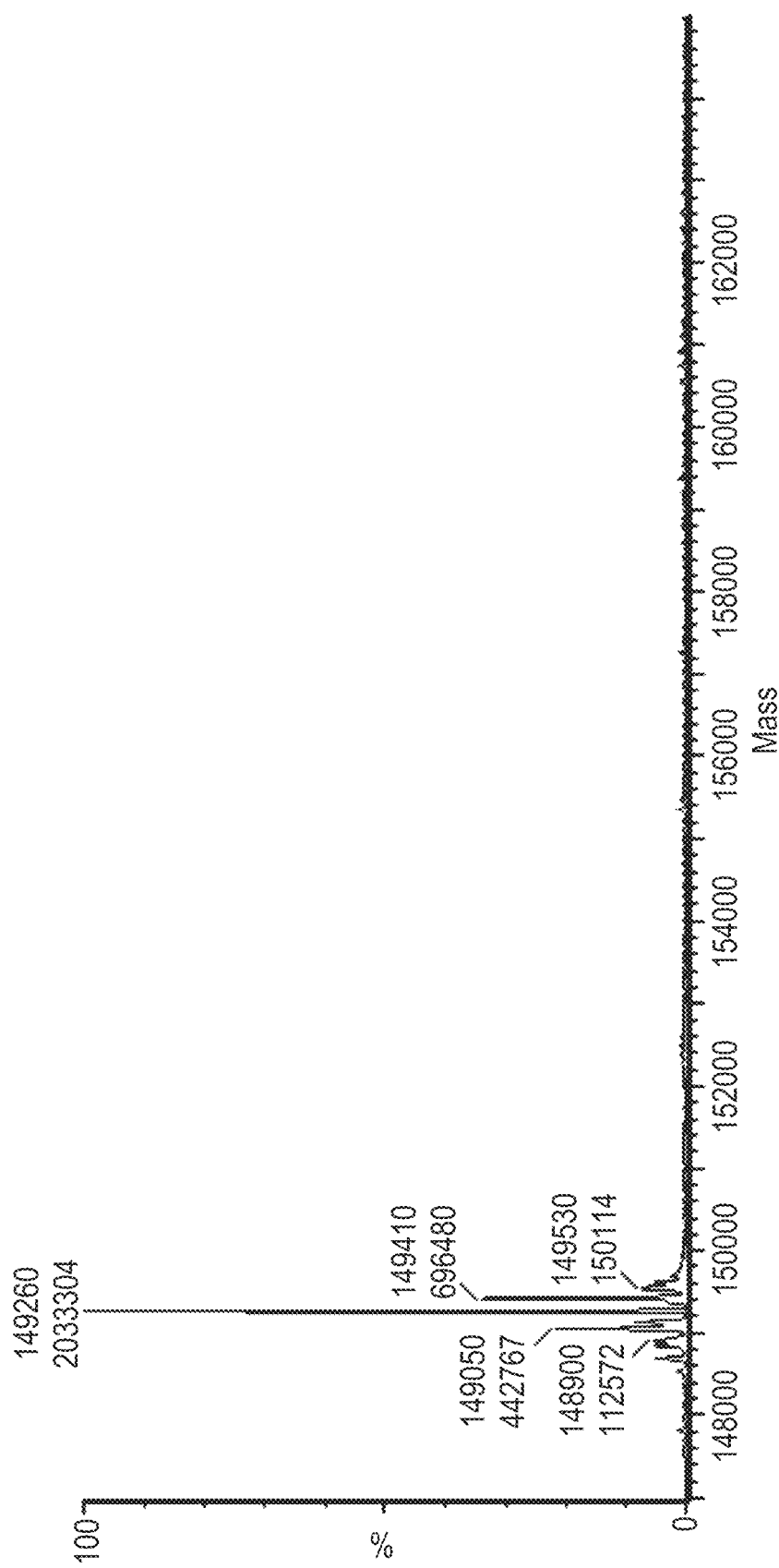

Specification includes a Sequence Listing.

Related U.S. Application Data

(60) Provisional application No. 61/584,675, filed on Jan. 9, 2012.

(51) Int. Cl.
| | | |
|---|---|---|
| *C07K 16/28* | (2006.01) | |
| *C07K 14/415* | (2006.01) | |
| *C12N 9/00* | (2006.01) | |
| *C07K 16/32* | (2006.01) | |
| *C07K 16/00* | (2006.01) | |
| *A61K 47/68* | (2017.01) | |
| *C07K 16/30* | (2006.01) | |
| *A61K 39/00* | (2006.01) | |

(52) U.S. Cl.
CPC ...... *A61K 47/6817* (2017.08); *A61K 47/6843* (2017.08); *A61K 47/6855* (2017.08); *C07K 14/415* (2013.01); *C07K 16/00* (2013.01); *C07K 16/2863* (2013.01); *C07K 16/30* (2013.01); *C07K 16/32* (2013.01); *C12N 9/0002* (2013.01); *A61K 2039/505* (2013.01); *C07K 2317/24* (2013.01); *C07K 2317/515* (2013.01); *C07K 2317/55* (2013.01); *C07K 2317/73* (2013.01); *C07K 2317/76* (2013.01); *C07K 2317/94* (2013.01)

(56) References Cited

FOREIGN PATENT DOCUMENTS

| WO | 2009136352 A1 | 11/2009 |
|---|---|---|
| WO | 2012007896 A1 | 1/2012 |
| WO | 2013072813 A2 | 5/2013 |

OTHER PUBLICATIONS

International Preliminary Report on Patentability for International Application No. PCT/IB2013/050131 dated Jul. 15, 2014.
International Search Report for International Application No. PCT/IB2013/050131 completed on May 23, 2013.
Written Opinion of the International Searching Authority for International Application No. PCT/IB2013/050131 dated Jun. 11, 2013.

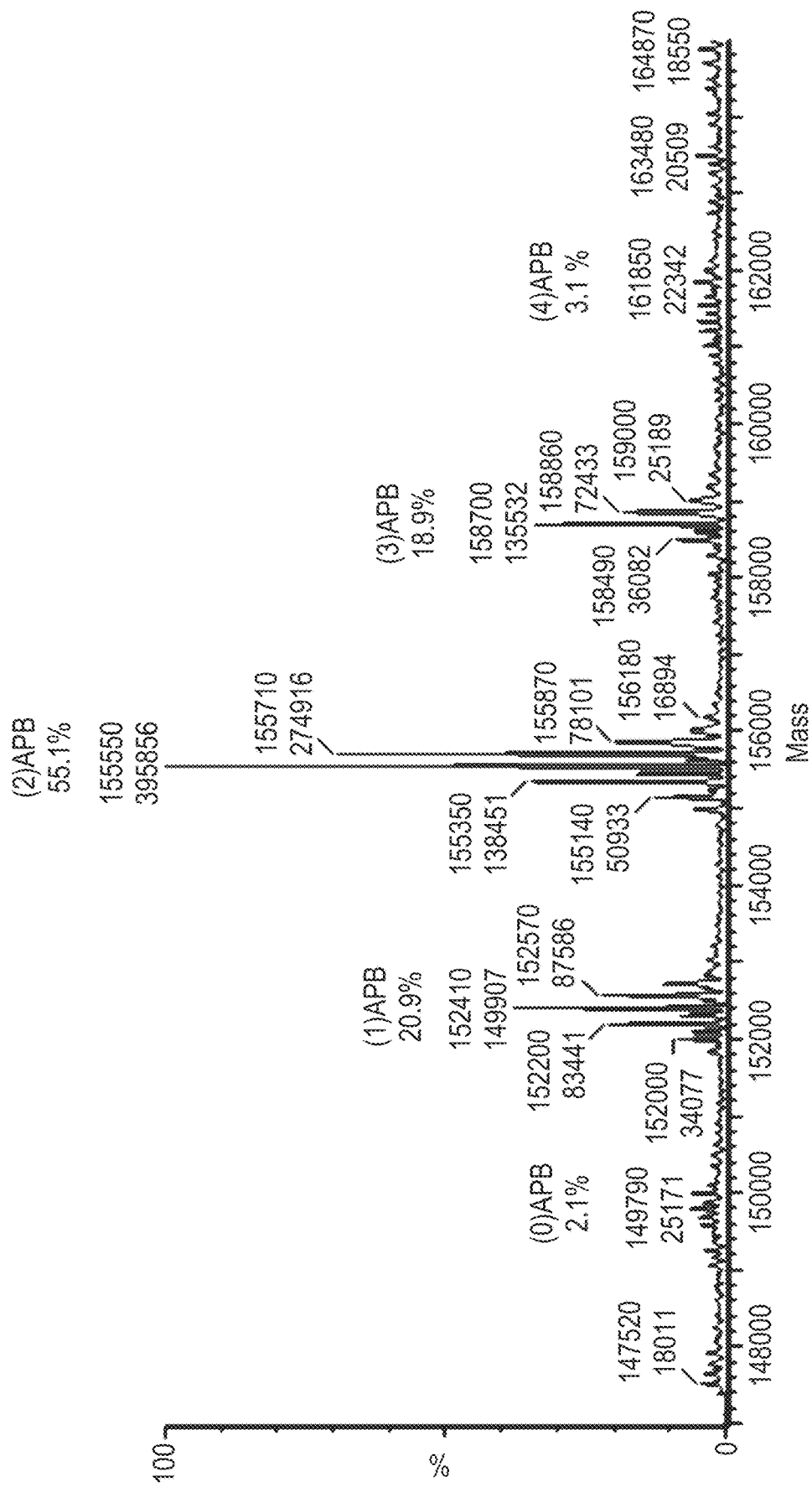

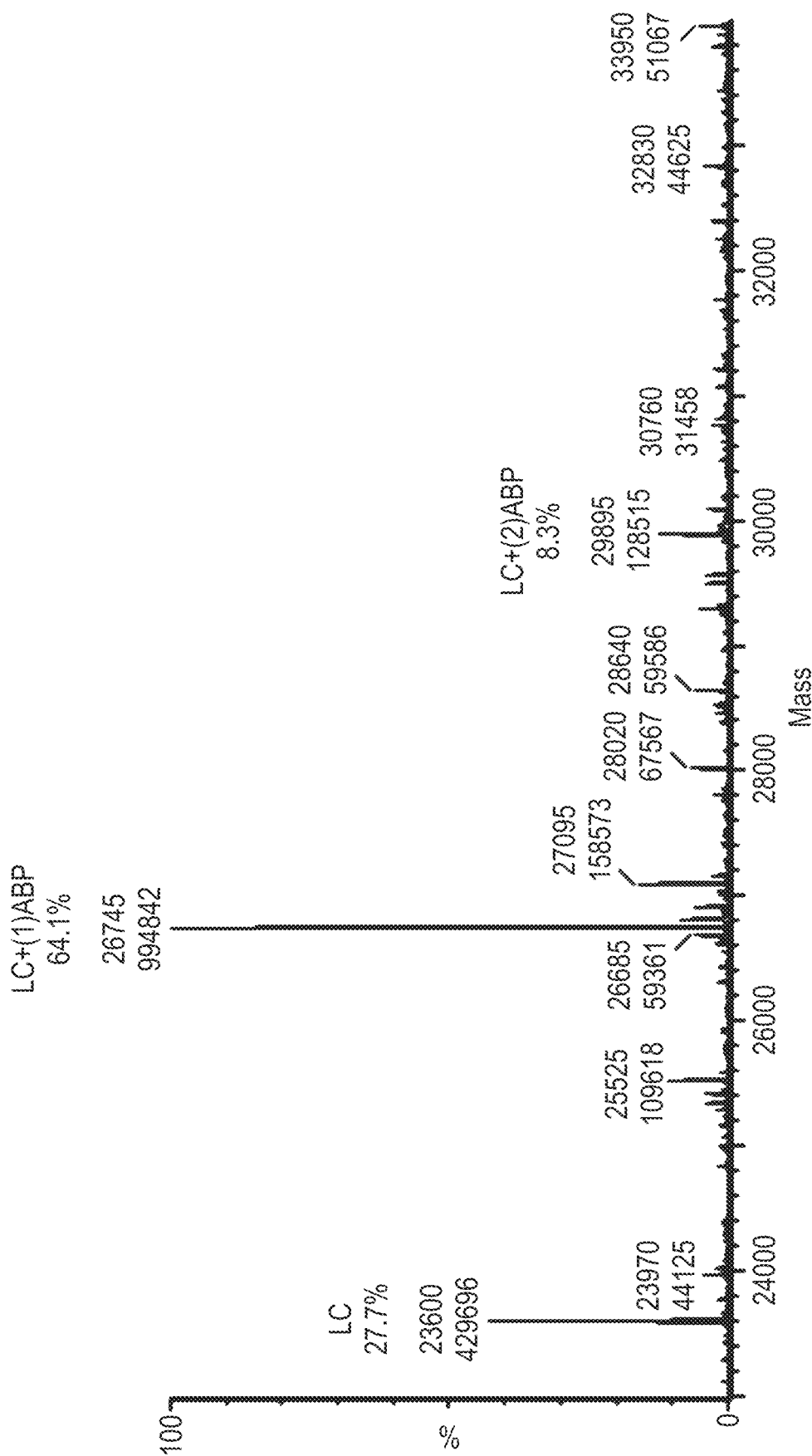

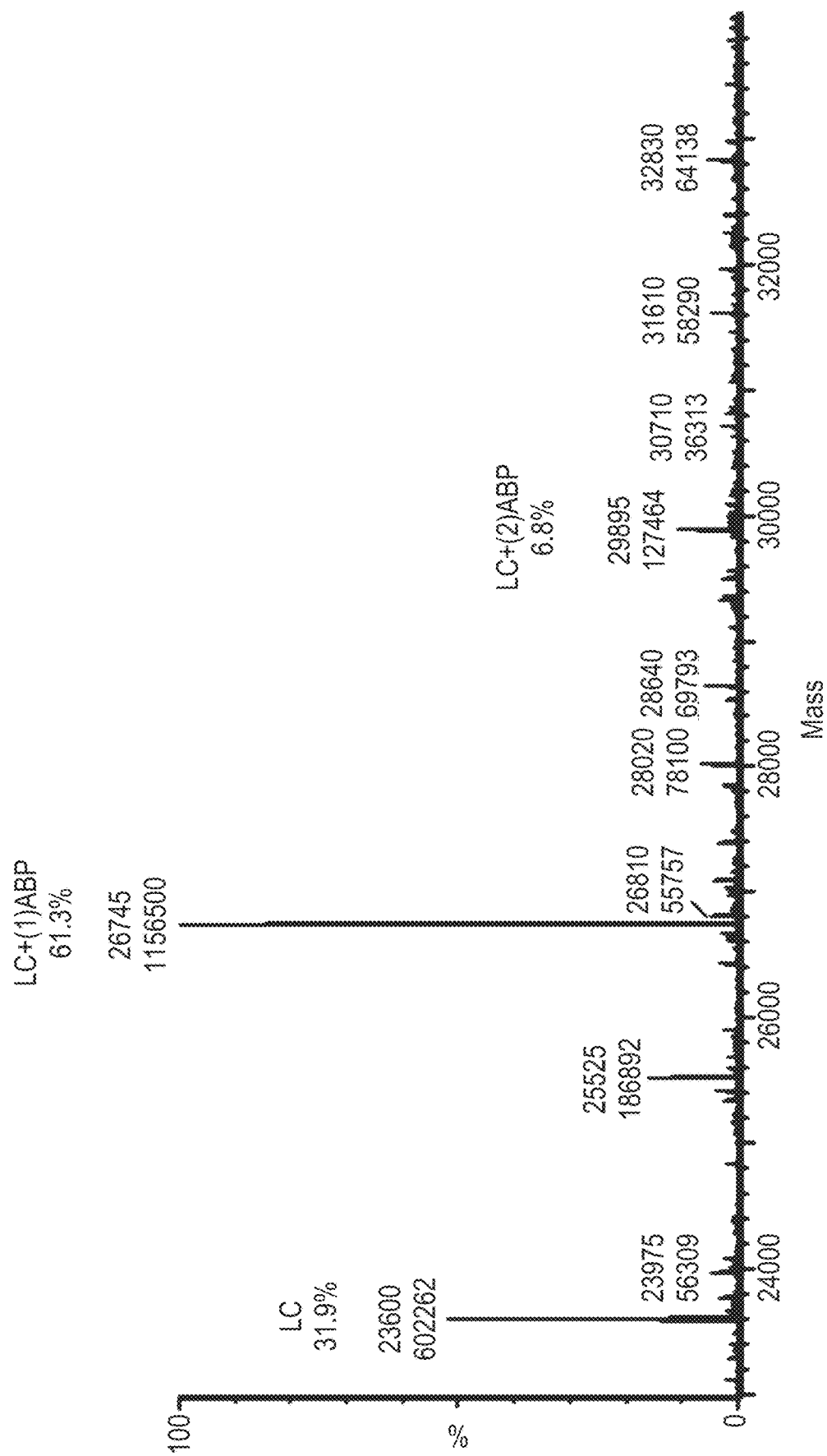

FIG. 3A

*LIGHT CHAIN*

DIQMTQSPSSLSASVGDRVTITCRASQDIRRDLGW•Y•(Y3)QQKPGKAPKRLIY•AASRLQSGVPSRF•SGSGSGTEF•TLTISSLQPEDF•ATY•Y•CLQHNNYPRTF•(Y10)GQGTKLVIKRTVAAPSVF•(Y11)IFPPSDEQLKSGTASVVCLLNNF•Y•(Y12)PREAKVQW•(Y13)KVDNALQSGNSQESVTEQDSKDSTY•(Y14)SLSSTLTLSKADY•(Y15)EKHKVY•(Y16)ACEVTHQGLSSPVTKSF•NRGEC

FIG. 3B

*HEAVY CHAIN*

(Y1)QVQLVESGGGLVKPGGSLRLSCAASGF•TF•SDY•Y•MSW•(Y6)IRQAPGKGLEW•VSY•ISSSGSTRDY•(Y9)ADSVKGRF•(Y10)TISRDNAKNSLY•LQMNSLRAEDTAVY•Y•CVRDGVETTF•Y•Y•Y•GMDVW•(Y20)GQGTTVTVSSASTKGPSVFPLAPCSRSTSESTAALGCLVKDY•FPEPVTVSW•NSGALTSGVHTFPAVLQS SGLY•SLSSVVTVPSSNF•GTQTY•(Y25)TCNVDHKPSNTKVDKTVERKCCVECPPCPAPPVAGPSVF•(Y26)L FPPKPKDTLMISRTPEVTCVVVDVSHEDPEVQF•NW•Y•(Y29)VDGVEVHNAKTKPREEQF•NSTF•RVVSVLTV VHQDW•(Y32)LNGKEY•(Y33)KCKVSNKGLPAPIEKTISKTKGQPREPQVY•(Y34)TLPPSREEMTKNQVSLT CLVKGF•YPSDIAVEW•ESNGQPENNY•(Y37)KTTPPMLDSDGSF•LY•(Y40)SKLTVDKSRW•QQGNVF•SCSVMHEALHNHY•(Y43)TQKSLSLSPG

FIG. 4A
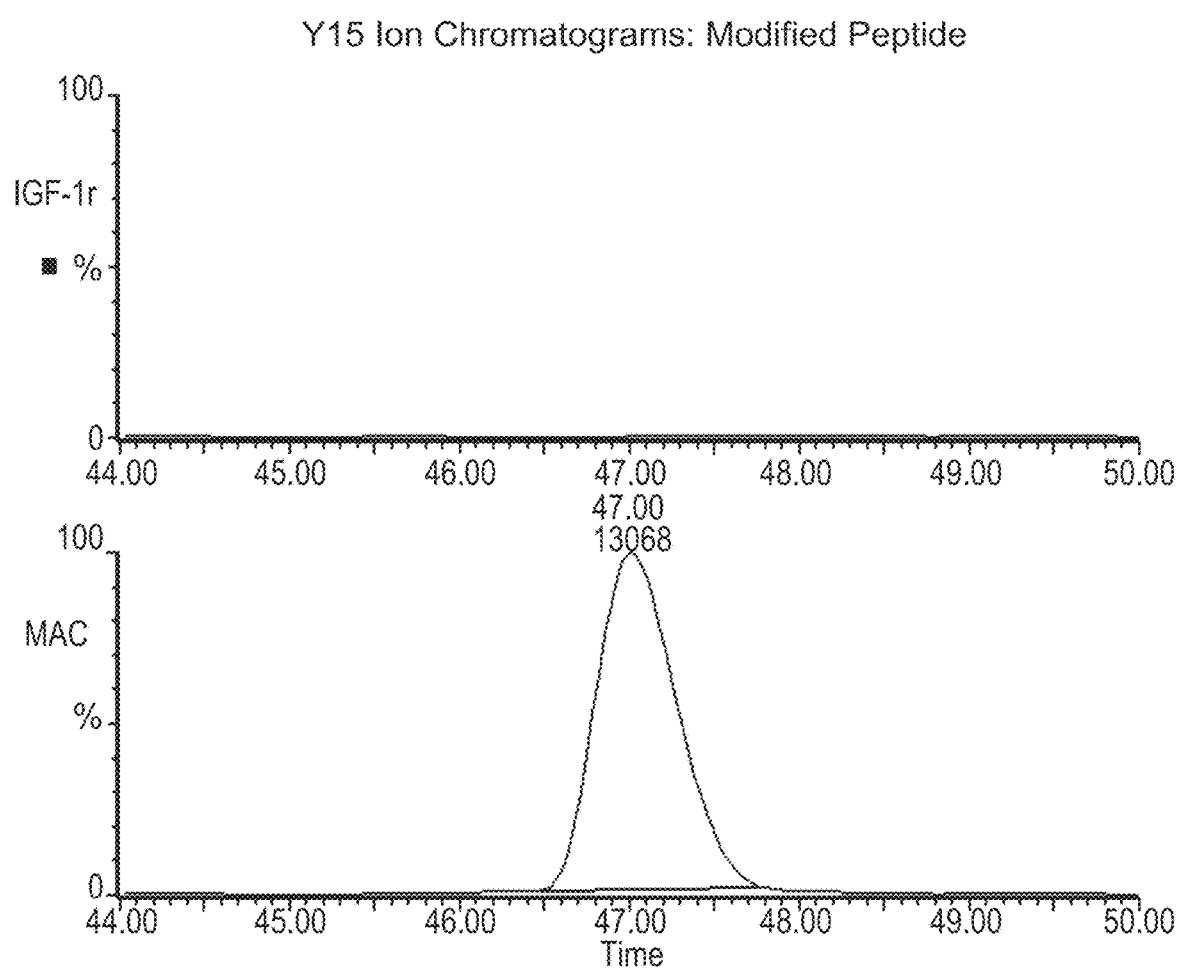
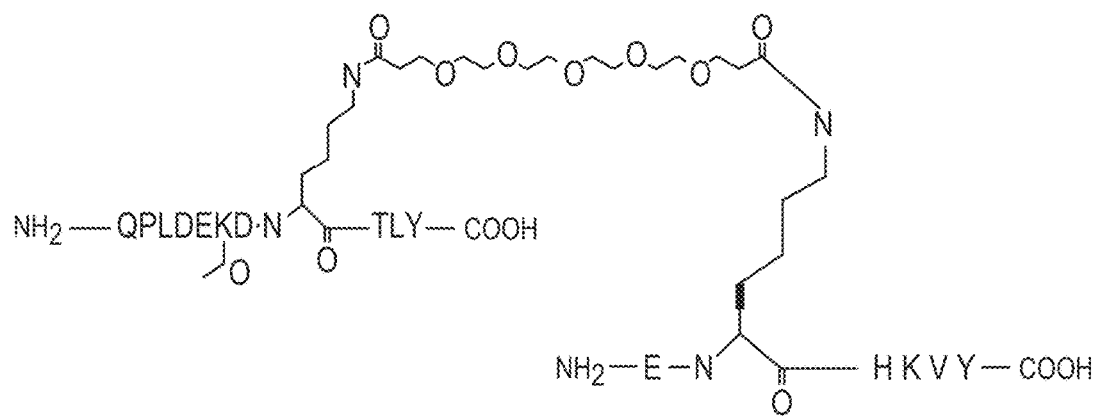
Modified Y15
Molecular Weight=2496.82

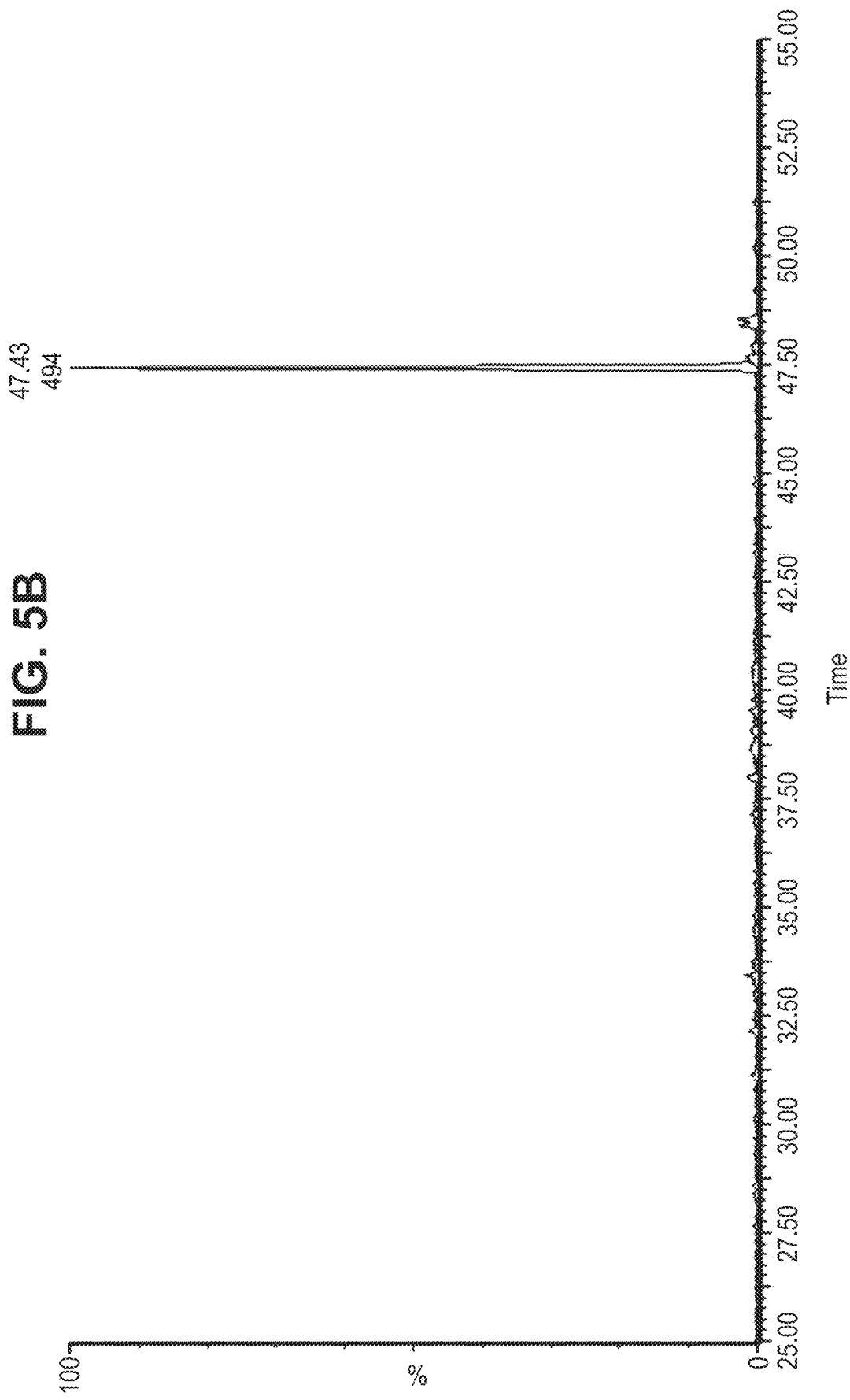

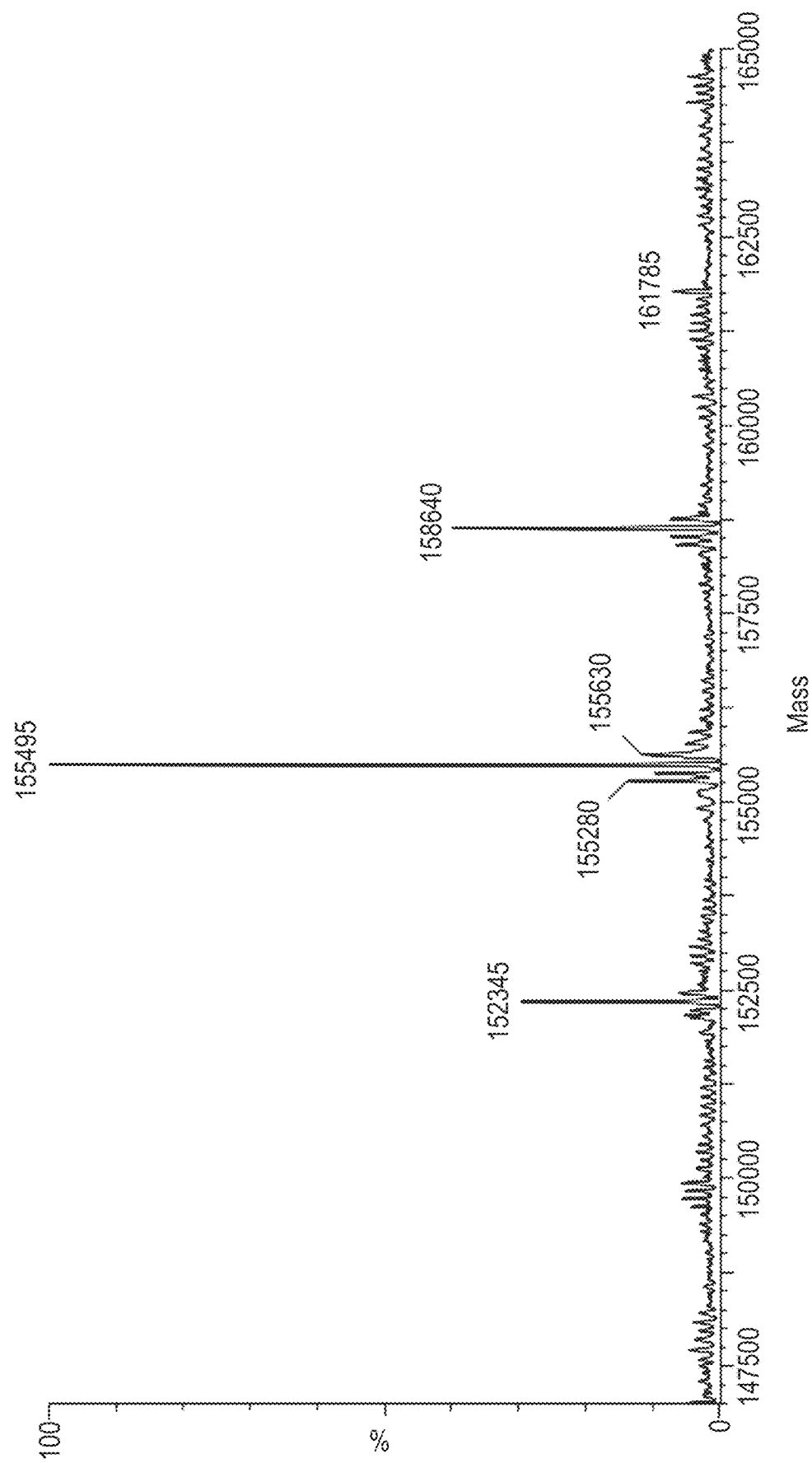

FIG. 8A

```
VL
            Fr1                                        CDR1               FR2             CDR2       FR3                                                CDR3         FR4
            1         2         3                                         4         5          6         7         8                                    9         1   1
            1234567890123456789012345678901234567890abcde234  567890123456  0123456  7890123456789012345678  901234567  8901234567
m38c2  DVVMTQTPLSLPVRLGDQASISC  RSSQSLLHTYGSPYLN      WYLQKPGQSPKLLIY  KVSNRFS  GVPDRFSGSGSGTDFTLRISRVEAEDLGVYFC  SQGTHLPYT  FGGGTKLEIK
         ***  *  *****  ***  ***  ********  *  **  *          **          *                             *           *        *****         *
h38c2  ELQMTQSPSSLSASVGDRVTITC  RSSQSLLHTYGSPYLN      WYLQKPGQSPKLLIY  KVSNRFS  GVPSRFSGSGSGTDFTLTISSLQPEDFAVYFC  SQGTHLPYT  FGGGTKVEIK
         **                    ********                  **           **  ***                                    * *****
DPK-9  DIQMTQSPSSLSASVGDRVTITC  RASQSISS------YLN      WYQQKPGKAPKLLIY  AASSLQS  GVPSRFSGSGSGTDFTLTISSLQPEDFATYYC  QQSYSTP
JK4                                                                                                                        LT  FGGGTKVEIK VH
            FR1                                        CDR1               FR2             CDR2                          FR3                                             CDR3            FR4
            1         2         3                                        4          5                                     6         7         8                         9             1    1
            1234567890123456789012345678901234567890  1ab2345  6789012345  012abc345678901234  5678901234abc  5678901234  56789012  34567890123
m38c2  EVKLVESGGGLVQPGGTMKLSCEISGLTFR  N--YWMS      WVRQSPEKGLEWVA  EIRLRSDNYATHYAESVKG  KFTISRDDSKSRLYLQMNSLRTEDTGIYYCKY  YFY-SFSY  WGQGTLVTVSA
         *                **  *  *  *               *             *  *                          *  **                     *  *  *        * **         *
h38c2  EVQLIESGGGLVQPGGSLRLSCAASGFTFS  N--YWMS      WVRQSPEKGLEWVS  EIRLRSDNYATHYAESVKG  RFTISRDNSKNTLYLQMNSLRAEDTGVYYCKT  YFY-SFSY  WGQGTLVTVSS
         **                            *****          **            ********                **                                *  **
DP-47  EVQLLESGGGLVQPGGSLRLSCAASGFTFS  S--YAMS      WVRQAPGKGLEWVS  AISG--SGGSTYYADSVKG  RFTISRDNSKNTLYLQMNSLRAEDTAVYYCAK
JH4                                                                                                                        YFDY  WGQGTLVTVSS
```

FIG. 8B

```
         A                                B                    C                   D
mCLκ  ---ADAAPTVSIF PPSSEQLTSG GASVVCFLNN FYPRDINVKW KIDGSERQNG VLNSWTDQDS  60
       * *  +       ***       *        * + *       + ****     ****        
hCLκ  ---TVAAPSVFIF PPSDEQLKSG TASVVCLLNN FYPREAKVQW KVDNALQSGN SQESVTEQDS  60
       * +          **+        ++       + +         *         ****        
hCLλ  GQPKAAPSVTLF PPSSEELQAN KATLVCLISD FYPGAVTVAW KADSSPVKAG -VETTTPSKQ  61
               E
mCLκ  KDSTYSMSST LTLTKDEYER HNSYTCEATH KTSTSPIVKS FNRNEC                106
       *         *+          *          *                                  
hCLκ  KDSTYSLSST LTLSKADYEK HKVYACEVTH QGLSSPVTKS FNRGEC                106
       *++       +   +      +  +       ****+     *                        
hCLλ  SNNKYAASSY LSLTPEQW-K HRSYSCQVTH EG-ST-VEKT VAPTEC                105
                              G
                              S
```

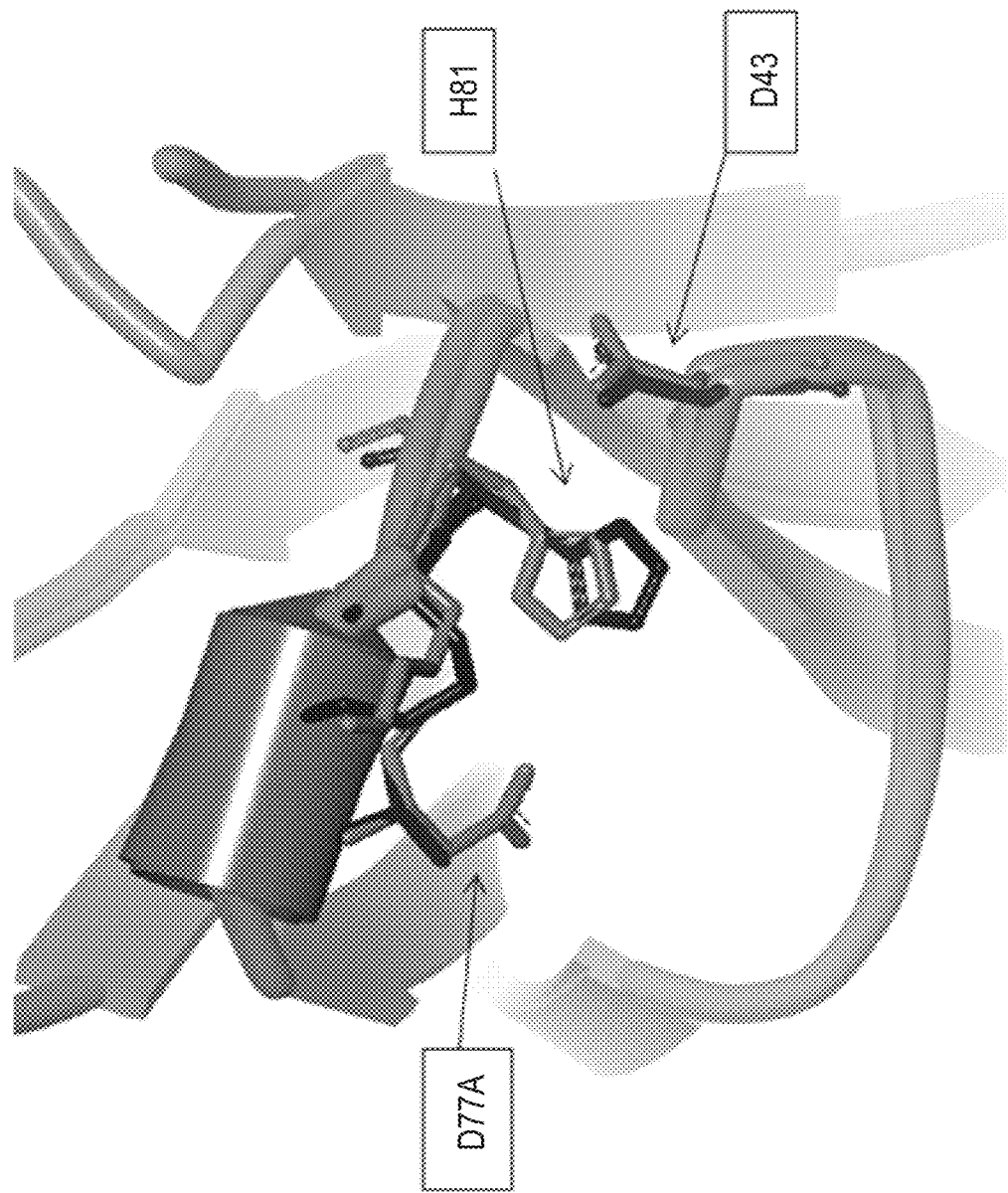

FIG. 16

```
              A                                 B                     C                      D hCHA1  ------AST-KGPSVFPL APSSKST---SGG TAALGCLVKD YFPEPVTVSW NS----GALTSG- VHTFPAVLQS
hCHA2  ------APELLGGPSVFLF PPKPKDTLMISR TPEVTCVVVD VSHEDPEVKF NWYVDGVEVHN AKTKPREEQY
hCHA3  ------GQP--REPQVYTL PPSREEM--TKN QVSLTCLVKG FYPSDIAVEW E---SNGQPENN YKTTPPVLDS
hCLK   ---------TVAAPTVFIF PPSDEQL--KSG TASVVCLLNN FYPREAKVQW K---VDNALQSGN SQESVTEQDS
             *    *                 *                             * hCLA   QLTVLGQPK-AAPSVTLF PPSSEEL---QAN KATLVCLISD FYPGAVTVAW K-ADSSPVKAG VETTTPSKQS

E                                 F                     G hCHA1  -SGLYSLSSV VTVPSSS--LG TQTYICNVNH KPSNTKVDKK VEPKSC-
hCHA2  -NSTYRVVSV LTVLHQDWLN GKEYKCKVSN KALPAPIEKT ISKAK--
hCHA3  -DGSFFLYSK LTVDKSRWQQ GNVFSCSVMH EALHNHYTQK SLSL---
hCLK   KDSTYSLSST LTLSKADYEK HKVYACEVTH QGLSSPVTKS FNRGEC-
hCLA   -NNKYAASSY LSLTPEQWKS HRSYSCQVTH EG--STVEKT VAPTECS
```

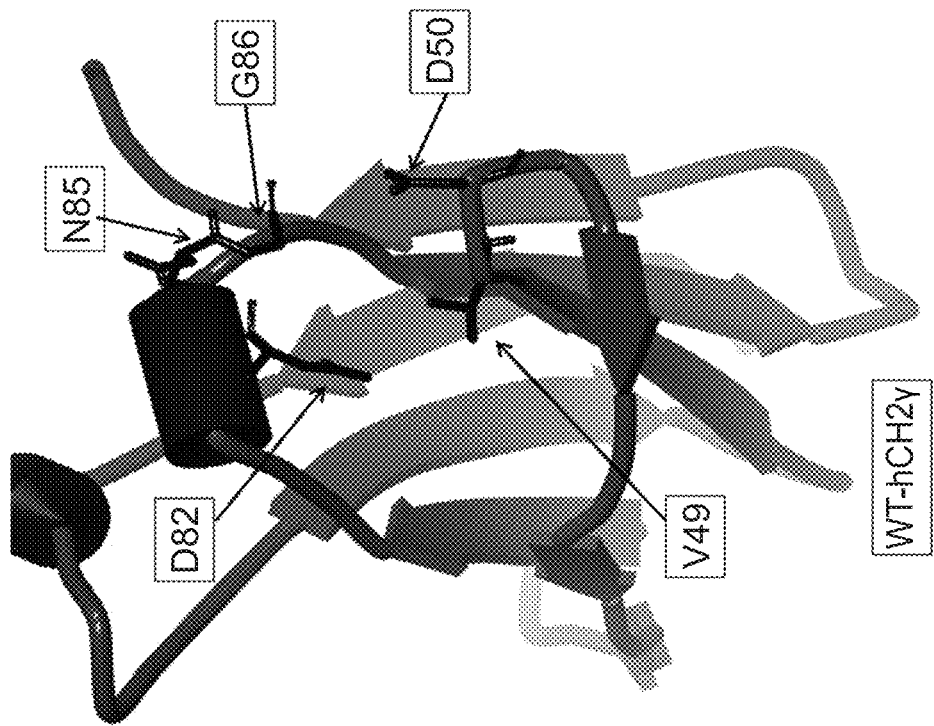
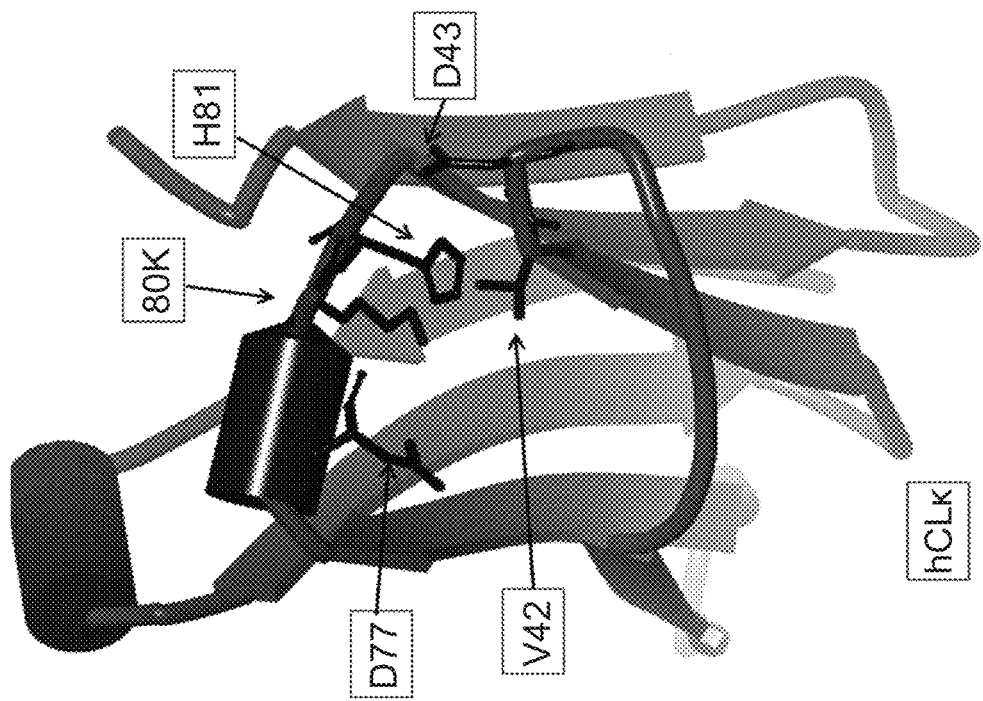

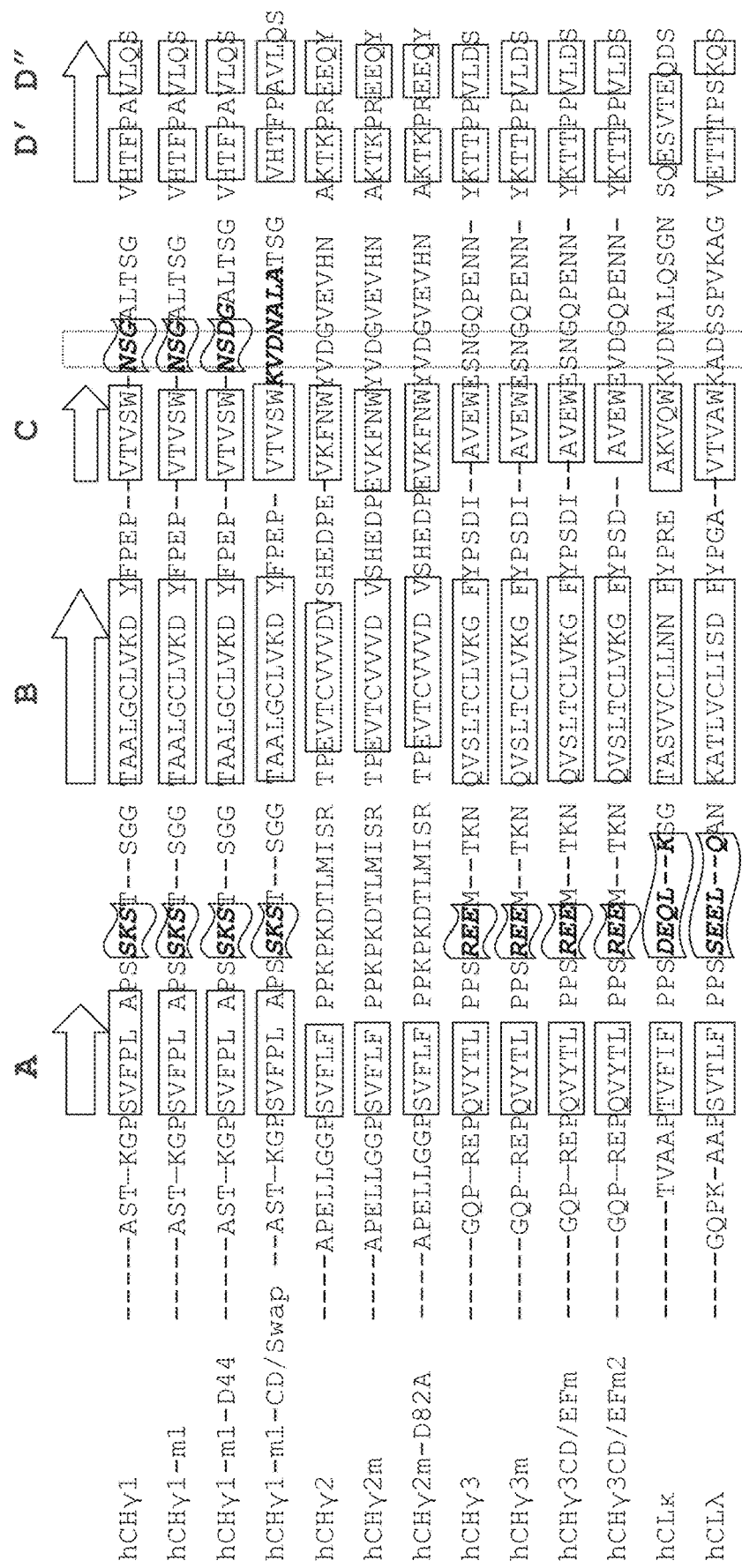

FIG. 32B

| | E | | | F | | G | |
|---|---|---|---|---|---|---|---|
| hCHγ1 | -SGLYSLSSV VTVL | PSSSLG | KH | TYICNVNHK | PSNTKVDKK | VEPKSC- |
| hCHγ1-m1 | -SGLYSLSSV VTVL | PSSSEK | KH | KYICNVNHK | PSNTKVDKK | VEPKSC- |
| hCHγ1-m1-D44 | -SGLYSLSSV VTVL | PSSSEK | KH | KYICNVNHK | PSNTKVDKK | VEPKSC- |
| hCHγ1-m1 CD/Wap | SGLYSLSSV VTVL | PSSSEK | KH | KYICNVNHK | PSNTKVDKK | VEPKSC- |
| hCHγ2 | -NSTYRVVSV LTVL | HQDWL | NGKEYKCKVSN | KALPAPIEKT | ISKAK- |
| hCHγ2m | -NSTYRVVSV LTVL | HQDWL | KHKEYKCKVSN | KALPAPIEKT | ISKAK- |
| hCHγ2m-D82A | -NSTYRVVSV LTVL | HQAWL | KHKEYKCKVSN | KALPAPIEKT | ISKAK- |
| hCHγ3 | -DGSFFLYSK LTVD | KSRWQ | QGNVFSCSVMH | EALHNHYTQK | SLSL- |
| hCHγ3m | -DGSFFLYSK LTVD | KSRWQ | KHNVFSCSVMH | EALHNHYTQK | SLSL- |
| hCHγ3CD/EFm | -DGSFFLYSK LTVD | KSAWQ | KHNVFSCSVMH | EALHNHYTQK | SLSL- |
| hCHγ3CD/EFm2 | -DGSFFLYSK LTVD | KSAWQ | KHNVFSCSVMH | EALHNHYTQK | SLSL- |
| hCLk | KDSTYSLSST LTLS | KADYE | KHKVYACEVTH | QGLSSPVTKS | FNRGEC |
| hCLλ | -NNKYAASSY LSLTP | EQWK | SHRSYSCQVTH | EG-STVEKTV | APTECS |

SEQUENCE LISTING

<160> NUMBER OF SEQ ID NOS: 260

<210> SEQ ID NO 1
<211> LENGTH: 451
<212> TYPE: PRT
<213> ORGANISM: Artificial Sequence
<220> FEATURE:
<223> OTHER INFORMATION: Synthetic Igfr mAb

<400> SEQUENCE: 1

```
Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Arg Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Gly Val Glu Thr Thr Phe Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
```

```
                355                 360                 365
Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Synthetic Igfr mAb

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
                20                  25                  30

Leu Gly Trp Tyr Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Leu Val Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 122
<212> TYPE: PRT
<213> ORGANISM: Artificial Sequence
<220> FEATURE:
<223> OTHER INFORMATION: Synthetic Igfr mAb
```

<400> SEQUENCE: 3

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Thr Arg Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Gly Val Glu Thr Thr Phe Tyr Tyr Tyr Tyr Gly Met
                100                 105                 110

Asp Val Trp Gly Gln Gly Thr Thr Val Thr
            115                 120
```

<210> SEQ ID NO 4
<211> LENGTH: 329
<212> TYPE: PRT
<213> ORGANISM: Homo sapiens

<400> SEQUENCE: 4

```
Val Ser Ser Ala Ser Thr Lys Gly Pro Ser Val Phe Pro Leu Ala Pro
1               5                   10                  15

Cys Ser Arg Ser Thr Ser Glu Ser Thr Ala Ala Leu Gly Cys Leu Val
            20                  25                  30

Lys Asp Tyr Phe Pro Glu Pro Val Thr Val Ser Trp Asn Ser Gly Ala
        35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Asn Phe Gly
65                  70                  75                  80

Thr Gln Thr Tyr Thr Cys Asn Val Asp His Lys Pro Ser Asn Thr Lys
                85                  90                  95

Val Asp Lys Thr Val Glu Arg Lys Cys Cys Val Glu Cys Pro Pro Cys
                100                 105                 110

Pro Ala Pro Pro Val Ala Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240
```

```
Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

```
<210> SEQ ID NO 5
<211> LENGTH: 108
<212> TYPE: PRT
<213> ORGANISM: Artificial Sequence
<220> FEATURE:
<223> OTHER INFORMATION: Synthetic Igfr mAb

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Leu Val Ile Lys Arg
            100                 105
```

```
<210> SEQ ID NO 6
<211> LENGTH: 106
<212> TYPE: PRT
<213> ORGANISM: Homo sapiens

<400> SEQUENCE: 6

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 7
<211> LENGTH: 106
<212> TYPE: PRT
<213> ORGANISM: Homo sapiens

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 106
<212> TYPE: PRT
<213> ORGANISM: Homo sapiens

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Val Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 9
<211> LENGTH: 106
<212> TYPE: PRT
<213> ORGANISM: Homo sapiens
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (82)..(82)
<223> OTHER INFORMATION: Xaa = any amino acid
<220> FEATURE:
<221> NAME/KEY: MISC_FEATURE
<222> LOCATION: (83)..(83)
<223> OTHER INFORMATION: Xaa = L or V

<400> SEQUENCE: 9

Thr Val Ala Ala Pro Ser Val Phe Ile Phe Pro Pro Ser Asp Glu Gln

```
                1               5                  10                 15
            Leu Lys Ser Gly Thr Ala Ser Val Val Cys Leu Leu Asn Asn Phe Tyr
                       20                   25                 30

Pro Arg Glu Ala Lys Val Gln Trp Lys Val Asp Asn Xaa Leu Gln Ser
                       35                   40                 45

Gly Asn Ser Gln Glu Ser Val Thr Glu Gln Asp Ser Lys Asp Ser Thr
                       50                   55                 60

Tyr Ser Leu Ser Ser Thr Leu Thr Leu Ser Lys Ala Asp Tyr Glu Lys
             65                   70                 75                 80

His Xaa Xaa Tyr Ala Cys Glu Val Thr His Gln Gly Leu Ser Ser Pro
                            85                   90                 95

Val Thr Lys Ser Phe Asn Arg Gly Glu Cys
                       100                  105

<210> SEQ ID NO 10
<211> LENGTH: 106
<212> TYPE: PRT
<213> ORGANISM: Homo sapiens
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (83)..(83)
<223> OTHER INFORMATION: Xaa = L or V

<400> SEQUENCE: 10

Thr Val Ala Ala Pro Ser Val Phe Ile Phe Pro Pro Ser Asp Glu Gln
             1               5                  10                 15

Leu Lys Ser Gly Thr Ala Ser Val Val Cys Leu Leu Asn Asn Phe Tyr
                       20                   25                 30

Pro Arg Glu Ala Lys Val Gln Trp Lys Val Asp Asn Xaa Leu Gln Ser
                       35                   40                 45

Gly Asn Ser Gln Glu Ser Val Thr Glu Gln Asp Ser Lys Asp Ser Thr
                       50                   55                 60

Tyr Ser Leu Ser Ser Thr Leu Thr Leu Ser Lys Ala Asp Tyr Glu Lys
             65                   70                 75                 80

His Lys Xaa Tyr Ala Cys Glu Val Thr His Gln Gly Leu Ser Ser Pro
                            85                   90                 95

Val Thr Lys Ser Phe Asn Arg Gly Glu Cys
                       100                  105

<210> SEQ ID NO 11
<211> LENGTH: 106
<212> TYPE: PRT
<213> ORGANISM: Homo sapiens
<220> FEATURE:
<221> NAME/KEY: MISC_FEATURE
<222> LOCATION: (82)..(82)
<223> OTHER INFORMATION: Xaa = any amino acid

<400> SEQUENCE: 11

Thr Val Ala Ala Pro Ser Val Phe Ile Phe Pro Pro Ser Asp Glu Gln
             1               5                  10                 15

Leu Lys Ser Gly Thr Ala Ser Val Val Cys Leu Leu Asn Asn Phe Tyr
                       20                   25                 30

Pro Arg Glu Ala Lys Val Gln Trp Lys Val Asp Asn Ala Leu Gln Ser
                       35                   40                 45

Gly Asn Ser Gln Glu Ser Val Thr Glu Gln Asp Ser Lys Asp Ser Thr
```

```
                50                  55                  60
Tyr Ser Leu Ser Ser Thr Leu Thr Leu Ser Lys Ala Asp Tyr Glu Lys
 65                  70                  75                  80

His Xaa Val Tyr Ala Cys Glu Val Thr His Gln Gly Leu Ser Ser Pro
                     85                  90                  95

Val Thr Lys Ser Phe Asn Arg Gly Glu Cys
                100                 105

<210> SEQ ID NO 12
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 12

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Arg
 65                  70                  75                  80

His Lys Val Tyr Ala Cys Glu Val Thr His Gln Gly Leu Ser Ser Pro
                     85                  90                  95

Val Thr Lys Ser Phe Asn Arg Gly Glu Cys
                100                 105

<210> SEQ ID NO 13
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 13

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Lys
 65                  70                  75                  80

His Arg Val Tyr Ala Cys Glu Val Thr His Gln Gly Leu Ser Ser Pro
                     85                  90                  95

Val Thr Lys Ser Phe Asn Arg Gly Glu Cys
                100                 105

<210> SEQ ID NO 14
<211> LENGTH: 106
<212> TYPE: PRT
<213> ORGANISM: Artificial Sequence
<220> FEATURE:
```

<223> OTHER INFORMATION: Mutant version of human CLk

<400> SEQUENCE: 14

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Arg
65                  70                  75                  80

His Arg Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 15
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 15

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Ala Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 16

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Ala

```
                65                  70                  75                  80
His Lys Val Tyr Ala Cys Glu Val Thr His Gln Gly Leu Ser Ser Pro
                    85                  90                  95
Val Thr Lys Ser Phe Asn Arg Gly Glu Cys
            100                 105
```

<210> SEQ ID NO 17
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 17

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

Ala Lys Val Tyr Ala Cys Glu Val Thr His Gln Gly Leu Ser Ser Pro
                    85                  90                  95

Val Thr Lys Ser Phe Asn Arg Gly Glu Cys
            100                 105
```

<210> SEQ ID NO 18
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 18

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Ala Val Tyr Ala Cys Glu Val Thr His Gln Gly Leu Ser Ser Pro
                    85                  90                  95

Val Thr Lys Ser Phe Asn Arg Gly Glu Cys
            100                 105
```

<210> SEQ ID NO 19
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 19

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Ala Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65              70                  75                  80

Ala Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 20
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 20

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Ala Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65              70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 21
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 21

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Ala Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65              70                  75                  80

His Lys Val Tyr Ala Cys Glu Val Thr His Gln Gly Leu Ser Ser Pro
```

```
                    85                  90                  95

Val Thr Lys Ser Phe Asn Arg Gly Glu Cys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 22

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Ala Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 23

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Ala Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 24

Thr Val Ala Ala Pro Ser Val Phe Ile Phe Pro Pro Ser Asp Glu Gln
1               5                   10                  15
```

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Ala Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 25
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 25

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ala
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 26
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 26

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Ala Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
```

```
              100                 105

<210> SEQ ID NO 27
<211> LENGTH: 22
<212> TYPE: PRT
<213> ORGANISM: Artificial Sequence
<220> FEATURE:
<223> OTHER INFORMATION: Ang2 binding peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Kac
<220> FEATURE:
<221> NAME/KEY: MISC_FEATURE
<222> LOCATION: (9)..(9)
<223> OTHER INFORMATION: Xaa = Kac
<220> FEATURE:
<221> NAME/KEY: MOD_RES
<222> LOCATION: (22)..(22)
<223> OTHER INFORMATION: AMIDATION

<400> SEQUENCE: 27

Gln Xaa Tyr Gln Pro Leu Asp Glu Xaa Asp Lys Thr Leu Tyr Asp Gln
1               5                   10                  15

Phe Met Leu Gln Gln Gly
            20

<210> SEQ ID NO 28
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 28

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Ala Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 29
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 29

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
```

```
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ala Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 30
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 30

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Ala Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 31
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 31

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Ala Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

```
<210> SEQ ID NO 32
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 32

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Ala Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 33
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 33

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

Ala Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 34
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 34

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
```

35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Ala Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 35
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 35

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Ala Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 36
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 36

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Ala Gly Glu Cys
            100                 105

<210> SEQ ID NO 37
<211> LENGTH: 106

```
<212> TYPE: PRT
<213> ORGANISM: Artificial Sequence
<220> FEATURE:
<223> OTHER INFORMATION: Mutant version of human CLk

<400> SEQUENCE: 37

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Ala Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 38
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 38

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Gly Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 39
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 39

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
```

```
                    50                  55                  60

Tyr Ser Leu Ser Ser Thr Leu Thr Leu Ser Lys Ala Val Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 40
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 40

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
             35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Leu Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 41
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 41

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
             35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Ile Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 42
<211> LENGTH: 106
<212> TYPE: PRT
<213> ORGANISM: Artificial Sequence
<220> FEATURE:

<223> OTHER INFORMATION: Mutant version of human CLk

<400> SEQUENCE: 42

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Pro Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 43
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 43

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Phe Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 44
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 44

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Trp Tyr Glu Lys

```
                65                  70                  75                  80
His Lys Val Tyr Ala Cys Glu Val Thr His Gln Gly Leu Ser Ser Pro
                    85                  90                  95

Val Thr Lys Ser Phe Asn Arg Gly Glu Cys
            100                 105
```

<210> SEQ ID NO 45
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 45

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Tyr Tyr Glu Lys
65                  70                  75                  80

His Lys Val Tyr Ala Cys Glu Val Thr His Gln Gly Leu Ser Ser Pro
                    85                  90                  95

Val Thr Lys Ser Phe Asn Arg Gly Glu Cys
            100                 105
```

<210> SEQ ID NO 46
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 46

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala His Tyr Glu Lys
65                  70                  75                  80

His Lys Val Tyr Ala Cys Glu Val Thr His Gln Gly Leu Ser Ser Pro
                    85                  90                  95

Val Thr Lys Ser Phe Asn Arg Gly Glu Cys
            100                 105
```

<210> SEQ ID NO 47
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 47

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Met Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 48
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 48

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Cys Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 49
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 49

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Ser Tyr Glu Lys
65                  70                  75                  80

His Lys Val Tyr Ala Cys Glu Val Thr His Gln Gly Leu Ser Ser Pro

```
                    85                  90                  95

Val Thr Lys Ser Phe Asn Arg Gly Glu Cys
            100                 105

<210> SEQ ID NO 50
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 50

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Thr Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 51
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 51

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Gln Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 52
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 52

Thr Val Ala Ala Pro Ser Val Phe Ile Phe Pro Pro Ser Asp Glu Gln
1               5                   10                  15
```

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asn Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 53
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 53

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Glu Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 54
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 54

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Arg Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys

```
                100             105

<210> SEQ ID NO 55
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 55

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100             105

<210> SEQ ID NO 56
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 56

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Ala Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100             105

<210> SEQ ID NO 57
<211> LENGTH: 105
<212> TYPE: PRT
<213> ORGANISM: Artificial Sequence
<220> FEATURE:
<223> OTHER INFORMATION: Mutant version of human CLk

<400> SEQUENCE: 57

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30
```

-continued

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 58
<211> LENGTH: 106
<212> TYPE: PRT
<213> ORGANISM: Mus musculus

<400> SEQUENCE: 58

Ala Asp Ala Ala Pro Thr Val Ser Ile Phe Pro Pro Ser Ser Glu Gln
 1               5                  10                  15

Leu Thr Ser Gly Gly Ala Ser Val Val Cys Phe Leu Asn Asn Phe Tyr
                20                  25                  30

Pro Arg Asp Ile Asn Val Lys Trp Lys Ile Asp Gly Ser Glu Arg Gln
            35                  40                  45

Asn Gly Val Leu Asn Ser Trp Thr Asp Gln Asp Ser Lys Asp Ser Thr
 50                  55                  60

Tyr Ser Met Ser Ser Thr Leu Thr Leu Thr Lys Asp Glu Tyr Glu Arg
 65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 59
<211> LENGTH: 106
<212> TYPE: PRT
<213> ORGANISM: Homo sapiens

<400> SEQUENCE: 59

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 60
<211> LENGTH: 107
<212> TYPE: PRT
<213> ORGANISM: Artificial Sequence

```
<220> FEATURE:
<223> OTHER INFORMATION: Fusion of human kappa and Lambda

<400> SEQUENCE: 60

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 61
<211> LENGTH: 117
<212> TYPE: PRT
<213> ORGANISM: Artificial Sequence
<220> FEATURE:
<223> OTHER INFORMATION: Fusion of human kappa and Lambda

<400> SEQUENCE: 61

Phe Gly Gly Gly Thr Lys Val Glu Ile Lys Arg Thr Val Ala Ala Pro
1               5                   10                  15

Ser Val Phe Ile Phe Pro Pro Ser Asp Glu Gln Leu Lys Ser Gly Thr
            20                  25                  30

Ala Ser Val Val Cys Leu Leu Asn Asn Phe Tyr Pro Arg Glu Ala Lys
        35                  40                  45

Val Gln Trp Lys Val Asp Asn Ala Leu Gln Ser Gly Asn Ser Gln Glu
    50                  55                  60

Ser Val Thr Glu Gln Asp Ser Lys Asp Ser Thr Tyr Ser Leu Ser Ser
65                  70                  75                  80

Thr Leu Thr Leu Ser Lys Ala Asp Tyr Glu Lys His Lys Val Tyr Ala
                85                  90                  95

Cys Glu Val Thr His Gln Gly Leu Ser Ser Pro Val Thr Lys Ser Phe
            100                 105                 110

Asn Arg Gly Glu Cys
        115

<210> SEQ ID NO 62
<211> LENGTH: 106
<212> TYPE: PRT
<213> ORGANISM: Artificial Sequence
<220> FEATURE:
<223> OTHER INFORMATION: Fusion of human kappa and Lambda

<400> SEQUENCE: 62

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45
```

```
Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

His Ser Arg Ser Tyr Ser Cys Gln Val Thr His Glu Gly Ser Thr Val
                 85                  90                  95

Glu Lys Thr Val Ala Pro Thr Glu Cys Ser
                100                 105
```

```
<210> SEQ ID NO 63
<211> LENGTH: 230
<212> TYPE: PRT
<213> ORGANISM: Artificial Sequence
<220> FEATURE:
<223> OTHER INFORMATION: Igfr mAb

<400> SEQUENCE: 63
```

```
Gln Val Gln Leu Val Glu Ser Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
                 35                  40                  45

Ser Tyr Ile Ser Ser Ser Gly Ser Thr Arg Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Asp Gly Val Glu Thr Thr Phe Tyr Tyr Tyr Tyr Gly Met
                100                 105                 110

Asp Val Trp Gly Gln Gly Thr Thr Val Thr Val Ser Ser Ala Ser Thr
                115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Asn Phe Gly Thr Gln Thr Tyr Thr Cys
                195                 200                 205

Asn Val Asp His Lys Pro Ser Asn Thr Lys Val Asp Lys Thr Val Glu
            210                 215                 220

Arg Lys Cys Cys Val Glu
225                 230
```

```
<210> SEQ ID NO 64
<211> LENGTH: 219
<212> TYPE: PRT
<213> ORGANISM: Artificial Sequence
<220> FEATURE:
<223> OTHER INFORMATION: Synthetic mAb

<400> SEQUENCE: 64
```

```
Glu Leu Gln Met Thr Gln Ser Pro Ser Ser Leu Ser Ala Ser Val Gly
 1               5                  10                  15
```

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 65
<211> LENGTH: 448
<212> TYPE: PRT
<213> ORGANISM: Artificial Sequence
<220> FEATURE:
<223> OTHER INFORMATION: Synthetic mAb

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 66
<211> LENGTH: 444
<212> TYPE: PRT
<213> ORGANISM: Artificial Sequence
<220> FEATURE:
<223> OTHER INFORMATION: Synthetic mAb

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 67
<211> LENGTH: 113
<212> TYPE: PRT
<213> ORGANISM: Artificial Sequence
<220> FEATURE:
<223> OTHER INFORMATION: Synthetic mAb

<400> SEQUENCE: 67
```

```
Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
                100                 105                 110

Arg
```

```
<210> SEQ ID NO 68
<211> LENGTH: 118
<212> TYPE: PRT
<213> ORGANISM: Artificial Sequence
<220> FEATURE:
<223> OTHER INFORMATION: Synthetic mAb

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
                100                 105                 110

Leu Val Thr Val Ser Ser
        115
```

```
<210> SEQ ID NO 69
<211> LENGTH: 112
<212> TYPE: PRT
<213> ORGANISM: Mus musculus

<400> SEQUENCE: 69

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
```

```
                 65                  70                  75                  80
Ser Arg Val Glu Ala Glu Asp Leu Gly Val Tyr Phe Cys Ser Gln Gly
                 85                  90                  95

Thr His Leu Pro Tyr Thr Phe Gly Gly Gly Thr Lys Leu Glu Ile Lys
            100                 105                 110

<210> SEQ ID NO 70
<211> LENGTH: 118
<212> TYPE: PRT
<213> ORGANISM: Mus musculus

<400> SEQUENCE: 70

Glu Val Lys Leu Val Glu Ser Gly Gly Gly Leu Val Gln Pro Gly Gly
1               5                   10                  15

Thr Met Lys Leu Ser Cys Glu Ile Ser Gly Leu Thr Phe Arg Asn Tyr
            20                  25                  30

Trp Met Ser Trp Val Arg Gln Ser Pro Glu Lys Gly Leu Glu Trp Val
        35                  40                  45

Ala Glu Ile Arg Leu Arg Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Thr Glu Asp Thr Gly Ile Tyr
                85                  90                  95

Tyr Cys Lys Tyr Tyr Phe Tyr Ser Phe Ser Tyr Trp Gly Gln Gly Thr
            100                 105                 110

Leu Val Thr Val Ser Ala
        115

<210> SEQ ID NO 71
<211> LENGTH: 450
<212> TYPE: PRT
<213> ORGANISM: Artificial Sequence
<220> FEATURE:
<223> OTHER INFORMATION: Synthetic mAb

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 72
<211> LENGTH: 120
<212> TYPE: PRT
<213> ORGANISM: Artificial Sequence
<220> FEATURE:
<223> OTHER INFORMATION: Synthetic mAb

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 73
<211> LENGTH: 330
<212> TYPE: PRT
<213> ORGANISM: Artificial Sequence
<220> FEATURE:
<223> OTHER INFORMATION: Synthetic mAb

<400> SEQUENCE: 73

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 74
<211> LENGTH: 214
<212> TYPE: PRT
<213> ORGANISM: Artificial Sequence
<220> FEATURE:
<223> OTHER INFORMATION: Synthetic mAb

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 75
<211> LENGTH: 108
<212> TYPE: PRT
<213> ORGANISM: Artificial Sequence
<220> FEATURE:
<223> OTHER INFORMATION: Synthetic mAb

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly

```
                   50                  55                  60
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg
                100                 105

<210> SEQ ID NO 76
<211> LENGTH: 108
<212> TYPE: PRT
<213> ORGANISM: Artificial Sequence
<220> FEATURE:
<223> OTHER INFORMATION: Synthetic mAb

<400> SEQUENCE: 76

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg
                100                 105

<210> SEQ ID NO 77
<211> LENGTH: 106
<212> TYPE: PRT
<213> ORGANISM: Artificial Sequence
<220> FEATURE:
<223> OTHER INFORMATION: Synthetic mAb

<400> SEQUENCE: 77

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
             35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Ala Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
                100                 105

<210> SEQ ID NO 78
<211> LENGTH: 106
<212> TYPE: PRT
<213> ORGANISM: Artificial Sequence
<220> FEATURE:
```

```
<223> OTHER INFORMATION: Synthetic mAb
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (77)..(77)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (83)..(83)
<223> OTHER INFORMATION: Xaa = V or L

<400> SEQUENCE: 78

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Xaa Tyr Glu Lys
65                  70                  75                  80

His Lys Xaa Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 79
<211> LENGTH: 15
<212> TYPE: PRT
<213> ORGANISM: Artificial Sequence
<220> FEATURE:
<223> OTHER INFORMATION: Synthetic peptide

<400> SEQUENCE: 79

Gly Gly Gly Gly Ser Gly Gly Gly Gly Ser Gly Gly Gly Gly Ser
1               5                   10                  15

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Gly Arg Gly Asp Ser Pro Lys
1               5

<210> SEQ ID NO 81
<211> LENGTH: 12
<212> TYPE: PRT
<213> ORGANISM: Artificial Sequence
<220> FEATURE:
<223> OTHER INFORMATION: Synthetic peptide

<400> SEQUENCE: 81

Asp Val Pro Lys Ser Asp Gln Phe Val Gly Leu Met
1               5                   10

<210> SEQ ID NO 82
```

```
<211> LENGTH: 27
<212> TYPE: PRT
<213> ORGANISM: Artificial Sequence
<220> FEATURE:
<223> OTHER INFORMATION: Synthetic peptide

<400> SEQUENCE: 82

Ser Lys Ala Asp Tyr Glu Lys His Lys Val Tyr Ala Cys Glu Val Thr
1               5                   10                  15

His Gln Gly Leu Ser Ser Pro Val Thr Lys Ser
            20                  25

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Ala Asp Tyr Glu Lys His Lys
1               5

<210> SEQ ID NO 84
<211> LENGTH: 19
<212> TYPE: PRT
<213> ORGANISM: Artificial Sequence
<220> FEATURE:
<223> OTHER INFORMATION: Synthetic peptide

<400> SEQUENCE: 84

His Lys Val Tyr Ala Cys Glu Val Thr His Gln Gly Leu Ser Ser Pro
1               5                   10                  15

Val Thr Lys

<210> SEQ ID NO 85
<211> LENGTH: 31
<212> TYPE: DNA
<213> ORGANISM: Artificial Sequence
<220> FEATURE:
<223> OTHER INFORMATION: Synthetic primer

<400> SEQUENCE: 85
caacaagatc tgccaccatg gacatgaggg t                                31

<210> SEQ ID NO 86
<211> LENGTH: 31
<212> TYPE: DNA
<213> ORGANISM: Artificial Sequence
<220> FEATURE:
<223> OTHER INFORMATION: Synthetic primer

<400> SEQUENCE: 86
caacagctag cctaacactc tcccctgttg a                                31

<210> SEQ ID NO 87
<211> LENGTH: 35
<212> TYPE: DNA
<213> ORGANISM: Artificial Sequence
<220> FEATURE:
<223> OTHER INFORMATION: Synthetic primer

<400> SEQUENCE: 87
caacaggtct cggccagcaa agcagactac gagaa                            35
```

```
<210> SEQ ID NO 88
<211> LENGTH: 34
<212> TYPE: DNA
<213> ORGANISM: Artificial Sequence
<220> FEATURE:
<223> OTHER INFORMATION: Synthetic primer

<400> SEQUENCE: 88
caacaggtct cctggccgtc agggtgctgc tgag                               34

<210> SEQ ID NO 89
<211> LENGTH: 35
<212> TYPE: DNA
<213> ORGANISM: Artificial Sequence
<220> FEATURE:
<223> OTHER INFORMATION: Synthetic primer

<400> SEQUENCE: 89
caacaggtct cagatctgcc accatgggat ggagc                              35

<210> SEQ ID NO 90
<211> LENGTH: 32
<212> TYPE: DNA
<213> ORGANISM: Artificial Sequence
<220> FEATURE:
<223> OTHER INFORMATION: Synthetic primer

<400> SEQUENCE: 90
caacaggtct catccgcttg atttccacct tg                                 32

<210> SEQ ID NO 91
<211> LENGTH: 29
<212> TYPE: DNA
<213> ORGANISM: Artificial Sequence
<220> FEATURE:
<223> OTHER INFORMATION: Synthetic primer

<400> SEQUENCE: 91
caacaggtct cacggaccgt ggccgctcc                                     29

<210> SEQ ID NO 92
<211> LENGTH: 29
<212> TYPE: DNA
<213> ORGANISM: Artificial Sequence
<220> FEATURE:
<223> OTHER INFORMATION: Synthetic primer

<400> SEQUENCE: 92
caacagctag cctatcagca ctcgccccg                                     29

<210> SEQ ID NO 93
<211> LENGTH: 106
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
```

```
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K or A
<220> FEATURE:
<221> NAME/KEY: MISC_FEATURE
<222> LOCATION: (65)..(65)
<223> OTHER INFORMATION: Xaa = K, R or N
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 93

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Ala Asp Xaa Ser Pro
        35                  40                  45

Xaa Xaa Xaa Gly Val Glu Thr Thr Xaa Pro Ser Lys Gln Ser Asn Asn
50                  55                  60

Xaa Tyr Ala Ala Ser Ser Tyr Leu Ser Leu Thr Pro Glu Gln Trp Xaa
65                  70                  75                  80

Ser His Xaa Ser Tyr Ser Cys Xaa Val Thr His Glu Gly Ser Thr Val
                85                  90                  95

Glu Lys Thr Val Ala Pro Xaa Glu Cys Ser
            100                 105

<210> SEQ ID NO 94
<211> LENGTH: 106
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = N or A
<220> FEATURE:
```

```
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 94

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Ala Asp Xaa Ser Pro
        35                  40                  45

Xaa Xaa Xaa Gly Val Glu Thr Thr Xaa Pro Ser Lys Gln Ser Asn Asn
50                  55                  60

Xaa Tyr Ala Ala Ser Ser Tyr Leu Ser Leu Thr Pro Glu Gln Trp Xaa
65                  70                  75                  80

Lys His Xaa Ser Tyr Ser Cys Xaa Val Thr His Glu Gly Ser Thr Val
            85                  90                  95

Glu Lys Thr Val Ala Pro Xaa Glu Cys Ser
            100                 105
```

```
<210> SEQ ID NO 95
<211> LENGTH: 106
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (80)..(80)
<223> OTHER INFORMATION: Xaa = G, A, I, L, V, S, T, M, N, Q, F, Y, W, D,
      or E
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 95

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
                20                  25                  30

Phe Tyr Pro Gly Xaa Val Xaa Val Ala Trp Lys Ala Asp Xaa Ser Pro
            35                  40                  45

Xaa Xaa Xaa Gly Val Glu Thr Thr Xaa Pro Ser Lys Gln Ser Asn Asn
```

```
                    50                  55                  60
Xaa Tyr Ala Ala Ser Ser Tyr Leu Ser Leu Thr Pro Glu Gln Trp Xaa
 65                  70                  75                  80

Lys His Xaa Ser Tyr Ser Cys Xaa Val Thr His Glu Gly Ser Thr Val
                 85                  90                  95

Glu Lys Thr Val Ala Pro Xaa Glu Cys Ser
            100                 105

<210> SEQ ID NO 96
<211> LENGTH: 105
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (77)..(77)
<223> OTHER INFORMATION: Xaa = R, L, S, G, Q, P, N, V, I, T, or M
<220> FEATURE:
<221> NAME/KEY: MISC_FEATURE
<222> LOCATION: (82)..(82)
<223> OTHER INFORMATION: Xaa = K or R
<220> FEATURE:
<221> NAME/KEY: MISC_FEATURE
<222> LOCATION: (87)..(87)
<223> OTHER INFORMATION: Xaa = Q or L
<220> FEATURE:
<221> NAME/KEY: MISC_FEATURE
<222> LOCATION: (102)..(102)
<223> OTHER INFORMATION: Xaa = A or T

<400> SEQUENCE: 96
```

-continued

```
Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Ala Asp Xaa Ser Pro
        35                  40                  45

Xaa Xaa Xaa Gly Val Glu Thr Thr Xaa Pro Ser Lys Gln Ser Asn Asn
50                      55                  60

Xaa Tyr Ala Ala Ser Ser Tyr Leu Ser Leu Thr Pro Xaa Gln Trp Lys
65                  70                  75                  80

His Xaa Ser Tyr Ser Cys Xaa Val Thr His Glu Gly Ser Thr Val Glu
            85                  90                  95

Lys Thr Val Ala Pro Xaa Glu Cys Ser
            100                 105
```

<210> SEQ ID NO 97
<211> LENGTH: 106
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (77)..(77)
<223> OTHER INFORMATION: Xaa = R, L, S, G, Q, P, N, V, I, T, or M
<220> FEATURE:
<221> NAME/KEY: MISC_FEATURE
<222> LOCATION: (80)..(80)
<223> OTHER INFORMATION: Xaa = G, A, I, L, V, S, T, M, N, Q, F, Y, W, D, or E -continued

```
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa =  Q or L
<220> FEATURE:
<221> NAME/KEY: MISC_FEATURE
<222> LOCATION: (103)..(103)
<223> OTHER INFORMATION: Xaa =  A or T

<400> SEQUENCE: 97

Gly Gln Pro Lys Ala Xaa Pro Xaa Val Thr Leu Phe Pro Pro Ser Ser
1               5                  10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Ala Asp Xaa Ser Pro
        35                  40                  45

Xaa Xaa Xaa Gly Val Glu Thr Thr Xaa Pro Ser Lys Gln Ser Asn Asn
    50                  55                  60

Xaa Tyr Ala Ala Ser Ser Tyr Leu Ser Leu Thr Pro Xaa Gln Trp Xaa
65                  70                  75                  80

Lys His Xaa Ser Tyr Ser Cys Xaa Val Thr His Glu Gly Ser Thr Val
                85                  90                  95

Glu Lys Thr Val Ala Pro Xaa Glu Cys Ser
            100                 105

<210> SEQ ID NO 98
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 98

Xaa Xaa Xaa Xaa Lys His
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
```

<222> LOCATION: (2)..(2)
<223> OTHER INFORMATION: Xaa = A, G, I, L, R, S, T, P, N, or M
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 99

Xaa Xaa Xaa Xaa Lys His
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = A, G, I, L, S, T, P, or M
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 100

Xaa Xaa Xaa Xaa Lys His
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (3)..(3)
<223> OTHER INFORMATION: Xaa = A, G, I, V, L, R, S, T, Q, P, N, M, H, or
      W

<400> SEQUENCE: 101

Lys Ala Xaa Tyr Glu Lys His
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (3)..(3)
<223> OTHER INFORMATION: Xaa = A, G, I, L, R, S, T, P, N, or M

<400> SEQUENCE: 102

Lys Ala Xaa Tyr Glu Lys His
1               5

```
<210> SEQ ID NO 103
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (3)..(3)
<223> OTHER INFORMATION: Xaa = A, G, I, L, S, T, P, or M

<400> SEQUENCE: 103

Lys Ala Xaa Tyr Glu Lys His
1               5

<210> SEQ ID NO 104
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (77)..(77)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (82)..(82)
<223> OTHER INFORMATION: Xaa = Any amino acid
<220> FEATURE:
<221> NAME/KEY: MISC_FEATURE
<222> LOCATION: (83)..(83)
<223> OTHER INFORMATION: Xaa = L or V

<400> SEQUENCE: 104

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Xaa Tyr Glu Lys
65                  70                  75                  80

His Xaa Xaa Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 105
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
```

```
<222> LOCATION: (77)..(77)
<223> OTHER INFORMATION: Xaa = A, G, I, L, R, S, T, P, N, or M
<220> FEATURE:
<221> NAME/KEY: MISC_FEATURE
<222> LOCATION: (82)..(82)
<223> OTHER INFORMATION: Xaa= Any amino acid
<220> FEATURE:
<221> NAME/KEY: MISC_FEATURE
<222> LOCATION: (83)..(83)
<223> OTHER INFORMATION: Xaa = L or V

<400> SEQUENCE: 105

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Xaa Tyr Glu Lys
65                  70                  75                  80

His Xaa Xaa Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 106
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (77)..(77)
<223> OTHER INFORMATION: Xaa = A, G, I, L, S, T, P, or M
<220> FEATURE:
<221> NAME/KEY: MISC_FEATURE
<222> LOCATION: (82)..(82)
<223> OTHER INFORMATION: Xaa = Any amino acid
<220> FEATURE:
<221> NAME/KEY: MISC_FEATURE
<222> LOCATION: (83)..(83)
<223> OTHER INFORMATION: Xaa = L or V

<400> SEQUENCE: 106

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Xaa Tyr Glu Lys
65                  70                  75                  80

His Xaa Xaa Tyr Ala Cys Glu Val Thr His Gln Gly Leu Ser Ser Pro
                85                  90                  95

Val Thr Lys Ser Phe Asn Arg Gly Glu Cys
```

<210> SEQ ID NO 107
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 107

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Glu Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 108
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 108

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asn Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 109
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 109

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Leu Asn Ala Leu Gln Ser
            35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 110
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 110

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

Asn Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 111
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 111

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

Gln Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 112
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 112

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

Tyr Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 113
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 113

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

Trp Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 114
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 114

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45
```

```
Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

Phe Lys Val Tyr Ala Cys Glu Val Thr His Gln Gly Leu Ser Ser Pro
                85                  90                  95

Val Thr Lys Ser Phe Asn Arg Gly Glu Cys
                100                 105
```

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = Any amino acid
<220> FEATURE:
<221> NAME/KEY: MISC_FEATURE
<222> LOCATION: (3)..(3)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (4)..(4)
<223> OTHER INFORMATION: Xaa = Any amino Acid
<220> FEATURE:
<221> NAME/KEY: MISC_FEATURE
<222> LOCATION: (5)..(5)
<223> OTHER INFORMATION: Xaa = Any amino Acid

<400> SEQUENCE: 115

```
Xaa Xaa Xaa Xaa Xaa Lys His
1               5
```

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = Any amino acid
<220> FEATURE:
<221> NAME/KEY: MISC_FEATURE
<222> LOCATION: (3)..(3)
<223> OTHER INFORMATION: Xaa = A, G, I, L, R, S, T, P, N, or M
<220> FEATURE:
<221> NAME/KEY: MISC_FEATURE
<222> LOCATION: (4)..(4)
<223> OTHER INFORMATION: Xaa = Any amino acid
<220> FEATURE:
<221> NAME/KEY: MISC_FEATURE
<222> LOCATION: (5)..(5)
<223> OTHER INFORMATION: Xaa = Any amino acid

<400> SEQUENCE: 116

```
Xaa Xaa Xaa Xaa Xaa Lys His
1               5
```

```
<210> SEQ ID NO 117
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = Any amino acid
<220> FEATURE:
<221> NAME/KEY: MISC_FEATURE
<222> LOCATION: (3)..(3)
<223> OTHER INFORMATION: Xaa = A, G, I, L, S, T, P, or M
<220> FEATURE:
<221> NAME/KEY: MISC_FEATURE
<222> LOCATION: (4)..(4)
<223> OTHER INFORMATION: Xaa = Any amino acid
<220> FEATURE:
<221> NAME/KEY: MISC_FEATURE
<222> LOCATION: (5)..(5)
<223> OTHER INFORMATION: Xaa = Any amino acid

<400> SEQUENCE: 117

Xaa Xaa Xaa Xaa Xaa Lys His
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = Any amino acid
<220> FEATURE:
<221> NAME/KEY: MISC_FEATURE
<222> LOCATION: (3)..(3)
<223> OTHER INFORMATION: Xaa = A, G, I, L, V, R, S, T, Q, P, N, M, H, or
      W
<220> FEATURE:
<221> NAME/KEY: MISC_FEATURE
<222> LOCATION: (4)..(4)
<223> OTHER INFORMATION: Xaa = Any aromatic amino acid
<220> FEATURE:
<221> NAME/KEY: MISC_FEATURE
<222> LOCATION: (5)..(5)
<223> OTHER INFORMATION: Xaa = Any amino acid

<400> SEQUENCE: 118

Xaa Xaa Xaa Xaa Xaa Lys His
1               5

<210> SEQ ID NO 119
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (43)..(43)
<223> OTHER INFORMATION: Xaa = D, E, N, or Q
```

-continued

```
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (76)..(76)
<223> OTHER INFORMATION: Xaa = Any amino acid
<220> FEATURE:
<221> NAME/KEY: MISC_FEATURE
<222> LOCATION: (77)..(77)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (78)..(78)
<223> OTHER INFORMATION: Xaa = any amino acid
<220> FEATURE:
<221> NAME/KEY: MISC_FEATURE
<222> LOCATION: (79)..(79)
<223> OTHER INFORMATION: Xaa = any amino acid
<220> FEATURE:
<221> NAME/KEY: MISC_FEATURE
<222> LOCATION: (82)..(82)
<223> OTHER INFORMATION: Xaa = any amino acid
<220> FEATURE:
<221> NAME/KEY: MISC_FEATURE
<222> LOCATION: (83)..(83)
<223> OTHER INFORMATION: Xaa = L or V

<400> SEQUENCE: 119

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Xaa Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Xaa Xaa Xaa Xaa Lys
65                  70                  75                  80

His Xaa Xaa Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 120
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (43)..(43)
<223> OTHER INFORMATION: Xaa = D, E, N, or Q
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (76)..(76)
<223> OTHER INFORMATION: Xaa = Any amino acid
<220> FEATURE:
<221> NAME/KEY: MISC_FEATURE
<222> LOCATION: (77)..(77)
<223> OTHER INFORMATION: Xaa = A, G, I, V, L, R, S, T, Q, P, N, M, H, or
      W
<220> FEATURE:
<221> NAME/KEY: MISC_FEATURE
```

<222> LOCATION: (78)..(78)
<223> OTHER INFORMATION: Xaa = Any aromatic amino acid
<220> FEATURE:
<221> NAME/KEY: MISC_FEATURE
<222> LOCATION: (79)..(79)
<223> OTHER INFORMATION: Xaa = Any amino acid
<220> FEATURE:
<221> NAME/KEY: MISC_FEATURE
<222> LOCATION: (82)..(82)
<223> OTHER INFORMATION: Xaa = Any amino acid
<220> FEATURE:
<221> NAME/KEY: MISC_FEATURE
<222> LOCATION: (83)..(83)
<223> OTHER INFORMATION: Xaa = L or V

<400> SEQUENCE: 120

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Xaa Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Xaa Xaa Xaa Xaa Lys
65                  70                  75                  80

His Xaa Xaa Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 121
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (43)..(43)
<223> OTHER INFORMATION: Xaa = D, E, N, or Q
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (76)..(76)
<223> OTHER INFORMATION: Xaa = Any amino acid
<220> FEATURE:
<221> NAME/KEY: MISC_FEATURE
<222> LOCATION: (77)..(77)
<223> OTHER INFORMATION: Xaa = A, G, I, L, S, T, P, or M
<220> FEATURE:
<221> NAME/KEY: MISC_FEATURE
<222> LOCATION: (78)..(78)
<223> OTHER INFORMATION: Xaa = Any amino acid
<220> FEATURE:
<221> NAME/KEY: MISC_FEATURE
<222> LOCATION: (79)..(79)
<223> OTHER INFORMATION: Xaa = Any amino acid
<220> FEATURE:
<221> NAME/KEY: MISC_FEATURE
<222> LOCATION: (82)..(82)
<223> OTHER INFORMATION: Xaa = Any amino acid
<220> FEATURE:
<221> NAME/KEY: MISC_FEATURE
<222> LOCATION: (83)..(83)
<223> OTHER INFORMATION: Xaa = L or V

<400> SEQUENCE: 121

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Xaa Asn Xaa Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Xaa Xaa Xaa Xaa Lys
65                  70                  75                  80

His Xaa Xaa Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 122
<211> LENGTH: 106
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (43)..(43)
<223> OTHER INFORMATION: Xaa = D, E, N, or Q
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (76)..(76)
<223> OTHER INFORMATION: Xaa = Any amino acid
<220> FEATURE:
<221> NAME/KEY: MISC_FEATURE
<222> LOCATION: (77)..(77)
<223> OTHER INFORMATION: Xaa = A, G, I, L, S, T, P, or M
<220> FEATURE:
<221> NAME/KEY: MISC_FEATURE
<222> LOCATION: (78)..(78)
<223> OTHER INFORMATION: Xaa = Any aromatic amino acid
<220> FEATURE:
<221> NAME/KEY: MISC_FEATURE
<222> LOCATION: (79)..(79)
<223> OTHER INFORMATION: Xaa = Any amino acid
<220> FEATURE:
<221> NAME/KEY: MISC_FEATURE
<222> LOCATION: (82)..(82)
<223> OTHER INFORMATION: Xaa = Any amino acid
<220> FEATURE:
<221> NAME/KEY: MISC_FEATURE
<222> LOCATION: (83)..(83)
<223> OTHER INFORMATION: Xaa = L or V

<400> SEQUENCE: 122

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Xaa Asn Xaa Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Xaa Xaa Xaa Xaa Lys
65                  70                  75                  80
```

```
His Xaa Xaa Tyr Ala Cys Glu Val Thr His Gln Gly Leu Ser Ser Pro
             85                  90                  95

Val Thr Lys Ser Phe Asn Arg Gly Glu Cys
            100                 105

<210> SEQ ID NO 123
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = A, G, I, L, V, R, S, T, Q, P, N, or M
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 123

Xaa Xaa Xaa Xaa Lys His
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = A, G, I, V, L, R, S, T, P, or M
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 124

Xaa Xaa Xaa Xaa Lys His
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = A, G, I, V, L, S, T, or M
```

```
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 125

Xaa Xaa Xaa Xaa Lys His
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic peptide based on IgG loop
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = A, G, I, L, S, T, or M
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 126

Xaa Xaa Xaa Xaa Lys His
1               5

<210> SEQ ID NO 127
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 127

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Ala Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Ala Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 128
<211> LENGTH: 106
<212> TYPE: PRT
<213> ORGANISM: Artificial Sequence
```

<220> FEATURE:
<223> OTHER INFORMATION: Mutant version of human CLk

<400> SEQUENCE: 128

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Ala Tyr Glu Lys
65                  70                  75                  80

Ala Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 129
<211> LENGTH: 106
<212> TYPE: PRT
<213> ORGANISM: Artificial Sequence
<220> FEATURE:
<223> OTHER INFORMATION: Mutant version of human CLk

<400> SEQUENCE: 129

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Ala Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Ala Tyr Glu Lys
65                  70                  75                  80

Ala Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 130
<211> LENGTH: 104
<212> TYPE: PRT
<213> ORGANISM: Artificial Sequence
<220> FEATURE:
<223> OTHER INFORMATION: Rabbit CLk

<400> SEQUENCE: 130

Arg Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 131
<211> LENGTH: 323
<212> TYPE: PRT
<213> ORGANISM: Artificial Sequence
<220> FEATURE:
<223> OTHER INFORMATION: Rabbit constant heavy chain

<400> SEQUENCE: 131

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Val Asp Val Ser Gln
130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Ser Lys Leu Ser Val
        275                 280                 285

Pro Thr Ser Glu Trp Gln Arg Gly Asp Val Phe Thr Cys Ser Val Met
290                 295                 300

His Glu Ala Leu His Asn His Tyr Thr Gln Lys Ser Ile Ser Arg Ser
305                 310                 315                 320

Pro Gly Lys

<210> SEQ ID NO 132
<211> LENGTH: 211
<212> TYPE: PRT
<213> ORGANISM: Artificial Sequence
<220> FEATURE:
<223> OTHER INFORMATION: Trastuzumab rabbit k1 chimera

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Asp Pro Val Ala
            100                 105                 110

Pro Thr Val Leu Ile Phe Pro Ala Ala Asp Gln Val Ala Thr Gly
        115                 120                 125

Thr Val Thr Ile Val Cys Val Ala Asn Lys Tyr Phe Pro Asp Val Thr
130                 135                 140

Val Thr Trp Glu Val Asp Gly Thr Thr Gln Thr Thr Gly Ile Glu Asn
145                 150                 155                 160

Ser Lys Thr Pro Gln Asn Ser Ala Asp Cys Thr Tyr Asn Leu Ser Ser
                165                 170                 175

Thr Leu Thr Leu Thr Ser Thr Gln Tyr Asn Ser His Lys Glu Tyr Thr
            180                 185                 190

Cys Lys Val Thr Gln Gly Thr Thr Ser Val Val Gln Ser Phe Asn Arg
        195                 200                 205

Gly Asp Cys
        210

<210> SEQ ID NO 133
<211> LENGTH: 443
<212> TYPE: PRT
<213> ORGANISM: Artificial Sequence
<220> FEATURE:
<223> OTHER INFORMATION: Trastuzumab rabbit IgG chimera

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Gly Gln Pro Lys Ala Pro Ser Val
            115                 120                 125
Phe Pro Leu Ala Pro Cys Cys Gly Asp Thr Pro Ser Ser Thr Val Thr
            130                 135                 140
Leu Gly Cys Leu Val Lys Gly Tyr Leu Pro Glu Pro Val Thr Val Thr
145                 150                 155                 160
Trp Asn Ser Gly Thr Leu Thr Asn Gly Val Arg Thr Phe Pro Ser Val
                165                 170                 175
Arg Gln Ser Ser Gly Leu Tyr Ser Leu Ser Ser Val Val Ser Val Thr
                180                 185                 190
Ser Ser Ser Gln Pro Val Thr Cys Asn Val Ala His Pro Ala Thr Asn
            195                 200                 205
Thr Lys Val Asp Lys Thr Val Ala Pro Ser Thr Cys Ser Lys Pro Thr
            210                 215                 220
Cys Pro Pro Pro Glu Leu Leu Gly Gly Pro Ser Val Phe Ile Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Asp Pro Glu Val Gln Phe Thr
                260                 265                 270
Trp Tyr Ile Asn Asn Glu Gln Val Arg Thr Ala Arg Pro Pro Leu Arg
            275                 280                 285
Glu Gln Gln Phe Asn Ser Thr Ile Arg Val Val Ser Thr Leu Pro Ile
            290                 295                 300
Ala His Gln Asp Trp Leu Arg Gly Lys Glu Phe Lys Cys Lys Val His
305                 310                 315                 320
Asn Lys Ala Leu Pro Ala Pro Ile Glu Lys Thr Ile Ser Lys Ala Arg
                325                 330                 335
Gly Gln Pro Leu Glu Pro Lys Val Tyr Thr Met Gly Pro Pro Arg Glu
            340                 345                 350
Glu Leu Ser Ser Arg Ser Val Ser Leu Thr Cys Met Ile Asn Gly Phe
            355                 360                 365
Tyr Pro Ser Asp Ile Ser Val Glu Trp Glu Lys Asn Gly Lys Ala Glu
            370                 375                 380
Asp Asn Tyr Lys Thr Thr Pro Ala Val Leu Asp Ser Asp Gly Ser Tyr
385                 390                 395                 400
Phe Leu Tyr Ser Lys Leu Ser Val Pro Thr Ser Glu Trp Gln Arg Gly
                405                 410                 415
Asp Val Phe Thr Cys Ser Val Met His Glu Ala Leu His Asn His Tyr
            420                 425                 430
Thr Gln Lys Ser Ile Ser Arg Ser Pro Gly Lys
            435                 440

<210> SEQ ID NO 134
<211> LENGTH: 104
<212> TYPE: PRT
<213> ORGANISM: Artificial Sequence
<220> FEATURE:
<223> OTHER INFORMATION: Mutant version of rabbit CLk

<400> SEQUENCE: 134
```

```
Arg Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
            35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Lys
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100
```

<210> SEQ ID NO 135
<211> LENGTH: 211
<212> TYPE: PRT
<213> ORGANISM: Artificial Sequence
<220> FEATURE:
<223> OTHER INFORMATION: Trastuzumab -rabbit k1 chimera

<400> SEQUENCE: 135

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Asp Pro Val Ala
            100                 105                 110

Pro Thr Val Leu Ile Phe Pro Pro Ala Ala Asp Gln Val Ala Thr Gly
            115                 120                 125

Thr Val Thr Ile Val Cys Val Ala Asn Lys Tyr Phe Pro Asp Val Thr
    130                 135                 140

Val Thr Trp Glu Val Asp Gly Thr Thr Gln Thr Thr Gly Ile Glu Asn
145                 150                 155                 160

Ser Lys Thr Pro Gln Asn Ser Ala Asp Cys Thr Tyr Asn Leu Ser Ser
                165                 170                 175

Thr Leu Thr Leu Thr Ser Thr Gln Tyr Asn Lys His Lys Glu Tyr Thr
            180                 185                 190

Cys Lys Val Thr Gln Gly Thr Thr Ser Val Val Gln Ser Phe Asn Arg
        195                 200                 205

Gly Asp Cys
    210
```

<210> SEQ ID NO 136
<211> LENGTH: 217
<212> TYPE: PRT
<213> ORGANISM: Artificial Sequence
<220> FEATURE:

<223> OTHER INFORMATION: Synthetic mAb

<400> SEQUENCE: 136

Gln Ala Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Val Phe Gly Gly Thr Gln Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 137
<211> LENGTH: 451
<212> TYPE: PRT
<213> ORGANISM: Artificial Sequence
<220> FEATURE:
<223> OTHER INFORMATION: Synthetic mAb

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Asp Ser Asp Val Trp Gly
            100                 105                 110

Arg Gly Thr Leu Val Thr Val Ser Ser Ala Ser Thr Lys Gly Pro Ser
        115                 120                 125

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 138
<211> LENGTH: 111
<212> TYPE: PRT
<213> ORGANISM: Artificial Sequence
<220> FEATURE:
<223> OTHER INFORMATION: Synthetic mAb

<400> SEQUENCE: 138

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

```
Tyr Gly Val His Trp Tyr Gln Gln Leu Pro Gly Thr Ala Pro Lys Leu
            35                  40                  45

Leu Ile Tyr Gly Asp Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Asn Ser
                 85                  90                  95

Leu Ser Gly Tyr Val Phe Gly Gly Gly Thr Gln Leu Thr Val Leu
                100                 105                 110

<210> SEQ ID NO 139
<211> LENGTH: 106
<212> TYPE: PRT
<213> ORGANISM: Homo sapiens

<400> SEQUENCE: 139

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 140
<211> LENGTH: 106
<212> TYPE: PRT
<213> ORGANISM: Artificial Sequence
<220> FEATURE:
<223> OTHER INFORMATION: Fusion of human kappa & lambda

<400> SEQUENCE: 140

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Lys His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 141
<211> LENGTH: 106
```

```
<212> TYPE: PRT
<213> ORGANISM: Artificial Sequence
<220> FEATURE:
<223> OTHER INFORMATION: Fusion of human kappa and lambda

<400> SEQUENCE: 141

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Ala Trp Lys
65                  70                  75                  80

Lys His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 142
<211> LENGTH: 106
<212> TYPE: PRT
<213> ORGANISM: Artificial Sequence
<220> FEATURE:
<223> OTHER INFORMATION: fusion of human kappa & lambda

<400> SEQUENCE: 142

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Val Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Lys His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 143
<211> LENGTH: 106
<212> TYPE: PRT
<213> ORGANISM: Artificial Sequence
<220> FEATURE:
<223> OTHER INFORMATION: fusion of human kappa & lambda

<400> SEQUENCE: 143

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Val Asp Ser Ser Pro
        35                  40                  45

Val Lys Ala Gly Val Glu Thr Thr Thr Pro Ser Lys Gln Ser Asn Asn
```

```
            50                  55                  60
Lys Tyr Ala Ala Ser Ser Tyr Leu Ser Leu Thr Pro Glu Ala Trp Lys
 65                  70                  75                  80

Lys His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 144
<211> LENGTH: 106
<212> TYPE: PRT
<213> ORGANISM: Artificial Sequence
<220> FEATURE:
<223> OTHER INFORMATION: fusion of human kappa & lambda

<400> SEQUENCE: 144

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Lys Ala Ala Tyr Glu
 65                  70                  75                  80

Lys His Lys Val Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 145
<211> LENGTH: 9
<212> TYPE: PRT
<213> ORGANISM: Artificial Sequence
<220> FEATURE:
<223> OTHER INFORMATION: Synthetic sequence from human lambda chain

<400> SEQUENCE: 145

Lys Ala Ala Tyr Glu Lys His Lys Val
 1               5

<210> SEQ ID NO 146
<211> LENGTH: 214
<212> TYPE: PRT
<213> ORGANISM: Artificial Sequence
<220> FEATURE:
<223> OTHER INFORMATION: Synthetic mAb

<400> SEQUENCE: 146

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Ala His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 147
<211> LENGTH: 98
<212> TYPE: PRT
<213> ORGANISM: Artificial Sequence
<220> FEATURE:
<223> OTHER INFORMATION: Synthetic mAb

<400> SEQUENCE: 147

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 148
<211> LENGTH: 98
<212> TYPE: PRT
<213> ORGANISM: Artificial Sequence
<220> FEATURE:
<223> OTHER INFORMATION: Synthetic mAb

<400> SEQUENCE: 148

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Glu Lys His Lys Val
65                  70                  75                  80

Tyr Ile Cys Asn Val Asn His Lys Pro Ser Asn Thr Lys Val Asp Lys
                85                  90                  95

Lys Val
```

<210> SEQ ID NO 149
<211> LENGTH: 99
<212> TYPE: PRT
<213> ORGANISM: Artificial Sequence
<220> FEATURE:
<223> OTHER INFORMATION: Synthetic mAb

<400> SEQUENCE: 149

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Asp Gly Ala Leu Thr
            35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Glu Lys His Lys
65                  70                  75                  80

Val Tyr Ile Cys Asn Val Asn His Lys Pro Ser Asn Thr Lys Val Asp
                85                  90                  95

Lys Lys Val
```

<210> SEQ ID NO 150
<211> LENGTH: 99
<212> TYPE: PRT
<213> ORGANISM: Artificial Sequence
<220> FEATURE:
<223> OTHER INFORMATION: Syntehtic mAb

<400> SEQUENCE: 150

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Tyr Glu Lys His Lys
65                  70                  75                  80

Val Tyr Ile Cys Asn Val Asn His Lys Pro Ser Asn Thr Lys Val Asp
                85                  90                  95

Lys Lys Val
```

<210> SEQ ID NO 151
<211> LENGTH: 100
<212> TYPE: PRT
<213> ORGANISM: Artificial Sequence
<220> FEATURE:
<223> OTHER INFORMATION: Syntehtic mAb

<400> SEQUENCE: 151

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Asp Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Tyr Glu Lys His
65                  70                  75                  80

Lys Val Tyr Ile Cys Asn Val Asn His Lys Pro Ser Asn Thr Lys Val
                85                  90                  95

Asp Lys Lys Val
            100

<210> SEQ ID NO 152
<211> LENGTH: 5
<212> TYPE: PRT
<213> ORGANISM: Artificial Sequence
<220> FEATURE:
<223> OTHER INFORMATION: hIGg1-CH1 segment removed

<400> SEQUENCE: 152

Leu Gly Thr Gln Thr
1               5

<210> SEQ ID NO 153
<211> LENGTH: 5
<212> TYPE: PRT
<213> ORGANISM: Artificial Sequence
<220> FEATURE:
<223> OTHER INFORMATION: M1 Insert

<400> SEQUENCE: 153

Glu Lys His Lys Val
1               5

<210> SEQ ID NO 154
<211> LENGTH: 6
<212> TYPE: PRT
<213> ORGANISM: Artificial Sequence
<220> FEATURE:
<223> OTHER INFORMATION: M2 Insert

<400> SEQUENCE: 154

Tyr Glu Lys His Lys Val
1               5

<210> SEQ ID NO 155
<211> LENGTH: 110
<212> TYPE: PRT
<213> ORGANISM: Artificial Sequence
<220> FEATURE:
<223> OTHER INFORMATION: Synthetic mAb

<400> SEQUENCE: 155

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45
```

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 156
<211> LENGTH: 110
<212> TYPE: PRT
<213> ORGANISM: Artificial Sequence
<220> FEATURE:
<223> OTHER INFORMATION: Synthetic mAb

<400> SEQUENCE: 156

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Lys His Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 157
<211> LENGTH: 107
<212> TYPE: PRT
<213> ORGANISM: Artificial Sequence
<220> FEATURE:
<223> OTHER INFORMATION: Synthetic mAb

<400> SEQUENCE: 157

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 158
<211> LENGTH: 107
<212> TYPE: PRT
<213> ORGANISM: Artificial Sequence
```

```
<220> FEATURE:
<223> OTHER INFORMATION: Synthetic mAb

<400> SEQUENCE: 158

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Lys His
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 159
<211> LENGTH: 451
<212> TYPE: PRT
<213> ORGANISM: Artificial Sequence
<220> FEATURE:
<223> OTHER INFORMATION: Synthetic mAb

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Tyr Glu Lys His Lys Val Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
```

```
                225                 230                 235                 240
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450

<210> SEQ ID NO 160
<211> LENGTH: 451
<212> TYPE: PRT
<213> ORGANISM: Artificial Sequence
<220> FEATURE:
<223> OTHER INFORMATION: Synthetic mAb

<400> SEQUENCE: 160

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
```

```
              130                 135                 140
Leu Gly Cys Leu Val Lys Asp Tyr Phe Pro Glu Pro Val Thr Val Ser
145                 150                 155                 160

Trp Asn Ser Asp Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Glu Lys His Lys Val Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 161
<211> LENGTH: 452
<212> TYPE: PRT
<213> ORGANISM: Artificial Sequence
<220> FEATURE:
<223> OTHER INFORMATION: Synthetic mAb

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

-continued

```
            35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Asp Gly Ala Leu Thr Ser Gly Val His Thr Phe Pro Ala
                    165                 170                 175

Val Leu Gln Ser Ser Gly Leu Tyr Ser Leu Ser Ser Val Val Thr Val
                180                 185                 190

Pro Ser Ser Ser Tyr Glu Lys His Lys Val Tyr Ile Cys Asn Val Asn
                195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
            450
```

<210> SEQ ID NO 162
<211> LENGTH: 450
<212> TYPE: PRT
<213> ORGANISM: Artificial Sequence
<220> FEATURE:
<223> OTHER INFORMATION: Synthetic mAb

<400> SEQUENCE: 162

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Lys His Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 163
<211> LENGTH: 450
<212> TYPE: PRT
<213> ORGANISM: Artificial Sequence
<220> FEATURE:
<223> OTHER INFORMATION: Synthetic mAb

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Lys His Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 164
<211> LENGTH: 39
<212> TYPE: PRT
<213> ORGANISM: Artificial Sequence
<220> FEATURE:
<223> OTHER INFORMATION: Synthetic Analog of Exendin 4
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = KSH

<400> SEQUENCE: 164

His Xaa Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 165
<211> LENGTH: 100
<212> TYPE: PRT
<213> ORGANISM: Artificial Sequence
<220> FEATURE:
<223> OTHER INFORMATION: Synthetic mAb

<400> SEQUENCE: 165

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

Phe Pro Glu Pro Val Thr Val Ser Trp Lys Val Asp Asn Ala Leu Ala
            35                  40                  45

Thr Ser Gly Val His Thr Phe Pro Ala Val Leu Gln Ser Ser Gly Leu
        50                  55                  60

Tyr Ser Leu Ser Ser Val Val Thr Val Pro Ser Ser Glu Lys His
65                  70                  75                  80

Lys Val Tyr Ile Cys Asn Val Asn His Lys Pro Ser Asn Thr Lys Val
                85                  90                  95

Asp Lys Lys Val
            100

<210> SEQ ID NO 166
<211> LENGTH: 7
<212> TYPE: PRT
<213> ORGANISM: Artificial Sequence
<220> FEATURE:
<223> OTHER INFORMATION: Synthetic Ig CD loop sequence

<400> SEQUENCE: 166

Lys Val Asp Asn Ala Leu Ala
1               5

<210> SEQ ID NO 167
<211> LENGTH: 110
<212> TYPE: PRT
<213> ORGANISM: Artificial Sequence
<220> FEATURE:
<223> OTHER INFORMATION: Synthetic mAb

<400> SEQUENCE: 167

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Ala Trp Leu Lys His Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 168
<211> LENGTH: 107
<212> TYPE: PRT
<213> ORGANISM: Artificial Sequence
<220> FEATURE:
<223> OTHER INFORMATION: Synthetic mAb

<400> SEQUENCE: 168

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Val Asp Gly Gln Pro Glu
        35                  40                  45

```
Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Ala Trp Gln Lys His
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 169
<211> LENGTH: 107
<212> TYPE: PRT
<213> ORGANISM: Artificial Sequence
<220> FEATURE:
<223> OTHER INFORMATION: Synthetic mAb

<400> SEQUENCE: 169

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
                 20                  25                  30

Tyr Pro Ser Asp Ile Ala Val Glu Trp Glu Leu Glu Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Ala Trp Gln Lys His
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 170
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R, H, D, E, G, or P
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R, H, D, E, G, or P
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R, H, D, E, G, or P

<400> SEQUENCE: 170

```
Xaa Xaa Xaa Xaa Lys His
 1               5
```

<210> SEQ ID NO 171
<211> LENGTH: 6

-continued

```
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, E, or G
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, E, or G
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, E, or G

<400> SEQUENCE: 171

Xaa Xaa Xaa Xaa Lys His
1               5

<210> SEQ ID NO 172
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 172

Xaa Xaa Xaa Xaa Lys His
1               5

<210> SEQ ID NO 173
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
```

```
                                W
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D,
      or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 173

Xaa Xaa Xaa Xaa Lys His
1               5

<210> SEQ ID NO 174
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 174

Xaa Xaa Xaa Xaa Lys His
1               5

<210> SEQ ID NO 175
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 175

Xaa Xaa Xaa Xaa Lys His
```

```
1               5

<210> SEQ ID NO 176
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 176

Xaa Xaa Xaa Xaa Lys His
1               5

<210> SEQ ID NO 177
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 177

Xaa Xaa Xaa Xaa Lys His
1               5

<210> SEQ ID NO 178
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
```

```
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 178

Xaa Xaa Xaa Xaa Lys His
1               5

<210> SEQ ID NO 179
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, S, T, M, N, Q, K, R, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 179

Xaa Xaa Xaa Xaa Lys His
1               5

<210> SEQ ID NO 180
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D,
      or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E
```

-continued

<400> SEQUENCE: 180

Xaa Xaa Xaa Xaa Lys His
1               5

<210> SEQ ID NO 181
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = , V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 181

Xaa Xaa Xaa Xaa Lys His
1               5

<210> SEQ ID NO 182
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 182

Xaa Xaa Xaa Xaa Lys His
1               5

<210> SEQ ID NO 183
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)

```
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 183

Xaa Xaa Xaa Xaa Lys His
1               5

<210> SEQ ID NO 184
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = N, Q, K, R, D, or E

<400> SEQUENCE: 184

Xaa Xaa Xaa Xaa Lys His
1               5

<210> SEQ ID NO 185
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = N, Q, K, R, D, or E
```

<400> SEQUENCE: 185

Xaa Xaa Xaa Xaa Lys His
1               5

<210> SEQ ID NO 186
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 186

Xaa Xaa Xaa Xaa Lys His
1               5

<210> SEQ ID NO 187
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, R, H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 187

Xaa Xaa Xaa Xaa Lys His
1               5

<210> SEQ ID NO 188
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE

```
<222> LOCATION: (1)..(1)
<223> OTHER INFORMATION: Xaa = A, V, L, I, S, T, M, or N
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 188

Xaa Xaa Xaa Xaa Lys His
1               5

<210> SEQ ID NO 189
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, or M
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 189

Xaa Xaa Xaa Xaa Lys His
1               5

<210> SEQ ID NO 190
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
```

```
<222> LOCATION: (4)..(4)
<223> OTHER INFORMATION: Xaa = A, V, L, I, S, T, M, N, Q, K, R, H, D, or
      E

<400> SEQUENCE: 190

Xaa Xaa Xaa Xaa Lys His
1               5

<210> SEQ ID NO 191
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, S, T, M, N, Q, K, R, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 191

Xaa Xaa Xaa Xaa Lys His
1               5

<210> SEQ ID NO 192
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D,
      or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 192

Xaa Xaa Xaa Xaa Lys His
1               5

<210> SEQ ID NO 193
<211> LENGTH: 6
<212> TYPE: PRT
<213> ORGANISM: Artificial Sequence
```

```
<220> FEATURE:
<223> OTHER INFORMATION: Ig EF
<220> FEATURE:
<221> NAME/KEY: MISC_FEATURE
<222> LOCATION: (1)..(1)
<223> OTHER INFORMATION: Xaa = A, V, L, I, S, T, M, N, Q, R, H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 193

Xaa Xaa Xaa Xaa Lys His
1               5

<210> SEQ ID NO 194
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, or Q
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 194

Xaa Xaa Xaa Xaa Lys His
1               5

<210> SEQ ID NO 195
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, or I
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
```

<223> OTHER INFORMATION: Xaa = A, V, L, I, S, T, M, N, Q, K, R, D, or E

<400> SEQUENCE: 195

Xaa Xaa Xaa Xaa Lys His
1               5

<210> SEQ ID NO 196
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, or I
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = N, Q, K, R, D, or E

<400> SEQUENCE: 196

Xaa Xaa Xaa Xaa Lys His
1               5

<210> SEQ ID NO 197
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = , G, I, V, L, R, S, T, Q, P, N, M, or H
<220> FEATURE:
<221> NAME/KEY: MISC_FEATURE
<222> LOCATION: (3)..(3)
<223> OTHER INFORMATION: Xaa  = A, V, L, I, F, W, Y, S, T, M, N, Q, K,
      R, H, D, or E
<220> FEATURE:
<221> NAME/KEY: MISC_FEATURE
<222> LOCATION: (4)..(4)
<223> OTHER INFORMATION: Xaa  = A, V, L, I, S, T, M, N, Q, K, R, H, D,
      or E

<400> SEQUENCE: 197

Xaa Xaa Xaa Xaa Lys His
1               5

<210> SEQ ID NO 198
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)

```
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = , G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, S, T, M, N, Q, K, R, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 198

Xaa Xaa Xaa Xaa Lys His
1               5

<210> SEQ ID NO 199
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, E, G, or P
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, E, G, or P
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, E, G, or P

<400> SEQUENCE: 199

Xaa Xaa Xaa Xaa Lys His
1               5

<210> SEQ ID NO 200
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, E, or G
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or
      W
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, E, or G
<220> FEATURE:
<221> NAME/KEY: MISC_FEATURE
```

<222> LOCATION: (4)..(4)
<223> OTHER INFORMATION: Xaa = A, V, L, I, F, W, Y, S, T, M, N, Q, K, R, H, D, E, or G

<400> SEQUENCE: 200

Xaa Xaa Xaa Xaa Lys His
1               5

<210> SEQ ID NO 201
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R, H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or W
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R, H, D, or E

<400> SEQUENCE: 201

Xaa Xaa Xaa Xaa Lys His
1               5

<210> SEQ ID NO 202
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R, H, D, or E
<220> FEATURE:
<221> NAME/KEY: MISC_FEATURE
<222> LOCATION: (2)..(2)
<223> OTHER INFORMATION: Xaa = A, G, I, V, L, R, S, T, Q, P, N, M, H, or W
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R, H, D, or E

<400> SEQUENCE: 202

Xaa Xaa Xaa Xaa Lys His
1               5

<210> SEQ ID NO 203
<211> LENGTH: 6
<212> TYPE: PRT

```
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, V, S, T, Q, P, N, M, or H
<220> FEATURE:
<221> NAME/KEY: MISC_FEATURE
<222> LOCATION: (3)..(3)
<223> OTHER INFORMATION: Xaa = L, I, F, W, Y, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 203

Xaa Xaa Xaa Xaa Lys His
1               5

<210> SEQ ID NO 204
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, V, S, T, Q, P, N, M, or H
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 204

Xaa Xaa Xaa Xaa Lys His
1               5

<210> SEQ ID NO 205
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
```

```
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 205

Xaa Xaa Xaa Xaa Lys His
1               5

<210> SEQ ID NO 206
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 206

Xaa Xaa Xaa Xaa Lys His
1               5

<210> SEQ ID NO 207
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D,
      or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 207

Xaa Xaa Xaa Xaa Lys His
1               5

<210> SEQ ID NO 208
<211> LENGTH: 6
<212> TYPE: PRT
<213> ORGANISM: Artificial Sequence
<220> FEATURE:
```

<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R, H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, Y, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or E

<400> SEQUENCE: 208

Xaa Xaa Xaa Xaa Lys His
1               5

<210> SEQ ID NO 209
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R, H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 209

Xaa Xaa Xaa Xaa Lys His
1               5

<210> SEQ ID NO 210
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R, H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

```
<400> SEQUENCE: 210

Xaa Xaa Xaa Xaa Lys His
1               5

<210> SEQ ID NO 211
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, S, T, P, or M
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = N, Q, K, R, D, or E

<400> SEQUENCE: 211

Xaa Xaa Xaa Xaa Lys His
1               5

<210> SEQ ID NO 212
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = N, Q, K, R, D, or E

<400> SEQUENCE: 212

Xaa Xaa Xaa Xaa Lys His
1               5

<210> SEQ ID NO 213
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
```

```
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 213

Xaa Xaa Xaa Xaa Lys His
1               5

<210> SEQ ID NO 214
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, R, H, D, or E
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 214

Xaa Xaa Xaa Xaa Lys His
1               5

<210> SEQ ID NO 215
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, or N
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 215
```

-continued

Xaa Xaa Xaa Xaa Lys His
1               5

<210> SEQ ID NO 216
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, or M
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 216

Xaa Xaa Xaa Xaa Lys His
1               5

<210> SEQ ID NO 217
<211> LENGTH: 6
<212> TYPE: PRT
<213> ORGANISM: Artificial Sequence
<220> FEATURE:
<223> OTHER INFORMATION: Ig EF Loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 217

Xaa Xaa Xaa Xaa Lys His
1               5

<210> SEQ ID NO 218
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:

```
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = A, V, L, I, S, T, M, N, Q, K, R, D, or E
<220> FEATURE:
<221> NAME/KEY: MISC_FEATURE
<222> LOCATION: (4)..(4)
<223> OTHER INFORMATION: Xaa = A, V, L, I, F, W, Y, S, T, M, N, Q, K, R,
      H, D, or E

<400> SEQUENCE: 218

Xaa Xaa Xaa Xaa Lys His
1               5

<210> SEQ ID NO 219
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, K, R, H, D, or
      E
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = L, I, F, W, Y, S, T, M, N, Q, K, R, H, D,
      or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 219

Xaa Xaa Xaa Xaa Lys His
1               5

<210> SEQ ID NO 220
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, Q, R, H, D, or E
<220> FEATURE:
<221> NAME/KEY: MISC_FEATURE
<222> LOCATION: (2)..(2)
<223> OTHER INFORMATION: Xaa = A, G, I, V, L, S, T, Q, P, N, M, or H
<220> FEATURE:
<221> NAME/KEY: MISC_FEATURE
<222> LOCATION: (3)..(3)
<223> OTHER INFORMATION: Xaa = L, I, F, W, Y, M, N, Q, K, R, H, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, H, D, or
      E

<400> SEQUENCE: 220

Xaa Xaa Xaa Xaa Lys His
1               5
```

```
<210> SEQ ID NO 221
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, S, T, M, N, or Q
<220> FEATURE:
<221> NAME/KEY: MISC_FEATURE
<222> LOCATION: (2)..(2)
<223> OTHER INFORMATION: Xaa = A, G, S, T, or M
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 221

Xaa Xaa Xaa Xaa Lys His
1               5

<210> SEQ ID NO 222
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, or I
<220> FEATURE:
<221> NAME/KEY: MISC_FEATURE
<222> LOCATION: (2)..(2)
<223> OTHER INFORMATION: Xaa = A, G, S, T, or M
<220> FEATURE:
<221> NAME/KEY: MISC_FEATURE
<222> LOCATION: (3)..(3)
<223> OTHER INFORMATION: Xaa = L, I, F, W, or Y
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 222

Xaa Xaa Xaa Xaa Lys His
1               5

<210> SEQ ID NO 223
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, or I
<220> FEATURE:
<221> NAME/KEY: MISC_FEATURE
<222> LOCATION: (2)..(2)
<223> OTHER INFORMATION: Xaa =  A, G, S, T, or M
<220> FEATURE:
<221> NAME/KEY: MISC_FEATURE
<222> LOCATION: (3)..(3)
<223> OTHER INFORMATION: Xaa =  L, I, F, W, or Y
<220> FEATURE:
```

```
<221> NAME/KEY: MISC_FEATURE
<222> LOCATION: (4)..(4)
<223> OTHER INFORMATION: Xaa =  N, Q, K, R, D, or E

<400> SEQUENCE: 223

Xaa Xaa Xaa Xaa Lys His
1               5

<210> SEQ ID NO 224
<211> LENGTH: 6
<212> TYPE: PRT
<213> ORGANISM: Artificial Sequence
<220> FEATURE:
<223> OTHER INFORMATION: Ig EF loop
<220> FEATURE:
<221> NAME/KEY: MISC_FEATURE
<222> LOCATION: (1)..(1)
<223> OTHER INFORMATION: Xaa = A, V, L, I, F, W, Y, S, T, M, N, Q, K, R,
      H, D, or E
<220> FEATURE:
<221> NAME/KEY: MISC_FEATURE
<222> LOCATION: (2)..(2)
<223> OTHER INFORMATION: Xaa = A, G, S, T, or M
<220> FEATURE:
<221> NAME/KEY: MISC_FEATURE
<222> LOCATION: (3)..(3)
<223> OTHER INFORMATION: Xaa = L, I, F, W, Y, N, Q, D, or E
<220> FEATURE:
<221> NAME/KEY: MISC_FEATURE
<222> LOCATION: (4)..(4)
<223> OTHER INFORMATION: Xaa = A, V, L, I, S, T, M, N, Q, K, R, D, or E

<400> SEQUENCE: 224

Xaa Xaa Xaa Xaa Lys His
1               5

<210> SEQ ID NO 225
<211> LENGTH: 75
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (42)..(42)
<223> OTHER INFORMATION: Xaa = V, I, or L
<220> FEATURE:
<221> NAME/KEY: MISC_FEATURE
<222> LOCATION: (43)..(43)
<223> OTHER INFORMATION: Xaa = D, E, N, or Q
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (75)..(75)
<223> OTHER INFORMATION: Xaa = Any amino acid

<400> SEQUENCE: 225

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Xaa Xaa Asn Xaa Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Xaa
65                  70                  75
```

<210> SEQ ID NO 226
<211> LENGTH: 25
<212> TYPE: PRT
<213> ORGANISM: Artificial Sequence
<220> FEATURE:
<223> OTHER INFORMATION: Mutant version of human CLk
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)
<223> OTHER INFORMATION: Xaa = L or V

<400> SEQUENCE: 226

Xaa Xaa Tyr Ala Cys Glu Val Thr His Gln Gly Leu Ser Ser Pro Val
1               5                   10                  15

Thr Lys Ser Phe Asn Arg Gly Glu Cys
            20                  25

<210> SEQ ID NO 227
<211> LENGTH: 76
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N

<400> SEQUENCE: 227

Gly Gln Pro Lys Ala Xaa Pro Xaa Val Thr Leu Phe Pro Pro Ser Ser
1               5               10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Ala Asp Xaa Ser Pro
        35              40                  45

Xaa Xaa Xaa Gly Val Glu Thr Thr Xaa Pro Ser Lys Gln Ser Asn Asn
    50                  55                  60

Xaa Tyr Ala Ala Ser Ser Tyr Leu Ser Leu Thr Pro
65                  70                  75

<210> SEQ ID NO 228
<211> LENGTH: 76
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (44)..(44)
<223> OTHER INFORMATION: Xaa = A, V, I, or L
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N

<400> SEQUENCE: 228

Gly Gln Pro Lys Ala Xaa Pro Xaa Val Thr Leu Phe Pro Pro Ser Ser
1               5               10                  15

Glu Glu Leu Gln Ala Asn Xaa Ala Thr Leu Val Cys Leu Ile Ser Asp
            20                  25                  30

```
Phe Tyr Pro Gly Xaa Val Xaa Val Ala Trp Lys Xaa Asp Xaa Ser Pro
            35              40                  45

Xaa Xaa Xaa Gly Val Glu Thr Thr Xaa Pro Ser Lys Gln Ser Asn Asn
 50                  55                  60

Xaa Tyr Ala Ala Ser Ser Tyr Leu Ser Leu Thr Pro
 65                  70                  75
```

<210> SEQ ID NO 229
<211> LENGTH: 76
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (44)..(44)
<223> OTHER INFORMATION: Xaa = V, I, or L
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N

<400> SEQUENCE: 229

```
Gly Gln Pro Lys Ala Xaa Pro Xaa Val Thr Leu Phe Pro Pro Ser Ser
 1               5                  10                  15

Glu Glu Leu Gln Ala Asn Xaa Ala Thr Leu Val Cys Leu Ile Ser Asp
             20                  25                  30

Phe Tyr Pro Gly Xaa Val Xaa Val Ala Trp Lys Xaa Asp Xaa Ser Pro
            35                  40                  45

Xaa Xaa Xaa Gly Val Glu Thr Thr Xaa Pro Ser Lys Gln Ser Asn Asn
 50                  55                  60
```

Xaa Tyr Ala Ala Ser Ser Tyr Leu Ser Leu Thr Pro
65                  70                  75

<210> SEQ ID NO 230
<211> LENGTH: 76
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N

<400> SEQUENCE: 230

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Val Asp Xaa Ser Pro
        35                  40                  45

Xaa Xaa Xaa Gly Val Glu Thr Thr Xaa Pro Ser Lys Gln Ser Asn Asn
    50                  55                  60

Xaa Tyr Ala Ala Ser Ser Tyr Leu Ser Leu Thr Pro
65                  70                  75

<210> SEQ ID NO 231
<211> LENGTH: 76
<212> TYPE: PRT
<213> ORGANISM: Artificial Sequence
<220> FEATURE:
<223> OTHER INFORMATION: Version of human CL Lambda

```
<220> FEATURE:
<221> NAME/KEY: MISC_FEATURE
<222> LOCATION: (44)..(44)
<223> OTHER INFORMATION: Xaa = A, V, I, or L

<400> SEQUENCE: 231
```

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Xaa Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro
65                  70                  75

```
<210> SEQ ID NO 232
<211> LENGTH: 76
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (44)..(44)
<223> OTHER INFORMATION: Xaa = V, I, or L

<400> SEQUENCE: 232
```

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Xaa Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro
65                  70                  75

```
<210> SEQ ID NO 233
<211> LENGTH: 76
<212> TYPE: PRT
<213> ORGANISM: Artificial Sequence
<220> FEATURE:
<223> OTHER INFORMATION: Version of human CL Lambda

<400> SEQUENCE: 233
```

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Val Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro
65                  70                  75

```
<210> SEQ ID NO 234
<211> LENGTH: 24
```

```
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (1)..(1)
<223> OTHER INFORMATION: Xaa = K or R
<220> FEATURE:
<221> NAME/KEY: MISC_FEATURE
<222> LOCATION: (6)..(6)
<223> OTHER INFORMATION: Xaa = Q or L
<220> FEATURE:
<221> NAME/KEY: MISC_FEATURE
<222> LOCATION: (21)..(21)
<223> OTHER INFORMATION: Xaa = A or T

<400> SEQUENCE: 234

Xaa Ser Tyr Ser Cys Xaa Val Thr His Glu Gly Ser Thr Val Glu Lys
1               5                   10                  15

Thr Val Ala Pro Xaa Glu Cys Ser
            20

<210> SEQ ID NO 235
<211> LENGTH: 24
<212> TYPE: PRT
<213> ORGANISM: Artificial Sequence
<220> FEATURE:
<223> OTHER INFORMATION: Version of human CL Lambda

<400> SEQUENCE: 235

Arg Ser Tyr Ser Cys Gln Val Thr His Glu Gly Ser Thr Val Glu Lys
1               5                   10                  15

Thr Val Ala Pro Thr Glu Cys Ser
            20

<210> SEQ ID NO 236
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (44)..(44)
<223> OTHER INFORMATION: Xaa = A, V, I, or L
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
```

```
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K , or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (78)..(78)
<223> OTHER INFORMATION: Xaa = A or Q
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 236

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
                20                  25                  30

Phe Tyr Pro Gly Xaa Val Xaa Val Ala Trp Lys Xaa Asp Xaa Ser Pro
            35                  40                  45

Xaa Xaa Xaa Gly Val Glu Thr Thr Xaa Pro Ser Lys Gln Ser Asn Asn
50                  55                  60

Xaa Tyr Ala Ala Ser Ser Tyr Leu Ser Leu Thr Pro Glu Xaa Trp Xaa
65                  70                  75                  80

Lys His Xaa Ser Tyr Ser Cys Xaa Val Thr His Glu Gly Ser Thr Val
                85                  90                  95

Glu Lys Thr Val Ala Pro Xaa Glu Cys Ser
            100                 105

<210> SEQ ID NO 237
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
```

```
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (44)..(44)
<223> OTHER INFORMATION: Xaa = V, I, or L
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (78)..(78)
<223> OTHER INFORMATION: Xaa = A or Q
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 237

Gly Gln Pro Lys Ala Xaa Pro Xaa Val Thr Leu Phe Pro Ser Ser
1               5                   10                  15

Glu Glu Leu Gln Ala Asn Xaa Ala Thr Leu Val Cys Leu Ile Ser Asp
                20                  25                  30

Phe Tyr Pro Gly Xaa Val Xaa Val Ala Trp Lys Xaa Asp Xaa Ser Pro
            35                  40                  45

Xaa Xaa Xaa Gly Val Glu Thr Thr Xaa Pro Ser Lys Gln Ser Asn Asn
    50                  55                  60

Xaa Tyr Ala Ala Ser Ser Tyr Leu Ser Leu Thr Pro Glu Xaa Trp Xaa
65                  70                  75                  80

Lys His Xaa Ser Tyr Ser Cys Xaa Val Thr His Glu Gly Ser Thr Val
                85                  90                  95

Glu Lys Thr Val Ala Pro Xaa Glu Cys Ser
```

```
<210> SEQ ID NO 238
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (78)..(78)
<223> OTHER INFORMATION: Xaa = A or Q
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 238

Gly Gln Pro Lys Ala Xaa Pro Xaa Val Thr Leu Phe Pro Pro Ser Ser
1               5                   10                  15
```

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Val Asp Xaa Ser Pro
        35                  40                  45

Xaa Xaa Xaa Gly Val Glu Thr Thr Xaa Pro Ser Lys Gln Ser Asn Asn
 50                  55                  60

Xaa Tyr Ala Ala Ser Ser Tyr Leu Ser Leu Thr Pro Glu Xaa Trp Xaa
 65                  70                  75                  80

Lys His Xaa Ser Tyr Ser Cys Xaa Val Thr His Glu Gly Ser Thr Val
                85                  90                  95

Glu Lys Thr Val Ala Pro Xaa Glu Cys Ser
            100                 105

<210> SEQ ID NO 239
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (44)..(44)
<223> OTHER INFORMATION: Xaa = A, V, I, or L
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE

```
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 239

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Xaa Asp Xaa Ser Pro
        35                  40                  45

Xaa Xaa Xaa Gly Val Glu Thr Thr Xaa Pro Ser Lys Gln Ser Asn Asn
    50                  55                  60

Xaa Tyr Ala Ala Ser Ser Tyr Leu Ser Leu Thr Pro Glu Ala Trp Xaa
65                  70                  75                  80

Lys His Xaa Ser Tyr Ser Cys Xaa Val Thr His Glu Gly Ser Thr Val
                85                  90                  95

Glu Lys Thr Val Ala Pro Xaa Glu Cys Ser
            100                 105

<210> SEQ ID NO 240
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
<222> LOCATION: (44)..(44)
<223> OTHER INFORMATION: Xaa = V, I, or L
<220> FEATURE:
<221> NAME/KEY: MISC_FEATURE
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
```

```
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 240

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
            20                  25                  30

Phe Tyr Pro Gly Xaa Val Xaa Val Ala Trp Lys Xaa Asp Xaa Ser Pro
        35                  40                  45

Xaa Xaa Xaa Gly Val Glu Thr Thr Xaa Pro Ser Lys Gln Ser Asn Asn
50                  55                  60

Xaa Tyr Ala Ala Ser Ser Tyr Leu Ser Leu Thr Pro Glu Ala Trp Xaa
65                  70                  75                  80

Lys His Xaa Ser Tyr Ser Cys Xaa Val Thr His Glu Gly Ser Thr Val
            85                  90                  95

Glu Lys Thr Val Ala Pro Xaa Glu Cys Ser
            100                 105

<210> SEQ ID NO 241
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (6)..(6)
<223> OTHER INFORMATION: Xaa = N or A
<220> FEATURE:
<221> NAME/KEY: MISC_FEATURE
<222> LOCATION: (8)..(8)
<223> OTHER INFORMATION: Xaa = S or T
<220> FEATURE:
<221> NAME/KEY: MISC_FEATURE
<222> LOCATION: (23)..(23)
<223> OTHER INFORMATION: Xaa = K, S, R, Q, or E
<220> FEATURE:
<221> NAME/KEY: MISC_FEATURE
<222> LOCATION: (37)..(37)
<223> OTHER INFORMATION: Xaa = A or V
<220> FEATURE:
<221> NAME/KEY: MISC_FEATURE
<222> LOCATION: (39)..(39)
<223> OTHER INFORMATION: Xaa = T or K
<220> FEATURE:
<221> NAME/KEY: MISC_FEATURE
```

```
<222> LOCATION: (46)..(46)
<223> OTHER INFORMATION: Xaa = S or G
<220> FEATURE:
<221> NAME/KEY: MISC_FEATURE
<222> LOCATION: (49)..(49)
<223> OTHER INFORMATION: Xaa = V, A, or I
<220> FEATURE:
<221> NAME/KEY: MISC_FEATURE
<222> LOCATION: (50)..(50)
<223> OTHER INFORMATION: Xaa = K or E
<220> FEATURE:
<221> NAME/KEY: MISC_FEATURE
<222> LOCATION: (51)..(51)
<223> OTHER INFORMATION: Xaa = A or T
<220> FEATURE:
<221> NAME/KEY: MISC_FEATURE
<222> LOCATION: (57)..(57)
<223> OTHER INFORMATION: Xaa = T, K, or A
<220> FEATURE:
<221> NAME/KEY: MISC_FEATURE
<222> LOCATION: (65)..(65)
<223> OTHER INFORMATION: Xaa = K, R, or N
<220> FEATURE:
<221> NAME/KEY: MISC_FEATURE
<222> LOCATION: (80)..(80)
<223> OTHER INFORMATION: Xaa = K or Q
<220> FEATURE:
<221> NAME/KEY: MISC_FEATURE
<222> LOCATION: (83)..(83)
<223> OTHER INFORMATION: Xaa = K or R
<220> FEATURE:
<221> NAME/KEY: MISC_FEATURE
<222> LOCATION: (88)..(88)
<223> OTHER INFORMATION: Xaa = Q or L
<220> FEATURE:
<221> NAME/KEY: MISC_FEATURE
<222> LOCATION: (103)..(103)
<223> OTHER INFORMATION: Xaa = A or T

<400> SEQUENCE: 241

Gly Gln Pro Lys Ala Xaa Pro Xaa Val Thr Leu Phe Pro Pro Ser Ser
1               5                   10                  15

Glu Glu Leu Gln Ala Asn Xaa Ala Thr Leu Val Cys Leu Ile Ser Asp
                20                  25                  30

Phe Tyr Pro Gly Xaa Val Xaa Val Ala Trp Lys Val Asp Xaa Ser Pro
            35                  40                  45

Xaa Xaa Xaa Gly Val Glu Thr Thr Xaa Pro Ser Lys Gln Ser Asn Asn
    50                  55                  60

Xaa Tyr Ala Ala Ser Ser Tyr Leu Ser Leu Thr Pro Glu Ala Trp Xaa
65                  70                  75                  80

Lys His Xaa Ser Tyr Ser Cys Xaa Val Thr His Glu Gly Ser Thr Val
                85                  90                  95

Glu Lys Thr Val Ala Pro Xaa Glu Cys Ser
            100                 105

<210> SEQ ID NO 242
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (44)..(44)
<223> OTHER INFORMATION: Xaa = A, V, I, or L
<220> FEATURE:
<221> NAME/KEY: MISC_FEATURE
<222> LOCATION: (78)..(78)
<223> OTHER INFORMATION: Xaa = A

<400> SEQUENCE: 242
```

Gly Gln Pro Lys Ala Ala Pro Ser Val Thr Leu Phe Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Xaa Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Xaa Trp Lys
65                  70                  75                  80

Lys His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 243
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (44)..(44)
<223> OTHER INFORMATION: Xaa = V, I, or L
<220> FEATURE:
<221> NAME/KEY: MISC_FEATURE
<222> LOCATION: (78)..(78)
<223> OTHER INFORMATION: Xaa = A

<400> SEQUENCE: 243

Gly Gln Pro Lys Ala Ala Pro Ser Val Thr Leu Phe Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Xaa Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Xaa Trp Lys
65                  70                  75                  80

Lys His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 244
<211> LENGTH: 106
<212> TYPE: PRT
<213> ORGANISM: Artificial Sequence
<220> FEATURE:
<223> OTHER INFORMATION: Version of human CL Lambda
<220> FEATURE:
<221> NAME/KEY: MISC_FEATURE
<222> LOCATION: (78)..(78)
<223> OTHER INFORMATION: Xaa = A

<400> SEQUENCE: 244

Gly Gln Pro Lys Ala Ala Pro Ser Val Thr Leu Phe Pro Ser Ser
1               5                   10                  15

Glu Glu Leu Gln Ala Asn Lys Ala Thr Leu Val Cys Leu Ile Ser Asp

```
                    20                  25                  30
Phe Tyr Pro Gly Ala Val Thr Val Ala Trp Lys Val Asp Ser Ser Pro
                35                  40                  45
Val Lys Ala Gly Val Glu Thr Thr Pro Ser Lys Gln Ser Asn Asn
        50                  55                  60
Lys Tyr Ala Ala Ser Ser Tyr Leu Ser Leu Thr Pro Glu Xaa Trp Lys
65                  70                  75                  80
Lys His Arg Ser Tyr Ser Cys Gln Val Thr His Glu Gly Ser Thr Val
                85                  90                  95
Glu Lys Thr Val Ala Pro Thr Glu Cys Ser
            100                 105
```

<210> SEQ ID NO 245
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (1)..(1)
<223> OTHER INFORMATION: Xaa = V, I, or L
<220> FEATURE:
<221> NAME/KEY: MISC_FEATURE
<222> LOCATION: (2)..(2)
<223> OTHER INFORMATION: Xaa = D, N, Q, or E
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 245

Xaa Xaa Xaa Xaa
1

<210> SEQ ID NO 246
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (1)..(1)
<223> OTHER INFORMATION: Xaa = V or I
<220> FEATURE:
<221> NAME/KEY: MISC_FEATURE
<222> LOCATION: (2)..(2)
<223> OTHER INFORMATION: Xaa = D, N, Q, or E
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid
<220> FEATURE:
<221> NAME/KEY: MISC_FEATURE
<222> LOCATION: (5)..(4)
<223> OTHER INFORMATION: Xaa = Any amino acid

<400> SEQUENCE: 246

Xaa Xaa Xaa Xaa
1

```
<210> SEQ ID NO 247
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (2)..(2)
<223> OTHER INFORMATION: Xaa = D, N, Q or E
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 247

Val Xaa Xaa Xaa
1

<210> SEQ ID NO 248
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (1)..(1)
<223> OTHER INFORMATION: Xaa = V, I, or L
<220> FEATURE:
<221> NAME/KEY: MISC_FEATURE
<222> LOCATION: (2)..(2)
<223> OTHER INFORMATION: Xaa = D or N
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 248

Xaa Xaa Xaa Xaa
1

<210> SEQ ID NO 249
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (1)..(1)
<223> OTHER INFORMATION: Xaa = V, I, or L
<220> FEATURE:
<221> NAME/KEY: MISC_FEATURE
<222> LOCATION: (2)..(2)
<223> OTHER INFORMATION: Xaa = Q or E
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 249
```

Xaa Xaa Xaa Xaa
1

<210> SEQ ID NO 250
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (1)..(1)
<223> OTHER INFORMATION: Xaa = V, I, or L
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 250

Xaa Asp Xaa Xaa
1

<210> SEQ ID NO 251
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 251

Val Asp Xaa Xaa
1

<210> SEQ ID NO 252
<211> LENGTH: 4
<212> TYPE: PRT
<213> ORGANISM: Artificial Sequence
<220> FEATURE:
<223> OTHER INFORMATION: Ig CD loop sequence
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 252

Leu Glu Xaa Xaa
1

<210> SEQ ID NO 253
<211> LENGTH: 4
<212> TYPE: PRT
<213> ORGANISM: Artificial Sequence
<220> FEATURE:
<223> OTHER INFORMATION: Ig CD loop sequence
<220> FEATURE:

<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 253

Ile Glu Xaa Xaa
1

<210> SEQ ID NO 254
<211> LENGTH: 219
<212> TYPE: PRT
<213> ORGANISM: Artificial Sequence
<220> FEATURE:
<223> OTHER INFORMATION: h38C2 LC-D185A

<400> SEQUENCE: 254

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Ala Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 255
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Any amino acid
<220> FEATURE:
<221> NAME/KEY: MISC_FEATURE
<222> LOCATION: (2)..(2)

```
<223> OTHER INFORMATION: Xaa = Any amino acid
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid

<400> SEQUENCE: 255

Xaa Xaa Xaa Xaa
1

<210> SEQ ID NO 256
<211> LENGTH: 6
<212> TYPE: PRT
<213> ORGANISM: Artificial Sequence
<220> FEATURE:
<223> OTHER INFORMATION: Synthetic

<400> SEQUENCE: 256

Glu Lys His Lys Val Tyr
1               5

<210> SEQ ID NO 257
<211> LENGTH: 93
<212> TYPE: PRT
<213> ORGANISM: Homo sapiens

<400> SEQUENCE: 257

Asp Ile Gln Met Thr Gln Ser Pro Ser Ser Leu Ser Ala Val Gly Asp
1               5                   10                  15

Arg Val Thr Ile Thr Cys Arg Ala Ser Gln Ser Ile Ser Ser Tyr Leu
            20                  25                  30

Asn Trp Tyr Gln Gln Lys Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro
                85                  90

<210> SEQ ID NO 258
<211> LENGTH: 12
<212> TYPE: PRT
<213> ORGANISM: Homo sapiens

<400> SEQUENCE: 258

Leu Thr Phe Gly Gly Gly Thr Lys Val Glu Ile Lys
1               5                   10

<210> SEQ ID NO 259
<211> LENGTH: 97
<212> TYPE: PRT
<213> ORGANISM: Homo sapiens

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val Lys
 50                  55                  60

Gly Arg Phe Thr Ile Ser Arg Asp Asn Ser Lys Asn Thr Leu Tyr Leu
 65              70                  75                  80

Gln Met Asn Ser Leu Arg Ala Glu Asp Thr Ala Val Tyr Tyr Cys Ala
             85                  90                  95

Lys

<210> SEQ ID NO 260
<211> LENGTH: 15
<212> TYPE: PRT
<213> ORGANISM: Homo sapiens

<400> SEQUENCE: 260

Tyr Phe Asp Tyr Trp Gly Gln Gly Thr Leu Val Thr Val Ser Ser
 1               5                  10                  15
```

MUTANT ANTIBODIES AND CONJUGATION THEREOF

CROSS-REFERENCE TO RELATED APPLICATIONS

This application is a continuation of U.S. patent application Ser. No. 13/736,029, filed Jan. 7, 2013, which claims the benefit of U.S. Provisional Patent Application No. 61/584,675, filed Jan. 9, 2012. The entire contents of each of the above-referenced patent applications are hereby incorporated by reference in their entirety.

BACKGROUND

The development of bifunctional therapeutics has great potential to augment combination therapy strategies. A bifunctional therapeutic can provide the benefit of a combination therapy by modulating 2 different pathways with one therapeutic entity. In addition, bifunctional therapeutics may also benefit from synergies between pathways and demonstrate increased activity compared to mono-functional agents. Furthermore, bifunctional therapeutics can provide benefits in terms of reduced manufacturing, storage, and shipping costs, as well as reducing the number of therapies given to the patient and simplifying dosage regimes.

The reference to any art in this specification is not, and should not be taken as, an acknowledgement of any form or suggestion that the referenced art forms part of the common general knowledge.

REFERENCE TO SEQUENCE LISTING

This application is being filed electronically via EFS-Web and includes an electronically submitted sequence listing in .txt format. The .txt file contains a sequence listing entitled "PC71862B_Sequence_Listing_ST25.txt" created on Jan. 29, 2021 and having a size of 265 kb. The sequence listing contained in this .txt file is part of the specification and is herein incorporated by reference in its entirety.

SUMMARY OF THE INVENTION

The present invention provides a polypeptide comprising an antibody constant domain, the antibody constant domain comprising residues K and H at positions corresponding to positions 80 and 81 of SEQ ID NO:6 when said antibody constant domain is aligned with the sequence of SEQ ID NO:6, and characterized in that the antibody constant domain further comprises a residue selected from the group consisting of A, G, I, V, L, R, S, T, Q, P, N, M, H, W at a position corresponding to position 77 of SEQ ID NO:6.

In some aspects, the invention provides an antibody constant domain comprising SEQ ID NO:98 (and all sequences herein described that fall within the scope of SEQ ID NO:98), wherein the position of SEQ ID NO:98 on said constant domain corresponds to residues 76-81 of SEQ ID NO:6 when the constant domain sequence is aligned with SEQ ID NO:6.

Sequences may be aligned by structural alignment, where the structure of the two polypeptides are known, or by sequence alignment; when sequence alignment is used, the method is preferably augmented using structural knowledge of homologous polypeptides whose structures are known.

The present invention provides a polypeptide comprising an antibody constant light domain, the antibody constant domain comprising residues K188 and H181 according to Kabat numbering, and characterized in that the antibody constant domain further comprises a residue selected from the group consisting of A, G, I, V, L, R, S, T, Q, P, N, M, H, W at a position corresponding to position 185 according to Kabat numbering.

The present invention provides a polypeptide comprising an immunoglobulin domain comprising 7 β-strands A, B, C, D, E, F, and G sequentially connected together by chains of connecting amino acids, wherein the β-strands are arranged so as to form a first β-sheet comprising β-strands A, B, D, and E, and a second β-sheet comprising β-strands C, F and G, said first and second β-sheets being covalently bonded together; wherein β-strands E and F are connected together by an EF chain, and said EF chain comprises the sequence, $X^1$-$X^2$-$X^3$-$X^4$-$K^5$-$H^6$ (SEQ ID NO:98), and wherein $X^1$, $X^3$ and $X^4$ are each independently any amino acid residue, and characterized in that $X^2$ is selected from the group consisting of A, G, I, V, L, R, S, T, Q, P, N, M, H, W, and pharmaceutically acceptable salts, stereoisomers, tautomers, solvates, and prodrugs thereof.

$X^2$ may be selected from the group consisting of A, G, I, L, R, S, T, P, N, and M (SEQ ID NO:99). $X^2$ may be selected from the group consisting of A, G, I, L, S, T, P, and M (SEQ ID NO:100). In some aspects, the EF chain comprises a sequence selected from the group consisting of sequence SEQ ID NO:101, SEQ ID NO:102, and SEQ ID NO:103. $X^2$ may be selected from the group consisting of A, G, I, V, L, R, S, T, Q, N, P, and M (SEQ ID NO:123). $X^2$ may be selected from the group consisting of A, G, I, V, L, R, S, T, P, and M (SEQ ID NO:124). $X^2$ may be selected from the group consisting of A, G, I, V, L, S, T, and M (SEQ ID NO:125). $X^2$ may be selected from the group consisting of A, G, I, L, S, T, and M (SEQ ID NO:126). $X^2$ may be S or T. $X^2$ may be A or G. $X^2$ may be I or L. The selections of $X^2$ described herein may also be applied to antibody constant domains of the invention, wherein position $X^2$ corresponds with residue 77 of SEQ ID NO:6, or residue 185 of a constant light domain according to Kabat numbering.

In some aspects, the EF chain comprises a sequence selected from the group consisting of SEQ ID NO:98, SEQ ID NO:99, SEQ ID NO:100, SEQ ID NO:101, SEQ ID NO:102, SEQ ID NO:103, SEQ ID NO:115, SEQ ID NO:116, SEQ ID NO:117, SEQ ID NO:123, SEQ ID NO:124, SEQ ID NO:125, and SEQ ID NO:126, and may further be selected from the group consisting of SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, and SEQ ID NO:224.

In some aspects, there may be a single residue difference when compared against residues 75-79 of SEQ ID NO:10; or SEQ ID NO:6. In some aspects, there may be up to 2 differences when compared against residues 75-79 of SEQ ID NO:10; or SEQ ID NO:6. In some aspects, there may be up to 2 differences when compared against residues 75-79 of SEQ ID NO:10; or SEQ ID NO:6. In some aspects, there may be up to 4 differences when compared against residues 75-79 of SEQ ID NO:10; or SEQ ID NO:6. In some aspects, there may be up two non-sequential differences when compared against residues 75-79 of SEQ ID NO:10; or SEQ ID NO:6. In some aspects, there may be up to three non-sequential differences when compared against residues 75-79 of SEQ ID NO:10; or SEQ ID NO:6.

In some aspects, there may be a single residue difference when compared against residues 76-79 of SEQ ID NO:10; or SEQ ID NO:6. In some aspects, there may be up to 2 differences when compared against residues 76-79 of SEQ ID NO:10; or SEQ ID NO:6. In some aspects, there may be up to 3 differences when compared against residues 76-79 of SEQ ID NO:10; or SEQ ID NO:6. In some aspects, there may be up to 4 differences when compared against residues 76-79 of SEQ ID NO:10; or SEQ ID NO:6. In some aspects, there may be up two non-sequential differences when compared against residues 76-79 of SEQ ID NO:10; or SEQ ID NO:6.

The polypeptide may comprise an EF α-helix located on the EF chain. In some aspects, one or more of residues $X^1$, $X^2$, $X^3$ and $X^4$ of SEQ ID NO:98 comprise part of the EF α-helix. In some aspects, two or more of residues $X^1$, $X^2$, $X^3$ and $X^4$ of SEQ ID NO:98 comprise part of the EF α-helix. In some aspects, three or more of residues $X^1$, $X^2$, $X^3$ and $X^4$ of SEQ ID NO:98 comprise part of the EF α-helix. In some aspects, all residues $X^1$, $X^2$, $X^3$ and $X^4$ of SEQ ID NO:98 comprise part of the EF α-helix. In some aspects, residues $K^5$ and $H^6$ of SEQ ID NO:98 do not form part of an α-helix. The selections of $X^1$, $X^2$, $X^3$, $X^4$, $K^5$, and $H^6$ described herein may also be applied to antibody constant domains of the invention, wherein positions $X^1$, $X^2$, $X^3$, $X^4$, $K^5$, and $H^6$ correspond with residues 76, 77, 78, 79, 800 and 81 of SEQ ID NO:6, or positions 184, 185, 186, 187, 188 and 189 of a constant light domain according to Kabat numbering.

In some aspects, the EF chain comprises a sequence selected from the group consisting of SEQ ID NO:99, SEQ ID NO:100, SEQ ID NO:101, SEQ ID NO:102, SEQ ID NO:103, SEQ ID NO:115, SEQ ID NO:116, SEQ ID NO:117, SEQ ID NO:118, SEQ ID NO:123, SEQ ID NO:124, SEQ ID NO:125, SEQ ID NO:126, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, and SEQ ID NO:224.

In some aspects of the invention, and with particular reference to all sequences in the application with variability at a residue corresponding to $X^1$, $X^1$ according to the above sequences may be selected from the group consisting of A, I, V, L, G, P, F, W, Y, S, T, C, M, N, Q, K, R, H, E, and D. In some aspects, $X^1$ may be selected from the group consisting of A, I, V, L, G, F, W, Y, S, T, C, M, N, Q, K, R, H, E, and D. In some aspects, $X^1$ may be selected from the group consisting of A, I, V, L, F, W, Y, S, T, C, M, N, Q, K, R, H, E, and D. In some aspects, $X^1$ may be selected from the group consisting of A, I, V, L, F, W, Y, S, T, M, N, Q, K, R, H, E, and D. In some aspects, $X^1$ may be selected from the group consisting of A, I, V, L, S, T, M, N, Q, K, R, H, E, and D. In some aspects, $X^1$ may be selected from the group consisting of A, I, V, L, S, T, M, N, Q, R, H, E, and D. $X^1$ may be selected from the group consisting of A, I, V, L, S, T, M, N, Q, E, and D. $X^1$ may be selected from the group consisting of A, I, V, L, S, T, M, N, Q, E, and D. The selections of $X^1$ described herein may also be applied to antibody constant domains of the invention, wherein position $X^1$ corresponds with residue 76 of SEQ ID NO:6, or residue 184 of a constant light domain according to Kabat numbering.

In some aspects of the invention, and with particular reference to all sequences in the application with variability at a residue corresponding to $X^3$, $X^3$ according to the above sequences may be selected from the group consisting of A, I, V, L, G, P, F, W, Y, S, T, C, M, N, Q, K, R, H, E, and D. $X^3$ may be selected from the group consisting of A, I, V, L, G, F, W, Y, S, T, C, M, N, Q, K, R, H, E, and D. $X^3$ may be selected from the group consisting of A, I, V, L, F, W, Y, S, T, C, M, N, Q, K, R, H, E, and D. $X^3$ may be selected from the group consisting of A, I, V, L, F, W, Y, S, T, M, N, Q, K, R, H, E, and D. $X^3$ may be selected from the group consisting of I, L, F, W, Y, S, T, M, N, Q, K, R, H, E, and D. $X^3$ may be selected from the group consisting of I, L, F, W, Y, M, N, Q, K, R, H, E, and D. $X^3$ may be selected from the group consisting of I, L, F, W, Y, N, Q, E, and D. $X^3$ may be selected from the group consisting of I, L, F, W, and Y. $X^3$ may be selected from the group consisting of F, W, and Y. $X^3$ may be selected from the group consisting of W and Y. The selections of $X^3$ described herein may also be applied to antibody constant domains of the invention, wherein position $X^3$ corresponds with residue 78 of SEQ ID NO:6, or residue 186 of a constant light domain according to Kabat numbering.

In some aspects of the invention, and with particular reference to all sequences in the application with variability at a residue corresponding to $X^4$, $X^4$ according to the above sequences may be selected from the group consisting of A, I, V, L, G, P, F, W, Y, S, T, C, M, N, Q, K, R, H, E, and D. $X^4$ may be selected from the group consisting of A, I, V, L, G, P, F, W, Y, S, T, M, N, Q, K, R, H, E, and D. $X^4$ may be selected from the group consisting of A, I, V, L, G, F, W, Y, S, T, M, N, Q, K, R, H, E, and D. $X^4$ may be selected from the group consisting of A, I, V, L, F, W, Y, S, T, M, N, Q, K, R, H, E, and D. $X^4$ may be selected from the group consisting of A, I, V, L, G, S, T, M, N, Q, K, R, H, E, and D. $X^4$ may be selected from the group consisting of A, I, V, L, S, T, M, N, Q, K, R, H, E, and D. $X^4$ may be selected from the group consisting of I, L, S, T, M, N, Q, K, R, E, and D. $X^4$ may be selected from the group consisting of S, T, M, N, Q, K, R, E, and D. $X^4$ may be selected from the group consisting of S, T, N, Q, K, R, E, and D. $X^4$ may be selected from the group consisting of N, Q, K, R, E, and D. $X^4$ may be selected from the group consisting of N, Q, K, R, and E. $X^4$ may be selected from the group consisting of, Q, K, and E. The selections of $X^4$ described herein may also be applied to antibody constant domains of the invention, wherein position $X^4$ corresponds with residue 79 of SEQ ID NO:6, or residue 187 of a constant light domain according to Kabat numbering.

In some aspects, the EF chain is between 6 and 12 residues long. In some aspects, the EF chain is between 7 and 12 residues long. In some aspects, the EF chain is between 8 and 12 residues long. In some aspects, the EF chain is between 9 and 12 residues long. In some aspects, the EF chain is between 6 and 11 residues long. In some aspects, the EF chain is between 6 and 10 residues long. In some aspects, the EF chain is between 6 and 9 residues long. In some aspects, the EF chain is between 7 and 11 residues long. In some aspects, the EF chain is between 7 and 10 residues long. In some aspects, the EF chain is between 8 and 10 residues long.

The EF chain may comprise an α-helix (the EF α-helix). The first residue of the EF α-helix may be located within the first 3 residues of the EF chain. The first residue of the EF α-helix may be located within the first 2 residues of the EF chain. The first residue of the EF α-helix may be located at residue of the EF chain. The EF α-helix may comprise at least residues $X^1$ and $X^2$ of SEQ ID NO:98 or one of the corresponding sequences herein that fall within the scope of SEQ ID NO:98. In some aspects, residues $K^5$ and $H^6$ corresponding to SEQ ID NO:98 are not within the α-helix. In some aspects, residues KH that correspond to positions 80 and 81 of SEQ ID NO:6 are not within the α-helix. In some aspects of the invention relating to antibody constant domains, the residue corresponding to position 77 of SEQ ID NO:6 falls within an α-helix.

In some aspects, the immunoglobulin domain of the invention, which may be a CL domain, further comprises the residue D, E, Q or N on the connecting chain between β-strands C and D; the CD chain. In some aspects, the CL domain further comprises the residue D, E, Q or N on the CD chain, the residue being positioned so as to allow its amino acid side chain interact with at least one of the side chains of $K^5$ or $H^6$ of SEQ ID NO:98. In some aspects, the polypeptide comprises a D, E, Q, or N residue located at the position corresponding to position 43 of SEQ ID NO:10 or SEQ ID NO:6, in some aspects, according to a BLAST sequence alignment. In some aspects, the residue is D, E or N. In some aspects, the residue is D or E. In some aspects the residue is D or N.

In some aspects, the β-strands C and D are connected together by a CD chain, comprising a CD motif C1-C2-C3-C4 (SEQ ID NO:255) wherein each of $C^1$, C2, C3 and C4 may be any amino acid, or further specified as set forth below. The CD motif may be selected from the group consisting of SEQ ID NO:245, SEQ ID NO:246, SEQ ID NO:247, SEQ ID NO:248, SEQ ID NO:249, SEQ ID NO:250, SEQ ID NO:251, SEQ ID NO:252, and SEQ ID NO:253, said CD motif beginning at the first or second residue of said CD chain. In some aspects, the CD motif begins at the first residue of the CD chain. In some aspects, the CD motif begins at the second residue of the CD chain. Favourably, the CD motif may not form part of an α-helix.

In some aspects, the residue $C^1$ of the CD motif may be selected from the group consisting of A, I, L, G, V, M, P, S, T, F, Y, W, N, Q, D, and E. In some aspects, the residue $C^1$ of the CD motif may be selected from the group consisting of I, L, V, M, P, F, Y, and W. In some aspects, the residue $C^1$ of the CD motif may be selected from the group consisting of I, L, V, P, F, Y, and W. In some aspects, the residue $C^1$ of the CD motif may be selected from the group consisting of I, L, V, P, F, and W. In some aspects, the residue $C^1$ of the CD motif may be selected from the group consisting of I, L, V, F, and W In some aspects, the residue $C^1$ of the CD motif may be selected from the group consisting of I, L, and V. In some aspects, the residue $C^1$ of the CD motif may be selected from the group consisting of L and V. In some aspects, the residue $C^1$ of the CD motif may be V. The selections of $C^1$ of the CD motif described herein may also be applied to antibody constant domains of the invention, wherein position $C^1$ of the CD motif corresponds with residue 42 of SEQ ID NO:6, or residue 150 of a constant light domain according to Kabat numbering.

In some aspects, the residue C2 of the CD motif may be selected from the group consisting of A, I, L, G, V, M, P, S, T, F, Y, W, N, Q, D, and E. In some aspects, the residue C2 of the CD motif may be selected from the group consisting of A, I, L, G, V, M, P, S, T, F, Y, W, N, Q, D, and E. In some aspects, the residue C2 of the CD motif may be selected from the group consisting of A, I, L, G, V, M, P, S, T, N, Q, D, and E. In some aspects, the residue C2 of the CD motif may be selected from the group consisting of A, I, L, V, M, P, S, T, N, Q, D, and E. In some aspects, the residue C2 of the CD motif may be selected from the group consisting of M, P, S, T, N, Q, D, and E. In some aspects, the residue C2 of the CD motif may be selected from the group consisting of S, T, N, Q, D, and E. In some aspects, the residue C2 of the CD motif may be selected from the group consisting of N, Q, D, and E. In some aspects, the residue C2 of the CD motif may be D. The selections of C2 of the CD motif described herein may also be applied to antibody constant domains of the invention, wherein position C2 of the CD motif corresponds with residue 43 of SEQ ID NO:6, or residue 151 of a constant light domain according to Kabat numbering.

In some aspects, the residue C3 of the CD motif may be selected from the group consisting of A, I, L, G, V, M, P, S, T, F, Y, W, N, Q, D, and E. In some aspects, the residue C3 of the CD motif may be selected from the group consisting of A, I, L, G, V, M, P, S, T, F, Y, W, N, Q, D, and E. In some aspects, the residue C3 of the CD motif may be selected from the group consisting of A, I, L, G, V, M, P, S, T, N, Q, D, and E. In some aspects, the residue C3 of the CD motif may be selected from the group consisting of A, I, L, V, M, P, S, T, N, Q, D, and E. In some aspects, the residue C3 of the CD motif may be selected from the group consisting of M, P, S, T, N, Q, D, and E. In some aspects, the residue C3 of the CD motif may be selected from the group consisting of S, T, N, Q, D, and E. In some aspects, the residue C3 of the CD motif may be selected from the group consisting of N, Q, D, and E. In some aspects, the residue C3 of the CD motif may be N. The selections of C3 of the CD motif described herein may also be applied to antibody constant domains of the invention, wherein position C3 of the CD motif corresponds with residue 44 of SEQ ID NO:6, or residue 152 of a constant light domain according to Kabat numbering.

In some aspects, the residue C4 of the CD motif may be selected from the group consisting of A, I, L, G, V, M, P, S, T, F, Y, W, N, Q, D, and E. In some aspects, the residue C4 of the CD motif may be selected from the group consisting of A, I, L, G, V, M, P, S, T, F, Y, W, N, Q, D, and E. In some aspects, the residue C4 of the CD motif may be selected from the group consisting of A, I, L, G, V, M, P, S, T, N, Q, D, E, K, R, and H. In some aspects, the residue C4 of the CD motif may be selected from the group consisting of A, I, L, V, G, M, P, S, T, N, Q, D, and E. In some aspects, the residue C4 of the CD motif may be selected from the group consisting of A, I, L, V, G, S, T, N, Q, D, and E. In some aspects, the residue C4 of the CD motif may be selected from the group consisting of A, V, Q, and S. In some aspects, the residue C4 of the CD motif may be selected from the group consisting of A and S. In some aspects, the residue C4 of the CD motif may be A. The selections of C4 of the CD motif described herein may also be applied to antibody constant domains of the invention, wherein position C4 of the CD motif corresponds with residue 45 of SEQ ID NO:6, or residue 153 of a constant light domain according to Kabat numbering.

In some aspects, the CD chain is between 6 and 12 residues long. In some aspects, the CD chain is between 7 and 12 residues long. In some aspects, the CD chain is between 8 and 12 residues long. In some aspects, the CD chain is between 9 and 12 residues long. In some aspects, the CD chain is between 6 and 11 residues long. In some aspects, the CD chain is between 6 and 10 residues long. In some aspects, the CD chain is between 6 and 9 residues long. In some aspects, the CD chain is between 7 and 11 residues long. In some aspects, the CD chain is between 7 and 10 residues long. In some aspects, the CD chain is between 8 and 10 residues long.

The immunoglobulin domain may be an antibody domain. The antibody domain may be an antibody constant domain. The antibody constant domain may be a constant heavy (CH) domain or constant light (CL) domain. Antibody CH domains may be selected from the group consisting of CHα1, CHα2, CHα3, CHδ1, CHδ2, CHδ3, CHε1, CHε2, CHε3, CHε4, CHγ1, CHγ2, CHγ3, CHμ1, CHμ2, CHμ3, and CHμ4.

In some aspects, the immunoglobulin domains of the invention are mammalian in origin (notwithstanding the method used to generate any artificially mutated or otherwise engineered versions). The mammalian species may be human, mouse, rabbit, rat, rodent, pig, cow, sheep, goat, donkey, horse, camel, primate, monkey, dog, or cat. The immunoglobulin domains of the invention, and other proteins such as antibodies to which they comprise or attached may be humanized.

In some aspects, the invention comprises mutant immunoglobulin domains, wherein a mutant is defined as sequence that has been engineered or altered to a sequence other than its natural canonical sequence, such that certain embodiments of polypeptides of the invention specifically excludes naturally occurring sequences that fall within the scope of the definition. In some aspects, therefore, the present invention relates to polypeptides of the invention comprising an EF chain that differs from their naturally occurring corresponding sequence.

The antibody domains of the invention may specifically exclude one or more natural IgA constant heavy domains (CHα1, CHα2, CHα3) from one or more species selected from the group consisting of Bornean orangutan and *Pongo pygmaeus*, and/or one or more natural IgM constant heavy domains (CHμ1, CHμ2, CHμ3, and CHμ4) from one or more species selected from the group consisting of mouse, rat, horse, *Equus caballus*, *Heterocephalus glaber*, bat, *Eptesicus fuscus*, and/or one or more natural IgE constant heavy domains (CHε1, CHε2, CHε3, and CHε4) from one or more species selected from the group consisting of human, chimp, monkey, *Erythrocebus patas*, mouse, rat, bat, *Cynopterus sphinx*, sheep, *Ovis aries*, echidna, and *Tachyglossus aculeatus*.

In some aspects, one or more constant heavy domains selected from the group consisting of CHα1, CHα2, CHα3, CHδ1, CHδ2, CHδ3, CHε1, CHε2, CHε3, CHε4, CHγ1, CHγ2, CHγ3, CHμ1, CHμ2, CHμ3, and CHμ4 from one or more of the species selected from the group consisting of human, mouse, rabbit, rat, rodent, pig, cow, sheep, goat, donkey, horse, camel, primate, monkey, dog, or cat are specifically excluded.

In some aspects, the invention provides an immunoglobulin domain, that may be a constant light chain (CL) domain, comprising 7 β-strands A, B, C, D, E, F, and G sequentially connected together by chains of amino acids, wherein the β-strands are arranged so as to form a first β-sheet comprising β-strands A, B, D, and E, and a second β-sheet comprising β-strands C, F and G, said first and second β-sheets being covalently bonded together; wherein the chain between β-strands E and F comprises the sequence $X^1$-$X^2$-$X^3$-$X^4$-$K^5$-$H^6$ (SEQ ID NO:98), and $X^1$, $X^3$ and $X^4$ are each independently any amino acid residue, and characterized in that $X^2$ is selected from the group consisting of A, G, I, V, L, R, S, T, Q, P, N, M, H, and W, and pharmaceutically acceptable salts, stereoisomers, tautomers, solvates, and prodrugs thereof. The invention also provides for pharmaceutical compositions and samples comprising CL domains of the invention. In some aspects, an α-helix is sequentially located on the connecting chain between β-strands E and F.

In part, aspects of the invention are based on the surprising discovery that site directed conjugation to a reactive KH group located on the EF chain of an immunoglobulin domain, that may be a constant light chain (CL) domain, is improved by a mutation 3 amino acid residues upstream that eliminates the presence of an acidic residue such as D or E, and that avoids introducing the aromatic residues F or Y, or other potential conjugation sites such as K or C.

Grafting a sequence of the invention onto the EF chain can impart increased specificity of conjugation on immunoglobulin domains, in particular, CL domains. This can be useful when conjugating Linkers and/or Effector Moieties onto immunoglobulin domains, and CL domains in general, and antibody and antigen-binding portions thereof in particular. In some aspects, therefore, the invention relates to a novel class of Multifunctional Antibody Conjugates (MACs), comprising an antibody, or antigen binding portion thereof, covalently conjugated to an Linker and/or Effector Moiety via a linker, characterized in that the antibody or antigen binding portion thereof comprises a polypeptide of the invention, and the linker is covalently bonded to the ε-amino group of the side chain of $K^5$ of SEQ ID NO:98.

In some aspects, the immunoglobulin domain of the invention, that may be a CL domain, is connected to a variable light chain (VL) domain. Together, these may comprise an antibody light chain.

In some aspects, the covalent bond between the first and second β-sheets is a disulfide bond. In some aspects, the disulfide bond is between β-strands B and F.

The CL domain may be a constant light chain kappa (CLκ), and may be of rat, mouse, monkey, rabbit, goat, sheep, cow, pig, horse, donkey, dog, cat, or human origin. In some aspects, the CLκ comprises a sequence selected from the group consisting of SEQ ID NO:37, SEQ ID NO:38, SEQ ID NO:39, SEQ ID NO:40, SEQ ID NO:41, SEQ ID NO:42, SEQ ID NO:44, SEQ ID NO:46, SEQ ID NO:47, SEQ ID NO:49, SEQ ID NO:50, SEQ ID NO:51, SEQ ID NO:52, SEQ ID NO:54, SEQ ID NO:104, SEQ ID NO:105, SEQ ID NO:106, SEQ ID NO:119, SEQ ID NO:120, SEQ ID NO:121, and SEQ ID NO:122.

In some aspects, the the CLκ comprises an N-terminal portion defined by SEQ ID NO:225 and a C' terminal portion defined by SEQ ID NO:226 contiguously connected together by an intermediate sequence selected from the group consisting of SEQ ID NO:99, SEQ ID NO:100, SEQ ID NO:101, SEQ ID NO:102, SEQ ID NO:103, SEQ ID NO:115, SEQ ID NO:116, SEQ ID NO:117, SEQ ID NO:118, SEQ ID NO:123, SEQ ID NO:124, SEQ ID NO:125, SEQ ID NO:126, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, and SEQ ID NO:224.

The immunoglobulin domain may be a CLλ domain, and may comprise a sequence selected from the group consisting of SEQ ID NO:60, SEQ ID NO:61, SEQ ID NO:141, SEQ ID NO:144, SEQ ID NO:143, SEQ ID NO:236, SEQ ID NO:237, SEQ ID NO:238, SEQ ID NO:239, SEQ ID NO:240, SEQ ID NO:241, SEQ ID NO:242, SEQ ID NO:243, and SEQ ID NO:244. In some aspects, the CLλ domain comprises a sequence selected from the group consisting of SEQ ID NO:60, SEQ ID NO:61, SEQ ID NO:143, SEQ ID NO:236, SEQ ID NO:237, SEQ ID NO:238, SEQ ID NO:239, SEQ ID NO:240, SEQ ID NO:241, SEQ ID NO:242, SEQ ID NO:243, and SEQ ID NO:244.

The CLλ may comprise an N' terminal portion defined by one of SEQ ID NO:227, SEQ ID NO:228, SEQ ID NO:229, SEQ ID NO:230, SEQ ID NO:231, SEQ ID NO:232, or SEQ ID NO:233 contiguously connected together by an intermediate sequence to a C' terminal portion defined by either of SEQ ID NO:234 or SEQ ID NO:235, the intermediate sequence being selected from the group consisting of SEQ ID NO:99, SEQ ID NO:100, SEQ ID NO:101, SEQ ID NO:102, SEQ ID NO:103, SEQ ID NO:115, SEQ ID NO:116, SEQ ID NO:117, SEQ ID NO:118, SEQ ID NO:123, SEQ ID NO:124, SEQ ID NO:125, SEQ ID NO:126, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, and SEQ ID NO:224.

In some embodiments where the immunoglobulin domain comprises a CLλ domain, the domain may further comprise a CD motif as described herein.

In some embodiments where the immunoglobulin domain comprises a CHγ1 domain, the domain may further comprise a CD motif as described herein.

In some embodiments where the immunoglobulin domain comprises a CHγ2 domain, the domain may further comprise a CD motif as described herein.

In some embodiments where the immunoglobulin domain comprises a CHγ3 domain, residue $X^2$ of the EF chain may not be R; in some aspects, the EF chain sequence may be selected from the group consisting of SEQ ID NO:100, SEQ ID NO:103, SEQ ID NO:117, SEQ ID NO:125, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, and SEQ ID NO:224. IN some aspects, the CD chain of a CHγ3 domain of the invention may further comprise a CD motif as described herein.

When conjugated to a linker suitable for conjugation to an Effector Moiety, the ε-amino group of the side chain of $K^5$ of SEQ ID NO:98 may be covalently attached to the linker.

In part, the invention is based on the surprising discovery that mutating CLκ-$D^{77}$ to one of A, G, I, V, L, R, S, T, Q, P, N, M, H, or W provides a significant increase in the degree of specificity of conjugation to CLκ-$K^{80}$.

Reaction of the Effector Moiety with the constant light domain of an antibody is particularly desirable to minimize, or prevent, any interference with binding of the Fc portion of the antibody to Fc receptors (such as FcγR and FcRn) or binding of the antibody to its respective target. Conversely, conjugation of the respective Effector Moiety to the Fc portion of an antibody may decrease the antibody half-life in vivo and/or its capacity to interact with the immune system (effector function). Conjugation of the Effector Moiety in the variable heavy chain (VH) or variable light chain (VL) region of the antibody carry a risk of diminishing the binding of the antibody to its cognate.

Preferential conjugation of the Effector Moiety to the CLκ or the constant light chain lambda (CLλ) domain simplifies the creation of MAC isotypes by allowing isotypic switches of the constant heavy chain (CH) domains of the antibody without affecting the conjugation sites of the Effector Moiety to the antibody.

The Linker and/or Effector Moiety may be covalently attached to the side chain of CLκ-$K^{80}$ (for example, a sequence selected from the group consisting of SEQ ID NO:104, SEQ ID NO:105, SEQ ID NO:106, SEQ ID NO:119, SEQ ID NO:120, SEQ ID NO:121, and SEQ ID NO:122.). The CL is located away from key regions of a typical antibody upon which it would form a part of, such as paratope region, FcRn binding domain, hinge, FcR binding domains; this provides the advantage that preferentially linking at these sites limits the amount of interference to antibody-antigen interaction when the MAC is conjugated to the Effector Moiety.

In some aspect, the CLκ region comprises at least residues 62-103 of SEQ ID NO:104, SEQ ID NO:105, SEQ ID NO:106, SEQ ID NO:107, SEQ ID NO:108, or SEQ ID NO:109, SEQ ID NO:119, SEQ ID NO:120, SEQ ID NO:121, or SEQ ID NO:122. In some aspects, CLκ-$x^{82}$ may be any amino acid. In some aspects, CLκ-$x^{82}$ may be selected from the group consisting of K, R, G, A, V, L, I, S, T, C, M, N, Q, D, E, H, F, W and Y. In some aspects, CLκ-$x^{82}$ may be G, A, V, L, or I. In some aspects, CLκ-$x^{82}$ may be K, R, N, or Q. In some aspects, CLκ-x$^{82}$ may be D, or E. In some aspects, CLκ-x$^{82}$ may be K, R, G, A, V, L, I, N, or Q. In some aspects, CLκ-x$^{82}$ may be D, or E. In some aspects, CLκ-x$^{82}$ may be K, R, G, A, V, L, I, N, Q, D or E. In some aspects, CLκ-x$^{82}$ may be D, or E. In some aspects, CLκ-x$^{82}$ may be H, F, W or Y. In some aspects CLκ-x$^{82}$ is not proline. In some aspects, CLκ-x$^{82}$ is K. In some aspects, CLκ-x$^{82}$ is R.

In some aspects, antibodies of the invention, or antigen-binding portions thereof, comprise an Effector Moiety conjugated to K$^5$ of SEQ ID NO:98 on both light chains. In some aspects, the Effector Moiety is conjugated to K$^5$ of SEQ ID NO:98 on one light chain only. In some aspects, the Effector Moiety is only conjugated to K$^5$ of SEQ ID NO:98. In some aspects, the Effector Moiety is conjugated at K$^5$ of SEQ ID NO:98 on one light chain and one other location on the antibody, or antigen-binding portions thereof. In some aspects, the Effector Moiety is conjugated at K$^5$ of SEQ ID NO:98 on one light chain and 2 other locations on the antibody, or antigen-binding portions thereof. In some aspects, the Effector Moiety is conjugated to K$^5$ of SEQ ID NO:98 on one light chain and 3 other locations on the antibody, or antigen-binding portions thereof. In some aspects, the Effector Moiety is conjugated to K$^5$ of SEQ ID NO:98 on both light chains, and at one other location. In some aspects, the Effector Moiety is conjugated at K$^5$ of SEQ ID NO:98 on both light chains, and at 2 other locations. In some aspects, the Effector Moiety is conjugated at K$^5$ of SEQ ID NO:98 on both light chains, and at 3 other locations.

In some aspects, the invention relates to a mutated Immunoglobulin (Ig) domain, comprising a substituted residue within the mutated Ig domain that corresponds to position 77 of SEQ ID NO:10; or SEQ ID NO:6, characterized in that the substituted residue is selected from the group consisting of A, G, I, V, L, R, S, T, M, Q, N, P, H, and W, provided that the mutated Ig domain further comprises residues K and H at positions corresponding to positions 80 and 81 respectively of SEQ ID NO:10; or SEQ ID NO:6. In some aspects, the mutated Ig domain comprises a sequence selected from the group consisting of SEQ ID NOs: 38, 39, 40, 41, 42, 44, 46, 47, 49, 50, 51, 52, 54, 98, 99, 100, 101, 102, 103, 104, 105, 106, 107, 108, 109, 115, 116, 117, 119, 120, 121, 122, 123, 124, 125, and 126.

Deposits

In some aspects, the invention provides for vectors and nucleic acids as desposited with the ATCC, polypeptides encoded by said vectors and nucleic acids, compositions comprising polypeptides encoded by said vectors and nucleic acids, and polypeptides expressed by said nucleic acids and vectors. The following materials have been deposited with the American Type Culture Collection, 10801 University Boulevard, Manassas, Virginia 20110-2209, USA (ATCC):

| Material | SEQ ID NO: | ATCC Accession No. | Date of Deposit |
|---|---|---|---|
| hCLk-Km(3)-D77A | 37 | PTA-13394 | Dec. 12, 2012 |
| h38C2-[LC-D185A] | 254 | PTA-13395 | Dec. 12, 2012 |

Vector hCLk-Km (3)-D77A is a TA cloning vector with a polynucleotide DNA insert encoding the human constant light chain kappa (Km(3)) domain with a D77A mutation, as set forth in SEQ ID NO:37, and vector h38C2-[LC-D185A] is a polynucleotide DNA insert encoding the humanized 38C2 light chain with a D77A mutation, as set forth in SEQ ID NO:254.

In some aspects, the invention provides for an isolated host cell that recombinantly produces an immunoglobulin domain of the present invention, or immunoglobulin domain-comprising protein or antibody of the present invention. The present invention provides for an isolated polynucleotide comprising a nucleotide sequence encoding proteins, domains and antibodies of the present invention, and vectors comprising said polynucleotides. Vectors of the present invention may comprise ATCC deposit sequences. In some aspects, the invention provides for a method of producing an antibody, immunoglobulin domain, or protein, comprising culturing a host cell under conditions that result in production of the antibody, immunoglobulin domain, or protein, and isolating the antibody, immunoglobulin domain, or protein, from the host cell or culture.

In some aspects, the present invention provide a polypeptide comprising a sequence selected from the group consisting of SEQ ID NO:37, SEQ ID NO:38, SEQ ID NO:39, SEQ ID NO:40, SEQ ID NO:41, SEQ ID NO:42, SEQ ID NO:44, SEQ ID NO:46, SEQ ID NO:47, SEQ ID NO:49, SEQ ID NO:50, SEQ ID NO:51, SEQ ID NO:52, SEQ ID NO:54, SEQ ID NO:60, SEQ ID NO:61, SEQ ID NO:77, SEQ ID NO:78, SEQ ID NO:94, SEQ ID NO:95, SEQ ID NO:96, SEQ ID NO:97, SEQ ID NO:104, SEQ ID NO:105, SEQ ID NO:106, SEQ ID NO:119, SEQ ID NO:120, SEQ ID NO:121, SEQ ID NO:122, SEQ ID NO:127, SEQ ID NO:128, SEQ ID NO:129, SEQ ID NO:134, SEQ ID NO:135, SEQ ID NO:140, SEQ ID NO:141, SEQ ID NO:142, SEQ ID NO:143, SEQ ID NO:144, SEQ ID NO:148, SEQ ID NO:149, SEQ ID NO:150, SEQ ID NO:151, SEQ ID NO:156, SEQ ID NO:158, SEQ ID NO:159, SEQ ID NO:160, SEQ ID NO:161, SEQ ID NO:163, SEQ ID NO:165, SEQ ID NO:167, SEQ ID NO:168, SEQ ID NO:169, SEQ ID NO:236, SEQ ID NO:237, SEQ ID NO:238, SEQ ID NO:239, SEQ ID NO:240, SEQ ID NO:241, and SEQ ID NO:254, or a polypeptide that is at least about 85%, or at least about 90%, or at least about 95%, or at least about 96%, or at least about 97%, or at least about 98%, or at least about 99% identical to one or more of the aforementioned sequences.

Samples and Compositions of the Invention

In some aspects, the invention provides for a composition or sample of an antibody or antigen binding portion thereof comprising a CL domain of the invention covalently conjugated to an Effector Moiety, wherein at least about 50% of the Effector Moiety in the composition or sample is conjugated to K$^5$ of SEQ ID NO:98. In some aspects, it is at least about 60%. In some aspects, it is at least about 70%. In some aspects, it is at least about 80%. In some aspects, it is at least about 90%.

In some aspects, the invention provides for a composition (or sample) of a antibody or antigen binding portion thereof comprising a CL domain of the invention, wherein at least about 50% of the antibody comprises an Effector Moiety covalently attached to K$^5$ of SEQ ID NO:98 on at least one light chain. In some aspects, it is at least about 60%. In some aspects, it is at least about 70%. In some aspects, it is at least about 80%. In some aspects, it is at least about 90%. In some aspects, the Effector Moiety is covalently conjugated to K$^5$ of SEQ ID NO:98 on both light chain constant regions.

In some aspects, the invention provides for a composition (or sample) of a antibody or antigen binding portion thereof comprising a CL domain of the invention covalently conjugated to an Effector Moiety, wherein at least about 30% of the sample comprises Effector Moieties conjugated at about 2 locations per antibody, and wherein at least one Effector Moiety conjugation site is $K^5$ of SEQ ID NO:98. In some aspects, the amount is about 40%. In some aspects, the amount is about 50%. In some aspects, the amount is about 60%. In some aspects, the amount is about 70%. In some aspects, the amount is about 80%. In some aspects, the amount is about 90%. In some aspects, the amount is about 95%. In some aspects, the amount is about 99%.

In some aspects, the invention provides for a composition (or sample) of a antibody or antigen binding portion thereof comprising a CL domain of the invention covalently conjugated to an Effector Moiety, wherein at least about 30% of the sample comprises Effector Moieties conjugated at about 3 locations per antibody, and wherein at least 2 Effector Moiety conjugation sites are $K^5$ of SEQ ID NO:98 on each light chain. In some aspects, the amount is about 40%. In some aspects, the amount is about 50%. In some aspects, the amount is about 60%. In some aspects, the amount is about 70%. In some aspects, the amount is about 80%. In some aspects, the amount is about 90%. In some aspects, the amount is about 95%. In some aspects, the amount is about 99%.

In some aspects, the invention provides for a composition (or sample) of a antibody or antigen binding portion thereof comprising a CL domain of the invention, wherein at least 50% of the light chain molecules are conjugated with at least one Effector Moiety at $K^5$ of SEQ ID NO:98. In some aspects, it is at least about 60%. In some aspects, it is at least about 65%. In some aspects, it is at least about 70%. In some aspects, it is at least about 75%. In some aspects, it is at least about 80%. In some aspects, it is at least about 85%. In some aspects, it is at least about 90%. In some aspects, it is at least about 95%.

In some aspects, the invention provides for a composition (or sample) of a antibody or antigen binding portion thereof comprising a CL domain of the invention conjugated to an Effector Moiety at $K^5$ of SEQ ID NO:98, wherein at least about 70% of the heavy chain molecules are unconjugated with the Effector Moiety. In some aspects, the amount is about 75%. In some aspects, the amount is about 80%. In some aspects, the amount is about 85%. In some aspects, the amount is about 90%. In some aspects, the amount is about 95%. In some aspects, the amount is about 99%. In some aspects, substantially all of the heavy chain molecules are unconjugated with the Effector Moiety.

In some aspects, the amount of individual light chain fragments that are unconjugated has a lower limit selected from the group consisting of about 1, 5, 10, 15, 20, 25, 30, 35, 40, 45, 50, and 55%, and an upper limit selected from the group consisting of about 5, 10, 15, 20, 25, 30, 35, 40, 45, 50, 55, and 60%. In some aspects, the amount of individual light chain fragments that are conjugated at one location has a lower limit selected from the group consisting of about 25, 30, 35, 40, 45, 50, and 55%, and an upper limit selected from the group consisting of about 30, 35, 40, 45, 50, 55, 60, 65, 70, 75, 80, 85, 90, and 95%. In some aspects, the amount of individual light chain fragments that are conjugated at 2 locations has a lower limit selected from the group consisting of about 1, 2, 3, 4, 5, 6, 7, 8, 9, 5, 10, 15, 20, and 25%, and an upper limit selected from the group consisting of about 5, 16, 7, 8, 9, 5, 10, 15, 20, 25, 30, 35, and 40%.

In some aspects, the amount of individual heavy chain fragments that are unconjugated has a lower limit selected from the group consisting of about 50, 55, 60, 65, 70, 75, and 80% and an upper limit selected from the group consisting of about 60, 65, 70, 75, 80, 85, 90, 95, and 99%. In some aspects, the amount of individual heavy chain fragments that are conjugated at one location has a lower limit selected from the group consisting of about 1, 2, 5, 10, 15, 20, and 25% and an upper limit selected from the group consisting of about 5, 10, 15, 20, 25, 30, 35, 40, and 50%. In some aspects, the amount of individual heavy chain fragments that are conjugated at 2 locations has a lower limit selected from the group consisting of about 0, 1, 2, 3, 4, 5, 10, and 15% and an upper limit selected from the group consisting of about 2, 3, 4, 5, 10, 15 and 20%.

In some aspects the number of conjugations per antibody in a sample or composition of the invention has a lower limit selected from the group consisting of about 0.5, 0.6, 0.7, 0.8, 0.9, 1, 1.1, 1.2, 1.3, 1.4, 1.5, 1.55, 1.6, 1.65, 1.7, 1.75, 1.8, 1.85, 1.9, 1.95 and 2, and an upper limit selected from the group consisting of about 1.6, 1.7, 1.75 1.8, 1.85, 1.9, 1.95, 2.0, 2.05, 2.1, 2.15, 2.2, 2.25, 2.3, 2.4, 2.5, 2.6, 2.7, 2.8, 2.9, 3.0, 3.5, 4.0, 4.5 and 5. In some aspects the number of conjugations per antibody in a sample or composition of the invention is between about 1.5 and about 2.5. In some aspects the number of conjugations per antibody in a sample or composition of the invention is between about 1.6 and about 2.4. In some aspects the number of conjugations per antibody in a sample or composition of the invention is between about 1.7 and about 2.3. In some aspects the number of conjugations per antibody in a sample or composition of the invention is between about 1.8 and about 2.2. In some aspects the number of conjugations per antibody in a sample or composition of the invention is an amount selected from the group consisting of about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.4 and about 2.5. In some aspects, the amount is about 1.7. In some aspects, the amount is about 1.8. In some aspects, the amount is about 1.9. In some aspects, the amount is about 2. In some aspects, the amount is about 2.1. In some aspects, the amount is about 2.1. In some aspects, the amount is about 2.3.

In some aspects of the invention, the number of conjugations per antibody is less than 2, with at least 50% of the antibody population having only a single conjugation per antibody. These samples are advantageous as they allow additional conjugation reactions to be targeted at the remaining CLκ site. In some aspects the number of conjugations per antibody in a sample or composition of the invention is between about 0.5 and about 1.5. In some aspects the number of conjugations per antibody in a sample or composition of the invention is between about 0.6 and about 1.4. In some aspects the number of conjugations per antibody in a sample or composition of the invention is between about 0.7 and about 1.3. In some aspects the number of conjugations per antibody in a sample or composition of the invention is between about 0.8 and about 1.2. In some aspects the number of conjugations per antibody in a sample or composition of the invention is between about 0.9 and about 1.1.

One of the advantages of the invention is that depending on the reagents and reaction conditions (especially the leaving group ester and molar ratio of linker:antibody), compositions and samples of the invention can be generated with a defined number of Effector Moieties relative to a defined number of antibodies. This can be especially useful when balancing the relative reactivities and therapeutic windows of the Effector Moiety and antibody. Moreover, in some situations, increasing the number of peptides or other Active Moieties per antibody beyond a certain threshold may not result in increased target binding or therapeutic effect. It is useful, therefore, to be able to control the number of peptides conjugated per antibody, and in doing so, direct the location of conjugation so as to minimize Fc or combining site interference. In some situations, therefore, aspects of the invention that allow for reduced conjugation, preferentially decorating only a single CLκ-$K^{80}$ can be advantageous. Furthermore, whereas conjugation to CLκ-$K^{80}$ is reliable and robust, conjugation to other antibody surface lysines, each of slightly different reactivity and pI can result in an heterogeneous sample of conjugated antibodies that can release conjugated molecules at inopportune or irregular times, such as during circulation and prior to delivery of the Effector Moiety to the target by antibody recognition (or delivery of the antibody to the target, by recognition with the Effector Moiety). This can be particularly undesirable with toxins (i.e. a cytotoxic agent with potential utility in killing tumors and tumor cells).

In some aspects, the toxin is an auristatin; a derivative of the natural product dolastatin 10 (MMAD). Representative auristatins include MMAE (N-methylvaline-valine-dolaisoleuine-dolaproline-norephedrine) and MMAF (N-methylvaline-valine-dolaisoleuine-dolaproline-phenylalanine).

In some aspects, the antibody targets a different target within the same pathway as the Effector Moiety. In some aspects, the antibody targets a different target to the Effector Moiety.

In some aspects, the VH and VL of antibody used for conjugation may be useful in the field of oncology. Suitable antibodies include; Rituximab, (Rituxan™), a chimeric, IgG1κ, anti-CD20 antibody, used to treat cancer and in particular non Hodgkin's lymphoma and also rheumatoid arthritis; Cetuximab (Erbitux™) a chimeric, IgG1κ, anti-EGF receptor antibody, used to treat cancer, and in particular colon, head & neck cancer.

In some aspects, the antibody used for conjugation may be useful in the field of auto-immune and other immunological disorders. Suitable antibodies include Infliximab (Remicade™) a chimeric, IgG1κ, anti-TNFα antibody, used to treat rheumatoid arthritis, ulcerative colitis, Crohn's disease, psoriasis, psoriatic arthritis, and ankylosing spondylitis; Adalimumab (Humira™) a human, IgG1κ, anti-TNFα antibody, used to treat rheumatoid arthritis, Crohn's disease, psoriasis, psoriatic arthritis, juvenile idiopathic arthritis and ankylosing spondylitis; Natalizumab (Tysabri™) a humanized, IgG4κ, anti-α4-integrin antibody used to treat multiple sclerosis, rheumatoid arthritis, psoriasis, juvenile idiopathic arthritis, psoriatic arthritis, ankylosing spondylitis, Crohn's disease; Omalizumab (Xolair™) a humanized, IgG1κ, anti-IgE antibody used to treat allergic asthma; Ranibizumab (Lucentis™) a humanized, IgG1κ, anti-VEGF antibody, used to treat wet AMD; and Palivizumab (Synagis™) a humanized, IgG1κ, anti-RSV antibody, used to treat infective diseases, including respiratory syncytical virus.

In some aspect, compounds and compositions of the invention may be used to treat the above mentioned conditions.

Effector Moieties

The Effector Moiety may be a therapeutic agent, protein, peptide, nucleic acid, aptamer, small molecule, protein agonist, protein antagonist, metabolic regulator, hormone, toxin, growth factor or other regulatory protein, or may be a diagnostic agent, such as an enzyme that may be easily detected or visualized, such as horseradish peroxidase.

In some aspects, the Effector Moiety may be a protein or peptide, and may be connected to the linker through a peptide-linking residue. The protein or peptide may comprise one or both of an amino-terminal capping group $R^1$ and a carboxyl-terminal capping group $R^2$. $R^1$ may be $CH_3$, $C(O)CH_3$, $C(O)CH_3$, $C(O)CH_2CH_3$, $C(O)CH_2CH_2CH_3$, $C(O)CH(CH_3)CH_3$, $C(O)CH_2CH_2CH_2CH_3$, $C(O)CH(CH_3)CH_2CH_3$, $C(O)C_6H_5$, $C(O)CH_2CH_2(CH_2CH_2O)_{1-5}$ Me, dichlorobenzoyl (DCB), difluorobenzoyl (DFB), pyridinyl carboxlate (PyC) or amido-2-PEG, an amino protecting group, a lipid fatty acid group or a carbohydrate. $R^2$ may be OH, $NH_2$, $NH(CH_3)$, $NHCH_2CH_3$, $NHCH_2CH_2CH_3$, $NHCH(CH_3)CH_3$, $NHCH_2CH_2CH_2CH_3$, $NHCH(CH_3)CH_2CH_3$, $NHC_6H_5$, $NHCH_2CH_2OCH_3$, $NHOCH_3$, $NHOCH_2CH_3$, a carboxy protecting group, a lipid fatty acid group or a carbohydrate.

The protein or peptide linking residue may be K, $K_{SH}$, lysine homologs, Dap, Dab, Orn, R, C, thiol containing residues, S, T, Y, D, E, N or Q. The protein or peptide may be connected to the linker through the amino terminus of the N-terminal amino acid. The protein or peptide may be connected to the linker through the carboxyl terminus of the C-terminal amino acid. An additional amino acid residue may be added to the N- or C-terminus in order to function as a linking residue, whether by connection through the amino acid side chain, or the amino or carboxyl terminus.

Linkers

In aspects of the invention relating to conjugates with Effector Moieties, in particular methods of preparing conjugates and MACs, it will be understood that the invention equally applies to conjugates with Linkers in the absence of Effector Moieties. An example of the utility of such conjugates would be as intermediates that may usefully used to prepate Effector Moiety-linker-polypeptide conjugates of the invention.

The Effector Moiety of the invention (such as a small molecule, aptamer, nucleic acid, protein, or peptide) may be covalently attached to the antibody or antigen binding portion thereof by a linker. The linker may be covalently attached to the peptide by an amino group of the side chain of the peptide-linking residue. This may be a lysine residue. In some embodiments, the linking residue is a thiol bearing residue, such as Cys or $K_{SH}$ and the linker is covalently attached to the peptide via the terminal thiol group of the linking residue.

The linker may be linear or branched (to allow for conjugation to more than one Effector Moiety per Conjugation Addition (CA)), and optionally includes one or more carbocyclic or heterocyclic groups. Linker length may be viewed in terms of the number of linear atoms between the Effector Moiety and Antibody, with cyclic moieties such as aromatic rings and the like to be counted by taking the shortest route around the ring. In some embodiments, the linker has a linear stretch of between 5-15 atoms, in other embodiments 15-30 atoms, in still other embodiments 30-50 atoms, in still other embodiments 50-100 atoms, and in still other embodiments 100-200 atoms. In some embodiments, the length of the linker is a range with a lower limit selected from the group consisting of 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 160, 170, 180, 190, and an upper limit selected from the group consisting of 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 160, 170, 180, 190, and 200.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

The linker may be a peptidyl linker. In some embodiments, the peptidyl linker may be between 3-20 amino acids long, such as repeats of a single amino acid residue (e.g. polyglycine) or combinations of amino acid residues to give a peptide linker which imparts favorable presentation of the Effector Moiety or pharmacokinetics. Peptidyl linkers that would be most compatible with the presence of activating groups may lack lysine and histidine residues. SEQ ID NO:79 is an exemplary peptidyl linker.

Alternatively, the linker may be a non-peptidyl linker. Typical examples of these types of linker would be those based on straight or branched chain hydrocarbons or polyethylene glycols of varying lengths. These may incorporate other groups to affect solubility, rigidity, isoelectric point, such as aromatic or non-aromatic rings, halogens, ketones, aldehydes, esters, sulfonyls, phosphate groups, and so on.

In some aspects of the invention, the linker may comprise the formula: —$X^1$-$Y^1$-Z—; wherein $X^1$ is the attachment group to the Effector Moiety (for example, via a peptide-linking residue), $Y^1$ is a spacer region, and Z is an attachment moiety to the side chain of a lysine residue on an antibody (for example, an anti-IGF1R antibody). In some aspects, the linker may be of the formula $X^1Y^1Z^*$ when unbound to the antibody, where $Z^*$ is a leaving group, such that when conjugated to the antibody, the leaving group $Z^*$ reacts with the conjugation site of the antibody to form the conjugated linker $X^1Y^1Z$.

$X^1$ may be selected so as to enable a specific directional covalent linking strategy to the Effector Moiety (for example, via the peptide-linking residue). In some aspects, $X^1$ may be selected from the group consisting of COOH, isocyanate, isothiocyanate, acyl azide, sulfonic acid, sulfonyl halide, aldehyde, ketone, epoxide, carbonate, arylating reagent, imidoester, amine group, and a malemide group. For example, where the peptide-linking residue comprises a nucleophilic group, $X^1$ may be an electrophilic group and vice versa. For example, if the peptide-linking residue side chain comprises an amine group, such as K, H, Ornithine, Dap, or Dab, $X^1$ may be COOH, or other similarly reactive electrophile, for example, an isocyanate, isothiocyanate, acyl azide, sulfonic acid or sulfonyl halide, aldehyde or ketone, epoxide, carbonate, arylating reagent or imidoester. If the peptide-linking residue is D or E, $X^1$ may comprise a nucleophilic group, such as an amine group. Either of these strategies permits a covalent bond to be formed between the $X^1$ group and the peptide-linking residue by amide bond formation strategies. For example, when $X^1$ is COOH, it may be activated as a pentafluorophenyl ester. In this case, reaction with an amine group on the peptide-linking peptide leads to amide bond formation, while the pentafluorophenol is a leaving group (which may be termed $X^{1*}$).

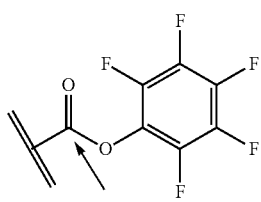

The arrow indicates the point of attachment to the peptide-linking residue and the parallel line represents the point of attachment to the $Y^1$ group of the linker.

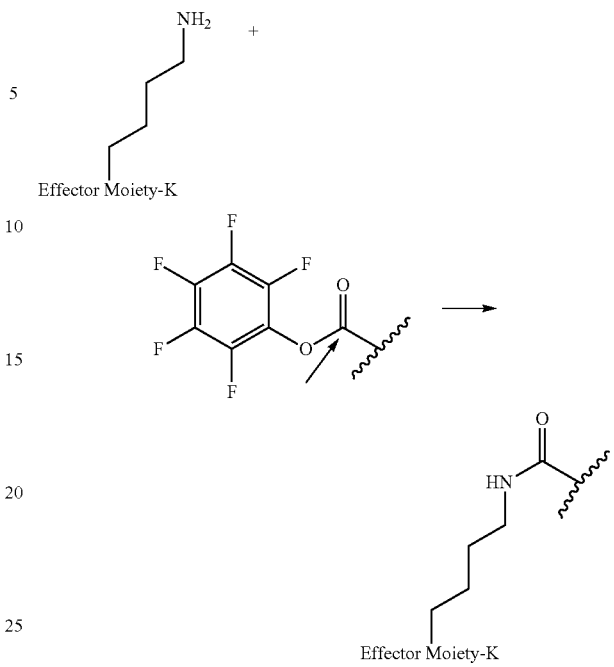

Where the peptide-linking group is C, homologs of C, or other thiol-group containing residues (such as $K_{SH}$), $X^1$ may comprise a malemide group, permitting a thiol-malemide addition reaction strategy to covalently link the $X^1$ group to the peptide-linking residue. In some aspects, $X^1$ may be maleimide:

wherein the arrow indicates the point of attachment to the peptide linking residue and the parallel line represents to attachment to the $Y^1$ group of the linker. For ease of nomenclature, linkers described herein that have been constructed using maleimide groups are described as maleimide-containing linkers, and may be titled MAL to indicate this, even though following construction of the linker, the maleimide group is generally converted to a succinimide ring.

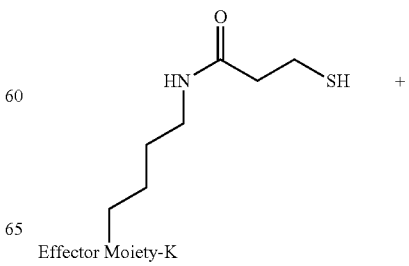

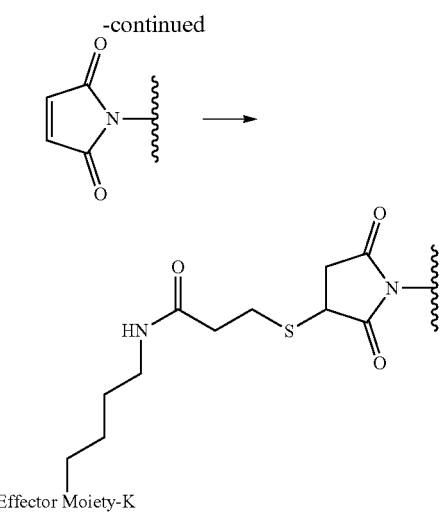

In some aspects, the linking residue is $K_{SH}$, and the $X^1$ group is maleimide. In some aspects, $X^1$ may comprise a pentafluorophenyl ester activated carboxyl function which may form an amide with the lysine side chain on the peptide.

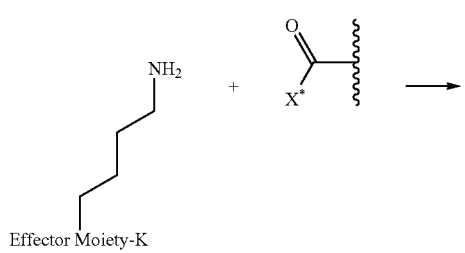

In some aspects, $X^1$ may comprise a thiol group, allowing a disulphide bridge to be formed between the peptide-linking residue and $X^1$ group.

In some embodiments, $Y^1$ is a biologically compatible connecting chain including any atom selected from the group consisting of C, H, N, O, P, S, F, Cl, Br, and I, and may comprise one or more amino acids, polymer or block co-polymer. $Y^1$ may be selected so as to provide an overall length of the linker of between 2-100 atoms. $Y^1$ may be selected so that the overall length of the linker is between 5 and 30 atoms. $Y^1$ may be selected so that the overall length of linker is 15-25 atoms. $Y^1$ may be selected so that the overall length of linker is between about 17 and about 19 atoms.

In some aspects, $Y^1$ may be an amino alkanoic acid, such as:

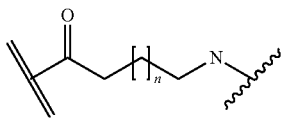

where n=0 to 20 in some aspects 1-10, in some aspects, 1-5, and in some aspects, 1 and in some aspects, 2.

In some aspects, $Y^1$ may be an alkanoic diacid, such as:

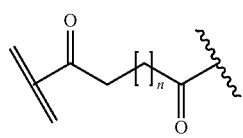

where n=0 to 20 in some aspects 1-10, in some aspects, 1-5, and in some aspects, 1 and in some aspects, 2.

In some aspects, $Y^1$ may be a polyglycine, such as:

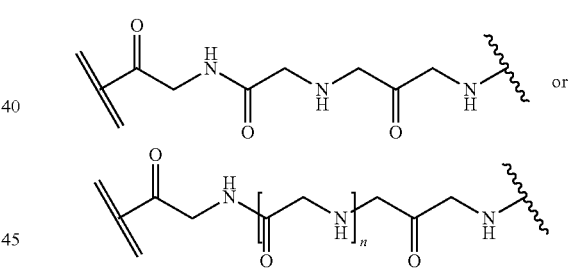

where n=0 to 10, in some aspects 1-10, in some aspects, 1-5, and in some aspects, 1 and in some aspects, 2.

In some aspects, $Y^1$, $X^1$—$Y^1$, $Y^1$—Z, and $X^1$—$Y^1$-Z may be selected from the group consisting of:

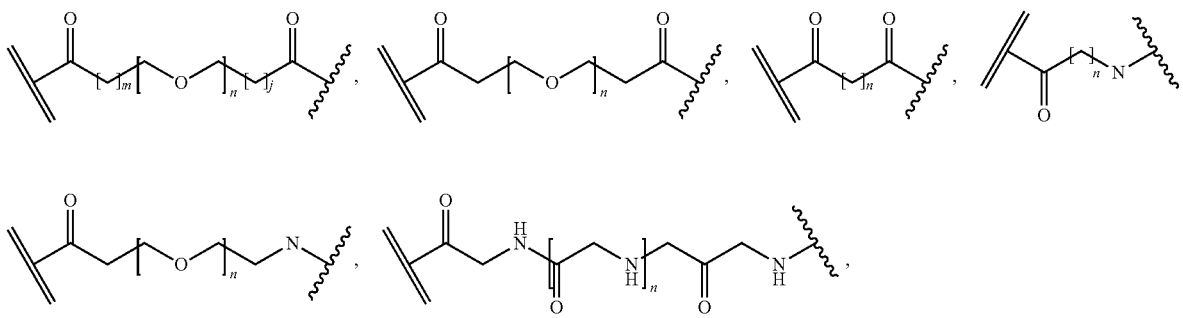

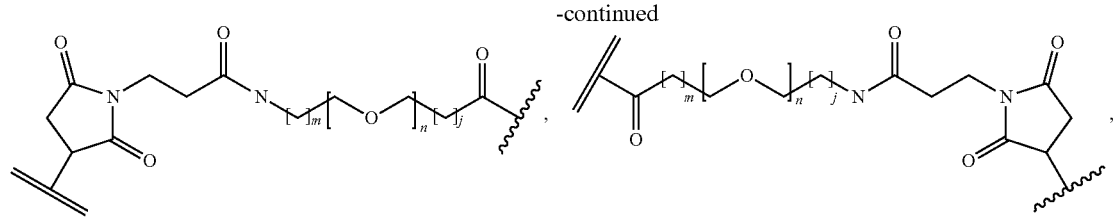

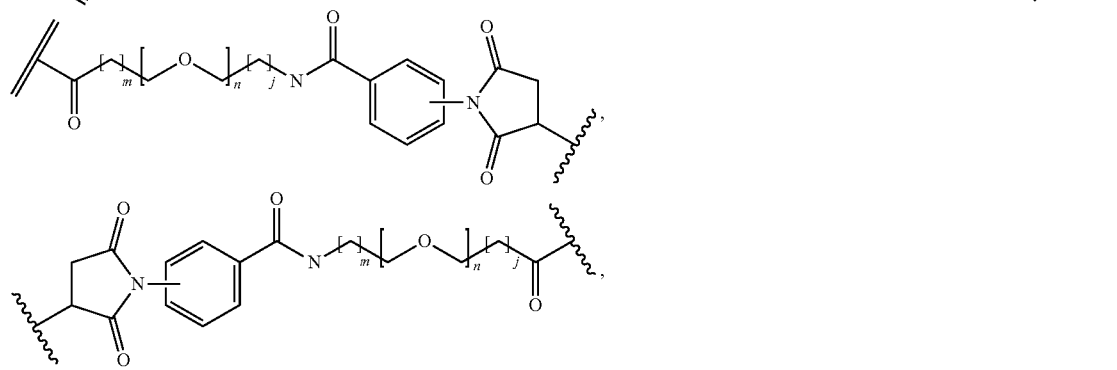

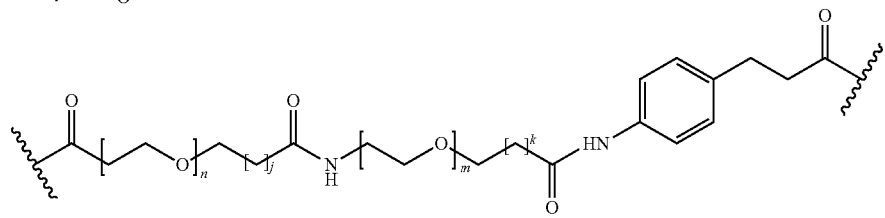

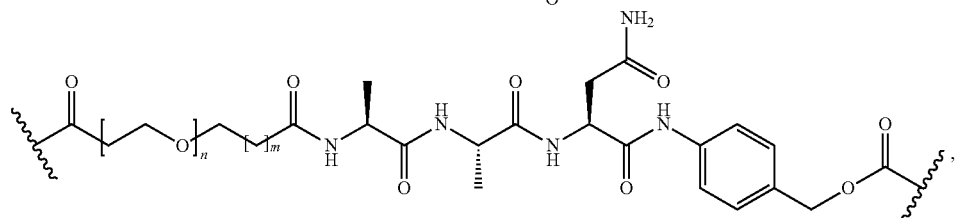

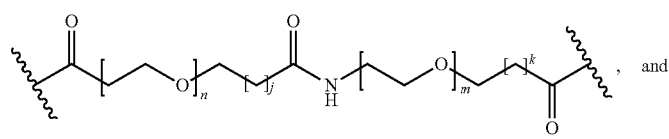

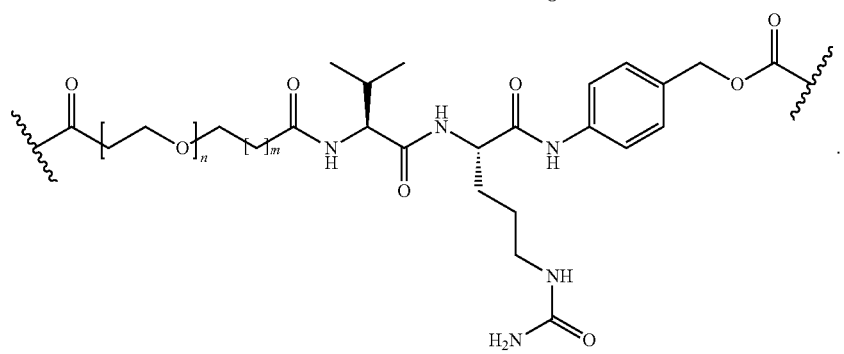

where m, n, j and k are each independently 0 to 30. In some aspects n=1-10, in some aspects, n=1-5. In some aspects, the lower limit of the range of values for n is selected from the group consisting of 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects m=1-10, in some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6. In some aspects k=1-10, in some aspects, k=1-5. In some aspects, the lower limit of the range of values for k is selected from the group consisting of 0, 1, 2, 3, 4, 5, 6, 7, 8, 9, 10, 11, 12, 13, 14, 15, 16, 17, 18, 19, and 20, and the upper limit for the range of values for k is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. K may be 1. K may be 2. K may be 3. K may be 4. K may be 5. K may be 6. In some aspects, the overall length of $Y^1$ does not exceed 200 atoms. In some aspects, the overall length of $Y^1$ does not exceed 150 atoms. In some aspects, the overall length of $Y^1$ does not exceed 100 atoms. In some aspects, the overall length of $Y^1$ does not exceed 50 atoms. In some aspects, the range of overall chain length of $Y^1$ in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100. In some aspects, the $X^1Y^1Z$ linker may be identical to the above $Y^1$ groups. In some aspects, the wavy line connects to the $X^1$ group. In some aspects, the parallel lines connect to the $X^1$ group. In some aspects, the wavy line connects to the Z group. In some aspects, the parallel lines connect to the Z group. In some aspects, the wavy line connects to the side chain of $CL\kappa\text{-}K^{80}$. In some aspects, the parallel lines connect to the side chain of $CL\kappa\text{-}K^{80}$. In some aspects, the wavy line connects to the Effector Moiety. In some aspects, the parallel lines connect to Effector Moiety. In some aspects, one of the wavy or parallel lines are points of attachment to a cleavable portion of the linker ($\Phi$).

Leaving Groups

Z* may be selected so as to enable a specific directional covalent linking strategy to a lysine side chain on the antibody. For example, Z may be COOH, or another similarly reactive electrophile to react with the ε-amino of the surface lysine side chains using one of a number of possible amide bond formation strategies.

In some aspects, Z* may be used to form an active ester. Active esters connect to amines, and can thus conjugate to the ε-amino of a lysine side chain of the antibody. The Z carboxyl function to enable the formation of the active ester will be present at the terminus of Y group. The alcoholic or phenolic function of the active ester acts as a leaving group Z* during the conjugation reaction, enabling connection with the lysine side chain on the antibody via generation of an amide.

In some embodiments, the Z* group comprises a structure of the formula:

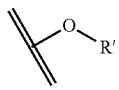

where R' is an aliphatic or aromatic group.

In some embodiments, the Z* group is of the formula:

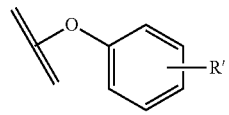

where R'=any of F, Cl, Br or I, nitro, cyano, trifluoromethyl, alone or in combination, and may be present in an amount of between 1 and 5. In some embodiments, $R^1$ may be a halogen, and 4 or 5 halogen atoms may be present. In some embodiments, there may be 4 $R^1$ atoms. In some embodiments, there may be 5 $R^1$ atoms. In some embodiments, Z* may be tetrafluorophenyl. In some embodiments, Z* may comprise the formula:

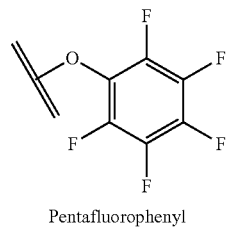

Pentafluorophenyl wherein the parallel line represents the point of attachment to the $Y^1$ portion of the linker.

In some embodiments, Z* may comprise the formula:

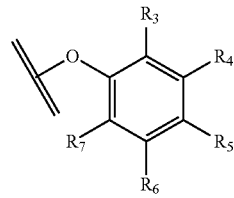

wherein $R^3$, $R^4$, $R^5$, $R^6$ and $R^7$ are each independently selected from the group consisting of F, CL, H and the formula $CR^8R^9R^{10}$, such that no more than two of $R^3$, $R^4$, $R^5$, $R^6$ and $R^7$ are H, and one of $R^3$, $R^4$, $R^5$, $R^6$ and $R^7$ is $CR^8R^9R^{10}$, and $R^8$, $R^9$, and $R^{10}$ are each independently selected from the group consisting of F, Cl and H such that no more than one of $R^8$, $R^9$ and $R^{10}$ may be H, and wherein the parallel line represents the point of attachment to the $Y^1$ portion of the linker. In some aspects, the group $CR^8R^9R^{10}$ is located at one of $R^4$, $R^5$ or $R^6$. In some aspects, the group $CR^8R^9R^{10}$ is located at $R^5$.

In some aspects, $R^3$, $R^4$, $R^5$, $R^6$ and $R^7$ are each independently selected from the group consisting of F, Cl, H and the formula $CR^8R^9R^{10}$, such that no more than one of $R^3$, $R^4$, $R^5$, $R^6$ and $R^7$ is H, and one of $R^3$, $R^4$, $R^5$, $R^6$ and $R^7$ is $CR^8R^9R^{10}$. In some aspects, $R^3$, $R^4$, $R^5$, $R^6$ and $R^7$ are each independently selected from the group consisting of F, Cl, and the formula $CR^8R^9R^{10}$, and one is $CR^8R^9R^{10}$.

In some aspects, $R^3$, $R^4$, $R^6$ and $R^7$ are each F. In some aspects, $R^8$, $R^9$, and $R^{10}$ are each independently selected from the group consisting of F and Cl. In some aspects, $R^8$, $R^9$, and $R^{10}$ are each F.

In some embodiments, Z* may comprise the formula:

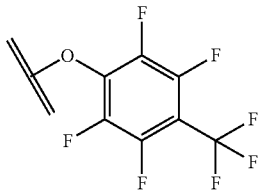

2,3,5,6-tetrafluoro-4-(trifluoromethyl)phenyl wherein the parallel line represents the point of attachment to the $Y^1$ portion of the linker.

In some aspects, the Z* group is of the formula:

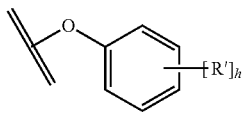

where $R'$=any of F, Cl, Br or I, nitro, cyano, trifluoromethyl, alone or in combination, and h=1, 2, 3, 4, or 5. In some embodiments, $R^1$ may be a halogen. In some embodiments, $R^1$ is F or Cl, and h=4 or 5. In some embodiments, $R^1$ is F or Cl, and h=5. In some embodiments, $R^1$ is F, and h=2, 3, 4 or 5. In some embodiments, $R^1$ is F, and h=3, 4 or 5. In some embodiments, $R^1$ is F, and h=4 or 5. In some embodiments, $R^1$ is F, and h=5. In some aspects, Z* may be selected from the group consisting of:

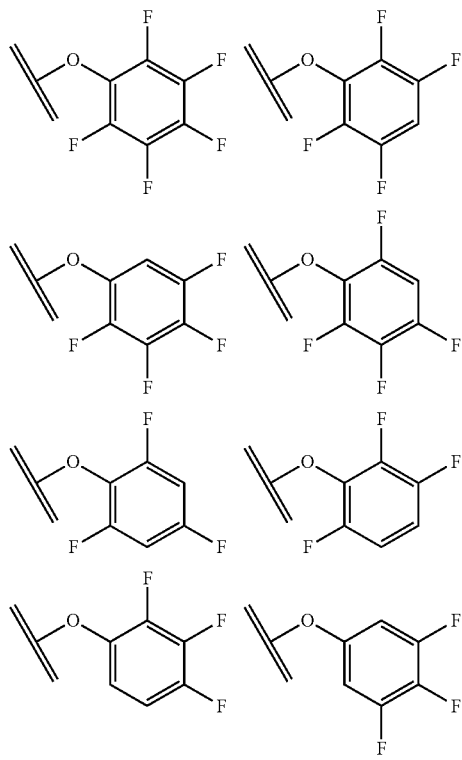

-continued

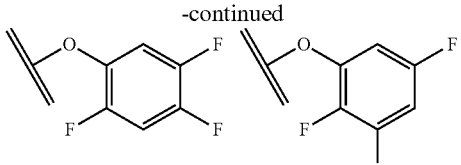

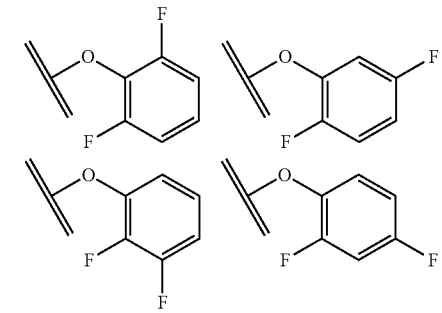

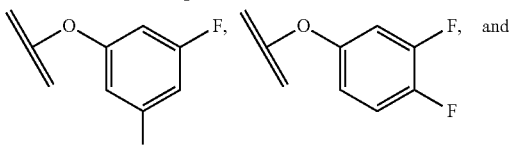

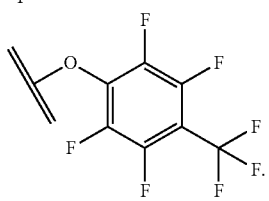

In some aspects, Z* may be selected from the group consisting of:

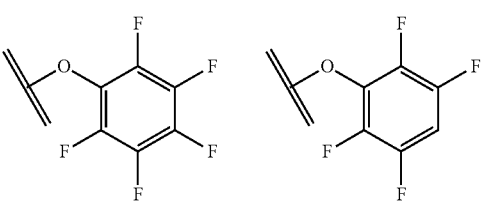

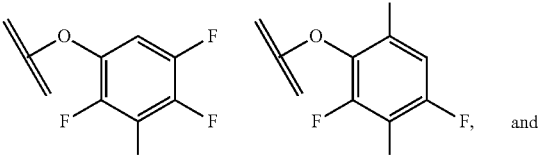

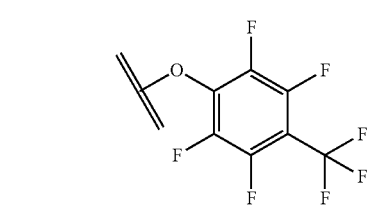

In some aspects, Z* may be selected from the group consisting of:

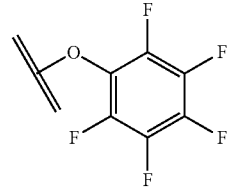 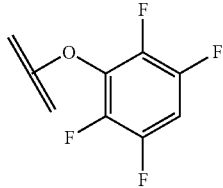

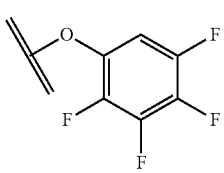 and 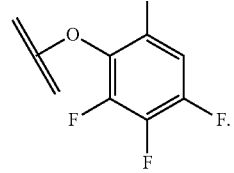

In some aspects, Z* may be selected from the group consisting of:

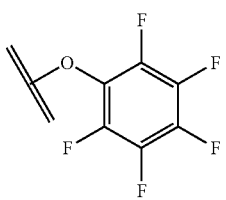 and 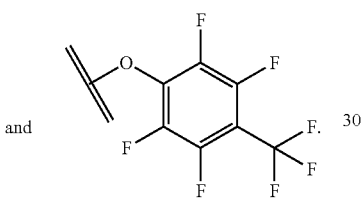

For such active esters, the leaving group is Z* and the Z group itself is the carbonyl attached to the $Y^1$ group. When reacted with the antibody, the Z* group forms an amide, as shown below,

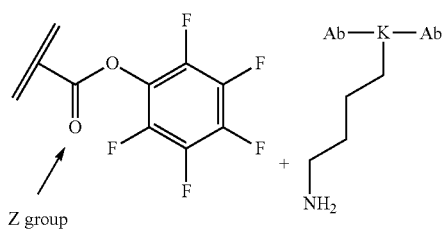

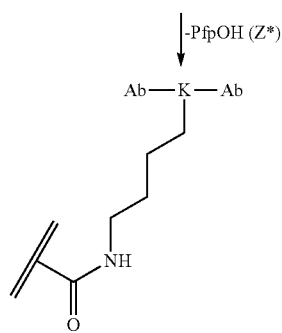

In some embodiments, Z is

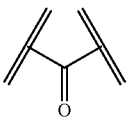

In some embodiments, the Z* group comprises a squarate ester such as

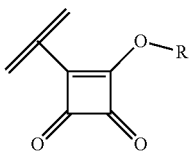

wherein R=aliphatic group or substituted aromatic and may be selected from the group consisting of:

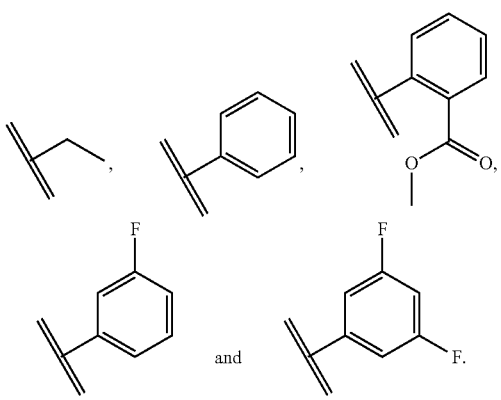

In some embodiments, the Z group comprises a Maleimide group:

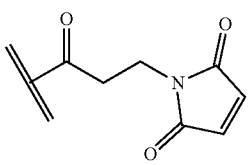

In some aspects, the $X^1*Y^1Z*$ linker comprises a Maleimide-PEG-PFP ester of the structure:

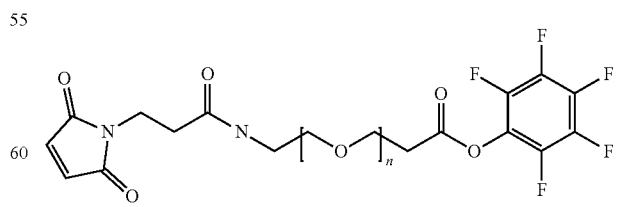

where n=1 to 12. In some aspects, n=1 to 5. In some aspects n=2. In some aspects n=1.

In some aspects, the $X^1*Y^1Z*$ linker comprises a structure selected from the group consisting of:

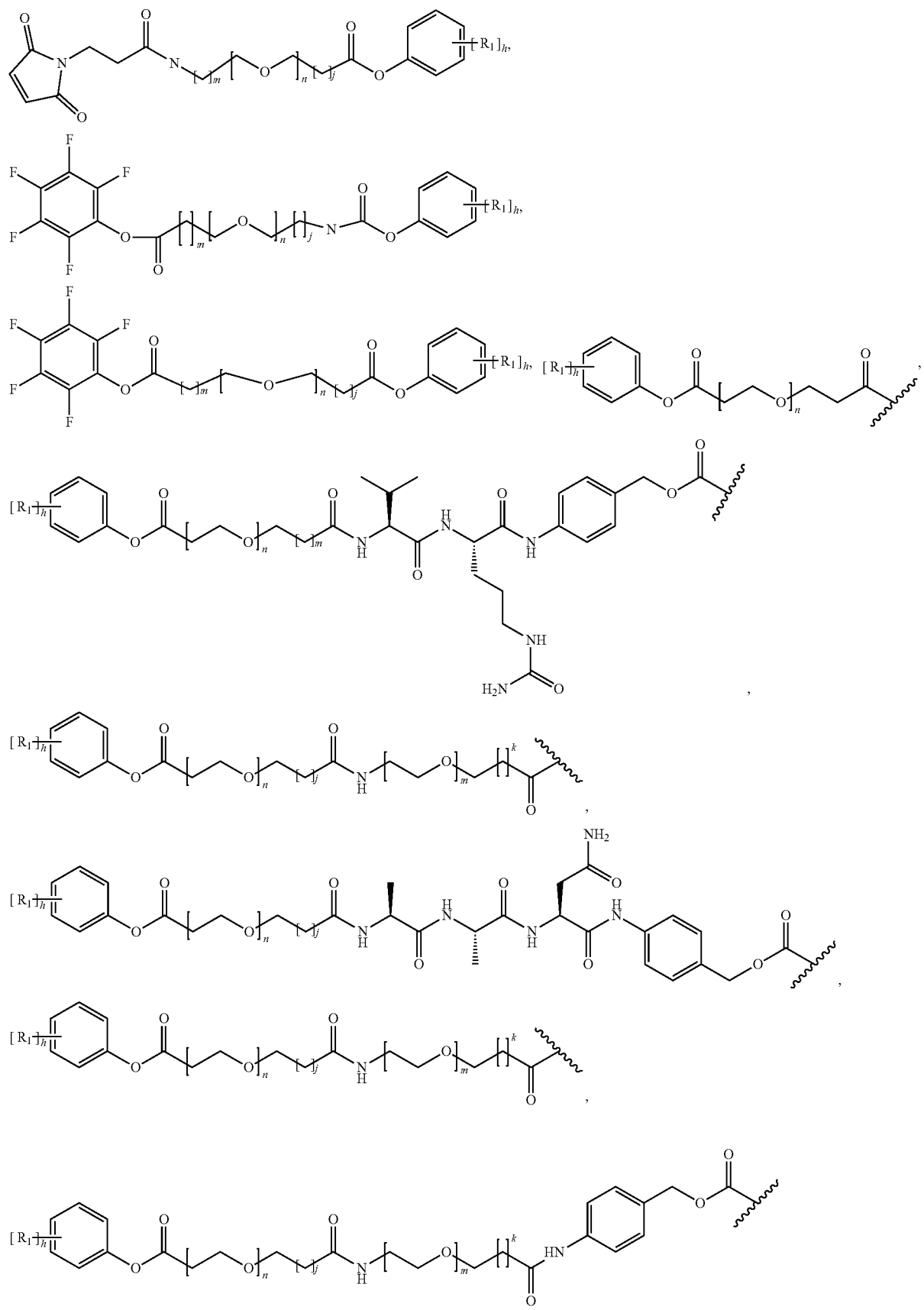

-continued

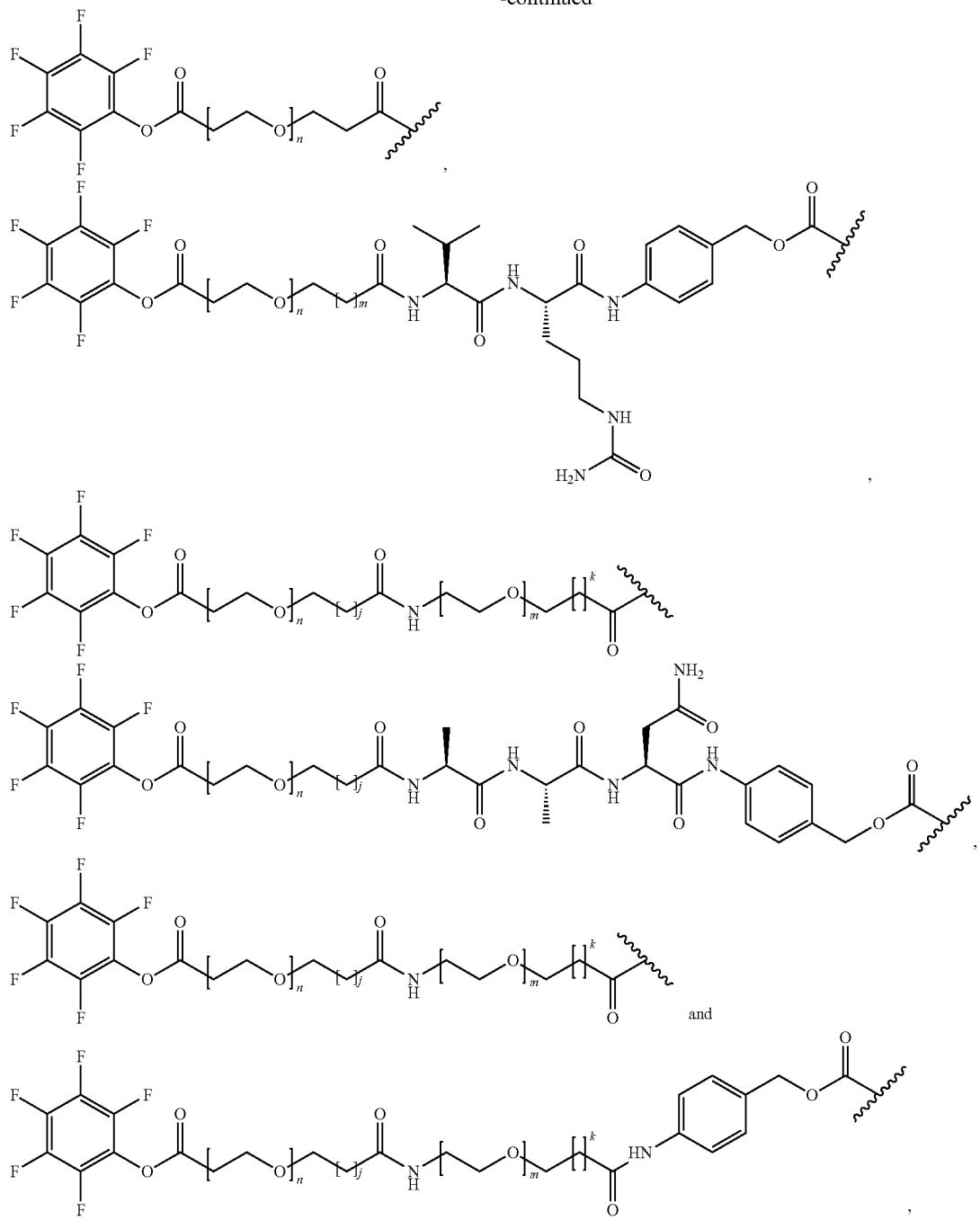

where m, n and j are each independently 0 to 30, R1 is F and h=2, 3, 4, or 5. In some aspects n=1-10, in some aspects, n=1-5. In some aspects, the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6.

In some aspects k=1-10, in some aspects, k=1-5. In some aspects, the lower limit of the range of values for k is selected from the group consisting of 0, 1, 2, 3, 4, 5, 6, 7, 8, 9, 10, 11, 12, 13, 14, 15, 16, 17, 18, 19, and 20, and the upper limit for the range of values for k is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. K may be 1. K may be 2. K may be 3. K may be 4. K may be 5. K may be 6. In some aspects, the overall length of $Y^1$ does not exceed 200 atoms. In some aspects, the overall length of $Y^1$ does not exceed 150 atoms. In some aspects, the overall length of $Y^1$ does not exceed 100 atoms. In some aspects, the overall length of $Y^1$ does not exceed 50 atoms. In some aspects, the range of overall chain length of $Y^1$ in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100.

In some aspects the MAC comprises a $X^1Y^1Z$ linker of the formula:

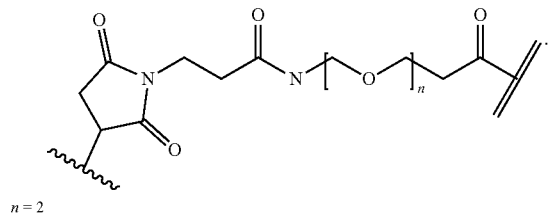

$n = 2$

In some aspects, the $X^{1*}Y^1Z^*$ linker comprises a PEG-bis-pentafluorophenyl ester of the formula:

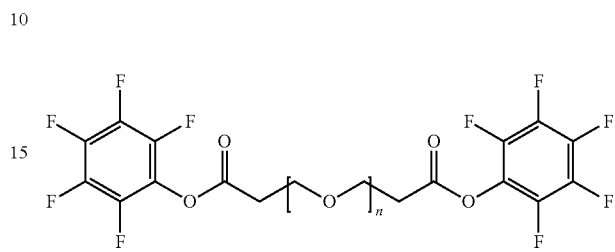

where n=1 to 25. In some aspects n=1 to 20. In some aspects n=1 to 10. In some aspects n=4. N=3, In some aspects n=1.

In some aspects the MAC comprises 2 peptides conjugated per antibody. In some aspects, one peptide is conjugated at each of the 2 $CL\kappa\text{-}K^{80}$ residues of the antibody or antigen binding fragment thereof.

In some aspects, the polypeptide of the invention comprises a formula selected from the group consisting of:

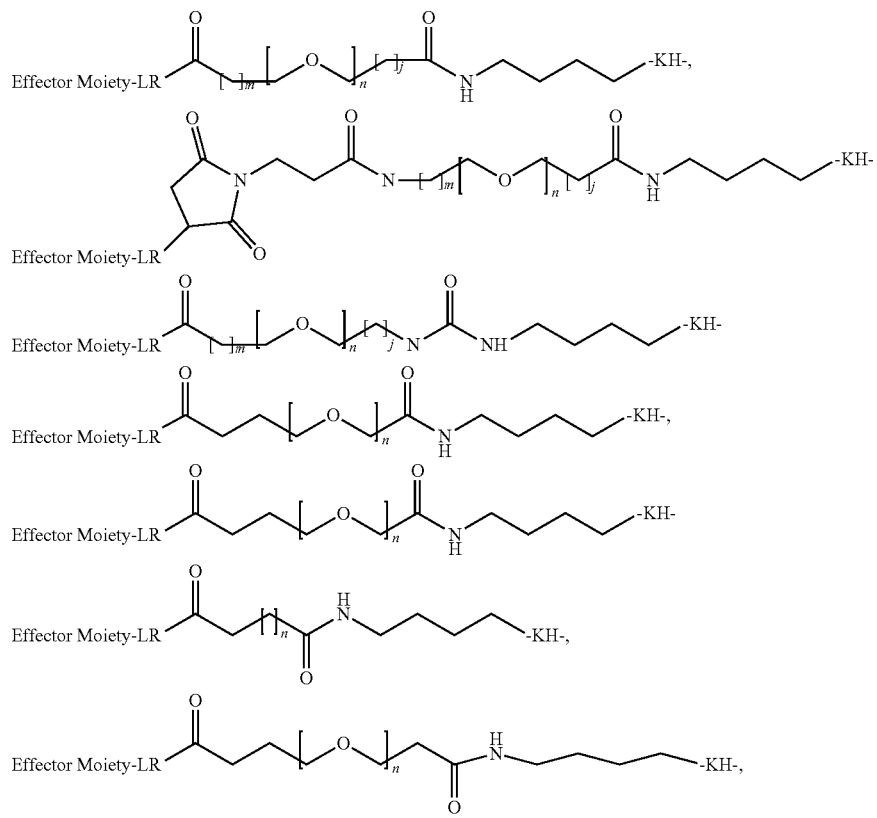

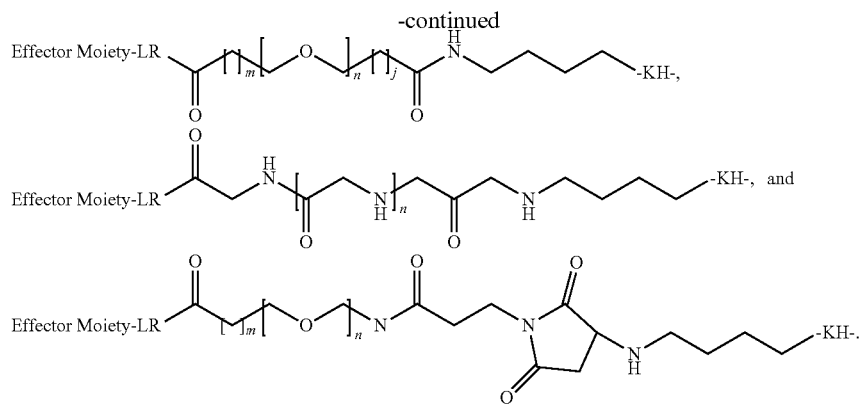

wherein —KH— is a covalent link to the side chain of $K^5$ of SEQ ID NO:98, Effector Moiety-LR is a covalent link to the Effector Moiety, and m, n and j are each independently 0-30. In some aspects n=1-10, in some aspects, n=1-5. In some aspects, the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects m=1-10, in some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6. In some aspects, the overall length of $Y^1$ does not exceed 200 atoms. In some aspects, the overall length of $Y^1$ does not exceed 150 atoms. In some aspects, the overall length of $Y^1$ does not exceed 100 atoms. In some aspects, the overall length of $Y^1$ does not exceed 50 atoms. In some aspects, the range of overall chain length of $Y^1$ in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100.

In some aspects, the linker is selected from the group consisting of

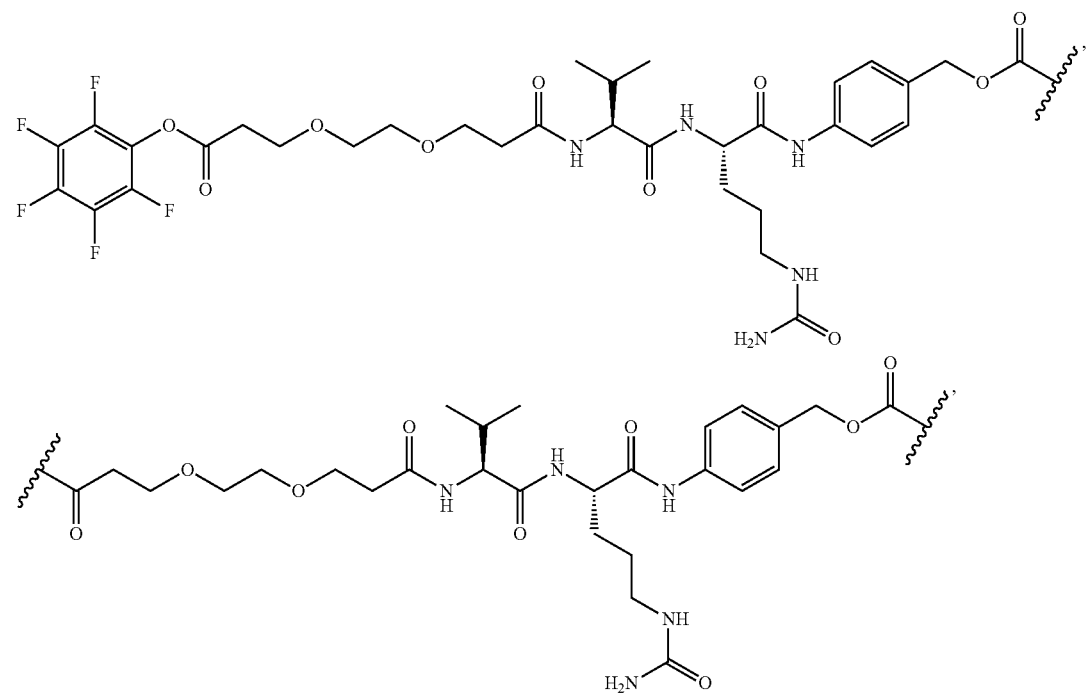

-continued
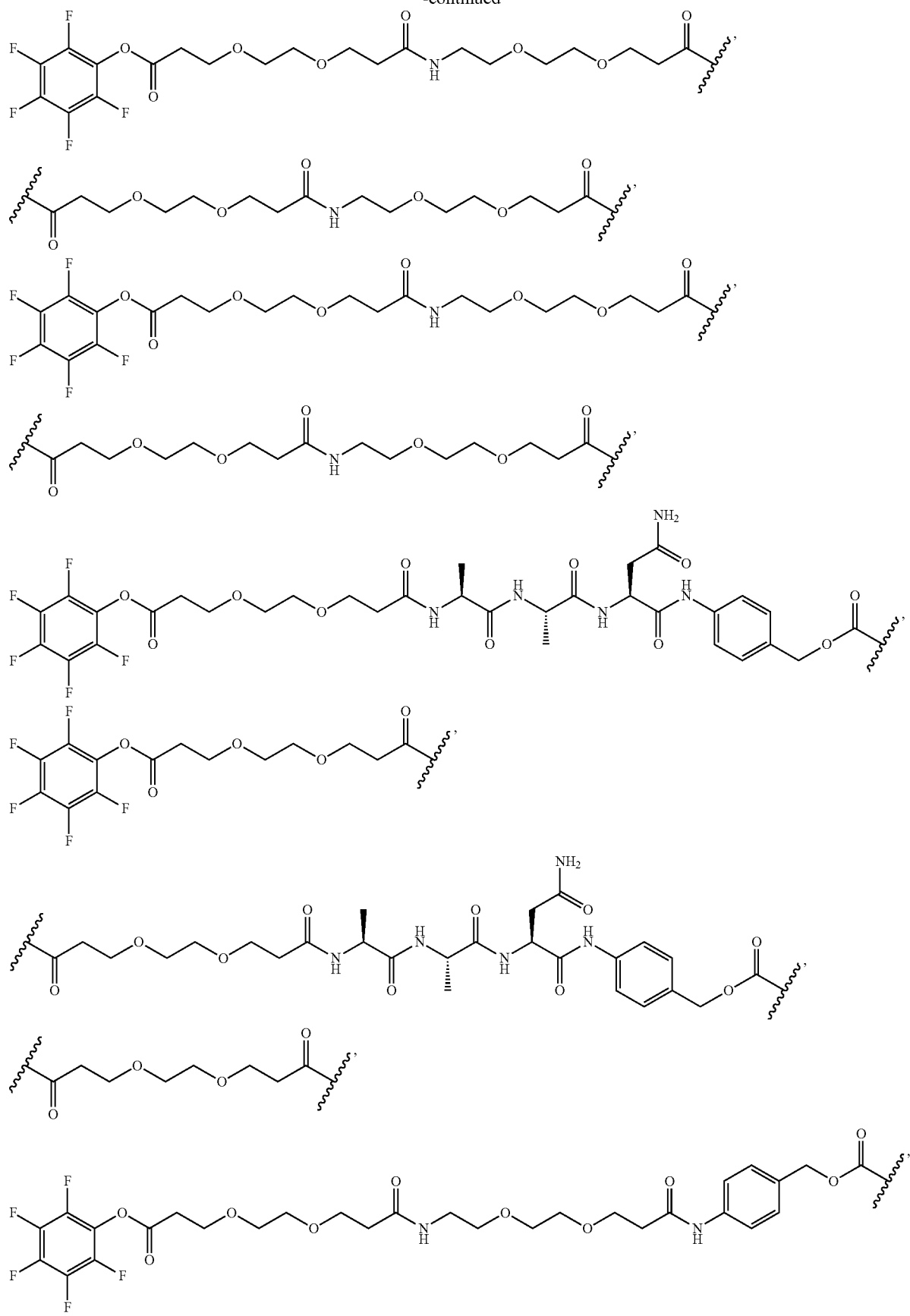

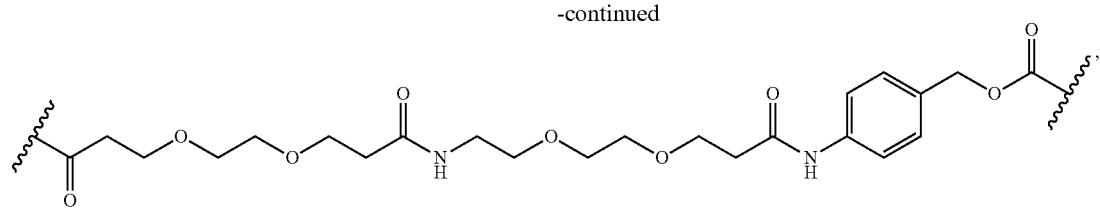

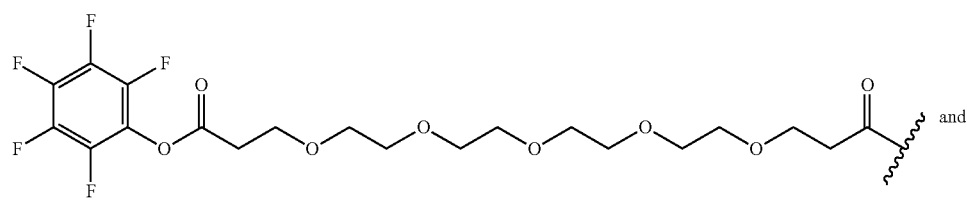 and

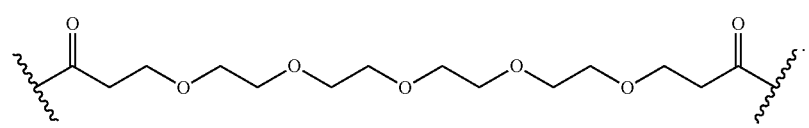

Cleavable Linkers

In some aspects, the invention provides for MACs as described herein comprising "non-cleavable" linkers. In other aspects, the invention provides for MACs comprising "cleavable" linkers. The term "cleavable linker" is used herein to describe a rapidly cleaved linker that is designed to be degraded by intracellular or extracellular enzymes or when subjected to changes in pH or redox environment so as to release the cargo at the desired location. For example, cleavable linkers may be preferentially stable in plasma, blood or serum, and less stable in intracellular environments.

Cleavable linkers can be formed by adding a cleavable portion ($\Phi$) to the $Y^1$ portion of the linker (or $P^1$ portion, where the linker is for a catalytic antibody combining site). Accordingly, the linkers would take the formula $X^1$-$\Phi$-$Y^1$-Z, $X^1$-$\Phi$-$Y^1$-Z*, and $P^1$-$\Phi$-$Q^1$-$W^1$.

A representative example of a cleavable portion of a linker is valine-citrulline p-aminobenzyl carbamate (VitCit-ABC) that is cleaved by intracellular proteases such as cathepsin B.

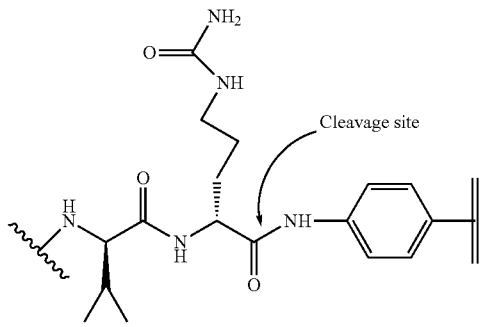

where the wavy line typically indicates the point of attachment to the $Y^1$ (or $Q^1$) portion of the linker, and the parallel line represents the point of attachment to the $X^1$ (or $P^1$) portion of the linker, or even to the Effector Moiety itself. In some aspects, of course, the wavy line may indicate the point of attachment to the $X^1$ or $P^1$ linker portion (or Effector Moiety), and the parallel line may indicate the point of attachment to the $Y^1$ or $Q^1$ portion of the linker.

Accordingly, in some aspects, the invention provides for linker of the formula:

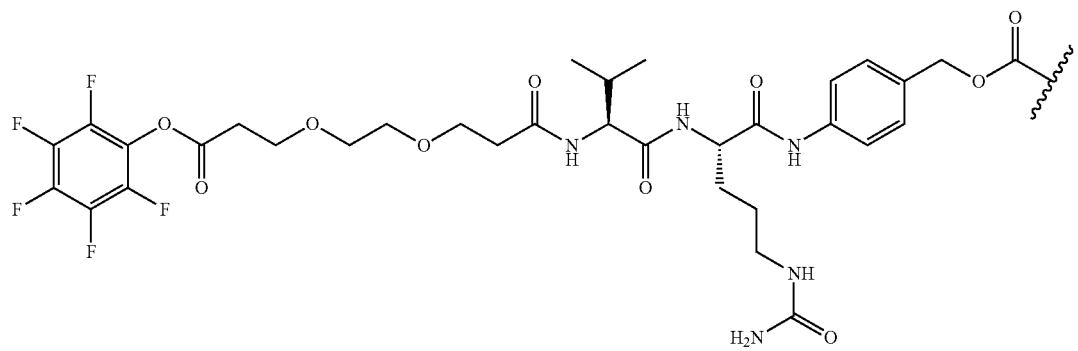

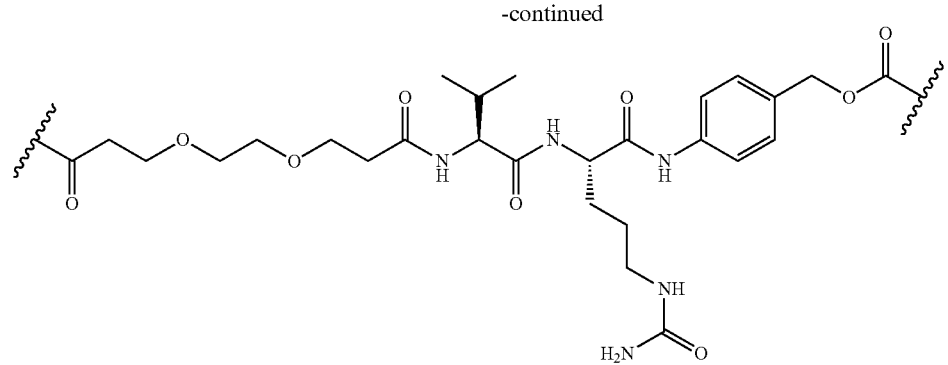
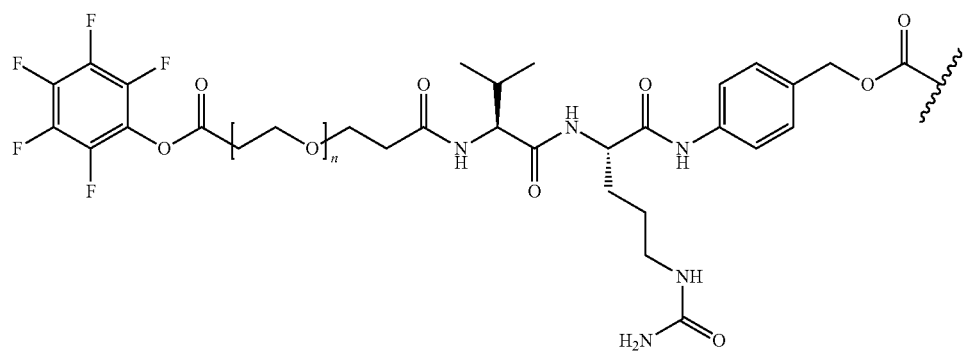
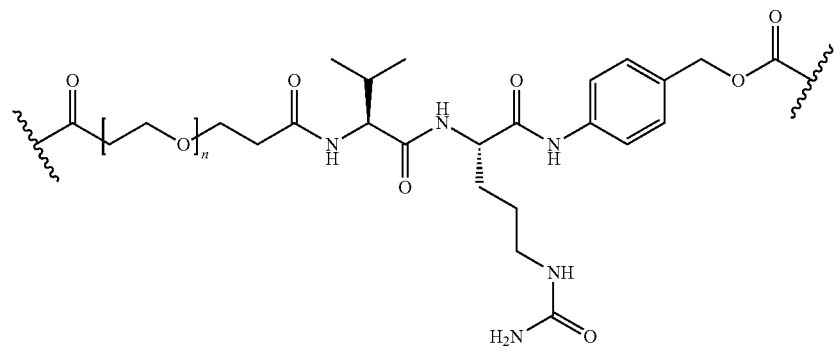
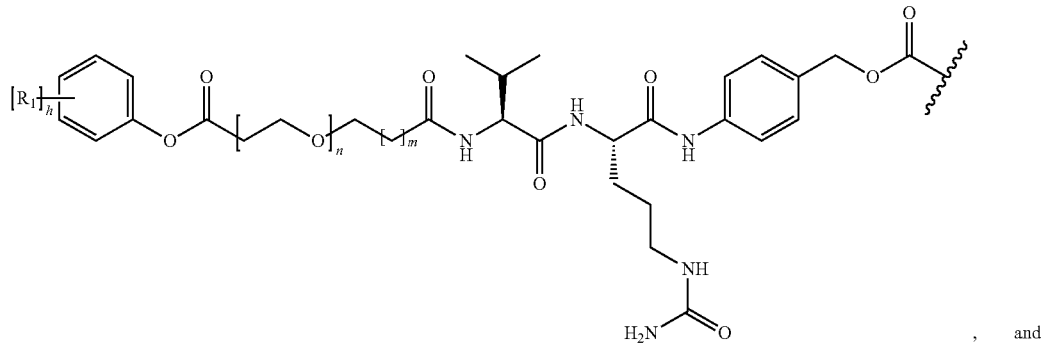
, and

-continued

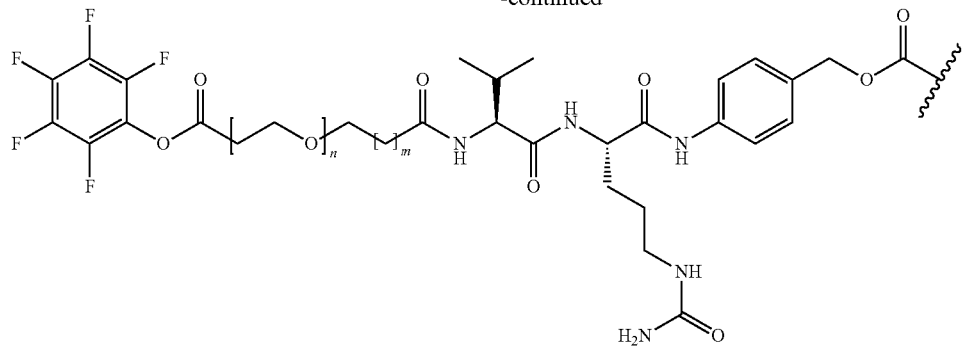

where m, n and j are each independently 0 to 30, R1 is F and h=2, 3, 4, or 5. In some aspects n=1-10, in some aspects, n=1-5. In some aspects, the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects m=1-10, in some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6. In some aspects k=1-10, in some aspects, k=1-5. In some aspects, the lower limit of the range of values for k is selected from the group consisting of 0, 1, 2, 3, 4, 5, 6, 7, 8, 9, 10, 11, 12, 13, 14, 15, 16, 17, 18, 19, and 20, and the upper limit for the range of values fork is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. K may be 1. K may be 2. K may be 3. K may be 4. K may be 5. K may be 6. In some aspects, the overall length of $Y^1$ does not exceed 200 atoms. In some aspects, the overall length of $Y^1$ does not exceed 150 atoms. In some aspects, the overall length of $Y^1$ does not exceed 100 atoms. In some aspects, the overall length of $Y^1$ does not exceed 50 atoms. In some aspects, the range of overall chain length of $Y^1$ in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100.

Use of Auristatin-Based Payloads

Auristatin-based effector moieties are also useful in connection with the targeted conjugation technology of the present invention when used in conjunction with the appropriate linker technology. Specifically, useful payloads include those disclosed in PCT/162012/056224 including all pharmaceutically acceptable salts, hydrates and free base forms.

Accordingly, the following effector moieties and linkers may be used in aspects of the invention:

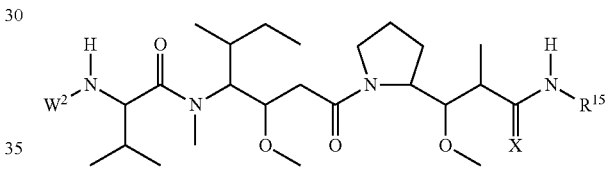

or a pharmaceutically acceptable salt or solvate thereof, wherein, independently for each occurrence, $W^2$ is

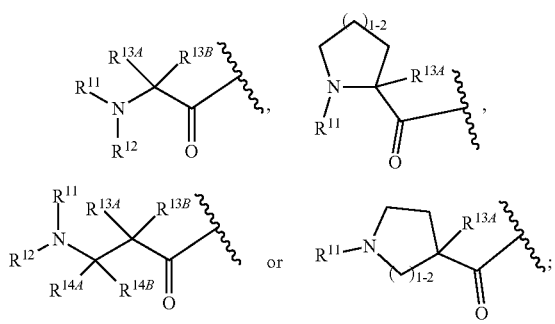

$R^{11}$ is

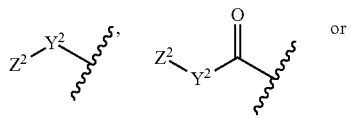

-continued

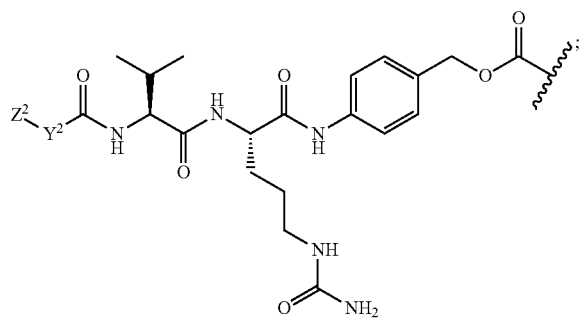

Y$^{12}$ is —C$_2$-C$_{20}$ alkylene-, —C$_2$-C$_{20}$ heteroalkylene-; —C$_3$-C$_8$ carbocyclo-, -arylene-, —C$_3$-C$_8$heterocyclo-, —C$_1$-C10 alkylene-arylene-, -arylene-C$_1$-C$_{10}$alkylene-, —C$_1$-C$_{10}$alkylene-(C$_3$-C$_8$carbocyclo)-, —(C$_3$-C$_8$carbocyclo)-C$_1$-C$_{10}$alkylene-, —C$_1$-C$_{10}$alkylene-(C$_3$-C$_8$heterocyclo)- or —(C$_3$-C$_8$ heterocyclo)-C$_1$-C$_{10}$alkylene-;

Z$^2$ is

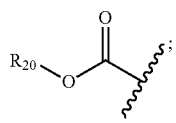

R$^{12}$ is hydrogen, C$_1$-C$_8$ alkyl or C$_1$-C$_8$ haloalkyl;

R$^{13A}$ and R$^{13B}$ are either of the following:
(i) R$^{13A}$ is hydrogen, C$_1$-C$_8$alkyl, C$_1$-C$_8$ haloalkyl, C$_3$-C$_8$ carbocyclyl, C$_1$-C$_{10}$ heterocyclyl, aryl, heteroaralkyl, aralkyl or halogen; and
R$^{13B}$ is C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl or aralkyl or halogen; or
(ii) R$^{13A}$ and R$^{13B}$ taken together are C$_2$-C$_8$ alkylene or C$_1$-C$_8$ heteroalkylene;

R$^{14A}$ and R$^{14B}$ are either of the following:
(i) R$^{14A}$ is hydrogen, C$_1$-C8alkyl, C$_1$-C$_8$ haloalkyl, C$_3$-C$_8$ carbocyclyl, C$_1$-C$_{10}$ heterocyclyl, aryl, heteroaralkyl or aralkyl; and
R$^{14B}$ is hydrogen, C$_1$-C$_8$ alkyl, C$_1$-C$_8$ haloalkyl, C$_3$-C$_8$ carbocyclyl, heterocyclyl, aryl, heteroaralkyl or aralkyl; or
(ii) R$^{14A}$ and R$^{14B}$ taken together are C$_2$-C$_8$ alkylene or C$_1$-C$_8$ heteroalkylene;

R$^{15}$ is

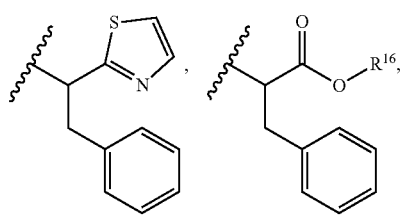

-continued

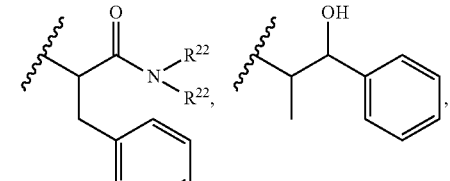

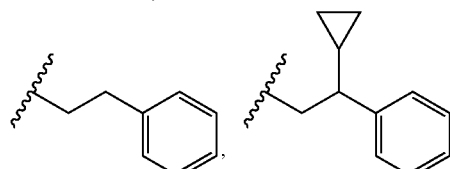

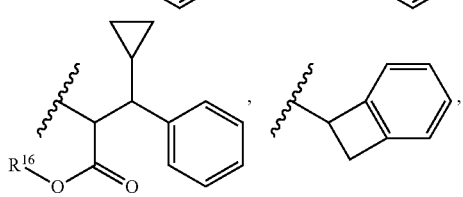

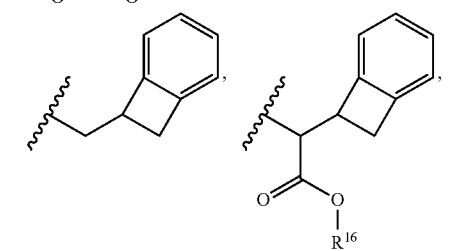

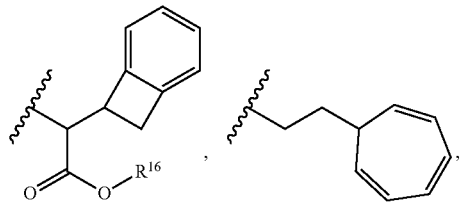

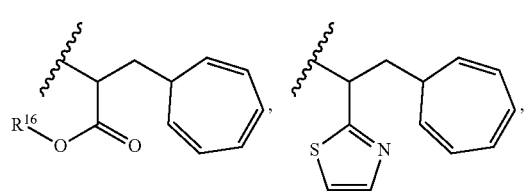

C$_1$-C$_{10}$ heterocyclyl, C3-C8 carbocycly and C$_6$-C$_{14}$ aryl optionally substituted with 1, 2, 3, 4 or 5 groups independently selected from the group consisting of —C$_1$-C$_8$ alkyl, —C$_1$-C$_8$ alkyl-N(R')$_2$, —C$_1$-C$_8$ alkyl-C(O)R', —C$_1$-C$_8$ alkyl-C(O)OR'—O—(C$_1$-C$_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, C$_1$-C$_8$ alkyl and unsubstituted aryl, or two R' can, together with the nitrogen to which they are attached, form a C$_1$-C$_{10}$ heterocyclyl;

or R[15] is

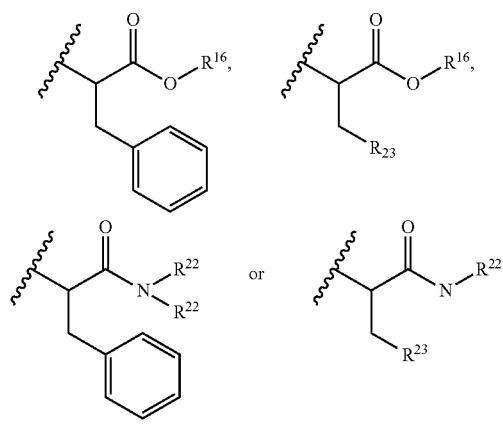

optionally substituted with 1, 2, 3, 4 or 5 groups independently selected from the group consisting of C$_1$-C$_8$ alkyl, —C$_1$-C$_8$ alkyl-N(R')$_2$, —C$_1$-C$_8$ alkyl-C(O)R', —C$_1$-C$_8$ alkyl-C(O)OR', —O—(C$_1$-C$_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR' and arylene-R', wherein each R' is independently selected from the group consisting of hydrogen, C$_1$-C$_8$ alkyl, C$_1$-C$_8$heterocyclyl, C$_1$-C$_{10}$alkylene-C$_3$-C$_8$heterocyclyl and aryl, or two R' can, together with the nitrogen to which they are attached, form a C$_1$-C$_{10}$ heterocyclyl;

R$^{16}$ is hydrogen, —C$_1$-C$_8$ alkyl, —C$_2$-C$_8$ alkenyl, —C$_2$-C$_8$ alkynyl or —C$_1$-C$_8$ haloalkyl;

R$^{22}$ is hydrogen, C$_1$-C$_4$ alkyl, C$_1$-C$_{10}$ heterocyclyl or C$_6$-C$_{14}$ aryl;

R$^{23}$ is C$_1$-C$_{10}$ heterocyclyl; and

R$^{17}$ is independently selected for each occurrence from the group consisting of F, Cl, I and Br;

R$^{20}$ is -aryl, —C$_1$-C$_{10}$alkylene-aryl, where aryl on R$^{10}$ comprising aryl is substituted with [R$^{17}$]$_h$;

h is 5; and

X is O or S;

provided that when R$^{13A}$ is hydrogen X is S.

In some aspects, the effector moieties may be selected from Table 73. In some aspects, the effector moiety is Toxin #54. In some aspects, the effector moiety is Toxin #115. In some aspects, the effector moiety is Toxin #69.

In some aspects, the Effector Moiety when conjugated to a linker of the invention comprises a formula selected from the group consisting of

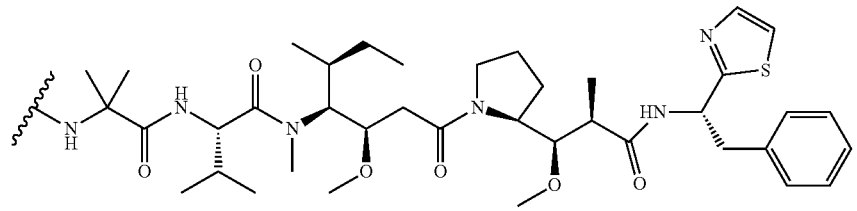

,

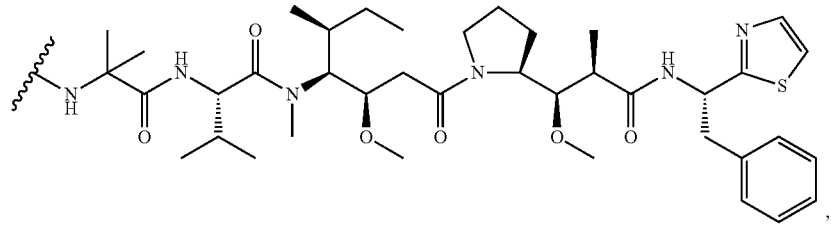

,

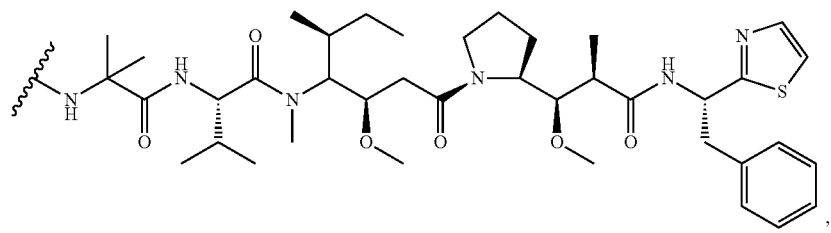

,

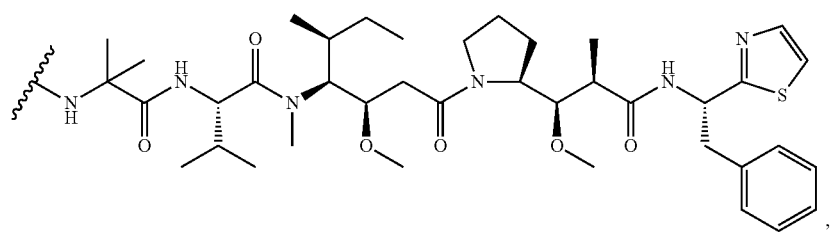

,

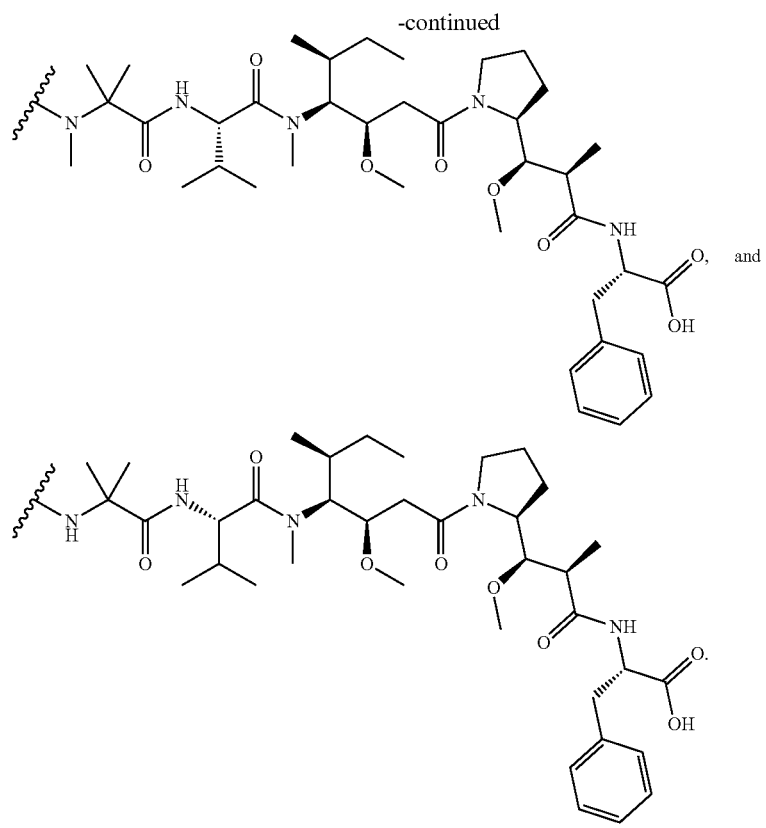
Effector Moieties conjugated to linkers useful in connection with the present invention include auristatin-based toxin-linkers such as those disclosed in PCT/162012/056224. In some aspects, the toxin-linkers of the invention may be selected from the group consisting of
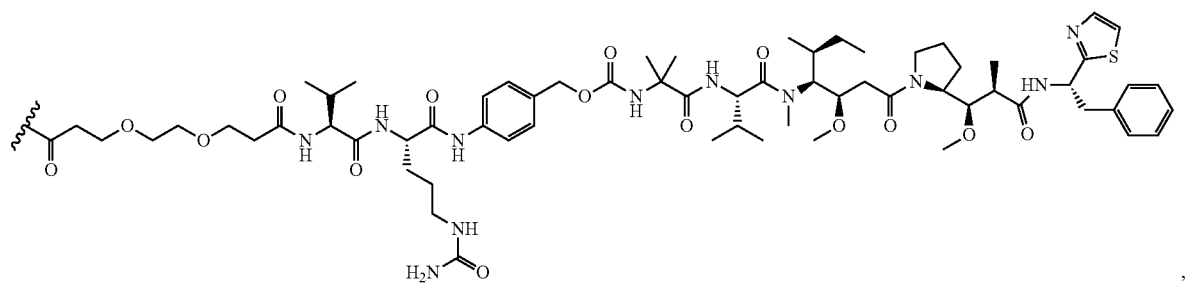
,
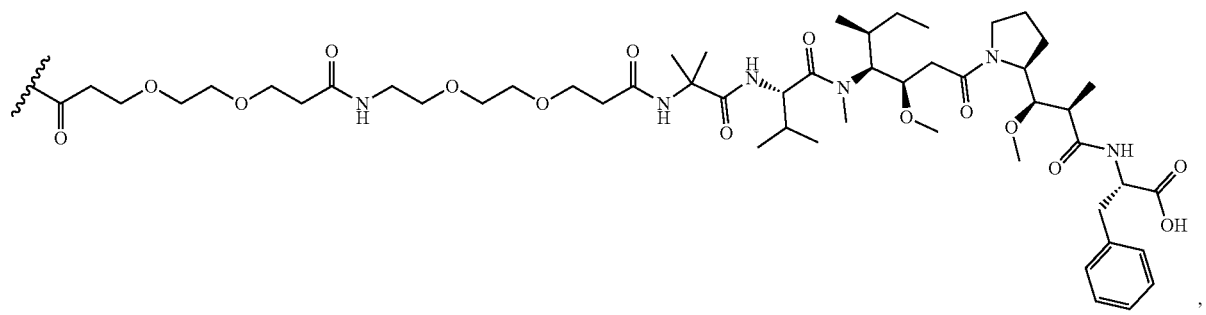
, -continued

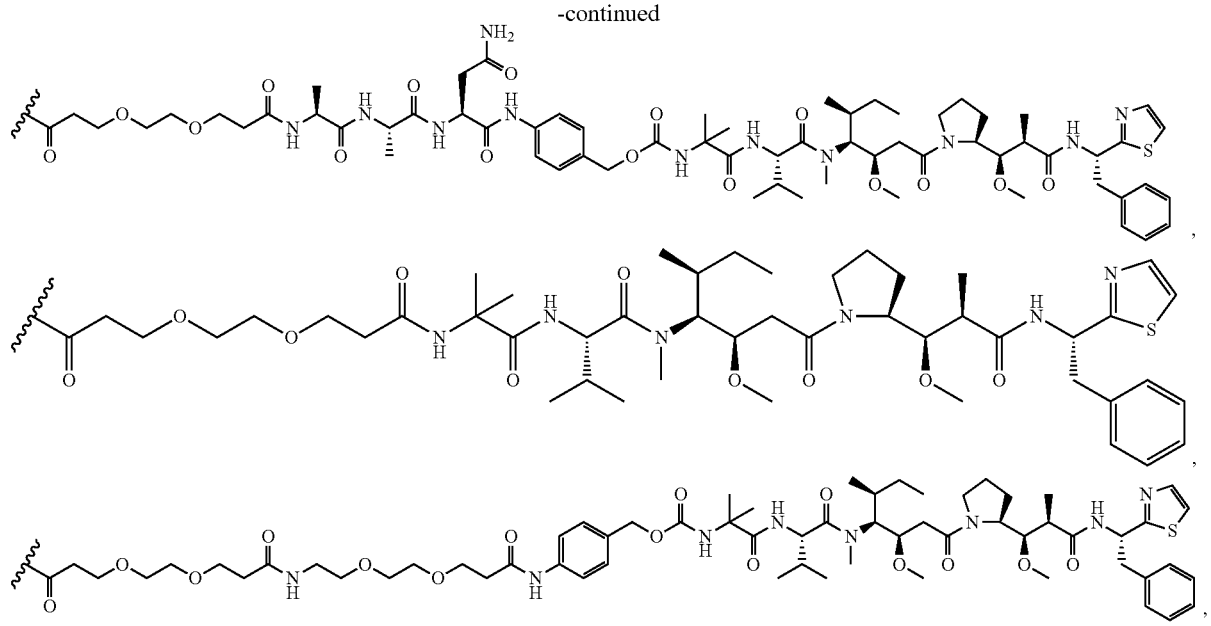

and

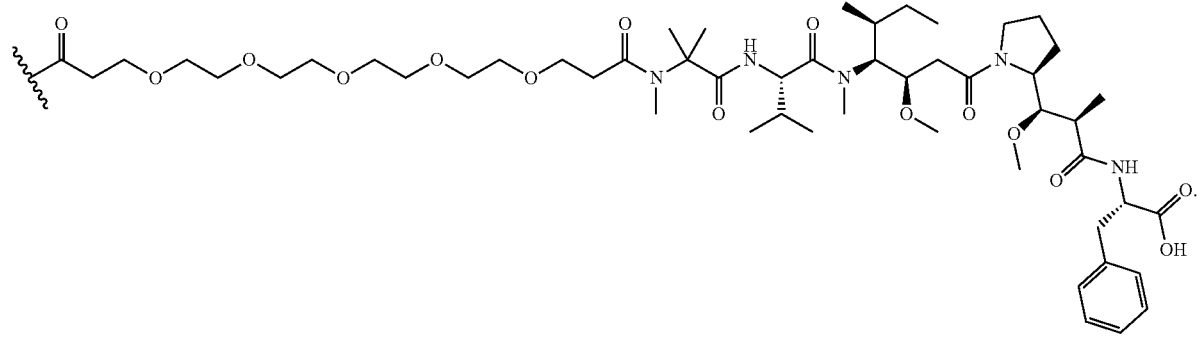

Methods of Conjugation

In some aspects, the invention provides for a method of preparing a multifunctional antibody conjugate (MAC) comprising an antibody or antigen binding portion, the antibody being covalently conjugated to at least one Effector Moiety through a linker attached to a side chain of $K^5$ of SEQ ID NO:98 (or SEQ ID herein disclosed falling within the scope of SEQ ID NO:98), or to a side chain of residue K on an antibody constant domain wherein the position of K corresponds with residue 77 of SEQ ID NO:6, or residue 185 of a constant light domain according to Kabat numbering;

said method comprising: covalently attaching the Effector Moiety to a linker terminating in a leaving group Z* of the formula:

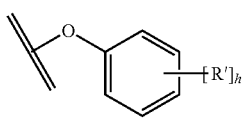

where $R^1$ is any of F, Cl, Br or I, nitro, cyano, trifluoromethyl, alone or in combination, and h=1, 2, 3, 4, or 5, and reacting the Effector Moiety-linker-leaving group complex so formed with the antibody at a molar ratio of between about 3.5:1 to about 4.5:1 of Effector Moiety:antibody. In some aspects, the molar ratio is about 3.7:1 to about 4.3:1. In some embodiments, $R^1$ may be a halogen. In some embodiments, $R^1$ is F or Cl, and h=4 or 5. In some embodiments, $R^1$ is F or Cl, and h=5. In some embodiments, $R^1$ is F, and h=2, 3, 4 or 5. In some embodiments, $R^1$ is F, and h=3, 4 or 5. In some embodiments, $R^1$ is F, and h=4 or 5. In some embodiments, $R^1$ is F, and h=5. In some aspects, Z* may be selected from the group consisting of:

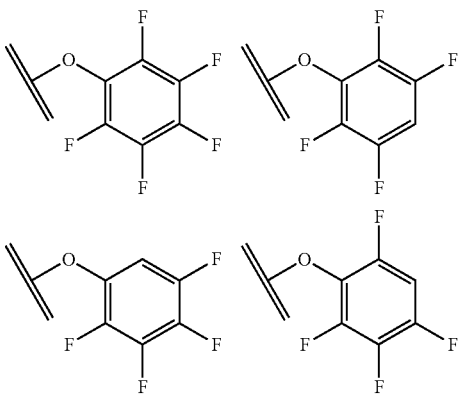

-continued

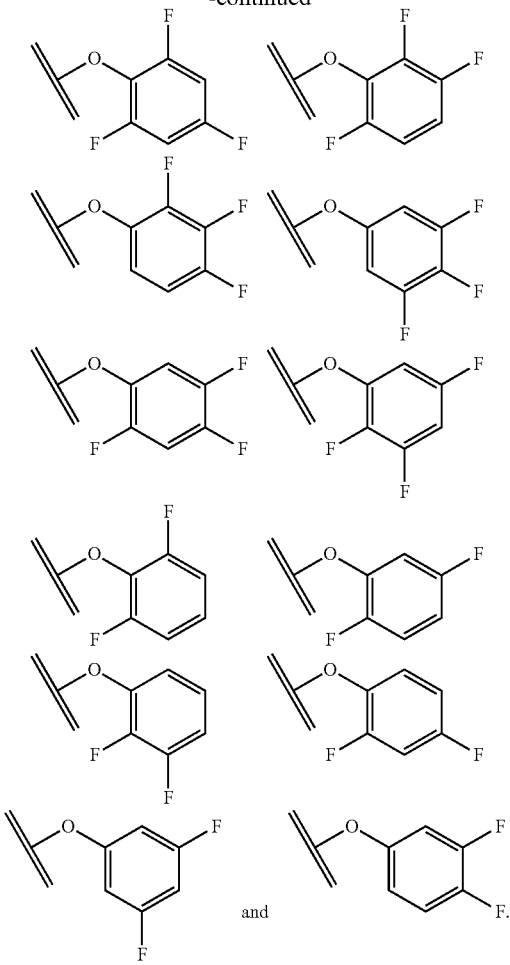

R¹ may be present in an amount of between 3 and 5. There may be 3 R¹ groups. R¹ may be present in an amount of between 4 and 5. There may be 4 R¹ groups. There may be R¹ groups. R¹ may be fluorine. R¹ may be chlorine. R¹ may be bromine. The leaving group may comprise the formula:

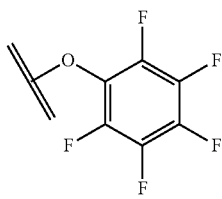

In some aspects, the invention provides for methods of producing a MAC, wherein the MAC comprises an antibody, or fragment thereof, covalently linked to at least one Effector Moiety that binds an additional target (such as peptide, small molecule, aptamer, nucleic acid molecule, or protein), characterised in that Effector Moiety comprises a linker with a PFP leaving group capable of reacting with the ε-amino of surface lysine residues of the antibody. In some aspects, the invention provides for a process for conjugating an Effector Moiety (such as a peptide) to a CL domain of the invention comprising SEQ ID NO:98, comprising conjugating the Effector Moiety with a linker comprising a leaving group of the formula:

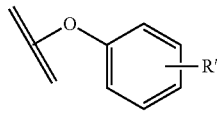

where R¹ is any of F, Cl, Br or I, nitro, cyano, trifluoromethyl, alone or in combination, and may be present in an amount of between 1 and 5 and reacting the leaving group with the side chain of $K^5$ of SEQ ID NO:98.

In some aspects, the method comprises combining an antibody or antigen binding portion thereof with an Effector Moiety, wherein the Effector Moiety is covalently attached to a linker comprising a PFP leaving group.

In some aspects, the molar ratio of Effector Moiety: antibody is between about 2.5 and about 4.6:1. In some aspects of the invention, the molar ratio is about 3.7:1, and about 4.3:1. In some aspects of the invention, the molar ratio of Effector Moiety:antibody is about 4:1. In some aspects, the molar ratio is between about 2:1 and about 7:1. In some aspects, the molar ratio is between about 3:1 and about 6:1. In some aspects, the molar ratio is between about 3:1 and about 7:1. In some aspects, the molar ratio is between about 3:1 and about 5:1.

In aspects of the invention where it is desirable to have less than 1.5 conjugations per antibody (such as where a single Effector Moiety is required) the molar ratio may be between about 1:1 and about 6:1, wherein the buffer comprises HEPES at a concentration of at least 0.02M. The concentration of HEPES may be between about 0.1M and about 1M. The concentration of HEPES may between about 0.1M and about 0.5M. In aspects of the invention where it is desirable to have less than 1.5 conjugations per antibody (such as where a single Effector Moiety is required) the molar ratio may be between about 1:1 and about 3:1.

In some aspects, the preferred molar ratio is a range with a lower limit selected from the group consisting of about 1, about 1.2, about 1.4, about 1.5, about 1.6, about 1.8, about 2, about 2.2, about 2.4, about 2.5, about 2.6, about 2.8, about 3, about 3.2, about 3.3, about 3.4, about 3.5, about 3.6, about 3.7, about 3.8, about 3.9, about 4.0, about 4.1, about 4.2, about 4.3, about 4.4. about 4.5, about 4.6, about 4.7, about 4.8, about 4.9, about 5, about 5.2, about 5.4, about 5.5, about 5.6, about 5.8, about 6, about 6.2, about 6.4, about 6.5, about 6.6, about 6.8, about 7, about 7.3, about 7.5, about 7.7, about 8, about 8.5, about 9, about 9.5, and about 10 to 1, and an upper limit selected from the group consisting of about 1.5, about 1.6, about 1.8, about 2, about 2.2, about 2.4, about 2.5, about 2.6, about 2.8, about 3, about 3.2, about 3.3, about 3.4, about 3.5, about 3.6, about 3.7, about 3.8, about 3.9, about 4.0, about 4.1, about 4.2, about 4.3, about 4.4. about 4.5, about 4.6, about 4.7, about 4.8, about 4.9, about 5, about 5.2, about 5.4, about 5.5, about 5.6, about 5.8, about 6, about 6.2, about 6.4, about 6.5, about 6.6, about 6.8, about 7, about 7.3, about 7.5, about 7.7, about 8, about 8.5, about 9, about 9.5, about 10, and about 15 to 1.

In some aspects, the invention further comprises conjugating the Effector Moiety and protein together for at least about 30 mins. In some aspects, the duration is at least about 60 mins. In some aspects, the duration is at least about 2 hrs. In some aspect, the invention further comprises conjugating the Effector Moiety and antibody at between about 4° C. and about 40° C. In some aspect, the invention further comprises conjugating the Effector Moiety and antibody at between about 10° C. and about 30° C. In some aspect, the invention further comprises conjugating the Effector Moiety and antibody at between about 15° C. and about 30° C. In some aspects, the reaction is conducted at about 18° C. to about 25° C. In some aspects, the reaction is conducted at about 22° C. In some aspects, the reaction is conducted at about room temperature.

In some aspects, the conjugation reaction takes place at between about pH 6.5 and about pH 8.0. In some aspects, the conjugation reaction takes place at between about pH 6.75 and about pH 8.0. In some aspects, the conjugation reaction takes place at about pH 7.7. In some aspects, the conjugation reaction takes place at about pH 7. In some aspects, the conjugation reaction takes place at about pH 7.2. In some aspects, the conjugation reaction takes place at about pH 7.5. In some aspects, the conjugation reaction takes place at between a range of pH values, whose lower limit is selected from the group consisting of 5.5, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 and 8, and whose upper limit is selected from the group consisting of 6.5, 6.6, 6.7, 6.8, 6.9, 7.0, 7.1, 7.2, 7.3, 7.4, 7.5, 7.6, 7.7, 7.8, 7.9, 8.0, 8.5, and 9.

In some aspects, the pH may be below 6.5; this may be particularly useful in applications were less than about 1.5 conjugations per antibody are required. In some aspects, the pH is between about 5.5 and about 6.5.

In some aspects, the salt concentration may be below about 0.2M. The salt may be a halide salt (F, Cl, Br, I) and may comprise a metal such as Li, Na, K, Be, Mg, Ca. The salt may be NaCl. The salt may be KCl. Salt concentrations of above about 0.1M may be used to limit the rate and/or number of conjugations per antibody. The salt concentration may be between about 0 and about 0.1M. The salt concentration may be between about 0 and about 0.5M. The salt concentration may be between about 0 and about 0.3M.

In some aspects, the method of the invention comprises formulating the antibody or antigen binding portion thereof in a formulation buffer at about pH 5.5. The formulation buffer may be sodium acetate and trehalose buffer. This buffer has the advantage of not containing any primary amines, and lends itself well to pH adjustment. The antibody may be present in an amount of about 15 to about 25 mg·ml$^{-1}$. In some aspects, the antibody may be present at an amount of 20 mg·ml$^{-1}$.

The pH of the formulation buffer may be adjusted to about pH 7.2 to about pH 8.0; in some embodiments, the formulation buffer may be adjusted to pH 7.7. The pH of the formulation buffer may be adjusted with a phosphate buffer. The phosphate buffer may be at a concentration of between about 40 mM and about 80 mM. The phosphate buffer may be at a concentration of between about 10 mM and about 200 mM.

In some aspects, the concentration of antibody during the conjugation reaction with the Effector Moiety/linker and leaving group Z* may be in a range where the lower limit of the range is selected from about 5, about 6, about 7, about 8, about 9, about 10, about 15, about 20, about 30, and about 40 mg·ml$^{-1}$, and the upper limit of the range is selected form the group consisting of about 7, about 8, about 9, about 10, about 15, about 20, about 30, about 40, about 50, about 60, about 70, about 80, about 90, about 100, about 150, about 200, about 500 mg·ml$^{-1}$.

The Effector Moiety may be reconstituted at a concentration of at least about 2 mg·ml$^{-1}$. The Effector Moiety may be reconstituted at a concentration of about 5 to about 20 mg·ml$^{-1}$ in diluted propylene glycol prior to use and, in some embodiments, may be at a concentration of 10 mg·ml$^{-1}$.

The conjugation reaction may be performed by combining the antibody or antigen binding portion thereof and the Effector Moiety at a molar ratio of 4 moles Effector Moiety to 1 mole of antibody and incubated at about 18° C. to about 25° C. for about 2 to about 24 hrs. In some embodiments, the conjugation reaction between antibody and Effector Moiety is at room temperature for 2 hrs. In some embodiments, the conjugation reaction is for at least about 2 hrs. In some embodiments, the conjugation reaction is for at least about 30 mins.

The reaction may be quenched and adjusted to about pH 5.0 to about pH 6.0. In some embodiments, the quenched reaction may be adjusted to pH 5.5. This may be accomplished using a succinate and glycine buffer at, for example, about pH 4.0. This buffer has advantages over other more common buffers such as TRIS, or other amino-acid buffers. The succinate assists in limiting aggregation and precipitation during diafiltration, which can be stressful on the conjugated molecule, and glycine contains an additional primary amine.

The reaction may be concentrated and unreacted Effector Moiety, related species (such as peptide where the linker was hydrolyzed by reaction with water solvent) and other unreacted elements of the reaction mixture (such as PFP) may be removed by diafiltration, for example, using a 50 kDa membrane or size exclusion chromatography into a succinate, glycine, sodium chloride, and trehalose buffer, pH 5.5 at 30 mg·ml$^{-1}$.

In some aspects, the method may comprise conjugating an Effector Moiety to CLκ-K$^{80}$. In some aspects, the invention comprises conjugating a Effector Moiety to an Ig domain, comprising mutating the CLλ so as to comprise a SEQ ID NO:98 on the EF connecting chain loop between β-strands E and F, attaching to the Effector Moiety a linker comprising a leaving group Z* as herein defined, and reacting said Effector Moiety-linker-leaving group complex with the side chain of K$^5$ of SEQ ID NO:98.

Pharmaceutical Compositions of the Invention

The invention provides a pharmaceutical composition comprising the MAC and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with antibodies in general. The preferred mode of administration is parenteral (e.g. intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The pharmaceutical composition may further comprise another component, such as an anti-tumour agent or an imaging reagent. Another aspect of the present invention provides kits comprising MACs of the invention and pharmaceutical compositions comprising these antibodies. A kit may include, in addition to the MAC or pharmaceutical composition, diagnostic or therapeutic agents. A kit may also include instructions for use in a diagnostic or therapeutic method. In some embodiments, the kit includes the antibody or a pharmaceutical composition thereof and a diagnostic agent. In other embodiments, the kit includes the antibody or a pharmaceutical composition thereof and one or more therapeutic agents, such as an additional antineoplastic agent, anti-tumour agent or chemotherapeutic agent.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compounds and compositions of the invention may be used in conjunction with established treatments for the relevant indication. Examples include 5-Flurouracil, irinotecan, oxilaplatin, cetuximab, sunitinib, and rituximab for the treatment of angiogenic disorders in particular, especially cancer. Other examples include ranibizumab, infliximab, adalimumab, natalizumab, omalizumab, and palivizumab.

Therapeutic Methods of the Invention

Therapeutic methods are also provided by the invention. A therapeutic method comprises administering a compound or composition of the invention to a subject in need thereof.

The invention provides for the use of compounds of the invention or pharmaceutical compositions of the invention in a method of inhibiting or reducing angiogenesis or for treating or preventing a disease or symptom associated with an angiogenic disorder. The invention provides methods of inhibiting or reducing angiogenesis or treating or preventing a disease or symptom associated with an angiogenic disorder comprising administering to a patient a therapeutically effective dose of compounds and compositions of the invention. Also provided are methods of delivering or administering compounds and compositions of the invention and methods of treatment using compounds and compositions of the invention. Also provided are methods of treating cancer comprising administering to the subject a therapeutically effective amount of a compound or pharmaceutical composition according to the invention. As used herein, an angiogenesis-mediated condition is a condition that is caused by abnormal angiogenesis activity or one in which compounds that modulate angiogenesis activity have therapeutic use. Diseases and conditions that may be treated and/or diagnosed with compounds and compositions of the invention include cancer, arthritis, hypertension, kidney disease, psoriasis, angiogenesis of the eye associated with ocular disorder, infection or surgical intervention, macular degeneration, diabetic retinopathy, and the like.

More specifically, examples of "cancer" when used herein in connection with the present invention include cancers of the lung (NSCLC and SCLC), the head or neck, the ovary, the colon, the rectum, the prostate, the anal region, the stomach, the breast, the kidney or ureter, the renal pelvis, the thyroid gland, the bladder, the brain, renal cell carcinoma, carcinoma of, neoplasms of the central nervous system (CNS), primary CNS lymphoma, non-Hodgkin's lymphoma, spinal axis tumours, carcinomas of the, oropharynx, hypopharynx, esophagus, pancreas, liver, gallbladder and bile ducts, small intestine, urinary tract; or lymphoma or a combination of one or more of the foregoing cancers. Still more specifically, examples of "cancer" when used herein in connection with the present invention include cancer selected from lung cancer (NSCLC and SCLC), breast cancer, ovarian cancer, colon cancer, rectal cancer, prostate cancer, cancer of the anal region, or a combination of one or more of the foregoing cancers.

In other embodiments, pharmaceutical compositions of the invention relate to non-cancerous hyperproliferative disorders such as, without limitation, age-related macular degeneration, restenosis after angioplasty or psoriasis. In another embodiment, the invention relates to pharmaceutical compositions for the treatment of a mammal that requires activation of IGF1R and/or Ang2, wherein the pharmaceutical composition comprises a therapeutically effective amount of an activating antibody of the invention and a pharmaceutically acceptable carrier. Pharmaceutical compositions of the invention may be used to treat osteoporosis, frailty or disorders in which the mammal secretes too little active growth hormone or is unable to respond to growth hormone.

As used herein, an "effective dosage" or "effective amount" of drug, compound, or pharmaceutical composition is an amount sufficient to affect any one or more beneficial or desired results. For prophylactic use, beneficial or desired results include eliminating or reducing the risk, lessening the severity, or delaying the outset of the disease, including biochemical, histological and/or behavioural symptoms of the disease, its complications and intermediate pathological phenotypes presenting during development of the disease. For therapeutic use, beneficial or desired results include clinical results such as reducing tumour size, spread, vasculature of tumours, or one or more symptoms of cancer or other diseases associated with increased angiogenesis, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, and horses.

Advantageously, therapeutic administration of compounds of the invention results in decrease in angiogenesis and/or in the case of cancers, stabilized or reduced tumour volume. Preferably, tumour volume is at least about 10% or about 15% lower than before administration of a MAC of the invention. More preferably, tumour volume is at least about 20% lower than before administration of the MAC. Yet more preferably, tumour volume is at least 30% lower than before administration of the MAC. Advantageously, tumour volume is at least 40% lower than before administration of the MAC. More advantageously, tumour volume is at least 50% lower than before administration of the MAC. Very preferably, tumour volume is at least 60% lower than before administration of the MAC. Most preferably, tumour volume is at least 70% lower than before administration of the MAC.

Administration of compounds of the invention in accordance with the method in the present invention can be continuous or intermittent, depending, for example, upon the recipient's physiological condition, whether the purpose of the administration is therapeutic or prophylactic, and other factors known to skilled practitioners. The administration of a compound of the invention may be essentially continuous over a preselected period of time or may be in a series of spaced doses.

Antibodies

The immunoglobulin (Ig) domain is a type of protein domain that consists of a 2-layer sandwich of between 7 and 9 antiparallel β-strands arranged in two β-sheets with a Greek key topology. A β-strand is a stretch of polypeptide chain typically 3 to 10 amino acids long with backbone in an almost fully extended conformation. B sheets consist of β-strands connected laterally by at least two or three backbone hydrogen bonds, forming a generally twisted, pleated sheet. The backbone switches repeatedly between the two β-sheets. Typically, the pattern is (N-terminal β-hairpin in sheet 1)-(β-hairpin in sheet 2)-(β-strand in sheet 1)-(C-terminal β-hairpin in sheet 2). The cross-overs between sheets form an "X", so that the N- and C-terminal hairpins are facing each other. Members of the Ig superfamily are found in hundreds of proteins of different functions. Examples include antibodies, the giant muscle kinase titin and receptor tyrosine kinases. Ig-like domains may be involved in protein-protein and protein-ligand interactions The α-helix is a right-handed coiled or spiral conformation of amino acids, in which every backbone N—H group donates a hydrogen bond to the backbone C═O group of the amino acid four residues earlier. This secondary structure is also sometimes called a classic Pauling-Corey-Branson α-helix. Among types of local structure in proteins, the α-helix is the most regular and the most predictable from sequence, as well as the most prevalent.

An immunoglobulin (Ig) is a tetrameric molecule. In a naturally occurring Ig, each tetramer is composed of 2 identical pairs of polypeptide chains, each pair having one "light" (about 25 kDa) and one "heavy" chain (about 50-70 kDa).

The amino-terminal portion of each chain includes a variable region, of about 100 to 110 or more amino acids primarily responsible for antigen recognition. The carboxy-terminal portion of each chain defines a constant region primarily responsible for effector function. Human light chains are classified as κ and λ light chains. Heavy chains are classified as α, δ, ε, γ, and μ, and define the antibody's isotype as IgA, IgD, IgE, IgG, IgM, respectively. Within light and heavy chains, the variable and constant regions are joined by a "J" region of about 12 or more amino acids, with the heavy chain also including a "D" region of about 10 more amino acids. The variable regions of each light/heavy chain pair form the antibody binding site such that an intact Ig has 2 binding sites.

Each domain in an antibody molecule has a similar structure of two β-sheets packed tightly against each other in a compressed antiparallel β-barrel. This conserved structure is termed the immunoglobulin (Ig) fold. The Ig fold of constant domains contains a 3-stranded β sheet packed against a 4-stranded β sheet, with each sheet separated by chains; these chains typically comprise α-helices, loops, turns, and short, sharp turns between two β-sheets called β-hairpins.

Ig chains exhibit the same general structure of relatively conserved framework regions (FR) joined by 3 hypervariable regions, also called complementarity determining regions or CDRs. The CDRs from the 2 chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)).

The identity of the amino acid residues in a particular antibody that make up a CDR can be determined using methods well known in the art. For example, antibody CDRs may be identified as the hypervariable regions originally defined by Kabat et al (Kabat et al., 1992, Sequences of Proteins of Immunological Interest, 5th ed., Public Health Service, NIH, Washington D.C.). The positions of the CDRs may also be identified as the structural loop structures originally described by Chothia and others (Chothia et al., 1989, Nature 342:877-883). Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding (Makabe et al., 2008, Journal of Biological Chemistry, 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, extended, AbM, contact, and/or conformational definitions.

The numbering of residues of the CLκ and CLλ domains can vary. For example, the numbering of the CLκ can begin at either LC-R$^{108}$ according to Kabat numbering (for example, R$^{108}$ of SEQ ID NO:2), or LC-T$^{109}$ according to Kabat numbering (for example, T$^{109}$ of SEQ ID NO:2). The numbering convention used herein is that provided by the Swiss-Prot group, a part of the Swiss Institute of Bioinformatics, and begins at LC-T$^{109}$. It will be appreciated that where a different numbering system is preferred, the numbering of specified residues of the invention may be adjusted accordingly. LC refers to Light Chain.

An "antibody" refers to an intact Ig or to an antigen binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), chimeric antibodies, diabodies and polypeptides that contain at least a portion of an Ig that is sufficient to confer specific antigen binding to the polypeptide. A Fab fragment is a monovalent fragment consisting of the VL, VH, CL and CH I domains; a F(ab')2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment consists of a VH domain or a VL domain (e.g. human, camelid, or shark).

In general, references to antibodies are to be construed as also referring to antigen binding portions thereof, and in particular, may include antigen binding portions thereof that comprise SEQ ID NO:98 between their E and F β-strands.

A single-chain antibody (scFv) is an antibody in which a VL and VH regions are paired to form a monovalent molecules via a synthetic linker that enables them to be made as a single protein chain. Diabodies are bivalent, bispecific antibodies in which VH and VL domains are expressed on a single polypeptide chain, but using a linker that is too short to allow for pairing between the 2 domains on the same chain, thereby forcing the domains to pair with complementary domains of another chain and creating 2 antigen binding sites. One or more CDRs may be incorporated into a molecule either covalently or noncovalently to make it an immunoadhesin. An immunoadhesin may incorporate the CDR (s) as part of a larger polypeptide chain, may covalently link the CDR (s) to another polypeptide chain, or may incorporate the CDR(s) noncovalently. The CDRs permit the immunoadhesin to specifically bind to a particular antigen of interest.

Mammalian light chains are of two types, κ and λ, and in any given antibody molecule only one type occurs. Approximately twice as many κ as λ molecules are produced in humans but in other mammals this ratio can vary. Each free light chain molecule contains approximately 220 amino acids in a single polypeptide chain that is folded to form the constant and variable region domains.

During B cell development, a recombination event at the DNA level joins a single variable (V) segment with a joining (J) segment; the constant (C) segment is later joined by splicing at the RNA level. Recombination of many different V segments with several J segments provides a wide range of antigen recognition. Additional diversity is attained by junctional diversity, resulting from the random additional of nucleotides by terminal deoxynucleotidyltransferase, and by somatic hypermutation, which occurs during B cell maturation in the spleen and lymph nodes. Constant kappa (CLκ) regions are encoded by a single gene, whereas lambda constant (CLλ) regions are encoded by multiple genes, and undergo splicing. Several markers associated with particular polymorphic species of CLλ are known: IgCLλ1 (Mcg marker); IGLC2-IgCLλ2 (Kern-Oz-marker); IgCLλ 3 (Kern-Oz+ marker), and IgCLλ7, for example. The skilled person can easily establish all of the polymorphisms so far identified in human CLλ chains. SEQ ID NO:93 incorporates many of the presently identified polymorphisms. The sequences of the present invention encompass other known polymorphisms of the CLκ and CLλ, and antibodies in general. Two polymorphic loci have been identified in the CLκ; CLκ-V/$A^{45}$ and CLκ-L/$V^{83}$. The three polymorphisms so far identified are: Km(1): CLκ-$V^{45}$/$L^{83}$; Km(1,2): CLκ-$A^{45}$/$L^{83}$; and Km(3): CLκ-$A^{45}$/$V^{83}$.

An antibody may have one or more binding sites. If there is more than one binding site, the binding sites may be identical to one another or may be different. For instance, a naturally-occurring Ig has 2 identical binding sites, a single-chain antibody or Fab fragment has one binding site, while a "bispecific" or "bifunctional" antibody has 2 different binding sites.

An "isolated antibody" is an antibody that (1) is not associated with naturally-associated components, including other naturally-associated antibodies, that accompany it in its native state, (2) is free of other proteins from the same species, (3) is expressed by a cell that does not naturally express the antibody, or is expressed by a cell from a different species, or (4) does not occur in nature.

The term "human antibody" includes all antibodies that have one or more variable and constant regions derived from human Ig sequences. In some embodiments of the present invention, all of the variable and constant domains of the anti-IGF1R antibody are derived from human Ig sequences (a fully human antibody). A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species.

The term "chimeric antibody" refers to an antibody that contains one or more regions from one antibody and one or more regions from one or more other antibodies.

The term "epitope" includes any protein determinant capable of specific binding to an Ig or T-cell receptor. Epitopic determinants usually consist of chemically active surface groupings of molecules such as amino acids or sugar side chains and usually have specific 3 dimensional structural characteristics, as well as specific charge characteristics. An antibody is said to specifically bind an antigen when the dissociation constant is <1 uM, preferably <100 nM and more preferably: <10 nM.

The term multifunctional antibody conjugate, or MAC, refers to an antibody as defined herein, or antigen binding portion thereof, covalently conjugated to at least one Effector Moiety that binds to a target. The Effector Moiety may be a peptide, small molecule, protein, nucleic acid molecule, toxin, aptamer, or antigen binding antibody or fragment thereof. References to conjugation of peptides and the like referred to throughout the specification generally applies to conjugation to proteins and (antigen binding) antibodies or fragments thereof.

Fully human antibodies are expected to minimize the immunogenic and allergic responses intrinsic to mouse or mouse-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations. In another embodiment, the invention provides a MAC comprising an antibody that does not bind complement.

In addition, fusion antibodies can be created in which 2 (or more) single-chain antibodies are linked to one another. This is useful if one wants to create a divalent or polyvalent antibody on a single polypeptide chain, or if one wants to create a bispecific antibody.

One type of derivatized antibody is produced by cross-linking 2 or more antibodies (of the same type or of different types; e. g. to create bispecific antibodies). Suitable cross-linkers include those that are heterobifunctional, having 2 distinctly reactive groups separated by an appropriate spacer (e. g., m-maleimidobenzoyl-N-hydroxysuccinimide ester) or homobifunctional (e. g. disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalene-sulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. When an antibody is labelled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labelled with biotin, and detected through indirect measurement of avidin or streptavidin binding. An antibody may be labelled with a magnetic agent, such as gadolinium. An antibody may also be labelled with a predetermined polypeptide epitope recognized by a secondary reporter (e. g. leucine zipper pair sequences, binding sites for secondary antibodies, metal binding domains, epitope tags). In some embodiments, labels are attached by spacer arms of various lengths to reduce potential steric hindrance.

The antibody may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

Antibody Specificity

In some embodiments comprising antigen binding domains, the antigen binding domain (for example, but not limited to, an antibody variable region having all 6 CDRs, or an equivalent region that is at least 90 percent identical to an antibody variable region) is chosen from: abagovomab, abatacept (ORENCIA®), abciximab (REOPRO®, c7E3

Fab), adalimumab (HUMIRA®), adecatumumab, alemtuzumab (CAMPATH®, MabCampath or Campath-1H), altumomab, afelimomab, anatumomab mafenatox, anetumumab, anrukizumab, apolizumab, arcitumomab, aselizumab, atlizumab, atorolimumab, bapineuzumab, basiliximab (SIMULECT®), bavituximab, bectumomab (LYMPHOSCAN®), belimumab (LYMPHO-STAT-B®), bertilimumab, besilesomab, βcept (ENBREL®), bevacizumab (AVASTIN®), biciromab brallobarbital, bivatuzumab mertansine, brentuximab vedotin (ADCETRIS®), canakinumab (ACZ885), cantuzumab mertansine, capromab (PROSTASCINT®), catumaxomab (REMOV ABC)), cedelizumab (CIMZIA®), certolizumab pegol, cetuximab (ERBITUX®), clenoliximab, dacetuzumab, dacliximab, daclizumab (ZENAPAX(®), denosumab (AMG 162), detumomab, dorlimomab aritox, dorlixizumab, duntumumab, durimulumab, durmulumab, ecromeximab, eculizumab (SOLIRIS®), edobacomab, edrecolomab (Mab17-1A, PANOREX®), efalizumab (RAPTIVA®), efungumab (MYCOGRAB®), elsilimomab, enlimomab pegol, epitumomab cituxetan, efalizumab, epitumomab, epratuzumab, erlizumab, ertumaxomab (REXOMUN®), etaracizumab (etaratuzumab, VITAXIN®, ABEGRIN™), exbivirumab, fanolesomab (NEUTROSPEC®), faralimomab, felvizumab, fontolizumab (HUZAF®), galiximab, gantenerumab, gavilimomab (ABX-CBL®), gemtuzumab ozogamicin (MYLOTARG®), golimumab (CNTO 148), gomiliximab, ibalizumab (TNX-355), ibritumomab tiuxetan (ZEVALIN®), igovomab, imciromab, infliximab (REMICAD E®), inolimomab, inotuzumab ozogamicin, ipilimumab (YERVOY®, MDX-010), iratumumab, keliximab, labetuzumab, lemalesomab, lebrilizumab, lerdelimumab, lexatumumab (HGS-ETR2, ETR2-ST01), lexitumumab, libivirumab, lintuzumab, lucatumumab, lumiliximab, mapatumumab (HGS-ETRI, TRM-I), maslimomab, matuzumab (EMD72000), mepolizumab (BOSATRIA®), metelimumab, milatuzumab, minretumomab, mitumomab, morolimumab, motavizumab (NUMAX™), muromonab (OKT3), nacolomab tafenatox, naptumomab estafenatox, natalizumab (TYSABRI®, ANTEGREN®), nebacumab, nerelimomab, nimotuzumab (THERACIM hR3®, THERA-CIM-hR3®, THERALOC®), nofetumomab merpentan (VERLUMA®), ocrelizumab, odulimomab, ofatumumab, omalizumab (XOLAIR®), oregovomab (OVAREX®), otelixizumab, pagibaximab, palivizumab (SYNAGIS®), panitumumab (ABX-EGF, VECTIBIX®), pascolizumab, pemtumomab (THERAGYN®), pertuzumab (2C4, OMNITARG®), pexelizumab, pintumomab, ponezumab, priliximab, pritumumab, ranibizumab (LUCENTIS®), raxibacumab, regavirumab, reslizumab, rituximab (RITUXAN®, MabTHERA®), rovelizumab, ruplizumab, satumomab, sevirumab, sibrotuzumab, siplizumab (MEDI-507), sontuzumab, stamulumab (Myo-029), sulesomab (LEUKOSCAN®), tacatuzumab tetraxetan, tadocizumab, talizumab, taplitumomab paptox, tefibazumab (AUREXIS®), telimomab aritox, teneliximab, teplizumab, ticilimumab, tocilizumab (ACTEMRA®), toralizumab, tositumomab, trastuzumab (HERCEPTIN®), tremelimumab (CP-675, 206), tucotuzumab celmoleukin, tuvirumab, urtoxazumab, ustekinumab (CNTO 1275), vapaliximab, veltuzumab, vepalimomab, visilizumab (NUVION®), volociximab (M200), votumumab (HUMASPECT®), zalutumumab, zanolimumab (HuMAX-CD4), ziralimumab, or zolimomab aritox.

In some embodiments comprising antigen binding domains, the antigen binding domain comprise a heavy and light chain variable domain having six CDRs, and/or compete for binding with an antibody selected from the preceding list. In some embodiments comprising antigen binding domains, the antigen binding domain binds the same epitope as the antibodies in the preceding list. In some embodiments comprising antigen binding domains, the antigen binding domain comprises a heavy and light chain variable domain having six total CDRs, and binds to the same antigen as the antibodies in the preceding list.

In some embodiments comprising antigen binding domains, the antigen binding domain comprises a heavy and light chain variable domain having six (6) total CDRs, and specifically binds to an antigen selected from: PDGFRα, PDGFRβ, PDGF, VEGF, VEGF-A, VEGF-B, VEGF-C, VEGF-D, VEGF-E, VEGF-F, VEGFR1, VEGFR2, VEGFR3, FGF, FGF2, HGF, KDR, flt-1, FLK-1, Ang-2, Ang-1, PLGF, CEA, CXCL13, Baff, IL-21, CCL21, TNF-α, CXCL12, SDF-I, bFGF, MAC-I, IL23p19, FPR, IGFBP4, CXCR3, TLR4, CXCR2, EphA2, EphA4, EphrinB2, EGFR (ErbBl), HER2(ErbB2 or pI85neu), HER3(ErbB3), HER4 ErbB4 or tyro2), SCI, LRP5, LRP6, RAGE, s100A8, s100A9, Nav1.7, GLPI, RSV, RSV F protein, Influenza HA protein, Influenza NA protein, HMGBI, CD16, CD19, CD20, CD21, CD28, CD32, CD32b, CD64, CD79, CD22, ICAM-I, FGFRI, FGFR2, HDGF, EphB4, GITR, β-amyloid, hMPV, PIV-I, PIV-2, OX40L, IGFBP3, cMet, PD-I, PLGF, Neprolysin, CTD, IL-18, IL-6, CXCL-13, IL-IRI, IL-15, IL-4R, IgE, PAI-I, NGF, EphA2, uPARt, DLL-4, αvβ5, αvβ6, α5β1, α3β1, interferon receptor type I and type II, CD 19, ICOS, IL-17, Factor II, Hsp90, IGF, IGF-I, IGF-II, CD 19, GM-CSF, PIV-3, CMV, IL-13, IL-9, and EBV.

In some embodiments comprising antigen binding domains, the antigen binding domain specifically binds to a member (receptor or ligand) of the TNF superfamily. Various molecules include, but are not limited to Tumor Necrosis Factor-α ("TNF-α"), Tumor Necrosis Factor-β ("TNF-β"), Lymphotoxin-α ("LT-α"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-I (also referred to as BlyS, BAFF or THANK), DR4, DR5 (also known as Apo-2, TRAIL-R2, TR6, Tango-63, hAPO8, TRICK2, or KILLER), DR6, DcRI, DcR2, DcR3 (also known as TR6 or M68), CART, HVEM (also known as ATAR or TR2), GITR, ZTNFR-5, NTR-I, TNFLI, CD30, LTBr, 4-1BB receptor and TR9.

In some embodiments comprising antigen binding domains, the antigen binding domain is capable of binding one or more targets chosen from 5T4, ABL, ABCB5, ABCFI, ACVRI, ACVRIB, ACVR2, ACVR2B, ACVRLI, ADORA2A, Aggrecan, AGR2, AICDA, AIFI, AIGI, AKAPI, AKAP2, AMH, AMHR2, angiogenin (ANG), ANGPTI, ANGPT2, ANGPTL3, ANGPTL4, Annexin A2, ANPEP, APC, APOCI, AR, aromatase, ATX, AXI, AZGPI (zinc-a-glycoprotein), B7.1, B7.2, B7-H1, BAD, BAFF, BAGI, BAII, BCR, BCL2, BCL6, BDNF, BLNK, BLRI (MDR15), BlyS, BMP1, BMP2, BMP3B (GDFIO), BMP4, BMP6, BMP7, BMP8, BMP9, BMP11, BMP12, BMPR1A, BMPR1B, BMPR2, BPAGI (plectin), BRCAI, C19orf10 (IL27w), C3, C4A, C5, C5R1, CANTI, CASPI, CASP4, CAVI, CCBP2 (D6/JAB61), CCLI (1-309), CCLI 1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22(MDC/STC-I), CCL23 (MPIF-I), CCL24 (MPIF-2/eotaxin-2), CCL25 (TECK), CCL26(eotaxin-3), CCL27 (CTACK/ILC), CCL28, CCL3 (MIP-la), CCL4 (MIP-Ib), CCL5(RANTES), CCL7 (MCP-3), CCL8 (mcp-2), CCNAI, CCNA2, CCNDI, CCNEI, CCNE2, CCRI (CKRI/HM145), CCR2 (mcp-IRB/RA), CCR3 (CKR3/CMKBR3), CCR4, CCR5(CMKBR5/ChemR13), CCR6 (CMKBR6/CKR-L3/STRL22/DRY6), CCR7 (CKR7/EBI1), CCR8 (CMKBR8/TERI/CKR-LI), CCR9 (GPR-9-6), CCRLI (VSHKI), CCRL2 (L-CCR), CD164, CD19, CDIC, CD20, CD200, CD-22, CD24, CD28, CD3, CD33, CD35, CD37, CD38, CD3E, CD3G, CD3Z, CD4, CD40, CD40L, CD44, CD45RB, CD46, CD52, CD69, CD72, CD74, CD79A, CD79B, CD8, CD80, CD81, CD83, CD86, CD105, CD137, CDHI (E-cadherin), CDCP1CDH10, CDH12, CDH13, CDH18, CDH19, CDH20, CDH5, CDH7, CDH8, CDH9, CDK2, CDK3, CDK4, CDK5, CDK6, CDK7, CDK9, CDKNIA (p21Wapl/Cipl), CDKNIB (p27Kipl), CDKNIC, CDKN2A (p16INK4a), CDKN2B, CDKN2C, CDKN3, CEBPB, CERI, CHGA, CHGB, Chitinase, CHSTIO, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLRI, CMKORI (RDCI), CNRI, COLI 8A1, COL1A1.COL4A3, COL6A1, CR2, Cripto, CRP, CSFI (M-CSF), CSF2 (GM-CSF), CSF3 (GCSF), CTLA4, CTL8, CTNNBI (b-catenin), CTSB (cathepsin B), CX3CL1 (SCYDI), CX3CR1 (V28), CXCLI(GROI), CXCLIO (IP-IO), CXCLII (I-TAC/IP-9), CXCL12 (SDFI), CXCL13, CXCL 14, CXCL 16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, Cyr61, CYSLTRI, c-Met, DAB2IP, DES, DKFZp451J0118, DNCLI, DPP4, E2F1, ECGFI5EDGI, EFNAI, EFNA3, EFNB2, EGF, ELAC2, ENG, endoglin, ENOI, EN02, EN03, EPHAI, EPHA2, EPHA3, EPHA4, EPHA5, EPHA6, EPHA7, EPHA8, EPHA9, EPHAIO, EPHBI, EPHB2, EPHB3, EPHB4, EPHB5, EPHB6, EPHRIN-AI, EPHRIN-A2, EPHRIN-A3, EPHRIN-A4, EPHRIN-A5, EPHRIN-A6, EPHRIN-BI, EPHRIN-B2, EPHRTN-B3, EPHB4, EPG, ERBB2 (Her-2), EREG, ERK8, Estrogen receptor, ESRI, ESR2, F3 (TF), FADD, farnesyltransferase, FasL, FASNf, FCER1A, FCER2, FCGR3A, FGF, FGFI (aFGF), FGFIO, FGFI 1, FGF12, FGF12B, FGF13, FGF14, FGF16, FGF17, FGF18, FGF19, FGF2 (bFGF), FGF20, FGF21 (such as mimAb1), FGF22, FGF23, FGF3 (int-2), FGF4 (HST), FGF5, FGF6 (HST-2), FGF7 (KGF), FGF8, FGF9, FGFR3, FIGF (VEGFD), FILI (EPSILON), FBLI (ZETA), FLJ12584, FLJ25530, FLRTI (fibronectin), FLTI, FLT-3, FOS, FOSLI(FRA-I), FY (DARC), GABRP (GABAa), GAGEBI, GAGECI, GALNAC4S-65T, GATA3, GD2, GD3, GDF5, GDF8, GFII, GGTI, GM-CSF, GNASI, GNRHI, GPR2 (CCRIO), GPR31, GPR44, GPR81 (FKSG80), GRCCIO (CIO), gremlin, GRP, GSN (Gelsolin), GSTPI, HAVCR2, HDAC, HDAC4, HDAC5, HDAC7A, HDAC9, Hedgehog, HGF, HIFIA, HIPI, histamine and histamine receptors, HLA-A, HLA-DRA, HM74, HMOXI, HSP90, HUMCYT2A, ICE-BERG, ICOSL, ID2, IFN-α, IFNAI, IFNA2, IFNA4, IFNA5, EFNA6, BFNA7, IFNBI, IFNgamma, IFNWI, IGBPI, IGFI, IGFIR, IGF2, IGFBP2, IGFBP3, IGFBP6, DL-I, ILIO, ILIORA, ILIORB, IL-1, ILIRI (CD121a), ILIR2(CD121b), IL-IRA, IL-2, IL2RA (CD25), IL2RB (CD122), IL2RG(CD132), IL-4, IL-4R(CD123), IL-5, IL5RA(CD125), IL3RB(CD131), IL-6, IL6RA (CD126), IR6RB(CD130), IL-7, IL7RA(CD127), IL-8, CXCRI (IL8RA), CXCR2 (IL8RB/CD128), IL-9, IL9R (CD129), IL-10, IL10RA(CD210), IL10RB(CDW210B), IL-11, ILI IRA, IL-12, IL-12A, IL-12B, IL-12RB1, IL-12RB2, IL-13, IL13RA1, IL13RA2, IL14, IL15, IL15RA, 1L16, IL17, IL17A, IL17B, IL17C, IL17R, IL18, IL18BP, IL18R1, IL18RAP, IL19, ILIA, ILIB, ILIFIO, IL1F5, IL1F6, IL1F7, IL1F8, DL1F9, ILIHYI, ILIRI, IL1R2, ILIRAP, ILIRAPLI, IL1RAPL2, ILIRLI, IL1RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, IL4R, IL6ST (glycoprotein 130), ILK, INHA, INHBA, INSL3, INSL4, IRAKI, IRAK2, ITGA1, ITGA2, ITGA3, ITGA6 (α 6 integrin), ITGAV, ITGB3, ITGB4 (β 4 integrin), JAKI, JAK3, JTB, JUN, K6HF, KAII, KDR, KIM-1, KITLG, KLF5 (GC Box BP), KLF6, KLKIO, KLK12, KLK13, KLK14, KLK15, KLK3, KLK4, KLK5, KLK6, KLK9, KRTI, KRT19 (Keratin 19), KRT2A, KRTHB6 (hair-specific type II keratin), LAMAS, LEP (leptin), Lingo-p75, Lingo-Troy, LPS, LRP5, LRP6, LTA (TNF-b), LTB, LTB4R (GPR16), LTB4R2, LTBR, MAC-MARCKS, MAG or Omgp, MAP2K7 (c-Jun), MCP-I, MDK, MIBI, midkine, MIF, MISRII, MJP-2, MK, MKI67 (Ki-67), MMP2, MMP9, MS4A1, MSMB, MT3 (metallothionectin-Ui), mTOR, MTSSI, MUCI (mucin), MYC, MYD88, NCK2, neurocan, neuregulin-1, neuropilin-1, NFKBI, NFKB2, NGFB (NGF), NGFR, NgR-Lingo, NgR-Nogo66 (Nogo), NgR-p75, NgR-Troy, NMEI (NM23A), NOTCH, NOTCHI, NOX5, NPPB, NROBI, NROB2, NRIDI, NR1D2, NR1H2, NR1H3, NR1H4, NR1I2, NR1I3, NR2C$_1$, NR2C$_2$, NR2E1, NR2E3, NR2F1, NR2F2, NR2F6, NR3C$_1$, NR3C$_2$, NR4A1, NR4A2, NR4A3, NR5A1, NR5A2, NR6A1, NRPI, NRP2, NT5E, NTN4, OCT-1, ODZ1, OPN1, OPN2, OPRDI, P2RX7, PAP, PARTI, PATE, PAWR, PCA3, PCDGF, PCNA, PDGFA, PDGFB, PDGFRA, PDGFRB, PECAMI, peg-asparaginase, PF4 (CXCL4), Plexin B2 (PLXNB2), PGF, PGR, phosphacan, PIAS2, PI3 Kinase, PIK3CG, PLAU (uPA), PLG5PLXDCI, PKC, PKC-β, PPBP (CXCL7), PPID, PRI, PRKCQ, PRKDI, PRL, PROC, PROK2, pro-NGF, prosaposin, PSAP, PSCA, PTAFR, PTEN, PTGS2 (COX-2), PTN, RAC2 (P21Rac2), RANK, RANK ligand, RARB, RGSI, RGS13, RGS3, RNFI10 (ZNF144), Ron, R0B02, RXR, selectin, S100A2, S100A8, S100A9, SCGB 1D2 (lipophilin B), SCGB2A1 (mammaglobin 2), SCGB2A2 (mammaglobin 1), SCYEI (endothelial Monocyte-activating cytokine), SDF2, SERPENA1, SERPINA3, SERPINBS (maspin), SERPINEI (PAI-I), SERPINFI, SHIP-I, SHIP-2, SHBI, SHB2, SHBG, SfcAZ, SLC2A2, SLC33A1, SLC43A1, SLIT2, SPPI, SPRRIB (SprI), ST6GAL1, STABI, STATE, STEAP, STEAP2, SULF-1, Sulf-2, TB4R2, TBX21, TCPIO, TDGFI, TEK, TGFA, TGFBI, TGFBIII, TGFB2, TGFB3, TGFBI, TGFBRI, TGFBR2, TGFBR3, THIL, THBSI (thrombospondin-1), THBS2/THBS4, THPO, TIE (Tie-1), TIMP3, tissue factor, TIKI2, TLR10, TLR2, TLR3, TLR4, TLR5, TLR6JLR7, TLR8, TLR9, TM4SF1, TNF, TNF-a, TNFAIP2 (B94), TNFAIP3, TNFRSFIIA, TNFRS-FIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (APO3L), TNFSF13 (April), TNFSF13B, TNFSF14 (HVEM-L), TNFSF15 (VEGI), TNFSF 18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TLR2, TLR4, TLR9, T0P2A (topoisomerase Iia), TP53, TPMI, TPM2, TRADD, TRAFI, TRAF2, TRAF3, TRAF4, TRAF5, TRAF6, TRKA, TREMI, TREM2, TRPC6, TROY, TSLP, TWEAK, Tyrosinase, uPAR, VEGF, VEGFB, VEGFC, versican, VHL C5, VLA-4, Wnt-1, XCLI (lymphotactin), XCL2 (SCM-Ib), XCRI (GPR5/CCXCRI), YYI, and ZFPM2.

Catalytic Antibodies

In some aspects of the invention, the MAC comprises a catalytic antibody, or antigen binding portion thereof. In some aspects, the antibody may be an aldolase antibody.

The contents of US2006205670 are incorporated herein by reference—in particular paragraphs [0153]-[0233], describing antibodies, useful fragments and variants and modifications thereof, combining sites and CDRs, antibody preparation, expression, humanization, amino acid modification, glycosylation, ADCC, CDC, increasing serum half life of antibodies, expression vectors, mammalian host systems, and folding, amongst other elements of antibody technology.

"Combining site", as used herein, (also known as the antibody binding site) refers to the region of the Ig or Ig domains that combine (or can combine) with the determinant of an appropriate antigen (or a structurally similar protein). The term generally includes the CDRs and the adjacent framework residues that are involved in antigen binding.

"Aldolase antibodies" as used herein, refers to antibodies containing combining site portions that, when unencumbered (for example by conjugation), catalyze an aldol addition reaction between an aliphatic ketone donor and an aldehyde acceptor. Aldolase antibodies are capable of being generated by immunization of an immune-responsive animal with an immunogen that includes a 1,3 diketone hapten of the formula:

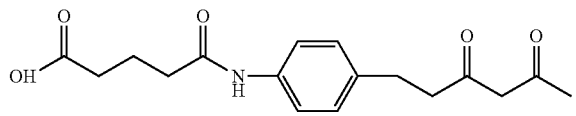 [SMILES: CC(=O)CC(=O)CCc1ccc(NC(=O)CCCC(=O)O)cc1]

coupled to a carrier protein, and further characterized by having a lysine with a reactive ε-amino group in the combining site of the antibody. Aldolase antibodies are further characterized by their catalytic activity being subject to inhibition with the 1,3-diketone hapten by formation of a complex between the 1,3-diketone hapten and the ε-amino group of the lysine of the catalytic antibody.

As discussed, in certain embodiments, certain antibodies that can be used to make MACs, compositions and samples of the invention may comprise a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue. The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site. In some embodiments, the amino acid is cysteine, and the reactive group of the side chain is a sulfhydryl group. In other embodiments, the amino acid residue is lysine, and the reactive group of the side chain is the ε-amino group. In some embodiments, the amino acid is $K^{93}$ on the heavy chain according to Kabat numbering. In some embodiments, the amino acid is on HC-$K^{99}$ of h38C2 according to the numbering of SEQ ID NOs: 65 and 66.

Catalytic antibodies are one source of antibodies with suitable combining sites that comprise one or more reactive amino acid side chains. Such antibodies include aldolase antibodies, β lactamase antibodies, esterase antibodies, and amidase antibodies.

One embodiment comprises an aldolase antibody such as the mouse monoclonal antibodies mAb 33F12 and mAb 38C2 (whose VL and VH comprise SEQ ID NO:68 and 69), as well as suitably chimeric and humanized versions of such antibodies (e.g. h38C2IgG1: SEQ ID NOs:64 and 65 and h38C2-IgG2: SEQ ID NOs:64 and 66). In favourable aspects, a heavy chain such as SEQ ID NO:65 or SEQ ID NO:66 is used in conjunction with the h38C2 VL (SEQ ID NO:67) fused to one of the CL domains of the invention comprising SEQ ID NO:98.

Mouse mAb 38C2 (and h38C2) has a reactive lysine near to but outside HCDR3, and is the prototype of a new class of catalytic antibodies that were generated by reactive immunization and mechanistically mimic natural aldolase enzymes. Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases.

Compounds of the invention may also be formed by linking a targeting agent to a reactive cysteine, such as those found in the combining sites of thioesterase and esterase catalytic antibodies. Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

The antibody may be a humanized antibody. Where compounds of the invention are covalently linked to the combining site of an antibody, and such antibodies are humanized, it is important that such antibodies be humanized with retention of high linking affinity for the W group. Various forms of humanized murine aldolase antibodies are contemplated. One embodiment uses the humanized aldolase catalytic antibody h38c2 IgG1 or h38c2 Fab with human constant domains CLκ and CH$\gamma_1$1. Human germline VLk gene DPK-9 and human Jk gene JK4 were used as frameworks for the humanization of the kappa light chain variable domain of m38c2, and human germline gene DP-47 and human JH gene JH4 were used as frameworks for the humanization of the heavy chain variable domain of m38c2. FIG. 8A illustrates a sequence alignment between the variable light and heavy chains in m38c2, h38c2, and human germlines. h38c2 may utilize IgG1, IgG2, IgG3, or IgG4 constant domains, including any of the allotypes thereof.

Another embodiment uses a chimeric antibody comprising the variable domains (VL and VH) of h38c2 (SEQ ID NOs: 67 and 68) and the constant domains from an IgG1, IgG2, IgG3, or IgG4 antibody that comprises a polypeptide of the invention comprising SEQ ID NO:98 between β-sheets E and F. The LC may comprise SEQ ID NO:254. The antibody may be a full-length antibody, Fab, Fab', F(ab')2, VH, VL, diabody, or minibody comprising VH and VL domains from h38c2. The antibody may be an antibody comprising the VL and VH domains from h38c2 and a constant domain selected from the group consisting of IgG1, IgG2, IgG3, and IgG4. The antibody may be a humanized version of a murine aldolase antibody comprising a constant region from a human IgG, IgA, IgM, IgD, or IgE antibody. In another embodiment, the antibody is a chimeric antibody comprising the VL and VH region from a murine aldolase antibody (e.g. SEQ ID NO:69 and 70) and a constant region from a human IgG, IgA, IgM, IgD, or IgE antibody, comprising a polypeptide of the invention comprising SEQ ID NO:98 between β-sheets E and F. In further embodiments, the antibody is a fully human version of a murine aldolase antibody comprising a polypeptide sequence from natural or native human IgG, IgA, IgM, IgD, or IgE antibody.

One embodiment uses h38c2 F(ab')$_2$. h38c2 F(ab')2 may be produced by the proteolytic digestion of h38c2 IgG1.

As used herein, "pharmacokinetics" refers to the concentration of an administered compound in the serum over time. Pharmacodynamics refers to the concentration of an administered compound in target and nontarget tissues over time and the effects on the target tissue (e.g., efficacy) and the non-target tissue (e.g., toxicity). Improvements in, for example, pharmacokinetics or pharmacodynamics can be designed for a particular targeting agent or biological agent, such as by using labile linkages or by modifying the chemical nature of any linker (e.g., changing solubility, charge, and the like). The term "$K_{off}$" refers to the off rate constant for dissociation of an antibody from the antibody/antigen complex. The term "$K_d$" refers to the dissociation constant of a particular antibody-antigen interaction.

In some aspects, the invention provides for pharmaceutically acceptable salts, stereoisomers, tautomers, solvates, and prodrugs of compounds, samples, compositions and pharmaceutical compositions of the invention.

Catalytic Antibody Linkers

Certain linkers suitable for connecting targeting agents (TA) to the combining site of catalytic antibodies (Catalytic Antibody Linkers: CAb-linkers) are disclosed in US2009098130, the contents of which are incorporated herein by reference. The term "targeting agents" is used herein to distinguish from the term "Effector Moiety" but it is apparent that the types of molecules attached at the end of a CAb-linker as a TA, or attached to the end of a MAC-linker as an Effector Moiety may be interchangable. In particular, aspects of US2009098130 pertaining to the general formulae describing (CAb-linkers, specific CAb-linker structure, synthesis of Cab-linkers and combinations of different elements of $P^1$, $Q^1$ and $W^1$, (therein classified as X, Y and Z groups respectively) as specifically and generally described therein are herein included.

The CAb-linker may be linear or branched, and optionally includes one or more carbocyclic or heterocyclic groups. CAb-linker length may be viewed in terms of the number of linear atoms, with cyclic moieties such as aromatic rings and the like to be counted by taking the shortest route around the ring. In some embodiments, the CAb-linker has a linear stretch of between 5-15 atoms, in other embodiments 15-30 atoms, in still other embodiments 30-50 atoms, in still other embodiments 50-100 atoms, and in still other embodiments 100-200 atoms. Other CAb-linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, and modulation of antibody binding, the ability to be incorporated into a micelle or liposome, and the like.

In some aspects the CAb-linker may be covalently linked to the side chain of the TA-linking residue. The linker may comprise the formula: $P^1$-$Q^1$-$W^1$; wherein $P^1$ is a biologically compatible connecting chain including any atom selected from the group consisting of C, H, N, O, P, S, F, Cl, Br, and I, and may comprise a polymer or block co-polymer, and is covalently linked to the linking residue (through side chain, amino terminus, or carboxyl terminus as appropriate) where the linker is linear, $Q^1$ is an optionally present recognition group comprising at least a ring structure; and $W^1$ is an attachment moiety comprising a covalent link to an amino acid side chain in a combining site of an antibody.

When present, $Q^1$ may have the optionally substituted structure:

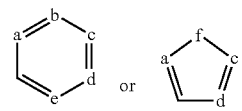

wherein a, b, c, d, and e are independently carbon or nitrogen; f is carbon, nitrogen, oxygen, or sulfur; $Q^1$ is attached to $P^1$ and $W^1$ independently at any 2 ring positions of sufficient valence; and no more than 4 of a, b, c, d, e, or f are simultaneously nitrogen and preferably a, b, c, d, and e in the ring structure are each carbon. In some aspects, $Q^1$ may be phenyl. Although not wishing to be bound by any theory, it is believed that the $Q^1$ group can assist in positioning the reactive group into a suitable antibody combining site so that the $W^1$ group can react with a reactive amino acid side chain.

The CAb-linker may be designed such that it contains a reactive group capable of covalently or non-covalently forming a bond with a macromolecule, such as an antibody, protein, or fragment thereof. The reactive group is chosen for use with a reactive residue in a particular combining site. For example, a chemical moiety for modification by an aldolase antibody may be a ketone, diketone, β lactam, active ester haloketone, lactone, anhydride, maleimide, α-haloacetamide, cyclohexyl diketone, epoxide, aldehyde, amidine, guanidine, imine, enamine, phosphate, phosphonate, epoxide, aziridine, thioepoxide, masked or protected diketone (ketal for example), lactam, haloketone, aldehyde, and the like.

In some embodiments, $W^1$, prior to conjugation with the side-chain of a residue in the combining site of an antibody, includes one or more C=O groups arranged to form an azetidinone, diketone, an acyl β-lactam, an active ester, a haloketone, a cyclohexyl diketone group, an aldehyde, a maleimide, an activated alkene, an activated alkyne or, in general, a molecule comprising a leaving group susceptible to nucleophilic or electrophilic displacement. Other groups may include a lactone, an anhydride, an α-haloacetamide, an imine, a hydrazide, or an epoxide. Exemplary linker electrophilic reactive groups that can covalently bond to a reactive nucleophilic group (e.g., a lysine or cysteine side chain) in a combining site of antibody include acyl β-lactam, simple diketone, succinimide active ester, maleimide, haloacetamide with linker, haloketone, cyclohexyl diketone, aldehyde, amidine, guanidine, imine, enamine, phosphate, phosphonate, epoxide, aziridine, thioepoxide, a masked or protected diketone (a ketal, for example), lactam, sulfonate, and the like, masked C=O groups such as imines, ketals, acetals, and any other known electrophilic group. In certain embodiments, the reactive group includes one or more C=O groups arranged to form an acyl β-lactam, simple diketone, succinimide active ester, maleimide, haloacetamide with linker, haloketone, cyclohexyl diketone, or aldehyde. $W^1$ may be a substituted alkyl, substituted cycloalkyl, substituted aryl, substituted arylalkyl, substituted heterocyclyl, or substituted heterocyclylalkyl, wherein at least one substituent is a 1,3-diketone moiety, an acyl lactam, an active ester, an α-haloketone, an aldehyde, a maleimide, a lactone, an anhydride, an α-haloacetamide, an amine, a hydrazide, or an epoxide. In some aspects, the $W^1$ group is covalently linked to a macromolecule scaffold that can provide increased half-life to the peptides of the invention. In some aspects, the $W^1$ group if present is covalently linked to the combining site of an antibody.

In some aspects, prior to conjugation (for example, with the combining site of an antibody), $W^1$ has the structure:

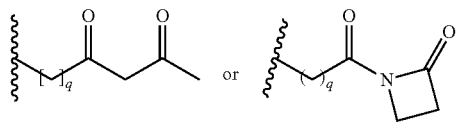

wherein q=0-5. q may be 1 or 2. q may be 1. In other aspects, q may be 2.

In some aspects, following conjugation with the antibody combining site, $W^1$ has the structure:

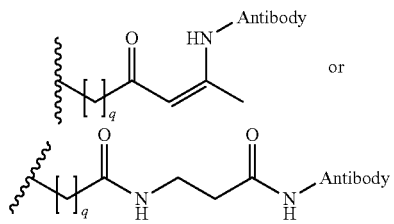

wherein q=0-5 and Antibody-N— is a covalent bond to a side chain in a combining site of an antibody. q may be 1 or 2. q may be 1. In other aspects, q may be 2.

$P^1$ may be a group comprising three components; $P^1p$-$P^1s$-$P^1y$, wherein $P^1p$ is a group specifically adapted to be combinable with the targeting agent, $P^1s$ is a spacer region of the $P^1$ group, and $P^1y$ is a group adapted to bind to the $W^1$ group. In some aspects, $P^1y$ is selected from an amide bond, an enamine bond, or a guanidinium bond. $P^1y$ may be selected so as to provide a hydrogen molecule adjacent (within two atoms) to the $Q^1$ group. While not wishing to be bound by theory, it is believed that the H atom can assist the $Q^1$ group recognition of a hydrophobic pocket through H-bond interaction, particularly in respect of the hydrophobic pocket of the binding cleft of a catalytic antibody, such as h38C2. Thus the amide bond, for example, may be orientated such that the NH group is directly bonded to the $Q^1$ group, providing the H of the NH group for hydrogen bonding. Alternatively, the C=O group of an amide may be bonded to the $Q^1$ group, with the H of the NH group about 2 atoms adjacent to the $Q^1$ group, but still available for H-bonding. In some embodiments, $P^1y$ is absent. In some embodiments the $P^1y$ group has the formula:

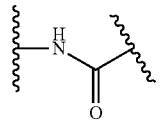

In some aspects, $P^1s$ is selected such that $P^1s$ does not provide any overly reactive groups. $P^1s$ may be selected so as to provide an overall length of the $P^1$ groups of between 2-15 atoms. $P^1s$ may be selected so that the overall length of the $P^1$ group is between 2 and 10 atoms. $X^1$ groups may be selected so that the overall length of $P^1$ group is 4-8 atoms. $P^1$ groups may be selected so that the overall length of the $P^1$ group is 5 atoms. $P^1$ groups may be selected so that the overall length of $P^1$ group is 6 atoms. In some aspects, $P^1$ groups may comprise one of the following formulae:

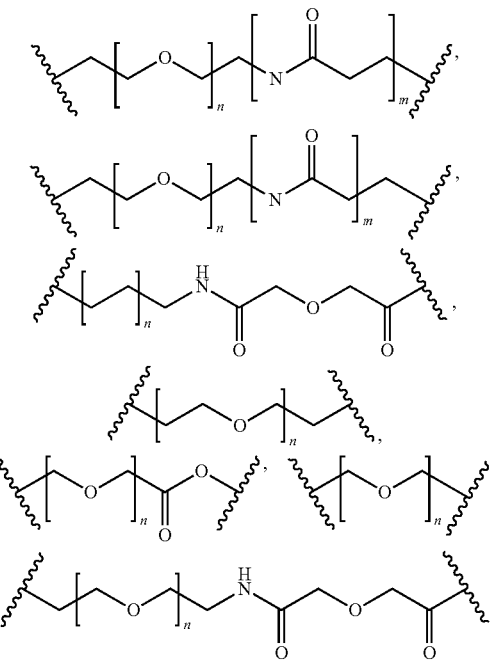

where n=1, 2, 3, 4, 5, 6, 7, 8, 9, or 10, and m is present or absent; n may be 1, 2, 3, 4, 5, or 6; n may be 1, 2, 3, or 4; n may be 1; n may be 2; n may be 3; n may be 4.

$P^1p$ ideally is selected so as to enable a specific directional covalent linking strategy to the linking residue of a targeting molecule (TA-linking residue), such as a peptide, protein, small molecule, nucleic acid or aptamer. For example, where the TA-linking residue comprises a nucleophilic group, $P^1p$ may be an electrophilic group and vice versa. For example, if the TA-linking residue side chain comprises an amine group, such as K, H, Y, orthinine, Dap, or Dab, Xp may be COOH, or other similarly reactive electrophile. If the TA-linking residue is D or E, $P^1p$ may comprise a nucleophilic group, such as an amine group. Either of these strategies permits a covalent bond to be formed between the $P^1p$ group and the TA-linking residue by amide bond formation strategies. Where the TA-linking group is an amine group, $P^1p$ may comprise the formula:

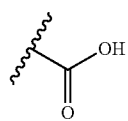 [SMILES: *C(=O)O]

$P^1$ may be an optionally present biologically compatible polymer or block copolymer. $P^1$ may be of the structure:

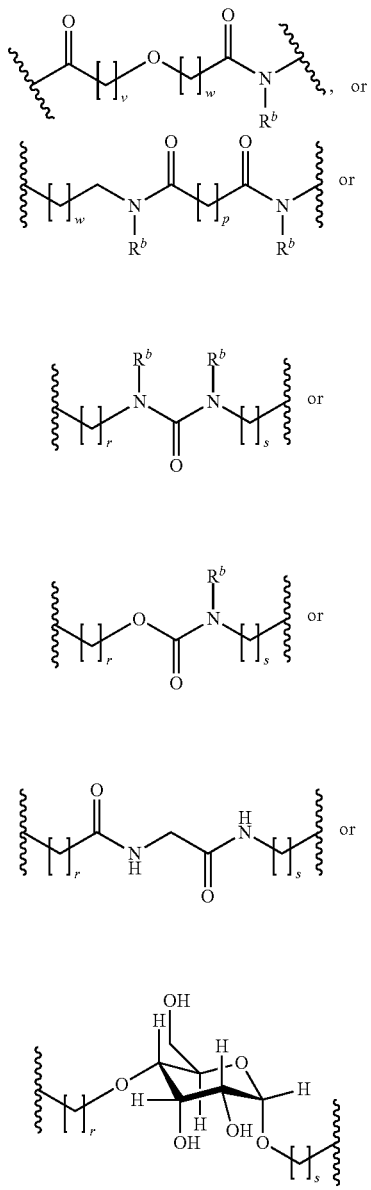

wherein p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, or 45; w, r, and s are each independently 0, 1, 2, 3, 4, 5, 6, 7, 8, 9, 10, 11, 12, 13, 14, 15, 16, 17, 18, 19 or 20; and Rb at each occurrence is independently hydrogen, substituted or unsubstituted $C_{1-10}$ alkyl, substituted or unsubstituted $C_{3-7}$ cycloalkyl-$C_{1-6}$ alkyl, or substituted or unsubstituted aryl-$C_{1-6}$ alkyl.

Where the TA-linking residue is C, homologs of C, or other thiol-group containing residues, $P^1p$ may comprise a maleimide group (or similar) permitting a thiol-maleimide addition reaction strategy to covalently link the $P^1p$ group to the TA-linking residue. In some aspects, $P^1p$ may also comprise a thiol group, allowing a disulphide bridge to be formed between the TA-linking residue and $P^1p$ group. In some aspects, $P^1p$ may be maleimide:

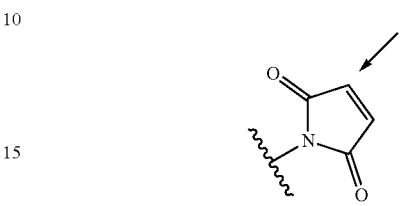

wherein the arrow indicates the point of attachment to the targeting molecule and the parallel line represents to attachment to the $Q^1$ group of the linker. Where the point of attachment to the targeting molecule comprises a cysteine residue, or other thiol bearing side chain, the mechanism of conjugation may be as follows:

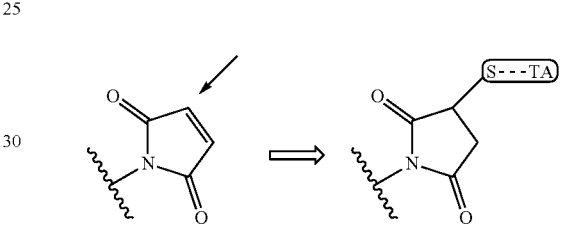

In some aspects, the $P^1p$ group comprises a substituted maleimide:

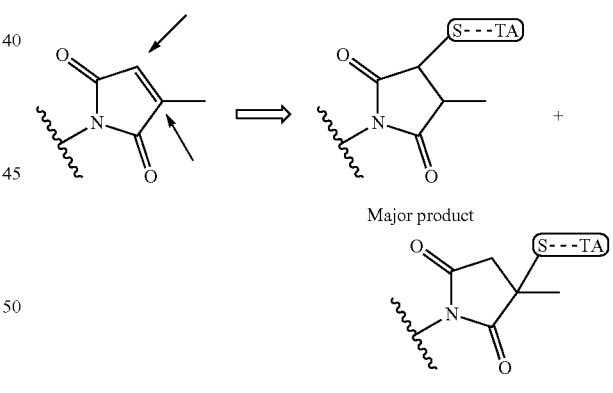

In some aspects, $P^1$ is

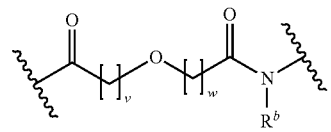

wherein v and w are selected such that the backbone length of $X^1$ is 6-12 atoms;

In some aspects, the TA-linker is of the formula:

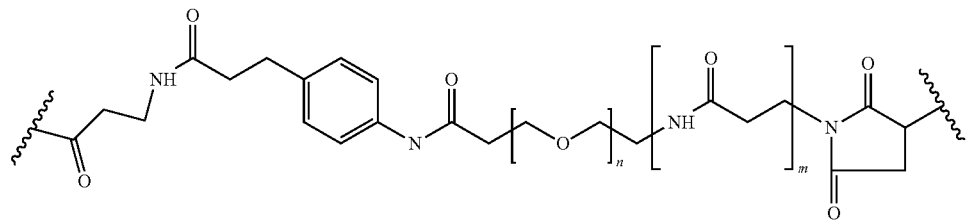

wherein n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some aspects, TA-linker is of the formula:

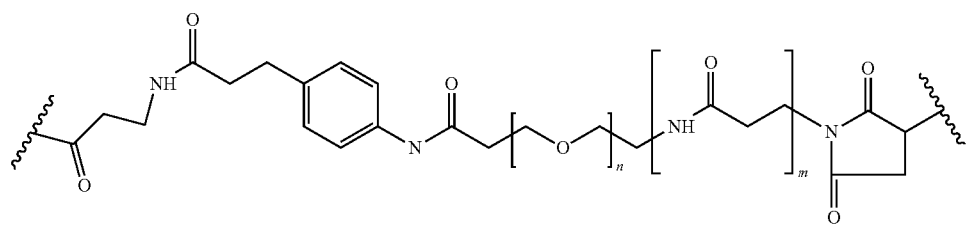

wherein n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some aspects, the $P^1$ portion of CA-linkers may be used as the $Y^1$, $X^1$-$Y^1$, $Y^1$-Z and $X^1$-$Y^1$-Z, portion of linkers for a MAC of the invention.

Peptides and Proteins

Acyl lysine, or $K_{ac}$ (also AcK) refers to:

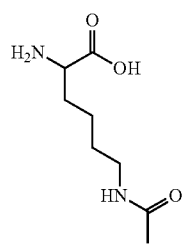

$K_{SH}$ refers to:

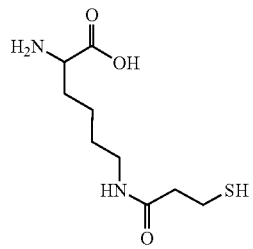

Aib (2-aminoisobutytric acid):

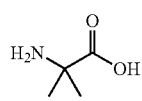

-continued

Diaminobutyric acid (Dab)

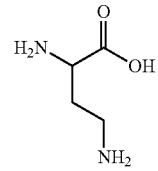

Diaminopropionic acid (Dap)

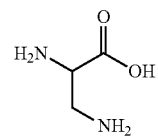

Homocysteine

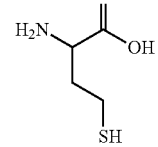

Homoserine

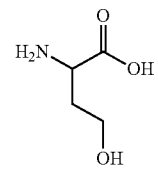

Ornithine

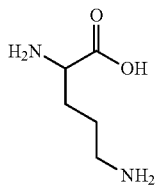

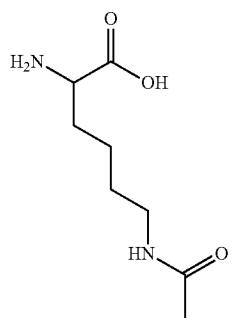

Diaminobutyric acid (Dab)

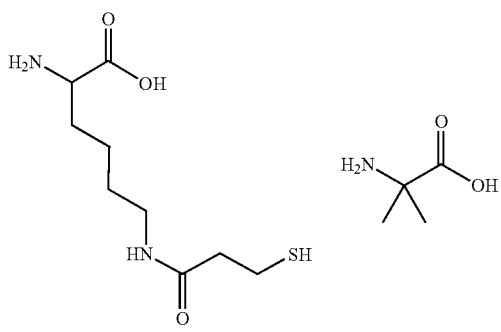

Diaminopropionic acid (Dap)

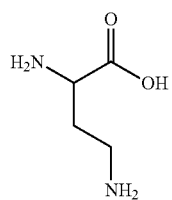

Homocysteine      Homoserine

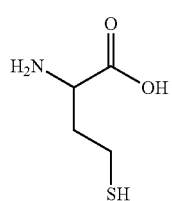

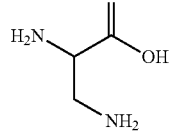

Ornithine

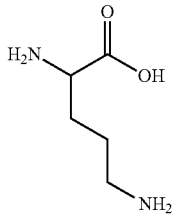

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. As used herein, the 20 natural, or conventional, amino acids and their abbreviations follow IUPAC single letter and three letter codes. "Polypeptide," "peptide," and "protein" are used interchangeably to refer to a polymer of amino acid residues. As used herein, these terms apply to amino acid polymers in which one or more amino acid residues is an artificial chemical analog of a corresponding naturally occurring amino acid. These terms also apply to naturally occurring amino acid polymers. Amino acids can be in the L-form or D-form as long as the binding and other desired characteristics of the peptide are maintained. A polypeptide may be monomeric or polymeric.

Unless indicated otherwise by a "D" prefix, e.g., D-Ala or N-Me-D-Ile, or written in lower case format, e.g., a, i, l, (D versions of Ala, Ile, Leu), the stereochemistry of the α-carbon of the amino acids and aminoacyl residues in peptides described in this specification and the appended claims is the natural or "L" configuration.

All peptide sequences are written according to the generally accepted convention whereby the α-N-terminal amino acid residue is on the left and the α-C-terminal amino acid residue is on the right. As used herein, the term "N-terminus" refers to the free α-amino group of an amino acid in a peptide, and the term "C-terminus" refers to the free α-carboxylic acid terminus of an amino acid in a peptide. A peptide which is N-terminated with a group refers to a peptide bearing a group on the α-amino nitrogen of the N-terminal amino acid residue. An amino acid which is N-terminated with a group refers to an amino acid bearing a group on the α-amino nitrogen.

As used herein, "halo," "halogen" or "halide" refers to F, Cl, Br or I.

As used herein, "biological activity" refers to the in vivo activities of a compound, composition, or other mixture, or physiological responses that result upon in vivo administration of a compound, composition or other mixture. Biological activity thus encompasses therapeutic effects, diagnostic effects and pharmaceutical activity of such compounds, compositions, and mixtures.

The term "biologically compatible" as used herein means something that is biologically inert or non reactive with intracellular and extra cellular biological molecules, and non toxic.

The term "alkyl" by itself or as part of another term refers to a straight chain or branched, saturated hydrocarbon having the indicated number of carbon atoms (e.g. "$C_1$-$C_8$" alkyl refer to an alkyl group having from 1 to 8 carbon atoms). When the number of carbon atoms is not indicated, the alkyl group has from 1 to 8 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

The phrase "substituted alkyl" refers to an alkyl group in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted alkyl" refers to a divalent unsubstituted alkyl group as defined above. Thus methylene, ethylene, and propylene are each examples of unsubstituted alkylenes. The phrase "substituted alkyl" refers to a divalent substituted alkyl group as defined above. Substituted or unsubstituted lower alkylene groups have from 1 to about 6 carbons.

The phrase "unsubstituted cycloalkyl" refers to cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and the like, as well as such rings substituted with straight and branched chain alkyl groups as defined above. Thus, the phrase would include methylcylcohexyl groups among others. The phrase does not include cyclic alkyl groups containing heteroatoms. Unsubstituted cycloalkyl groups may be bonded to one or more carbon atom(s), oxygen atom(s), nitrogen atom(s), and/or sulfur atom(s) in the parent compound. In some embodiments unsubstituted cycloalkyl groups have from 3 to 20 carbon atoms. In other embodiments, such unsubstituted alkyl groups have from 3 to 8 carbon atoms while in others, such groups have from 3 to 7 carbon atoms.

The phrase "substituted cycloalkyl" has the same meaning with respect to unsubstituted cycloalkyl groups that substituted alkyl groups have with respect to unsubstituted alkyl groups. Thus, the phrase includes, but is not limited to, oxocyclohexyl, chlorocyclohexyl, hydroxycyclopentyl, and chloromethylcyclohexyl groups.

The term "aryl," by itself or an part of another term, means a substituted or unsubstituted monovalent carbocyclic aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted carbocyclic aromatic group (e.g., an aryl group) can be substituted with one or more, preferably 1 to 5, of the following groups: $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$ and —CN; wherein each R' is independently selected from —H, $C_1$-$C_8$ alkyl and unsubstituted aryl. In some embodiments, a substituted carbocyclic aromatic group can further include one or more of: —NHC(=NH)NH$_2$, —NHCONH$_2$, —S(=O)$_2$R' and —SR'. "Arylene" is the corresponding divalent moiety.

The term "substituted alkyl" means an alkyl in which one or more hydrogen atoms are each independently replaced with a substituent. Typical substituents include, but are not limited to, —X, —R, —O—, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3^{2-}$, PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, $C_1$-$C_{20}$ alkyl, $C_1$-$C_{20}$ heteroalkyl, $C_8$-$C_{20}$ aryl, $C_3$-$C_8$ heterocyclyl, a protecting group or a prodrug moiety. Aryl, alkylene and heteroalkylene groups as described above may also be similarly substituted.

The term "aralkyl" by itself or part of another term, means an alkyl group, as defined above, substituted with an aryl group, as defined above.

The term "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethylene-CH$_2$CH$_2$—), 1,3-propylene (—CH$_2$CH$_2$CH$_2$—), 1,4-butylene (—CH$_2$CH$_2$CH$_2$CH$_2$—), and the like. A "C$_1$-C$_{10}$" straight chain alkylene is a straight chain, saturated hydrocarbon group of the formula —(CH$_2$)$_{1-10}$—. Examples of a C$_1$-C$_{10}$ alkylene include methylene, ethylene, propylene, butylene, pentylene, hexylene, heptylene, octylene, nonylene and decalene.

The term "heteroalkylene" by itself or as part of another substituent means a divalent group derived from heteroalkyl (as discussed above). For heteroalkylene groups, heteroatoms can also occupy either or both of the chain termini.

The term "C$_3$-C$_8$ heterocyclyl" by itself or as part of another term, refers to a monovalent substituted or unsubstituted aromatic or non-aromatic monocyclic, bicyclic or tricyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Unless otherwise noted, the heterocyclyl is attached to its pendant group at any heteroatom or carbon atom that results in a stable structure. Representative examples of a C$_3$-C$_8$ heterocyclyl include, but are not limited to, tetrahyrofuranyl, oxetanyl, pyranyl, pyrrolidinyl, piperidinyl, benzofuranyl, benzothiophene, indolyl, benzopyrazolyl, pyrrolyl, thiophenyl (thiopene), furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C$_3$-C$_8$ heterocyclyl can be substituted with up to seven groups including, but not limited to, C$_1$-C$_8$ alkyl, C$_1$-C$_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(═O)$_2$R', —S(O)R', halogen, —N$_3$, —NH$_2$, —NH(R'), —N(R')$_2$ and —CN; wherein each R' is independently selected from —H, C$_1$-C$_8$ alkyl, C$_1$-C$_8$ heteroalkyl and aryl. In some embodiments, a substituted heterocyclyl can also include one or more of: —NHC(═NH)NH$_2$, —NHCONH$_2$, —S(═O)$_2$R' and —SR'. "Heterocyclo" is the corresponding divalent moiety.

The term "C$_3$-C$_8$ carbocyclyl" by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative C$_3$-C$_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(111)pentane, and bicyclo(222)octane. A C$_3$-C$_8$ carbocyclyl group can be unsubstituted or substituted with up to seven groups including, but not limited to, C$_1$-C$_8$ alkyl, C$_1$-C$_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(═O)$_2$R', —S(═O)R', —OH, -halogen, —N$_3$, —NH$_2$, —NH(R'), —N(R$^1$)$_2$ and —CN; where each R' is independently selected from —H, C$_1$-C$_8$ alkyl, C$_1$-C$_8$ heteroalkyl and aryl. "C$_3$-C$_8$ carbocyclo" is the corresponding divalent moiety.

The term "heteroaralkyl" by itself or part of another term, means an alkyl group, as defined above, substituted with an aromatic heterocyclyl group, as defined above. Heteroaralclo is the corresponding divalent moiety.

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Connecting chain", or "chain" as herein used refers to the sequences of amino acids in any tertiary structural form other than a β-strand that connect the individual β-strands of an immunoglobulin domain. The terms encompass the structural motifs of α-helices, turns, loops, and β-hairpins. The terms "α-helices", "turns", "loops", and "β-hairpins" have the meaning commonly ascribed to them in the art so as to be able to distinguish between the four distinct three dimensional structural motifs.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

The term "conservative amino acid substitution" refers to a substitution of a native amino acid residue with a nonnative residue such that there is little or no effect on the polarity or charge of the amino acid residue at that position. For example, a conservative substitution results from the replacement of a non-polar residue in a polypeptide with any other non-polar residue.

Structural Alignment

Structural alignments, which are usually specific to protein and sometimes RNA sequences, use information about the secondary and tertiary structure of the protein or RNA molecule to aid in aligning the sequences. These methods are used for two or more sequences and typically produce local alignments; however, because they depend on the availability of structural information, they can only be used for sequences whose corresponding structures are known (usually through X-ray crystallography or NMR spectroscopy). Because both protein and RNA structure is more evolutionarily conserved than sequence, structural alignments can be more reliable between sequences that are very distantly related and that have diverged so extensively that sequence comparison cannot reliably detect their similarity. Where there is no available structural data on one of the proteins, a comparison can still be made if structural data is available on one or preferably more closely related proteins, such as immunoglobulins across species, and in particular antibody constant domains across species and subtype.

Structural alignments are used as the "gold standard" in evaluating alignments for homology-based protein structure prediction because they explicitly align regions of the protein sequence that are structurally similar rather than relying exclusively on sequence information.

The DALI method, or distance matrix alignment, is a fragment-based method for constructing structural alignments based on contact similarity patterns between successive hexapeptides in the query sequences. It can generate pairwise or multiple alignments and identify a query sequence's structural neighbors in the Protein Data Bank (PDB). It has been used to construct the FSSP structural alignment database (Fold classification based on Structure-Structure alignment of Proteins, or Families of Structurally Similar Proteins). A DALI webserver can be accessed at EBI DALI and the FSSP is located at The Dali Database.

SSAP (sequential structure alignment program) is a dynamic programming-based method of structural alignment that uses atom-to-atom vectors in structure space as comparison points. It has been extended since its original description to include multiple as well as pairwise alignments, and has been used in the construction of the CATH (Class, Architecture, Topology, Homology) hierarchical database classification of protein folds. The CATH database can be accessed at CATH Protein Structure Classification.

The combinatorial extension method of structural alignment generates a pairwise structural alignment by using local geometry to align short fragments of the two proteins being analyzed and then assembles these fragments into a larger alignment. Based on measures such as rigid-body root mean square distance, residue distances, local secondary structure, and surrounding environmental features such as residue neighbor hydrophobicity, local alignments called "aligned fragment pairs" are generated and used to build a similarity matrix representing all possible structural alignments within predefined cutoff criteria. A path from one protein structure state to the other is then traced through the matrix by extending the growing alignment one fragment at a time. The optimal such path defines the combinatorial-extension alignment. A web-based server implementing the method and providing a database of pairwise alignments of structures in the Protein Data Bank is located at the Combinatorial Extension website.

Sequence Alignment

Where structural alignment with sequences of the invention is not possible, for example due to an absence of target sequence NMR or crystal structure data, sequence alignment may be used. The skilled person is familiar with sequence alignment tools (such as BLAST, CLUSTAL and others known to the skilled person, such as those described herein), and is able to align sequences, particularly antibody constant domain sequences according to known structural motifs, especially due to the large number of exemplary structural studies already existent for immunoglobulin domains, antibodies and antibody constant domains in particular, across subtype and species.

Computational approaches to sequence alignment generally fall into two categories: global alignments and local alignments. Calculating a global alignment is a form of global optimization that "forces" the alignment to span the entire length of all query sequences. By contrast, local alignments identify regions of similarity within long sequences that are often widely divergent overall. Local alignments are often preferable, but can be more difficult to calculate because of the additional challenge of identifying the regions of similarity. A variety of computational algorithms have been applied to the sequence alignment problem. These include slow but formally correct methods like dynamic programming and also efficient, heuristic algorithms or probabilistic methods designed for large-scale database search, that do not guarantee to find best matches.

Global alignments, which attempt to align every residue in every sequence, are most useful when the sequences in the query set are similar and of roughly equal size. A general global alignment technique is the Needleman-Wunsch algorithm, which is based on dynamic programming. Local alignments are more useful for dissimilar sequences that are suspected to contain regions of similarity or similar sequence motifs within their larger sequence context. The Smith-Waterman algorithm is a general local alignment method also based on dynamic programming.

Pairwise sequence alignment methods are used to find the best-matching piecewise (local) or global alignments of two query sequences. The three primary methods of producing pairwise alignments are dot-matrix methods, dynamic programming, and word methods; however, multiple sequence alignment techniques can also align pairs of sequences. Although each method has its individual strengths and weaknesses, all three pairwise methods have difficulty with highly repetitive sequences of low information content—especially where the number of repetitions differ in the two sequences to be aligned. One way of quantifying the utility of a given pairwise alignment is the 'maximum unique match' (MUM), or the longest subsequence that occurs in both query sequence. Longer MUM sequences typically reflect closer relatedness. Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux et al., Nuc. Acids Res. 12: 387 (1984); Genetics Computer Group, University of Wisconsin, Madison, WI), BLASTP, BLASTN, and FASTA (Atschul et al., J. Mol. Biol. 215: 403-10 (1990)). The BLAST X program is publicly available from the National Center for Biotechnology Information (NCBI) and other sources (Altschul et al., BLAST Manual (NCB NLM NIH, Bethesda, MD); Altschul et al., 1990, supra). The well-known Smith Waterman algorithm may also be used to determine identity.

By way of example, using the computer algorithm GAP (Genetics Computer Group), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. Preferred parameters for polypeptide sequence comparison include the following: Algorithm: Needleman and Wunsch, J. Mol. Biol. 48: 443-53 (1970). Comparison matrix: BLOSUM 62 from Henikoff et al., Proc. Natl. Acad. Sci. U.S.A. 89: 10915-19 (1992).

Other exemplary algorithms, gap opening penalties, gap extension penalties, comparison matrices, thresholds of similarity, etc. may be used by those of skill in the art, including those set forth in the Program Manual, WisconsinPackage, Version 9, September, 1997. The particular choices to be made will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

SEQUENCE LIST

| SEQ | Description | Sequence |
|---|---|---|
| 1 | Heavy Chain 2.12.1.fx CDRs underlined | QVQLVESGGG LVKPGGSLRL SCAAS<u>GFTFS DYYMS</u>WIRQA PGKGLEWVS<u>Y ISSSGSTRDY ADSVKG</u>RFTI SRDNAKNSLY LQMNSLRAED TAVYYCVR<u>DG VETTFYYYYY GMDV</u>WGQGTT VTVSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE CPPCPAPPVA GPSVFLFPPK PKDTLMISRT PEVTCVVVDV SHEDPEVQFN WYVDGVEVHN AKTKPREEQF NSTFRVVSVL TVVHQDWLNG KEYKCKVSNK GLPAPIEKTI SKTKGQPREP QVYTLPPSRE EMTKNQVSLT CLVKGFYPSD IAVEWESNGQ PENNYKTTPP MLDSDGSFFL YSKLTVDKSR WQQGNVFSCS VMHEALHNHY TQKSLSLSPGK |
| 2 | Light Chain 2.12.1.fx CDRs underlined | DIQMTQSPSS LSASVGDRVT IT<u>CRASQDIR RDLGW</u>YQQKP GKAPKRLIY<u>A ASRLQS</u>GVPS RFSGSGSGTE FTLTISSLQP EDFATYYC<u>LQ HNNYPRT</u>FGQ GTKLVIKRTV AAPSVFIFPP SDEQLKSGTA SVVCLLNNFY PREAKVQWKV DNALQSGNSQ ESVTEQDSED STYSLSSTLT LSKADYEKHK VYACEVTHQG LSSPVTKSFN RGEC |
| 3 | HC variable 2.12.1.fx | QVQLVESGGG LVKPGGSLRL SCAAS<u>GFTFS DYYMS</u>WIRQA PGKGLEWVS<u>Y ISSSGSTRDY ADSVKG</u>RFTI SRDNAKNSLY LQMNSLRAED TAVYYCVR<u>DG VETTFYYYYY GMDV</u>WGQGTT VT |
| 4 | HC constant 2.12.1.fx | VSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE CPPCPAPPVA GPSVFLFPPK PKDTLMISRT PEVTCVVVDV SHEDPEVQFN WYVDGVEVHN AKTKPREEQF NSTFRVVSVL TVVHQDWLNG KEYKCKVSNK GLPAPIEKTI SKTKGQPREP QVYTLPPSRE EMTKNQVSLT CLVKGFYPSD IAVEWESNGQ PENNYKTTPP MLDSDGSFFL YSKLTVDKSR WQQGNVFSCS VMHEALHNHY TQKSLSLSPGK |
| 5 | LC variable 2.12.1.fx | DIQMTQSPSS LSASVGDRVT IT<u>CRASQDIR RDLGW</u>YQQKP GKAPKRLIY<u>A ASRLQS</u>GVPS RFSGSGSGTE FTLTISSLQP EDFATYYC<u>LQ HNNYPRT</u>FGQ GTKLVIKR |
| 6 | Human CLκ1-106 (Km(3) $X^{45}$ = A/$X^{83}$ = V $K^{80}$ bold & underlined 2.12.1.fx | TVAAPSVFIF PPSDEQLKSG TASVVCLLNN FYPREAKVQW KVDN<u>A</u>LQSGN SQESVTEQDS <u>K</u>DSTYSLS<u>S</u>T LTLSKA<u>D</u>YE<u>K</u> HK<u>V</u>YACEVTH QGLSSPVTKS FNRGEC |
| 7 | Human CLκ 1-106 Km(1,2) $X^{45}$ = A/$X^{83}$ = L $K^{80}$ bold & underlined | TVAAPSVFIF PPSDEQLKSG TASVVCLLNN FYPREAKVQW KVDN<u>A</u>LQSGN SQESVTEQDS <u>K</u>DSTYSLS<u>S</u>T LTLSKA<u>D</u>YE<u>K</u> HK<u>L</u>YACEVTH QGLSSPVTKS FNRGEC |
| 8 | Human CLκ 1-106 (Km(1, 2) $X^{45}$ = A/$X^{83}$ = L $K^{80}$ bold & underlined | TVAAPSVFIF PPSDEQLKSG TASVVCLLNN FYPREAKVQW KVDN<u>V</u>LQSGN SQESVTEQDS <u>K</u>DSTYSLS<u>S</u>T LTLSKA<u>D</u>YE<u>K</u> HK<u>L</u>YACEVTH QGLSSPVTKS FNRGEC |
| 9 | hCLκ 1-106 $X^{82}$ = any AA $X^{45}$ = V/A $X^{83}$ = L/V | TVAAPSVFIF PPSDEQLKSG TASVVCLLNN FYPREAKVQW KVDN<u>x</u>LQSGN SQESVTEQDS KDSTYSLSST LTLSKADYEK H<u>xx</u>YACEVTH QGLSSPVTKS FNRGEC |
| 10 | Human CLκ 1-106 $X^{45}$ = V/A $X^{83}$ = L/V | TVAAPSVFIF PPSDEQLKSG TASVVCLLNN FYPREAKVQW KVDNxLQSGN SQESVTEQDS KDSTYSLSST LTLSKADYEK HKxYACEVTH QGLSSPVTKS FNRGEC |
| 11 | Human CLκ 1-106 $X^{82}$ = any aa | TVAAPSVFIF PPSDEQLKSG TASVVCLLNN FYPREAKVQW KVDNALQSGN SQESVTEQDS KDSTYSLSST LTLSKADYEK HxVYACEVTH QGLSSPVTKS FNRGEC |
| 12 | Human CLk.$K^{80}$R | TVAAPSVFIF PPSDEQLKSG TASVVCLLNN FYPREAKVQW KVDNALQSGN SQESVTEQDS KDSTYSLSST LTLSKADYE<u>R</u> HKVYACEVTH QGLSSPVTKS FNRGEC |
| 13 | Human CLk.$K^{82}$R | TVAAPSVFIF PPSDEQLKSG TASVVCLLNN FYPREAKVQW KVDNALQSGN SQESVTEQDS KDSTYSLSST LTLSKADYEK H<u>R</u>VYACEVTH QGLSSPVTKS FNRGEC |
| 14 | Human CLk.$K^{80}$R/$K^{82}$R | TVAAPSVFIF PPSDEQLKSG TASVVCLLNN FYPREAKVQW KVDNALQSGN SQESVTEQDS KDSTYSLSST LTLSKADYE<u>R</u> H<u>R</u>VYACEVTH QGLSSPVTKS FNRGEC |

SEQUENCE LIST

| SEQ | Description | Sequence |
|---|---|---|
| 15 | Human CLk.$D^{43}A$ | TVAAPSVFIF PPSDEQLKSG TASVVCLLNN FYPREAKVQW KVANALQSGN SQESVTEQDS KDSTYSLSST LTLSKADYEK HKVYACEVTH QGLSSPVTKS FNRGEC |
| 16 | Human CLk.$K^{80}A$ | TVAAPSVFIF PPSDEQLKSG TASVVCLLNN FYPREAKVQW KVDNALQSGN SQESVTEQDS KDSTYSLSST LTLSKADYEA HKVYACEVTH QGLSSPVTKS FNRGEC |
| 17 | Human CLk.$H^{81}A$ | TVAAPSVFIF PPSDEQLKSG TASVVCLLNN FYPREAKVQW KVDNALQSGN SQESVTEQDS KDSTYSLSST LTLSKADYEK AKVYACEVTH QGLSSPVTKS FNRGEC |
| 18 | Human CLk.$K^{82}A$ | TVAAPSVFIF PPSDEQLKSG TASVVCLLNN FYPREAKVQW KVDNALQSGN SQESVTEQDS KDSTYSLSST LTLSKADYEK HAVYACEVTH QGLSSPVTKS FNRGEC |
| 19 | Human CLk.$D^{43}A/H^{81}A$ | TVAAPSVFIF PPSDEQLKSG TASVVCLLNN FYPREAKVQW KVANALQSGN SQESVTEQDS KDSTYSLSST LTLSKADYEK AKVYACEVTH QGLSSPVTKS FNRGEC |
| 20 | Human CLk.$K^{41}A$ | TVAAPSVFIF PPSDEQLKSG TASVVCLLNN FYPREAKVQW AVDNALQSGN SQESVTEQDS KDSTYSLSST LTLSKADYEK HKVYACEVTH QGLSSPVTKS FNRGEC |
| 21 | Human CLk.$V^{42}A$ | TVAAPSVFIF PPSDEQLKSG TASVVCLLNN FYPREAKVQW KADNALQSGN SQESVTEQDS KDSTYSLSST LTLSKADYEK HKVYACEVTH QGLSSPVTKS FNRGEC |
| 22 | Human CLk.$N^{44}A$ | TVAAPSVFIF PPSDEQLKSG TASVVCLLNN FYPREAKVQW KVDAALQSGN SQESVTEQDS KDSTYSLSST LTLSKADYEK HKVYACEVTH QGLSSPVTKS FNRGEC |
| 23 | Human CLk.$L^{46}A$ | TVAAPSVFIF PPSDEQLKSG TASVVCLLNN FYPREAKVQW KVDNAAQSGN SQESVTEQDS KDSTYSLSST LTLSKADYEK HKVYACEVTH QGLSSPVTKS FNRGEC |
| 24 | Human CLk.$Q^{47}A$ | TVAAPSVFIF PPSDEQLKSG TASVVCLLNN FYPREAKVQW KVDNALASGN SQESVTEQDS KDSTYSLSST LTLSKADYEK HKVYACEVTH QGLSSPVTKS FNRGEC |
| 25 | Human CLk.$S^{48}A$ | TVAAPSVFIF PPSDEQLKSG TASVVCLLNN FYPREAKVQW KVDNALQAGN SQESVTEQDS KDSTYSLSST LTLSKADYEK HKVYACEVTH QGLSSPVTKS FNRGEC |
| 26 | Human CLk.$N^{50}A$ | TVAAPSVFIF PPSDEQLKSG TASVVCLLNN FYPREAKVQW KVDNALQSGA SQESVTEQDS KDSTYSLSST LTLSKADYEK HKVYACEVTH QGLSSPVTKS FNRGEC |
| 27 | ANG 2 binding peptide X1 = $COCH_3$ X3 and x10 = $K_{ac}$ X24 = $NH^2$ | xQxYQPLDEx DKTLYDQFML QQGx |
| 28 | Human CLk.$L^{73}A$ | TVAAPSVFIF PPSDEQLKSG TASVVCLLNN FYPREAKVQW KVDNALQSGN SQESVTEQDS KDSTYSLSST LTASKADYEK HKVYACEVTH QGLSSPVTKS FNRGEC |
| 29 | Human CLk.$S^{74}A$ | TVAAPSVFIF PPSDEQLKSG TASVVCLLNN FYPREAKVQW KVDNALQSGN SQESVTEQDS KDSTYSLSST LTLAKADYEK HKVYACEVTH QGLSSPVTKS FNRGEC |
| 30 | Human CLk.$K^{75}A$ | TVAAPSVFIF PPSDEQLKSG TASVVCLLNN FYPREAKVQW KVDNALQSGN SQESVTEQDS KDSTYSLSST LTLSAADYEK HKVYACEVTH QGLSSPVTKS FNRGEC |
| 31 | Human CLk.$Y^{78}A$ | TVAAPSVFIF PPSDEQLKSG TASVVCLLNN FYPREAKVQW KVDNALQSGN SQESVTEQDS KDSTYSLSST LTLSKADAEK HKVYACEVTH QGLSSPVTKS FNRGEC |
| 32 | Human CLk.$E^{79}A$ | TVAAPSVFIF PPSDEQLKSG TASVVCLLNN FYPREAKVQW KVDNALQSGN SQESVTEQDS KDSTYSLSST LTLSKADYAK HKVYACEVTH QGLSSPVTKS FNRGEC |

-continued

| SEQ | Description | Sequence |
|---|---|---|
| 33 | Human CLk.H$^{81}$A | TVAAPSVFIF PPSDEQLKSG TASVVCLLNN FYPREAKVQW KVDNALQSGN SQESVTEQDS KDSTYSLSST LTLSKADYEK AKVYACEVTH QGLSSPVTKS FNRGEC |
| 34 | Human CLk.V$^{83}$A | TVAAPSVFIF PPSDEQLKSG TASVVCLLNN FYPREAKVQW KVDNALQSGN SQESVTEQDS KDSTYSLSST LTLSKADYEK HKAYACEVTH QGLSSPVTKS FNRGEC |
| 35 | Human CLk.Y$^{84}$A | TVAAPSVFIF PPSDEQLKSG TASVVCLLNN FYPREAKVQW KVDNALQSGN SQESVTEQDS KDSTYSLSST LTLSKADYEK HKVAACEVTH QGLSSPVTKS FNRGEC |
| 36 | Human CLk.R$^{103}$A | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNAGEC |
| 37 | Human CLk.D$^{77}$A | TVAAPSVFIF PPSDEQLKSG TASVVCLLNN FYPREAKVQW KVDNALQSGN SQESVTEQDS KDSTYSLSST LTLSKAAYEK HKVYACEVTH QGLSSPVTKS FNRGEC |
| 38 | Human CLk.D$^{77}$G | TVAAPSVFIF PPSDEQLKSG TASVVCLLNN FYPREAKVQW KVDNALQSGN SQESVTEQDS KDSTYSLSST LTLSKAGYEK HKVYACEVTH QGLSSPVTKS FNRGEC |
| 39 | Human CLk.D$^{77}$V | TVAAPSVFIF PPSDEQLKSG TASVVCLLNN FYPREAKVQW KVDNALQSGN SQESVTEQDS KDSTYSLSST LTLSKAVYEK HKVYACEVTH QGLSSPVTKS FNRGEC |
| 40 | Human CLk.D$^{77}$L | TVAAPSVFIF PPSDEQLKSG TASVVCLLNN FYPREAKVQW KVDNALQSGN SQESVTEQDS KDSTYSLSST LTLSKALYEK HKVYACEVTH QGLSSPVTKS FNRGEC |
| 41 | Human CLk.D$^{77}$I | TVAAPSVFIF PPSDEQLKSG TASVVCLLNN FYPREAKVQW KVDNALQSGN SQESVTEQDS KDSTYSLSST LTLSKAIYEK HKVYACEVTH QGLSSPVTKS FNRGEC |
| 42 | Human CLk.D$^{77}$P | TVAAPSVFIF PPSDEQLKSG TASVVCLLNN FYPREAKVQW KVDNALQSGN SQESVTEQDS KDSTYSLSST LTLSKAPYEK HKVYACEVTH QGLSSPVTKS FNRGEC |
| 43 | Human CLk.D$^{77}$F | TVAAPSVFIF PPSDEQLKSG TASVVCLLNN FYPREAKVQW KVDNALQSGN SQESVTEQDS KDSTYSLSST LTLSKAFYEK HKVYACEVTH QGLSSPVTKS FNRGEC |
| 44 | Human CLk.D$^{77}$W | TVAAPSVFIF PPSDEQLKSG TASVVCLLNN FYPREAKVQW KVDNALQSGN SQESVTEQDS KDSTYSLSST LTLSKAWYEK HKVYACEVTH QGLSSPVTKS FNRGEC |
| 45 | Human CLk.D$^{77}$Y | TVAAPSVFIF PPSDEQLKSG TASVVCLLNN FYPREAKVQW KVDNALQSGN SQESVTEQDS KDSTYSLSST LTLSKAYYEK HKVYACEVTH QGLSSPVTKS FNRGEC |
| 46 | Human CLk.D$^{77}$H | TVAAPSVFIF PPSDEQLKSG TASVVCLLNN FYPREAKVQW KVDNALQSGN SQESVTEQDS KDSTYSLSST LTLSKAHYEK HKVYACEVTH QGLSSPVTKS FNRGEC |
| 47 | Human CLk.D$^{77}$M | TVAAPSVFIF PPSDEQLKSG TASVVCLLNN FYPREAKVQW KVDNALQSGN SQESVTEQDS KDSTYSLSST LTLSKAMYEK HKVYACEVTH QGLSSPVTKS FNRGEC |
| 48 | Human CLk.D$^{77}$C | TVAAPSVFIF PPSDEQLKSG TASVVCLLNN FYPREAKVQW KVDNALQSGN SQESVTEQDS KDSTYSLSST LTLSKACYEK HKVYACEVTH QGLSSPVTKS FNRGEC |
| 49 | Human CLk.D$^{77}$S | TVAAPSVFIF PPSDEQLKSG TASVVCLLNN FYPREAKVQW KVDNALQSGN SQESVTEQDS KDSTYSLSST LTLSKASYEK HKVYACEVTH QGLSSPVTKS FNRGEC |
| 50 | Human CLk.D$^{77}$T | TVAAPSVFIF PPSDEQLKSG TASVVCLLNN FYPREAKVQW KVDNALQSGN SQESVTEQDS KDSTYSLSST LTLSKATYEK HKVYACEVTH QGLSSPVTKS FNRGEC |
| 51 | Human CLk.D$^{77}$Q | TVAAPSVFIF PPSDEQLKSG TASVVCLLNN FYPREAKVQW KVDNALQSGN SQESVTEQDS KDSTYSLSST LTLSKAQYEK HKVYACEVTH QGLSSPVTKS FNRGEC |

| SEQ | Description | Sequence |
|---|---|---|
| 52 | Human CLk.D$^{77}$N | TVAAPSVFIF PPSDEQLKSG TASVVCLLNN FYPREAKVQW KVDNALQSGN SQESVTEQDS KDSTYSLSST LTLSKANYEK HKVYACEVTH QGLSSPVTKS FNRGEC |
| 53 | Human CLk.D$^{77}$E | TVAAPSVFIF PPSDEQLKSG TASVVCLLNN FYPREAKVQW KVDNALQSGN SQESVTEQDS KDSTYSLSST LTLSKAEYEK HKVYACEVTH QGLSSPVTKS FNRGEC |
| 54 | Human CLk.D$^{77}$R | TVAAPSVFIF PPSDEQLKSG TASVVCLLNN FYPREAKVQW KVDNALQSGN SQESVTEQDS KDSTYSLSST LTLSKARYEK HKVYACEVTH QGLSSPVTKS FNRGEC |
| 55 | Human CLk.D$^{77}$K | TVAAPSVFIF PPSDEQLKSG TASVVCLLNN FYPREAKVQW KVDNALQSGN SQESVTEQDS KDSTYSLSST LTLSKAKYEK HKVYACEVTH QGLSSPVTKS FNRGEC |
| 56 | Human CLk.D$^{43}$A | TVAAPSVFIF PPSDEQLKSG TASVVCLLNN FYPREAKVQW KVANALQSGN SQESVTEQDS KDSTYSLSST LTLSKADYEK HKVYACEVTH QGLSSPVTKS FNRGEC |
| 57 | Human CLλ | GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTEC |
| 58 | mCLκ | ADAAPTVSIF PPSSEQLTSG GASVVCFLNN FYPRDINVKW KIDGSERQNG VLNSWTDQDS KDSTYSMSST LTLTKDEYER HNSYTCEATH KTSTSPIVKS FNRNEC |
| 59 | hAbλTest LC Light chain constant region (lambda) | GQPKAAPSVTLFPPSSEELQANKATLVCLISDFYPGAVTVAWKADSSPVKAGVET TTPSKQSNNKYAASSYLSLTPEQWKSHRSYSCQVTHEGSTVEKTVAPTECS |
| 60 | hAbλTest-λκ | *RTVAAPSVFIEPPSDEQLKSGTASVVCLLNNFYPREAKVQWKVENALQSGNSQES VTEQDSKDSTYSLSSTLTLSKADYEKHKVYACEVTHQGLSSPVTKSFNRGEC* |
| 61 | hAbλTest-λκJ | *KVEIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNRG EC* |
| 62 | hAbλTest S$^{81}$H/H$^{82}$S | GQPKAAPSVTLFPPSSEELQANKATLVCLISDFYPGAVTVAWKADSSPVKAGVET TTPSKQSNNKYAASSYLSLTPEQWKHS**RSYSCQVTHEGSTVEKTVAPTECS |
| 63 | 2.12.1.fx Fab HC | QVQLVESGGG LVKPGGSLRL SCAASGFTFS DYYMSWIRQA PGKGLEWVSY ISSSGSTRDY ADSVKGRFTI SRDNAKNSLY LQMNSLRAED TAVYYCVRDG VETTFYYYYY GMDVWGQGTT VTVSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE |
| 64 | h38C2-IgG1 LC | <u>ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IK</u>RTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 65 | h38C2-IgG1 HC | <u>EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSSAS</u> TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC RAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 66 | h38C2-IgG2 HC | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSSAS TKGPSVFPLA PCSRSTSEST AALGCLVKDY FPEPVTVSWN SGALTSGVHT FPAVLQSSGL YSLSSVVTVT SSNFGTQTYT CNVDHKPSNT KVDKTVERKC CVECPPCPAP PVAGPSVFLF PPKPKDTLMI SRTPEVTCVV VDVSHEDPEV QFNWYVDGVE VHNAKTKPRE EQFNSTFRVV SVLTVVHQDW LNGKEYKCKV SNKGLPSSIE KTISKTKGQP REPQVYTLPP SREEMTKNQV SLTCLVKGFY PSDIAVEWES NGQPENNYKT TPPMLDSDGS FFLYSKLTVD KSRWQQGNVF SCSVMHEALH NHYTQKSLSL SPGK |

-continued

| SEQ | Description | Sequence |
|---|---|---|
| 67 | VL h38C2 | ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IKR |
| 68 | VH h38C2 | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSS |
| 69 | VL m38C2 | DVVMTQTPLS LPVRLGDQAS ISCRSSQSLL HTYGSPYLNW YLQKPGQSPK LLIYKVSNRF SGVPDRFSGS GSGTDFTLRI SRVEAEDLGV YFCSQGTHLP YTFGGGTKLE IK |
| 70 | VH m38C2 | EVKLVESGGG LVQPGGTMKL SCEISGLTFR NYWMSWVRQS PEKGLEWVAE IRLRSDNYAT HYAESVKGKF TISRDDSKSR LYLQMNSLRT EDTGIYYCKY YFYSFSYWGQ GTLVTVSA |
| 71 | Trastuzumab HC | EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 72 | Trastuzumab VH | EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS |
| 73 | Trastuzumab CH | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 74 | Trastuzumab LC | DIQMTQSPSS LSASVGDRVT ITCRASQDVN TAVAWYQQKP GKAPKLLIYS ASFLYSGVPS RFSGSRSGTD FTLTISSLQP EDFATYYCQQ HYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 75 | Trastuzumab VL | DIQMTQSPSS LSASVGDRVT ITCRASQDVN TAVAWYQQKP GKAPKLLIYS ASFLYSGVPS RFSGSRSGTD FTLTISSLQP EDFATYYCQQ HYTTPPTFGQ GTKVEIKR |
| 76 | Trastuzumab CL | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNRGEC |
| 77 | Trastuzumab D77A CL | TVAAPSVFIF PPSDEQLKSG TASVVCLLNN FYPREAKVQW KVDNALQSGN SQESVTEQDS KDSTYSLSST LTLSKAAYEK HKVYACEVTH QGLSSPVTKS FNRGEC |
| 78 | Trastuzumab D77x CL X45 = V/A; X77 = A, G, I, V, L, R, S, T, Q, P, N, M, H, W; X83 = V/L | TVAAPSVFIF PPSDEQLKSG TASVVCLLNN FYPREAKVQW KVDNxLQSGN SQESVTEQDS KDSTYSLSST LTLSKAxYEK HKxYACEVTH QGLSSPVTKS FNRGEC |
| 79 | (Gly$_4$Ser)$_3$ | GGGGSGGGG SGGGGS |
| 80 | Test peptide-1 | GRGDSPK |
| 81 | Test peptide-2 | DVPKSDQFVG LM |
| 82 | Cleavage example | SKADYEK HKVYACEVTH QGLSSPVTKS |
| 83 | Trypsin cleavage product 1 | ADYEK HK |
| 84 | Trypsin cleavage product 2 | HKVYACEVTH QGLSSPVTK |

-continued

| SEQ | Description | Sequence |
|---|---|---|
| 85 | 2.12.1.fx.LC.FOR | CAA CAA GAT CTG CCA CCA TGG ACA TGA GGG T |
| 86 | 2.12.1.fx.LC.REV | CAA CAG CTA GCC TAA CAC TCT CCC CTG TTG A |
| 87 | L181A.FOR | CAA CAG GTC TCG GCC AGC AAA GCA GAC TAC GAG AA |
| 88 | L181A.REV | CAA CAG GTC TCC TGG CCG TCA GGG TGC TGC TGA G |
| 89 | TRAST.VL.FOR | CAA CAG GTC TCA GAT CTG CCA CCA TGG GAT GGA GC |
| 90 | TRAST.VL.REV | CAA CAG GTC TCA TCC GCT TGA TTT CCA CCT TG |
| 91 | TRAST.CL.D185A.FOR | CAA CAG GTC TCA CGG ACC GTG GCC GCT CC |
| 92 | TRAST.CL.D185A.REV | CAA CAG CTA GCC TAT CAG CAC TCG CCC CG |
| 93 | CLλ consensus<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; x80 = K/Q:<br>x83 = K/R; x88 = Q/L;<br>x103 = A/T | GQPKAxPxVT LFPPSSEELQ ANxATLVCLI SDFYPGxVxV AWKADxSPxx<br>xGVETTxPSK QSNNxYAASS YLSLTPEQWx SHxSYSCxVT HEGSTVEKTV<br>APxECS |
| 94 | CLλ consensus<br>S81K<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; x80 = K/Q:<br>x83 = K/R; x88 = Q/L;<br>x103 = A/T | GQPKAxPxVT LFPPSSEELQ ANxATLVCLI SDFYPGxVxV AWKADxSPxx<br>xGVETTxPSK QSNNxYAASS YLSLTPEQWx KHxSYSCxVT HEGSTVEKTV<br>APxECS |
| 95 | CLλ consensus;<br>K80X/S81K<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; x80 = G,<br>A, I, L, V, S, T, M,<br>N, Q, F, Y, W, D, or<br>E x83 = K/R; x88 = Q/L;<br>x103 = A/T | GQPKAxPxVT LFPPSSEELQ ANxATLVCLI SDFYPGxVxV AWKADxSPxx<br>xGVETTxPSK QSNNxYAASS YLSLTPEQWx KHxSYSCxVT HEGSTVEKTV<br>APxECS |
| 96 | CLλ consensus<br>E77x/S81Δ<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; $x^{77}$ =<br>R/L/S/G/Q/P/N/V/I/T/<br>M; x83 = K/R; x88 = Q/L;<br>x103 = A/T | GQPKAxPxVT LFPPSSEELQ ANxATLVCLI SDFYPGxVxV AWKADxSPxx<br>xGVETTxPSK QSNNxYAASS YLSLTPxQWK -HxSYSCxVT HEGSTVEKTV<br>APxECS |
| 97 | CLλ consensus;<br>$E^{77}x/K^{80}X/S^{81}K$<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A; | GQPKAxPxVT LFPPSSEELQ ANxATLVCLI SDFYPGxVxV AWKADxSPxx<br>xGVETTxPSK QSNNxYAASS YLSLTPxQWx KHxSYSCxVT HEGSTVEKTV<br>APxECS |

-continued

| SEQ | Description | Sequence |
|---|---|---|
| | x65 = K/R/N; x77 = R, L, S, G, Q, P, N, V, I, T, and M x80 = G, A, I, L, V, S, T, M, N, Q, F, Y, W, D, or E x83 = K/R; x88 = Q/L; x103 = A/T | |
| 98 | $X^1$ = any aa; $X^2$ = A, G, I, V, L, R, S, T, Q, P, N, M, H, W; $X^3$ = any aa; $X^4$ = any aa. | xxxxKH |
| 99 | $X^1$ = any aa; $X^2$ = A, G, I, L, R, S, T, P, N, M; $X^3$ = any aa; $X^4$ = any aa. | xxxxKH |
| 100 | $X^1$ = any aa; $X^2$ = A, G, I, L, S, T, P, M; $X^3$ = any aa; $X^4$ = any aa. | xxxxKH |
| 101 | $X^3$ = A, G, I, V, L, R, S, T, Q, P, N, M, H, W. | KAxYEKH |
| 102 | $X^3$ = A, G, I, L, R, S, T, P, N, M. | KAxYEKH |
| 103 | $X^3$ = A, G, I, L, S, T, P, M. | KAxYEKH |
| 104 | hCLκ 1-106 $X^{45}$ = V/A $x^{77}$ = A, G, I, V, L, R, S, T, Q, P, N, M, H, W; $X^{82}$ = any AA; $X^{83}$ = L/V | TVAAPSVFIF PPSDEQLKSG TASVVCLLNN FYPREAKVQW KVDNxLQSGN SQESVTEQDS KDSTYSLSST LTLSKAxYEK HxxYACEVTH QGLSSPVTKS FNRGEC |
| 105 | hCLκ 1-106 $X^{45}$ = V/A $x^{77}$ = A, G, I, L, R, S, T, P, N, M; $X^{82}$ = any AA $X^{83}$ = L/V | TVAAPSVFIF PPSDEQLKSG TASVVCLLNN FYPREAKVQW KVDNxLQSGN SQESVTEQDS KDSTYSLSST LTLSKAxYEK HxxYACEVTH QGLSSPVTKS FNRGEC |
| 106 | hCLκ 1-106 $X^{45}$ = V/A $x^{77}$ = A, G, I, L, S, T, P, M; $X^{82}$ = any AA $X^{83}$ = L/V | TVAAPSVFIF PPSDEQLKSG TASVVCLLNN FYPREAKVQW KVDNxLQSGN SQESVTEQDS KDSTYSLSST LTLSKAxYEK HxxYACEVTH QGLSSPVTKS FNRGEC |
| 107 | Human CLk.$D^{43}$E | TVAAPSVFIF PPSDEQLKSG TASVVCLLNN FYPREAKVQW KVENALQSGN SQESVTEQDS KDSTYSLSST LTLSKADYEK HKVYACEVTH QGLSSPVTKS FNRGEC |
| 108 | Human CLk.$D^{43}$N | TVAAPSVFIF PPSDEQLKSG TASVVCLLNN FYPREAKVQW KVNNALQSGN SQESVTEQDS KDSTYSLSST LTLSKADYEK HKVYACEVTH QGLSSPVTKS FNRGEC |
| 109 | Human CLk.$D^{43}$L | TVAAPSVFIF PPSDEQLKSG TASVVCLLNN FYPREAKVQW KVLNALQSGN SQESVTEQDS KDSTYSLSST LTLSKADYEK HKVYACEVTH QGLSSPVTKS FNRGEC |
| 110 | Human CLk.$H^{81}$N | TVAAPSVFIF PPSDEQLKSG TASVVCLLNN FYPREAKVQW KVDNALQSGN SQESVTEQDS KDSTYSLSST LTLSKADYEK NKVYACEVTH QGLSSPVTKS FNRGEC |
| 111 | Human CLk.$H^{81}$Q | TVAAPSVFIF PPSDEQLKSG TASVVCLLNN FYPREAKVQW KVDNALQSGN SQESVTEQDS KDSTYSLSST LTLSKADYEK QKVYACEVTH QGLSSPVTKS FNRGEC |
| 112 | Human CLk.$H^{81}$Y | TVAAPSVFIF PPSDEQLKSG TASVVCLLNN FYPREAKVQW KVDNALQSGN SQESVTEQDS KDSTYSLSST LTLSKADYEK YKVYACEVTH QGLSSPVTKS FNRGEC |

| SEQUENCE LIST | | |
|---|---|---|
| SEQ | Description | Sequence |
| 113 | Human CLκ.H$^{81}$W | TVAAPSVFIF PPSDEQLKSG TASVVCLLNN FYPREAKVQW KVDNALQSGN SQESVTEQDS KDSTYSLSST LTLSKADYEK WKVYACEVTH QGLSSPVTKS FNRGEC |
| 114 | Human CLκ.H$^{81}$F | TVAAPSVFIF PPSDEQLKSG TASVVCLLNN FYPREAKVQW KVDNALQSGN SQESVTEQDS KDSTYSLSST LTLSKADYEK FKVYACEVTH QGLSSPVTKS FNRGEC |
| 115 | $X^1$ = any aa; $X^2$ = any aa; $X^3$ = A, G, I, V, L, R, S, T, Q, P, N, M, H, W; $X^4$ = any aa; $X^5$ = any aa. | xxxxxKH |
| 116 | $X^1$ = any aa; $X^2$ = any aa; $X^3$ = A, G, I, L, R, S, T, P, N, M; $X^4$ = any aa; $X^5$ = any aa. | xxxxxKH |
| 117 | $X^1$ = any aa; $X^2$ = any aa; $X^3$ = A, G, I, L, S, T, P, M; $X^4$ = any aa; $X^5$ = any aa. | xxxxxKH |
| 118 | $X^1$ = any aa; $X^2$ = any aa; $X^3$ = A, G, I, V, L, R, S, T, Q, P, N, M, H, W; $X^4$ = any aromatic amino acid; $X^5$ = any aa. | xxxxxKH |
| 119 | hCLκ 1-106 x43 = D, E, N, Q; $X^{45}$ = V/A; x76 = any aa; $x^{77}$ = A, G, I, V, L, R, S, T, Q, P, N, M, H, W; x78 = any aa; x79 = any aa; $X^{82}$ = any AA; $X^{83}$ = L/V | TVAAPSVFIF PPSDEQLKSG TASVVCLLNN FYPREAKVQW KVDNxLQSGN SQESVTEQDS KDSTYSLSST LTLSKxxxxK HxxYACEVTH QGLSSPVTKS FNRGEC |
| 120 | hCLκ 1-106 x43 = D, E, N, Q; $X^{45}$ = V/A; x76 = any aa; $x^{77}$ = A, G, I, V, L, R, S, T, Q, P, N, M, H, W; x78 = any aromatic aa; x79 = any aa; $X^{82}$ = any AA; $X^{83}$ = L/V | TVAAPSVFIF PPSDEQLKSG TASVVCLLNN FYPREAKVQW KVDNxLQSGN SQESVTEQDS KDSTYSLSST LTLSKxxxxK HxxYACEVTH QGLSSPVTKS FNRGEC |
| 121 | hCLκ 1-106 x43 = D, E, N, Q; $X^{45}$ = V/A; x76 = any aa; $x^{77}$ = A, G, I, L, S, T, P, M; x78 = any aa; x79 = any aa; $X^{82}$ = any AA; $X8^3$ = L/V | TVAAPSVFIF PPSDEQLKSG TASVVCLLNN FYPREAKVQW KVDNxLQSGN SQESVTEQDS KDSTYSLSST LTLSKxxxxK HxxYACEVTHQGLSSPVTKS FNRGEC |
| 122 | hCLκ 1-106 x43 = D, E, N, Q; $X^{45}$ = V/A; x76 = any aa; $x^{77}$ = A, G, I, L, S, T, P, M; x78 = any aromatic aa; x79 = any aa; $X^{82}$ = any AA; $X^{83}$ = L/V | TVAAPSVFIF PPSDEQLKSG TASVVCLLNN FYPREAKVQW KVDNxLQSGN SQESVTEQDS KDSTYSLSST LTLSKxxxxK HxxYACEVTH QGLSSPVTKS FNRGEC |
| 123 | $X^1$ = any aa; $X^2$ = A, G, I, V, L, R, S, T, Q, P, N, M; $X^3$ = any aa; $X^4$ = any aa. | xxxxKH |
| 124 | $X^1$ = any aa; $X^2$ = A, G, I, V, L, R, S, T, P, M; $X^3$ = any aa; $X^4$ = any aa. | xxxxKH |

-continued

| SEQUENCE LIST | | |
|---|---|---|
| SEQ | Description | Sequence |
| 125 | X$^1$ = any aa; X$^2$ = A, G, I, V, L, S, T, M; X$^3$ = any aa; X$^4$ = any aa. | xxxxKH |
| 126 | X$^1$ = any aa; X$^2$ = A, G, I, L, S, T, M; X$^3$ = any aa; X$^4$ = any aa. | xxxxKH |
| 127 | kappa light chain D$^{43}$A/D$^{77}$A | TVAAPSVFIF PPSDEQLKSG TASVVCLLNN FYPREAKVQW KVA̲NALQSGN SQESVTEQDS KDSTYSLSST LTLSKAA̲YEK HKVYACEVTH QGLSSPVTKS FNRGEC |
| 128 | Human CLk D77A/H81A | TVAAPSVFIF PPSDEQLKSG TASVVCLLNN FYPREAKVQW KVDNALQSGN SQESVTEQDS KDSTYSLSST LTLSKAA̲YEK A̲KVYACEVTH QGLSSPVTKS FNRGEC |
| 129 | Human CLk D43A/D77A/H81A | TVAAPSVFIF PPSDEQLKSG TASVVCLLNN FYPREAKVQW KVA̲NALQSGN SQESVTEQDS KDSTYSLSST LTLSKAA̲YEK A̲KVYACEVTH QGLSSPVTKS FNRGEC |
| 130 | Rabbit CLκ | RDPVAPTVLI FPPAADQVAT GTVTIVCVAN KYFPDVTVTW EVD̲GTTQTTG IENSKTPQNS ADCTYNLSST LTLTSTQYNS̲ H̲KEYTCKVTQ GTTSVVQSFN RGDC |
| 131 | Rabbit Constant Heavy Chain rCH | GQPKAPSVFP LAPCCGDTPS STVTLGCLVK GYLPEPVTVT WNSGTLTNGV RTFPSVRQSS GLYSLSSVVS VTSSSQPVTC NVAHPATNTK VDKTVAPSTC SKPTCPPPEL LGGPSVFIFP PKPKDTLMIS RTPEVTCVVV DVSQDDPEVQ FTWYINNEQV RTARPPLREQ QFNSTIRVVS TLPIAHQDWL RGKEFKCKVH NKALPAPIEK TISKARGQPL EPKVYTMGPP REELSSRSVS LTCMINGFYP SDISVEWEKN GKAEDNYKTT PAVLDSDGSY FLYSKLSVPT SEWQRGDVFT CSVMHEALHN HYTQKSISRS PGK |
| 132 | Trastuzumab -rabbit k1 chimera (variable domain) rTrast-LC | _DIQMTQSPSS_ _LSASVGDRVT_ _ITCRASQDVN_ _TAVAWYQQKP_ _GRAPKLLIYS_ _ASFLYSGVPS_ _RFSGSRSGTD_ _FTLTISSLQP_ _EDFATYYCQQ_ _HYTTPPTFGQ_ _GTKVEIK_RDP VAPTVLIFPP AADQVATGTV TIVCVANKYF PDVTVTWEVD GTTQTTGIEN SKTPQNSADC TYNLSSTLTL TSTQYNSHKE YTCKVTQGTT SVVQSFNRGD C |
| 133 | Trastuzumab rabbit IgG chimera (variable domain) rTrast-HC | _EVQLVESGGG_ _LVQPGGSLRL_ _SCAASGFNIK_ _DTYIHWVRQA_ _PGKGLEWVAR_ _IYPTNGYTRY_ _ADSVKGRFTI_ _SADTSKNTAY_ _LQMNSLRAED_ _TAVYYCSRWG_ _GDGFYAMDYW_ _GQGTLVTVSS_ GQPKAPSVFP LAPCCGDTPS STVTLGCLVK GYLPEPVTVT WNSGTLTNGV RTFPSVRQSS GLYSLSSVVS VTSSSQPVTC NVAHPATNTK VDKTVAPSTC SKPTCPPPEL LGGPSVFIFP PKPKDTLMIS RTPEVTCVVV DVSQDDPEVQ FTWYINNEQV RTARPPLREQ QFNSTIRVVS TLPIAHQDWL RGKEFKCKVH NKALPAPIEK TISKARGQPL EPKVYTMGPP REELSSRSVS LTCMINGFYP SDISVEWEKN GKAEDNYKTT PAVLDSDGSY FLYSKLSVPT SEWQRGDVFT CSVMHEALHN HYTQKSISRS PGK |
| 134 | Rabbit CLκ-S80K | RDPVAPTVLI FPPAADQVAT GTVTIVCVAN KYFPDVTVTW EVD̲GTTQTTG IENSKTPQNS ADCTYNLSST LTLTSTQYNK̲ H̲KEYTCKVTQ GTTSVVQSFN RGDC |
| 135 | Trastuzumab -rabbit k1 chimera S188K(variable domain) rTrastLC-[rCLk-S80K] | _DIQMTQSPSS_ _LSASVGDRVT_ _ITCRASQDVN_ _TAVAWYQQKP_ _GRAPKLLIYS_ _ASFLYSGVPS_ _RFSGSRSGTD_ _FTLTISSLQP_ _EDFATYYCQQ_ _HYTTPPTFGQ_ _GTKVEIK_RDP VAPTVLIFPP AADQVATGTV TIVCVANKYF PDVTVTWEVD GTTQTTGIEN SKTPQNSADC TYNLSSTLTL TSTQYNK̲HKE YTCKVTQGTT SVVQSFNRGD C |
| 136 | hIL22 LC | _QAVLTQPPSV_ _SGAPGQRVTI_ _SCTGSSSNIG_ _AGYGVHWYQQ_ _LPGTAPKLLI_ _YGDSNRPSGV_ _PDRFSGSKSG_ _TSASLAITGL_ _QAEDEADYYC_ _QSYDNSLSGY_ _VFGGGTQLTV_ _LG_QPKAAPSV TLFPPSSEEL QANKATLVCL ISDFYPGAVT VAWKADSSPV KAGVETTTPS KQSNNKYAAS SYLSLTPEQW KSHRSYSCQV THEGSTVEKT VAPTECS |
| 137 | hIL22 HC | _QVQLVQSGAE_ _VKKPGASVKV_ _SCKASGYTFT_ _NYYMHWVRQA_ _PGQGLEWVGW_ _INPYTGSAFY_ _AQKFRGRVTM_ _TRDTSISTAY_ _MELSRLRSDD_ _TAVYYCAREP_ _EKFDSDDSDV_ _WGRGTLVTVS_ SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K |

-continued

| SEQ | Description | Sequence |
|---|---|---|
| 138 | hIL22 VL | QAVLTQPPSV SGAPGQRVTI SCTGSSSNIG AGYGVHWYQQ LPGTAPKLLI YGDSNRPSGV PDRFSGSKSG TSASLAITGL QAEDEADYYC QSYDNSLSGY VFGGGTQLTV L |
| 139 | hIL22 lambda constant | GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |
| 140 | hIL22-[CLλ-S⁸¹K] | GQPKA APSVTLFPPS SEELQANKAT LVCLISDFYP GAVTVAWKAD SSPVKAGVET TTPSKQSNNK YAASSYLSLT PEQWKKHRSY SCQVTHEGST VEKTVAPTEC S |
| 141 | hIL22-[CLλ-Q⁷⁸A/S⁸¹K | GQPKA APSVTLFPPS SEELQANKAT LVCLISDFYP GAVTVAWKAD SSPVKAGVET TTPSKQSNNK YAASSYLSLT PEAWKKHRSY SCQVTHEGST VEKTVAPTEC S |
| 142 | hIL22-[CLλA⁴⁴V/S⁸¹K] | GQPKA APSVTLFPPS SEELQANKAT LVCLISDFYP GAVTVAWKVD SSPVKAGVET TTPSKQSNNK YAASSYLSLT PEQWKKHRSY SCQVTHEGST VEKTVAPTEC S |
| 143 | hIL22-[CLλ-A⁴⁴V/Q⁷⁸A/S⁸¹K] | GQPKA APSVTLFPPS SEELQANKAT LVCLISDFYP GAVTVAWKVD SSPVKAGVET TTPSKQSNNK YAASSYLSLT PEAWKKHRSY SCQVTHEGST VEKTVAPTEC S |
| 144 | hIL22-[CLλ-λ⁷⁶⁻⁸⁴/145] | GQPKA APSVTLFPPS SEELQANKAT LVCLISDFYP GAVTVAWKAD SSPVKAGVET TTPSKQSNNK YAASSYLSLT KAAYEKHKVY SCQVTHEGST VEKTVAPTEC S |
| 145 | CLK 9-aa loop | KAAYEKHKV |
| 146 | Trastuzumab LC K188A (variable domain) | *DIQMTQSPSS LSASVGDRVT ITCRASQDVN TAVAWYQQKP GKAPKLLIYS ASFLYSGVPS RFSGSRSGTD FTLTISSLQP EDFATYYCQQ HYTTPPTFGQ GTKVEIK*RTV AAPSVFIFPP SDEQLKSGTA SVVCLLNNFY PREAKVQWKV DNALQSGNSQ ESVTEQDSKD STYSLSSTLT LSKADYEAHK VYACEVTHQG LSSPVTKSFN RGEC |
| 147 | hIGg1-CH1 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKV |
| 148 | hIGgq-CH1-m1 | ASTKGPSVFP LAPSSKSTSG GTAALGCLVK DYFPEPVTVS WNSGALTSGV HTFPAVLQSS GLYSLSSVVT VPSSSEKHKV YICNVNHKPS NTKVDKKV |
| 149 | hIGgq-CH1-m1-D44 | ASTKGPSVFP LAPSSKSTSG GTAALGCLVK DYFPEPVTVS WNSDGALTSG VHTFPAVLQS SGLYSLSSVV TVPSSSEKHK VYICNVNHKP SNTKVDKKV |
| 150 | hIGg1-CH1-m2 | ASTKGPSVFP LAPSSKSTSG GTAALGCLVK DYFPEPVTVS WNSGALTSGV HTFPAVLQSS GLYSLSSVVT VPSSSYEKHK VYICNVNHKP SNTKVDKKV |
| 151 | hIGg1-CH1-m2-D44 | ASTKGPSVFP LAPSSKSTSG GTAALGCLVK DYFPEPVTVS WNSDGALTSG VHTFPAVLQS SGLYSLSSVV TVPSSSYEKH KVYICNVNHK PSNTKVDKKV |
| 152 | hIGg1-CH1 Δ fragment | LGTQT |
| 153 | M1 insert fragment | EKHKV |
| 154 | M2 insert fragment | YEKHKV |
| 155 | hIGg1-CH2 | APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |
| 156 | hIGg1-CH2m | APELLGGPSV FLFPPKPKDT LMISRTPEVT CVVVDVSHED PEVKFNWYVD GVEVHNAKTK PREEQYNSTY RVVSVLTVLH QDWLKHKEYK CKVSNKALPA PIEKTISKAK |
| 157 | hIGg1-H3 | GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 158 | hIGg1-CH3m | GQPREPQVYT LPPSREEMTK NQVSLTCLVK GFYPSDIAVE WESNGQPENN YKTTPPVLDS DGSFFLYSKL TVDKSRWQKH NVFSCSVMHE ALHNHYTQKS LSLSPGK |

| SEQ | Description | Sequence |
|---|---|---|
| 159 | Trastuzumab CH1-m2 | *EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS* ASTKGPSVFP LAPSSKSTSG GTAALGCLVK DYFPEPVTVS WNSGALTSGV HTFPAVLQSS GLYSLSSVVT VPSSSYEKHK VYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 160 | Trastuzumab CH1-m1-D44 | *EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS* ASTKGPSVFP LAPSSKSTSG GTAALGCLVK DYFPEPVTVS WNSDGALTSG VHTFPAVLQS SGLYSLSSVV TVPSSSEKHK VYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 161 | Trastuzumab CH1-m2-D44 | *EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS* ASTKGPSVFP LAPSSKSTSG GTAALGCLVK DYFPEPVTVS WNSDGALTSG VHTFPAVLQS SGLYSLSSVV TVPSSSYEKH KVYICNVNHK PSNTKVDKKV EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 162 | Trastuzumab CH2m | *EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS* ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLKHK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 163 | Trastuzumab CH3m | *EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS* ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QKHNVFSCSV MHEALHNHYT QKSLSLSPGK |
| 164 | Ex4 homologue x2 is Aib X14 = KSH | HxEGTFTSDL SKQxEEEAVR LFIEWLKNGG PSSGAPPPS |
| 165 | hIgG1-CH1-T78K/Q79K/CD loop swap | ASTKGPSVFP LAPSSKSTSG GTAALGCLVK DYFPEPVTVS WKVDNALATS GVHTFPAVLQ SSGLYSLSSV TVTPSSSEKH KVYICNVNHK PSNTKVDKKV |
| 166 | hIgG1-CH1-CD insert | KVDNALA |
| 167 | hIGg1-CH2m-D82A/N85K/G86H | APELLGGPSV FLFPPKPKDT LMISRTPEVT CVVVDVSHED PEVKFNWYVD GVEVHNAKTK PREEQYNSTY RVVSVLTVLH QAWLKHKEYK CKVSNKALPA PIEKTISKAK |
| 168 | hIGg1-CH3m-CD1/EF | GQPREPQVYT LPPSREEMTK NQVSLTCLVK GFYPSDIAVE WEVDGQPENN YKTTPPVLDS DGSFFLYSKL TVDKSAWQKH NVFSCSVMHE ALHNHYTQKS LSLSPGK |
| 169 | hIGg1-CH3m-CD2/EF | GQPREPQVYT LPPSREEMTK NQVSLTCLVK GFYPSDIAVE WELEGQPENN YKTTPPVLDS DGSFFLYSKL TVDKSAWQKH NVFSCSVMHE ALHNHYTQKS LSLSPGK |

| SEQ | Description | Sequence |
|---|---|---|
| 170 | $X^1$ = A, V, L, I, F, W, Y, S, T, M, N, Q, K, R, H, D, E, G, P. $X^2$ = A, G, I, V, L, R, S, T, Q, P, N, M, H, W. $X^3$ = A, V, L, I, F, W, Y, S, T, M, N, Q, K, R, H, D, E, G, P; $X^4$ = A, V, L, I, F, W, Y, S, T, M, N, Q, K, R, H, D, E, G, P; | xxxxKH<br>X1 X3 X4 not cys |
| 171 | $X^1$ = A, V, L, I, F, W, Y, S, T, M, N, Q, K, R, H, D, E, G. $X^2$ = A, G, I, V, L, R, S, T, Q, P, N, M, H, W. $X^3$ = A, V, L, I, F, W, Y, S, T, M, N, Q, K, R, H, D, E, G; $X^4$ = A, V, L, I, F, W, Y, S, T, M, N, Q, K, R, H, D, E, G; | xxxxKH<br>X1 X3 X4 not Cys, Pro |
| 172 | $X^1$ = A, V, L, I, F, W, Y, S, T, M, N, Q, K, R, H, D, E. $X^2$ = A, G, I, V, L, R, S, T, Q, P, N, M, H, W. $X^3$ = A, V, L, I, F, W, Y, S, T, M, N, Q, K, R, H, D, E; $X^4$ = A, V, L, I, F, W, Y, S, T, M, N, Q, K, R, H, D, E; | xxxxKH<br>X1 X3 X4 no Cis, Pro, Gly |
| 173 | $X^1$ =10 A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, S, T, M, N, Q, K, R, H, D, E; $X^4$ = A, V, L, I, F, W, Y, S, T, M, N, Q, K, R, H, D, E; | xxxxKH<br>X1 X3 X4 not C, P, G<br>X3 is not A or V |
| 174 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, M, N, Q, K, R, H, D, E; $X^4$ = A, V, L, I, F, W, Y, S, T, M, N, Q, K, R, H, D, E; | xxxxKH<br>X1 X3 X4 not C, P, G<br>X3 is not A or V, S or T |
| 175 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, N, Q, D, E; | xxxxKH<br>X1 X3 X4 not C, P, G<br>X3 is not A, V, S or T, M, K, R, H |

SEQUENCE LIST

| SEQ | Description | Sequence |
|---|---|---|
| | $X^4$ = A, V, L, I, F, W, Y, S, T, M, N, Q, K, R, H, D, E; | |
| 176 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, $X^4$ = A, V, L, I, F, W, Y, S, T, M, N, Q, K, R, H, D, E; | xxxxKH<br>X1 X3 X4 not C, P, G<br>X3 is not C, G, P, A, V, S or T, M, K, R, H, N, Q, D, or E; |
| 177 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, $X^4$ = A, V, L, I, F, W, Y, S, T, M, N, Q, K, R, H, D, E; | xxxxKH<br>X1 X3 X4 not C, P, G<br>X3 is Y or W |
| 178 | $X^1$ = A, V, L, I, F, W, Y, S, T, M, N, Q, K, R, H, D, E. $X^2$ = A, G, I, V, L, R, S, T, Q, P, N, M, H, W. $X^3$ = A, V, L, I, F, W, Y, S, T, M, N, Q, K, R, H, D, E; $X^4$ = A, V, L, I, S, T, M, N, Q, K, R, H, D, E; | xxxxKH<br>X1 X3 X4 not C, P, G<br>X4 is not F, Y, W |
| 179 | $X^1$ = A, V, L, I, F, W, Y, S, T, M, N, Q, K, R, H, D, E. $X^2$ = A, G, I, V, L, R, S, T, Q, P, N, M, H, W. $X^3$ = A, V, L, I, S, T, M, N, Q, K, R, D, E; $X^4$ = A, V, L, I, F, W, Y, S, T, M, N, Q, K, R, H, D, E; | xxxxKH<br>X1 X3 X4 not C, P, G<br>X4 is not F, W, Y, H |
| 180 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, S, T, M, N, Q, K, R, H, D, E; $X^4$ = A, V, L, I, S, T, M, N, Q, K, R, H, D, E; | xxxxKH<br>X1 X3 X4 not C, P, G<br>X3 is not A or V<br>X4 is not F, Y, W |
| 181 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, M, N, Q, K, R, H, D, E; | xxxxKH<br>X1 X3 X4 not C, P, G<br>X3 is not A or V, S or T<br>X4 is not F, Y, W |

SEQUENCE LIST

| SEQ | Description | Sequence |
|---|---|---|
| | $X^4$ = A, V, L, I, S, T, M, N, Q, K, R, H, D, E; | |
| 182 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, N, Q, D, E; $X^4$ = A, V, L, I, S, T, M, N, Q, K, R, D, E; | xxxxKH<br>X1 X3 X4 not C, P, G<br>X3 is not A, V, S or T, M, K, R, H<br>X4 is not F, Y, W, or H |
| 183 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, $X^4$ = A, V, L, I, S, T, M, N, Q, K, R, D, E; | xxxxKH<br>X1 X3 X4 not C, P, G<br>X3 is not C, G, P, A, V, S or T, M, K, R, H, N, Q, D, or E;<br>X4 is not F, Y, W, or H |
| 184 | $X^1$ = A, V, L, I, F, W, Y, S, T, M, N, Q, K, R, H, D, E. $X^2$ = A, G, I, V, L, R, S, T, Q, P, N, M, H, W. $X^3$ = L, I, F, W, Y, $X^4$ = N, Q, K, R, D, E; | xxxxKH<br>X1 X3 X4 not C, P, G<br>X3 is Y or W<br>X4 is E, K, D, R, N, or Q. |
| 185 | $X^1$ = A, V, L, I, F, W, Y, S, T, M, N, Q, K, R, H, D, E. $X^2$ = A, G, I, V, L, R, S, T, Q, P, N, M, H, W. $X^3$ = A, V, L, I, F, W, Y, S, T, M, N, Q, K, R, H, D, E; $X^4$ = N, Q, K, R, D, E; | xxxxKH<br>X1 X3 X4 not C, P, G<br>X4 is E, K, D, R, N, or Q. |
| 186 | $X^1$ = A, V, L, I, S, T, M, N, Q, K, R, H, D, E. $X^2$ = A, G, I, V, L, R, S, T, Q, P, N, M, H, W. $X^3$ - A, V, L, I, F, W, Y, S, T, M, N, Q, K, R, H, D, E; $X^4$ = A, V, L, I, F, W, Y, S, T, M, N, Q, K, R, H, D, E; | xxxxKH<br>X1 X3 X4 not C, P, G<br>X1 is not aromatic |
| 187 | $X^1$ = A, V, L, I, S, T, M, N, Q, R, H, D, E. $X^2$ = A, G, I, V, L, R, S, T, Q, P, N, M, H, W. $X^3$ = A, V, L, I, F, W, Y, S, T, M, N, Q, K, R, H, D, E; $X^4$ = A, V, L, I, F, W, Y, S, T, M, N, Q, K, R, H, D, E; | xxxxKH<br>X1 X3 X4 not C, P, G<br>X1 is not aromatic or K |

-continued

| SEQUENCE LIST | | |
|---|---|---|
| SEQ | Description | Sequence |
| 188 | $X^1$ = A, V, L, I, S, T, M, N. $X^2$ = A, G, I, V, L, R, S, T, Q, P, N, M, H, W. $X^3$ = A, V, L, I, F, W, Y, S, T, M, N, Q, K, R, H, D, E; $X^4$ = A, V, L, I, F, W, Y, S, T, M, N, Q, K, R, H, D, E; | xxxxKH<br>X1 X3 X4 no c, p, g<br>X1 is not aromatic or K, or charged |
| 189 | $X^1$ = A, V, L, I, M. $X^2$ = A, G, I, V, L, R, S, T, Q, P, N, M, H, W. $X^3$ = A, V, L, I, F, W, Y, S, T, M, N, Q, K, R, H, D, E; $X^4$ = A, V, L, I, F, W, Y, S, T, M, N, Q, K, R, H, D, E; | xxxxKH<br>X1 X3 X4 not C, P, G<br>X1 is hydrophilic |
| 190 | $X^1$ = A, V, L, I, S, T, M, N, Q, K, R, H, D, E. $X^2$ = A, G, I, V, L, R, S, T, Q, P, N, M, H, W. $X^3$ = A, V, L, I, F, W, Y, S, T, M, N, Q, K, R, H, D, E; $X^4$ = A, V, L, I, S, T, M, N, Q, K, R, H, D, E; | xxxxKH<br>X1 X3 X4 not C, P, G<br>X1 is not aromatic<br>X4 is not F, Y, W |
| 191 | $X^1$ = A, V, L, I, S, T, M, N, Q, K, R, H, D, E. $X^2$ = A, G, I, V, L, R, S, T, Q, P, N, M, H, W. $X^3$ = A, V, L, I, S, T, M, N, Q, K, R, D, E; $X^4$ = A, V, L, I, F, W, Y, S, T, M, N, Q, K, R, H, D, E; | xxxxKH<br>X1 X3 X4 not C, P, G<br>X1 is not aromatic<br>X4 is not F, W, Y, H |
| 192 | $X^1$ = A, V, L, I, S, T, M, N, Q, K, R, H, D, E. $X^2$ = A, G, I, V, L, R, S, T, Q, P, N, M, H, W. $X^3$ = L, I, F, W, Y, S, T, M, N, Q, K, R, H, D, E; $X^4$ = A, V, L, I, S, T, M, N, Q, K, R, H, D, E; | xxxxKH<br>X1 X3 X4 not C, P, G<br>X1 is not aromatic<br>X3 is not A or V<br>X4 is not F, Y, W |
| 193 | $X^1$ = A, V, L, I, S, T, M, N, Q, R, H, D, E. $X^2$ = A, G, I, V, L, R, S, T, Q, P, N, M, H, W. $X^3$ = L, I, F, W, Y, M, N, Q, K, R, H, D, E; $X^4$ = A, V, L, I, S, T, M, N, Q, K, R, H, D, E; | xxxxKH<br>X1 X3 X4 not C, P, G<br>X1 is not aromatic or K<br>X3 is not A or V, S or T<br>X4 is not F, Y, W |

| SEQ | Description | Sequence |
|---|---|---|
| 194 | $X^1$ = A, V, L, I, S, T, M, N, Q. $X^2$ = A, G, I, V, L, R, S, T, Q, P, N, M, H, W. $X^3$ = L, I, F, W, Y, N, Q, D, E; $X^4$ = A, V, L, I, S, T, M, N, Q, K, R, D, E; | xxxxKH X1 X3 X4 not C, P, G X1 is not aromatic, K or charged X3 is not A, V, S or T, M, K, R, H X4 is not F, Y, W, or H |
| 195 | $X^1$ = A, V, L, I. $X^2$ = A, G, I, V, L, R, S, T, Q, P, N, M, H, W. $X^3$ = L, I, F, W, Y, $X^4$ = A, V, L, I, S, T, M, N, Q, K, R, D, E; | xxxxKH X1 X3 X4 not C, P, G X1 is hydrophilic X3 is not C, G, P, A, V, S or T, M, K, R, H, N, Q, D, or E; X4 is not F, Y, W, or H |
| 196 | $X^1$ = A, V, L, I. $X^2$ = A, G, I, V, L, R, S, T, Q, P, N, M, H, W. $X^3$ = L, I, F, W, Y, $X^4$ = N, Q, K, R, D, E; | xxxxKH X1 X3 X4 not C, P, G X1 is hydrophilic X3 is Y or W X4 is E, K, D, R, N, or Q. |
| 197 | $X^1$ = A, V, L, I, F, W, Y, S, T, M, N, Q, K, R, H, D, E. $X^2$ = A, G, I, V, L, R, S, T, Q, P, N, M, H. $X^3$ = A, V, L, I, F, W, Y, S, T, M, N, Q, K, R, H, D, E; $X^4$ = A, V, L, I, S, T, M, N, Q, K, R, H, D, E; | xxxxKH X1 X3 X4 not C, P, G X2 = is not W X4 is not F, Y, W |
| 198 | $X^1$ = A, V, L, I, F, W, Y, S, T, M, N, Q, K, R, H, D, E. $X^2$ = A, G, I, V, L, R, S, T, Q, P, N, M, H, W. $X^3$ = A, V, L, I, S, T, M, N, Q, K, R, D, E; $X^4$ = A, V, L, I, F, W, Y, S, T, M, N, Q, K, R, H, D, E; | xxxxKH X1 X3 X4 not C, P, G X2 is not W X4 is not F, W, Y, H |
| 199 | $X^1$ = A, V, L, I, F, W, Y, S, T, M, N, Q, K, R, H, D, E, G, P. $X^2$ = A, G, I, V, L, R, S, T, Q, P, N, M, H, W. $X^3$ = A, V, L, I, F, W, Y, S, T, M, N, Q, K, R, H, D, E, G, P; $X^4$ = A, V, L, I, F, W, Y, S, T, M, N, Q, K, R, H, D, E, G, P; | xxxxKH X1 X3 X4 not C, P, G X2 is not W |
| 200 | $X^1$ = A, V, L, I, F, W, Y, S, T, M, N, Q, K, R, H, D, E, G. $X^2$ = A, G, I, V, L, R, S, T, Q, P, N, M, H, W. $X^3$ = A, V, L, I, F, W, Y, S, T, M, N, Q, | xxxxKH X1 X3 X4 not C, P, G X2 is not W |

-continued

| SEQ | Description | Sequence |
|---|---|---|
| | K, R, H, D, E, G;<br>X⁴ = A, V, L, I, F,<br>W, Y, S, T, M, N, Q,<br>K, R, H, D, E, G; | |
| 201 | X¹ = A, V, L, I, F,<br>W, Y, S, T, M, N, Q,<br>K, R, H, D, E.<br>X² = A, G, I, V, L,<br>R, S, T, Q, P, N, M,<br>H, W.<br>X³ = A, V, L, I, F,<br>W, Y, S, T, M, N, Q,<br>K, R, H, D, E;<br>X⁴ = A, V, L, I, F,<br>W, Y, S, T, M, N, Q,<br>K, R, H, D, E; | xxxxKH<br>X1 X3 X4 not C P, G<br>X2 is not W |
| 202 | X¹ = A, V, L, I, F,<br>W, Y, S, T, M, N, Q,<br>K, R, H, D, E.<br>X² = A, G, I, V, L,<br>R, S, T, Q, P, N, M,<br>H, W.<br>X³ = L, I, F, W, Y,<br>S, T, M, N, Q, K, R,<br>H, D, E;<br>X⁴ = A, V, L, I, F,<br>W, Y, S, T, M, N, Q,<br>K, R, H, D, E; | xxxxKH<br>X1 X3 X4 not C P, G<br>X2 is not W<br>X3 is not A or V |
| 203 | X¹ = A, V, L, I, F,<br>W, Y, S, T, M, N, Q,<br>K, R, H, D, E.<br>X² = A, G, V, S, T,<br>Q, P, N, M, H.<br>X³ = L, I, F, W, Y,<br>M, N, Q, K, R, H, D,<br>E;<br>X⁴ = A, V, L, I, F,<br>W, Y, S, T, M, N, Q,<br>K, R, H, D, E; | xxxxKH<br>X1 X3 X4 not C P, G<br>X2 is not W, I, L, R<br>X3 is not A or V, S or T |
| 204 | X¹ = A, V, L, I, F,<br>W, Y, S, T, M, N, Q,<br>K, R, H, D, E.<br>X² = A, G, V, S, T,<br>Q, P, N, M, H.<br>X³ = L, I, F, W, Y,<br>N, Q, D, E;<br>X⁴ = A, V, L, I, F,<br>W, Y, S, T, M, N, Q,<br>K, R, H, D, E; | xxxxKH<br>X1 X3 X4 not C P, G<br>X2 is not W, I, L, R<br>X3 is not A, V, S or T, M, K, R, H |
| 205 | X¹ = A, V, L, I, F,<br>W, Y, S, T, M, N, Q,<br>K, R, H, D, E.<br>X² = A, G, S, T, P,<br>M.<br>X³ = L, I, F, W, Y,<br>X⁴ = A, V, L, I, F,<br>W, Y, S, T, M, N, Q,<br>K, R, H, D, E; | xxxxKH<br>X1 X3 X4 not C P, G<br>X2 is A, G, P, S, T, M<br>X3 is not C, G, P, A, V, S or T, M, K, R, H, N, Q, D,<br>or E; |
| 206 | X¹ = A, V, L, I, F,<br>W, Y, S, T, M, N, Q,<br>K, R, H, D, E.<br>X² = A, G, S, T, P,<br>M.<br>X³ = L, I, F, W, Y,<br>X⁴ = A, V, L, I, F,<br>W, Y, S, T, M, N, Q,<br>K, R, H, D, E; | xxxxKH<br>X1 X3 X4 not C P, G<br>X2 is A, G, P, S, T, M<br>X3 is Y or W |

-continued

| SEQUENCE LIST | | |
|---|---|---|
| SEQ | Description | Sequence |
| 207 | $X^1$ = A, V, L, I, F, W, Y, S, T, M, N, Q, K, R, H, D, E. $X^2$ = A, G, S, T, P, M. $X^3$ = L, I, F, W, Y, S, T, M, N, Q, K, R, H, D, E; $X^4$ = A, V, L, I, S, T, M, N, Q, K, R, H, D, E; | xxxxKH<br>X1 X3 X4 not C, P, G<br>X2 is A, G, P, S, T, M<br>X3 is not A or V<br>X4 is not F, Y, W |
| 208 | $X^1$ = A, V, L, I, F, W, Y, S, T, M, N, Q, K, R, H, D, E. $X^2$ = A, G, S, T, P, M. $X^3$ = L, I, F, W, Y, M, N, Q, K, R, H, D, E; $X^4$ = A, V, L, I, S, T, M, N, Q, K, R, H, D, E; | xxxxKH<br>X1 X3 X4 not C, P, G<br>X2 is A, G, P, S, T, M<br>X3 is not A or V, S or T<br>X4 is not F, Y, W |
| 209 | $X^1$ = A, V, L, I, F, W, Y, S, T, M, N, Q, K, R, H, D, E. $X^2$ = A, G, S, T, P, M. $X^3$ = L, I, F, W, Y, N, Q, D, E; $X^4$ = A, V, L, I, S, T, M, N, Q, K, R, D, E; | xxxxKH<br>X1 X3 X4 not C, P, G<br>X2 is A, G, P, S, T, M<br>X3 is not A, V, S or T, M, K, R, H<br>X4 is not F, Y, W, or H |
| 210 | $X^1$ = A, V, L, I, F, W, Y, S, T, M, N, Q, K, R, H, D, E. $X^2$ = A, G, S, T, P, M. $X^3$ = L, I, F, W, Y, $X^4$ = A, V, L, I, S, T, M, N, Q, K, R, D, E; | xxxxKH<br>X1 X3 X4 not C, P, G<br>X2 is A, G, P, M, S, T<br>X3 is not C, G, P, A, V, S or T, M, K, R, H, N, Q, D, or E;<br>X4 is not F, Y, W, or H |
| 211 | $X^1$ = A, V, L, I, F, W, Y, S, T, M, N, Q, K, R, H, D, E. $X^2$ = A, G, S, T, P, M. $X^3$ = L, I, F, W, Y, $X^4$ = N, Q, K, R, D, E; | xxxxKH<br>X1 X3 X4 not C, P, G<br>X2 is A, G, P, M, S, T<br>X3 is Y or W<br>X4 is E, K, D, R, N, or Q. |
| 212 | $X^1$ = A, V, L, I, F, W, Y, S, T, M, N, Q, K, R, H, D, E. $X^2$ = A, G, I, V, L, S, T, Q, P, N, M, H. $X^3$ = A, V, L, I, F, W, Y, S, T, M, N, Q, K, R, H, D, E; $X^4$ = N, Q, K, R, D, E; | xxxxKH<br>X1 X3 X4 not C, P, G<br>X2 is not W or R,<br>X4 is E, K, D, R, N, or Q. |
| 213 | $X^1$ = A, V, L, I, S, T, M, N, Q, K, R, H, D, E. $X^2$ = A, G, I, V, L, S, T, Q, P, N, M, H. $X^3$ = A, V, L, I, F, W, Y, S, T, M, N, Q, K, R, H, D, E; | xxxxKH<br>X1 X3 X4 not C, P, G<br>W2 is not W or R<br>X1 is not aromatic |

-continued

| SEQUENCE LIST | | |
|---|---|---|
| SEQ | Description | Sequence |
| | $X^4$ = A, V, L, I, F, W, Y, S, T, M, N, Q, K, R, H, D, E; | |
| 214 | $X^1$ = A, V, L, I, S, T, M, N, Q, R, H, D, E.<br>$X^2$ = A, G, I, V, L, S, T, Q, P, N, M, H.<br>$X^3$ = A, V, L, I, F, W, Y, S, T, M, N, Q, K, R, H, D, E;<br>$X^4$ = A, V, L, I, F, W, Y, S, T, M, N, Q, K, R, H, D, E; | xxxxKH<br>X1 X3 X4 not C, P, G<br>X1 is not aromatic or K<br>X2 is not W or R |
| 215 | $X^1$ = A, V, L, I, S, T, M, N.<br>$X^2$ = A, G, I, V, L, S, T, Q, P, N, M, H.<br>$X^3$ = A, V, L, I, F, W, Y, S, T, M, N, Q, K, R, H, D, E;<br>$X^4$ = A V, L, I, F, W, Y, S, T, M, N, Q, K, R, H, D, E; | xxxxKH<br>X1 X3 X4 not C, P, G<br>X1 is not aromatic or K, or charged<br>X2 = is not W or R |
| 216 | $X^1$ = A, V, L, I, M.<br>$X^2$ = A, G, I, V, L, S, T, Q, P, N, M, H.<br>$X^3$ = A, V, L, I, F, W, Y, S, T, M, N, Q, K, R, H, D, E;<br>$X^4$ = A, V, L, I, F, W, Y, S, T, M, N, Q, K, R, H, D, E; | xxxxKH<br>X1 X3 X4 not C, P, G<br>X1 is hydrophilic<br>X2 is not W or R |
| 217 | $X^1$ = A, V, L, I, S, T, M, N, Q, K, R, H, D, E.<br>$X^2$ = A, G, I, V, L, S, T, Q, P, N, M, H.<br>$X^3$ = A, V, L, I, F, W, Y, S, T, M, N, Q, K, R, H, D, E;<br>$X^4$ = A, V, L, I, S, T, M, N, Q, K, R, H, D, E; | xxxxKH<br>X1 X3 X4 not C, P, G<br>X1 is not aromatic<br>X2 is not W or R<br>X4 is not F, Y, W |
| 218 | $X^1$ = A, V, L, I, S, T, M, N, Q, K, R, H, D, E.<br>$X^2$ = A, G, I, V, L, S, T, Q, P, N, M, H.<br>$X^3$ = A, V, L, I, S, T, M, N, Q, K, R, D, E;<br>$X^4$ = A, V, L, I, F, W, Y, S, T, M, N, Q, K, R, H, D, E; | xxxxKH<br>X1 X3 X4 not C, P, G<br>X1 is not aromatic<br>X2 is not W, or R<br>X4 is not F, W, Y, H |
| 219 | $X^1$ = A, V, L, I, S, T, M, N, Q, K, R, H, D, E.<br>$X^2$ = A, G, I, V, L, S, T, Q, P, N, M, H.<br>$X^3$ = L, I, F, W, Y, S, T, M, N, Q, K, R, H, D, E;<br>$X^4$ = A, V, L, I, S, T, M, N, Q, K, R, H, D, E; | xxxxKH<br>X1 X3 X4 not C, P, G<br>X1 is not aromatic<br>Is not W or R<br>X3 is not A or V<br>X4 is not F, Y, W |
| 220 | $X^1$ = A, V, L, I, S, T, M, N, Q, R, H, D, | xxxxKH<br>X1 X3 X4 not C, P, G |

-continued

| SEQUENCE LIST | | |
|---|---|---|
| SEQ | Description | Sequence |
| | E.<br>$X^2$ = A, G, I, V, L, S, T, Q, P, N, M, H.<br>$X^3$ = L, I, F, W, Y, M, N, Q, K, R, H, D, E;<br>$X^4$ = A, V, L, I, S, T, M, N, Q, K, R, H, D, E; | X1 is not aromatic or K<br>X2 is not W or R<br>X3 is not A or V, S or T<br>X4 is not F, Y, W |
| 221 | $X^1$ = A, V, L, I, S, T, M, N, Q.<br>$X^2$ = A, G, S, T, M.<br>$X^3$ = L, I F, W, Y, N, Q, D, E;<br>$X^4$ = A, V, L, I, S, T, M, N, Q, K, R, D, E; | xxxxKH<br>X1 X3 X4 not C, P, G<br>X1 is not aromatic, K or charged<br>X2 is A, G, P, S, T, M<br>X3 is not A, V, S or T, M, K, R, H<br>X4 is not F, Y, W, or H |
| 222 | $X^1$ = A, V, L, I.<br>$X^2$ = A, G, S, T, M.<br>$X^3$ = L, I, F, W, Y,<br>$X^4$ = A, V, L, I, S, T, M, N, Q, K, R, D, E; | xxxxKH<br>X1 X3 X4 not C, P, G<br>X1 is hydrophilic<br>X2 is A, G, P, S, T, M<br>X3 is not C, G, P, A, V, S or T, M, K, R, H, N, Q, D, or E;<br>X4 is not F, Y, W, or H |
| 223 | $X^1$ = A, V, L, I.<br>$X^2$ = A, G, S, T, M.<br>$X^3$ = L, I, F, W, Y,<br>$X^4$ = N, Q, K, R, D, E; | xxxxKH<br>X1 X3 X4 not C, P, G<br>X2 is A, G, P, S, T, M<br>X1 is hydrophilic<br>X3 is Y or W<br>X4 is E, K, D, R, N, or Q. |
| 224 | $X^1$ = A, V, L, I, F, W, Y, S, T, M, N, Q, K, R, H, D, E.<br>$X^2$ = A, G, S, T, M.<br>$X^3$ = L, I, F, W, Y, N, Q, D, E;<br>$X^4$ = A, V, L, I, S, T, M, N, Q, K, R, D, E; | xxxxKH<br>X1 X3 X4 not C, P, G<br>X2 is A, G, P, S, T, M<br>X3 is not A, V, S or T, M, K, R, H<br>X4 is not F, Y, W, or H |
| 225 | hCLκ 1-75 x42-V, I, L, x43 = D, E, N, Q; $X^{45}$ = V/A; x75-any amino acid | TVAAPSVFIF PPSDEQLKSG TASVVCLLNN FYPREAKVQW KxxNxLQSGN SQESVTEQDS KDSTYSLSST LTLSx |
| 226 | hCLK 81-106 $X^1$ = any AA; $X^2$ = L/V | xxYACEVTH QGLSSPVTKS FNRGEC |
| 227 | CLλ consensus 1-76<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; | GQPKAxPxVT LFPPSSEELQ ANxATLVCLI SDFYPGxVxV AWKADxSPxx xGVETTxPSK QSNNxYAASS YLSLTP |
| 228 | CLλ consensus 1-76, x44 inc A<br>X6 = N/A; X8 = S/T;<br>x23 = K/S/R/Q/E;<br>x37 = A/V; X39 = T/K;<br>X44 is A, V, I, L<br>X46 = S/G; x49 = V/A/I;<br>x50 = K/E; x51 = A/T;<br>x57 = T/K/A;<br>x65 = K/R/N; | GQPKAxPxVT LFPPSSEELQ ANxATLVCLI SDFYPGxVxV AWKxDxSPxx xGVETTxPSK QSNNxYAASS YLSLTP |
| 229 | CLλ consensus 1-76, X44 no A | GQPKAxPxVT LFPPSSEELQ ANxATLVCLI SDFYPGxVxV AWKxDxSPxx xGVETTxPSK QSNNxYAASS YLSLTP |

SEQUENCE LIST

| SEQ | Description | Sequence |
|---|---|---|
| | X6 = N/A; X8 = S/T;<br>x23 = K/S/R/Q/E;<br>x37 = A/V; X39 = T/K;<br>x44 = V, I L<br>X46 = S/G; x49 = V/A/I;<br>x50 = K/E; x51 = A/T;<br>x57 = T/K/A;<br>x65 = K/R/N; | |
| 230 | CLλ consensus<br>1-76, X44 = V<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; | GQPKAxPxVT LFPPSSEELQ ANxATLVCLI SDFYPGxVxV AWKVDxSPxx<br>xGVETTxPSK QSNNxYAASS YLSLTP |
| 231 | CLλ 1-76<br>X44 is A, V, I, L | GQPKAAPSVT LFPPSSEELQ ANKATLVCLI SDFYPGAVTV AWKxDSSPVK<br>AGVETTTPSK QSNNKYAASS YLSLTP |
| 232 | CLλ 1-76<br>X44 is V, I, L | GQPKAAPSVT LFPPSSEELQ ANKATLVCLI SDFYPGAVTV AWKxDSSPVK<br>AGVETTTPSK QSNNKYAASS YLSLTP |
| 233 | CLλ 1-76<br>X44 is V | GQPKAAPSVT LFPPSSEELQ ANKATLVCLI SDFYPGAVTV AWKVDSSPVK<br>AGVETTTPSK QSNNKYAASS YLSLTP |
| 234 | CLλ consensus 83-103<br>x1 = K/R; x6 = Q/L;<br>x21 = A/T | xSYSCxVTHE GSTVEKTVAP xECS |
| 235 | CLλ 83-103 | RSYSCQVTHE GSTVEKTVAP TECS |
| 236 | CLλ consensus<br>S81K, x44 = AVIL,<br>X6 = N/A; X8 = S/T;<br>x23 = K/S/R/Q/E;<br>x37 = A/V; X39 = T/K;<br>x44 A, V, I, L<br>X46 = S/G; x49 = V/A/I;<br>x50 = K/E; x51 = A/T;<br>x57 = T/K/A;<br>x65 = K/R/N; Q78 = A/Q<br>x80 = K/Q; x83 = K/R;<br>x88 = Q/L; x103 = A/T | GQPKAxPxVT LFPPSSEELQ ANxATLVCLI SDFYPGxVxV AWKxDxSPxx<br>xGVETTxPSK QSNNxYAASS YLSLTPExWx KHxSYSCxVT HEGSTVEKTV<br>APxECS |
| 237 | CLλ consensus<br>S81K, X44 = VIL,<br>X6 = N/A; X8 = S/T;<br>x23 = K/S/R/Q/E;<br>x37 = A/V; X39 = T/K;<br>x44 V, I, L<br>X46 = S/G; x49 = V/A/I;<br>x50 = K/E; x51 = A/T;<br>x57 = T/K/A;<br>x65 = K/R/N; X78 = A/Q<br>x80 = K/Q; x83 = K/R;<br>x88 = Q/L; x103 = A/T | GQPKAxPxVT LFPPSSEELQ ANxATLVCLI SDFYPGxVxV AWKxDxSPxx<br>xGVETTxPSK QSNNxYAASS YLSLTPExWx KHxSYSCxVT HEGSTVEKTV<br>APxECS |
| 238 | CLλ consensus<br>S81K, x44 = V,<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; x78 = A/Q<br>x80 = K/Q; x83 = K/R;<br>x88 = Q/L; x103 = A/T | GQPKAxPxVT LFPPSSEELQ ANxATLVCLI SDFYPGxVxV AWKVDxSPxx<br>xGVETTxPSK QSNNxYAASS YLSLTPExWx KHxSYSCxVT HEGSTVEKTV<br>APxECS |
| 239 | CLλ consensus<br>S81K, x44 = AVIL, A78<br>X6 = N/A; X8 = S/T; | GQPKAxPxVT LFPPSSEELQ ANxATLVCLI SDFYPGxVxV AWKxDxSPxx<br>xGVETTxPSK QSNNxYAASS YLSLTPEAWx KHxSYSCxVT HEGSTVEKTV<br>APxECS |

SEQUENCE LIST

| SEQ | Description | Sequence |
|---|---|---|
| | x23 = K/S/R/Q/E;<br>x37 = A/V; X39 = T/K;<br>x44 A, V, I, L<br>X46 = S/G; x49 = V/A/I;<br>x50 = K/E; x51 = A/T;<br>x57 = T/K/A;<br>x65 = K/R/N;<br>x80 = K/Q; x83 = K/R;<br>x88 = Q/L; x103 = A/T | |
| 240 | CLλ consensus<br>S81K, X44 = VIL, A78<br>X6 = N/A; X8 = S/T;<br>x23 = K/S/R/Q/E;<br>x37 = A/V; X39 = T/K;<br>x44 V, I, L<br>X46 = S/G; x49 = V/A/I;<br>x50 = K/E; x51 = A/T;<br>x57 = T/K/A;<br>x65 = K/R/N; x80 = K/Q:<br>x83 = K/R; x88 = Q/L;<br>x103 = A/T | GQPKAxPxVT LFPPSSEELQ ANxATLVCLI SDFYPGxVxV AWKxDxSPxx xGVETTxPSK QSNNxYAASS YLSLTPEAWx KHxSYSCxVT HEGSTVEKTV APxECS |
| 241 | CLλ consensus<br>S81K, x44 = V, A78<br>X6 = N/A; X8 = S/T;<br>x23 = K/S/R/Q/E;<br>x37 = A/V; X39 = T/K;<br>X46 = S/G; x49 = V/A/I;<br>x50 = K/E; x51 = A/T;<br>x57 = T/K/A;<br>x65 = K/R/N; x80 = K/Q:<br>x83 = K/R; x88 = Q/L;<br>x103 = A/T | GQPKAxPxVT LFPPSSEELQ ANxATLVCLI SDFYPGxVxV AWKVDxSPxx xGVETTxPSK QSNNxYAASS YLSLTPEAWx KHxSYSCxVT HEGSTVEKTV APxECS |
| 242 | CLλ<br>X44 is A, V, I, L<br>X78 is A. | GQPKAAPSVT LFPPSSEELQ ANKATLVCLI SDFYPGAVTV AWKxDSSPVK AGVETTTPSK QSNNKYAASS YLSLTPExWK KHRSYSCQVT HEGSTVEKTV APTECS |
| 243 | CLλ<br>X44 is V, I, L<br>X78 is A | GQPKAAPSVT LFPPSSEELQ ANKATLVCLI SDFYPGAVTV AWKxDSSPVK AGVETTTPSK QSNNKYAASS YLSLTPExWK KHRSYSCQVT HEGSTVEKTV APTECS |
| 244 | CLλ<br>X44 is V<br>X78 is A | GQPKAAPSVT LFPPSSEELQ ANKATLVCLI SDFYPGAVTV AWKVDSSPVK AGVETTTPSK QSNNKYAASS YLSLTPExWK KHRSYSCQVT HEGSTVEKTV APTECS |
| 245 | CD motif<br>X1 is V, I or L<br>X2 is D, N, Q, E<br>X3, x4 is any AA | xxxx |
| 246 | CD motif<br>X1 is V or I<br>X2 is D, N, Q, E<br>X3, x4 is any AA | xxxx |
| 247 | CD motif<br>X2 is D, N, Q, E X3,<br>x4 is any AA | Vxxx |
| 248 | CD motif<br>X1 is V, I or L<br>X2 is D, or N<br>X3, x4 is any AA | xxxx |
| 249 | CD motif<br>X1 is V, I or L<br>X2 is Q or E<br>X3, x4 is any AA | xxxx |
| 250 | CD motif<br>X1 is V, I or L<br>X3, x4 is any AA | xDxx |

SEQUENCE LIST

| SEQ | Description | Sequence |
|---|---|---|
| 251 | CD motif<br>X3, x4 is any AA | VDxx |
| 252 | CD motif<br>X3, x4 is any AA | LExx |
| 253 | CD motif<br>X3, x4 is any AA | IExx |
| 254 | h38C2-[LC-D185A] | ELQMTQSPSS LSASVGDRVT ITCRSSQSLL HTYGSPYLNW YLQKPGQSPK<br>LLIYKVSNPF SGVPSRFSGS GSGTDFTLTI SSLQPEDFAV YFCSQGTHLP<br>YTFGGGTKVE IKRTVAAPSV FIFPPSDEQL KSGTASVVCL LNNFYPREAK<br>VQWKVDNALQ SGNSQESVTE QDSKDSTYSL SSTLTLSKAA YEKHKVYACE<br>VTHQGLSSPV TKSFNRGEC |
| 255 | CD motif<br>X1, x2, x3, x4 = any amino acid | xxxx |

DETAILED DESCRIPTION OF FIGURES

Figure 1B:
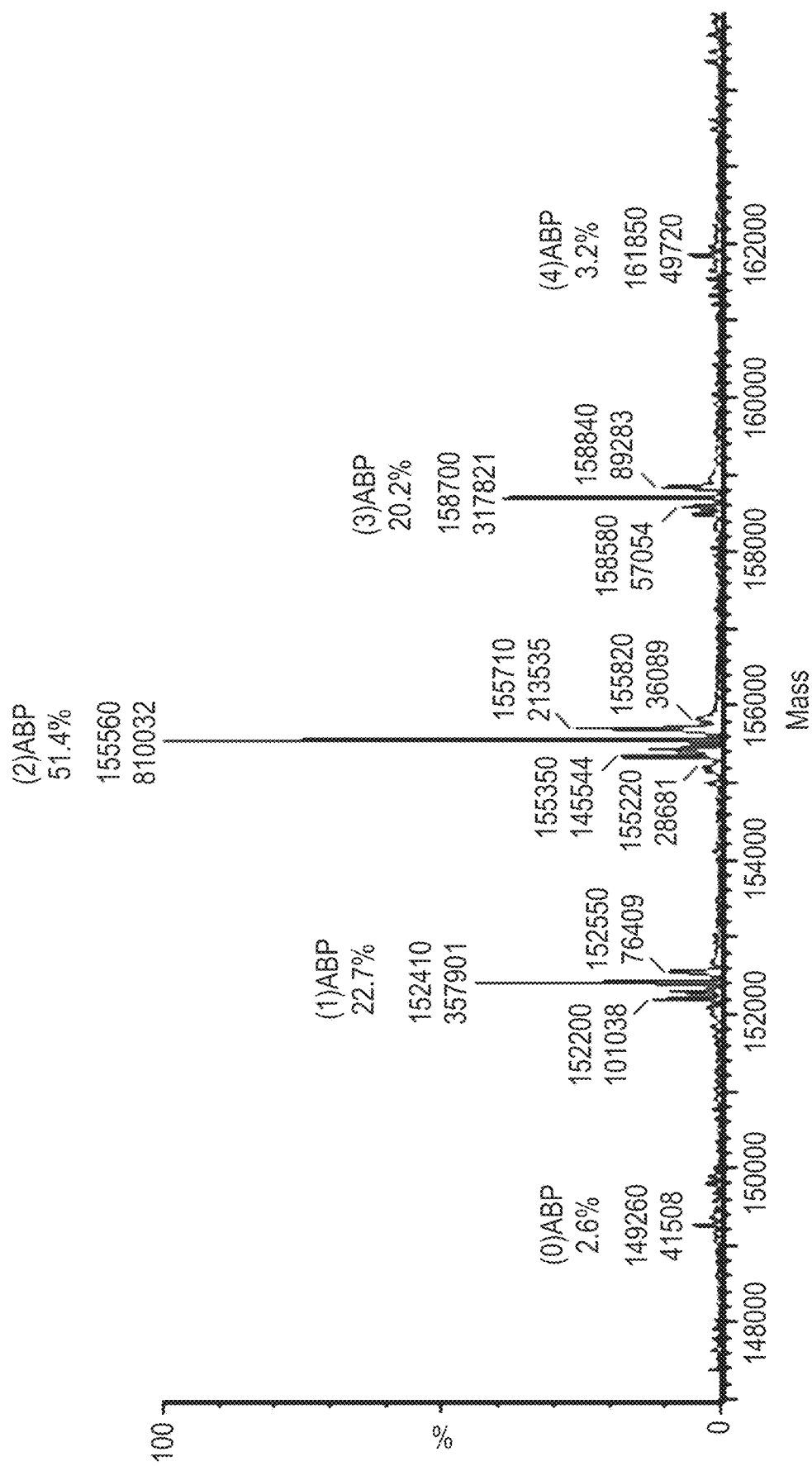
Figure 1C:
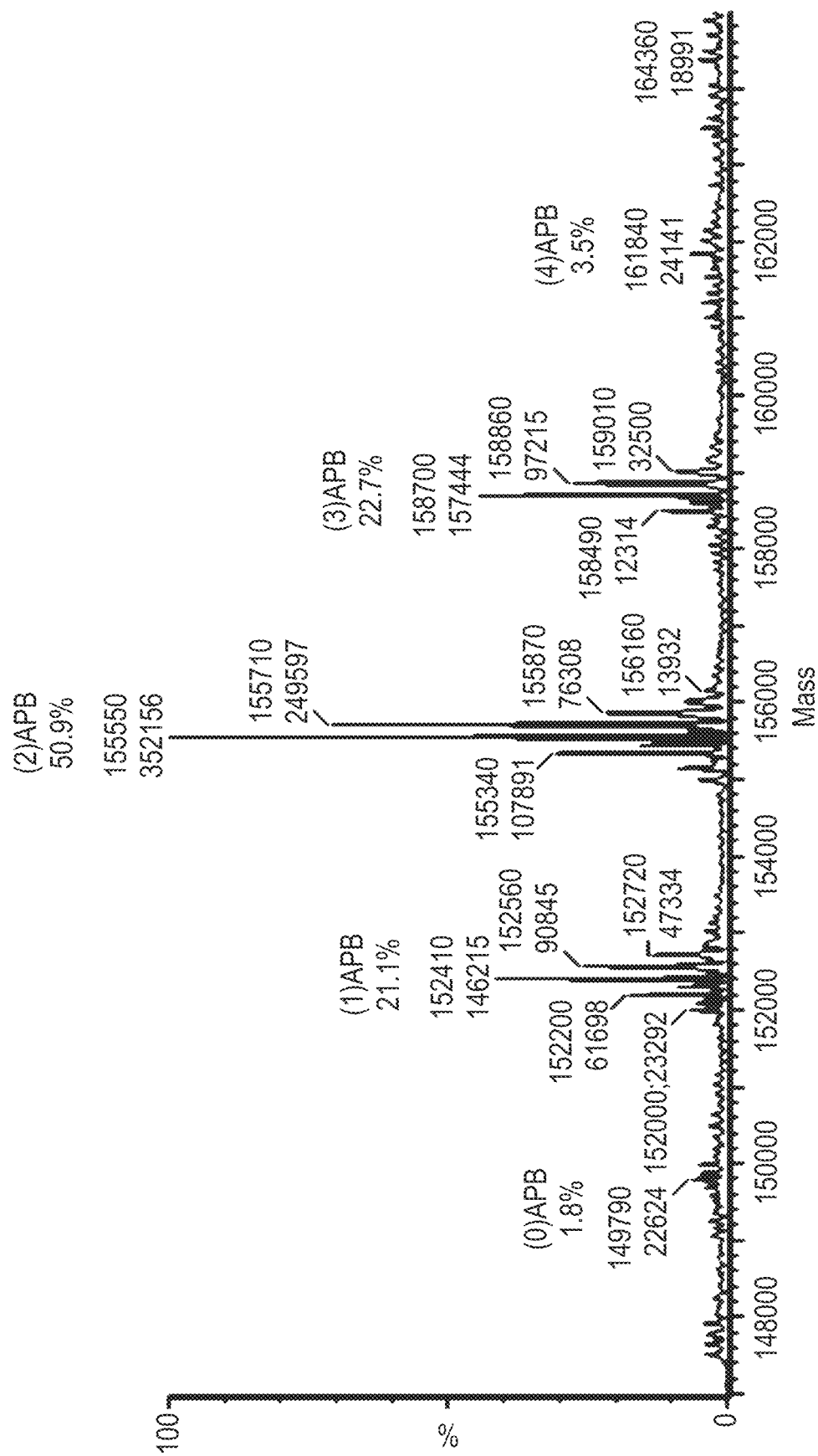

FIGS. 1A, 1B, 1C, and 1D: Intact molecular weight analysis of MAC by mass spectrometry demonstrates that multiple peptides are attached to the anti-IGF1R antibody 2.12.1.fx. FIG. 1A: mass spectrometry data of anti-IGF1R antibody 2.12.1.fx. FIG. 1B-1D: mass spectrometry data of MAC-2, showing replicate experiments of 3 individual lots.

Figure 2A:
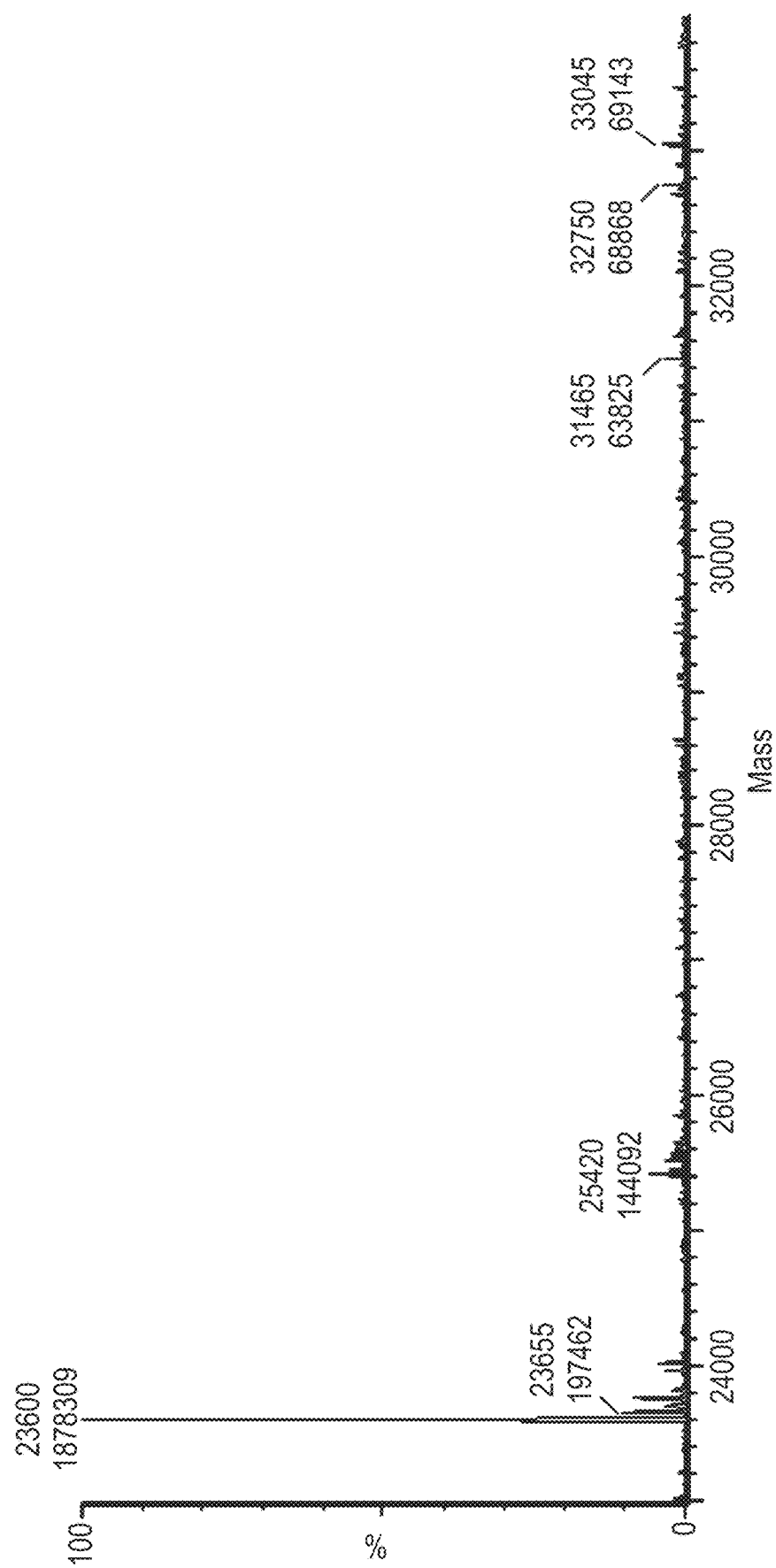
Figure 2B:
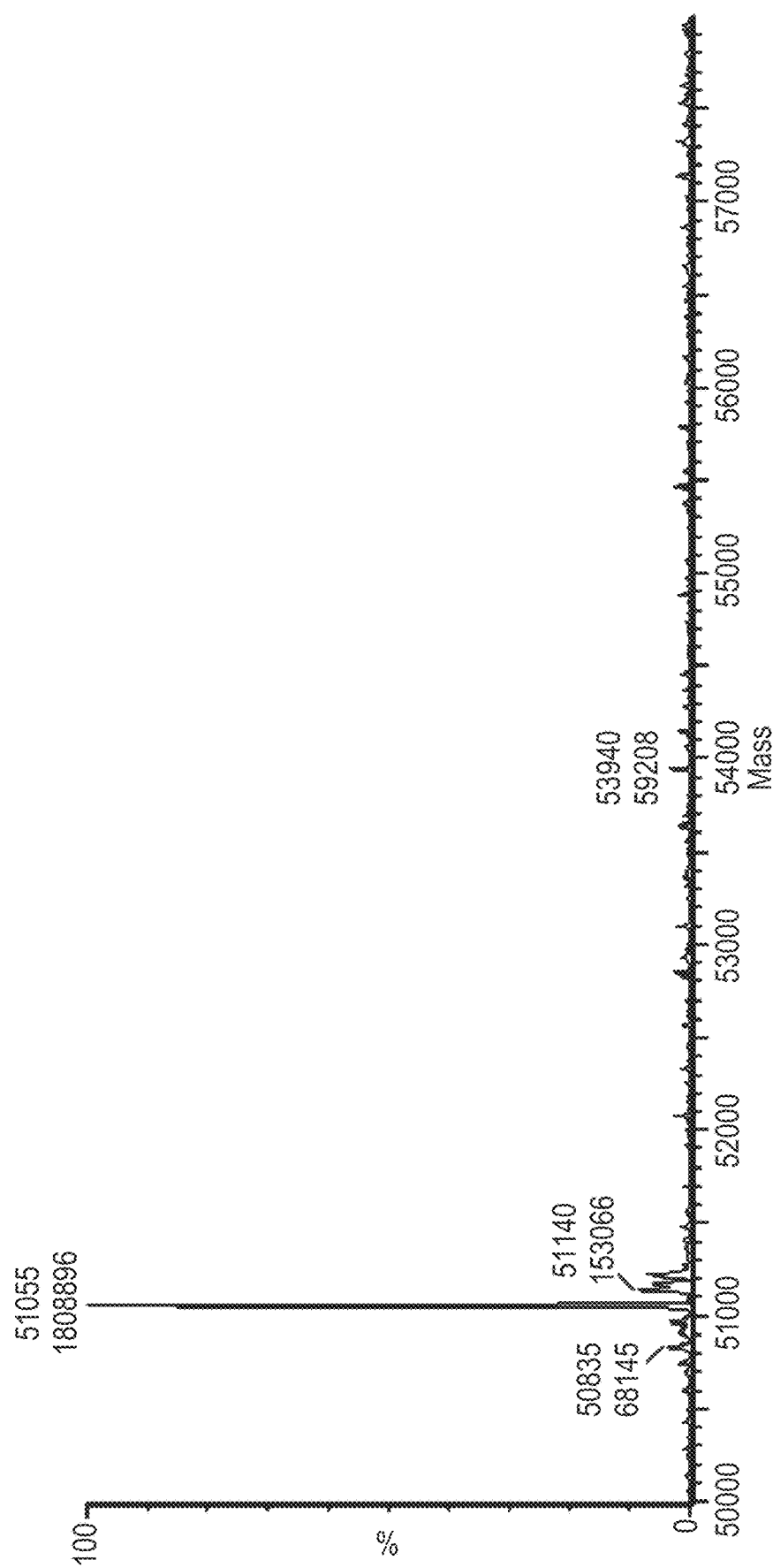
Figure 2D:
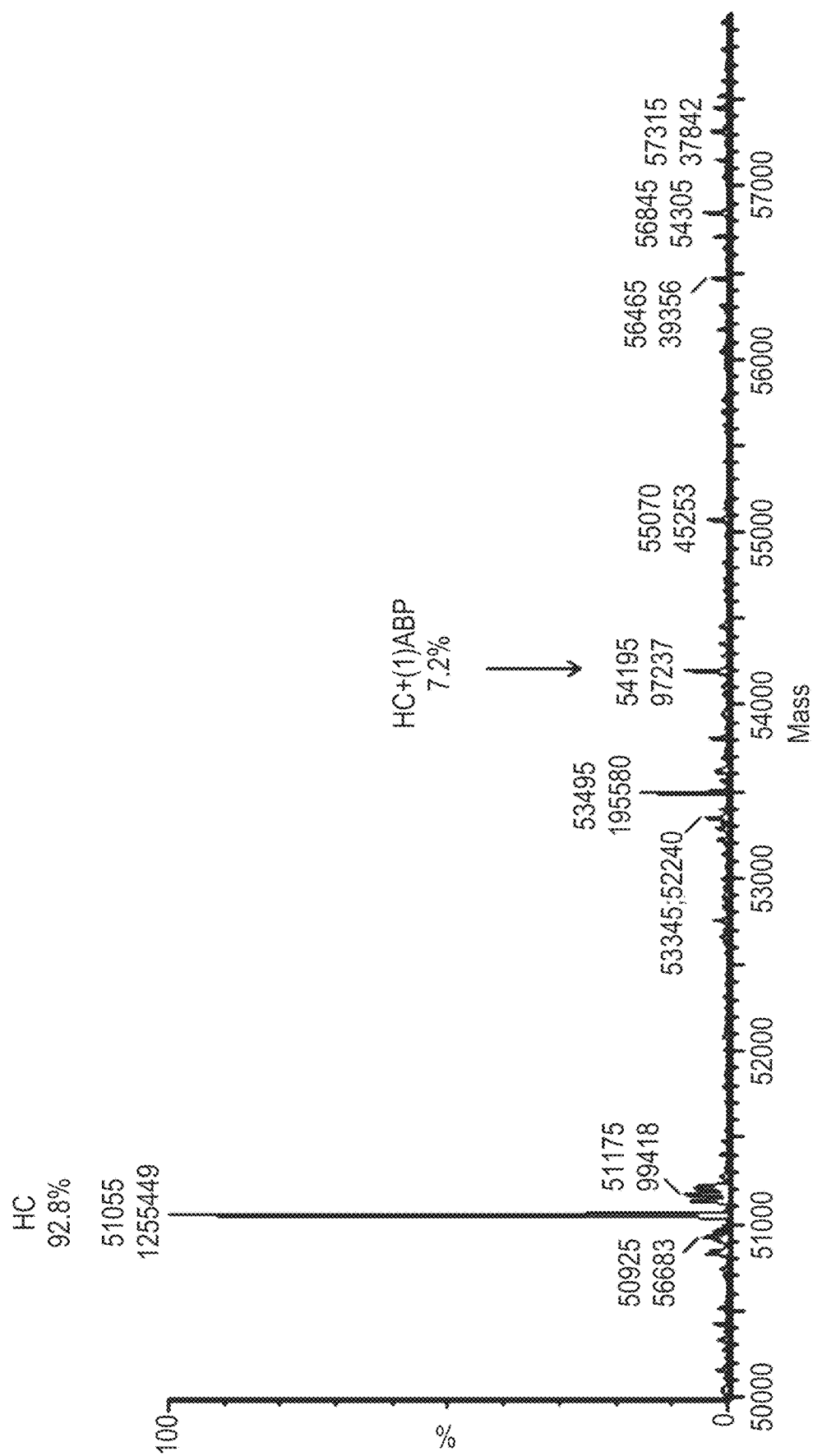
Figure 2E:
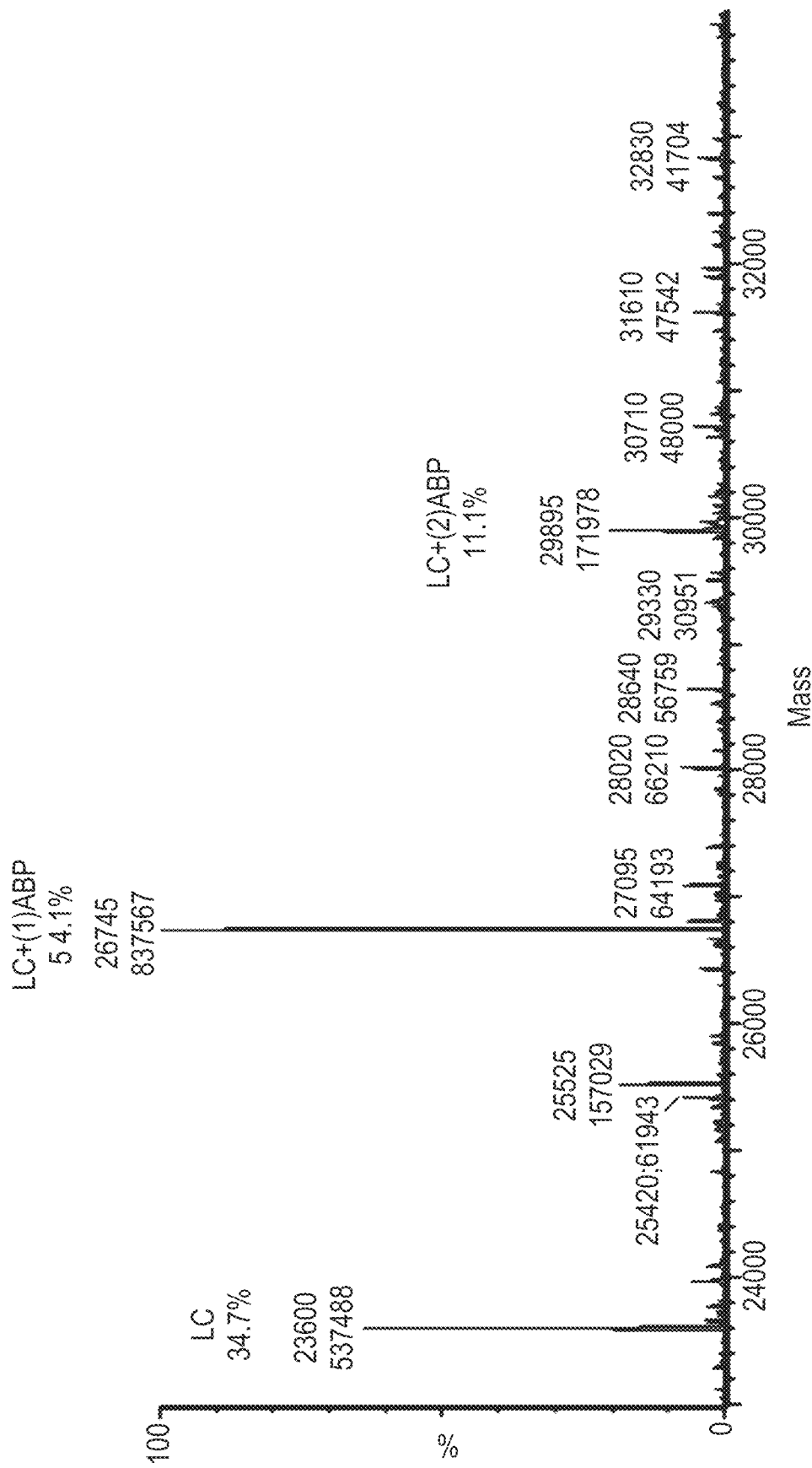
Figure 2F:
Figure 2H:
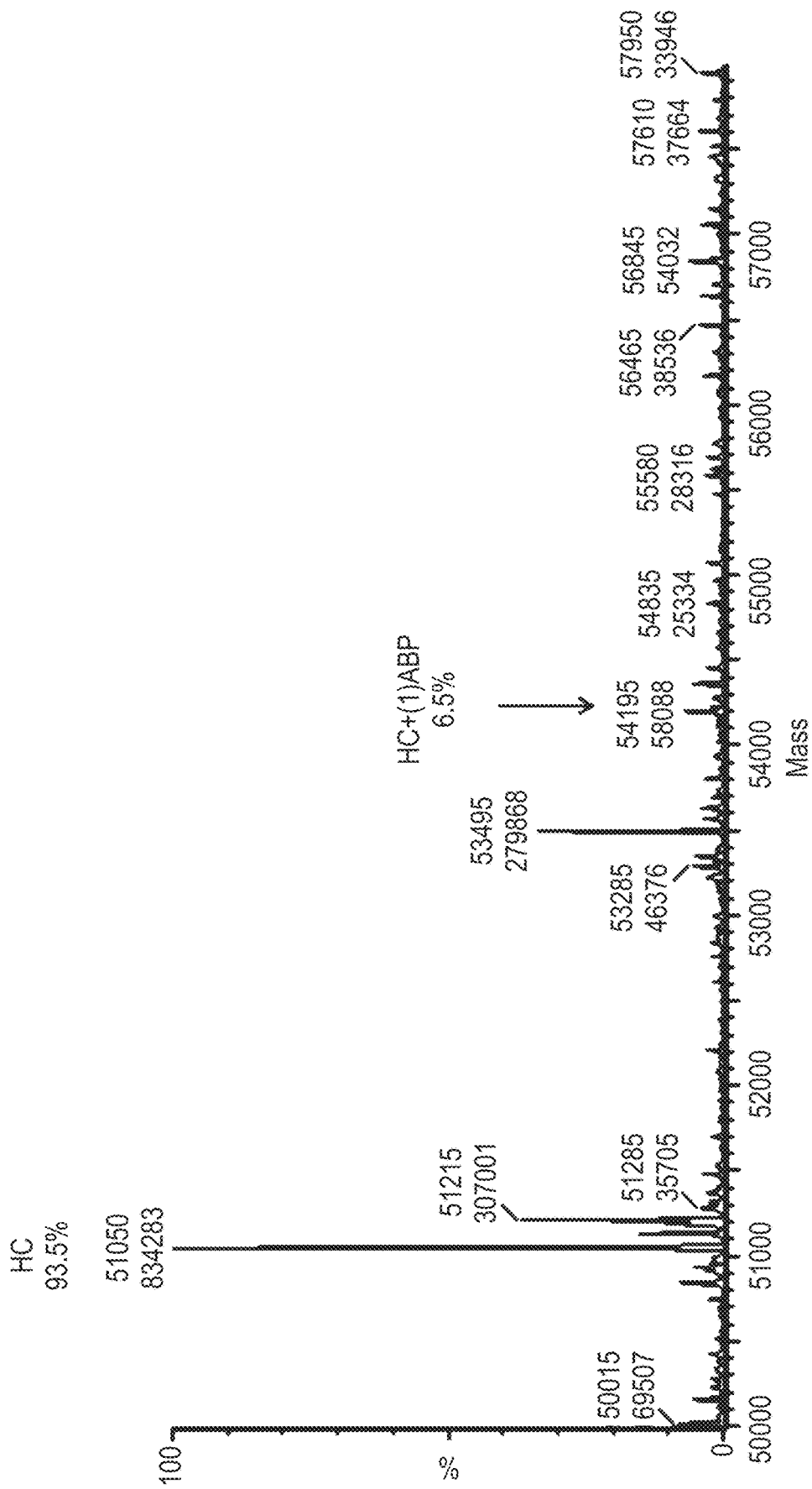

FIGS. 2A, 2B, 2C, 2D, 2E, 2F, 2G, and 2H: Mass spectrometry data of 2.12.1.fx (IGF1R) and 3 lots of MAC-2 (MAC) where the disulfide bonds have been reduced. FIG. 2A: Mass spectrometry data of 2.12.1.fx (IGF1R), light chain. FIG. 2B: Mass spectrometry data of 2.12.1.fx (IGF1R), heavy chain. FIG. 2C: mass spectrometry data of light chain of MAC-2, lot-1. FIG. 2D: mass spectrometry data of heavy chain of MAC-2, lot-1. FIG. 2E: mass spectrometry data of light chain of MAC-2, lot-2. FIG. 2F: mass spectrometry data of heavy chain of MAC-2, lot-2. FIG. 2G: mass spectrometry data of light chain of MAC-2, lot-3. FIG. 2H: mass spectrometry data of heavy chain of MAC-2, lot-3.

FIG. 3A: Amino acid sequence of light chain of antibody 2.12.1.fx with chymotrypsin cleavage sites noted with bullets. Chymotryptic fragments that contain a Lys residue (site of potential conjugation) are labeled by number from the N-terminus. The Y15 fragment of the light chain is underlined. FIG. 3B: Amino acid sequence of heavy chain of antibody 2.12.1.fx with chymotrypsin cleavage sites noted with bullets. Chymotryptic fragments that contain a Lys residue (site of potential conjugation) are labeled by number from the N-terminus.

Figure 4B:
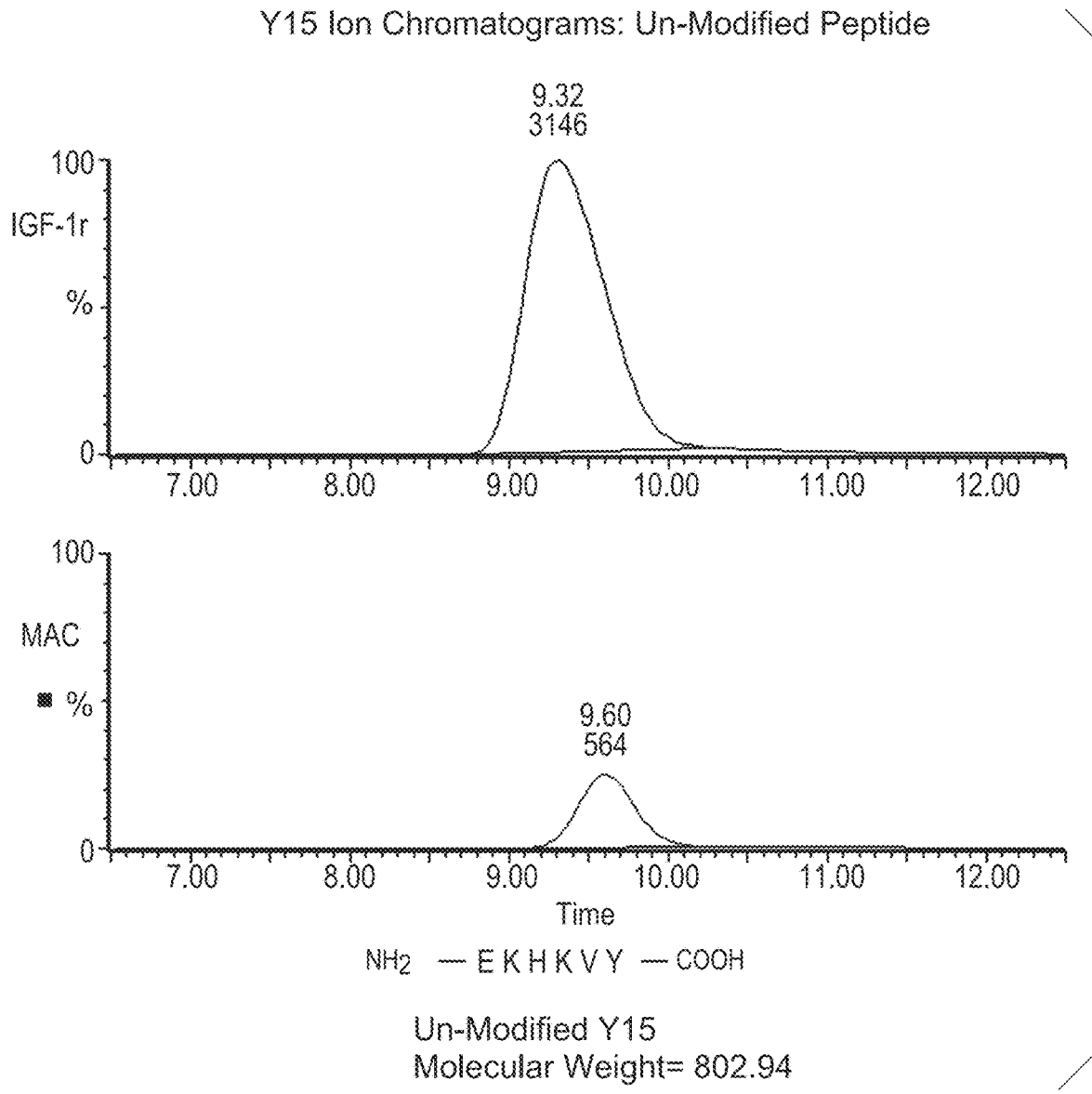

FIG. 4A: Mass spectrometry data of a conjugated lysine-containing peptide: light chain Y15, showing mass spectrometry data for unconjugated anti-IGF1R antibody 2.12.1.fx (IGF1r) and MAC-2 (MAC), as well as a representation of the Y15 fragment. FIG. 4B: Mass spectrometry data of un-conjugated light chain Y15 fragment, showing mass spectrometry data for unconjugated anti-IGF1R antibody 2.12.1.fx (IGF1r) and MAC-2 (MAC), as well as a representation of the Y15 fragment.

Figure 5A:
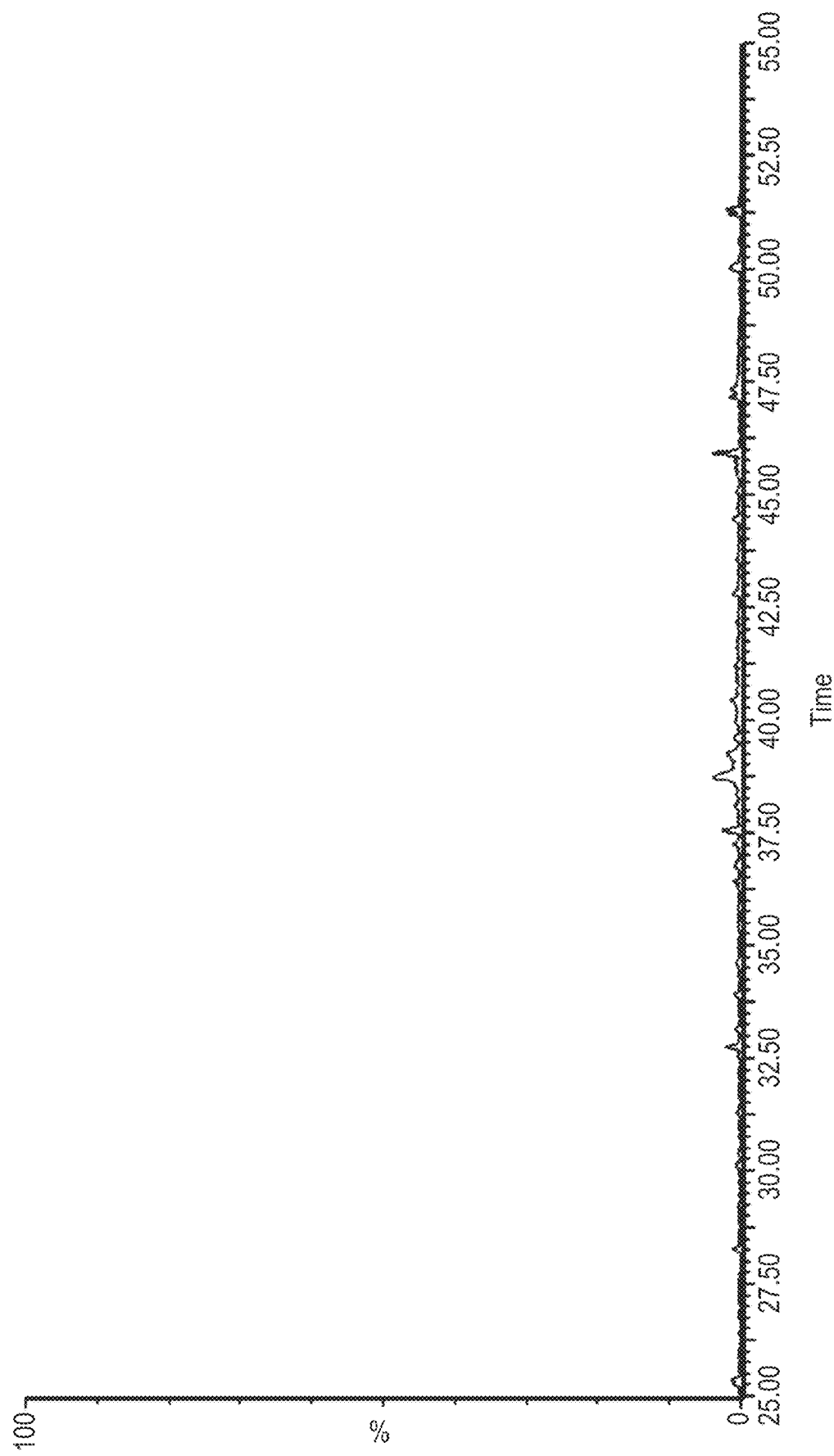

FIG. 5A: The selected ion LCMS chromatogram data for the tryptic fragment of 2.12.1.fx. FIG. 5B: The selected ion LCMS chromatogram data for the tryptic fragment when LC-K$^{188}$ is modified with ABP of MAC-2.

Figure 6A:
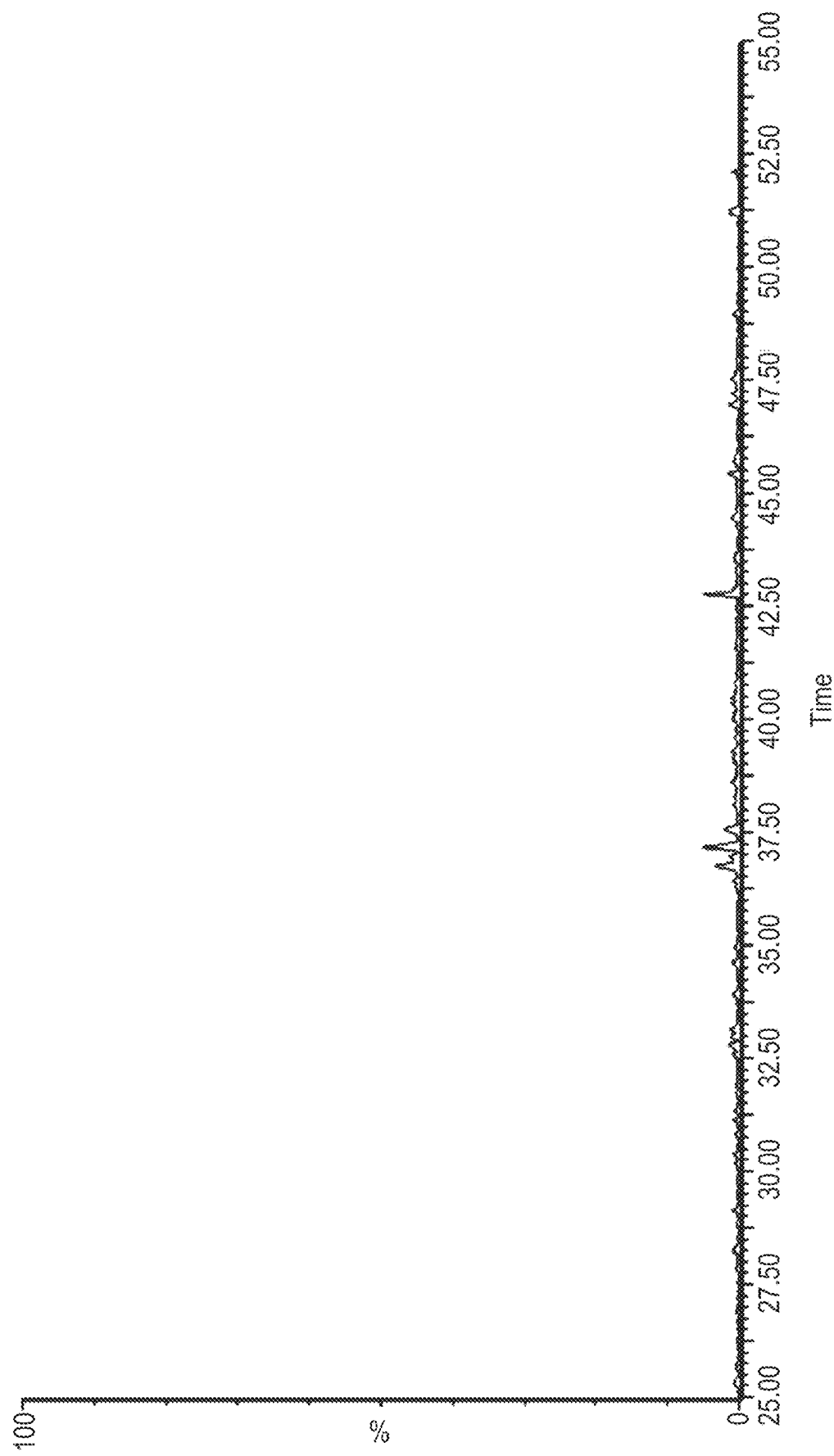
Figure 6B:
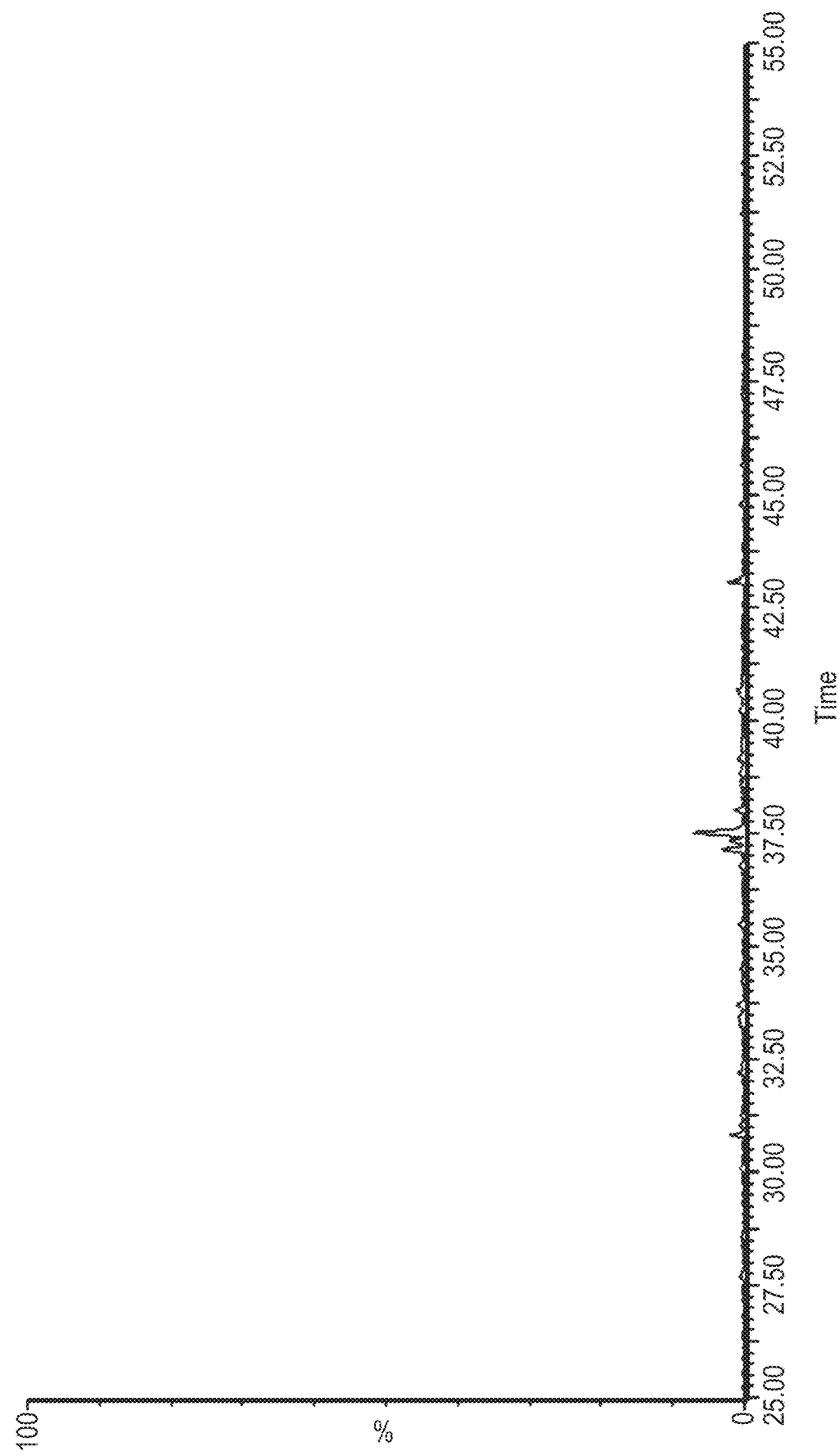

FIG. 6A: The selected ion LCMS chromatogram data for the tryptic fragment of 2.12.1.fx. FIG. 6B: The selected ion LCMS chromatogram data for the tryptic peptide when LC-K$^{190}$ is modified with ABP of MAC-2.

Figure 7B:
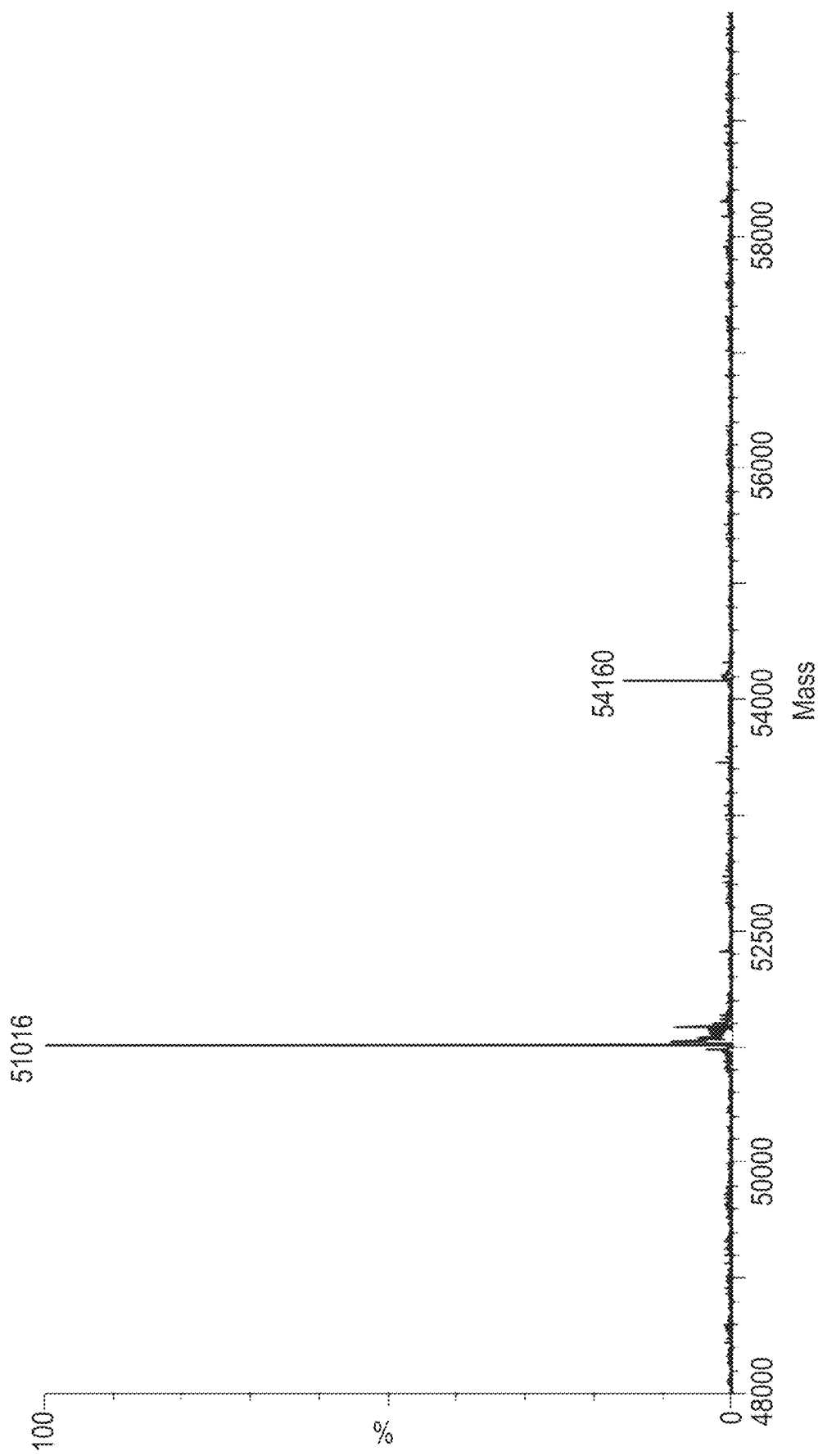
Figure 7C:
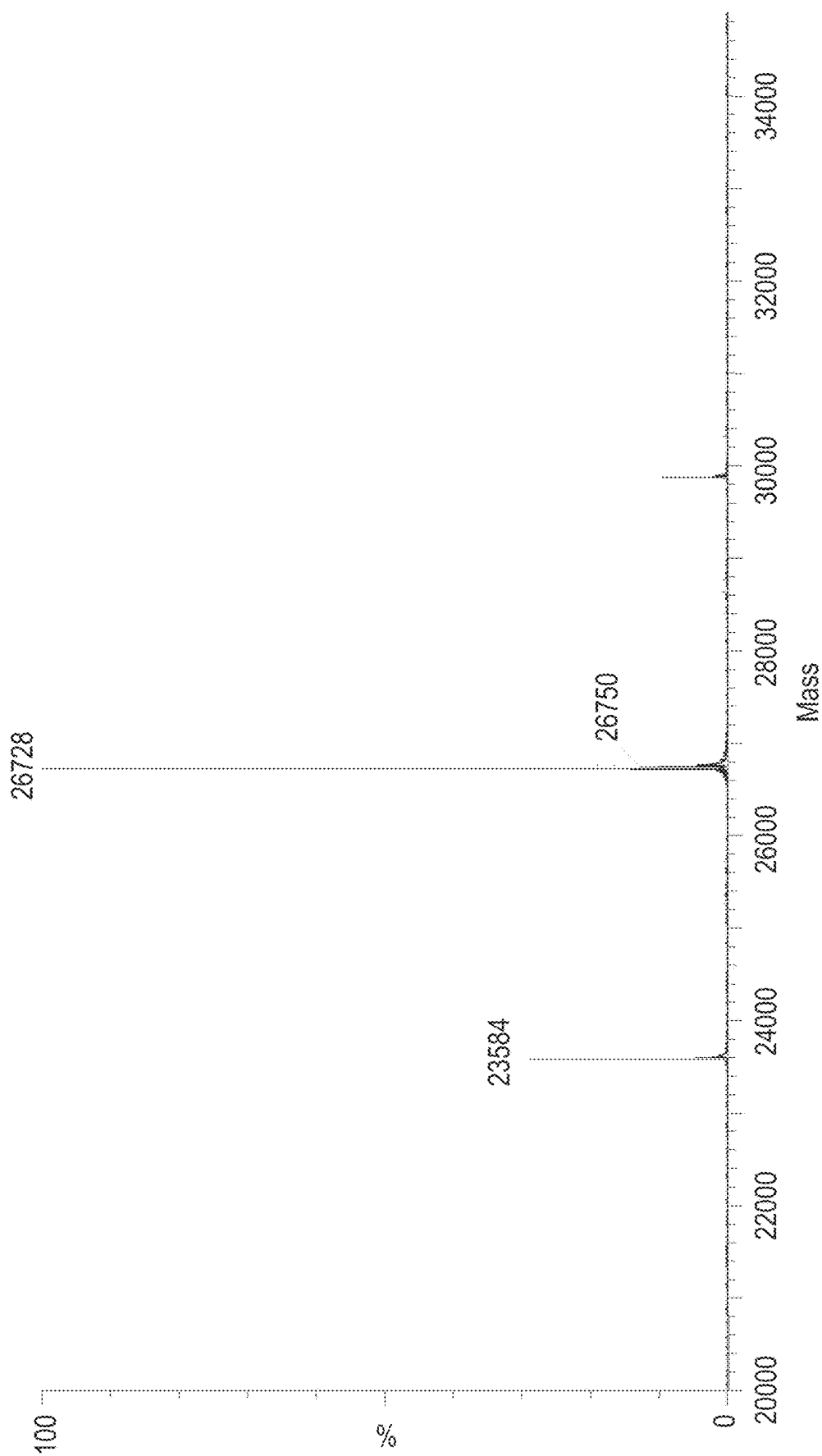

FIG. 7A: Mass spectra of intact MAC-2. FIG. 7B: Mass spectra of reduced heavy chain for MAC-2. FIG. 7C: Mass spectra of reduced light chain for MAC-2.

FIG. 8A: Amino acid sequence alignment of the variable domains of m38c2, h38c2, and human germlines. Framework regions (FR) and complementarity determining regions (CDR) are defined according to Kabat et al. Asterisks mark differences between m38c2 and h38c2 or between h38c2 and the human germlines.

FIG. 8B: Amino acid sequence alignment of murine constant light chain kappa region (mCLκ), human constant light chain kappa region (hCLκ), and human constant light chain lambda region (hCLλ). Differences between mCLκ and hCLκ; and between hCLκ and hCLλ; are shown as asterisks, and conserved substitutions are shown as crosses. β-strands A-G are underlined. The turn between β-strands A and B and the α-helix between β-strands E and F are each indicated in italics. Di-sulfide bond-forming cysteines between the first β-sheet (made up of β-strands ABDE; single underline) and the second β-sheet (made up of β-strands CGF, double underline) are indicated by §. Known polymorphic loci in the human sequences are indicated in bold.

Figure 9A:
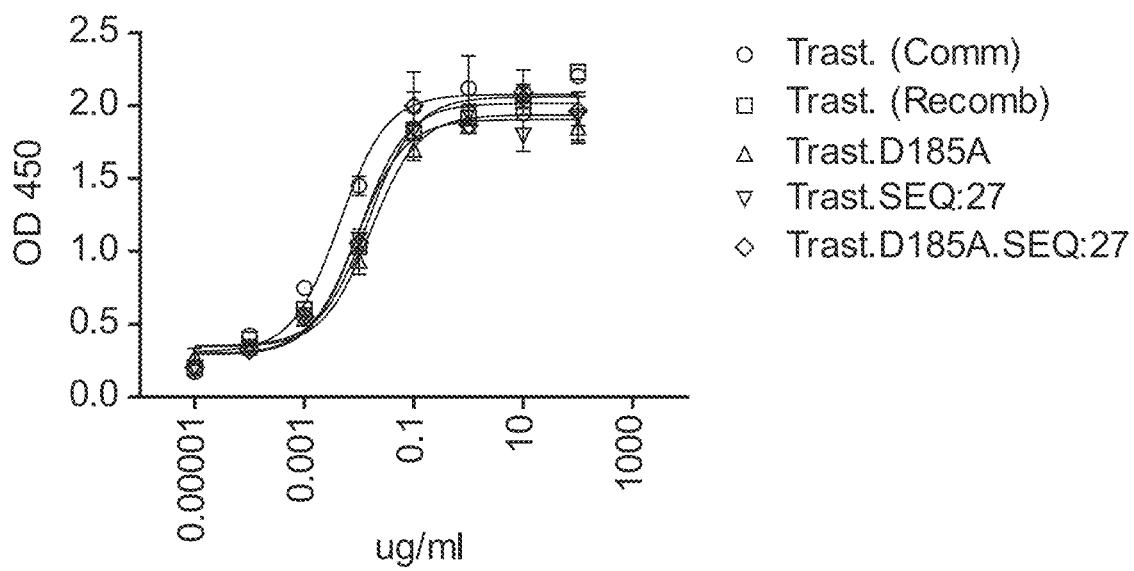
Figure 9B:
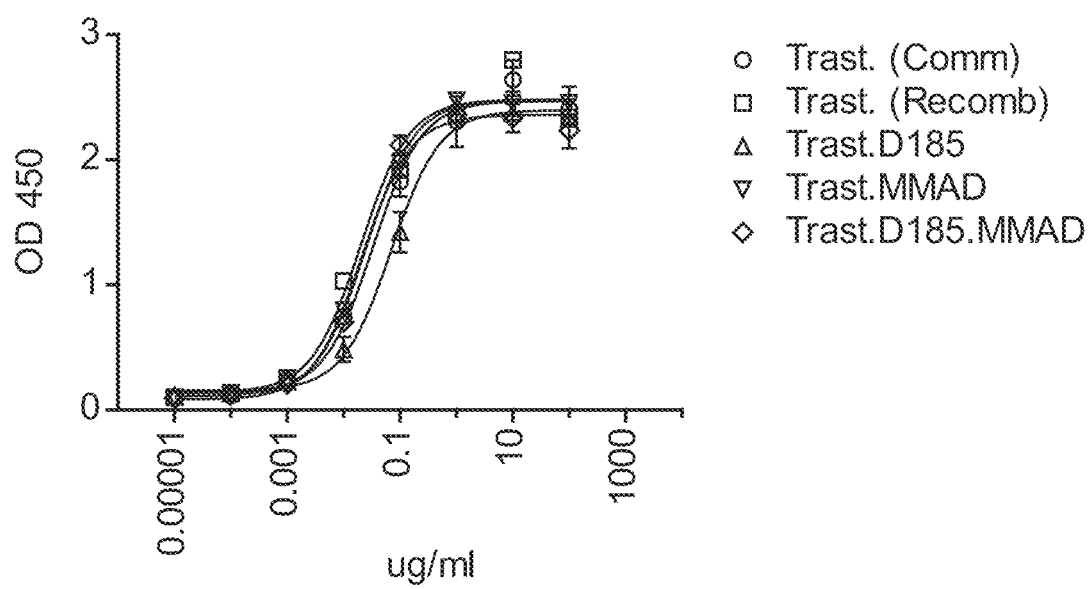

FIG. 9A: Binding ELISA data for HER2 receptor binding of trastuzumab and trastuzumab-[CLκ-D$^{185}$A] conjugation products to [PEG$_5$-K$^{11}$-SEQ:27]. FIG. 9B: Binding ELISA data for HER2 receptor binding of trastuzumab and trastuzumab-[CLκ-D$^{185}$A] conjugation products to MMAD toxin.

Figure 10A:
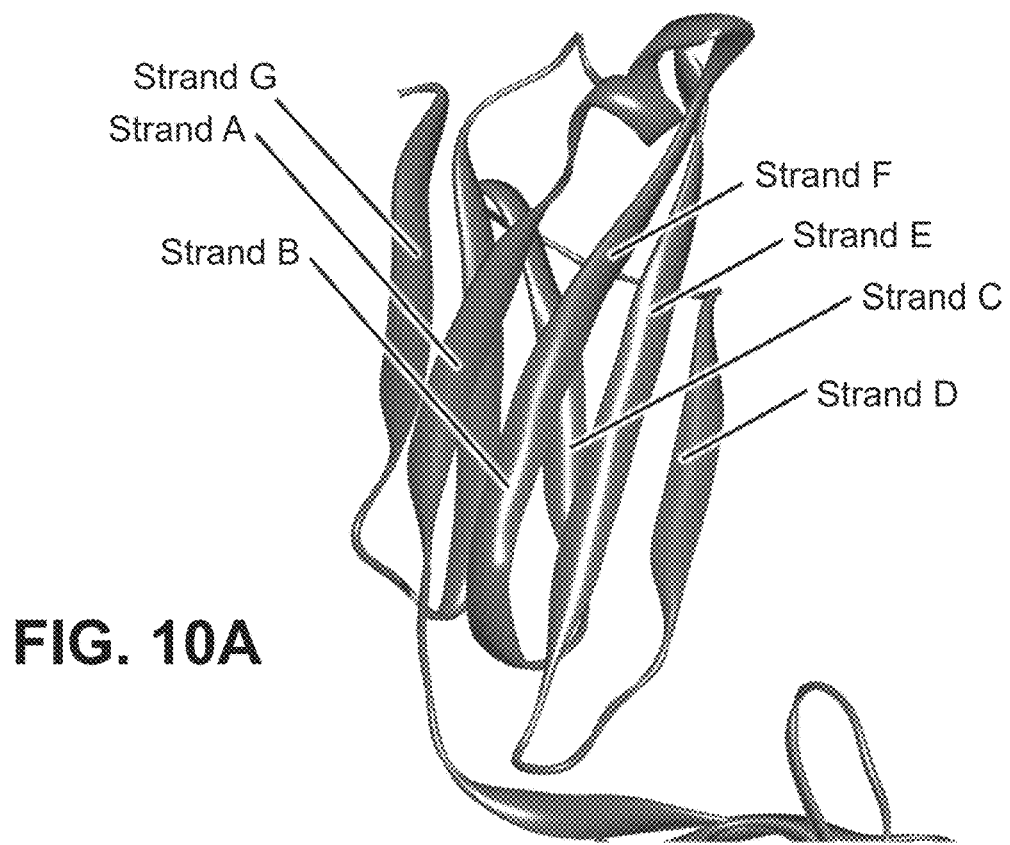
Figure 10B:
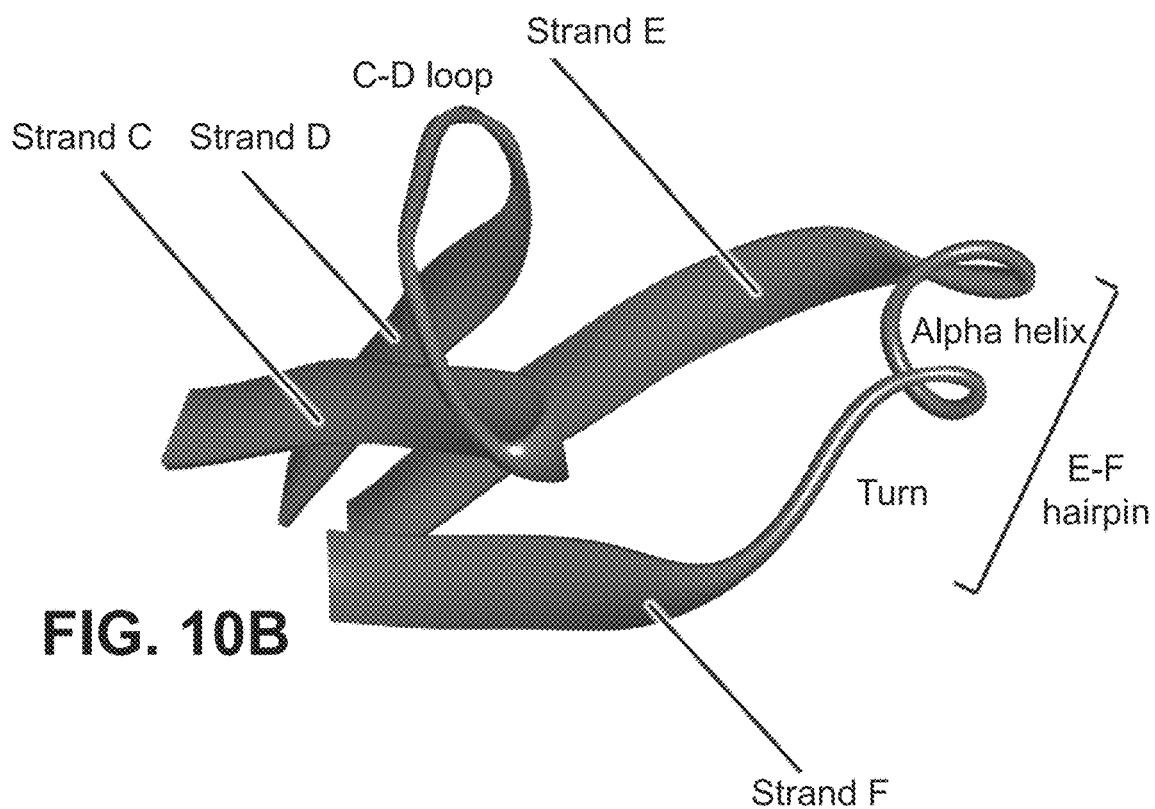

FIG. 10A: representation of a constant Ig domain showing the 7 β-strands forming the two β-sheets. FIG. 10B: close up of the α-helix between β-sheets E and F.

Figure 11:
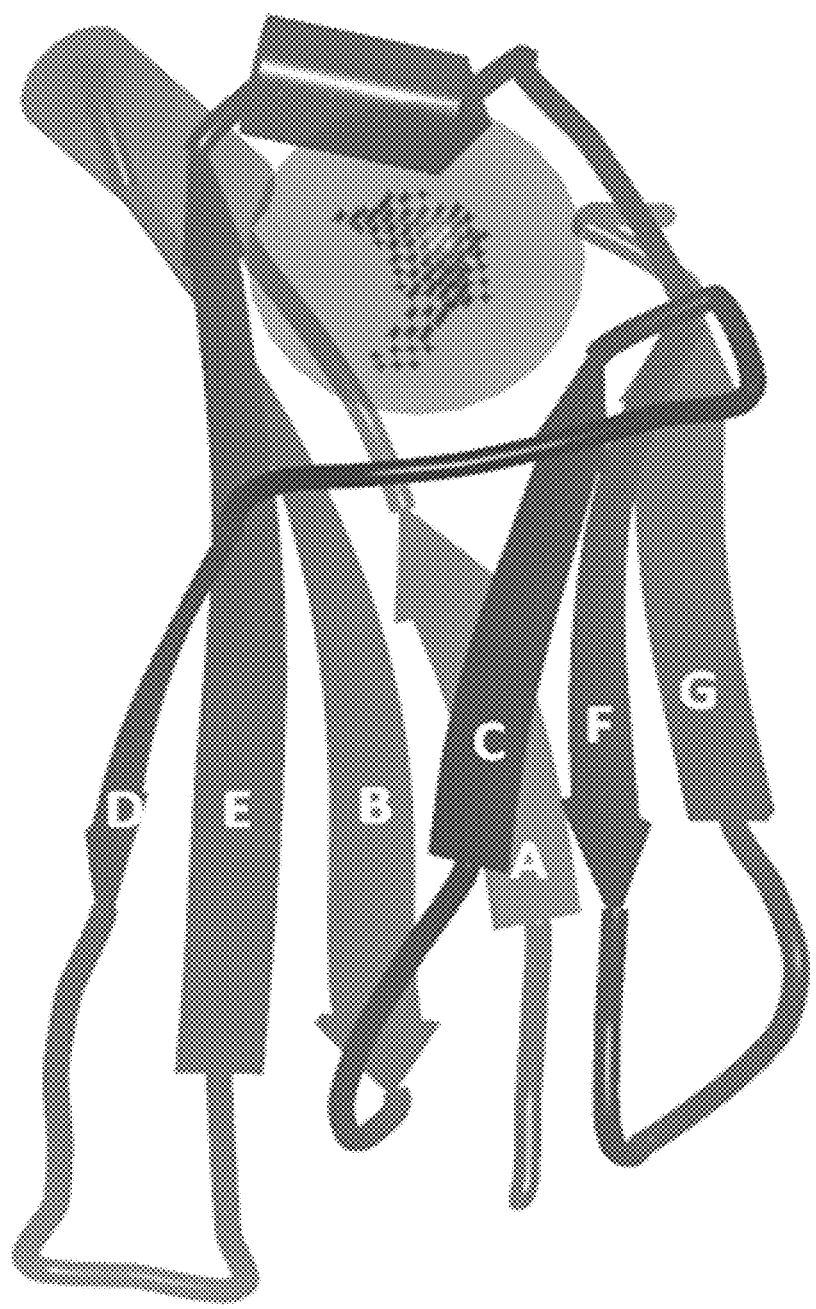

FIG. 11. Crystal structure-based minimized ribbon representation of CLκ, showing the halo-phenyl ester reactive 'binding site' (small jacks) within the overall steric 'binding pocket' created by the 3D structure. B-strands are labeled.

Figure 12:
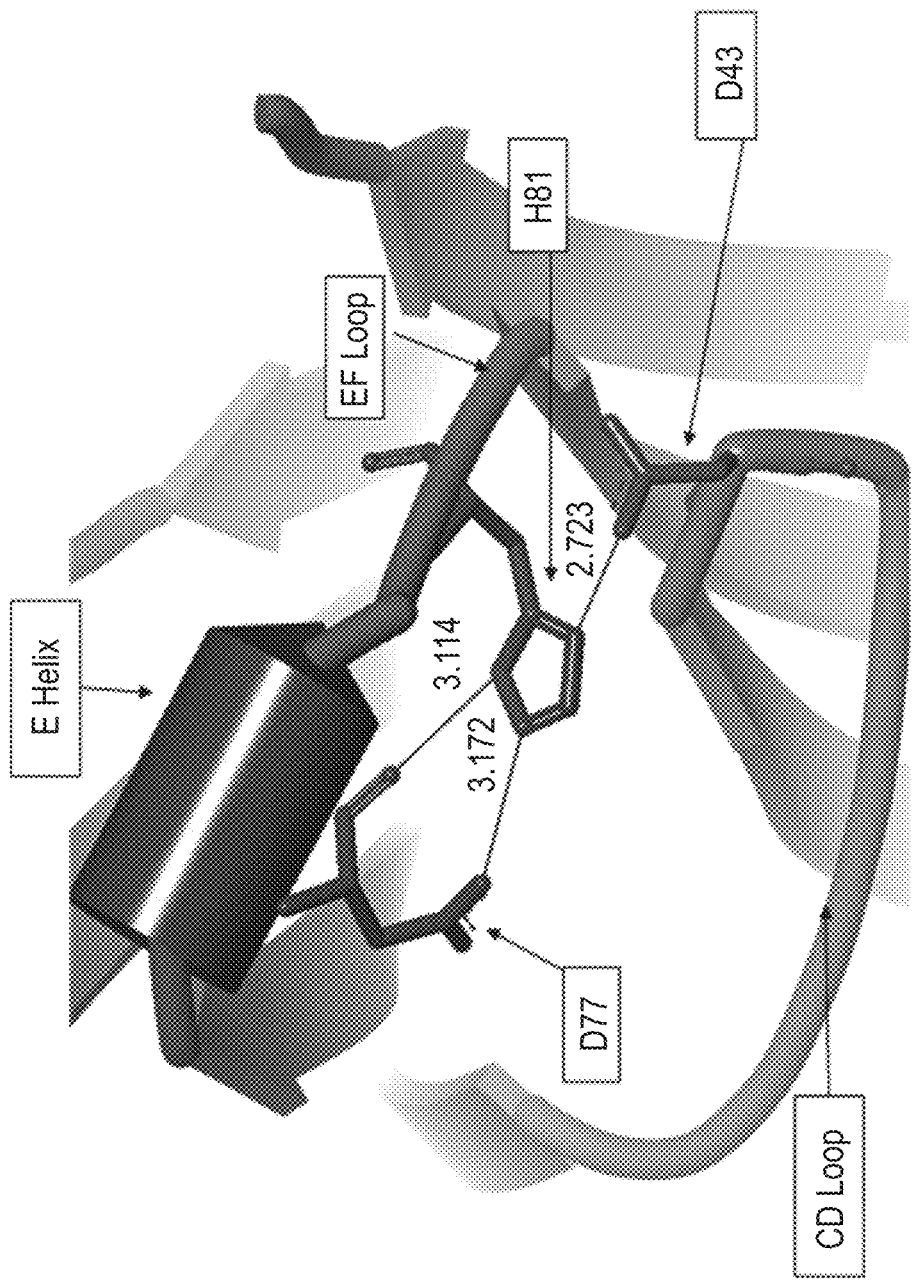

FIG. 12. Crystal structure-based minimized ribbon representation of the CLκ 'binding pocket', showing CLκ-D$^{77}$ and CLκ-D$^{43}$ (as a stick model) in the hydrogen bond with CLκ-H$^{81}$ Nε or Nδ, and atomic distances in Å.

Figure 13B:
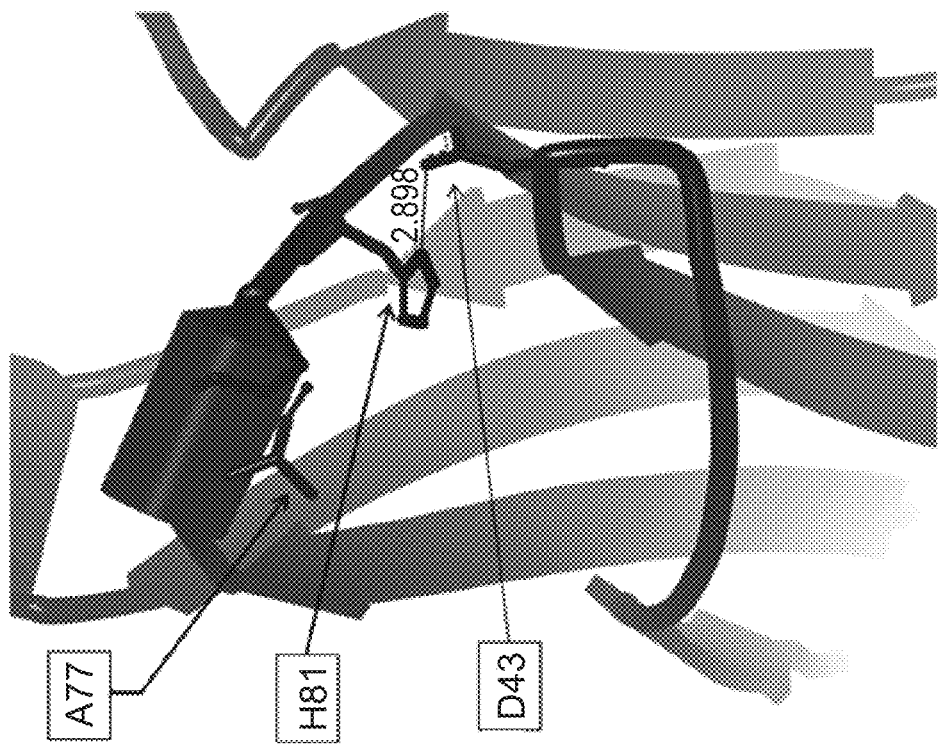
Figure 13A:
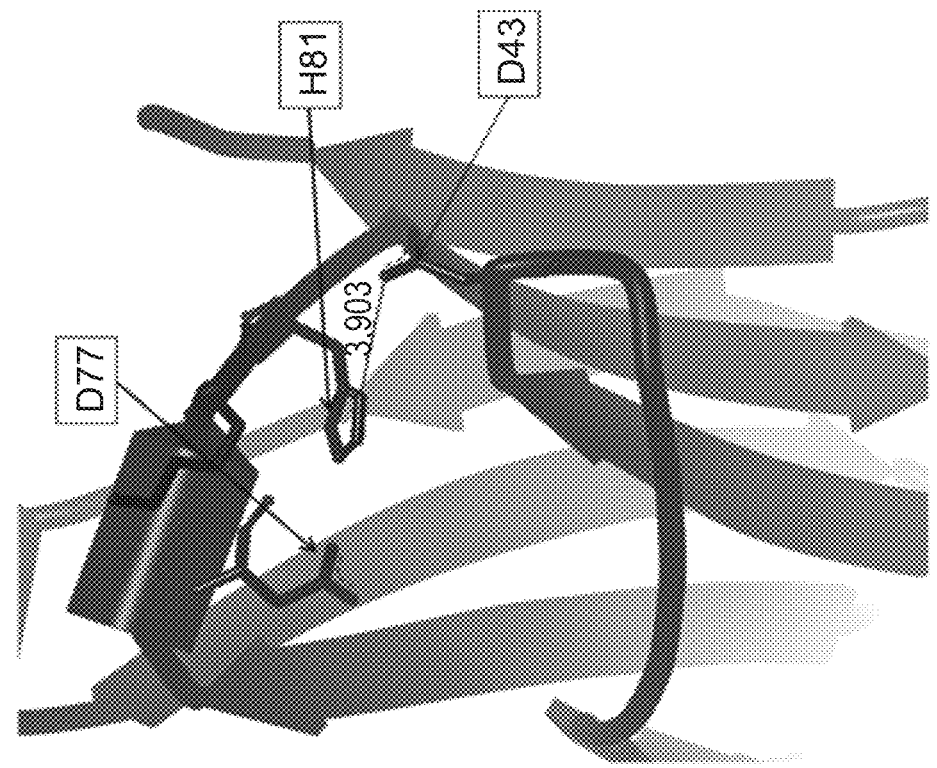

FIGS. 13A and 13B. Crystal structure-based minimized ribbon representation of the CLκ and CLκ-D$^{77}$A mutant 'binding pockets'. The distance between carbonyl oxygen of CLκ-D$^{43}$ and Nδ of CLκ-H$^{81}$ differs by 1 Å between the CLκ and CLκ-D$^{77}$A mutant, pointing to the predominance of catalytically active CLκ-H$^{81}$ tautomer Nδ in the CLκ-D$^{77}$A mutant. In addition, the modeling identifies a clear increase in the overall size of the pocket in CLκ-D$^{77}$A mutant, which is represented by the figure. FIG. 13C. Crystal structure-based ribbon representation of the CLκ (grey) and CLκ-D$^{77}$A mutant (black) 'binding pockets' superimposed over each other. In the CLκ-D$^{77}$A mutant, CLκ-H$^{81}$ is shifted toward CLκ-D$^{43}$ by the hydrogen bond interactions, as CLκ-D$^{77}$A is unable to form a hydrogen bond with Nε of CLκ-H$^{81}$.

Figure 14:
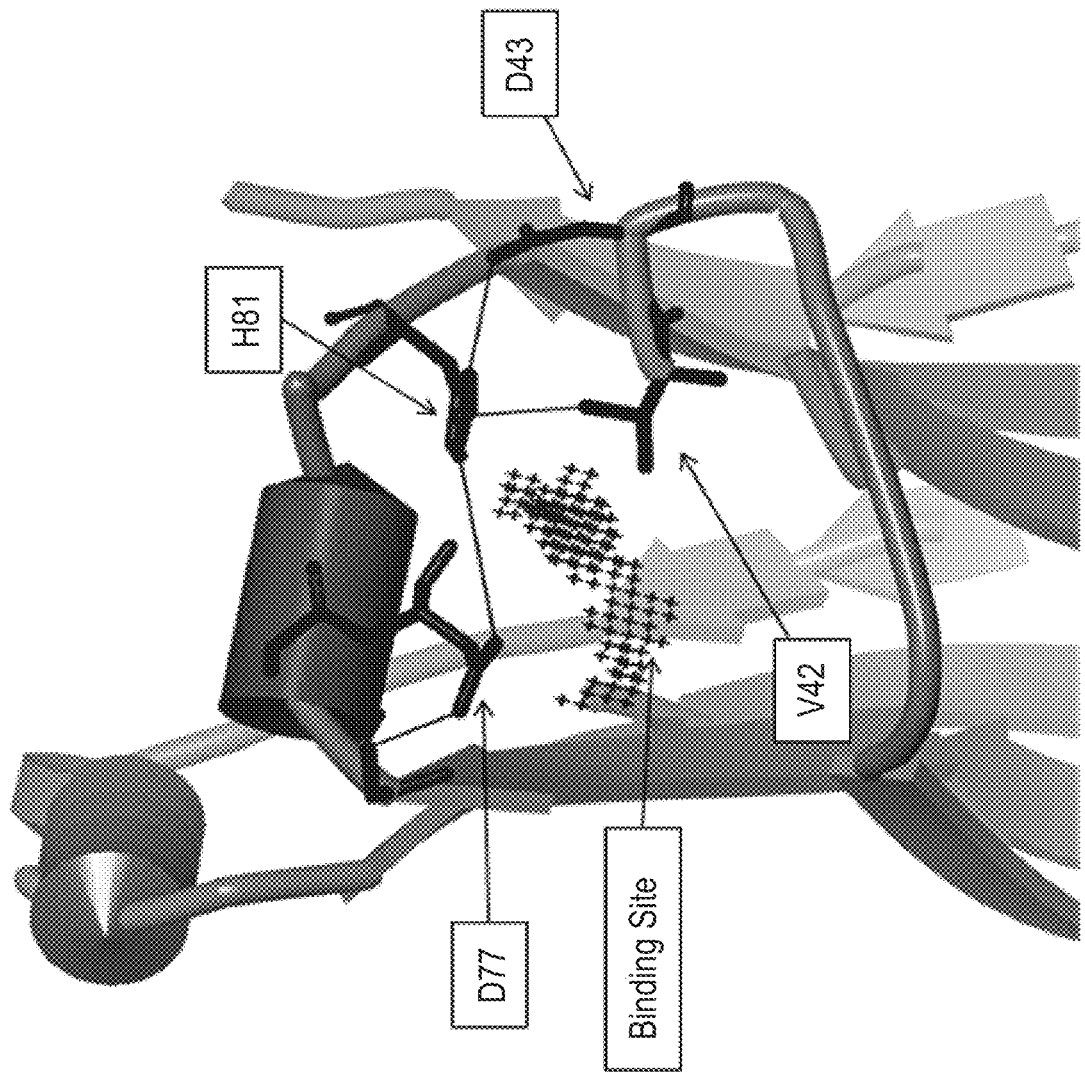

FIG. 14. Crystal structure-based minimized ribbon representation of the CLκ 'binding pocket'. The binding site is depicted as a small jacks. The π electron stacking interactions with CLκ-H$^{81}$ are shown, maintaining the imidazole ring at the optimum position in relation to the incoming halo-phenyl ester substrate.

Figure 15A:
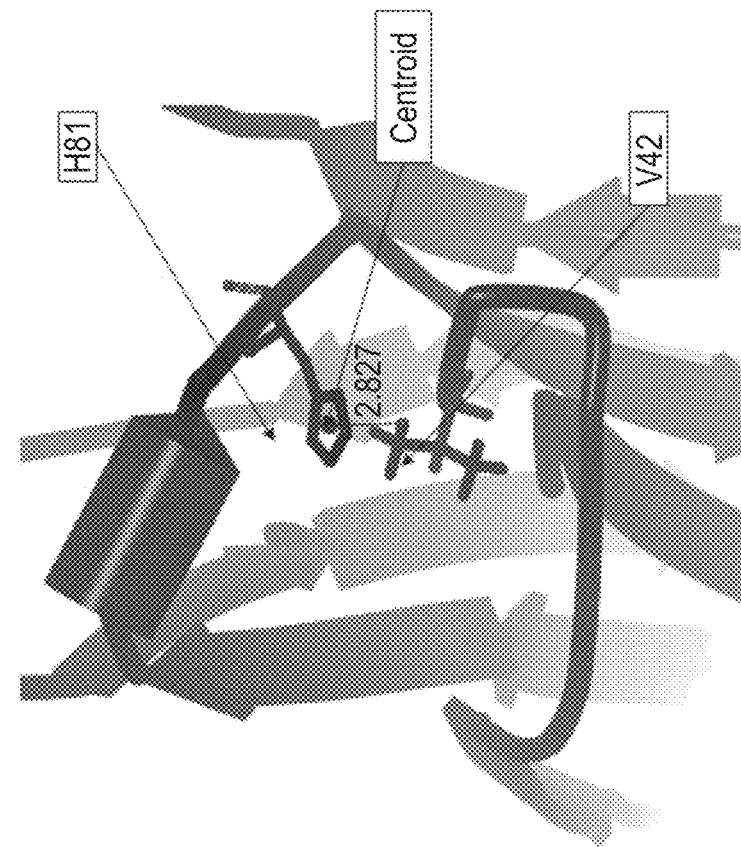
Figure 15B:
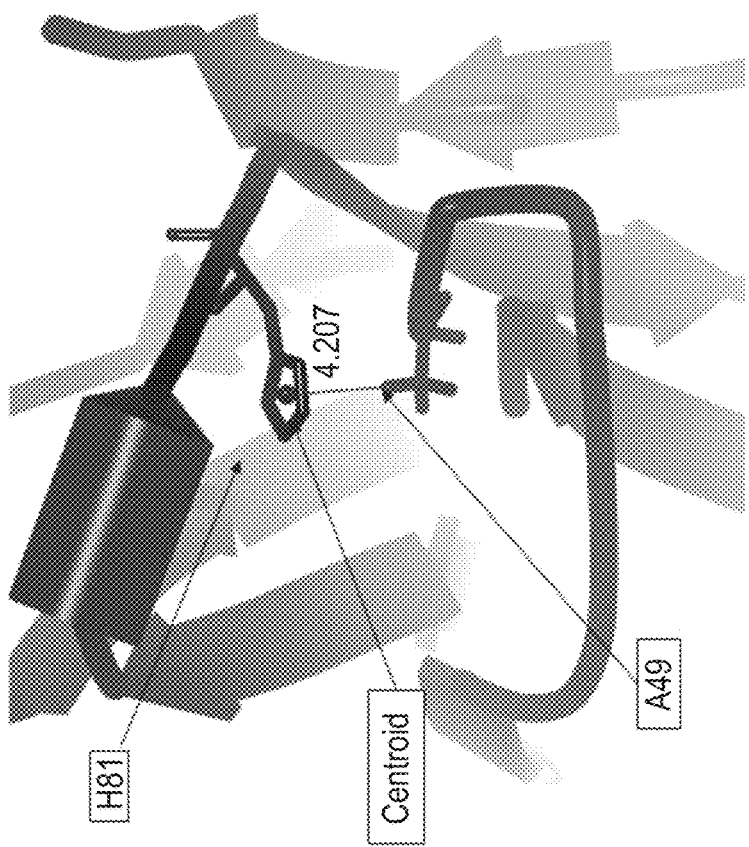

FIGS. 15A and 15B. Crystal structure-based minimized ribbon representation of the CLκ and CLλ 'binding pockets. FIG. 15A shows the 7-electron interactions between CLκ-V$^{42}$ and CLκ-H$^{81}$, assisting in maintaining the CLκ-H$^{81}$ imidazole ring and the Nε electron pair at the plane needed for nucleophilic attack during catalytic reaction. The distance between the center of CLκ-H$^{81}$ imidazole ring and each of the hydrogen atoms on the CLκ-V$^{42}$ are 2.8 Å allowing for strong interactions. In FIG. 15B, CLλ-A$^{49}$ is shown at a distance of 4.2 Å from CLλ-H$^{82}$ (identified as H81 in the figure for the purposes of clarity of comparison). This distance is modeled as likely too far to have a significant influence on the position or tautomeric form of CLλ-H$^{82}$.

FIG. 16. Sequence alignment of hCHλ1, hCHλ2, hCHλ3, hCLκ and hCLλ. β-strands of the CLκ are indicated as underlined regions. α-helices are indicated in italics.

Figure 17:
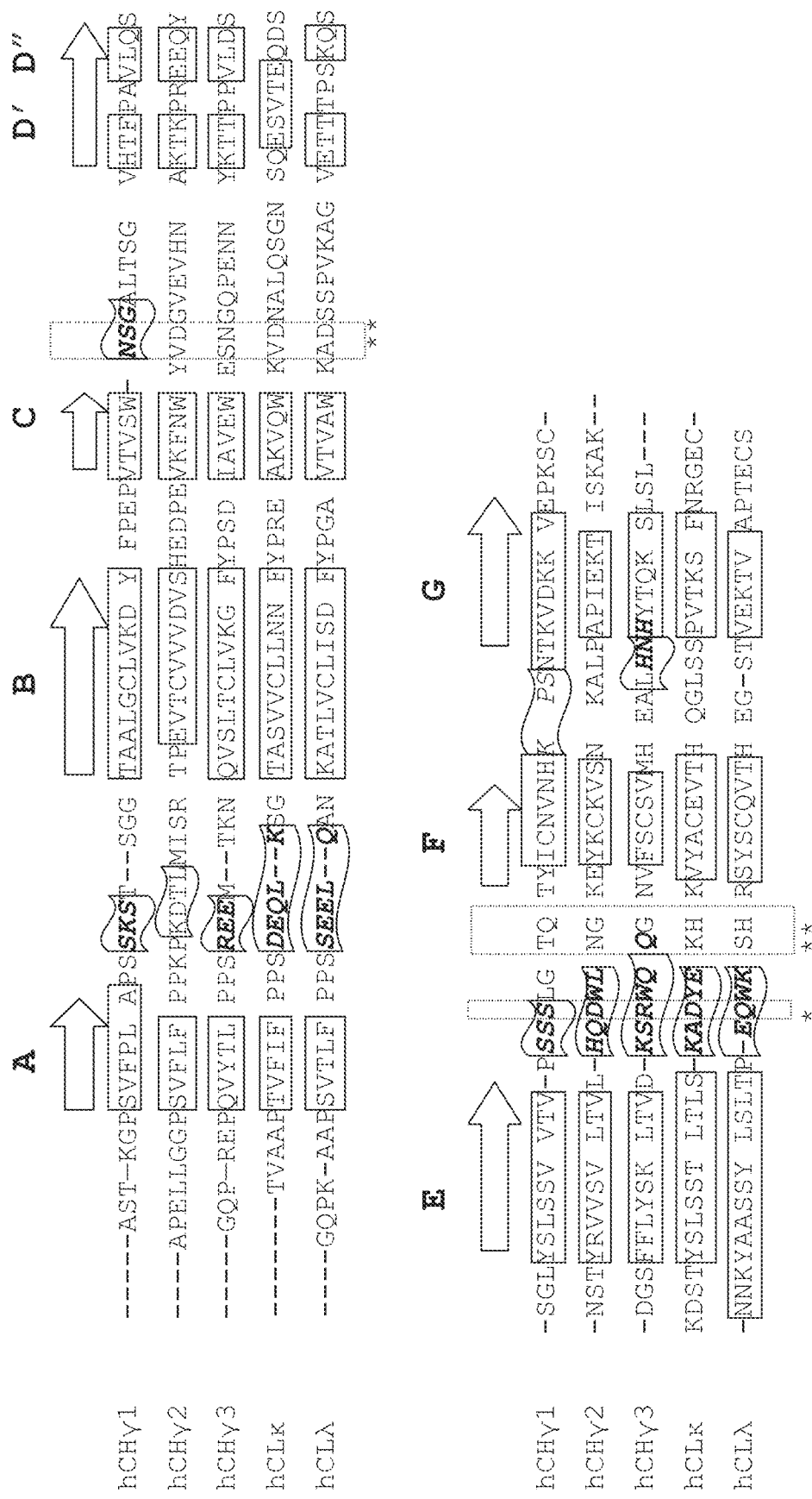

FIG. 17. Crystal structure based alignment of sequences of hCHλ1, hCHλ2, hCHλ3, hCLκ and hCLλ according to minimized 3D homology. β-strands are indicated as boxed regions, α-helices are indicated within wavy scrolls. Key residues corresponding to CLκ-V$^{42}$, CLκ-D$^{43}$, CLκ-D$^{77}$, CLκ-K$^{80}$, and CLκ-H$^{81}$ are identified with rectangular dotted-line boxes extending vertically between sequences. The crystal structure modeling of the domains that generated this alignment suggested a short break in the D β-strand in the hCHλ1, hCHλ2, hCHλ3, and hCLλ domains. Other modeling and crystal structure analysis indicates that most, if not all antibody constant domains comprise 7 β-strands, and the D β-strand is contiguous. The two D β-strands modeled herein have accordingly been indicated as D' and D''. FIGS. 18B-31B, depicting CLλ, and CHγ domains, are orientated such that the D β-strand is on the lower left of the structure pointing downwards, and lying against the E β-strand. The D' and D'' β-strands together can be seen to occupy approximately the same relative position as the CLκ D β-strand (β-strands D and D', D'' labelled in FIG. 18 as a point of reference).

Figure 18B:
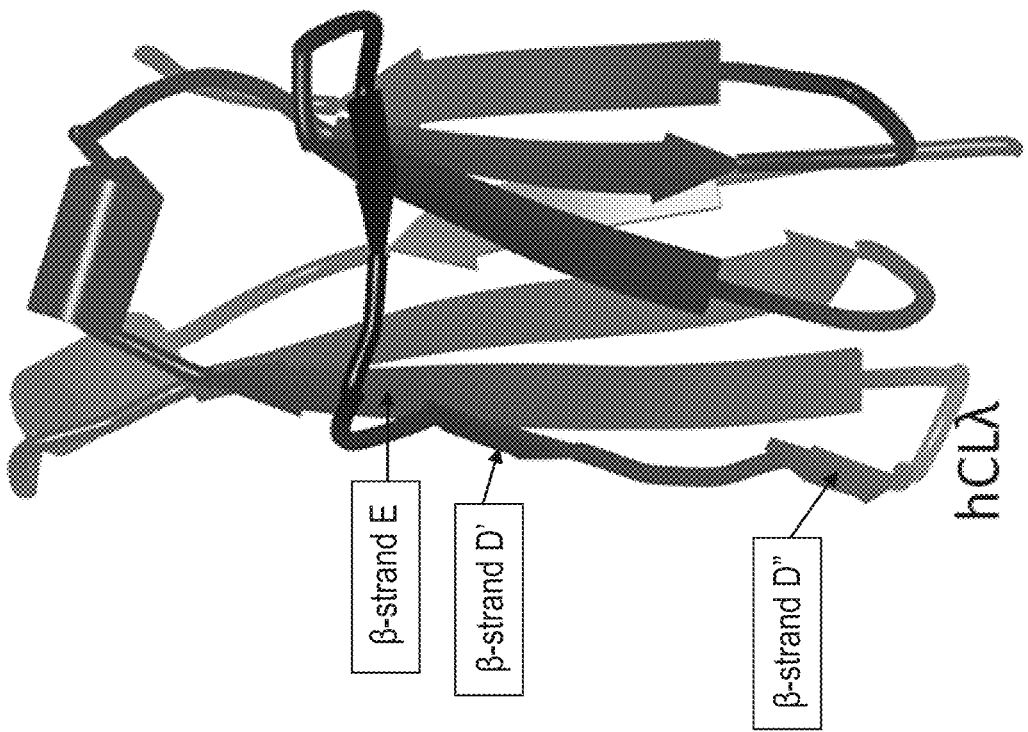
Figure 18A:
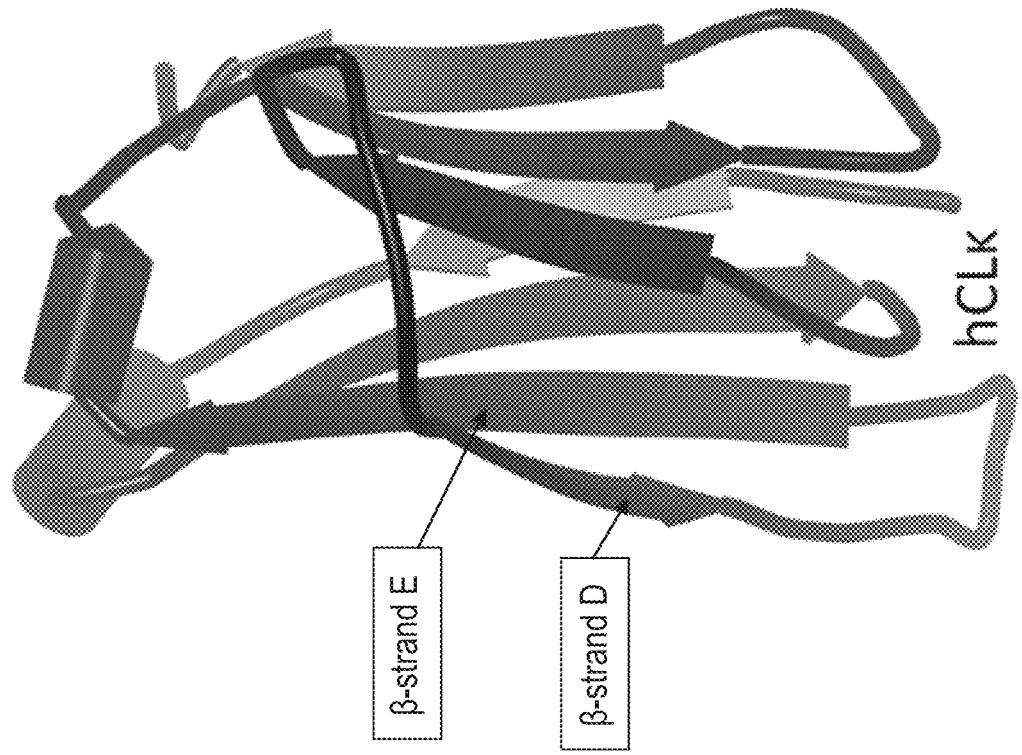

FIGS. 18A and 18B. Crystal structure-based minimized ribbon representation of the hCLκ (A) and hCLλ (B) domains.

Figure 19A:
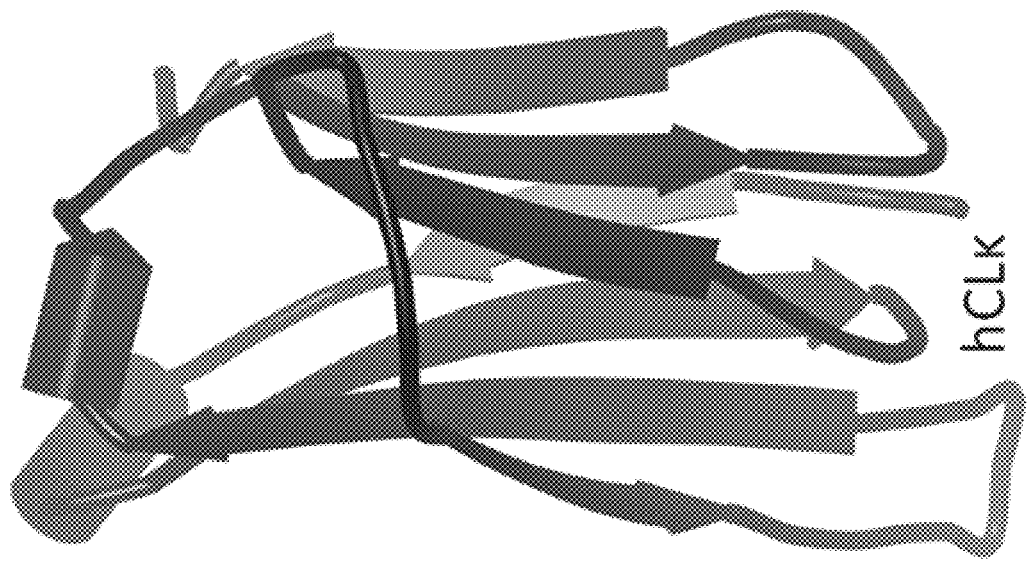
Figure 19B:
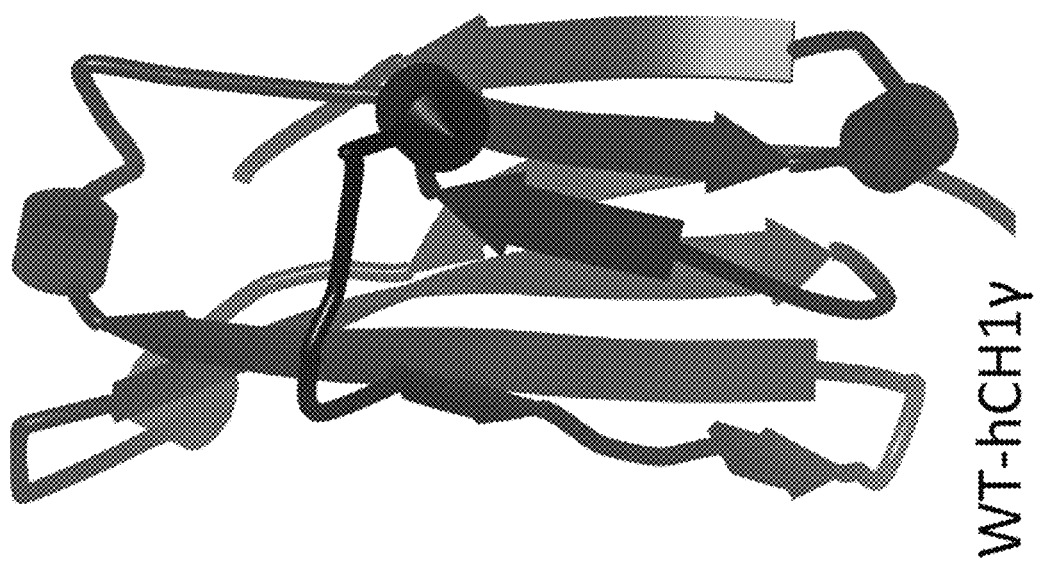

FIGS. 19A and 19B. Crystal structure-based minimized ribbon representation of the hCLκ (A) and WT-hCHγ1 (B) domains.

Figure 20B:
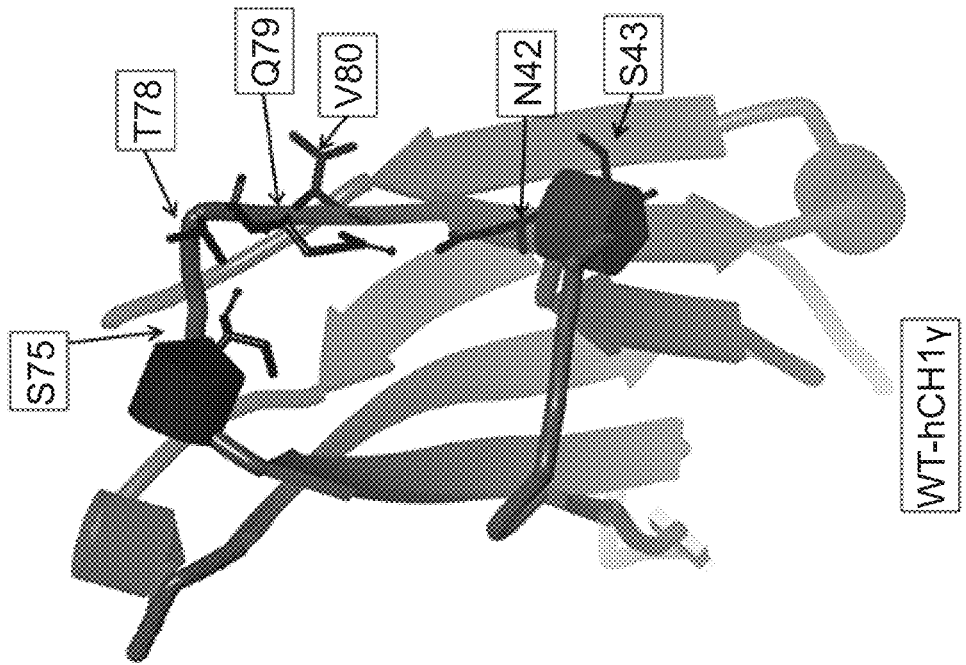
Figure 20A:
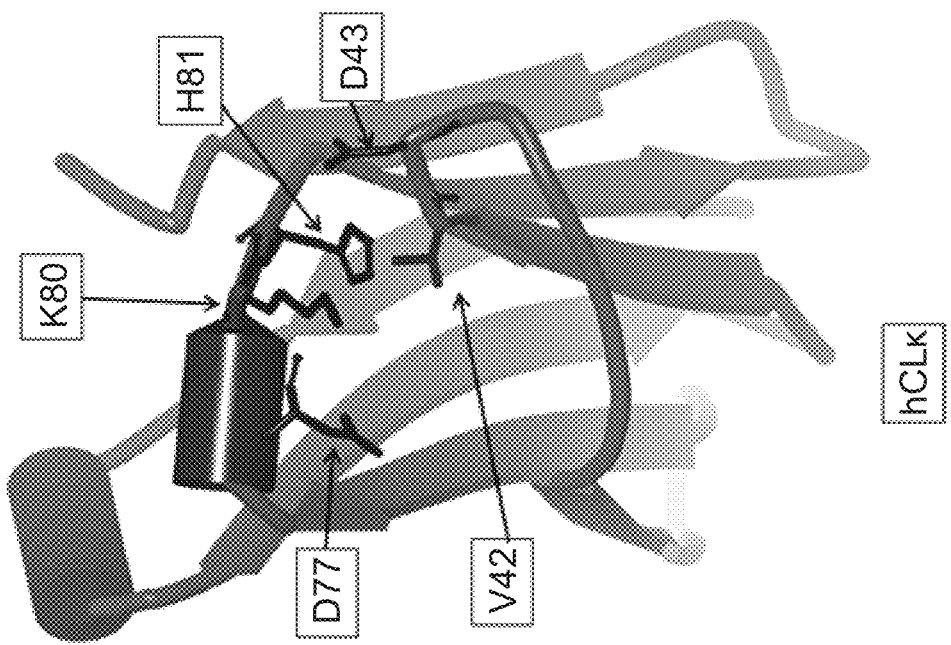

FIGS. 20A and 20B. Crystal structure-based minimized ribbon representation of the hCLκ (A) and WT-hCHγ1 (B) domains, showing the sidechain location of significant residues.

Figure 21B:
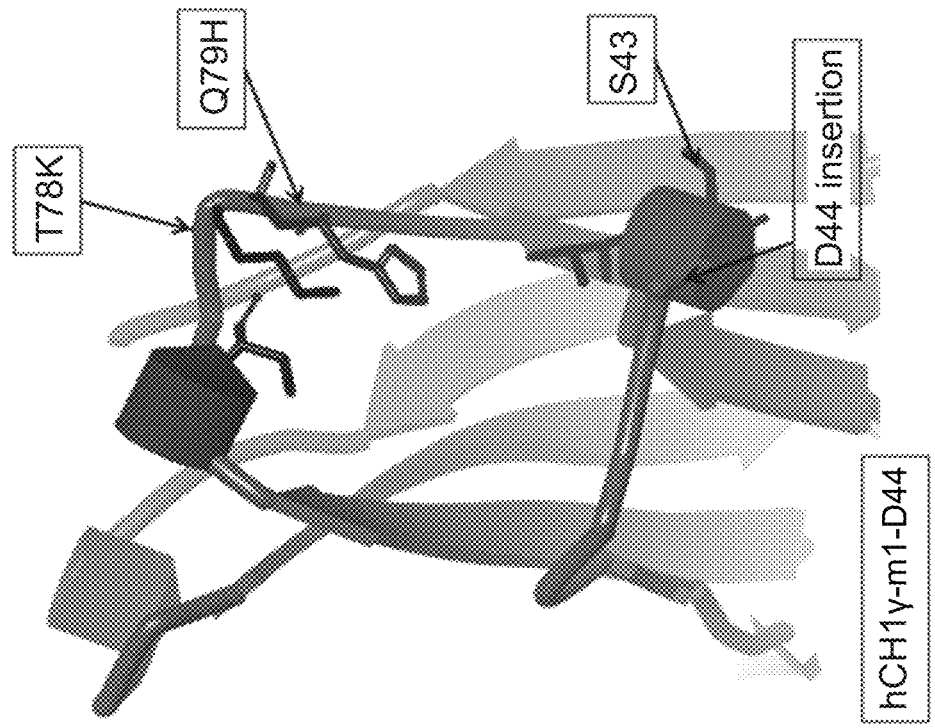
Figure 21A:
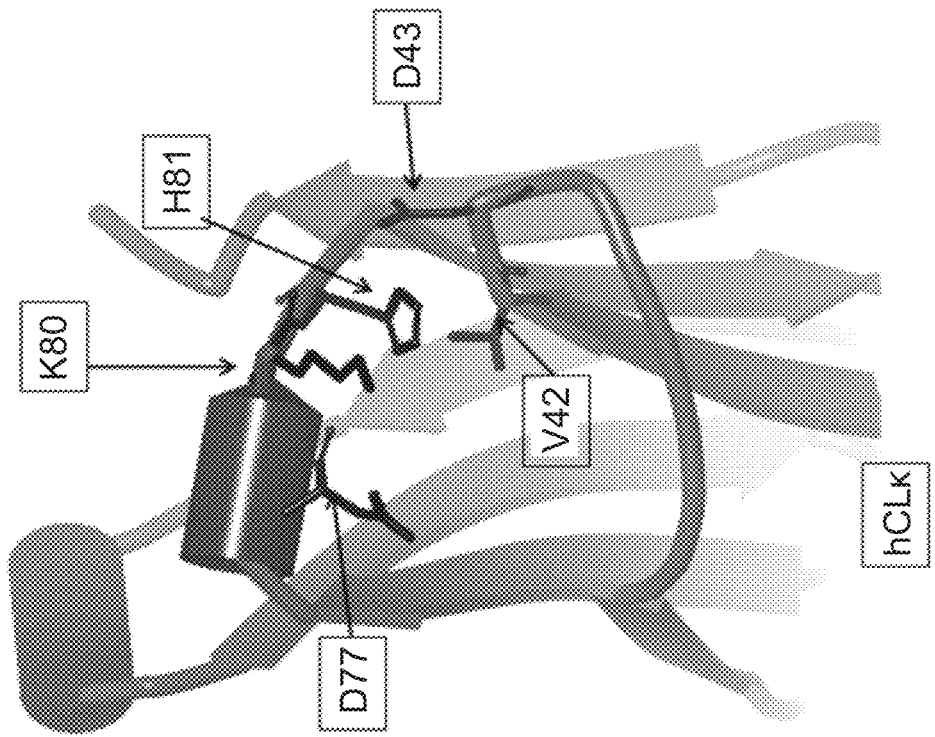

FIGS. 21A and 21B. Crystal structure-based minimized ribbon representation of the hCLκ (A) and hCHγ1-m1-D44 mutant (B) domains, showing the sidechain location of significant residues.

Figure 22A:
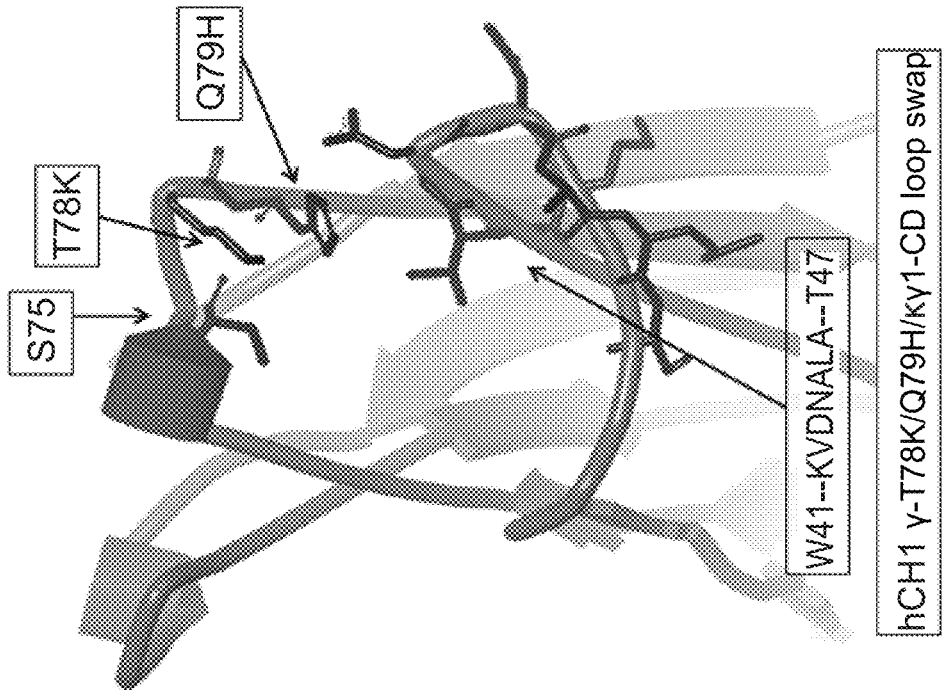
Figure 22B:
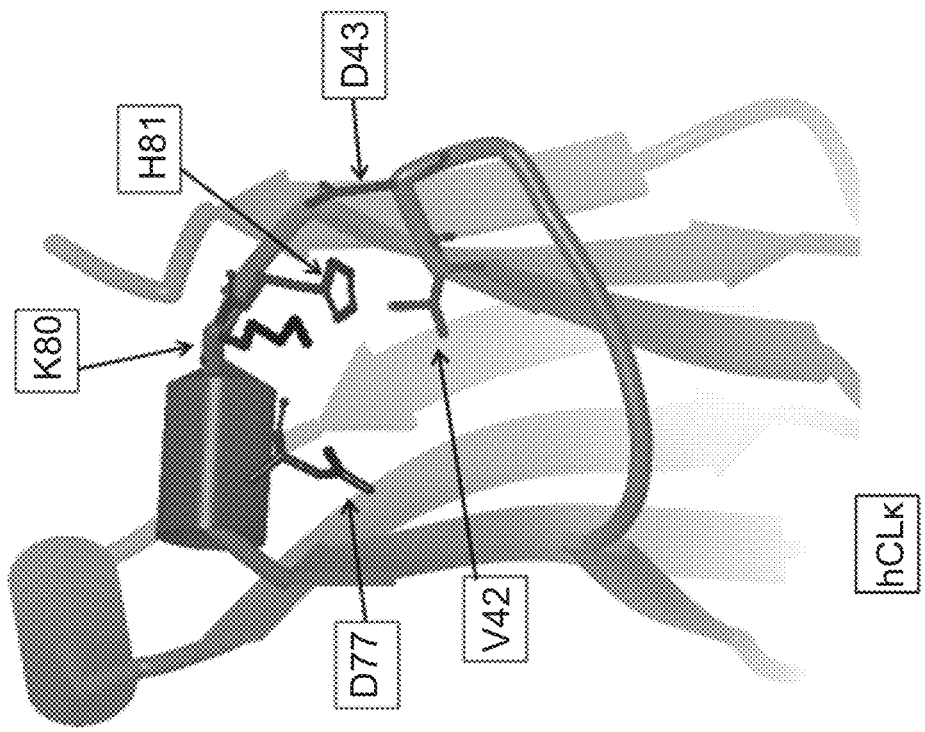

FIGS. 22A and 22B. Crystal structure-based minimized ribbon representation of the hCLκ (A) and hCHγ1-T78K/Q79H/CD loop swap mutant (B) domains, showing the sidechain location of significant residues.

Figure 23A:
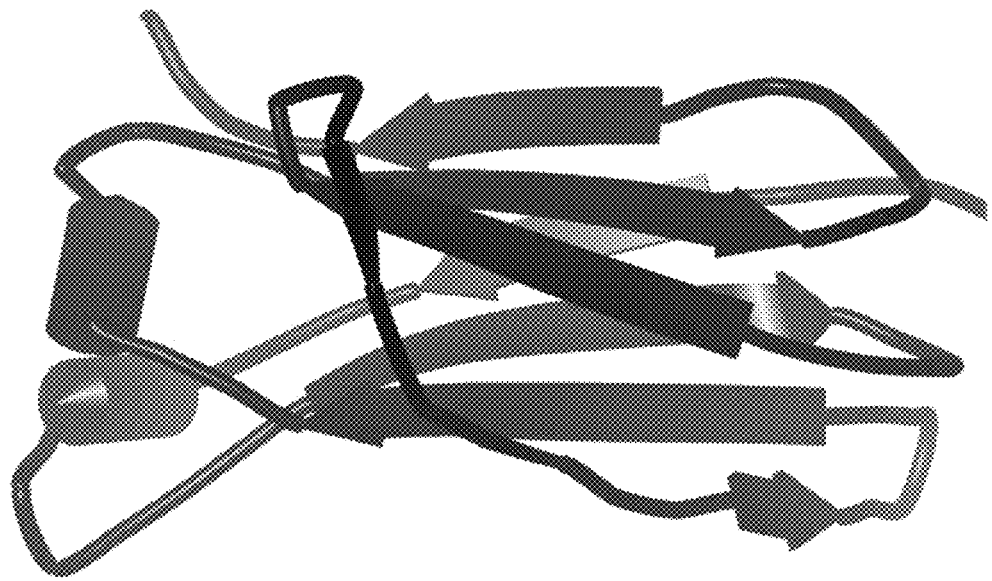
Figure 23B:
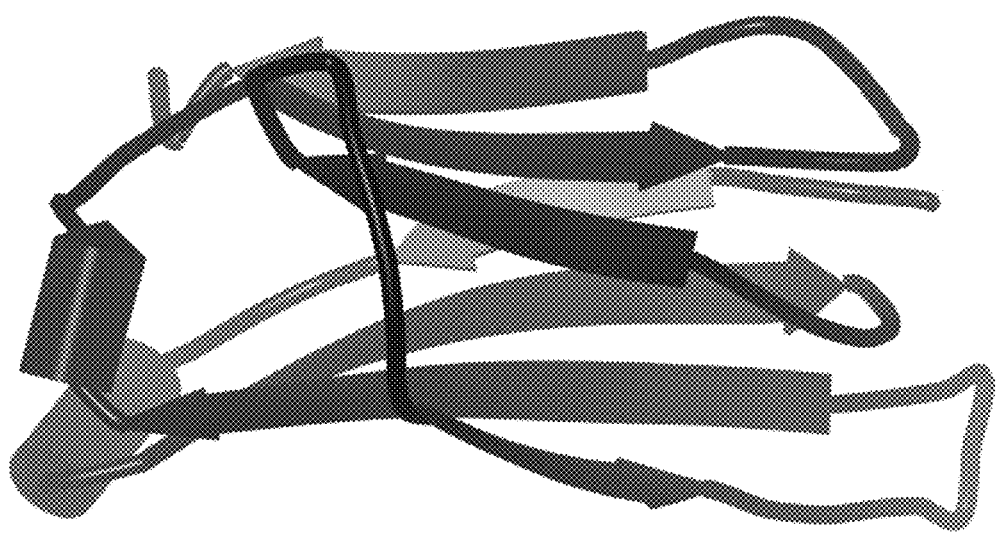

FIGS. 23A and 23B. Crystal structure-based minimized ribbon representation of the hCLκ (A) and WT-hCHγ2 (B) domains.

FIGS. 24A and 24B. Crystal structure-based minimized ribbon representation of the hCLκ (A) and WT-hCHγ2 (B) domains, showing the sidechain location of significant residues.

Figure 25B:
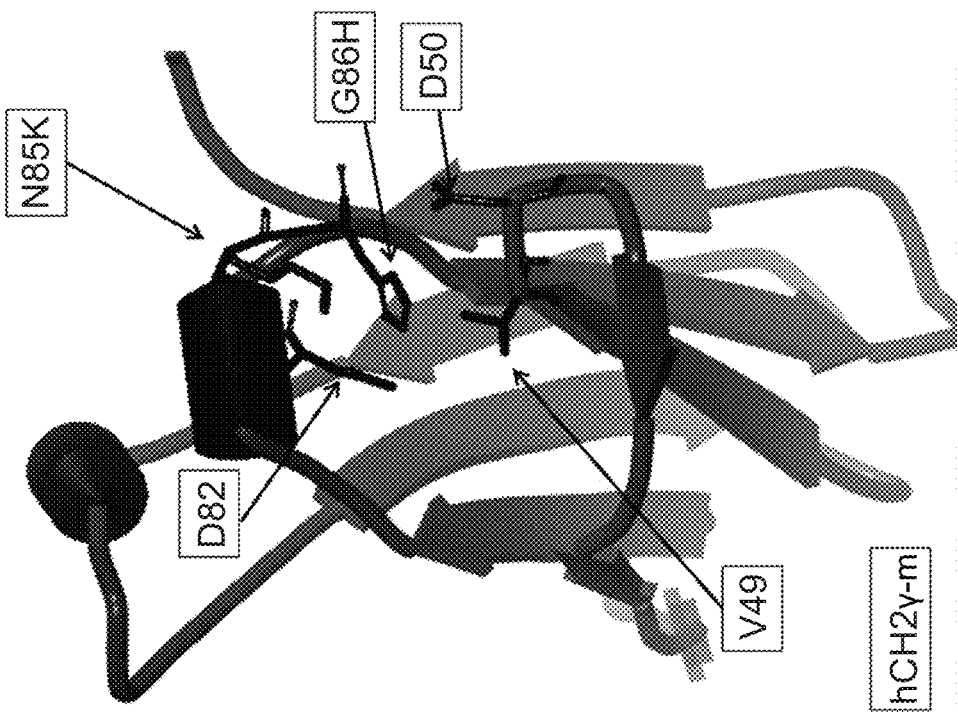
Figure 25A:
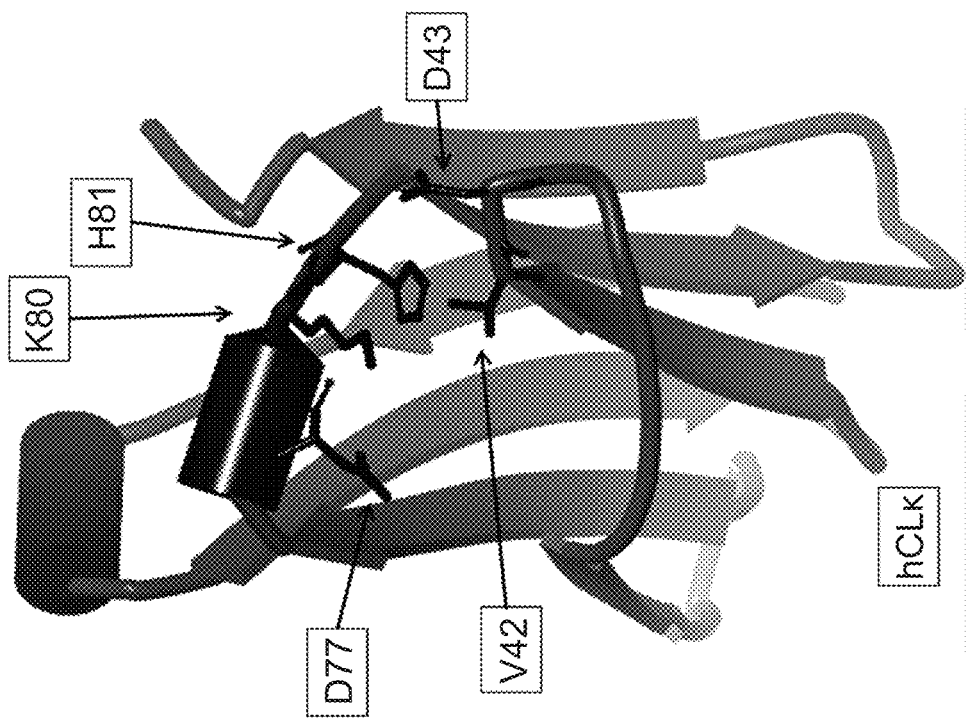

FIG. 25A and FIG. 25B. Crystal structure-based minimized ribbon representation of the hCLκ (A) and hCHγ2m mutant (B) domains, showing the sidechain location of significant residues.

Figure 26A:
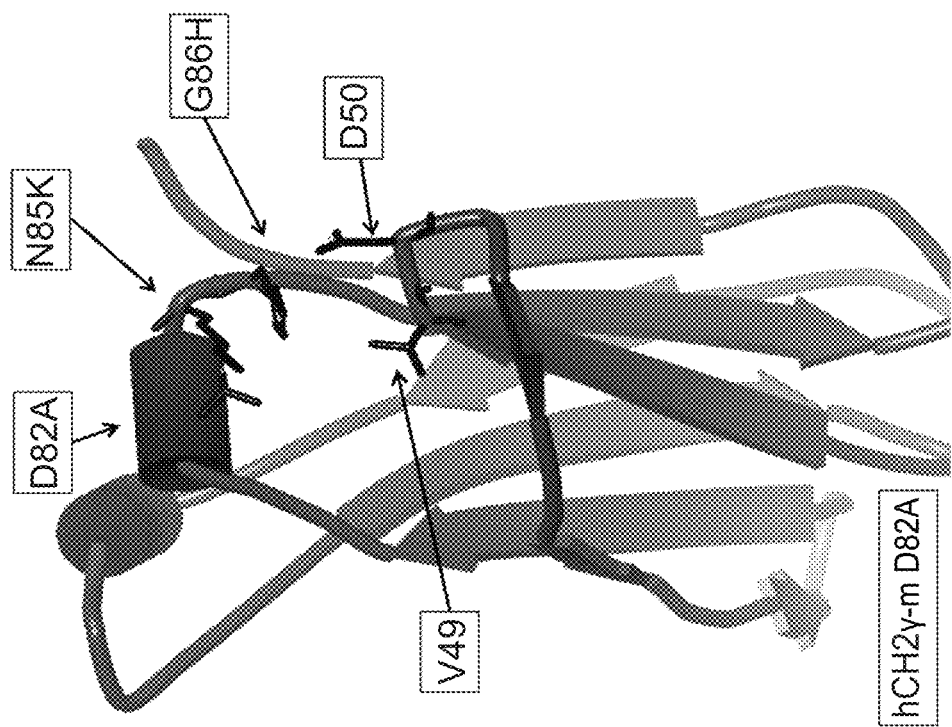
Figure 26B:
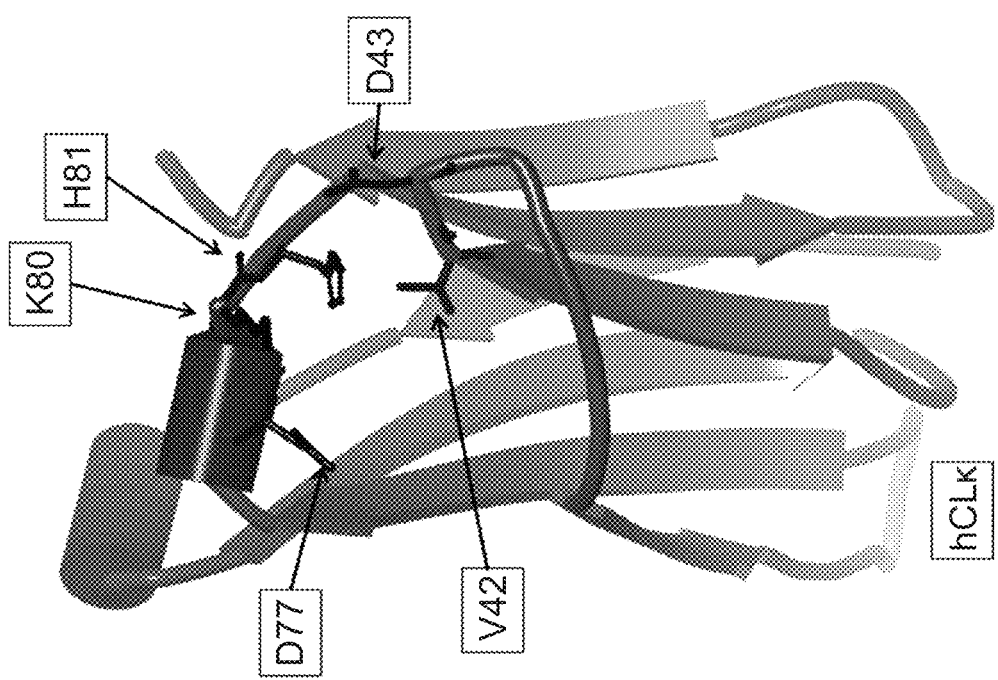

FIGS. 26A and 26B. Crystal structure-based minimized ribbon representation of the hCLκ (A) and hCHγ2m-D$^{82}$A mutant (B) domains, showing the sidechain location of significant residues.

Figure 27B:
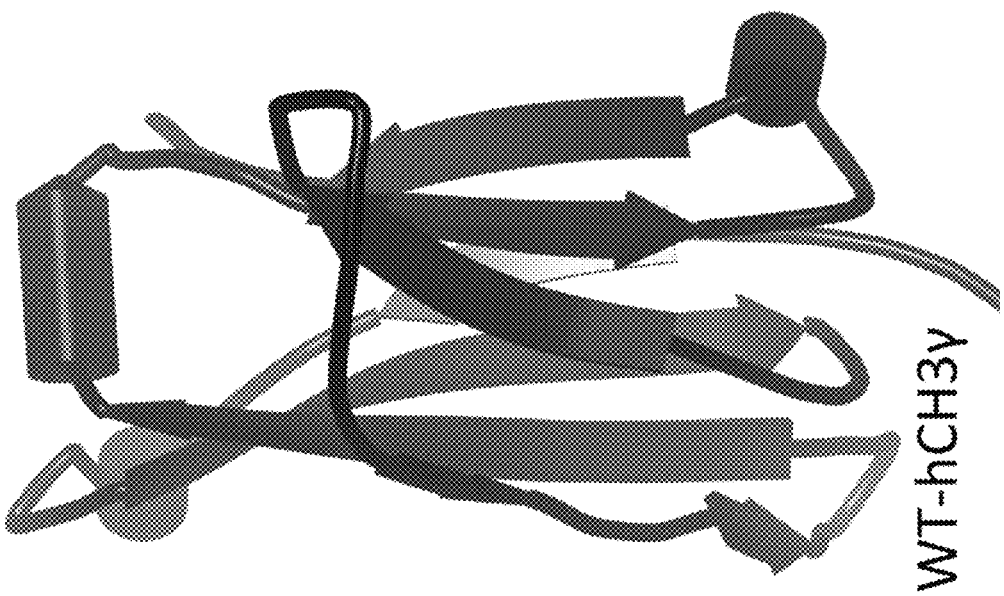
Figure 27A:
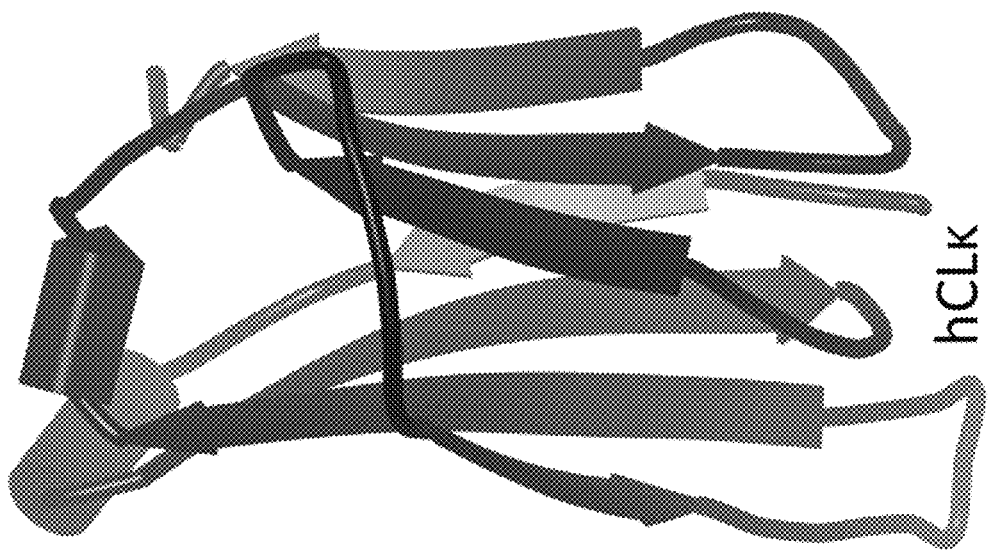

FIGS. 27A and 27B. Crystal structure-based minimized ribbon representation of the hCLκ (A) and WT-hCHγ3 (B) domains.

Figure 28A:
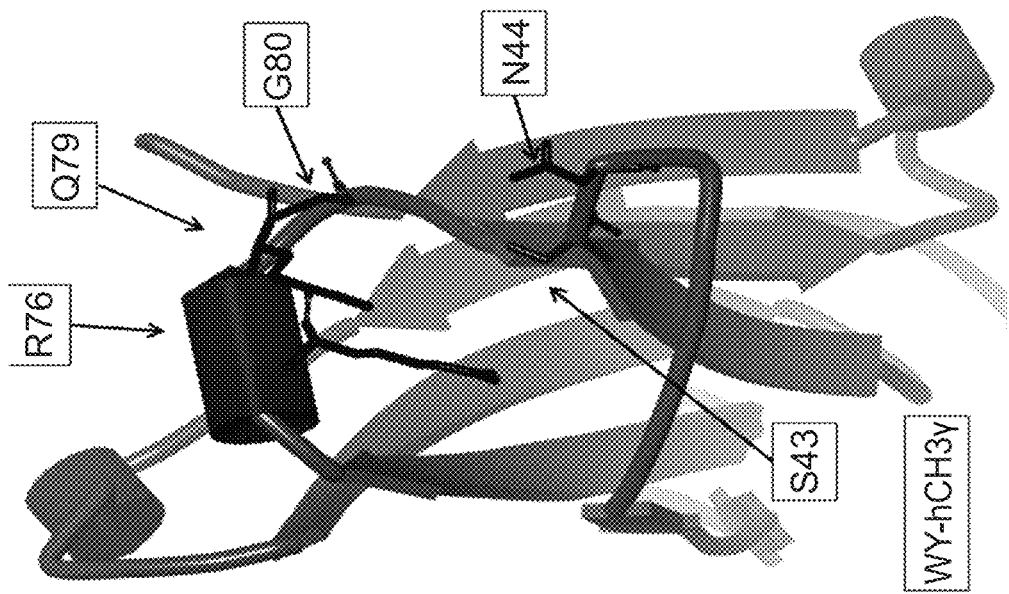
Figure 28B:
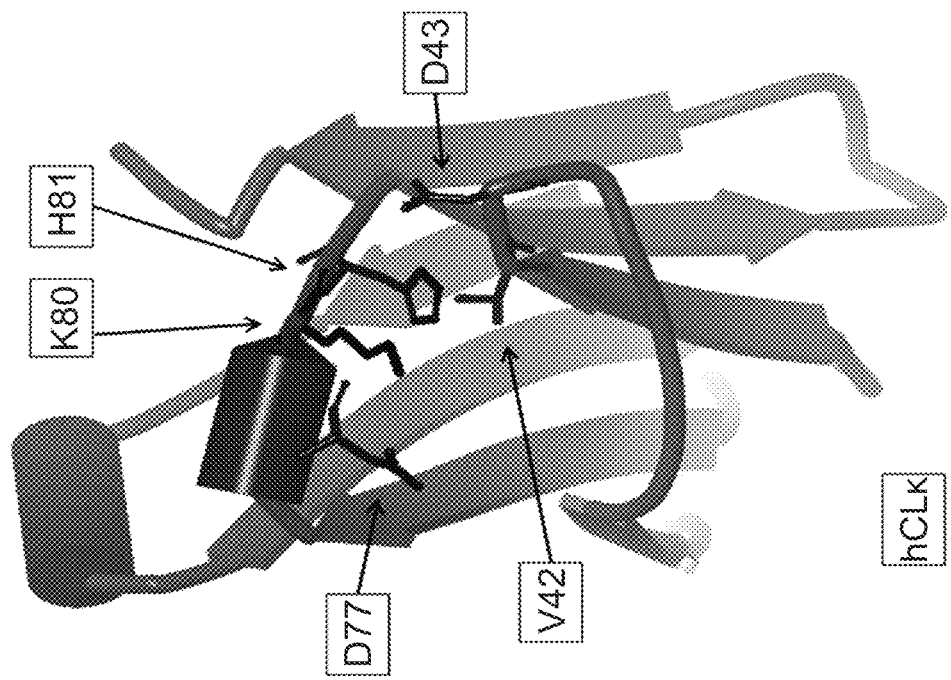

FIGS. 28A and 28B. Crystal structure-based minimized ribbon representation of the hCLκ (A) and WT-hCHγ3 (B) domains, showing the sidechain location of significant residues.

Figure 29B:
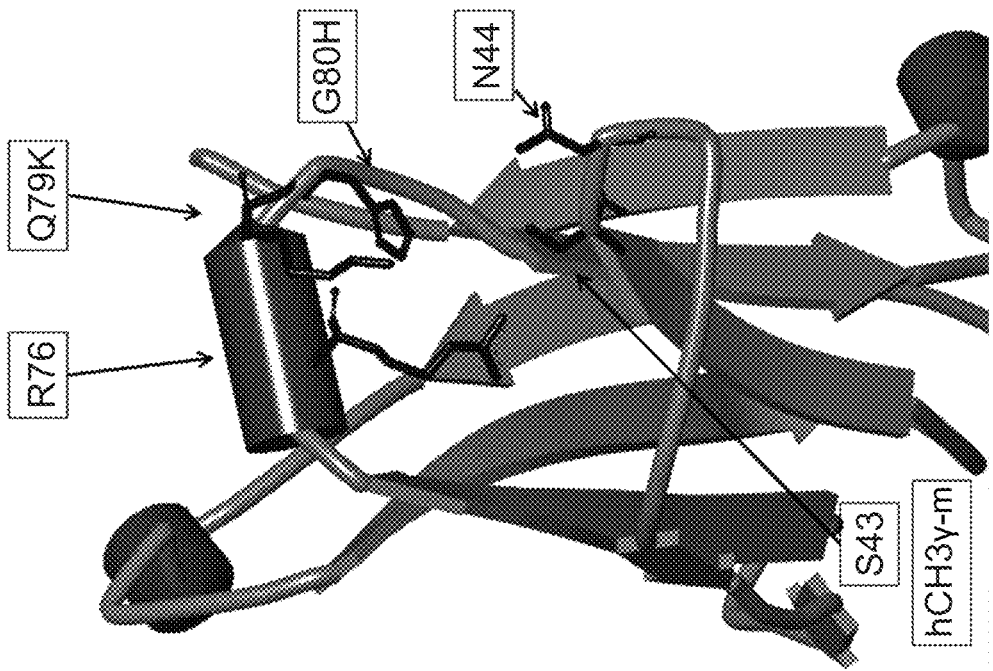
Figure 29A:
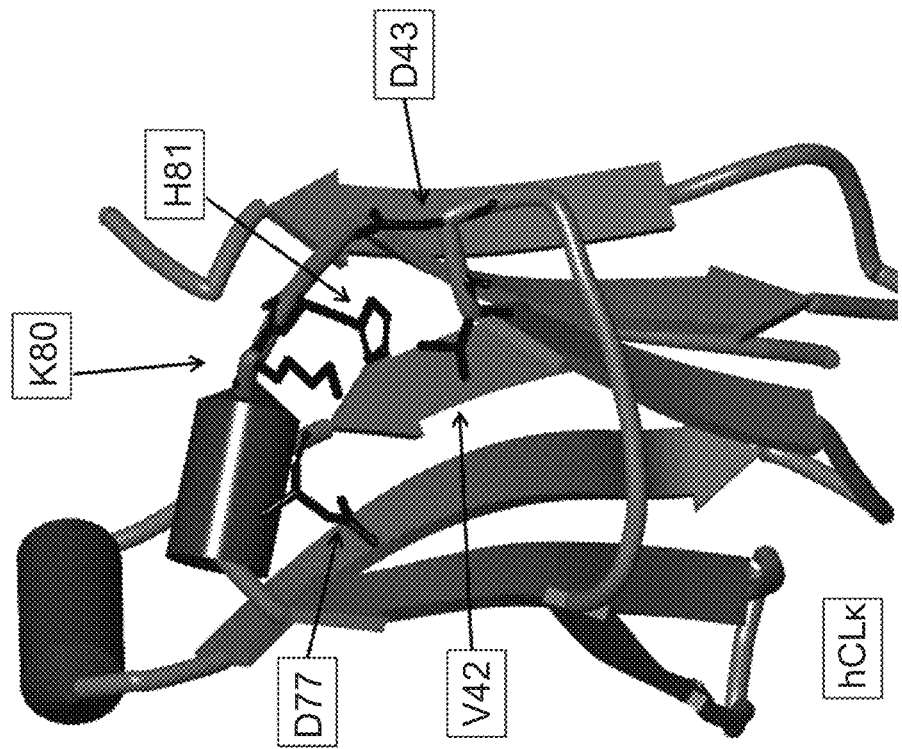

FIGS. 29A and 29B. Crystal structure-based minimized ribbon representation of the hCLκ (A) and hCHγ3m mutant (B) domains, showing the sidechain location of significant residues.

Figure 30B:
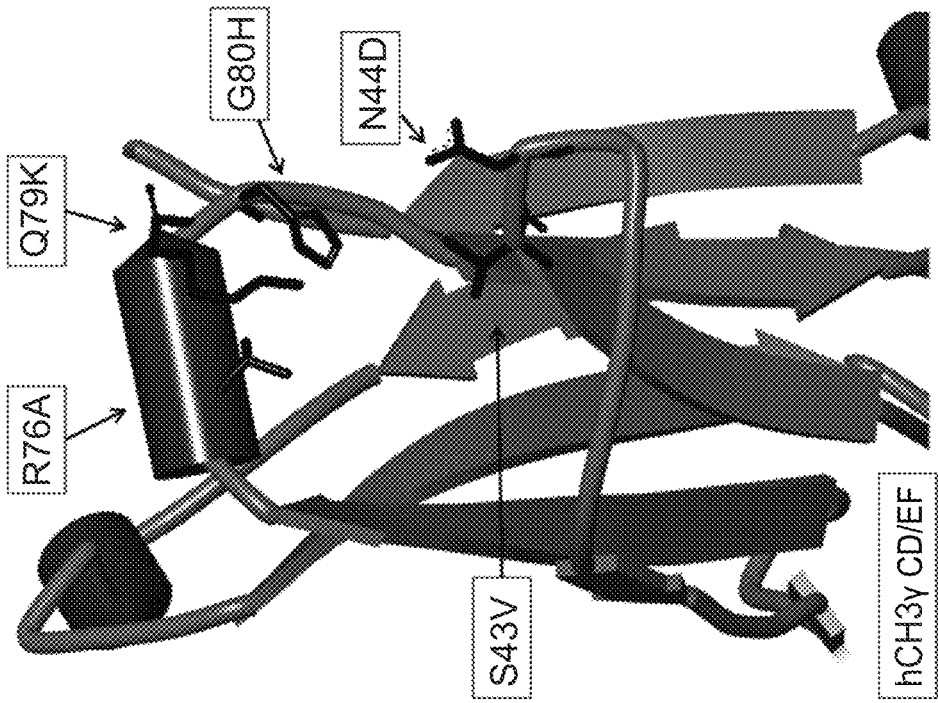
Figure 30A:
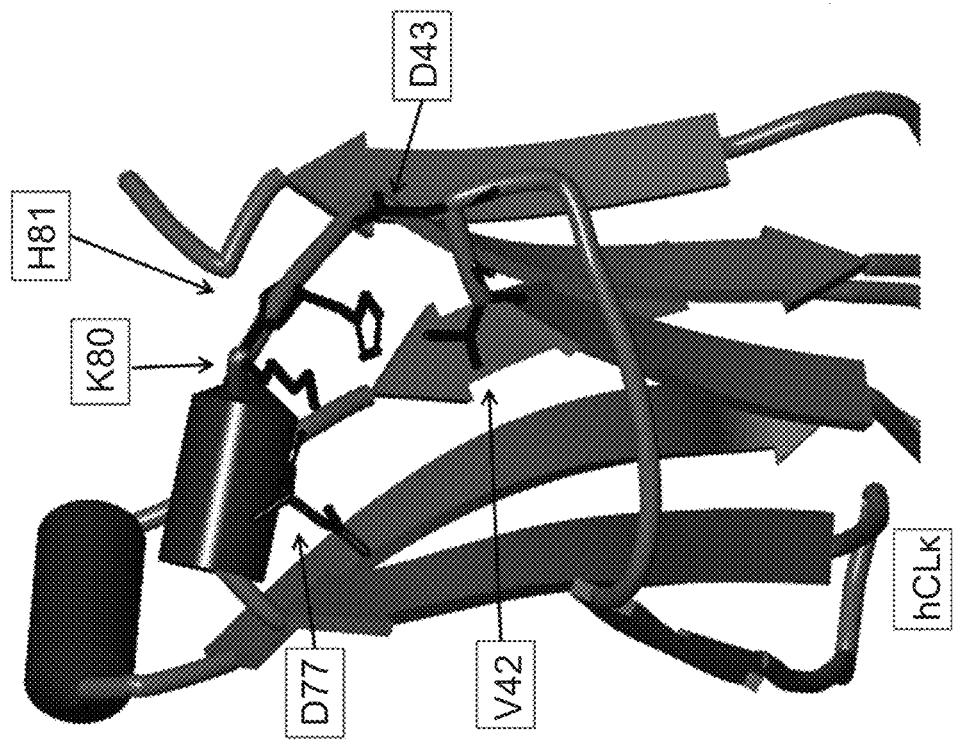

FIGS. 30A and 30B. Crystal structure-based minimized ribbon representation of the hCLκ (A) and hCHγ3m CD/EF mutant (B) domains, showing the sidechain location of significant residues.

Figure 31A:
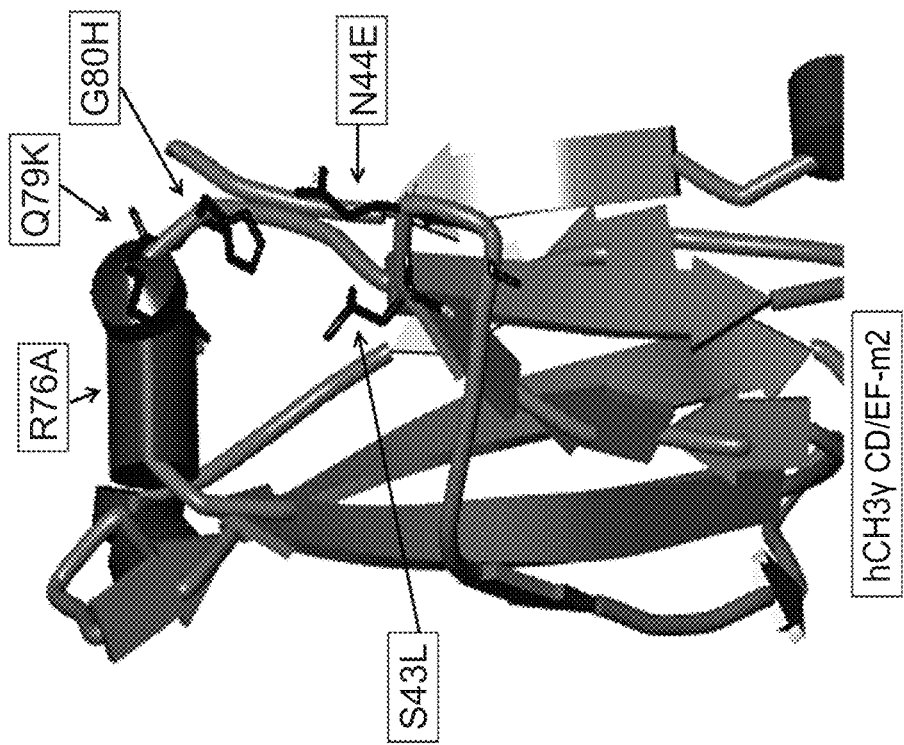
Figure 31B:
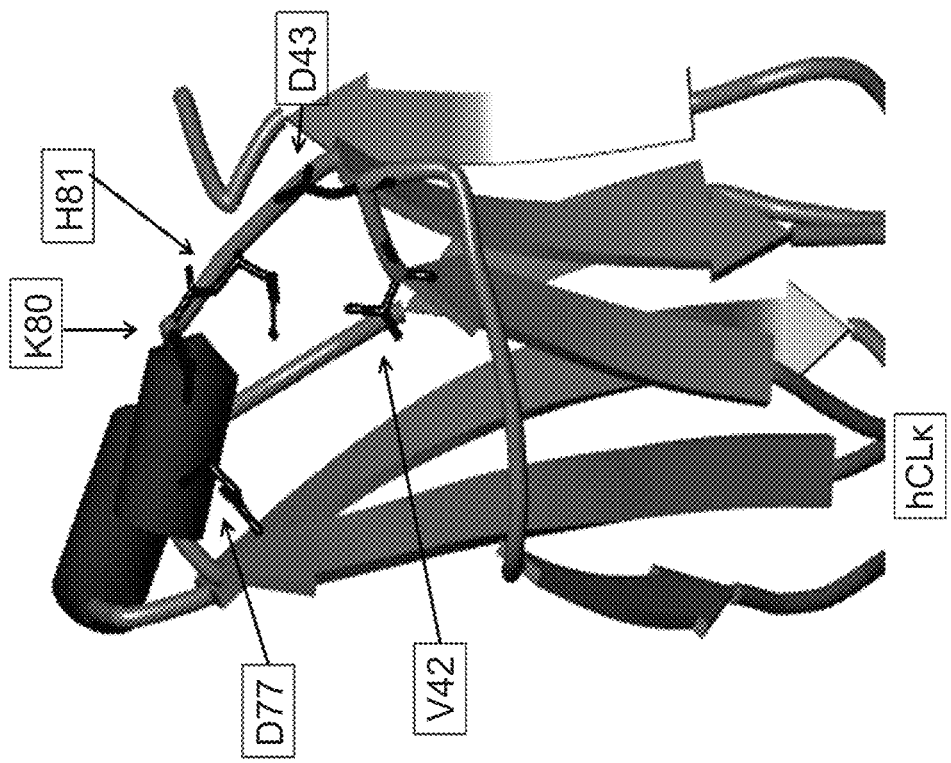

FIGS. 31A and 31B. Crystal structure-based minimized ribbon representation of the hCLκ (A) and hCHγ3m CD/EF-m2 mutant (B) domains, showing the sidechain location of significant residues.

FIGS. 32A and 32B. Alignment of CHγ1, CHγ2, and CHγ3 with their respective mutants and proposed mutant, together with CLκ and CLλ.

EXAMPLES

In order that this invention may be better understood, the following examples are set forth. These examples are for purposes of illustration only and are not to be construed as limiting the scope of the invention in any manner.

Description of Conjugation Additions (CA), Average CA

Conjugation additions (CA) are measured on an antibody scaffold using intact mass measurement by mass spectrometry. Upon conjugation, the overall mass of the intact product increases by the mass and number of additions of the conjugated peptide, toxin, etc. If multiple additions occur then a distribution of conjugate forms is observed in a mass spectra and the observed signal intensity of each conjugate form gives a quantitative measurement. This analysis is routinely presented in a table by listing each CA form as a percentage of all the observed CA forms. Average CA (e.g.:

the overall number of CA present on a scaffold) is an additional value that describes the average conjugate load. An example is provided below of 2 conjugated drug products. Example 1 has an even distribution of CA with an average CA=2.00. Example 2 has a distribution that heavily favors the presence of 2 CA with a minimal amount of other conjugation forms. The average CA is similar between these examples (2.13 vs. 2.00); however, Example 1 is a more heterogeneous product comprised of more conjugation forms, while Example 2 is a more homogeneous product that contains mostly 2 CA.

TABLE 1

|  | 0 CA % | 1 CA % | 2 CA % | 3 CA % | 4 CA % | Average CA |
|---|---|---|---|---|---|---|
| Example 1 | 11 | 22 | 33 | 22 | 11 | 2.00 |
| Example 2 | 2 | 4 | 77 | 12 | 5 | 2.13 |

A similar analytical treatment is also possible on these antibody scaffolds after disulfide bonds have been reduced to generate free light chains and heavy chains. Measurement of the intact mass of conjugated light/heavy chains can provide information about the location of CA on these respective subunits.

Explanation of Directional Conjugation to CLκ-$K^{80}$

To determine site specific attachment of drug conjugates to an antibody scaffold, a peptide map is produced. Peptide maps are the analysis of a protein sequence in detail to characterize peptide produced following a proteolytic digestion of the conjugated drug product. Once the protein is digested then the resulting peptides are analyzed by reversed phase liquid chromatography with mass spectrometry detection (RPLC/MS). The presence of conjugate additions on discreet amino acid residues is observed as a corresponding mass shift compared to the un-conjugated peptide. This process has been repeated on multiple antibodies conjugated with multiple conjugate additions using PFP reactive esters to target lysine residues. (Data is presented below, and also in WO2012007896, whose contents are herein incorporated entirely). In these studies, the following observations were consistent: 1—conjugate additions were observed more frequently on the LC than the HC, 2-CLκ-$K^{80}$ is the specific preferred residue that is modified, 3—multiple other locations are also modified on both the LC and HC; however, each alternative site is modified at a low level. To summarize, halo-phenyl ester conjugation results in preferred modification of CLκ-$K^{80}$ and additional conjugation is distributed at a low level across multiple residues. For this reason, the conjugation process is generally optimized to result in high % CA values for 2 conjugate additions because this promotes a product that is fully conjugated at a single location on each LC. While elevated % CA levels of 0-1 conjugates result in preferable CLκ-$K^{80}$ modification, these conjugate forms also represent a significant amount of un-reacted scaffold. Products that display average CA values significantly greater than 2 suggest the presence of conjugate additions that are not targeted at discreet residues. When HC and LC are reduced and analysed separately, the % value of 1 CA indicates the % conjugation on single LC species, and is thus reliable indicator of the efficiency of conjugation to the CLκ-$K^{80}$ residue.

Example 1 Exemplary Synthesis of Peptides Used in the Invention

Scheme 1: Solid phase synthesis of a peptide chain usaing Fmoc chemistry (exemplified with a typical Ang2-binding peptide (ABP) SEQ ID NO: 27. TFA/water/phenol/triisopropylsilane (90:4:4:2). Rink Amide Resin. Steps for SPPS using Fmoc chemistry: (i)Fmoc removal with 20% piperidine/DMF, (ii) Amino acid coupling; HBTU:Amino acid: HOBt:NMM ratio relative to resin amine loading is 5:5:5:20. Solvent used was NMP, (iii) Repeat steps for each amino acid coupling. X = acid-labile side chain protecting group. Completed assembly of fully-protected, resin-bound peptide:

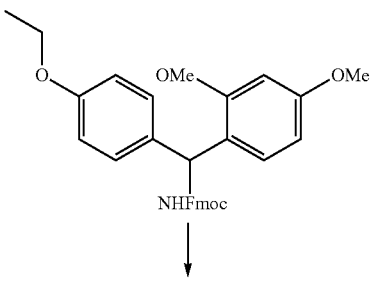

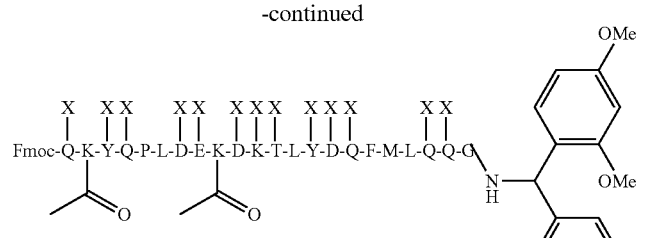
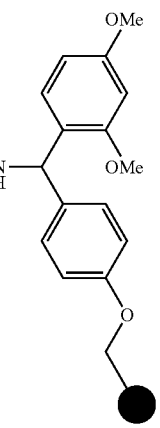
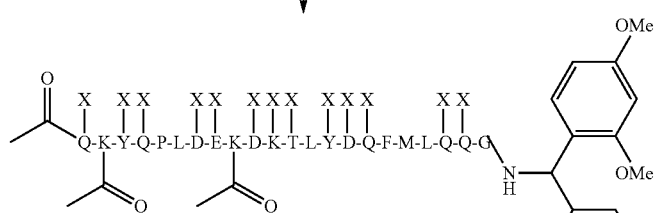
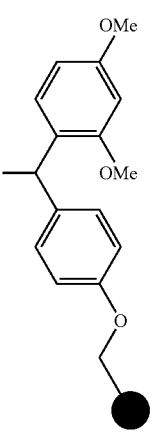
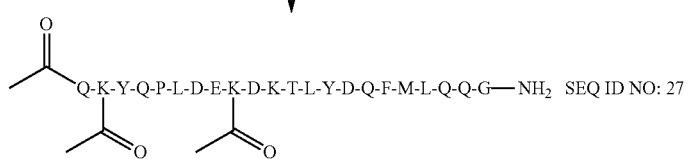 SEQ ID NO: 27
Synthesis of Peptide-Thiol-Linker Compounds
Scheme 2: Synthesis of SEQ ID NO: 27-$K_{SH}^{11}$
($K^{11}$ substituted with linking residue $K_{SH}$). S-Trityl-mercaptopropionic acid/HBTU/NMM (5:5:10 ratio with respect to peptide). Trityl-protected thiol Ang2 peptide intermediate.
TFA/DCM/TIPS (5:93:2 ratio). Thiol bearing Ang2 modified peptide.
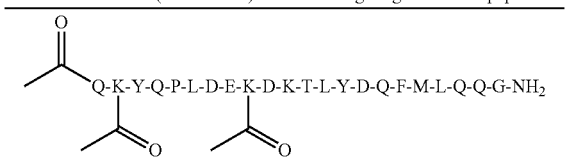
SEQ ID NO: 27
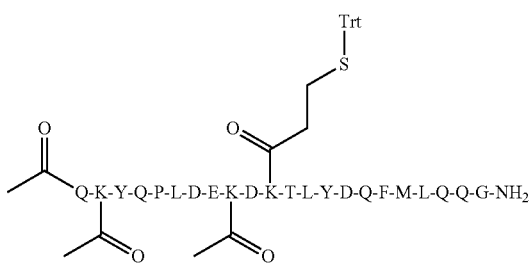
SEQ ID NO: 27-$K_{SH}^{11}$-Trt

-continued

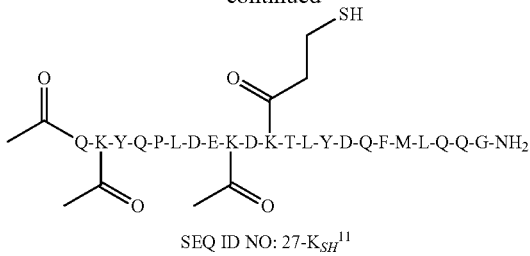

SEQ ID NO: 27-K$_{SH}$[11]

An Ang2-binding peptide (ABP; SEQ ID NO:27) (284 mg, 0.1 mmol) was dissolved in dimethylformamide (0.5 ml) with stirring. Separately, S-Trityl-mercaptopropionic acid (MPA, 62 mg, approx 0.125 mmol), HBTU (48 mg, 0.125 mmol) and N-methylmorpholine (0.025 ml, 0.25 mmol) were stirred in DMF (0.5 ml) for 5 min until dissolved. The ABP solution and activated MPA solutions were mixed together for 2 hrs. Progress of the reaction was monitored by LCMS. After 2 hrs, the solution was slowly added to ice-cold ether (40 ml) to precipitate the ABP-S-trityl-MPA product. The white precipitate was collected by filtration then dried. The solid residue was then dissolved in a solution of trifluoroacetic acid in dichloromethane (1:10, 10 ml), with triisopropylsilane (TIPS) added (0.050 ml) and stirred for 1 hr. The solution was evaporated under reduced pressure to a light-yellow oil then the crude thiol peptide precipitated by the addition of ice-cold ether. The product was collected by centrifugation and dried in vacuo. The residue was dissolved in 50% aqueous acetonitrile then lyophilized to yield the crude thiol peptide (approx 80% pure by HPLC analysis). The crude thiol peptide was purified by semi-preparative HPLC to yield 145 mg of SEQ ID NO:27-K$_{SH}$[11].

Generation of Ang-2-Binding-Peptide-Thiol Intermediates

Peptide chain assembly was conducted on a 0.1 mmol scale. The resin used was Fmoc-Rink-PL resin (150 mg, 0.67 mmol/g substitution). Standard Fmoc chemistry protocols were used to assemble the peptide. Fmoc removal was with 20% piperidine/DMF for 3×5 min. and all resin washing steps used DMF. To incorporate the amino acids, a single coupling step was employed for each residue, using HBTU/HOBt/NMM activation, for a 2 hr period. The Linking Residue (K$_{SH}$) was incorporated as Fmoc-Lys(N$^\varepsilon$-mercaptopropionate-S-Trt)-OH. Upon chain assembly, the N-terminal Fmoc group was removed and the peptidoresin capped by acetylation. The final resin was washed with DCM and dried overnight in vacuo.

Acidolytic removal of protecting groups and cleavage of the peptide from the resin was achieved using a cocktail of TFA/water/dithiothreitol/triisopropylsilane (ratio 90:4:4:2, 5 ml) for 2 hrs. The solution was filtered from the resin and the resin washed with another 5 ml of neat TFA. The combined filtrates were evaporated to a syrup then addition of ice-cold ether precipitated a white powder. The powder was collected by centrifugation then dissolved in 50% aqueous acetonitrile (20 ml), frozen and lyophilized overnight.

A preparative HPLC column was pre-equilibrated with dilute aqueous TFA and acetonitrile. The crude ABP-thiol intermediates (i.e. ABP with K$_{SH}$ as linking residue) was dissolved in DMF (3 ml), then adsorbed onto the column and eluted by applying a gradient of acetonitrile in dilute TFA. Fractions were collected automatically by mass (M=1465). Elution from the column was monitored by UV, the fractions obtained were analyzed by analytical RP-HPLC.

Example 2 Conjugation Strategies 5 different conjugation strategies were considered for conjugating peptides to antibodies (exemplary structures are shown using SEQ ID NO:27-K$_{SH}$[11] and 2.12.1.fx) (full details are provided in the Examples of PCT/US2011/053092, filed 11 Jul. 2011, whose contents are hereby incorporated entirely). Briefly, NHS esters, maleimide, squarate esters, AZD and halo-phenyl esters were all investigated as potential mechanisms to develop directional conjugation to antibodies.

[NHS-PEG5-SEQ: 27-K[11]]

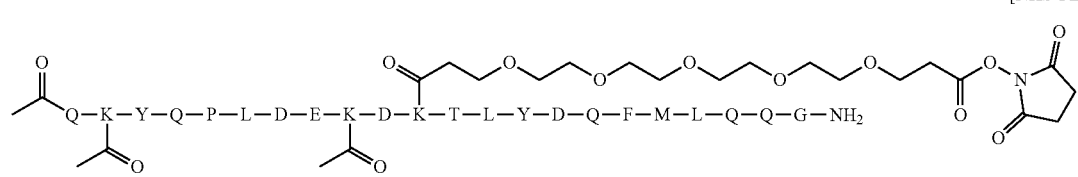

[Squarate-SEQ: 27-K[11]]

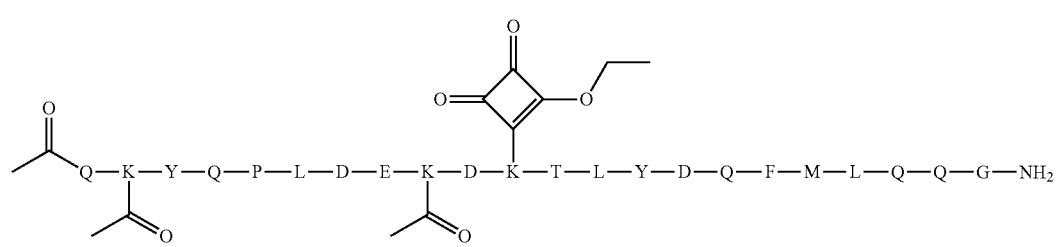

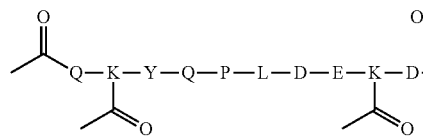
[Mal-PEG4-SEQ: 27-K[11]]

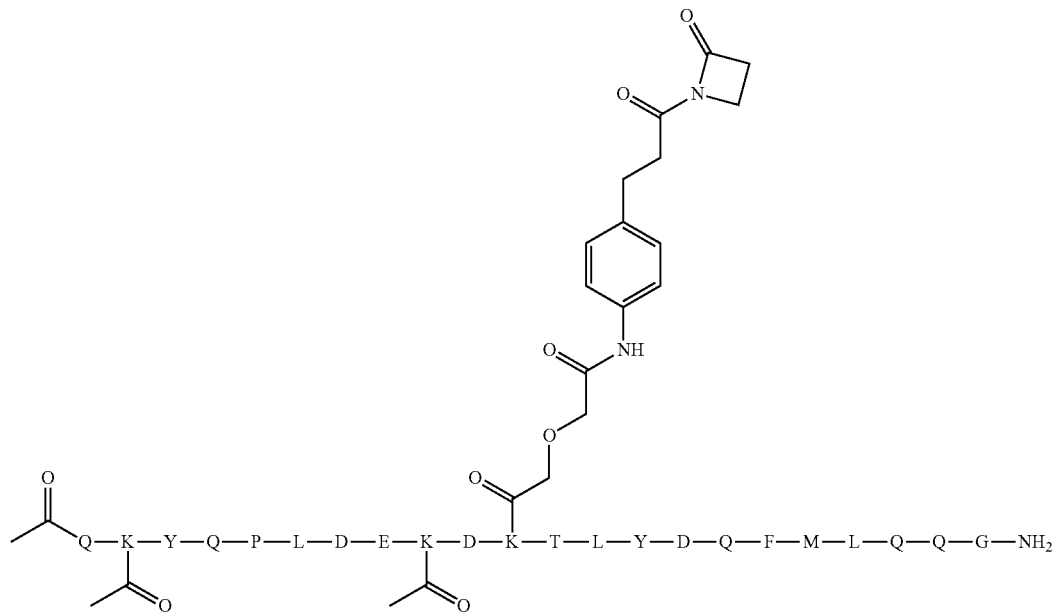
[AZD-SEQ: 27-K[11]]

NHS esters suffered from the problems of slowly converting to a free acid form, where the NHS ester is converted to an inactive carboxyl. It was concluded that although some success was obtained with NHS esters, it appeared that the aqueous lability of the resulting NHS-ester may limit their application in subsequent conjugation reactions. Further tests of NHS-PEG$_2$-MAL are shown below (comprising Z* group Z13).

The ethyl squarates conjugate well to free thiols but poorly to free amines on proteins and antibodies unless the pH is above 9.

In general, the maleimide-activated peptides did not conjugate well to proteins or antibodies which lack either an endogenous thiol (derived from a free cysteine side chain) or a thiol introduced by other chemical means, e.g. via Traut's reagent.

AZD reacted slowly with antibody amino groups, and attempts to increase the pH to 7-9 yielded low levels of conjugation and high levels of AZD hydrolysis (in order to increase the nucleophilic tendency of the antibody surface lysines by decreasing their charge, as the pKa of surface lysines is about 9.1 to 11.2).

Example 3 Synthesis of Pentafluorophenyl Esters (PFP)

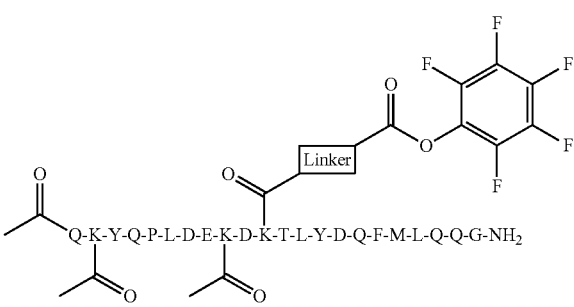

The present invention also provides for the use of pentafluorophenyl (PFP; Z*=Z1) esters to form relatively stable Effector Moiety-linker complexes. This method has several advantages over other approaches in that the PFP group can be introduced in solution easily from a stable activated peptide product, which itself can be purified using standard HPLC methods with little PFP ester hydrolysis observed.

The present invention provides a synthetic route whereby an activated ester group, such as PFP, can be coupled directly to a side chain lysine on the peptide by either a chemoselective reaction (using thiol/maleimide chemistry)

or by using a bis-active ester reagent, which forms an amide with the peptide side chain but leaves the other end as the active ester.

In some embodiments, the strategy may be a bis-acid PEG with each acid activated as a PFP ester. In organic solutions, with some base present, the end of the bis-PFP linker reacted with the N-ε-amino side chain of lysine in the required tether position to form a stable amide linkage, while the other end maintained the other PFP group. One potential problem with this strategy is the possibility of forming peptide dimers, where a peptide would add to each of the PFP moieties present at each end of the linker. In some aspects, the present invention overcomes this additional problem by altering the stoichiometry and addition of the respective peptide and bis-PEG-PFP linker. One solution provided by the invention is to have an excess of the bis-Pfp linker in solution and slowly add the peptide in solution, such that an excess of linker over peptide is always present. By having a ratio of between about 3.7:1 to about 4.3:1, or in some embodiments, a ratio of about 4:1, of linker over peptide, the required PFP-activated peptide can be synthesized with no dimer present. The synthesis scheme for [PFP-PEG$_5$-K$^{11}$-SEQ:27] is shown below in Scheme 3.

Synthesis of [PFP-PEG$_5$-K$^{11}$-SEQ:27]

to dryness to give a pale yellow light oil. Analysis by TLC and HPLC indicated a pure product with correct MS=670. The product was used in the next step without further purification. The product is stable for several months at −20° C.

SEQ ID NO:27 (730 mg) was dissolved in anhydrous dimethylformamide (8 ml) and N-methylmorpholine (0.05 ml) added. An aliquot of neat bis-dPEG$_5$-OPfp reagent (0.5 ml) was placed in a glass vial (20 ml). With vigorous stirring, the SEQ ID NO:27/NMM solution was added in 4×2 ml aliquots to the bis-dPEG$_5$-OPfp reagent over 2 hr, then the final mixture stirred for a further 1 hr. Progress of the conversion to [PFP-PEG$_5$-K$^{11}$-SEQ:27] product was monitored by analytical HPLC. At the end of the reaction, the solution was filtered and directly purified by semi-

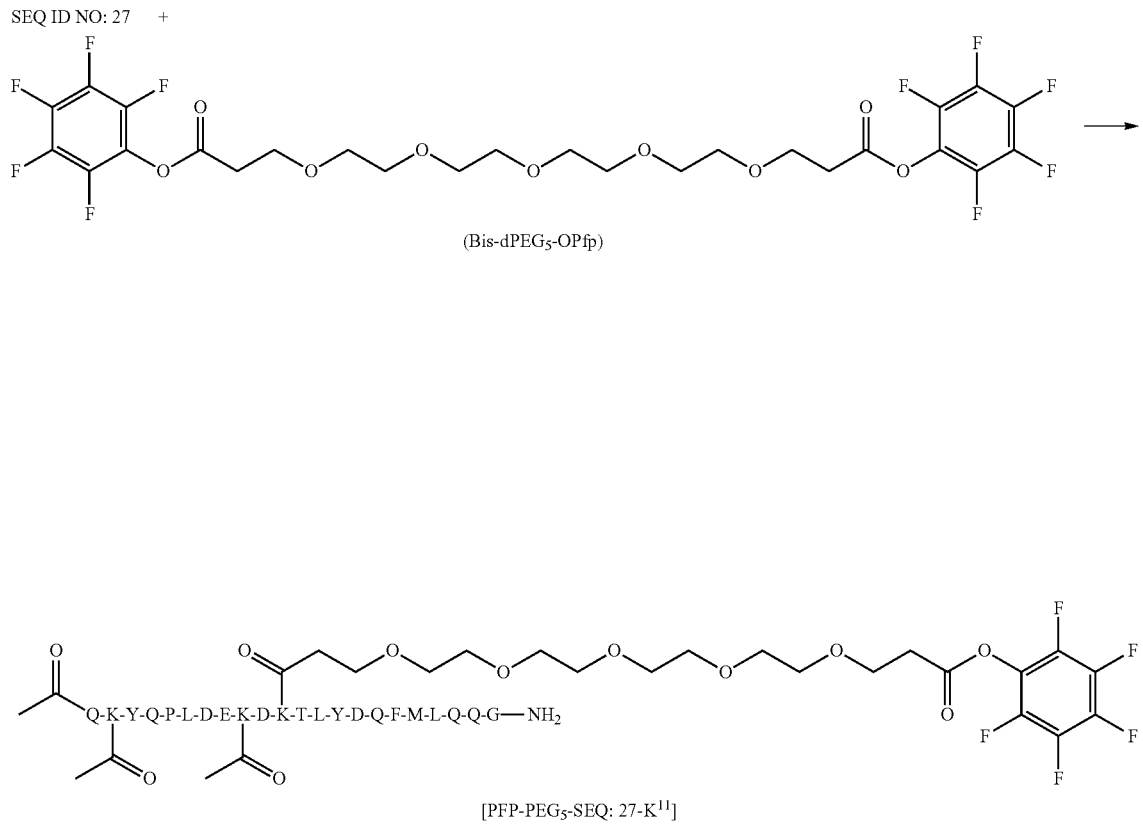

Bis-dPEG$_5$-acid (1 mmol, 338 mg) was dissolved in anhydrous dichloromethane (5 ml) then pentafluorophenol (2 mmol, 368 mg) was added, along with dicyclohexycarbodiimide (1 mmol, 208 mg). The solution was stirred overnight at RT. After this time, the fine white dicyclohexylurea side-product was filtered off and the filtrate evaporated preparative HPLC on a 1" C8 column. The purest fractions (>95% by analytical HPLC) were combined and lyophilized to give 400 mg (48% yield) of final [PFP-PEG$_5$-K$^{11}$-SEQ: 27] peptide-linker product. A similar mechanism can be used to generate [PFP-PEG$_2$-MAL-K$_{SH}$$^{11}$-SEQ:27] (see Scheme 4).

Synthesis of [PFP-PEG$_2$-K$_{SH}^{11}$-SEQ:27]

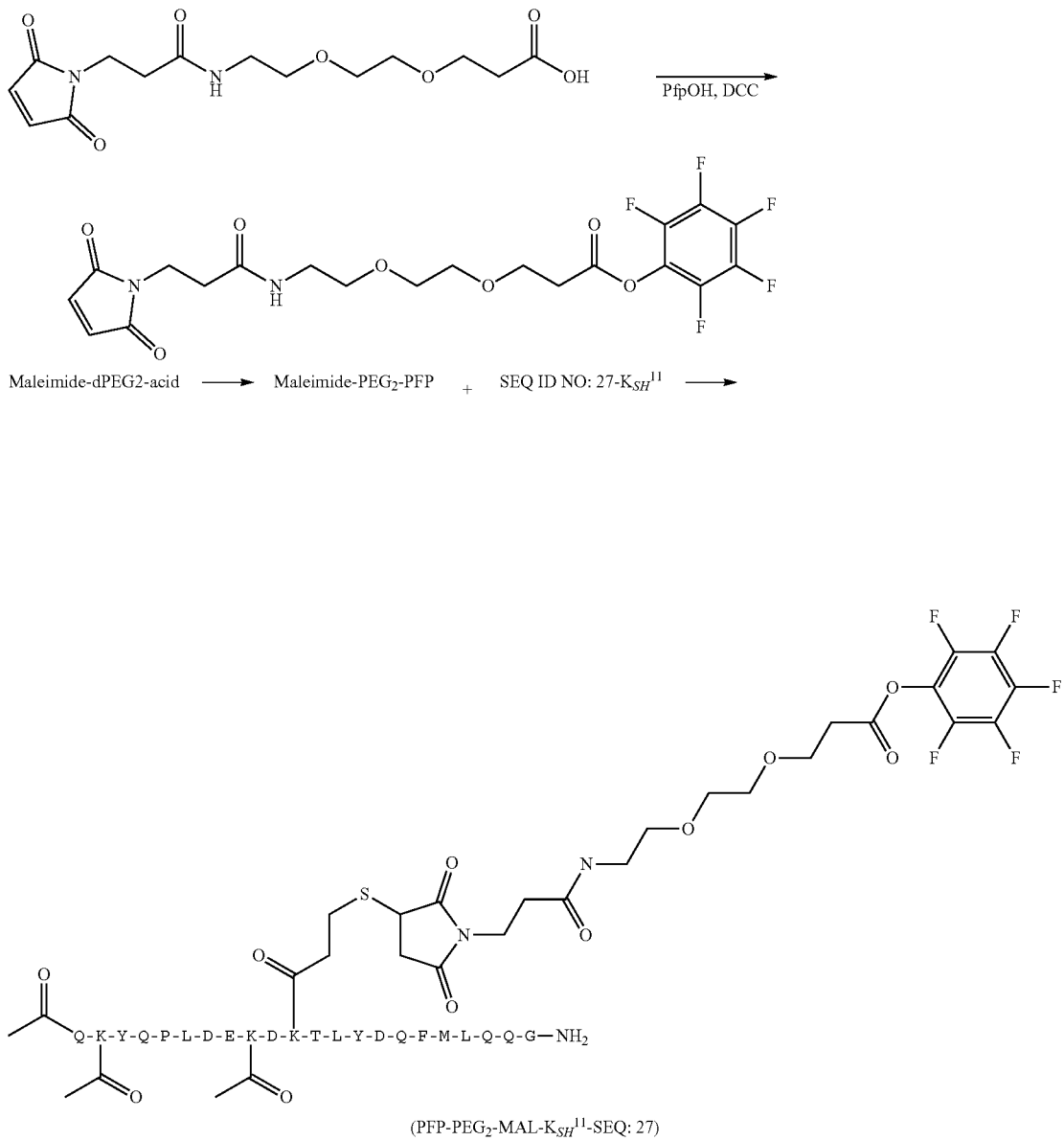

Maleimide-dPEG$_2$-acid (328 mg, 1 mmol, Quanta Biodesign), pentafluorophenol (0.103 ml, 1 mmol, PFP) and dicyclohexylcarbodiimide (206 mg, 1 mmol, DCC) were dissolved in dry DCM (10 ml) and stirred for 1 hr at RT. The fine white precipitate (DCU side-product) that formed was removed by filtration and the filtrate evaporated to dryness in vacuo. The product was obtained as a fine white powder in high yield (490 mg, quantitative). Purity was >95% by analytical HPLC; MS showed [M+H]$^+$=495.

A sample (30-40 mg) of SEQ ID NO:27-K$_{SH}^{11}$ was dissolved in anhydrous DMF (2 ml). Maleimide-PEG$_2$-PFP (20 mg) was added along with N-methylmorpholine (5 mL). The reaction was stirred and monitored at RT by HPLC to follow the time-course of product formation. The complete conversion of starting peptide to PFP-activated product was observed within the first 2 hrs. The solution was filtered and the product peak directly isolated by semi-preparative HPLC. In each case, the product was isolated in approximately 40% yield after lyophilization.

Example 4 Antibody Conjugation

The MAC-1 and MAC-2 exemplary antibody-Effector Moiety conjugates were made by conjugating the antibody 2.12.1.fx (SEQ ID NO:1 and SEQ ID NO:2) with an Ang2 binding peptide (SEQ ID NO:27). MAC-1 comprises 2.12.1.fx conjugated to [PFP-PEG$_2$-MAL-K$_{SH}^{11}$-SEQ:27] to yield 2.12.1.fx-[PEG$_2$-MAL-K$_{SH}^{11}$-SEQ:27] and MAC-2 comprises 2.12.1.fx conjugated to [PFP-PEG$_5$-K$^{11}$-SEQ:27] to yield 2.12.1.fx-[PEG$_5$-K$^{11}$-SEQ:27].

Generation of MAC-1
Scheme 5: Reaction of [PFP-PEG$_2$-MAL-K$_{SH}$$^{11}$-SEQ: 27] with a lysine side chain of an antibody (Ab-K-Ab): Where the antibody is 2:12.1fx, the MAC is MAC-1.
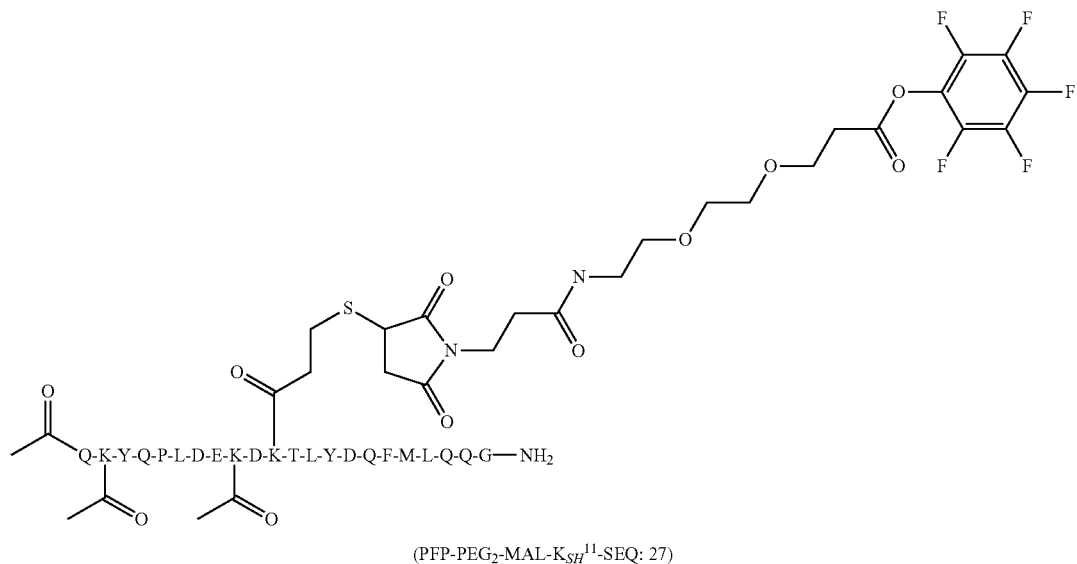
(PFP-PEG$_2$-MAL-K$_{SH}$$^{11}$-SEQ: 27)
Generation of MAC-2
Scheme 6: Reaction of [PFP-PEG$_5$-K$^{11}$-SEQ: 27] with a lysine side chain of an antibody (Ab-K-Ab): Where the antibody is 2.12.1.fx, the MAC is MAC-2.
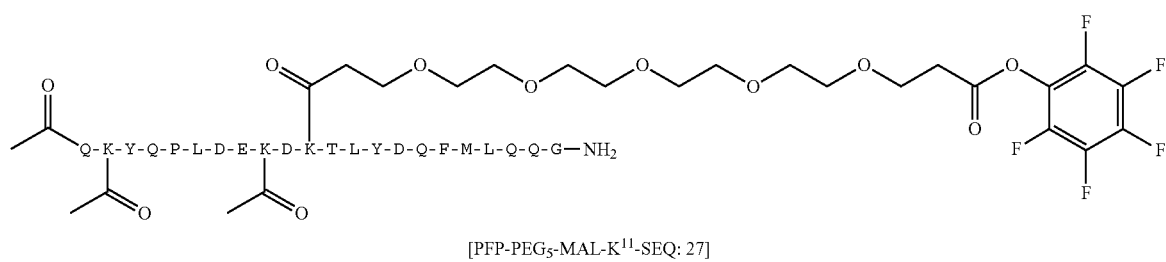
[PFP-PEG$_5$-MAL-K$^{11}$-SEQ: 27]
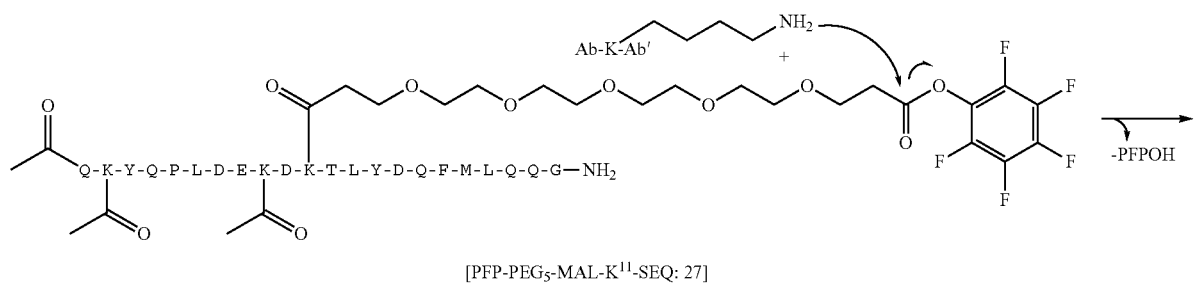
[PFP-PEG$_5$-MAL-K$^{11}$-SEQ: 27]

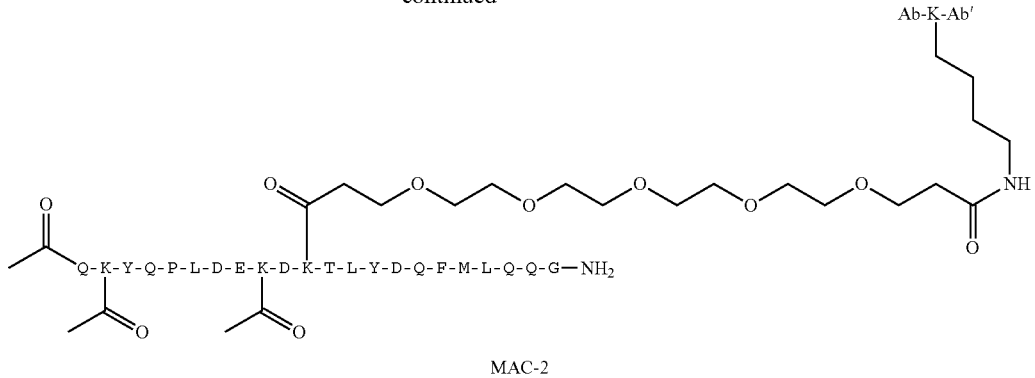

MAC-2

The number of peptide conjugations per 2.12.1.fx antibody in a sample of each MAC was calculated (see Table 2).

TABLE 2

Conjugation profile of MAC-1 and MAC-2.

| | Conjugation Additions (CA) (%) | | | | | |
|---|---|---|---|---|---|---|
| | 0 | 1 | 2 | 3 | 4 | Avg CA |
| MAC-1 | 3 | 26 | 42 | 25 | 3 | 1.97 |
| MAC-2 | 2 | 20 | 47 | 26 | 5 | 2.12 |

Example 5 Optimizing Conditions for PFP-Based Conjugation

A series of assays were run to establish optimal reaction conditions for directed conjugation. At the end of each reaction conjugation, the reaction was quenched with a succinate and glycine buffer, lowering the pH to approximately 5.5 and quenching any free peptide or peptide/linker. MAC-2 analysis was conducted by measuring the intact molecular weight (MW) of the MAC using electrospray time-of-flight mass spectrometry detection following protein separation from salts and excipients through a size exclusion chromatography column.

Temperature 2.12.1.fx antibody was adjusted to 18 mg·ml$^{-1}$ at pH 7.7 with a phosphate buffer to a final concentration of 0.06M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 4.3:1 and allowed to react for 2 hrs at 18, 22, or 25° C. Results are presented in Table 3.

TABLE 3

Reaction temperature in 0.06M phosphate at 4.3:1 peptide:antibody.

| | CA (%) | | | | | |
|---|---|---|---|---|---|---|
| Temp | 0 | 1 | 2 | 3 | 4 | Avg CA |
| 18 C. | 1 | 16 | 51 | 23 | 8 | 2.21 |
| 22 C. | 3 | 15 | 57 | 21 | 5 | 2.11 |
| 25 C. | 2 | 12 | 53 | 25 | 7 | 2.24 |

Reaction pH 2.12.1.fx antibody was adjusted to 18 mg·ml$^{-1}$ at pH 6.5, 6.75, 7.0, 7.25, 7.5, 7.75, or 8.0 with a phosphate buffer to a final concentration of 0.06M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 4.3:1 and allowed to react for 2 hrs at RT. The results are presented in Table 4.

TABLE 4 pH in 0.06M sodium phosphate buffer at 4.3:1 peptide:antibody.

| | CA (%) | | | | | |
|---|---|---|---|---|---|---|
| pH | 0 | 1 | 2 | 3 | 4 | Avg CA |
| 6.5 | 7 | 42 | 41 | 9 | 0 | 1.51 |
| 6.75 | 3 | 31 | 52 | 12 | 3 | 1.83 |
| 7.0 | 3 | 24 | 53 | 16 | 4 | 1.94 |
| 7.25 | 2 | 18 | 54 | 22 | 5 | 2.12 |
| 7.5 | 2 | 12 | 57 | 23 | 7 | 2.23 |
| 7.75 | 3 | 15 | 55 | 22 | 6 | 2.15 |
| 8.0 | 1 | 14 | 52 | 29 | 4 | 2.21 |

2.12.1.fx was adjusted to 2 mg·ml$^{-1}$ at pH 7.0, 7.5 and 8.0 with a HEPES buffer to a final concentration of 0.02M. [PFP-PEG$_5$-K$^{11}$-SEQ:27] was reconstituted in DMSO to 10 mg·ml$^{-1}$. [PFP-PEG$_5$-K$^{11}$-SEQ:27] was added to 2.12.1.fx at a molar ratio of 5:1 and allowed to react overnight at RT. The results are presented in Table 5. The level of conjugation decreased above pH 8.0

TABLE 5 pH in 0.02M HEPES Buffer at 5:1 peptide:antibody.

| | ABP Additions (%) | | | | | |
|---|---|---|---|---|---|---|
| pH | 0 | 1 | 2 | 3 | 4 | Avg CA |
| 7 | 2 | 21 | 41 | 28 | 4 | 2.03 |
| 7.5 | 3 | 22 | 44 | 26 | 5 | 2.08 |
| 8 | 9 | 30 | 42 | 17 | 2 | 1.73 |

Duration of Conjugation Reaction 2.12.1.fx was adjusted to 18 mg·ml$^{-1}$ at pH 7.7 with a phosphate buffer to a final concentration of 0.06M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 4.3:1 and allowed react for 30, 60, 120, 180, 240, 300, or 2400 mins at room temperature (Table 6).

TABLE 6

Duration of conjugation reaction in 0.06M sodium phosphate at 4.3:1 peptide:antibody.

| Time (mins) | CA (%) 0 | 1 | 2 | 3 | 4 | Avg CA |
|---|---|---|---|---|---|---|
| 30 | 6 | 38 | 44 | 13 | 0 | 1.64 |
| 60 | 1 | 22 | 52 | 21 | 3 | 2.02 |
| 120 | 0 | 15 | 50 | 29 | 6 | 2.24 |
| 180 | 1 | 12 | 51 | 31 | 5 | 2.28 |
| 240 | 1 | 9 | 51 | 33 | 5 | 2.33 |
| 300 | 1 | 9 | 50 | 35 | 5 | 2.35 |
| 2400 | 1 | 10 | 48 | 35 | 6 | 2.35 |

Molar Ratio of Peptide to Protein 2.12.1.fx was adjusted 18 mg·ml$^{-1}$ to pH 7.5 with a HEPES buffer to a final concentration of 0.2M HEPES. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 1, 2, 3, 4, and 5:1 (Table 7), and reacted for at least 2 hrs at RT, but the high concentration of HEPES buffer resulted in decreased conjugation.

TABLE 7

Molar ratio of peptide to protein 1:1-5:1 in 0.2M HEPES.

| Peptide:2.12.1.fx | 0 | 1 | 2 | 3 | 4 | 5 | 6 | 7 | Avg CA |
|---|---|---|---|---|---|---|---|---|---|
| 1:1 | 80 | 20 | 0 | 0 | 0 | 0 | 0 | 0 | 0.20 |
| 2:1 | 60 | 35 | 5 | 0 | 0 | 0 | 0 | 0 | 0.45 |
| 3:1 | 39 | 49 | 12 | 0 | 0 | 0 | 0 | 0 | 0.73 |
| 4:1 | 27 | 51 | 19 | 3 | 0 | 0 | 0 | 0 | 0.98 |
| 5:1 | 11 | 47 | 37 | 5 | 0 | 0 | 0 | 0 | 1.36 |

2.12.1.fx was adjusted 18 mg·ml$^{-1}$ to pH 7.7 with a phosphate buffer to a final concentration of 0.06M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 5, 7, 10, 12, and 15:1 (Table 8) and allowed to react for 2 hrs at RT to generate a MAC with a higher level of conjugation.

TABLE 8

Molar ratio of peptide to protein 7:1-15:1 in 0.06M sodium phosphate.

| Peptide:2.12.1.fx | 0 | 1 | 2 | 3 | 4 | 5 | 6 | 7 | Avg CA |
|---|---|---|---|---|---|---|---|---|---|
| 7:1 | 1 | 1 | 29 | 39 | 17 | 10 | 2 | 0 | 3.06 |
| 10:1 | 1 | 1 | 18 | 33 | 25 | 19 | 3 | 0 | 3.49 |
| 12:1 | 3 | 1 | 11 | 22 | 26 | 26 | 8 | 3 | 3.92 |
| 15:1 | 1 | 2 | 9 | 19 | 23 | 32 | 12 | 3 | 4.22 |

To further optimize the molar ratio of 2.12.1.fx and [PFP-PEG$_5$-K$^{11}$-SEQ:27], 2.12.1.fx was adjusted 18 mg·ml$^{-1}$ to pH 7.7 with a phosphate buffer to a final concentration of 0.06 M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx antibody at a molar ratio of 2.5, 2.8, 3.1, 3.4, 3.7, 4.0, 4.3, or 4.6:1 (Table 9) and allowed to react for 2 hrs at RT.

TABLE 9

Molar ratio of peptide to protein 2.5:1-4.6:1 in 0.06M sodium phosphate.

| Peptide:2.12.1.fx | 0 | 1 | 2 | 3 | 4 | 5 | 6 | 7 | Avg CA |
|---|---|---|---|---|---|---|---|---|---|
| 2.5:1 | 14 | 53 | 30 | 4 | 0 | 0 | 0 | 0 | 1.25 |
| 2.8:1 | 10 | 45 | 37 | 8 | 0 | 0 | 0 | 0 | 1.43 |
| 3.1:1 | 7 | 39 | 45 | 8 | 0 | 0 | 0 | 0 | 1.53 |
| 3.4:1 | 5 | 40 | 44 | 11 | 0 | 0 | 0 | 0 | 1.61 |
| 3.7:1 | 4 | 25 | 51 | 15 | 5 | 0 | 0 | 0 | 1.92 |
| 4.0:1 | 2 | 26 | 55 | 15 | 2 | 0 | 0 | 0 | 1.89 |
| 4.3:1 | 1 | 24 | 55 | 16 | 4 | 0 | 0 | 0 | 1.98 |
| 4.6:1 | 2 | 19 | 56 | 19 | 5 | 0 | 0 | 0 | 2.08 |

2.12.1.fx was adjusted to 2 mg·ml$^{-1}$ at pH 7.0 with a HEPES buffer to a final concentration of 0.02M. [PFP-PEG$_5$-K$^{11}$-SEQ:27] was reconstituted in DMSO to 10 mg·ml$^{-1}$. [PFP-PEG$_5$-K$^{11}$-SEQ:27] was added to 2.12.1.fx at a molar ratio of 5, 6, 7, 8, 10:1 and allowed to react overnight at RT. The results are presented in Table 10.

TABLE 10

Molar ratio of peptide to protein 5:1-10:1 in 0.02M HEPES.

| Peptide:2.12.1.fx | 0 | 1 | 2 | 3 | 4 | 5 | 6 | 7 | Avg CA |
|---|---|---|---|---|---|---|---|---|---|
| 5:1 | 2 | 21 | 49 | 24 | 4 | 0 | 0 | 0 | 2.07 |
| 6:1 | 2 | 15 | 42 | 32 | 9 | 0 | 0 | 0 | 2.31 |
| 7:1 | 1 | 11 | 34 | 42 | 13 | 0 | 0 | 0 | 2.57 |
| 8:1 | 0 | 9 | 32 | 42 | 16 | 1 | 0 | 0 | 2.68 |
| 10:1 | 0 | 4 | 21 | 47 | 25 | 4 | 0 | 0 | 3.07 |

Conjugation Profile of 2.12.1.Fx at Various Protein Concentrations

The conjugation profiles of 2.12.1.fx with [PFP-PEG$_5$-K$^{11}$-SEQ:27] at various concentrations were analyzed. 2.12.1.fx was concentrated to >50 mg/mL, diluted to the desired concentration with 20 mM sodium acetate, 200 mM trehalose pH 5.5, and spiked with 60 mM sodium phosphate pH 7.7. [PFP-PEG$_5$-K$^{11}$-SEQ:27] was resuspended with 50% propylene glycol and mixed with the antibody at a 4.3:1 molar ratio and allowed to react overnight at RT. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a peptide. Relative quantitation of multiple conjugation species is performed by measuring the signal magnitude. Table 11 shows the conjugation profile of 2.12.1.fx with peptide at various concentrations of antibody. At antibody concentrations 10 mg/mL to 50 mg/mL, the conjugation occurs at a distribution between 0-5 addition with an average of 1.8 or greater additions. At antibody concentrations 0.5 to 5 mg/mL, the conjugation occurs at a distribution between 0-3 additions with an average of 1.5 or less additions.

TABLE 11

Effect of antibody concentration.

| Antibody Concentration (mg/ml) | CA (%) | | | | | | Avg CA |
|---|---|---|---|---|---|---|---|
| | 0 | 1 | 2 | 3 | 4 | 5 | |
| 0.5 | 65 | 32 | 3 | — | — | — | 0.37 |
| 1 | 44 | 44 | 12 | — | — | — | 0.67 |
| 5 | 10 | 41 | 40 | 8 | — | — | 1.45 |
| 10 | 3 | 30 | 47 | 17 | 2 | 1 | 1.87 |
| 15 | 1 | 24 | 51 | 20 | 3 | 1 | 2.02 |
| 20 | 1 | 16 | 57 | 22 | 2 | 1 | 2.11 |
| 30 | 2 | 20 | 55 | 20 | 3 | 1 | 2.04 |
| 40 | 2 | 21 | 53 | 22 | 2 | 0 | 2.04 |
| 50 | 2 | 19 | 50 | 24 | 4 | 1 | 2.11 |

Reaction Buffer Selection 2.12.1.fx was adjusted to 18 mg·ml$^{-1}$ at pH 7.7 with a sodium carbonate, sodium borate, or sodium phosphate buffer to a final concentration of 0.05M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 1, 2, 3, 4, or 5:1 and allowed to react for 2 hrs at RT. The low reaction pH resulted in the reduced level of conjugation (Table 12).

TABLE 12

Buffer and pH alterations.

| Buffer | CA (%) | | | | | Avg CA |
|---|---|---|---|---|---|---|
| | 0 | 1 | 2 | 3 | 4 | |
| 50 mM sodium carbonate pH 7.4 | 2 | 24 | 48 | 26 | 0 | 1.98 |
| 50 mM sodium borate pH 7.0 | 1 | 17 | 45 | 31 | 5 | 2.20 |
| 50 mM sodium phosphate pH 7.0 | 10 | 48 | 38 | 4 | 0 | 1.36 |

2.12.1.fx was adjusted to 18 mg·ml$^{-1}$ at pH 7.5, 7.7 and 8.0 with a sodium borate and sodium phosphate buffer to a final concentration of 0.04 M. [PFP-PEG$_5$-K$^{11}$-SEQ:27] was reconstituted in a propylene glycol solution to 10 mg·ml$^{-1}$ and added to 2.12.1.fx at a molar ratio of 4.3:1, and reacted for 2 hrs at RT (Table 13).

TABLE 13

Buffer and pH alterations.

| Buffer | CA (%) | | | | | Avg CA |
|---|---|---|---|---|---|---|
| | 0 | 1 | 2 | 3 | 4 | |
| Phosphate, pH 7.5 | 1 | 21 | 53 | 21 | 3 | 2.02 |
| Phosphate, pH 7.7 | 0 | 15 | 50 | 29 | 6 | 2.26 |
| Phosphate, pH 8.0 | 1 | 14 | 52 | 29 | 4 | 2.21 |
| Borate, pH 7.5 | 46 | 44 | 10 | 0 | 0 | 0.64 |
| Borate, pH 7.7 | 22 | 51 | 23 | 4 | 0 | 1.09 |
| Borate, pH 8.0 | 1 | 17 | 48 | 30 | 4 | 2.19 |

2.12.1.fx was adjusted to 18 mg·ml$^{-1}$ at pH 7.7 with a phosphate buffer to a final concentration of 0.04 M, 0.06 M, or 0.08 M sodium phosphate. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 4.3:1 and allowed to react for 2 hrs at RT. The results are presented in Table 14.

TABLE 14

Concentration of phosphate.

| Concentration (mM) of phosphate at pH 7.7 | CA (%) | | | | | Avg CA |
|---|---|---|---|---|---|---|
| | 0 | 1 | 2 | 3 | 4 | |
| 40 | 2 | 23 | 54 | 16 | 4 | 1.95 |
| 60 | 2 | 28 | 51 | 15 | 4 | 1.91 |
| 80 | 2 | 29 | 51 | 13 | 4 | 1.86 |

Effect of Buffer Constituents on Conjugation

Propylene glycol: 2.12.1.fx was adjusted to 18 mg·ml$^{-1}$ at pH 7.7 with a phosphate buffer to a final concentration of 0.06 M sodium phosphate. [PFP-PEG$_5$-K$^{11}$-SEQ:27] was reconstituted in a propylene glycol solution to 20 mg·ml$^{-1}$ (5% propylene glycol in the conjugation reaction). [PFP-PEG$_5$-K$^{11}$-SEQ:27] was added to 2.12.1.fx at a molar ratio of 4.3:1 and spiked with an additional 0 to 15% propylene glycol (final propylene glycol percentage of 5, 10, 15, and 20%) and allowed to react for 2 hrs at RT. The results are presented in Table 15.

TABLE 15

Percent of propylene glycol in 0.06M sodium phosphate.

| Percent (%) Propylene Glycol | CA (%) | | | | | Avg CA |
|---|---|---|---|---|---|---|
| | 0 | 1 | 2 | 3 | 4 | |
| 5 | 2 | 18 | 55 | 20 | 5 | 2.08 |
| 10 | 2 | 20 | 53 | 21 | 5 | 2.09 |
| 15 | 2 | 23 | 49 | 20 | 5 | 2.01 |
| 20 | 4 | 23 | 50 | 19 | 4 | 1.96 |

NaCl: 2.12.1.fx was adjusted to 2 mg·ml$^{-1}$ at pH 7.0 with a HEPES buffer to a final concentration of 0.02M in the presence and absence of 0.14M NaCl. [PFP-PEG$_5$-K$^{11}$-SEQ:27] was reconstituted in DMSO to 10 mg·ml$^{-1}$. [PFP-PEG$_5$-K$^{11}$-SEQ:27] was added to 2.12.1.fx at a molar ratio of 5:1 and allowed to react overnight at RT. The level of conjugation decreases in the presence of NaCl (Table 16).

TABLE 16

Concentration of sodium chloride in 0.02M HEPES.

| Concentration of sodium chloride (mM) | ABP Additions (%) | | | | | Avg CA |
|---|---|---|---|---|---|---|
| | 0 | 1 | 2 | 3 | 4 | |
| 0 | 2 | 21 | 41 | 28 | 4 | 2.03 |
| 0.14 | 9 | 34 | 42 | 14 | 1 | 1.64 |

HEPES: 2.12.1.fx was adjusted to 2 mg·ml$^{-1}$ at pH 7.0 with a HEPES buffer to a final concentration of 0.2 M and 0.02 M. [PFP-PEG$_5$-K$^{11}$-SEQ:27] was reconstituted in 50% propylene glycol to 10 mg·ml$^{-1}$. [PFP-PEG$_5$-K$^{11}$-SEQ:27] was added to 2.12.1.fx at a molar ratio of 5:1 and allowed to react 2 hrs at RT. The results are presented in Table 17. The level of conjugation is reduced at 0.2M HEPES buffer.

TABLE 17

HEPES concentration.

| Concentration of HEPES (mM) | ABP Additions (%) | | | | | Avg CA |
|---|---|---|---|---|---|---|
| | 0 | 1 | 2 | 3 | 4 | |
| 0.02 | 2 | 35 | 47 | 16 | 0 | 1.77 |
| 0.2 | 21 | 49 | 26 | 4 | 0 | 1.13 |

DMSO: 2.12.1.fx was adjusted to 15 mg·ml$^{-1}$ at pH 7.7 with sodium phosphate buffer to a final concentration of 0.06 M and DMSO was added to a final concentration of 30%. [PFP-PEG$_5$-K$^{11}$-SEQ:27] was reconstituted in a propylene glycol solution to 10 mg·ml$^{-1}$. [PFP-PEG$_5$-K$^{11}$-SEQ:27] was added to 2.12.1.fx at a molar ratio of 4:1 and allowed to react for 2 hrs at RT. The results are presented in Table 18.

TABLE 18

DMSO in 0.06M sodium phosphate.

| Percent of DMSO | ABP Additions (%) | | | | | Avg CA |
|---|---|---|---|---|---|---|
| | 0 | 1 | 2 | 3 | 4 | |
| 0 | 3 | 28 | 49 | 14 | 6 | 1.92 |
| 30 | 8 | 28 | 32 | 22 | 10 | 1.98 |

Discussion of Conjugation Reaction Parameters

When the molar ratio of Effector Moiety (in this example, a peptide) to antibody is reduced below about 3.5:1, the level of conjugation is decreased, as seen in Table 9. Alternatively, Table 10 shows that increasing the molar ratio results in an increased level of conjugation. Increasing the number of peptides per antibody generally decreases the binding efficiency of the antibody (in this case 2.12.1 fx) to its antigen (in this case the IGF1R receptor), therefore the molar ratio of peptide to antibody was optimized to maximise both antibody-antigen, and peptide-cognate binding.

It was also found that varying the conjugation buffer can alter the conjugation pattern. Amine-containing excipients are less preferable in general as they can react with the PFP group. Buffers such as carbonate and borate can be used for conjugation but were avoided as their pKa (boric acid with a pKa ~9 and carbonate with two pKa of ~6 and ~11) were far from the conjugation pH of 7.7 that was identified as optimal for MAC-1 and MAC-2 (Table 12). The level of conjugation is not only dependent on the chemical conditions of the reaction but also based on time. After 2 hrs, most of the PFP-activated peptide had reacted with the antibody or the PFP Z* has hydrolyzed (Table 6).

The PFP-activated peptide/linker reacted quickly with lysine side chain amino groups. Conjugation was performed at pH 6.5 to 8 in phosphate buffer to increase the nucleophilic tendency of the antibody surface lysines by decreasing their charge (the pKa of lysines on the surface proteins is about 9.1 to 11.2) as shown in Tables 4 and 5.

Optimal conditions for conjugation of MAC-1 and MAC-2 are described as follows: 2.12.1.fx antibody was adjusted to pH 7.7 with a phosphate buffer to a final concentration of 0.06M sodium phosphate. [PFP-PEG$_5$-K$^{11}$-SEQ:27] was reconstituted in a propylene glycol solution to 10 mg·ml$^{-1}$ (final propylene glycol concentration in reaction is 10%). [PFP-PEG$_5$-K$^{11}$-SEQ:27] was added to 2.12.1.fx antibody at a molar ratio of 4.3:1 and allowed to react for 2 hrs at RT. The reaction was quenched with a succinate and glycine buffer, lowering the pH to approximately 6.0 and quenching any free peptide. In some aspects, the reaction may be concentrated and peptide-related species (such as peptides where the linker was hydrolyzed by reaction with water solvent) and other elements of the reaction mixture (such as PFP) may be removed by diafiltration, for example, using a 50 kDa membrane or size exclusion chromatography into a succinate, glycine, sodium chloride, and trehalose buffer, pH 5.5 at 30 mg/ml.

The conjugation conditions listed above were varied to determine the range of each process parameter. Parameter ranges were set based on variability that may occur during the conjugation and/or were expanded until greater than 10% change in species population was observed. Table 19 summarizes the parameters that result in similar conjugation profiles for MAC-2.

TABLE 19

Process parameters optimized for MAC-2.

| Parameters tested | Range tested | Desirable range | Optimum |
|---|---|---|---|
| Temperature | 18-25° C. | 18-25° C. | RT |
| Reaction pH | 6.5 to 8.0 | pH 7.25-8.0 | 7.7 |
| Reaction duration | 30-2400 mins | 180-2400 mins | >about 2 hrs |
| Molar ratio of Peptide to Antibody | 2.5 to 4.6 | 3.7:1 to 4.3:1 | 4.3:1 |
| 2.12.1.fx concentration added to the reaction | 0.5 to 50 mg/mL | 10 to 50 mg/mL | 20 mg/mL |
| Phosphate concentration in the reaction buffer | 40 to 80 mM | 40-80 mM | 60 mM |
| Final propylene glycol concentration | 5 to 20% | 5-20% | 10% |

Example 6 Location of Conjugated Peptides on Antibody

The MAC-2 drug product molecule consists of a distribution of 1-4 [PEG$_5$-K$^{11}$-SEQ:27] molecules attached to the 2.12.1.fx antibody. This was determined by measuring the intact molecular weight (MW) of MAC-2 using electrospray, time-of-flight mass spectrometry detection following protein separation from salts and excipients through a size exclusion chromatography column. Mass spectrometry data that demonstrated the MW of the 2.12.1.fx and 3 lots of MAC-2 are shown in FIG. 2. FIG. 1A shows 2.12.1.fx before conjugation. This is a uniform molecule that displays a single MW. The MAC-2 lots display a distribution of conjugated peptides to 2.12.1.fx; between 1-4 conjugation additions (CA) are observed. The relative amount of each form is consistent between lots and the most common form in each lot has 2 peptides (SEQ ID NO:27) attached to each individual 2.12.1.fx antibody.

By reducing disulfide bonds in the 2.12.1.fx antibody, light and heavy chains are observed separately. Disulfide reduction is performed by treating the intact 2.12.1.fx antibody with 20 mM tris(2-carboxyethyl) phosphine (TCEP). The resulting mixture of heavy and light chains is analyzed for intact molecular weight as described above. The data shown in FIG. 2 provides evidence toward the location of the ABP on 2.12.1.fx. The majority of light chain (>65%) in the MAC-2 lots are conjugated. Most of the conjugated light chain contains 1CA. 2CA is also observed at a lower level. Almost all observed heavy chain (>90%) is unmodified, which suggests that very few of the conjugated peptides are located on the heavy chain.

Peptide mapping was used to determine the precise location of conjugation. The procedure was as follows: an aliquot of MAC-2 was denatured with 8M Guanidine-hydrochloride, disulfide bonds were reduced with TCEP, and the resulting cysteine sulphydryls were alkylated with Iodo-acetamide. This treated protein sample was then digested with the protease chymotrypsin (1:125 protease:MAC ratio by weight). The resulting chymotryptic peptides were then detected individually by mass spectrometry after separation through a C8 liquid chromatography column. With this technique, MAC-2 was digested by chymotrypsin on the heavy and light chains into fragments at the locations noted in the sequence (with bullets) in FIG. 3. Liquid chromatography-mass spectrometry (LC-MS) detection of the MW of each peptide was then used to determine which Lysine residues are modified by a conjugated peptide. If a fragment was modified by attachment of conjugated peptide, its MW was shifted accordingly.

Fragments Y1, Y6, Y9, Y10, Y20, Y25, Y26, Y29, Y32, Y33, Y34, Y37, Y40 and Y43 of the heavy chain contain Lys residues. Of these, peptide conjugation was detected at Y6, Y10, Y25, Y33, and Y37. Fragments Y3, Y10, Y11, Y12, Y13, Y14, Y15, and Y16 of the light chain contain Lys residues. Of these, conjugation was detected at Y3, Y13, and Y15.

The light chain fragment referred to as Y15 (the 15th chymotryptic fragment on the light chain from the N-terminus) was found to be conjugated based on the data shown in FIG. 4. The MW of the modified Y15 fragment in MAC was clearly detected. In the un-conjugated 2.12.1.fx sample, there was no evidence of modified Y15 fragment. The unmodified Y15 fragment was observed in both MAC-2 and 2.12.1.fx. The magnitude of this fragment is higher in the 2.12.1.fx sample because this entire fragment is present in the un-modified form. As this fragment is conjugated in MAC-2, the observed level of un-modified Y15 decreases, which is seen in FIG. 4 as a peak with a smaller area.

The amount of conjugation of [SEQ:27-$K^{11}$-PEG5] observed on light chain fragment Y15 in MAC-2 is estimated by measuring the decreased peak area of un-modified Y15. After normalizing the signal intensity such that unconjugated 2.12.1.fx showed 100%, 3 independent lots of MAC-2 showed 17%, 27% and 22% unconjugated Y15 fragments respectively.

The observed magnitude of Y15 in the MAC samples was normalized to the magnitude of Y15 in the 2.12.1.fx sample. Between 75-85% of the Y15 fragments are determined as modified in MAC-2. Considering that MAC-2 contains mostly 1-2 conjugation additions, this suggests that most of the conjugation in MAC-2 is located at one of the 2 K residues of light chain fragment Y15 (LC-$K^{188}$ or LC-$K^{190}$). The location of fragment Y15 in relation to the sequence of 2.12.1.fx is shown in FIG. 3.

Trypsin enzymatic digestion was used to discriminate between LC-$K^{188}$ and LC-$K^{190}$ (trypsin has specificity for the C-terminus of K and R). As trypsin does not digest conjugated K residues, the enzymatic digestion generates different peptide lengths, depending on which K residue is conjugated. Examination of LCMS data from MAC-2 that was digested with trypsin provides evidence that the peptide attaches specifically to LC-$K^{188}$. No evidence of modified LC-$K^{190}$ was observed.

MAC-2 was reduced with TCEP and denatured with guanidine hydrochloride as described above. The protein concentration was adjusted to 2 mg/ml and the pH to 7.8 with Tris digestion buffer. Purified trypsin was added at a 1:125 protease:MAC ratio by weight and incubated at 30° C. for 4 hrs. Samples were stored at −20° C. until analyzed by LCMS. Fragment samples were separated on a C18 reversed phase column using water/acetonitrile+0.1% TFA mobile phases. Detection of fragments was monitored both by UV 214 nm and ESI-TOF mass spectrometry. All data analysis was performed using MassLynx software.

The formation of fragments upon trypsin digestion of MAC-2 depends on the site of peptide conjugation. Lysines are the targeted residue for conjugation. Data shown in FIGS. 1-4 indicates that the predominant site of peptide binding is either LC-$K^{188}$ or LC-$K^{190}$. The scheme below shows the trypsin digestion reactions that would occur upon conjugation at either 2.12.1.fx-[LC-$K^{188}$] or 2.12.1.fx-[LC-$K^{190}$].

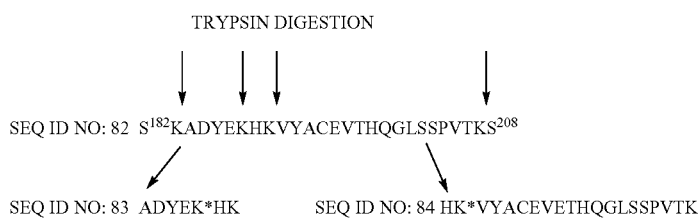

TRYPSIN DIGESTION

SEQ ID NO: 82  $S^{182}$KADYEKHKVYACEVTHQGLSSPVTKS$^{208}$

SEQ ID NO: 83  ADYEK*HK

SEQ ID NO: 84  HK*VYACEVETHQGLSSPVTK

The chemical structures of the two potential digestion fragments in question are as follows:

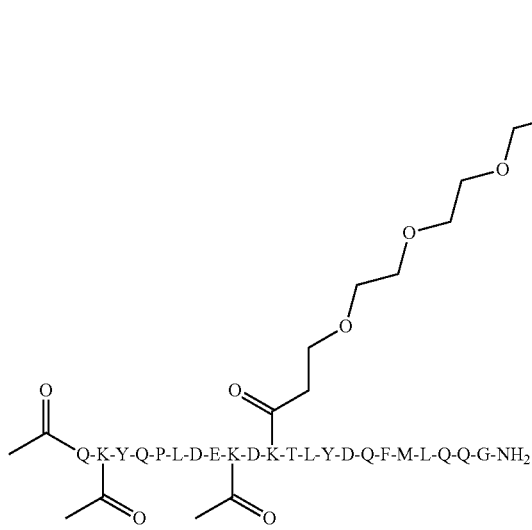

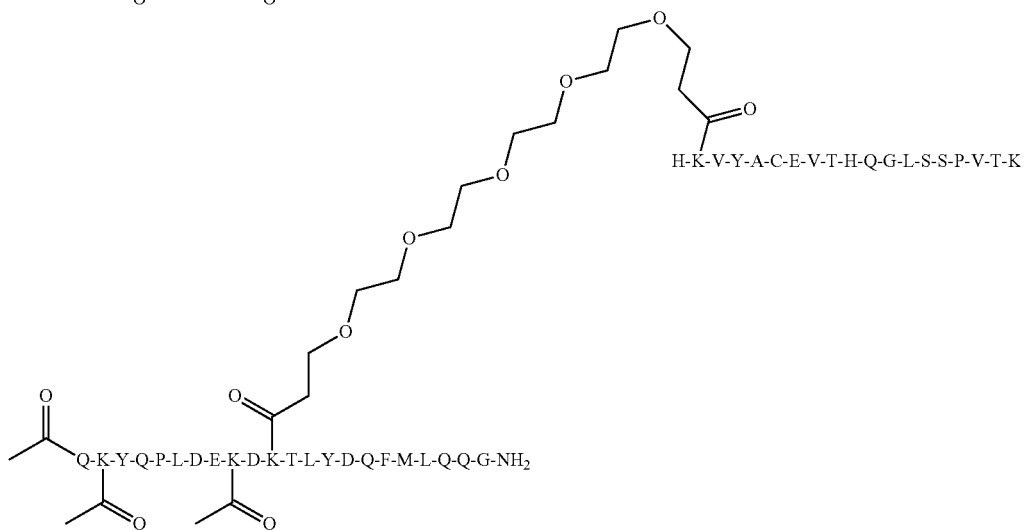

FIG. 5 shows the selected ion LCMS chromatogram data for the trypsin peptide when LC-$K^{188}$ is conjugated to the peptide. FIG. 6 shows the selected ion LCMS chromatogram data for the trypsin fragment when LC-$K^{190}$ is modified with a conjugated peptide. These data suggest that only LC-$K^{188}$ alone is conjugated; this situation results in a significant signal that is detected in MAC-2 but is absent in the 2.12.1.fx control experiment. The results from modification at LC-$K^{190}$ do not provide any data that is unique compared to the negative control.

In contrast to what may be expected, the peptide/linker appears to preferentially decorate LC-$K^{188}$ of the light chain of 2.12.1.fx. This has the surprising advantage that the Fc portion of the 2.12.1.fx antibody is unaffected. Tests show that the resulting PK of MAC-2 is approximately equal to the PK of unconjugated 2.12.1.fx. Promiscuous, non-specific conjugation to multiple sites on an antibody can result in a product with lower PK. The directional conjugation of the invention, exemplified by MAC-1 and MAC-2, provide the advantage of minimizing some of the possible deleterious effects that can be caused by promiscuous, non-specific conjugation, including lower PK. LC-$K^{188}$ is the same residue as CLκ-$K^{80}$ (i.e. $K^{80}$ of SEQ ID NO:6), as the Light Chain (LC) comprises the variable region as well as the constant light kappa chain (CLκ).

To establish the reproducibility of the process, the experiment was repeated. MAC-2 was diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a conjugated peptide/linker. Relative quantitation of multiple conjugation species is performed by measuring the signal magnitude. FIG. 7A shows a representative spectrum of MAC-2; the calculations used for quantitation are shown in Table 20. The average conjugation addition for the intact MAC-2 is calculated as 2.11 using the following formula: SUMPRODUCT (Number of Conjugation Additions (CA), Percent per CA). This example demonstrates conjugation of peptides occurring as a distribution between 0-4 peptide additions with the largest form being 2 peptide additions and the average number of peptide additions is 2.11. Replicate analysis by multiple individuals demonstrates that the profile of conjugation is consistent and reproducible.

TABLE 20

Weighted average of conjugation additions: 2.11.

| Conjugation additions | Predicted mass | Intensity | Percent |
|---|---|---|---|
| 0 | 149210 | 1615 | 1% |
| 1 | 152350 | 20533 | 17% |
| 2 | 155490 | 69395 | 56% |
| 3 | 158630 | 27708 | 22% |
| 4 | 161770 | 4818 | 4% |
|  |  | 124069 | 100% |

The extent of peptide conjugation was examined separately on the light and heavy chains of 2.12.1.fx. MAC-2 was denatured and disulfide bonds were reduced using guanidine hydrochloride and dithiothreitol. The resulting free light and heavy chains were analyzed using LCMS to determine the conjugation profile on each. FIGS. 7B and 7C show a representative spectrum of each chain; the calculation used for quantitation are shown in Table 21. The average conjugation additions (Avg CA) for the reduced heavy chain MAC-2 is calculated as 0.14 and the Avg CA for the reduced light chain MAC-2 is calculated at 0.86 using the following formula: SUMPRODUCT (Number of Conjugation Additions (CA), Percent per CA). These data demonstrate that the location of conjugation is higher on the light chain; the most abundant form on the light chain contains one peptide addition and the light chain contains an average of 0.86 peptide additions. Conjugation on the heavy chain is observed at a significantly lower level. Replicate analysis of this experiment by multiple individuals demonstrates that the profile of conjugation is consistent and reproducible.

TABLE 21

Peptide mapping characterization of MAC-2 identifying specific location of conjugation.

| Mass (Da) | Conj. Additions | Species | Intensity | Percent | Avg CA |
|---|---|---|---|---|---|
| 51020 | 0 | HC | 102093 | 86% |  |
| 54165 | 1 | HC + (1x) ABP-1 | 16204 | 14% |  |
|  |  | Total HC | 118297 | 100% | 0.14 |
| 23584 | 0 | LC | 19752 | 21% |  |
| 26729 | 1 | LC + (1x) ABP-1 | 68757 | 72% |  |
| 29874 | 2 | LC + (2x) ABP-2 | 6561 | 7% |  |
|  |  | Total LC | 95070 | 100% | 0.86 |

MAC-2 was reduced with dithiothreitol and cysteine residues were alkylated by carboxymethylation with iodoacetamide. Chymotrypsin was used for proteolytic digestion. Digested fragments in solution were analyzed using liquid chromatography mass spectrometry (LCMS). Individual fragments were separated over a C18 HPLC column and their accurate mass is measured in a Quadrupole Time-of-Flight (Q-ToF) mass spectrometer. The resulting fragment mass was used to identify unmodified fragments or fragments modified with a conjugated peptide. This experiment was interpreted by focusing on chymotryptic fragments that contain a lysine residue, as these were possible sites for peptide conjugation. Table 22 shows a listing of all such fragments. Blank entries are fragments that are not detected using this technique. Detected fragments that are observed with a peptide modifier are considered potential sites of conjugation.

The table entries for Table 17 are explained below:

Fragment number: Chymotrypsin fragment numbering from the N-terminus; joined fragments (i.e. Y1-2) indicate a missed cleavage site.

Start/End: Numbering of the fragment location from the N-terminus.

Peptide Mass (Da): Theoretical mass of the fragment listed in Daltons.

Retention Time (Control/Analyte): Time of chromatographic retention/elution in the LCMS fragment mapping experiment.

MS Signal Intensity (Control/Analyte): Magnitude of observed signal observed by MS.

Mass Error-ppm (Control/Analyte): Comparison of theoretical vs. observed mass of the fragment; values >10, and especially closer to zero (0) demonstrate better mass accuracy.

Modifiers: Potential covalent additions to the fragment; peptide-antibody binding fragment of Lys residue, CAM-carboxymethylation of Cysteine residue.

Asterisks indicate the modified (e.g. conjugated) version of the respective fragment. Pep indicates a conjugated peptide.

Directional conjugation of a peptide to the Y15 fragment is demonstrated by quantitating the conjugation level. The following analysis was performed on each of the peptide fragments that were observed having conjugation during the peptide mapping experiment of the 2.12.1.fx reference product. The ratio of observed signal intensity for the unmodified peptide in the non-conjugated control (2.12.1.fx antibody scaffold—no conjugation) compared to the conjugated reference product (MAC-2) is shown in Table 23. The unmodified signal is used because a direct comparison of the same peptide signal is possible in each sample. For example, an unconjugated peptide would be expected to have the same observed signal intensity in the control vs. product samples resulting in a ratio of one (1). Conjugation would result in a decrease in the observed amount of unmodified peptide in the product sample which would be indicated by a ratio greater than one (1). The data in Table 23 was further normalized to correct for sample and experimental variation between the control and product. Table 23 demonstrates that light chain peptide Y15 is conjugated at a significantly higher level than each of the other conjugated peptides. This suggests that conjugation occurs in a directional manner and is not randomly distributed across K residues.

TABLE 22

Peptide mapping characterization of MAC-2 heavy chain reference product.

| Fragment Number | Start | End | Peptide Mass (Da) | Retention Time Control | Retention Time Analyte | MS Signal Intensity Control | MS Signal Intensity Analyte | Mass Error (ppm) Control | Mass Error (ppm) Analyte | Modifiers |
|---|---|---|---|---|---|---|---|---|---|---|
| Y1 | 1 | 27 | 2617.3533 | | | | | | | |
| Y1-2 | 1 | 29 | 2865.4695 | | | | | | | |
| Y5-6 | 34 | 47 | 1657.8398 | | | | | | | |
| Y6 | 37 | 47 | 1253.688 | 19.2 | 19.2 | 516640 | 583534 | 1.9 | −1.1 | |
| Y6-7 | 37 | 50 | 1602.8518 | 22.1 | 22.1 | 26537 | 37988 | −1.6 | −2.2 | |
| Y6-7* | 37 | 50 | 3295.7017 | | 21.8 | | 6316 | | −19.4 | Pep(1) |
| Y8-9 | 51 | 68 | 1931.9337 | 16.5 | 16.5 | 60894 | 85742 | −2.2 | 0.4 | |
| Y9 | 61 | 68 | 878.461 | 11.3 | 11.3 | 376224 | 412997 | 0 | −1 | |
| Y9-10 | 61 | 80 | 2241.1501 | | | | | | | |
| Y10 | 69 | 80 | 1380.6997 | 13.3 | 13.3 | 261813 | 299847 | −1.1 | 0.7 | |
| Y10* | 69 | 80 | 3073.5498 | | 23.4 | | 6350 | | −8.7 | Pep (1) |
| Y10-011 | 69 | 94 | 2972.4661 | | | | | | | |
| Y19-20 | 111 | 157 | 4748.2773 | | | | | | | |
| Y20 | 116 | 157 | 4160.0405 | | | | | | | |
| Y20-21 | 116 | 166 | 5202.5527 | | | | | | | |
| Y20-21* | 116 | 166 | 5316.5957 | 34.1 | | 6445 | | 0.5 | | CAM(2) |
| Y24-25 | 202 | 245 | 4702.2109 | | | | | | | |
| Y25 | 207 | 245 | 4151.9722 | | | | | | | |
| Y25* | 207 | 245 | 4437.0796 | 20.9 | 20.9 | 1495322 | 1800079 | 1.1 | −3.1 | CAM(5) |
| Y25* | 207 | 245 | 6129.9297 | | 24.4 | | 6652 | | −4.5 | CAM(5) Pep(1) |
| Y25-26 | 207 | 279 | 7985.9092 | | | | | | | |
| Y26 | 246 | 279 | 3851.9478 | | | | | | | |
| Y26-27 | 246 | 281 | 4152.0698 | | | | | | | |
| Y28-29 | 282 | 300 | 2245.1128 | | | | | | | |
| Y29 | 283 | 300 | 2082.0493 | 14.6 | 14.6 | 20665 | 16662 | −0.6 | −3.8 | |
| Y29-30 | 283 | 304 | 2531.2405 | | | | | | | |
| Y31-32 | 305 | 323 | 2241.1907 | | | | | | | |
| Y32 | 318 | 323 | 722.3599 | 7.9 | 7.9 | 93966 | 96639 | 0.1 | 2.6 | |
| Y32 | 318 | 323 | 722.3599 | 17.7 | 18.4 | 37943 | 12802 | 11.4 | 30.6 | |
| Y32 | 318 | 323 | 722.3599 | 18.4 | | 11761 | | 23.8 | | |
| Y32-33 | 318 | 353 | 4028.188 | | | | | | | |
| Y33 | 324 | 353 | 3323.8386 | 20 | | 5422 | | 3.1 | | |
| Y33* | 324 | 353 | 3380.8601 | 19.7 | 19.7 | 2196329 | 2497507 | −2.5 | −3.1 | CAM(1) |
| Y33* | 324 | 353 | 5073.71 | | 24 | | 5973 | | 1.3 | CAM(1) Pep(1) |
| Y33-34 | 324 | 376 | 5883.1577 | | | | | | | |
| Y34 | 354 | 376 | 2577.3293 | | | | | | | |
| Y34-35 | 354 | 385 | 3637.8159 | | | | | | | |
| Y34-35* | 354 | 385 | 3694.8374 | 33 | 32.9 | 10095 | 20682 | 1.9 | −2.4 | CAM(1) |
| Y36-37 | 386 | 408 | 2527.0808 | | | | | | | |
| Y37 | 396 | 408 | 1394.6388 | 19.6 | 19.6 | 62942 | 71902 | −0.9 | −0.4 | |
| Y37-38 | 396 | 409 | 1541.7072 | 25.1 | 25.1 | 827336 | 878570 | 0 | −1.9 | |
| Y37-38* | 396 | 409 | 3234.5571 | | 29.7 | | 7749 | | −5.3 | Pep(1) |
| Y39-40 | 410 | 421 | 1494.8195 | | | | | | | |
| Y40 | 412 | 421 | 1218.672 | 15.8 | 15.8 | 77917 | 88243 | −0.3 | −1.6 | |
| Y40-41 | 412 | 427 | 1891.9905 | 20.3 | 20.3 | 107513 | 149676 | 0.2 | −2 | |
| Y42-43 | 428 | 450 | 2525.1792 | | | | | | | |
| Y43 | 441 | 450 | 1016.5502 | | | | | | | |
| Y2-3 | 36 | 49 | 1688.9725 | 16.2 | 16.2 | 145374 | 170451 | −1.7 | −2.6 | |
| Y2-3* | 36 | 49 | 3381.8225 | | 24.2 | | 7192 | | −9.2 | Pep(1) |
| Y3 | 37 | 49 | 1525.9093 | 15.5 | 15.5 | 331068 | 393638 | −2.7 | −2.9 | |
| Y3* | 37 | 49 | 3218.7593 | | 24 | | 28193 | | −9 | Pep(1) |
| Y3-4 | 37 | 62 | 2882.6355 | | | | | | | |
| Y9-10 | 88 | 116 | 3244.729 | | | | | | | |
| Y10 | 99 | 116 | 1871.0992 | | | | | | | |
| Y10-11 | 99 | 139 | 4331.335 | | | | | | | |
| Y11 | 117 | 139 | 2478.2463 | | 22.8 | | 47035 | | −5.9 | |
| Y11-12 | 117 | 148 | 3635.8445 | | | | | | | |
| Y12 | 140 | 148 | 1175.6088 | | | | | | | |
| Y12-13 | 140 | 173 | 3886.8245 | | | | | | | |
| Y13 | 149 | 173 | 2729.2263 | 13.1 | 13.1 | 1140556 | 1218022 | −1.1 | 0.1 | |
| Y13* | 149 | 173 | 4422.0762 | | 21.4 | | 8424 | | −6.5 | Pep(1) |
| Y13-14 | 149 | 186 | 4095.9243 | | | | | | | |
| Y14 | 174 | 186 | 1384.7086 | | | | | | | |
| Y14-15 | 174 | 192 | 2169.1318 | | | | | | | |
| Y15 | 187 | 192 | 802.4337 | 7.5 | 7.5 | 275639 | 62720 | −1.9 | −0.2 | |
| Y15* | 187 | 192 | 2495.2837 | | 20.9 | | 936267 | | −9.8 | Pep(1) |
| Y15-16 | 187 | 209 | 2574.29 | | | | | | | |
| Y16 | 193 | 209 | 1789.8668 | 18.7 | | 5400 | | 4.4 | | |
| Y16* | 193 | 209 | 1846.8883 | 18.1 | 18.1 | 169490 | 235914 | −1.7 | −2.5 | CAM(1) |
| Y16-17 | 193 | 214 | 2349.0842 | 17.8 | | 9211 | | 0.1 | | |

TABLE 23

Directional conjugation of peptide to Y15 fragment on the light chain.

| Fragment | Unmodified Intensity Ratio: Control/Analyte-normalized |
|---|---|
| Light Y3 | 1.000 |
| Light Y13 | 1.112 |
| Light Y15 | 5.218 |
| Heavy Y6 | 0.831 |
| Heavy Y10 | 1.038 |
| Heavy Y25 | 0.988 |
| Heavy Y33 | 1.045 |
| Heavy Y37 | 1.120 |

Example 7 Demonstration of Potency of MAC Products

Full details of in vitro and in vivo assays of MAC-1 and MAC-2 are provided in the Examples of PCT/US2011/053092 (WO2012/007896). Ang2-h38C2-IgG1 was used as a control in certain examples. The generation and structure of the Ang2-h38C2 is fully described as compound 43 in WO2008056346, whose contents is incorporated herein, with particular reference to aspects referring to the generation of compound 43. Briefly, the structure is as follows:

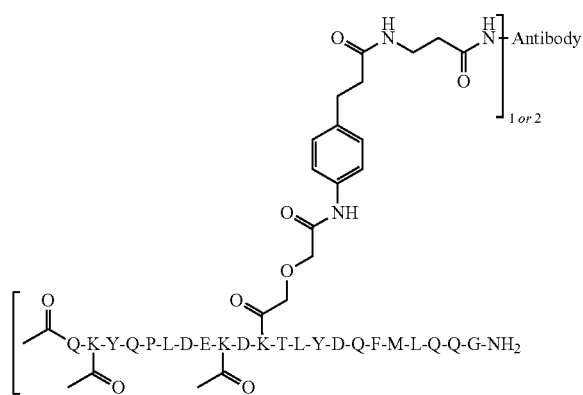

wherein the linker is covalently attached to the ε-amino group of HC-$K^{99}$ ($K^{93}$ according to Kabat numbering) of the combining site of the antibody and the antibody is h38C2-IgG1 (SEQ ID NO:64 and 65) (SEQ ID NO:189 and SEQ ID NO:190 of WO2008/056346).

In summary, MAC-1 and MAC-2 were able to bind Ang2 and prevent its binding to Tie2 as shown in an Ang2 competition assay, and both MAC-1 and MAC-2 have similar activity as the parental anti-IGF1R antibody (2.12.1.fx) for competing with IGF1 for IGF1R binding (Table 24). Surprisingly, in comparison with Ang2-h38c2, MAC-1 and MAC-2 both showed an increase in ability to competitively bind Ang2. Therefore, conjugation of limited Ang2 peptides does not appear to change the innate binding and inhibition of the antibody, and may in some cases improve the Effector Moiety activity.

The MACs were tested for the ability to downregulate IGF1R levels on a human colon carcinoma cell line Colo205. Cells were treated for 3 hrs in culture with titration of MAC compounds. Cells were collected and IGF1R surface expression determined by flow cytometry. The percentage of IGF1R downregulated as compared to negative control hIgG2 was determined (Table 23).

TABLE 24

Ability of MAC-1 and MAC-2 to bind & modulate IGF1R and Ang2.

| | Ang2 $IC_{50}$ (nM) | IGF1R $IC_{50}$ (nM) | IGF1R phosphorylation $IC_{50}$ (nM) | % IGF1R down-regulated |
|---|---|---|---|---|
| MAC-1 | 0.092 ± 0.049 | 5.1 ± 1.1 | 150.7 ± 59.6 | 43 ± 5 |
| MAC-2 | 0.057 ± 0.022 | 6.1 ± 1.1 | 91.4 ± 40.2 | 50 ± 5 |
| 2.12.1.fx antibody | nd | 3.8 ± 0.8 | 48.7 ± 14.0 | 48 ± 3 |
| Ang2-h38c2-IgG1 | 0.582 ± 0.242 | nd | nd | nd |

It was also demonstrated that conjugating 2 peptides per antibody was ideal in terms of effecting IGF1R autophosphorylation and downregulation and that conjugating more or less than 2 peptides per antibody lessens the ability of the MAC to effect these functions.

To assess the effect of the number of peptides per antibody on the ability of 2.12.1.fx to modulate IGF1R activity, 2 samples of MAC-1 were prepared where the reaction conditions were set to provide either reduced conjugation (MAC-1 low) or increased conjugation (MAC-1 high) (Table 25). The samples were analysed for the ability to downregulate and phosphorylate IGF1R (Table 25). There is a significant difference in the ability of the MAC-1 high as compared with MAC-1 low to effectively modulate the IGF1R pathway. Conjugation of greater than about 2 peptides per antibody limits the functional activity of the MAC to both inhibit IGF1R autophosphorylation and induce IGF1R downregulation, compared to conjugation of about 2 or less peptides per antibody. Therefore, in order to efficiently modulate 2 different biological pathways in one bifunctional entity, conjugation of about 2 peptides per antibody may be ideal (depending on peptide's and target's pharmacokinetic profile).

TABLE 25

Analysis of MAC-1-High and MAC-1 Low.

| | Ang2 $IC_{50}$ (nM) | % IGF1R down-regulated | Phosphorylation IGF1R $IC_{50}$ (nM) | CA (%) 0 | 1 | 2 | 3 | 4 | 5 | Avg CA |
|---|---|---|---|---|---|---|---|---|---|---|
| MAC-1 Low | 0.103 | 32 ± 1 | 12.8 | 14 | 42 | 32 | 12 | 0 | 0 | 1.42 |
| MAC-1 High | 0.035 | 9 ± 2 | >300 | 0 | 4 | 19 | 41 | 32 | 5 | 3.18 |
| 2.12.1.fx | nd | 36 ± 3 | 3.5 | | | | | | | |
| Ang2-h38c2-IgG1 | 0.252 | nd | nd | | | | | | | |

Example 8 In Vivo Pharmacokinetics

PK studies were conducted using male Swiss Webster mice and 2 male Cynomolgus monkeys (*Macaca fascicularis*). Full details of PK studies are provided in the Examples of PCT/US2011/053092. In mouse, MAC-1 and MAC-2 demonstrated similar residence time as the parental anti-IGF1R antibody with 1β phase half-lives of 383-397 hrs. The MAC-1 and MAC-2 Ang2 binding capability demonstrated similar residence time as Ang2-h38c2 with T½ of 105-120 hrs in mouse in single dose IV studies. In cynomolgus monkey, MAC-2 demonstrated a slightly shorter residence time as the parental anti-IGF1R antibody with T½ of 100.4 hrs. The MAC-2 Ang2 binding capability demonstrated similar residence time as Ang2-h38c2 with T½ of 97.8 hrs.

TABLE 26

Single-dose PK of IV administered MACs at 10 mg/mkg in mouse and cynomolgus monkey. α-IGF1R antibody dosed at 10 mg/kg in mouse, and 5 mg/kg in monkey.

| Compound (mg · Kg$^{-1}$) | Mouse β-T ½ (hr) | | Monkey T ½ (hr) | |
| --- | --- | --- | --- | --- |
| | Ang2 | IGF1R | Ang2 | IGF1R |
| Ang2-h38c2, (10) | 95.2 | — | 95.3 | — |
| α-IGF1R antibody, (10), (5) | — | 390 | — | 146.4 |
| MAC-1, (10) | 105 | 383 | NT | NT |
| MAC-2, (10) | 120 | 397 | 97.8 | 100.4 |

NT: not tested.

Example 9 In Vivo Pharmacology

The anti-tumour activity of MAC-2 was evaluated in the Colo205 (human colon adenocarcinoma) or MDA-MB-435 (melanoma) xenograft model. Full details of tumour studies are provided in the Examples of PCT/US2011/053092 (WO2012/007896). Weekly administration of Ang2-h38c2 or anti-IGF1R antibody (2.12.1.fx) inhibited Colo205 tumour growth. Combination of weekly administered Ang2-h38c2 and anti-IGF1R antibody showed an additive benefit on inhibiting Colo205 tumour growth. Weekly administration of MAC-2 alone showed similar benefit as the combination. In a separate study, MAC-2 dose-dependently inhibited Colo205 tumour growth and final tumour weights.

At day 28, tumour microvessel density after compound treated was significantly reduced (~42%) by MAC-2 (10 mg/kg, once weekly) in comparison with the Vehicle-treated group confirming the anti-angiogenic activity of the MAC-2 treatment.

To investigate whether MAC-2 targets both Ang2 and IGF1R in vivo, the effects of MAC-2 on Ang2 and IGF1R expression levels were assessed in 2 independent Colo205 xenograft tumors treated with Vehicle, Ang2-h38c2, IGF1R antibody (2.12.1.fx) or MAC-2 (dose response ranging from 0.3 mg/kg to 10 mg/kg). The results showed that Ang2 and IGF1R immunoreactivity was significantly reduced by MAC-2 treatment in a dose-dependent manner (1, 3 and 10 mg/kg) in comparison with the Vehicle-treated group. The effect of MAC-2 on IGF1R levels was similar to that observed for an IGF1R antagonizing antibody. In addition, the levels of phosphorylated IGF1R were reduced in tumours from MAC-2 treated animals. These data demonstrate that MAC-2 treatment affects both Ang2 and IGF1R pathways in Colo205 xenograft model. MAC-2 treatment did not affect body weight gain and mice appeared to be in good health throughout the studies. The anti-tumor efficacy of MAC-2 was also evaluated in an MDA-MB-435 melanoma xenograft model. Weekly administration of MAC-2 (3 and 20 mg/kg IP) resulted in a significant 40% reduction (day 67) in tumor growth in the MDA-MB-435 model. Thus, MAC-2 demonstrates significant anti-tumor efficacy in 2 different human xenograft tumor models.

Example 10 Peptide Conjugation Profile of Various Antibodies

The conjugation profiles of several different antibodies with peptides were analyzed, using SEQ ID NO:27 and PEG$_5$ as an exemplary peptide and linker respectively. All antibodies tested were human or fully humanized IgG antibodies with well defined and characterized antigen interactions. hAbλTest comprises a CLλ (hIL22: SEQ ID NOs:136 and 137), whereas 2.12.1.fx, mAbκTest1 (an IgG2 anti-Alk1 antibody, as disclosed in U.S. Pat. No. 7,537,762, incorporated herein by reference), h38C2-IgG1 (SEQ ID NO:64 and 65) and h38C2-IgG2 (SEQ ID NO:64 and 66) each comprise CLκ. Each of the antibodies were buffer exchanged into 20 mM HEPES, pH 7.0 and concentrated to 5-20 mg/mL. [PFP-PEG$_5$-K$^{11}$-SEQ:27] was resuspended with 50% propylene glycol and mixed with the relevant antibody at a 4.3:1 molar ratio and allowed to react for at least 2 hrs at RT. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple peptide conjugation sites are observed as distinct signals separated by the mass difference of a bound peptide. Relative quantitation of multiple peptide conjugation species is performed by measuring the signal magnitude. Table 22 shows the peptide conjugation profile of various antibodies For antibodies containing a CLκ, peptide conjugation occurs at a distribution between 0-4 peptide additions with the largest form being 2 to 3 peptide additions. In contrast, for the CLλ comprising antibody, hAbλTest, conjugation of the peptide occurs at a distribution between 0-4 peptides additions with the largest form being 1 to 2 peptide additions.

The extent of peptide conjugation was examined separately on the light and heavy chains. Each sample was denatured and disulfide bonds were reduced using guanidine hydrochloride and dithiothreitol. The resulting free light and heavy chains were analyzed using LCMS to determine the conjugation profile on each. The peptide conjugation profile on the light and heavy chain of various antibodies is shown in Table 27. On 2.12.1.fx and hAbκTest1, the data demonstrate that the location of conjugation is higher on the light chain; the most abundant form on the light chain contains 1 peptide addition. Conjugation on the heavy chain is observed at a significantly lower level. On h38C2-IgG1 and h38C2-IgG2, comparable levels of conjugation are observed on the light and heavy chain, with a slight conjugation preference on the light chain. On a CLλ containing antibody (hAbλTest; comprising SEQ ID NOs:136 and 137)), the majority of the conjugation occurs on the heavy chain with a low level of conjugation observed on the light chain.

TABLE 27

Conjugation profile of various antibodies.

| Antibody | CA (%) | | | | | Avg CA | Light Chain % CA | | | Heavy chain % CA | | |
| --- | --- | --- | --- | --- | --- | --- | --- | --- | --- | --- | --- | --- |
| | 0 | 1 | 2 | 3 | 4 | | 0 | 1 | 2 | 0 | 1 | 2 |
| 2.12.1.fx | 1 | 15 | 53 | 26 | 5 | 2.2 | 20 | 70 | 9 | 84 | 16 | 0 |
| hAbλTest | 10 | 37 | 37 | 11 | 6 | 1.66 | 95 | 5 | 0 | 74 | 22 | 4 |
| hAbκTest1 | 7 | 10 | 35 | 27 | 14 | 2.55 | 11 | 74 | 14 | 87 | 13 | 0 |
| h38C2 IgG1 | 1 | 3 | 28 | 55 | 13 | 2.75 | 49 | 46 | 4 | 70 | 30 | 0 |
| h38C2 IgG2 | | 4 | 6 | 31 | 44 | 2.6 | 61 | 35 | 4 | 73 | 27 | 0 |

Each of the antibodies 2.12.1.fx, hAbλTest and hAbκTest1 was assessed after the conjugation process to determine the effect of the conjugation additions on the ability of the antibody scaffold to retain its receptor binding (compared to native mAb) (Table 28). The results show that the directional conjugation of peptides to the test antibodies did not appear to alter the antibody binding.

TABLE 28

Antibody binding to respective native antigen before and after conjugation.

| Antibody | Antigen binding | |
|---|---|---|
| | Native (IC$_{50}$, nM) | After conjugation (IC$_{50}$, nM) |
| 2.12.1.fx | 3.2 | 5.7 |
| hAbλTest | 0.4 | 1.7 |
| hAbκTest1 | 59 | 53 |

Example 11 Peptide Conjugation Profile of an IgG2-κ Antibody

The conjugation profile of an IgG2 κ antibody (hABκTest2) with a 39-mer peptide was analyzed (SEQ ID NO:164). The antibody was concentrated to 8 mg/mL and buffered exchanged into 40 mM HEPES pH 8.0. The peptide was resuspended with 100% DMSO and mixed with the antibody at a 5.0:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple peptide conjugation sites are observed as distinct signals separated by the mass difference of a peptide. Relative quantitation of multiple peptide conjugation species is performed by measuring the signal magnitude. Table 29 shows the peptide conjugation profile of hAbκTest2 with the 39-mer peptide. The conjugation of peptide occurs at a distribution between 0-4 CA with an average of 2.03 CA, and is consistent with directional conjugation on the CLκ-K$^{80}$.

TABLE 29

Conjugation profile of 39-mer peptide and hAbκTest2.

| Antibody scaffold | Binding Peptide | % CA | | | | | Avg CA |
|---|---|---|---|---|---|---|---|
| | | 0 | 1 | 2 | 3 | 4 | |
| hAbκTest2 | 39-mer peptide | 1 | 22 | 53 | 18 | 5 | 2.03 |

In a separate experiment, the 39-mer peptide was conjugated to h38C2-IgG2 with MAL-PEG2-PFP as described above, at different molar concentrations. In addition, binding of the cognate receptor for the 39-mer peptide was assayed. The results (Table 30) shown are consistent with directional conjugation at CLκ-K$^{80}$. Moreover, increasing the average number of peptides per antibody did not substantially increase overall binding to the target. This demonstrates that in certain scenarios, increasing the conjugation per antibody may not increase target binding, demonstrating one of the advantages of the invention; control of the number of peptides conjugating per antibody can help achieve the maximum target binding per unit peptide.

TABLE 30

Conjugation profile of 39-mer peptide and H38C2-IgG2.

| 39-mer peptide: h38C2-IgG2 mole ratio | CA (%) | | | | Avg # Conjugates | Peptide target: EC50 (nM) |
|---|---|---|---|---|---|---|
| | 0 | 1 | 2 | 3 | | |
| 2:1 | 57 | 32 | 10 | 0 | 0.52 | 0.99 |
| 2.5:1 | 19 | 56 | 25 | 0 | 1.06 | 1.06 |
| 4:1 | 20 | 25 | 35 | 20 | 1.55 | 1.01 |
| 5:1 | 0 | 16 | 45 | 40 | 2.26 | 0.82 |

Example 12 Conjugation of Biotin to 2.12.1.fx Fab

The conjugation profile of the Fab region of 2.12.1.fx (SEQ ID NOs:4 and 64) with PFP-Biotin was analyzed. The antibody Fab was concentrated to 20 mg/mL and buffered exchanged into 20 mM sodium acetate+200 mM trehalose, pH 5.5 and spiked with 60 mM sodium phosphate pH 7.7. PFP-Biotin was resuspended with 100% DMSO and mixed with the antibody at successive molar ratios and allowed to react overnight at room temperature. All samples were diluted to 2 mg/ml and analyzed as an intact conjugated protein by size exclusion chromatography-mass spectrometry (SEC-MS) to determine the number and quantitation of conjugate forms. This technique measures the molecular weight of each protein form; multiple conjugation sites are observed as distinct signals separated by the mass difference of a conjugated peptide. Relative quantitation of multiple conjugation species is performed by measuring the signal magnitude. Table 31 shows the conjugation profile of 2.12.1.fx Fab with PFP-Biotin at molar ratios. The conjugation of occurs at a distribution between 0-2 additions as the molar ratio increases. The lower number of molecules per antibody was consistent with earlier results, based on the molar ratio used. This demonstrates the flexibility of the process to control the amount of conjugation by altering reaction parameters.

TABLE 31

Conjugation profile of Biotin to 2.12.1.fx Fab.

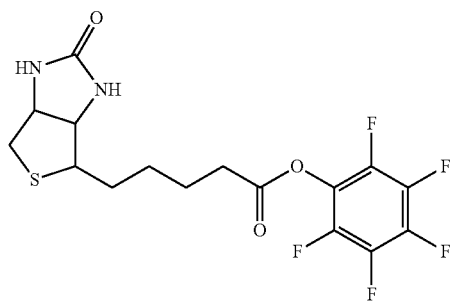 [SMILES: O=C1NC2CSC(CCCCC(=O)Oc3c(F)c(F)c(F)c(F)c3F)C2N1]

Biotin-PFP

| Binding Peptide | Peptide:Antibody Molar Ratio | % CA | | | | Avg CA |
|---|---|---|---|---|---|---|
| | | 0 | 1 | 2 | 3 | |
| Biotin-PFP | 1:1 | 54 | 46 | — | — | 0.46 |
| Biotin-PFP | 1.5:1 | 42 | 51 | 7 | — | 0.65 |
| Biotin-PFP | 2:1 | 34 | 55 | 10 | — | 0.76 |
| Biotin-PFP | 3:1 | 28 | 55 | 17 | — | 0.88 |
| Biotin-PFP | 4:1 | 21 | 46 | 26 | 8 | 1.21 |

Example 12 Conjugation of Biotin to h38C2-IgG1

The antibody h38C2-IgG1 was adjusted to 20 mg/mL with HEPES buffer pH 7.5 to a final concentration of 0.02 M. Biotin-PFP was reconstituted in water to 10 mg/mL and added to h38C2-IgG1 at a molar ratio of 5:1 and allowed to react at room temperature for 2 hrs. The unreacted PFP-Biotin was removed by size exclusion chromatography and buffer exchanged into a histidine, glycine, and sucrose buffer pH 6.5. The samples were diluted to 2 mg/ml and analyzed as an intact conjugated protein by size exclusion chromatography-mass spectrometry (SEC-MS) to determine the number and quantitation of conjugate forms of the protein. Table 32 shows the conjugation profile of h38C2-IgG1 with Biotin-PFP. Conjugation of h38C2-IgG1 occurs at a distribution between 0-3 CA with an average of 1.1 conjugations. Increased conjugation would be possible following optimization of the reaction conditions. The reactivity of VH-$K^{99}$ ($K^{93}$ according to Kabat numbering) on h38C2-IgG1 was confirmed to be >95% when reacted with the catalytic antibody test compound CATC-1, and analyzed via reversed phase chromatography.

TABLE 32

Conjugation of Biotin and h38C2-IgG1.

CATC-1

| Antibody | 0 | 1 | 2 | 3 | Avg CA |
|---|---|---|---|---|---|
| h38C2-IgG1 | 16 | 61 | 20 | 3 | 1.1 |

Example 13 Conjugation Profile of 2.12.1.fx and CLκ-$K^{80}$, CLκ-$K^{82}$ Mutants Based on peptide mapping, there are 2 Lys in Y15 fragment. In order to distinguish the active conjugation site, CLκ-$K^{80}$ and CLκ-$K^{82}$ were mutated to R respectively or in combination. Mutants of the test antibody, 2.12.1.fx, were generated following protocols described in QuickChange site-directed mutagenesis kit (Stratagene®). Mutations were introduced by oligonucleotide primers and confirmed by DNA sequencing. The mutated mAbs were transiently expressed in HEK 293 cells, and purified using Protein A affinity column. The purified mAbs were characterized using MS. SEQ ID NOs:12, 13 and 14 show the mutant CLκ sequences.

The antibody was buffer exchanged to 0.02M HEPES buffer pH 7.5 or 6.5 at 2 mg/mL. If the pH was 6.5, the antibody was then spiked with 60 mM sodium phosphate pH 7.7. [PFP-$PEG_5$-$K^{11}$-SEQ:27] was resuspended with 50% propylene glycol and mixed with the protein at a 4.3:1 molar ratio and allowed to react overnight at RT. All samples were diluted to 2 mg/ml and analyzed as an intact conjugated protein by size exclusion chromatography—mass spectrometry (SEC-MS) to determine the number and quantitation of conjugate forms of the protein. This technique measures the molecular weight of each protein form; multiple conjugation sites are observed as distinct signals separated by the mass difference of a conjugated protein. Relative quantitation of multiple protein conjugation species is performed by measuring the signal magnitude. Table 33 shows the conjugation profile of unmodified 2.12.1.fx, 2.12.1.fx-[CLκ-$K^{80}$R] (CLκ: SEQ ID NO:12), 2.12.1.fx-[CLκ-$K^{82}$R] (CLκ: SEQ ID NO:13), and 2.12.1.fx-[CLκ-$K^{80}$R-$K^{82}$R] (CLκ: SEQ ID NO:14). CLκ-$K^{80}$R mutant showed reduced conjugation. CLκ-$K^{82}$R had similar conjugation as the unconjugated 2.12.1.fx. The conjugation of MAC-2 was lower than observed in other assays due using a combination HEPES/phosphate buffer.

TABLE 33

Conjugation profile of 2.12.1.fx, $K^{80}$ and $R^{82}$ mutants.

| LC SEQ ID NO: | Mutants | CA (%) | | | | | Avg CA |
|---|---|---|---|---|---|---|---|
| | | 0 | 1 | 2 | 3 | 4 | |
| 6 | MAC-2 | 14 | 49 | 31 | 5 | 1 | 1.29 |
| 12 | K80R | 82 | 14 | 4 | 0 | 0 | 0.22 |
| 13 | K82R | 11 | 46 | 36 | 6 | 0 | 1.37 |
| 14 | K80R/K82R | 51 | 37 | 9 | 3 | 0 | 0.63 |

Example 14 Elucidation of Directional Conjugation Mechanism on $K^{80}$

CLκ-$H^{81}$ side chain is very close to the ε-amino group of CLκ-$K^{80}$. Since His is often involved in proton transfer reactions, CLκ-$H^{81}$ is very likely required for CLκ-$K^{80}$ conjugation. In order to study the role of CLκ-$H^{81}$ in CLκ-$K^{80}$ site specific conjugation, the imidazole ring was eliminated by a CLκ-$H^{81}$A mutation. CLκ-$D^{43}$A and CLκ-$D^{43}$A/$H^{81}$A mutants were made to study the role of CLκ-$D^{43}$ in site specific conjugation and the combined effect of CLκ-$D^{43}$ and CLκ-$H^{81}$.

Mutants were generated following protocols described in QuickChange site-directed mutagenesis kit (Stratagene®). Mutations were introduced by oligonucleotide primers and confirmed by DNA sequencing. The mutated mAbs were transiently expressed in HEK 293 cells, and purified using protein A affinity column. The purified mAbs were characterized using MS. The following 2.12.1.fx I CLκ mutants were generated: CLκ-$D^{43}$A (SEQ ID NO:15), CLκ-$K^{80}$A (SEQ ID NO:16), CLκ-$H^{81}$A (SEQ ID NO:17), CLκ-$K^{82}$A (SEQ ID NO:18) and CLκ-$D^{43}$A/$H^{81}$A (SEQ ID NO:19).

Each of the antibodies was buffer exchanged to 20 mM sodium acetate, 200m trehalose pH 5.5 at 20 mg/ml. The proteins were then spiked with 60 mM sodium phosphate pH 7.7. [PFP-$PEG_5$-$K^{11}$-SEQ:27] was resuspended with 50% propylene glycol and mixed with the antibody at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a conjugated peptide. Relative quantitation of multiple conjugation species is performed by measuring the signal magnitude. Table 34 shows the conjugation profile of 2.12.1.fx, 2.12.1.fx-[CLκ-$D^{43}$A], 2.12.1.fx-[CLκ-$K^{80}$A], 2.12.1.fx-[CLκ-$H^{81}$A], 2.12.1.fx-[CLκ-$K^{82}$A], and 2.12.1.fx-[CLκ-D43A/$H^{81}$A] mutants. All the mutants showed reduced average conjugation level compared to the unmodified 2.12.1.fx antibody, except for CLκ-K$^{80}$A, which maintained directional conjugation.

The extent of conjugation was examined separately on the light and heavy chains. Each sample was denatured and disulfide bonds were reduced using guanidine hydrochloride and dithiothreitol. The resulting free light and heavy chains were analyzed using LCMS to determine the conjugation profile on each. The conjugation profile on the light and heavy chain of 2.12.1.fx and mutants are shown in Table 34. All the mutants listed in the table showed reduced conjugation level on light chain compared to the unmodified 2.12.1.fx except CLκ-K$^{80}$A. The heavy chain conjugation level of the mutants was at the similar level as the unmodified 2.12.1.fx. The % of 1-LC % relative to the respective WT run is shown in the right column, as described in Table 34.

Example 16 hAbλTest1 Mutants: Motif Modification

To establish whether the short motif "KH" was sufficient for MAC formation in the corresponding region of the CLλ, a mutant with simple sequence switch of residues CLλ$^{81/82}$ in hAbλTest to place a histidine beside K$^{80}$ was made, hence "K$^{80}$S$^{81}$H$^{82}$" became "K$^{80}$H$^{81}$S$^{82}$". Mutants were generated following protocols described in QuickChange site-directed mutagenesis kit (Stratagene). Mutations were introduced by oligonucleotide primers and confirmed by DNA sequencing. The mutated antibody constructs were transiently expressed in HEK 293 cells, and purified using Protein A affinity column. The purified antibodies were characterized using MS. The hAbλTest-[CLλ-S$^{81}$H/H$^{82}$S] (CL: SEQ ID NO:62) mutant bound to its ligand as well as the parent hAbλTest antibody did (Table 36).

TABLE 34

Conjugation profile of MAC-2 and K$^{80}$A, D$^{43}$ and H$^{81}$ mutants.

| LC SEQ ID NO: | Mutants | CA (%) 0 | 1 | 2 | 3 | 4 | Avg CA | LC CA% 0 | 1 | 2 | LC Avg CA-LC | HC CA % 0 | 1 | 2 | HC Avg CA-HC | 1 LC WT % |
|---|---|---|---|---|---|---|---|---|---|---|---|---|---|---|---|---|
| 6 | MAC-2 | 1 | 15 | 53 | 26 | 5 | 2.2 | 23 | 69 | 8 | 0.85 | 86 | 14 | 0 | 0.14 | |
| 15 | D$^{43}$A | 17 | 38 | 31 | 14 | 0 | 1.41 | 68 | 30 | 1 | 0.33 | 79 | 21 | 0 | 0.21 | 43 |
| 16 | K$^{80}$A | 56 | 31 | 10 | 4 | 0 | 0.61 | 89 | 11 | 0 | 0.11 | 91 | 9 | 0 | 0.09 | 16 |
| 17 | H$^{81}$A | 34 | 44 | 17 | 6 | 0 | 0.95 | 89 | 11 | 0 | 0.11 | 78 | 22 | 0 | 0.22 | 16 |
| 18 | K$^{82}$A | 9 | 7 | 31 | 37 | 16 | 2.42 | 8 | 77 | 15 | 1.06 | 83 | 17 | 0 | 0.17 | 111 |
| 19 | D$^{43}$A/H$^{81}$A | 34 | 39 | 18 | 9 | 0 | 1.02 | 83 | 17 | 0 | 0.17 | 87 | 13 | 0 | 0.13 | 25 |

Example 15 Lambda/Kappa Substitution

The CLλ in hAbλTest1 (SEQ ID NOs:136 and 137) was substituted with CLκ to determine whether this increased the level, directionality and/or control of CL-specific conjugation. The CLλ/CLκ domain substitution hybrid constructs were generated using overlap PCR. The VLλ and CLκ were PCR amplified using hAbλTest and a κ mAb light chain as templates separately. These 2 PCR products were mixed as templates; hAbλTest1 forward primer and LCLκ reverse primer were used in overlap PCR reaction to amplify the full length hAbλTestVL/CLκ DNA. The hybrid antibody constructs were transiently expressed in HEK 293 cells, and purified using Protein A affinity column. The purified antibodies were characterized using MS. The hAbλTest CLκ hybrid bound to its cognate ligand similarly to the native mAb (hAbλTest) (Table 35). SEQ ID NOs:59, 60 and 61 are the light chain constant regions from hAbλTest, hAbλTest-λκ (with λJ), and hAbλTest-λκJ (with κJ).

TABLE 35

Antibody: Antigen binding of lambda/Kappa substitution.

| hAbλTest1 Mutants | LC SEQ ID NO: | Inhibition of IL22 binding to antigen (IC$_{50}$, nM) |
|---|---|---|
| hAbλTest (CONTROL) | 59 | 0.4 |
| hAλTest-λκ | 60 | 0.3 |
| hAbλTest-λκJ | 61 | 0.3 |

TABLE 36 hAbλTest-S$^{81}$H/H$^{82}$S.

| hAbλTest1 Mutants | LC SEQ ID NO: | Ligand binding (IC$_{50}$, nM) |
|---|---|---|
| hAbλTest (CONTROL) | 59 | 0.3 |
| hAbλTest-S$^{81}$H/H$^{82}$S | 62 | 0.4 |

Example 17 Conjugation Profile of hAbλTest1 Mutants

Each antibody (hAbλTest, hAbλTest-λκ, hAbλTest-λκJ and hAbλTest-[CLλ-S$^{81}$H/H$^{82}$S]) was buffer exchanged to 20 mM sodium acetate, 200m trehalose pH 5.5 at 20 mg/ml. The proteins were then spiked with 60 mM sodium phosphate pH 7.7. [PFP-PEG$_5$-K$^{11}$-SEQ:27] was resuspended with 50% propylene glycol and mixed with the antibody at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple peptide conjugation sites are observed as distinct signals separated by the mass difference of a peptide. Relative quantitation of multiple peptide conjugation species is performed by measuring the signal magnitude. Table 37 shows the overall level of conjugation has been increased in the 2 LC-switched hybrids (λκ and λκJ— the former includes a λ J fragment, the latter includes a κ J fragment). The conjugation level increases over the hAbλTest control's average CA, going from 1.66 to 2.19 (λκ) and 2.53 (λκJ) respectively. The mutant had little effect compared to the native sequence, suggesting that "KH" motif alone is not sufficient for MAC formation.

The extent of peptide conjugation was examined separately on the light and heavy chains (Table 37). Each sample was denatured and disulfide bonds were reduced using guanidine hydrochloride and dithiothreitol. The resulting free light and heavy chains were analyzed using LCMS to determine the conjugation profile on each. In the reduced analyses, the LC of native hAbλTest has only 5% 1CA but this jumps dramatically to 58% 1CA for hAbλTest-λκ and 63% 1CA for hAbλTest-λκJ. The LC switch had little effect on the level of HC conjugation, which remained fairly constant (except for λκJ, where HC conjugation increased moderately). Again, the mutant had little effect compared to the native sequence, suggesting that "KH" motif alone is not sufficient for MAC formation. The % of 1-LC % relative to the respective WT run is shown in the right column, as described in Table 37.

was examined by MS of the intact conjugates, and the degree of peptide addition to both the light and heavy chains were also determined by MS following reduction of the intact conjugate and separation of the light and heavy chains.

The structure and designations of the alternatively activated esters are shown below. The alternatively activated peptides were synthesized using the same strategies and methods shown above. Briefly, each activated group was incorporated into a MAL-PEG$_2$-Z* linker, where Z* represented the new leaving group replacing PFP. To synthesize the above compounds, a sample (30-40 mg) of the purified ABP-thiol peptide (i.e. ABP with $K_{SH}$ as linking residue) was dissolved in anhydrous DMF (2 ml). MAL-PEG$_2$-Z* (20 mg) was added along with N-methylmorpholine (5 mL). The reaction was stirred and monitored at RT by HPLC to follow the time-course of product formation. The complete conversion of starting peptide to activate-ester linked ABP product was observed within 2-6 hrs. The solution was

TABLE 37

Conjugation profile of hAbATest mutants.

| hAbλTest Mutants | LC SEQ ID NO: | CA (%) 0 | 1 | 2 | 3 | 4 | Avg CA | LC CA% 0 | 1 | 2 | Avg CA-LC | HC CA % 0 | 1 | 2 | Avg CA-HC | 1LC WT % |
|---|---|---|---|---|---|---|---|---|---|---|---|---|---|---|---|---|
| hAbλTest | 59 | 10 | 37 | 37 | 11 | 6 | 1.66 | 95 | 5 | 0 | 0.05 | 74 | 22 | 4 | 0.3 | |
| hAbλTest-λκ | 60 | 3 | 18 | 43 | 29 | 7 | 2.19 | 42 | 58 | 0 | 0.58 | 78 | 22 | 0 | 0.22 | 1160 |
| hAbλTest-λκJ | 61 | 2 | 11 | 34 | 36 | 17 | 2.53 | 33 | 63 | 4 | 0.71 | 64 | 36 | 0 | 0.36 | 1260 |
| hAbλTest-S$^{81}$H/H$^{82}$S | 62 | 7 | 34 | 37 | 16 | 6 | 1.79 | 82 | 18 | 0 | 0.18 | 79 | 21 | 0 | 0.21 | 360 |

The receptor binding attributes of these conjugated forms was also assessed to determine the effect of conjugation with [PFP-PEG$_5$-K$^{11}$-SEQ:27] on the ability of the conjugated antibodies to still bind to their ligand (Table 38).

TABLE 38

Antibody: Antigen binding of lambda at antibodies.

| SEQ ID NO: 27 conjugated hAbλTest1 Mutants | LC SEQ ID NO: | Inhibition of IL22 binding to antigen (IC$_{50}$, nM) |
|---|---|---|
| hAbλTest | 59 | 1.7 |
| hAbλTest-λκ | 60 | 1.5 |
| hAbλTest-λκJ | 61 | 1.6 |
| hAbλTest1-S$^{81}$H/H$^{82}$S | 62 | 1.6 |

Example 18 MAC Generation Using Different Leaving Groups

To investigate if the degree of activation and/or structure of the active ester leaving group was important in defining the directional conjugation effect, a series of alternatively activated ester analogs of [PFP-PEG$_2$-MAL-K$_{SH}$$^{11}$-SEQ:27] were synthesized. The distribution of the conjugate product filtered and the product peak directly isolated by semi-preparative HPLC. The products were isolated in yields ranging from approximately 30-50%, after lyophilization.

The conjugation reactions were carried out under the standard conditions. Briefly, the 2.12.1.fx antibody solution was prepared by diluting the 2.12.1.fx solution with sodium phosphate, pH 7.7 to a final concentration of 0.06M. Separately, the peptide solution was prepared by dissolving the peptide to 20 mg/ml in propylene glycol, then diluting this solution to 10 mg/ml with water. For the conjugation reaction, the peptide and antibody solutions were mixed at a 4:1 molar ratio for the prescribed period. For the time-course studies, samples of the conjugation solution were quenched at various time points by mixing a sample of the conjugation reaction with a solution of 40 mM succinic acid, 200 mM glycine, pH 4.0 (1:1, v/v). Time-course of the conjugation reactions were followed by HPLC. SEQ ID NO:27 was used as an exemplary peptide.

TABLE 39

Reactive esters - intact conjugation at 24 hrs.

Z*—PEG$_2$—MAL—K$_{SH}$[11]—SEQ: 27

| CA | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6-DFP | Z12 1 NAP |
|---|---|---|---|---|---|---|---|---|---|---|---|---|
| 0 | 3  | 32 | 17 | 100 | 81 | 38 | 73 | 34 | 20 | 41 | 50 | 100 |
| 1 | 34 | 45 | 43 | 0   | 19 | 45 | 25 | 40 | 36 | 42 | 39 | 0 |
| 2 | 51 | 20 | 30 | 0   | 0  | 16 | 2  | 18 | 31 | 15 | 11 | 0 |
| 3 | 12 | 3  | 11 | 0   | 0  | 2  | 0  | 5  | 12 | 3  | 0  | 0 |

Table 39 shows the final product distribution of the intact conjugates 24 hrs after initiation of the conjugation reaction. The results show that some of esters did not react at all (Z4, Z12), others reacted sluggishly (e.g. Z5), while several gave profiles approaching that of PFP (Z1) (e.g. Z3).

Conjugation Kinetics

The rates of addition over time for each of the final conjugates are shown in Tables 39, 40, 41, and 42. OCA represents underivatized 2.12.1.fx antibody, whereas 1, 2 or 3CA represents additions of 1, 2 or 3 peptides to the 2.12.1.fx antibody at each of the time periods examined.

TABLE 40

Conjugation kinetics of different Z* groups yielding 0 CA.

| 0CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6-DFP | Z12 1 nap |
|---|---|---|---|---|---|---|---|---|---|---|---|---|
| 0  | 84 | 97 | 94 | 100 | 100 | 100 | 100 | 95 | 95 | 96 | 100 | 100 |
| 1  | 5  | 83 | 58 | 100 | 100 | 95  | 96  | 43 | 24 | 79 | 93  | 100 |
| 2  | 4  | 75 | 40 | 100 | 100 | 89  | 93  | 42 | 20 | 67 | 88  | 100 |
| 4  | 4  | 62 | 27 | 100 | 96  | 81  | 88  | 40 | 20 | 54 | 79  | 100 |
| 24 | 3  | 32 | 17 | 100 | 81  | 38  | 73  | 34 | 20 | 41 | 50  | 100 |

TABLE 41

Conjugation kinetics of different Z* groups yielding 1 CA.

| 1CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6-DFP | Z12 1 nap |
|---|---|---|---|---|---|---|---|---|---|---|---|---|
| 0  | 16 | 3  | 6  | 0 | 0  | 0  | 0  | 5  | 5  | 5  | 0  | 0 |
| 1  | 38 | 17 | 36 | 0 | 0  | 5  | 4  | 39 | 39 | 21 | 8  | 0 |
| 2  | 37 | 25 | 45 | 0 | 0  | 11 | 7  | 39 | 38 | 29 | 12 | 0 |
| 4  | 33 | 34 | 43 | 0 | 4  | 19 | 12 | 42 | 39 | 37 | 21 | 0 |
| 24 | 34 | 45 | 43 | 0 | 19 | 45 | 25 | 40 | 36 | 42 | 39 | 0 |

TABLE 42

Conjugtion kinetics of different Z* arouos yielding 2 CA.

| 2CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6-DFP | Z12 1 nap |
|---|---|---|---|---|---|---|---|---|---|---|---|---|
| 0 | 0 | 0 | 0 | 0 | 0 | 0 | 0 | 0 | 0 | 0 | 0 | 0 |
| 1 | 49 | 0 | 6 | 0 | 0 | 0 | 0 | 15 | 27 | 0 | 0 | 0 |
| 2 | 50 | 0 | 14 | 0 | 0 | 0 | 0 | 16 | 30 | 4 | 0 | 0 |
| 4 | 52 | 4 | 25 | 0 | 0 | 0 | 0 | 15 | 29 | 9 | 0 | 0 |
| 24 | 51 | 20 | 30 | 0 | 0 | 16 | 2 | 18 | 31 | 15 | 11 | 0 |

TABLE 43

Conjugation kinetics of different Z* groups yielding 3 CA.

| 3CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6-DFP | Z12 1 nap |
|---|---|---|---|---|---|---|---|---|---|---|---|---|
| 0 | 0 | 0 | 0 | 0 | 0 | 0 | 0 | 0 | 0 | 0 | 0 | 0 |
| 1 | 8 | 0 | 0 | 0 | 0 | 0 | 0 | 3 | 11 | 0 | 0 | 0 |
| 2 | 10 | 0 | 2 | 0 | 0 | 0 | 0 | 3 | 12 | 0 | 0 | 0 |
| 4 | 12 | 0 | 5 | 0 | 0 | 0 | 0 | 4 | 12 | 0 | 0 | 0 |
| 24 | 12 | 3 | 11 | 0 | 0 | 2 | 0 | 5 | 12 | 3 | 0 | 0 |

Light and Heavy Chain Distribution

The extent of peptide conjugation for each of the alternatively activated esters was examined separately on the light and heavy chains. Each sample was denatured and disulfide bonds were reduced using guanidine hydrochloride and dithiothreitol. The resulting free light and heavy chains were analyzed using LCMS to determine the conjugation profile on each. The peptide conjugation profile on the light and heavy chain of 2.12.1.fx and mutants are shown in Table 44. Almost all of the activated peptides listed in the table showed reduced conjugation level on light chain compared to the compound using PFP (Z1), except 2,3,6-trifluorophenyl (Z3), which showed a similar level of conjugation. Activated esters derived from N-hydroxysuccinimide (NHS), i.e. N-Hydroxyl-5-norbornene-2,3-dicarboxylic acid imide and 2-hydroxyl-isoindoline-1,3-dione (Z8 and Z9) showed a greater propensity for heavy chain derivatization.

TABLE 44

Summary of activated ester results.

| Z* # | Z* Name | Z* Structure | Time course of conjugation adducts [separate 24 hr expt in bold] | | | | | | Reduced conjugation at 24 hr | | | | | |
|---|---|---|---|---|---|---|---|---|---|---|---|---|---|---|
| 1 | Penta Fluoro Phenyl | | CA | 0 | 1 | 2 | 4 | 24 | LC | LC + 1CA | L + 2CA | HC | HC + 1CA | HC + 2CA |
| | | | 0 | 84 | 5 | 4 | 4 | 3 | 30 | 64 | 7 | 94 | 6 | — |
| | | | 1 | 16 | 38 | 37 | 33 | 34 | | | | | | |
| | | | 2 | 0 | 49 | 50 | 52 | 51 | | | | | | |
| | | | 3 | 0 | 8 | 10 | 12 | 12 | | | | | | |
| 2 | 2,3,4-trifluoro-phenyl | | CA | 0 | 1 | 2 | 4 | 24 | LC | LC + 1CA | L + 2CA | HC | HC + 1CA | HC + 2CA |
| | | | 0 | 97 | 83 | 75 | 62 | 32 | 59 | 41 | — | 94 | 6 | — |
| | | | 1 | 3 | 17 | 25 | 34 | 45 | | | | | | |
| | | | 2 | 0 | 0 | 0 | 4 | 20 | | | | | | |
| | | | 3 | 0 | 0 | 0 | 0 | 3 | | | | | | |
| 3 | 2,3,6-trifluoro-phenyl | | CA | 0 | 1 | 2 | 4 | 24 | LC | LC + 1CA | L + 2CA | HC | HC + 1CA | HC + 2CA |
| | | | 0 | 94 | 58 | 40 | 27 | 17 | 30 | 64 | 7 | 90 | 10 | — |
| | | | 1 | 6 | 36 | 45 | 43 | 43 | | | | | | |
| | | | 2 | 0 | 6 | 14 | 25 | 30 | | | | | | |
| | | | 3 | 0 | 0 | 2 | 5 | 11 | | | | | | |
| 4 | 2,3,6-trichloro-phenyl | | CA | 0 | 1 | 2 | 4 | 24 | LC | LC + 1CA | L + 2CA | HC | HC + 1CA | HC + 2CA |
| | | | 0 | 100 | 100 | 100 | 100 | 100 | 95 | 5 | — | 100 | — | — |
| | | | 1 | 0 | 0 | 0 | 0 | 0 | | | | | | |
| | | | 2 | 0 | 0 | 0 | 0 | 0 | | | | | | |
| | | | 3 | 0 | 0 | 0 | 0 | 0 | | | | | | |

TABLE 44-continued

Summary of activated ester results.

| Z* # | Z* Name | Z* Structure | Time course of conjugation adducts [separate 24 hr expt in bold] | | | | | | Reduced conjugation at 24 hr | | | | | |
|---|---|---|---|---|---|---|---|---|---|---|---|---|---|---|
| 5 | 2,6 dichlorophenyl | 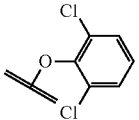 | CA 0 1 2 3 | 0 100 0 0 0 | 1 100 0 0 0 | 2 100 0 0 0 | 4 96 4 0 0 | 24 81 19 0 0 | LC 89 | LC + 1CA 11 | L + 2CA — | HC 100 | HC + 1CA — | HC + 2CA — |
| 6 | 2,4 DiCl Napthalene | 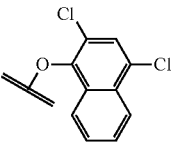 | CA 0 1 2 3 | 0 100 0 0 0 | 1 95 5 0 0 | 2 89 11 0 0 | 4 81 19 0 0 | 24 38 45 16 2 | LC 66 | LC + 1CA 34 | L + 2CA — | HC 95 | HC + 1CA 5 | HC + 2CA — |
| 7 | 5,7-dichloroquinolin-8-yl | 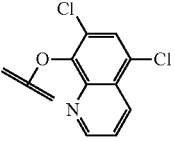 | CA 0 1 2 3 | 0 100 0 0 0 | 1 96 4 0 0 | 2 93 7 0 0 | 4 88 12 0 0 | 24 73 25 2 0 | LC 92 | LC + 1CA 8 | L + 2CA — | HC 95 | HC + 1CA 5 | HC + 2CA — |
| 8 | N-Hydroxyl-5-norbornene-2,3-dicarboxylic acid imide | 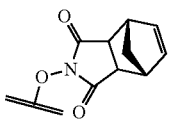 | CA 0 1 2 3 | 0 95 5 0 0 | 1 43 39 15 3 | 2 42 39 16 3 | 4 40 42 15 4 | 24 38 40 18 5 | LC 77 | LC + 1CA 23 | L + 2CA — | HC 82 | HC + 1CA 18 | HC + 2CA — |
| 9 | 2-hydroxyl-isoindoline-1,3-dione | 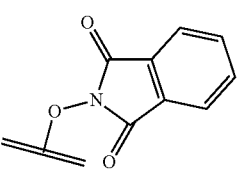 | CA 0 1 2 3 | 0 95 5 0 0 | 1 24 39 27 11 | 2 20 38 30 12 | 4 20 39 29 12 | 24 20 36 31 12 | LC 70 | LC + 1CA 30 | L + 2CA — | HC 50 | HC + 1CA 50 | HC + 2CA — |
| 10 | 4-nitrophenyl | 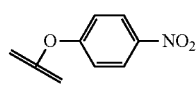 | CA 0 1 2 3 | 0 96 5 0 0 | 1 79 21 0 0 | 2 67 29 4 0 | 4 54 37 9 0 | 24 41 42 15 3 | LC 68 | LC + 1CA 32 | L + 2CA — | HC 92 | HC + 1CA 8 | HC + 2CA — |
| 11 | 2,6-difluorophenyl |  | CA 0 1 2 3 | 0 100 0 0 0 | 1 93 8 0 0 | 2 88 12 0 0 | 4 79 29 0 0 | 24 50 39 11 0 | | | | | | |
| 12 | 1-naphthyl | 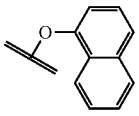 | CA 0 1 2 3 | 0 100 0 0 0 | 1 100 0 0 0 | 2 100 0 0 0 | 4 100 0 0 0 | 24 100 0 0 0 | | | | | | |

Example 19

Further examples of alternatively activated esters are shown in Table 45. The time-course of conjugation of several analogs of PFP esters were examined. By decreasing the number and position of the fluorine groups in PFP, less reactive active ester forms can be synthesized and investigated. 2,3,5,6-tetrafluorophenyl ester and 2,4,6-trifluorophenyl ester were both tested after conjugation to [PEG$_2$-MAL-K$_{SH}$$^{11}$-SEQ:27]. 1-hydroxyl-pyrrolidine-2,5-dione (NHS) was conjugated to [PEG$_5$-K$^{11}$-SEQ:27].

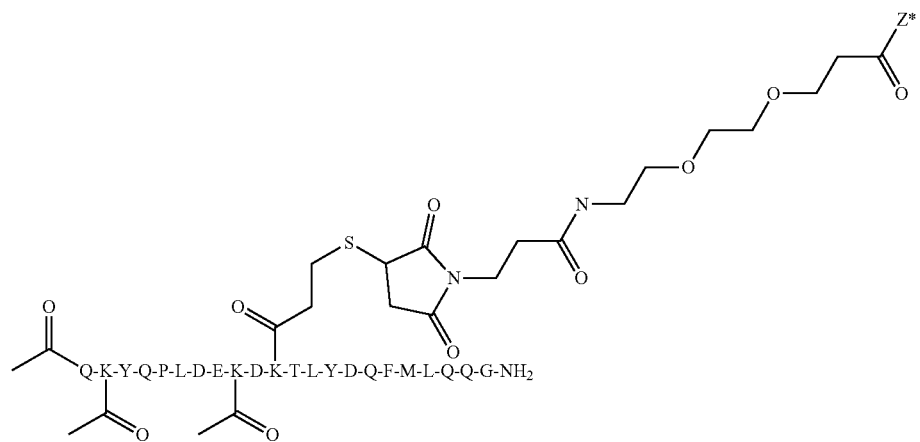

[Z*-PEG₂-MaL-K$_{SH}^{11}$-SEQ: 27]

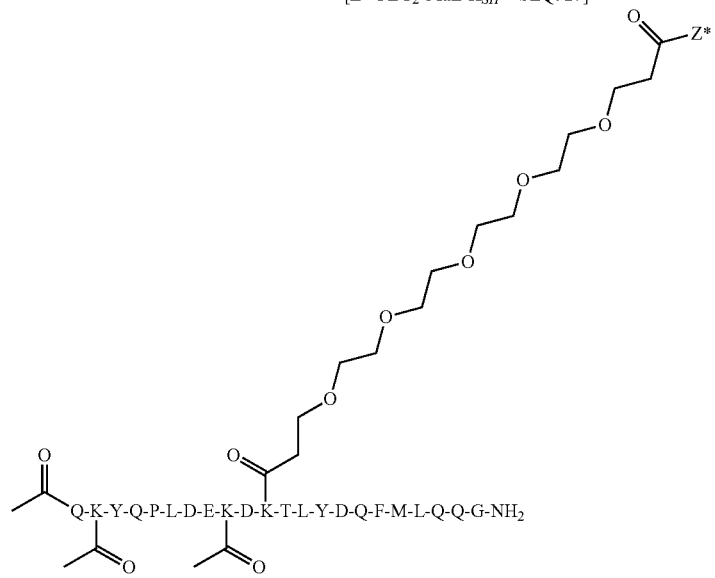

[Z*-PEG₅-K¹¹-SEQ: 27]

After 2 hrs conjugation, these less activated forms gave lower overall conjugation to 2.12.1.fx than PFP. NHS group also showed lower overall conjugation. NHS and PFP-containing peptides were conjugated to 2.12.1.fx. The reduced forms were analyzed to see the distribution at 2 hrs. PFP showed a much greater propensity for light chain derivatization (77% overall to LC, only 6% to heavy) compared to 1-hydroxyl-pyrrolidine-2,5-dione (NHS) (31% overall to LC, but 34% overall to heavy).

TABLE 45

Alternatively activated esters - further examples.

| | Name | Structure | CA at 2 hr | | Active esters—reduced analysis of conjugation at 2 hr | | | | | |
|---|---|---|---|---|---|---|---|---|---|---|
| | | | CA | 2 hr | LC | LC + 1CA | LC + 2CA | HC | HC + 1CA | HC + 2CA |
| 1 | Penta Fluoro Phenyl | 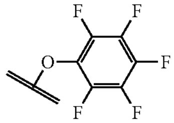 | 0 | 3 | 23 | 72 | 5 | 94 | 6 | 0 |
| | | | 1 | 40 | | | | | | |
| | | | 2 | 42 | | | | | | |
| | | | 3 | 14 | | | | | | |
| | | | 4 | 1 | | | | | | |

TABLE 45-continued

Alternatively activated esters - further examples.

| Name | Structure | CA at 2 hr | | Active esters—reduced analysis of conjugation at 2 hr | | | | | | |
|---|---|---|---|---|---|---|---|---|---|---|
| | | | | LC | LC + 1CA | LC + 2CA | HC | HC + 1CA | HC + 2CA | |
| 13 1-hydroxyl-pyrrolidine-2,5-dione (NHS) | 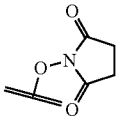 | CA<br>0<br>1<br>2<br>3<br>4 | 2 hr<br>18<br>44<br>24<br>12<br>3 | 70 | 28 | 3 | 66 | 31 | 3 | |
| 14 2,3,5,6-tetra-fluoro-phenyl | 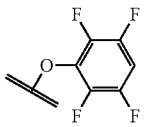 | CA<br>0<br>1<br>2<br>3<br>4 | 2 hr<br>21<br>44<br>29<br>5<br>2 | | | | | | | |
| 15 2,4,6-trifluoro phenyl | 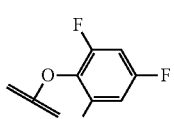 | CA<br>0<br>1<br>2<br>3<br>4 | 2 hr<br>80<br>27<br>2<br>0<br>0 | | | | | | | |

Compounds Z1-Z15 represent a variety of different structural types of active ester. It is enlightening to consider the series of fluorinated aromatic active esters, which have a different number and pattern of substitution of fluorine atoms around the aromatic ring (compounds Z1, Z2, Z3, Z11, Z14 and Z15) and consider how their structure influences their reactivity and propensity for protein derivatization. The kinetics of the antibody-conjugation of these derivatives can be conveniently compared at the 2 hr timepoint, when the pentafluorophenyl (Z1) reaction has gone to completion. With an increasing level of fluorine substitution around the ring, there is an increasing level of overall conjugation and a concomitant decrease in unreacted antibody. The rate of reaction is directly related to the pKa of the fluorinated phenol leaving group, with the most acidic phenols giving higher reaction rates. The rates of conjugation are Z1>Z14>Z3>Z15>Z2>Z11. The subtle effects of the fluorine substitution patterns can be seen by comparing compounds Z2, Z3 and Z15.

The structure of the active ester also significantly affected the directionality of the conjugation reaction. In general, the fluorinated aromatic esters showed a marked propensity towards light chain derivatization (principally $CL\kappa\text{-}K^{80}$ as previously mentioned). In contrast, several esters based on N-hydroxysuccinimide derivatives (Z8, Z9 and Z13) showed less preference, with often greater levels of heavy chain derivatization observed.

Example 20

The rate of conjugation between MAC-1 ($PEG_2$-MAL-mercaptopropionyl linker between the peptide and PFP activating group) and MAC-2 (straight-chained $PEG_5$ linker between the peptide and PFP activating group) was assessed. Table 46 compares these activated peptides to 2.12.1x. The results show that the activated peptides behave very similarly in terms of the rate and extent of derivatization, despite their slightly different linker structures.

TABLE 46

Comparison of conjugation between MAC-1 and MAC-2.

| | MAC-2 | | | | | MAC-1 | | | | |
|---|---|---|---|---|---|---|---|---|---|---|
| Intact time (min) | OCA | 1CA | 2CA | 3CA | 4CA | OCA | 1CA | 2CA | 3CA | 4CA |
| 0 | 72 | 27 | 1 | 0 | 0 | 82 | 18 | 1 | 0 | 0 |
| 10 | 26 | 56 | 17 | 1 | 0 | 29 | 49 | 20 | 2 | 0 |
| 20 | 13 | 53 | 29 | 5 | 0 | 15 | 47 | 33 | 5 | 0 |
| 30 | 9 | 51 | 32 | 8 | 1 | 9 | 43 | 40 | 8 | 0 |
| 40 | 7 | 45 | 39 | 9 | 1 | 8 | 41 | 41 | 8 | 2 |
| 50 | 6 | 43 | 39 | 11 | 1 | 7 | 41 | 42 | 9 | 2 |
| 60 | 5 | 41 | 40 | 11 | 2 | 6 | 36 | 45 | 11 | 2 |
| 70 | 4 | 40 | 40 | 14 | 2 | 6 | 35 | 46 | 11 | 2 |
| 80 | 3 | 38 | 44 | 14 | 2 | 5 | 36 | 47 | 10 | 2 |
| 90 | 4 | 37 | 45 | 13 | 1 | 6 | 35 | 46 | 12 | 2 |
| 100 | 4 | 40 | 41 | 13 | 2 | 6 | 35 | 46 | 11 | 2 |
| 110 | 3 | 40 | 42 | 14 | 1 | 6 | 34 | 46 | 12 | 3 |
| 120 | 4 | 37 | 44 | 13 | 1 | 5 | 35 | 46 | 12 | 2 |

Example 21 Effect of Linker Length

The effect on the final conjugate distribution profile of having different lengths of linker was examined. Compounds were synthesized with different PEG length linkers joining the peptide to the PFP group. The results for the addition to 2.12.1.fx of 0, 1, 2, 3 and 4 peptides are summarized in Table 47. Overall, changing the length of the PEG linker had generally little effect on the distribution of conjugates obtained.

TABLE 47

Effect of linker length.

$Y^1 =$

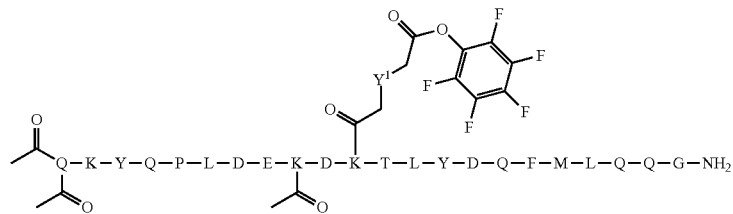

| n | CA (%) | | | | |
|---|---|---|---|---|---|
| | 0 | 1 | 2 | 3 | 4 |
| 2 | 8 | 39 | 44 | 8 | 0 |
| 3 | 6 | 34 | 47 | 10 | 2 |
| 5 | 4 | 37 | 44 | 13 | 1 |
| 7 | 4 | 35 | 49 | 11 | 0 |
| 9 | 3 | 28 | 49 | 19 | 2 |
| 13 | 3 | 32 | 54 | 10 | 0 |
| 17 | 6 | 37 | 51 | 7 | 0 |
| 21 | 4 | 43 | 45 | 5 | 2 |
| 25 | 11 | 44 | 38 | 7 | 0 |

Structure of Example 21 compounds.
2.12.1fx was conjugated to

[PFP—PEG$_n$—K$^{11}$ - SEQ: 27]

Example 22 Conjugation of Alternative Peptide Sequences

To confirm the applicability of the invention across other peptide sequences, SEQ ID NO:80 and SEQ ID NO:81 (Test-peptides-1, and -2) were conjugated. SEQ ID NOs:80 and 81 were conjugated with [PFP-PEG$_5$] and then the 2.12.1.fx under conditions previously optimized for reaction with [PFP-PEG$_5$-K$^{11}$-SEQ:27]. The results of analysis of the conjugation profile and LC/HC conjugation are shown in Table 48. SEQ ID NO:80 and SEQ ID NO:81 both showed directional conjugation to the light chain. On further analysis of the LC/HC distributions, similar profiles to that of MAC-2 were observed, with around 70% LC derivatization and less than 10% on the HC.

TABLE 48

Conjugation profile of SEQ ID NO 80 and SEQ ID NO: 81.

| SEQ ID NO: | % CA | | | | | LC % CA | | | HC % CA | | |
|---|---|---|---|---|---|---|---|---|---|---|---|
| | 0 | 1 | 2 | 3 | 4 | LC | LC +1 | LC +2 | HC | HC +1 | HC +2 |
| 27 | 2 | 24 | 55 | 17 | 3 | 24 | 65 | 11 | 91 | 9 | — |
| 80 | 11 | 39 | 43 | 8 | 0 | 32 | 68 | — | 95 | 5 | — |
| 81 | 8 | 35 | 48 | 10 | 0 | 29 | 71 | — | 94 | 6 | — |

TABLE 48-continued

Conjugation profile of SEQ ID NO 80 and SEQ ID NO: 81.

| SEQ ID NO: | % CA | | | | | LC % CA | | | HC % CA | | |
|---|---|---|---|---|---|---|---|---|---|---|---|
| | 0 | 1 | 2 | 3 | 4 | LC | LC +1 | LC +2 | HC | HC +1 | HC +2 |

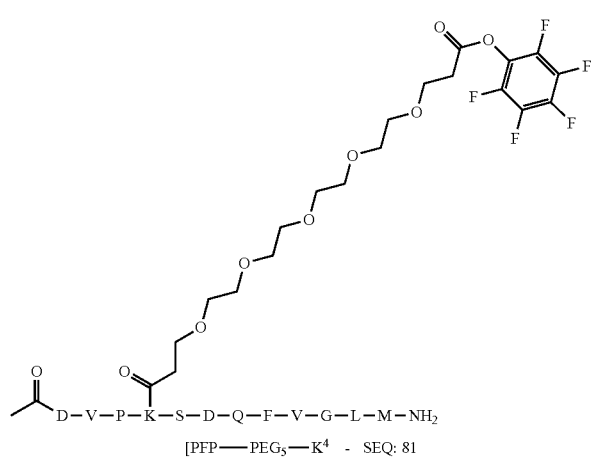

[PFP—PEG₅—K⁷ - SEQ: 80]

[PFP—PEG₅—K⁴ - SEQ: 81]

Example 23 Summary of Peptide Conjugation Analysis

Peptide mapping experiments were performed on a range of protein/conjugate combinations for the purpose of confirming the important parameters that lead to directional conjugation at CLκ-K⁸⁰ on antibody light chains. Table 49 lists the results of the peptide mapping experiments performed. For each study parameter, the peptide mapping procedure described earlier was used. "*" indicates a high level of directional conjugation to CLκ-K⁸⁰. "" and to a lesser extent, "*", indicates directional conjugation is still observed, but may show differences, such as slower reaction conditions, less overall conjugation, or averaging at one light chain only, and so may be more suitable to special circumstances, such as generating MACs with between 0.5 and 1.5 peptide per antibody (for example). "-" indicates that these reaction conditions did not appear favorable towards directional conjugation at CLκ-K⁸⁰.

As CLκ-K⁸⁰ was observed in MAC-2 to be the location of directional conjugation, peptide mapping studies on alternative parameters focused on this location. Detailed peptide mapping data for each study parameter is not included, but significant conjugation levels at other K residues was not observed, and observations of other MACs were consistent with directional conjugation at CLκ-K⁸⁰.

CLκ-K⁸⁰R and CLκ-K⁸⁰A mutations of 2.12.1.fx resulted in the loss of directional conjugation at this site; suggesting an essential role for this specific residue. CLκ-K⁸²R, and CLκ-K⁸²A mutations did not hinder directional conjugation to CLκ-K⁸⁰, and may even enhance it. Of the other study parameters examined, at least a portion of the sub-type of light chain constant region was observed to have a significant impact on directional conjugation; at least a portion of the light chain sub-type kappa was determined to be necessary. Conjugation onto a CLλ sub-type (using an exemplary A containing antibody, hAbλTest1), did not demonstrate directional conjugation. When the CLλ of hAbλTest1 was mutated to a CLκ, directional conjugation at K⁸⁰ was recovered.

TABLE 49

Summary of directional conjugation at $CL_K\text{-}K^{80}$.

| Antibody | LC | Mutations/ Differences Vs MAC1/2 | SEQ ID NO | Linker | Z* | Directional conjugation |
|---|---|---|---|---|---|---|
| 2.12.1.fx | κ | | 27 | PEG$_2$-MAL | PFP | * * * |
| 2.12.1.fx | κ | | 27 | PEG$_5$ | PFP | * * * |
| 2.12.1.fx Fab | κ | | 27 | PEG$_5$ | PFP | * * * |
| h38C2-IgG1 | κ | | 27 | PEG$_5$ | PFP | * * * |
| h38C2-IgG2 | κ | | 27 | PEG$_5$ | PFP | * * * |
| hAbλTest | λ | K$^{80}$SH | 27 | PEG$_5$ | PFP | — |
| hAbκTest1 | κ | | 27 | PEG$_5$ | PFP | * * * |
| hAbκTest3 | κ | | 39-mer | PEG$_5$ | PFP | * * * |
| hAbλTest | λκ | | 27 | PEG$_5$ | PFP | * * * |
| hAbλTest | λκJ | | 27 | PEG$_5$ | PFP | * * * |
| 2.12.1.fx | κ | K$^{80}$R | 27 | PEG$_5$ | PFP | — |
| 2.12.1.fx | κ | K$^{82}$R | 27 | PEG$_5$ | PFP | * * * |
| 2.12.1.fx | κ | K$^{80}$R/R$^{82}$R | 27 | PEG$_5$ | PFP | — |
| 2.12.1.fx | κ | D$^{43}$A | 27 | PEG$_5$ | PFP | * * |
| 2.12.1.fx | κ | K$^{80}$A | 27 | PEG$_5$ | PFP | — |
| 2.12.1.fx | κ | H$^{81}$A | 27 | PEG$_5$ | PFP | — |
| 2.12.1.fx | κ | H$^{82}$A | 27 | PEG$_5$ | PFP | * * * |
| 2.12.1.fx | κ | D$^{43}$A/H$^{81}$A | 27 | PEG$_5$ | PFP | — |
| hAbλTest1 | λ | S$^{81}$H/H$^{82}$S | 27 | PEG$_5$ | PFP | — |
| 2.12.1.fx | κ | | 39-mer | PEG$_5$ | PFP | * * * |
| 2.12.1.fx | κ | | 80 | PEG$_5$ | PFP | * * * |
| 2.12.1.fx | κ | | 81 | PEG$_5$ | PFP | * * * |
| h38C2-IgG2 | κ | | 39-mer | PEG$_5$ | PFP | * * * |
| 2.12.1.fx Fab | κ | | biotin | PEG$_5$ | PFP | * * * |
| 2.12.1.fx | κ | | 27 | PEG$_2$-MAL | PFP | * * * |
| 2.12.1.fx | κ | | 27 | PEG$_2$-MAL | 2,3,4 TFP (2) | * * |
| 2.12.1.fx | κ | | 27 | PEG$_2$-MAL | 2,3,6 TFP (3) | * * |
| 2.12.1.fx | κ | | 27 | PEG$_2$-MAL | 2,3,6 TCP (4) | — |
| 2.12.1.fx | κ | | 27 | PEG$_2$-MAL | 2,6 DCP (5) | — |
| 2.12.1.fx | κ | | 27 | PEG$_2$-MAL | 2,4 DCN (6) | * |
| 2.12.1.fx | κ | | 27 | PEG$_2$-MAL | 5,7 DCQ (7) | — |
| 2.12.1.fx | κ | | 27 | PEG$_2$-MAL | NH-5-N2,3DI (8) | * |
| 2.12.1.fx | κ | | 27 | PEG$_2$-MAL | 2Hi1,3 DIO (9) | * |
| 2.12.1.fx | κ | | 27 | PEG$_2$-MAL | 4NP (10) | * * |
| 2.12.1.fx | κ | | 27 | PEG$_2$-MAL | 2,6 DFP (11) | * * |
| 2.12.1.fx | κ | | 27 | PEG$_2$-MAL | NAP (12) | — |
| 2.12.1.fx | κ | | 27 | PEG$_2$-MAL | 1HP 2,5D (13) | * |
| 2.12.1.fx | κ | | 27 | PEG$_2$-MAL | 2,3,5,6 TFP (14) | * * |
| 2.12.1.fx | κ | | 27 | PEG$_2$-MAL | 2,4,6 TFP (15) | * * |
| 2.12.1.fx | κ | | 27 | PEG$_2$-MAL | Squarate | * |
| 2.12.1.fx | κ | | 27 | PEG$_2$-MAL | AZD | * |
| 2.12.1.fx | κ | | 27 | PEG$_{2-17}$ | PFP | * * * |
| 2.12.1.fx | κ | | 27 | PEG$_{17-21}$ | PFP | * * |
| 2.12.1.fx | κ | | 27 | PEG$_{25}$ | PFP | * * |

Example 24 Examination of CLκ-D$^{77}$

Residues geographically close to the CLκ-K$^{80}$ in the 3-D structure were examined. Initial Crystal structure analysis suggested the possibility that CLκ-D$^{77}$ could form a salt bridge with CLκ-K$^{80}$, which could have an impact on the CLκ-K$^{80}$ directional conjugation. In order to study the effect of CLκ-D$^{77}$ on conjugation to CLκ-K$^{80}$, CLκ-D$^{77}$ was mutated to CLκ-A$^{77}$ on the 2.12.1.fx antibody to create 2.12.1.fx-[CLκ-D$^{77}$A] (CLκ of SEQ ID NO:37). The CLκ-D$^{77}$A mutation was generated on an antibody light chain following protocols described in QuickChange site-directed mutagenesis kit (Stratagene®). The mutation was introduced by oligonucleotide primers and confirmed by DNA sequencing. 2.12.1.fx-[CLκ-D$^{77}$A] was transiently expressed in HEK 293 cells, and purified using Protein A affinity column. The purified mAbs were characterized using MS.

2.12.1.fx and 2.12.1.fx-[CLκ-D$^{77}$A] (1 mg reaction size) were adjusted to 18 mg/ml to pH 7.7 with a phosphate buffer to a final concentration of 0.06M sodium phosphate. The exemplary test peptide-linker pair [PFP-PEG$_5$-K$^{11}$-SEQ:27] was reconstituted in a propylene glycol solution to 10 mg/ml. [PFP-PEG$_5$-K$^{11}$-SEQ:27] was added to antibody at a molar ratio of 4.3:1 and allowed to react for 2 hrs at RT. The conjugated product was diluted to 2 mg/ml and analyzed as an intact conjugated protein by SEC-MS to determine the number and quantitation of conjugate forms of the protein. Relative quantitation of multiple peptide-linker conjugation species was performed by measuring the signal magnitude.

Table 50 compares the conjugation profile of [2.12.1.fx]-[PEG$_5$-K$^{11}$-SEQ:27] and [2.12.1.fx-[CLκ-D$^{77}$A]-[PEG$_5$-K$^{11}$-SEQ:27]. The conjugation profile of [2.12.1.fx]-[PEG$_5$-K$^{11}$-SEQ:27] occurs as a distribution between 0-4 peptide additions with the largest form being 2 peptide additions and the average number of peptide additions is 2.16. The profile changes when the residue CLκ-D$^{77}$ is mutated to CLκ-A$^{77}$ in the scaffold protein; the average number of peptide additions rises to 2.38 and significantly less single peptide addition is observed. This result suggests that the single point mutation CLκ-D$^{77}$A has the effect of increasing the overall conjugation to the scaffold. In both conditions replicate analysis (n=3) demonstrates that the conjugations profiles observed are reproducible.

The extent of peptide conjugation was examined separately on the light and heavy chains of 2.12.1.fx and 2.12.1.fx-[CLκ-D$^{77}$A]. The produced MACs were denatured and disulfide bonds were reduced using guanidine hydrochloride and dithiothreitol. The resulting free light and heavy chains were analyzed using LCMS to determine the conjugation profile on each. Table 50 demonstrates that the average conjugation is higher on the light chain of 2.12.1.fx-[CLκ-D$^{77}$A] than 2.12.1.fx; the average conjugate addition value for 2.12.1.fx-[CLκ-D$^{77}$A] is 1.15 compared to 0.85 for 2.12.1.fx. In addition, unconjugated light chain is undetected in 2.12.1.fx-[CLκ-D$^{77}$A]. Conjugation on the heavy chain is observed at a significantly lower level. The majority of observed heavy chain for both 2.12.1.fx and 2.12.1.fx-[CLκ-D$^{77}$A] is unconjugated; this is especially true in the case of 2.12.1.fx-[CLκ-D$^{77}$A] heavy chain. These results suggest that the CLκ-D$^{77}$A mutation alters the light chain to make it significantly more susceptible to conjugation. Replicate analysis of this experiment by multiple scientists is shown in Table 50 which demonstrates that the profile of conjugation is consistent and reproducible.

technique. Detected fragments that were observed with a [PEG$_5$-K$^{11}$-SEQ:27] modifier are considered potential sites of peptide conjugation.

2 [PEG$_5$-K$^{11}$-SEQ:27]-conjugated fragments were detected using LCMS peptide mapping of the 2.12.1.fx-[CLκ-D$^{77}$A]-[PEG$_5$-K$^{11}$-SEQ:27] product. Both of these conjugated fragments were present on the light chain of the 2.12.1.fx-[CLκ-D$^{77}$A] antibody. In comparison, 8 fragments conjugated to [PEG$_5$-K$^{11}$-SEQ:27] were detected in 2.12.1.fx-[PEG$_5$-K$^{11}$-SEQ:27].

Overall, these results suggest that conjugation levels in the CLκ-D$^{77}$A mutant are elevated at fewer conjugation sites, possibly suggesting increased conjugation specificity relative to the unmutated antibody. Further, structural analysis has shown that the CLκ-D$^{77}$ residue is in close proximity (<10 Ås) to the identified major conjugation site CLκ-K$^{80}$. It was speculated that an electrostatic interaction, possibly a salt bridge, could exist between the carboxylic acid of CLκ-D$^{77}$ and the primary amine of CLκ-K$^{80}$. The CLκ-D$^{77}$A mutation would disrupt such an electrostatic interaction, resulting in the reactive amine on CLκ-K$^{80}$ being more exposed and susceptible to conjugation with the reactive esters of the invention. Although subsequent analysis coupled with sophisticated modeling helped build a more complete picture of the reaction site, and indicated that CLκ-D$^{77}$ exerted its effect primarily through its interaction with CLκ-H$^{81}$, the initial hypothesis of an interaction between CLκ-D$^{77}$ and CLκ-K$^{80}$ was helpful in underlining the significance of the CLκ-D$^{77}$ residue.

The observed conjugation sites in the 2.12.1.fx-[CLκ-D$^{77}$A]-[PEG$_5$-K$^{11}$-SEQ:27] product are light chain chymotrypsin fragments Y3 and Y15. Analysis of the signal intensities for these fragments suggests that fragment Y15, which carries the CLκ-K$^{80}$ residue, is the primary conjugation site. Fragment Y15 is only observed as an [PEG$_5$-K$^{11}$-SEQ:27]-modified fragment at a very high signal intensity (1118572 counts, Table 52), whilst the unmodified form of Y15 is not observed, suggesting that all or nearly all of fragment Y15 exists in the modified form. Fragment Y3 is observed in both the [PEG$_5$-K$^{11}$-SEQ:27]-modified and unmodified forms; unmodified Y3 signal intensities in 2.12.1.fx-[PEG$_5$-K$^{11}$-SEQ:27] and 2.12.1.fx-[CLκ-D$^{77}$A]-

TABLE 50

Analysis of conjugation of [PEG$_5$-K$^{11}$-SEQ: 27] to Abs 2.12.1.fx (WT) and 2.12.1.fx-[CLK-D77A]. Rep = replicate. AvReps is the average of the results of the three replicate experiments, with the standard deviation shown beneath (StdDev). Ab % CA shows % conjugations additions per antibody, followed by the average CA per antibody. Reduced light and heavy chain analysis also shown, with respective average CA per chain. CLκ-D$^{77}$A shows 123% rate of LC % 1CA species compared to native CLκ.

| Ab | Ab % CA | | | | | Avg. CA | LC % CA | | | Avg. CA | HC % CA | | Avg. CA |
|---|---|---|---|---|---|---|---|---|---|---|---|---|---|
| | 0 | 1 | 2 | 3 | 4 | | 0 | 1 | 2 | | 0 | 1 | |
| WT | | | | | | | | | | | | | |
| Rep1 | 1 | 17 | 56 | 22 | 4 | 2.11 | 21 | 72 | 7 | 0.86 | 86 | 14 | 0.14 |
| Rep2 | 2 | 14 | 54 | 25 | 5 | 2.18 | 25 | 67 | 8 | 0.83 | 85 | 15 | 0.15 |
| Rep3 | 2 | 13 | 55 | 25 | 6 | 2.2 | 23 | 69 | 8 | 0.85 | 85 | 15 | 0.15 |
| Av.Rep | 2 | 15 | 55 | 24 | 5 | 2.16 | 23 | 69 | 8 | 0.85 | 85 | 15 | 0.15 |
| StdDev | 1 | 2 | 1 | 2 | 1 | 0.05 | 2 | 3 | 1 | 0.02 | 1 | 1 | 0.01 |
| D$^{77}$A | | | | | | | | | | | | | |
| Rep1 | 5 | 4 | 54 | 30 | 8 | 2.32 | 0 | 84 | 16 | 1.16 | 94 | 6 | 0.06 |
| Rep2 | 6 | 4 | 43 | 36 | 12 | 2.44 | 0 | 85 | 15 | 1.15 | 94 | 6 | 0.06 |
| Rep3 | 3 | 3 | 56 | 31 | 7 | 2.37 | 0 | 86 | 14 | 1.14 | 94 | 6 | 0.06 |
| AvRep | 5 | 4 | 51 | 32 | 9 | 2.38 | 0 | 85 | 15 | 1.15 | 94 | 6 | 0.06 |
| StdDev | 2 | 1 | 7 | 3 | 3 | 0.06 | 0 | 1 | 1 | 0.01 | 0 | 0 | 0.00 |

Example 25 Peptide Mapping Characterization of 2.12.1.Fx-[CLκ-D$^{77}$A]-[SEQ:27-K$^{11}$-PEG5] Heavy and Light Chain Reference Product 2.12.1.fx-[CLκ-D$^{77}$A]-[PEG$_5$-K$^{11}$-SEQ:27] conjugated antibody was reduced with dithiothreitol and cysteine residues were alkylated by carboxymethylation with iodoacetamide. Chymotrypsin was used for proteolytic digestion. Digested fragments in solution were analyzed using LCMS. Individual fragments were separated over a C18 HPLC column and their accurate mass was measured in a Q-Tof mass spectrometer. The resulting fragment mass was used to identify unmodified fragments or fragments modified with a [PEG$_5$-K$^{11}$-SEQ:27] conjugation group. This experiment was interpreted by focusing on chymotryptic fragments that contain a lysine residue and are therefore possible sites for peptide conjugation. Tables 51 and 52 list of all such fragments on the heavy chain and light chains respectively. Blank entries are fragments that were not detected using this

[PEG$_5$-K$^{11}$-SEQ:27] are within 15%. [PEG$_5$-K$^{11}$-SEQ:27]-modified Y3 is observed at a relatively low level (9737 counts, Table 52).

The table entries for Tables 51 and 52 are explained below:

Fragment number: Chymotrypsin fragments numbering from the N-terminus; joined fragments (ie—Y1-2) indicate a missed cleavage site.

Start/End: Numbering of the fragment location from the N-terminus.

Fragment Mass (Da): Theoretical mass of the fragment listed in Daltons.

Retention Time (Control/Analyte): Time of chromatographic retention/elution in the LCMS peptide mapping experiment.

MS Signal Intensity (Control/Analyte): Magnitude of observed signal observed by MS.

Mass Error-ppm (Control/Analyte): Comparison of theoretical vs. observed mass of the peptide fragment; values closer to zero (0) demonstrate better mass accuracy. The control protein for Retention Time, MS signal intensity and Mass Error is 2.12.1.fx-[CLκ-D$^{77}$A] and the analyte protein in each case is 2.12.1.fx-[CLκ-D$^{77}$A]+[PEG$_5$-K$^{11}$-SEQ:27].

Modifiers: Potential covalent additions to the fragment; [PEG$_5$-K$^{11}$-SEQ:27]-antibody binding peptide of Lysine residue, CAM-carboxymethylation of Cysteine residue.

TABLE 51

Peptide mapping characterization of 2.12.1.fx-[CLκ-D$^{77}$A]-[PEG$_5$-K$^{11}$-SEQ: 27] heavy chain referenceproduct.

| Fragment Number | Start | End | Fragment Mass (Da) | Retention Time Control | Retention Time Analyte | MS Signal Intensity Control | MS Signal Intensity Analyte | Mass Error (ppm) Control | Mass Error (ppm) Analyte | Modifiers |
|---|---|---|---|---|---|---|---|---|---|---|
| Y1 | 1 | 27 | 2617.3533 | | | | | | | |
| Y1-2 | 1 | 29 | 2865.4695 | | | | | | | |
| Y5-6 | 34 | 47 | 1657.8398 | | | | | | | |
| Y6 | 37 | 47 | 1253.688 | 19.2 | 19.2 | 516640 | 548267 | 1.9 | 0 | |
| Y6-7 | 37 | 50 | 1602.8518 | 22.1 | 22.1 | 26537 | 31229 | −1.6 | −2 | |
| Y8-9 | 51 | 68 | 1931.9337 | 16.5 | 16.5 | 60894 | 82459 | −2.2 | 0.5 | |
| Y9 | 61 | 68 | 878.461 | 11.3 | 11.4 | 376224 | 403402 | 0 | −0.3 | |
| Y9-10 | 61 | 80 | 2241.1501 | | | | | | | |
| Y10 | 69 | 80 | 1380.6997 | 13.3 | 13.3 | 261813 | 286406 | −1.1 | 0.3 | |
| Y10-011 | 69 | 94 | 2972.4661 | | | | | | | |
| Y19-20 | 111 | 157 | 4748.2773 | | | | | | | |
| Y20 | 116 | 157 | 4160.0405 | | | | | | | |
| Y20-21 | 116 | 166 | 5202.5527 | | | | | | | |
| Y20-21* | 116 | 166 | 5316.5957 | 34.1 | 34.1 | 6445 | 8275 | 0.5 | −5.7 | CAM(2) |
| Y24-25 | 202 | 245 | 4702.2109 | | | | | | | |
| Y25 | 207 | 245 | 4151.9722 | | | | | | | |
| Y25* | 207 | 245 | 4437.0796 | 20.9 | 20.9 | 1495322 | 1771622 | 1.1 | 0.7 | CAM(5) |
| Y25-26 | 207 | 279 | 7985.9092 | | | | | | | |
| Y26 | 246 | 279 | 3851.9478 | | | | | | | |
| Y26-27 | 246 | 281 | 4152.0698 | | | | | | | |
| Y28-29 | 282 | 300 | 2245.1128 | | | | | | | |
| Y29 | 283 | 300 | 2082.0493 | 14.6 | 14.6 | 20665 | 18618 | −0.6 | −0.2 | |
| Y29-30 | 283 | 304 | 2531.2405 | | | | | | | |
| Y31-32 | 305 | 323 | 2241.1907 | | | | | | | |
| Y32 | 318 | 323 | 722.3599 | 7.9 | 7.9 | 93966 | 81618 | 0.1 | 3 | |
| Y32 | 318 | 323 | 722.3599 | 17.7 | 18.4 | 37943 | 11371 | 11.4 | 27.1 | |
| Y32 | 318 | 323 | 722.3599 | 18.4 | | 11761 | | 23.8 | | |
| Y32-33 | 318 | 353 | 4028.188 | | | | | | | |
| Y33 | 324 | 353 | 3323.8386 | 20 | | 5422 | | 3.1 | | |
| Y33* | 324 | 353 | 3380.8601 | 19.7 | 19.7 | 2196329 | 2374835 | −2.5 | −3.8 | CAM(1) |
| Y33-34 | 324 | 376 | 5883.1577 | | | | | | | |
| Y34 | 354 | 376 | 2577.3293 | | | | | | | |
| Y34-35 | 354 | 385 | 3637.8159 | | | | | | | |
| Y34-35* | 354 | 385 | 3694.8374 | 33 | 33 | 10095 | 10026 | 1.9 | −2 | CAM(1) |
| Y36-37 | 386 | 408 | 2527.0808 | | | | | | | |
| Y37 | 396 | 408 | 1394.6388 | 19.6 | 19.6 | 62942 | 65871 | −0.9 | −1.6 | |
| Y37-38 | 396 | 409 | 1541.7072 | 25.1 | 25.1 | 827336 | 874876 | 0 | −3.8 | |
| Y39-40 | 410 | 421 | 1494.8195 | | | | | | | |
| Y40 | 412 | 421 | 1218.672 | 15.8 | 15.8 | 77917 | 78774 | −0.3 | 0.2 | |
| Y40-41 | 412 | 427 | 1891.9905 | 20.3 | 20.3 | 107513 | 150305 | 0.2 | 0.1 | |
| Y42-43 | 428 | 450 | 2525.1792 | | | | | | | |
| Y43 | 441 | 450 | 1016.5502 | | | | | | | |

TABLE 52

Peptide mapping characterization of 2.12.1.fx-[CLκ-D$^{77}$A]-[PEG$_5$-K$^{11}$-SEQ: 27] light chain reference product.

| Fragment Number | Start | End | Peptide Mass (Da) | Retention Time Control | Retention Time Analyte | MS Signal Intensity Control | MS Signal Intensity Analyte | Mass Error (ppm) Control | Mass Error (ppm) Analyte | Modifiers |
|---|---|---|---|---|---|---|---|---|---|---|
| Y2-3 | 36 | 49 | 1688.9725 | 16.2 | 16.2 | 145374 | 172582 | −1.7 | −1.1 | |
| Y3 | 37 | 49 | 1525.9093 | 15.5 | 15.5 | 331068 | 390175 | −2.7 | −2.4 | |
| Y3* | 37 | 49 | 3218.7593 | | 24 | | 9737 | | −6.8 | [SEQ: 27-K11-PEG5](1) |
| Y3-4 | 37 | 62 | 2882.6355 | | | | | | | |
| Y9-10 | 88 | 116 | 3244.729 | | | | | | | |
| Y10 | 99 | 116 | 1871.0992 | | | | | | | |
| Y10-11 | 99 | 139 | 4331.335 | | | | | | | |
| Y11 | 117 | 139 | 2478.2463 | | 22.8 | | 61217 | | −1.7 | |
| Y11* | 117 | 139 | 2535.2678 | | 21.5 | | 5127 | | −16.8 | CAM(1) |
| Y11-12 | 117 | 148 | 3635.8445 | | | | | | | |
| Y12 | 140 | 148 | 1175.6088 | | | | | | | |
| Y12-13 | 140 | 173 | 3886.8245 | | | | | | | |
| Y13 | 149 | 173 | 2729.2263 | 13.1 | 13.1 | 1140556 | 1153543 | −1.1 | −1.8 | |
| Y13-14 | 149 | 186 | 4051.9346 | | | | | | | |
| Y14 | 174 | 186 | 1340.7188 | | | | | | | |
| Y14-15 | 174 | 192 | 2125.1418 | | | | | | | |
| Y15 | 187 | 192 | 802.4337 | 7.5 | | 275639 | | −1.9 | | |
| Y15* | 187 | 192 | 2495.2837 | | 20.9 | | 1118572 | | −6.3 | [SEQ: 27-K11-PEG5](1) |
| Y15-16 | 187 | 209 | 2574.29 | | | | | | | |
| Y16 | 193 | 209 | 1789.8668 | 18.7 | | 5400 | | 4.4 | | |
| Y16* | 193 | 209 | 1846.8883 | 18.1 | 18.1 | 169490 | 246823 | −1.7 | −2.2 | CAM(1) |
| Y16-17 | 193 | 214 | 2349.0842 | 17.8 | | 9211 | | 0.1 | | |

Example 26 Examination of CLκ-D$^{77}$ Mutations

CLκ-D$^{77}$ residue of 2.12.1.fx antibody was mutated to each of the other 18 amino acids in addition to the CLκ-D$^{77}$A mutation. The CLκ-D$^{77}$G (SEQ ID NO:38), CLκ-D$^{77}$L (SEQ ID NO:40), CLκ-D$^{77}$S (SEQ ID NO:49), CLκ-D$^{77}$E (SEQ ID NO:53), and CLκ-D$^{77}$R (SEQ ID NO:54) and mutants were generated following protocols described in QuickChange site-directed mutagenesis kit (Stratagene®). Mutations were introduced by oligonucleotide primers and confirmed by DNA sequencing. The other 13 mutants on the CLκ-D$^{77}$ site (CLκ-D$^{77}$V (SEQ ID NO:39), CLκ-D$^{77}$I (SEQ ID NO:41), CLκ-D$^{77}$P (SEQ ID NO:42), CLκ-D$^{77}$F (SEQ ID NO:43), CLκ-D$^{77}$W (SEQ ID NO:44), CLκ-D$^{77}$Y (SEQ ID NO:45), CLκ-D$^{77}$H (SEQ ID NO:46), CLκ-D$^{77}$M (SEQ ID NO:47), CLκ-D$^{77}$C (SEQ ID NO:48), CLκ-D$^{77}$T (SEQ ID NO:50), CLκ-D$^{77}$Q (SEQ ID NO:51), CLκ-D$^{77}$N (SEQ ID NO:52), CLκ-D$^{77}$K (SEQ ID NO:55)) were generated following protocols described in Quick PCR Cloning Kit (BPS Bioscience). Mutations were introduced by oligonucleotide primers and cloned to a modified p2.12.1.fxP4 vector (Invitrogen) cut with BglII and NheI. Insert DNA were confirmed by DNA sequencing. The mutated mAbs were transiently expressed in HEK 293 cells, and purified using protein A affinity column. The purified mAbs were characterized using MS.

2.12.1.fx and 2.12.1.fx mutants were adjusted 18 mg/ml to pH 7.7 with a phosphate buffer to a final concentration of 0.06 M sodium phosphate. [PFP-PEG$_5$-K$^{11}$-SEQ:27] was reconstituted in a propylene glycol solution to 10 mg/ml. The peptide/linker was added to antibody at a molar ratio of 4.3:1 and allowed to react for 2 hrs at RT.

Table 53 describes the overall conjugation profile of the CLκ-D$^{77}$ mutants. CLκ-D$^{77}$C aggregated due to an introduction of a free cysteine, and the results were not interpretable. Mutations CLκ-D$^{77}$W, CLκ-D$^{77}$M, CLκ-D$^{77}$H, CLκ-D$^{77}$Q, CLκ-D$^{77}$N, and CLκ-D$^{77}$V did not change the overall conjugation profile compared to wild-type 2.12.1.fx. Mutations CLκ-D$^{77}$F, CLκ-CLκ-D$^{77}$K, CLκ-D$^{77}$Y, and CLκ-D$^{77}$E decreased the overall level of conjugation. Mutations CLκ-D$^{77}$P, CLκ-D$^{77}$I, CLκ-D$^{77}$T, CLκ-D$^{77}$R, CLκ-D$^{77}$L, CLκ-D$^{77}$S, and CLκ-D$^{77}$G increased the level of conjugation.

Analysis of the reduced LC and HC showed that only the mutations CLκ-D$^{77}$F, CLκ-D$^{77}$K, CLκ-D$^{77}$Y, CLκ-D$^{77}$E, and CLκ-D$^{77}$C resulted in reduced levels of conjugation on the light chain. The levels of conjugation on the light chain increased (and conjugation on the heavy slightly decreased) for CLκ-D$^{77}$M, CLκ-D$^{77}$H, CLκ-D$^{77}$Q, CLκ-D$^{77}$N, CLκ-D$^{77}$W and CLκ-D$^{77}$V. Mutations CLκ-D$^{77}$P, CLκ-D$^{77}$I, CLκ-D$^{77}$T, CLκ-D$^{77}$R, CLκ-D$^{77}$L, CLκ-D$^{77}$S, and CLκ-D$^{77}$G increased the level of conjugation on the light chain by reducing the level of unconjugated light chain. CLκ-D$^{77}$K increased the level of 2 conjugates on the light chain due to the introduction of another lysine, a potential conjugation site.

TABLE 53

Conjugation analysis of CLκ-D$^{77}$ mutants to alternative amino acids (data is separated within the table according to the protein amount used during the conjugation reaction, or because the conjugation reaction was set up at a different time). The decreased level of conjugation for the tests run at 0.5 and 0.25 mg/ml was due to the low levels of the antibody. Ab % CA shows % conjugations additions per antibody, followed by the average CA per antibody. Reduced light and heavy chain analysis also shown, with respective average CA per chain. The % of 1-LC % relative to the respective WT run is shown in the right column: for example, D$^{77}$Q, 1-LC % value of 81 is 126% of the respective WT 1-LC % of 69 for that experimental run. All samples were tested with 1 mg Ab, except the run including D$^{77}$M, D$^{77}$F and D$^{77}$H (0.5 mg), and the run including D$^{77}$W and D$^{77}$C (0.25 mg).

| Ab | Ab % CA 0 | 1 | 2 | 3 | 4 | Avg. CA | LC % CA 0 | 1 | 2 | Avg. CA | HC % CA 0 | 1 | Avg. CA | 1LC WT % |
|---|---|---|---|---|---|---|---|---|---|---|---|---|---|---|
| WT | 1 | 16 | 54 | 24 | 4 | 2.14 | 19 | 69 | 13 | 0.94 | 88 | 12 | 0.12 | |
| D$^{77}$R | 6 | 12 | 41 | 26 | 15 | 2.33 | 8 | 87 | 5 | 0.96 | 94 | 6 | 0.06 | 126 |
| D$^{77}$L | 5 | 5 | 53 | 28 | 10 | 2.33 | 1 | 88 | 11 | 1.11 | 91 | 9 | 0.09 | 127 |
| D$^{77}$E | 8 | 27 | 39 | 18 | 8 | 1.90 | 32 | 57 | 10 | 0.78 | 84 | 16 | 0.78 | 82 |
| D$^{77}$S | 5 | 6 | 47 | 29 | 12 | 2.36 | 0 | 92 | 8 | 1.08 | 94 | 6 | 0.06 | 133 |
| D$^{77}$G | 7 | 7 | 44 | 28 | 13 | 2.34 | 0 | 91 | 9 | 1.09 | 92 | 8 | 0.08 | 131 |
| WT | 2 | 24 | 50 | 21 | 3 | 1.99 | 24 | 66 | 10 | 0.85 | 90 | 10 | 0.1 | |
| D$^{77}$Q | 2 | 10 | 78 | 10 | | 1.96 | 15 | 81 | 4 | 0.88 | 96 | 4 | 0.04 | 122 |
| D$^{77}$P | 3 | 4 | 63 | 24 | 7 | 2.26 | 5 | 88 | 7 | 1.02 | 96 | 4 | 0.04 | 133 |
| D$^{77}$K | 9 | 30 | 36 | 17 | 8 | 1.84 | 34 | 45 | 21 | 0.86 | 93 | 7 | 0.07 | 68 |
| D$^{77}$N | 3 | 8 | 79 | 11 | | 1.98 | 11 | 83 | 6 | 0.94 | 96 | 4 | 0.04 | 125 |
| D$^{77}$Y | 28 | 41 | 19 | 11 | | 1.14 | 54 | 42 | 4 | 0.51 | 89 | 11 | 0.11 | 63 |
| D$^{77}$V | 6 | 10 | 63 | 21 | | 1.98 | 13 | 79 | 9 | 0.96 | 95 | 5 | 0.05 | 119 |
| D$^{77}$I | 3 | 4 | 63 | 24 | 7 | 2.27 | 6 | 85 | 9 | 1.03 | 93 | 7 | 0.07 | 128 |
| D$^{77}$T | 3 | 11 | 59 | 18 | 9 | 2.17 | 8 | 88 | 4 | 0.97 | 95 | 5 | 0.05 | 133 |
| WT | 4 | 30 | 44 | 20 | 3 | 1.88 | 28 | 63 | 10 | 0.82 | 89 | 11 | 0.11 | |
| D$^{77}$M | 4 | 15 | 67 | 14 | | 1.90 | 16 | 81 | 3 | 0.87 | 96 | 4 | 0.04 | 132 |
| D$^{77}$F | 21 | 42 | 24 | 13 | | 1.29 | 54 | 42 | 4 | 0.49 | 86 | 14 | 0.14 | 66 |
| D$^{77}$H | 5 | 16 | 60 | 19 | | 1.92 | 16 | 75 | 9 | 0.93 | 94 | 6 | 0.06 | 119 |
| WT | 5 | 36 | 47 | 12 | | 1.66 | 30 | 60 | 10 | 0.8 | 90 | 10 | 0.1 | |
| D$^{77}$W | 8 | 29 | 46 | 18 | | 1.73 | 20 | 75 | 4 | 0.84 | 91 | 9 | 0.09 | 125 |
| D$^{77}$C | | | | | | | 60 | 37 | 2 | 0.42 | 95 | 5 | 0.05 | 61 |

Example 27 Effects of Other Mutations to the CHκ Region on Conjugation

In addition to CLκ-D$^{77}$A, other residues within 10A distance to CLκ-K$^{80}$ were mutated to alanine: CLκ-K$^{41}$A (SEQ ID NO:20), V$^{42}$A (SEQ ID NO:21), CLκ-D$^{43}$A (SEQ ID NO:56), CLκ-N$^{44}$A (SEQ ID NO:22), CLκ-L$^{48}$A (SEQ ID NO:23), CLκ-Q$^{47}$A (SEQ ID NO:24), CLκ-S$^{48}$A (SEQ ID NO:25), CLκ-N$^{80}$A (SEQ ID NO:26), CLκ-L$^{73}$A (SEQ ID NO:28), CLκ-S$^{74}$A (SEQ ID NO:29), CLκ-K$^{75}$A (SEQ ID NO:30), CLκ-Y$^{78}$A (SEQ ID NO:31), CLκ-E$^{79}$A (SEQ ID NO:32), CLκ-H$^{81}$A (SEQ ID NO:33), CLκ-V$^{83}$A (SEQ ID NO:34), CLκ-Y$^{84}$A (SEQ ID NO:35), and CLκ-R$^{103}$A (SEQ ID NO:36) were also mutated to Ala. The data of CLκ-D$^{43}$A and CLκ-H$^{81}$A are discussed in Example 14.

The L$^{73}$A mutant was introduced to 2.12.1.fx CLκ using the three way ligation method. A primer specific to the 5' end of 2.12.1.fx-LC (2.12.1.fx.LC.FOR: SEQ ID NO:85) and a reverse primer containing the desired L$^{73}$A mutation (L181A.REV: SEQ ID NO:88) were used to PCR the first half of the 2.12.1.fx-LC using 2.12.1.fx-LC DNA as the PCR template. This PCR fragment was then digested using restriction enzymes BglII and BsaI. A forward primer containing CLκ-L$^{73}$A mutation (L181A.FOR: SEQ ID NO:87) paired with the reverse primer specific to the 3' end of 2.12.1.fx-LC (2.12.1.fx.LC.REV: SEQ ID NO:86) were used to PCR amplify the second half of 2.12.1.fx-LC DNA fragments carrying mutation using 2.12.1.fx-LC DNA as the PCR template. This PCR fragment was then digested using restriction enzymes BsaI and NheI. The two restriction enzyme digested PCR fragments were ligated with a modified p2.12.1.fxP4 plasmid (Invitrogen®) cut with BglII and NheI. The insert sequence was confirmed by DNA sequencing. 2.12.1.fx-[CLκ-L$^{73}$A] (i.e. comprising SEQ ID NO:28) was transiently expressed in HEK 293 cells, and purified using protein A affinity column. The purified mAbs were characterized using MS.

The CLκ-V$^{42}$A and CLκ-K$^{75}$A mutants were generated by overlap PCR. Mutations were introduced by oligonucleotide primers. Primer specific to the 5' end of 2.12.1.fx-LC (2.12.1.fx.LC.FOR) paired a reverse primer carrying the desired mutation, and a forward primer carrying the desired mutation paired with the reverse primer specific to the 3' end of 2.12.1.fx light chain (2.12.1.fx.LC.FOR) were used to PCR amplify 2.12.1.fx-LC DNA fragments using 2.12.1.fx-LC as template. These two PCR products were mixed as templates; 2.12.1.fx-LC forward primer and reverse primer were used in overlap PCR reaction to amplify the full length 2.12.1.fx-LC DNA with desired mutation. The PCR was then digested with restriction enzyme BglII and NheI. The digested PCR was ligated with a modified p2.12.1.fxP4 plasmid (Invitrogen®) cut with BglII and NheI. The insert sequence was confirmed by DNA sequencing. The mutated mAbs were transiently expressed in HEK 293 cells, and purified using protein A affinity column. The purified mAbs were characterized using MS.

The other mutants were generated on 2.12.1.fx-LC following protocols described in QuickChange site-directed mutagenesis kit (Stratagene®). Mutations were introduced by oligonucleotide primers and confirmed by DNA sequencing. The mutated mAbs were transiently expressed in HEK 293 cells, and purified using protein A affinity column. The purified mAbs were characterized using MS.

2.12.1.fx and 2.12.1.fx mutants (1 mg reaction size) were adjusted 18 mg/ml to pH 7.7 with a phosphate buffer to a final concentration of 0.06 M sodium phosphate. [PFP-PEG$_5$-K$^{11}$-SEQ:27] was reconstituted in a propylene glycol solution to 10 mg/ml. The peptide/linker was added to the antibody at a molar ratio of 4.3:1 and allowed to react for 2 hrs at room temperature.

Table 54 compares the conjugation profile of 2.12.1.fx-[PEG$_5$-K$^{11}$-SEQ:27] with 2.12.1.fx-[CLκ-mutants]-[PEG$_5$-K$^{11}$-SEQ:27]. The conjugation profile of 2.12.1.fx-[PEG$_5$-K$^{11}$-SEQ:27] occurs as a distribution between 0-4 peptide additions with the largest form being 2 peptide additions. The profile changes when the residues are mutated to Ala in the scaffold protein; the average number of [PEG$_5$-K$^{11}$-SEQ:27] additions either decreased (CLκ-V$^{42}$A, CLκ-L$^{46}$A, CLκ-S$^{74}$A, CLκ-Y$^{78}$A and CLκ-Y$^{84}$A) or increased (CLκ-Q$^{47}$A, CLκ-N$^{50}$A and CLκ-D$^{77}$A/E$^{79}$A double mutants) compared to their corresponding 2.12.1.fx-[PEG$_5$-K$^{11}$-SEQ:27] controls. When comparing the conjugation profile of CLκ-D$^{77}$A/E$^{79}$A with CLκ-E$^{79}$A, the significant increase of average [PEG$_5$-K$^{11}$-SEQ:27] additions to the antibody is mainly contributed by the CLκ-D$^{77}$A mutation.

The extent of [PEG$_5$-K$^{11}$-SEQ:27] conjugation was examined separately on the light and heavy chains of 2.12.1.fx and 2.12.1.fx-[CLκ-mutants]. The MACs were denatured and disulfide bonds were reduced using guanidine hydrochloride and dithiothreitol. The resulting free light and heavy chains were analyzed using LCMS to determine the conjugation profile on each. Table 54 demonstrates that the 1CA on the light chain of 2.12.1.fx-[CLκ-Q$^{47}$A] and -[CLκ-N$^{50}$A] are higher than 2.12.1.fx. The average CAs are 0.84 and 0.85 compared to 0.78 of the 2.12.1.fx antibody. Both CLκ-Q$^{47}$A and CLκ-N$^{80}$A mutants have over 70% 1CA compared to the 59% 1CA of the 2.12.1.fx wild type antibody. In addition, the unconjugated light chain levels of these two mutants were reduced from 31% of the wild type antibody to 22% and 19%. The V$^{42}$A had reduced level of light chain conjugation. The average light chain CA is 0.45 with 59% unconjugated light chain and 37% 1CA. The % of 1-LC % relative to the respective WT run is shown in the right column, as described in Table 54.

Conjugation of CLκ-V$^{42}$A, CLκ-Q$^{47}$A and CLκ-N$^{80}$A to [PEG$_5$-K$^{11}$-SEQ:27] were repeated, and the results are shown at the bottom of the table. The elevated levels of light chain conjugation in CLκ-Q$^{47}$A and CLκ-N$^{80}$A and reduced light chain conjugation in CLκ-V$^{42}$A were confirmed by both intact and reduced LC-MS analysis. Overall, the conjugation data suggests that CLκ-V$^{42}$, CLκ-D$^{43}$ and CLκ-H$^{81}$ all have an impact on for PFP directional conjugation at CLκ-K$^{80}$.

TABLE 54

Conjugation analysis of 2.12.1.fx variants conjugated to [SEQ: 27-K$^{11}$-PEG5], showing amino acid mutants within10 Ås of light chain K$^{80}$. Ab % CA shows % conjugations additions per antibody, followed by the average CA per antibody. Reduced light and heavy chain analysis also shown, with respective average CA per chain. The % of 1-LC % relative to the respective WT run is shown in the right column, as described in Table 53.

| Ab | AB % CA | | | | | Avg. CA | LC % CA | | | Avg. CA | HC % CA | | Avg. CA | 1LC WT % |
|---|---|---|---|---|---|---|---|---|---|---|---|---|---|---|
|  | 0 | 1 | 2 | 3 | 4 |  | 0 | 1 | 2 |  | 0 | 1 |  |  |
| WT | 5 | 40 | 43 | 10 | 2 | 1.63 | 31 | 59 | 9 | 0.78 | 90 | 10 | 0.1 |  |
| K$^{41}$A | 6 | 32 | 49 | 10 | 2 | 1.70 | 28 | 65 | 7 | 0.78 | 90 | 10 | 0.1 | 110 |
| V$^{42}$A | 26 | 45 | 21 | 8 |  | 1.11 | 59 | 37 | 4 | 0.45 | 90 | 10 | 0.1 | 63 |
| N$^{44}$A | 9 | 37 | 40 | 10 | 4 | 1.6 | 31 | 63 | 6 | 0.75 | 93 | 7 | 0.07 | 107 |
| L$^{46}$A | 14 | 42 | 35 | 9 |  | 1.4 | 35 | 62 | 3 | 0.68 | 95 | 5 | 0.05 | 105 |
| Q$^{47}$A | 6 | 27 | 53 | 9 | 4 | 1.78 | 22 | 73 | 5 | 0.84 | 95 | 5 | 0.05 | 124 |
| S$^{48}$A | 6 | 34 | 46 | 9 | 4 | 1.72 | 34 | 59 | 7 | 0.73 | 93 | 7 | 0.07 | 100 |
| N$^{50}$A | 4 | 23 | 56 | 13 | 4 | 1.89 | 19 | 76 | 4 | 0.85 | 95 | 5 | 0.05 | 129 |
| L$^{73}$A | 12 | 36 | 33 | 13 | 7 | 1.69 | 41 | 55 | 3 | 0.62 | 87 | 13 | 0.13 | 93 |
| S$^{74}$A | 11 | 42 | 39 | 7 |  | 1.43 | 35 | 61 | 5 | 0.7 | 96 | 4 | 0.04 | 103 |
| K$^{75}$A | 12 | 38 | 41 | 9 |  | 1.48 | 35 | 62 | 3 | 0.68 | 93 | 7 | 0.07 | 105 |
| D$^{77}$A-E$^{79}$A | 3 | 7 | 71 | 15 | 4 | 2.1 | 5 | 87 | 8 | 1.04 | 95 | 5 | 0.05 | 147 |
| V$^{83}$A- | 9 | 35 | 39 | 11 | 6 | 1.7 | 33 | 61 | 6 | 0.73 | 86 | 14 | 0.14 | 103 |
| WT | 2 | 23 | 49 | 22 | 4 | 2.03 | 34 | 60 | 5 | 0.71 | 81 | 19 | 0 |  |
| E$^{79}$A | 6 | 13 | 51 | 24 | 6 | 2.12 | 21 | 73 | 6 | 0.86 | 85 | 15 | 0 | 122 |
| R$^{103}$A | 4 | 18 | 51 | 20 | 6 | 2.06 | 23 | 70 | 7 | 0.83 | 82 | 18 | 0 | 117 |
| WT | 1 | 17 | 51 | 25 | 5 | 2.16 | 14 | 77 | 9 | 0.96 | 84 | 16 | 0.16 |  |
| D$^{77}$A | 4 | 6 | 60 | 23 | 7 | 2.23 | 0 | 86 | 13 | 1.13 | 92 | 8 | 0.08 | 112 |
| V$^{42}$A | 13 | 28 | 29 | 21 | 9 | 1.86 | 49 | 42 | 9 | 0.61 | 86 | 14 | 0.14 | 55 |
| Q$^{47}$A | 6 | 7 | 58 | 21 | 9 | 2.2 | 8 | 85 | 7 | 0.99 | 91 | 9 | 0.09 | 110 |
| N$^{50}$A | 7 | 8 | 51 | 25 | 9 | 2.2 | 10 | 81 | 9 | 0.99 | 90 | 10 | 0.1 | 105 |

Example 28 Analysis of CLκ-D$^{43}$A and CLκ-H$^{81}$A Mutants

In order to determine whether the charge, hydrogen bond or the size of CLκ-D$^{43}$ are important to the CLκ-K$^{80}$ directional conjugation, CLκ-D$^{43}$ was mutated to CLκ-D$^{43}$A (SEQ ID NO:107), CLκ-D$^{43}$E (SEQ ID NO:108) and CLκ-D$^{43}$L (SEQ ID NO:109) respectively. The mutants were generated on 2.12.1.fx antibody light chain following protocols described in QuickChange site-directed mutagenesis kit (Stratagene®). Mutations were introduced by oligonucleotide primers and confirmed by DNA sequencing. The mutated mAbs were transiently expressed in HEK 293 cells, and purified using protein A affinity column. The purified mAbs were characterized using MS.

Similarly, in order to assess the role of CLκ-H$^{81}$, the following mutant versions of the test antibody 2.12.1.fx were assessed: CLκ-H$^{81}$N (SEQ ID NO:110), CLκ-H$^{81}$Q (SEQ ID NO:111), CLκ-H$^{81}$Y (SEQ ID NO:112), CLκ-H$^{81}$W (SEQ ID NO:113) and CLκ-H$^{81}$F (SEQ ID NO:114).

2.12.1.fx antibody and 2.12.1.fx-[CLκ-mutant]antibodies (1 mg reaction size) were adjusted 18 mg/ml to pH 7.7 with a phosphate buffer to a final concentration of 0.06 M sodium phosphate. [PFP-PEG$_5$-K$^{11}$-SEQ:27] was reconstituted in a propylene glycol solution to 10 mg/ml. The peptide/linker was added to antibody at a molar ratio of 4.3:1 and allowed to react for 2 hrs at RT.

CLκ-D$^{43}$N has the similar overall conjugation and light chain levels (Table 55) compared to the wild type antibody. CLκ-D$^{43}$E and CLκ-D$^{43}$L showed reduced overall conjugation level light chain conjugation level.

CLκ-H$^{81}$N, CLκ-H$^{81}$Q, CLκ-H$^{81}$Y, CLκ-H$^{81}$W and CLκ-H$^{81}$F mutants showed reduced overall conjugation level light chain conjugation level, suggesting that the imidazole ring is required for the PFP directional conjugation. The conjugation reaction does not involve the 7-stacking interaction nor the H-bonds formed with Nε2 or Nδ11 of the imidazole ring.

Example 29 2.12.1.Fx-[CLκ-D″A] Conjugation Using Different Reactive Esters 2.12.1.fx and 2.12.1.fx-[CLκ-D$^{77}$A] were conjugated to [PEG$_5$-K$^{11}$-SEQ:27] using different reactive esters (see Examples 18 and 19) (results shown in Table 56). For all of the different activated esters, the 2.12.1.fx-[CLκ-D$^{77}$A] mutant gave a higher level of intact average CA upon conjugation compared to the wt 2.12.1.fx. Another clear trend was that the level of 0 and 1 CA in the wild type 2.12.1.fx was markedly decreased in the 2.12.1.fx-[CLκ-D$^{77}$A] mutant for each of the activated esters, and that the level of 2 CA was increased in each case for most activated esters, except for Z9.

The results of the reduced LC/HC analyses showed a further obvious trend comparing the 2.12.1.fx and 2.12.1.fx-[CLκ-D$^{77}$A] conjugation results. In each case, the degree of underivatized LC decreased, substantially in some cases. This was accompanied by a concomitant increase in the level of 1 CA on the LC, again for each different active ester, so that overall the average amount of derivatization on the LC increased. The general trend for the LC was that the amount of 1CA increased by the amount that OCA decreased, as the amount of 2CA present in each case was essentially unchanged.

In considering the HC, another trend was apparent in that the already low amount of 1CA derivatization for each active ester was further decreased. The outlier in this trend was Z9, the only non-phenolic ester. This ester shows little of the directional conjugation effect towards CLκ-K$^{80}$ compared to the other phenolic esters and the levels of both LC and HC derivatization are similar, with only a minor improvement in directionality imparted by the 2.12.1.fx-[CLκ-D$^{77}$A] mutant. Overall, the 2.12.1.fx-[CLκ-D$^{77}$A] mutant provides clear evidence of improved directional LC conjugation compared to native 2.12.1.fx fora range of activated esters

TABLE 55

2.12.1.fx variants conjugated to [PEG$_5$-K$^{11}$-SEQ: 27]

(WT is 2.12.1.1fx). Ab % CA shows % conjugations additions per antibody, followed by the average CA per antibody. Reduced light and heavy chain analysis also shown, with respective average CA per chain. The % of 1-LC % relative to the respective WT run is shown in the right column, as described in Table 53.

| | Ab % CA | | | | | Avg | LC % CA | | | Avg | HC % CA | | | Avg | 1LC |
|---|---|---|---|---|---|---|---|---|---|---|---|---|---|---|---|
| Ab | 0 | 1 | 2 | 3 | 4 | CA | 0 | 1 | 2 | CA | 0 | 1 | 2 | CA | WT % |
| WT | 2 | 23 | 49 | 22 | 4 | 2.03 | 34 | 60 | 5 | 0.71 | 81 | 19 | 0 | 0.19 | |
| D$^{43}$N | 7 | 24 | 39 | 21 | 8 | 2.00 | 34 | 59 | 7 | 0.73 | 84 | 16 | 0 | 0.16 | 98 |
| D$^{43}$L | 14 | 33 | 34 | 19 | 0 | 1.57 | 55 | 40 | 5 | 0.50 | 74 | 26 | 0 | 0.26 | 67 |
| D$^{43}$E | 9 | 33 | 37 | 17 | 4 | 1.75 | 44 | 48 | 8 | 0.63 | 74 | 26 | 4 | 0.34 | 80 |
| H$^{81}$N | 32 | 41 | 20 | 7 | 0 | 1.04 | 84 | 16 | 0 | 0.16 | 70 | 26 | 5 | 0.35 | 27 |
| H$^{81}$Q | 29 | 40 | 21 | 11 | 0 | 1.14 | 82 | 17 | 1 | 0.19 | 73 | 27 | 0 | 0.27 | 28 |
| H$^{81}$Y | 27 | 40 | 24 | 8 | 0 | 1.14 | 80 | 20 | 0 | 0.20 | 70 | 26 | 4 | 0.35 | 33 |
| H$^{81}$W | 29 | 45 | 19 | 8 | 0 | 1.05 | 85 | 15 | 0 | 0.15 | 69 | 26 | 5 | 0.36 | 25 |
| H$^{81}$F | 13 | 41 | 30 | 15 | 0 | 1.48 | 79 | 21 | 0 | 0.21 | 70 | 30 | 0 | 0.30 | 35 |

TABLE 56

Analysis of 2.12.1.fx.-[CLκ-D$^{77}$A] conjugation to [PEG$_5$-K$^{11}$-SEQ: 27] using different reactive esters (see Examples 26 and 27). Ab % CA shows the overall % of conjugation additions per antibody, with reduced light chain and heavy chain analysis also shown (LC % CAN, HC % CA). and Δ indicates the difference between the WT and D$^{185}$A mutant results for Ab % CA. The % of 1-LC % relative to the respective WT run is shown in the right column, as described in Table 53.

| Z# | Ab | Ab % CA | | | | | Avg CA | Δ | LC % | | | Avg. CA | | | | Avg. CA | 1LC WT % |
|---|---|---|---|---|---|---|---|---|---|---|---|---|---|---|---|---|---|
| | | 0 | 1 | 2 | 3 | 4 | | | 0 | 1 | 2 | | 0 | 1 | 2 | | |
| 1 | WT | 1 | 17 | 51 | 25 | 5 | 2.16 | 0.07 | 14 | 77 | 9 | 0.96 | 84 | 16 | | 0.16 | |
| | D$^{77}$A | 4 | 6 | 60 | 23 | 7 | 2.23 | | 0 | 86 | 13 | 1.13 | 92 | 8 | | 0.08 | 112 |
| 2 | WT | 15 | 43 | 33 | 9 | | 1.36 | 0.72 | 49 | 49 | 3 | 0.54 | 84 | 16 | | 0.16 | |
| | D$^{77}$A | 7 | 14 | 53 | 19 | 8 | 2.09 | | 16 | 81 | 3 | 0.87 | 90 | 10 | | 0.1 | 33 |
| 10 | WT | 23 | 44 | 26 | 7 | | 1.18 | 0.73 | 60 | 38 | 2 | 0.42 | 81 | 19 | | 0.19 | |
| | D$^{77}$A | 6 | 27 | 43 | 18 | 6 | 1.91 | | 29 | 67 | 4 | 0.74 | 89 | 11 | | 0.11 | 176 |
| 3 | WT | 7 | 32 | 39 | 18 | 5 | 1.82 | 0.43 | 44 | 48 | 7 | 0.63 | 79 | 21 | | 0.21 | |
| | D$^{77}$A | 6 | 11 | 46 | 25 | 12 | 2.25 | | 12 | 79 | 9 | 0.97 | 90 | 10 | | 0.1 | 165 |
| 6 | WT | 15 | 46 | 30 | 9 | | 1.34 | 0.71 | 41 | 52 | 7 | 0.66 | 88 | 12 | | 0.12 | |
| | D$^{77}$A | 6 | 21 | 44 | 20 | 9 | 2.05 | | 18 | 73 | 8 | 0.9 | 93 | 7 | | 0.07 | 140 |
| 9 | WT | 7 | 29 | 35 | 21 | 8 | 1.94 | 0.26 | 57 | 34 | 9 | 0.51 | 56 | 34 | 10 | 0.54 | |
| | D$^{77}$A | 10 | 19 | 29 | 27 | 15 | 2.20 | | | 47 | 44 | 9 | 0.63 | 61 | 32 | 7 | 0.46 | 129 |

Example 30 Trastuzumab (Herceptin®) Conjugation

In order to confirm that the improved directional conjugation to CLκ-K$^{80}$ caused by CLκ-D$^{77}$ mutation can be applied to other antibodies comprising CLκ, D$^{77}$A mutation was also inserted to the CLκ of trastuzumab (hTrast). Trastuzumab light chain and heavy chain DNA were synthesized based on the amino acid sequences on Drug Bank, Accession Number DB00072 (BIOD00098, BTD00098).

hTrast-[CLκ-D$^{77}$A] mutant was generated in two steps. First, D$^{77}$A mutation was generated on an antibody light chain following protocols described in QuickChange site-directed mutagenesis kit (Stratagene®). Mutations were introduced by oligonucleotide primers and confirmed by DNA sequencing. The VL of trastuzumab was ligated with the CL of the antibody with D$^{77}$A mutation. Primer pair TRAST.VL.FOR (SEQ ID NO:89) and TRAST.VL.REV (SEQ ID NO:90) were used to amplify trastuzumab VL. The PCR fragment was digested with BglII and BsaI. Primer pair TRAST.CL.D185A.FOR (SEQ ID NO:91) and TRAST.CL.D185.A.REV (SEQ ID NO:92) were used to amplify CL with D$^{77}$A mutation. The resulting PCR fragment was digested with BsaI and NheI. Restriction enzyme digested PCR fragments were ligated with a modified p2.12.1.fxP4 plasmid (Invitrogen®) cut with BglII and NheI. The insert sequence was confirmed by DNA sequencing. The mutated mAb was transiently expressed in HEK 293 cells, and purified using protein A affinity column. The purified mAb was characterized using MS.

Trastuzumab and hTrast-[CLκ-D$^{77}$A] (1 mg reaction size) were adjusted 18 mg/ml to pH 7.7 with a phosphate buffer to a final concentration of 0.06 M sodium phosphate. [PFP-PEG$_5$-K$^{11}$-SEQ:27] was reconstituted in a propylene glycol solution to 10 mg/ml. The peptide/linker was added to antibody at a molar ratio of 4.3:1 and allowed to react for 2 hrs at RT.

Table 57 compares the conjugation profile of trastuzumab-[PEG$_5$-K$^{11}$-SEQ:27] with hTrast-[CLκ-D$^{77}$A]-[PEG$_5$-K$^{11}$-SEQ:27]. The conjugation profile of trastuzumab-[PEG$_5$-K$^{11}$-SEQ:27] occurs as a distribution between 0-4 peptide additions with the average number of peptide additions being 1.75. The profile changes following the D$^{77}$A mutation; the average number of peptide additions rises to 2.18 and significantly less overall levels of 0 and 1 peptide addition is observed. This result suggests that the single point mutation CLκ-D$^{77}$A has the effect of increasing the overall conjugation to the scaffold, as seen in the test antibody 2.12.1.fx.

The reduced light and heavy chain analysis demonstrates that the average conjugation is higher on the light chain of hTrast-[CLκ-D$^{77}$A] than unmodified trastuzumab; the average light chain conjugate addition value for hTrast-[CLκ-D$^{77}$A] is 1.01 compared to 0.70 for trastuzumab. In addition, unconjugated light chain is significantly reduced in hTrast-[CLκ-D$^{77}$A]. Conjugation on the heavy chain is observed at a significantly lower level. The majority of observed heavy chain for both trastuzumab and hTrast-[CLκ-D$^{77}$A] is unconjugated; this is especially true in the case of hTrast-[CLκ-D$^{77}$A] heavy chain. These results suggest that the CLκ-D$^{77}$A mutation alters the light chain to make it significantly more susceptible to conjugation.

TABLE 57

Analysis of conjugation of [PEG$_5$-K$^{11}$-SEQ: 27] to Abs trastuzumab (WT) and hTrast-[CLκ-D$^{77}$A]. Rep = replicate. AvReps is the average of the results of the three replicate experiments, with the standard deviation shown beneath (StdDev). Ab % CA shows % conjugations additions per antibody, followed by the average CA per antibody. Reduced light and heavy chain analysis also shown.

| Ab | Ab % CA | | | | | Avg. CA | LC % CA | | | Avg. CA | HC % CA | | Avg. CA |
|---|---|---|---|---|---|---|---|---|---|---|---|---|---|
| | 0 | 1 | 2 | 3 | 4 | | 0 | 1 | 2 | | 0 | 1 | |
| WT | | | | | | | | | | | | | |
| Rep1 | 6 | 33 | 42 | 15 | 5 | 1.80 | 35 | 65 | ND | 0.65 | 85 | 15 | 0.15 |
| Rep2 | 7 | 34 | 39 | 14 | 6 | 1.79 | 26 | 74 | ND | 0.74 | 84 | 16 | 0.16 |

TABLE 57-continued

Analysis of conjugation of [PEG$_5$-K$^{11}$-SEQ: 27] to Abs trastuzumab
(WT) and hTrast-[CLκ-D$^{77}$A]. Rep = replicate. AvReps is the average of the results
of the three replicate experiments, with the standard deviation shown beneath
(StdDev). Ab % CA shows % conjugations additions per antibody, followed by the
average CA per antibody. Reduced light and heavy chain analysis also shown.

| Ab | Ab % CA | | | | | Avg. | LC % CA | | | Avg. | HC % CA | | Avg. |
|---|---|---|---|---|---|---|---|---|---|---|---|---|---|
| WT | 0 | 1 | 2 | 3 | 4 | CA | 0 | 1 | 2 | CA | 0 | 1 | CA |
| Rep3 | 9 | 38 | 38 | 11 | 5 | 1.65 | 30 | 70 | ND | 0.7 | 82 | 18 | 0.18 |
| Av. Rep | 7 | 35 | 40 | 13 | 5 | 1.75 | 30 | 70 | | 0.70 | 84 | 16 | 0.16 |
| StdDev | 2 | 3 | 2 | 2 | 1 | 0.08 | 5 | 5 | | 0.05 | 2 | 2 | 0.02 |
| D$^{77}$A | | | | | | | 5 | 92 | 3 | 0.99 | 94 | 6 | 0.06 |
| Rep1 | 4 | 5 | 66 | 20 | 6 | 2.19 | 1 | 94 | 5 | 1.04 | 91 | 9 | 0.09 |
| Rep2 | 3 | 5 | 65 | 21 | 6 | 2.22 | 3 | 95 | 2 | 0.99 | 94 | 6 | 0.06 |
| Rep3 | 3 | 8 | 69 | 17 | 4 | 2.12 | 3 | 94 | 3 | 1.01 | 93 | 7 | 0.07 |
| AvRep | 3 | 6 | 67 | 19 | 5 | 2.18 | 2 | 2 | 2 | 0.03 | 2 | 2 | 0.02 |
| StdDev | 1 | 2 | 2 | 2 | 1 | 0.05 | 5 | 92 | 3 | 0.99 | 94 | 6 | 0.06 |

Example 31 Conjugation of Trastuzumab with MMAD

Table 58 compares the conjugation profile of trastuzumab-[PEG$_5$-MMAD] (Auristatin derivative) with hTrast-[CLκ-D$^{77}$A]-[PEG$_5$-MMAD].

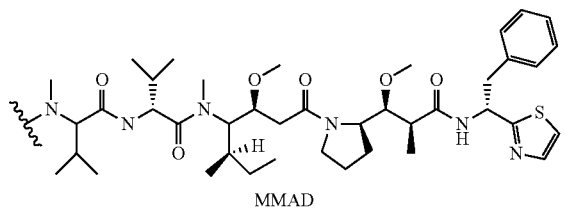

MMAD

The conjugation profile of trastuzumab-[PEG$_5$-MMAD] occurs as a distribution between 0-4 conjugations per antibody with the largest form being 2 conjugations and the average number of conjugations is 1.65. When CLκ-D$^{77}$A is mutated, the average number of conjugations rises to 2.00 and significantly less overall levels of 0 and 1 MMAD addition is observed. This result suggests that the single point mutation CLκ-D$^{77}$A has the effect of increasing the overall conjugation to the scaffold and that this technology is applicable to an antibody toxin conjugation model.

Reduced heavy and light chain analysis demonstrates that the average conjugation is higher on the light chain of hTrast-[CLκ-D$^{77}$A] than unmodified trastuzumab; the average light chain conjugate addition value for hTrast-[CLκ-D$^{77}$A] is 0.88 compared to 0.56 for trastuzumab. In addition, unconjugated light chain is significantly reduced in hTrast-[CLκ-D$^{77}$A]. Conjugation on the heavy chain is observed at a significantly lower level. The majority of observed heavy chain for both trastuzumab and hTrast-[CLκ-D$^{77}$A] is unconjugated; this is especially true in the case of hTrast-[CLκ-D$^{77}$A] heavy chain. These results suggest that the CLκ-D$^{77}$A mutation alters the light chain to make it significantly more susceptible to conjugation.

TABLE 58

Analysis of [PEG$_5$-MMAD] conjugation to trastuzumab (WT) and
hTrast-[CLκ-D$^{77}$A], also showing reduced LC and HC analysis. Ab % CA shows %
conjugations additions per antibody, followed by the average CA per antibody.
Reduced light and heavy chain analysis also shown. The % of 1-LC % relative to the
respective WT run is shown in the right column, as described in Table 53.

| hTrast conjugated | Percent CA | | | | | Avg. CA | LC % CA | | | Avg. CA | HC % CA | | Avg. CA | 1LC |
|---|---|---|---|---|---|---|---|---|---|---|---|---|---|---|
| to MMAD | 0 | 1 | 2 | 3 | 4 | | 0 | 1 | 2 | | 0 | 1 | | WT % |
| WT | 8 | 35 | 42 | 13 | 2 | 1.65 | 45 | 54 | 1 | 0.56 | 76 | 23 | 0.23 | |
| D$^{77}$A | 1 | 16 | 65 | 16 | 1 | 2.00 | 11 | 88 | | 0.88 | 84 | 14 | 0.14 | 163 |

Example 32 Ability of Conjugated Trastuzumab to Bind Targets

The ability of trastuzumab and hTrast-[CLκ-D$^{77}$A], unconjugated and conjugated to either [PEG$_5$-K$^{11}$-SEQ:27] or [PEG$_5$-MMAD] and to bind to the Her2 receptor was studied using a Her2 binding ELISA assay. Half well ELISA plates were coated with 1 ug/ml of Fc-ErbB2 fusion protein in PBS and incubated at 4° C. overnight. Plates were washed 3 with KPL wash buffer and subsequently blocked with Superblock for 1 hr at RT. 10× serial dilutions of samples were prepared in Superblock, with a top concentration of 100 μg/ml. Samples were added to wells and plates were incubated for 1 hr at RT. Plates were washed 3× with KPL wash buffer. Bound samples were detected by incubating with a 1:1000 dilution of anti-human Fab-HRP secondary antibody for 1 hr at RT. Plates were again washed 3× with KPL wash buffer and HRP was detected with TMB substrate. The reaction was stopped with 2M H$_2$SO$_4$ and OD was measured at 450 nm on a Spectramax plate reader.

FIGS. 9A and 9B demonstrate that commercial trastuzumab, trastuzumab generated from the available sequence, and hTrast-[CLκ-D$^{77}$A], as well as trastuzumab and hTrast-[CLκ-D$^{77}$A] when bound to either of [PEG$_5$-K$^{11}$-SEQ:27] or [PEG$_5$-MMAD] each display similar Her2 binding characteristics. These result suggest that conjugation, primarily at CLκ-K$^{80}$, does not significantly interfere with the receptor binding function of the native antibody.

Example 33 Comparison of PFP and NHS Conjugation Strategies

Trastuzumab was conjugated to [PEG$_5$-MMAD] using two separate strategies: directional conjugation to CLκ-K$^{80}$ using PFP ester (Z1) as the Z* group (generating trastuzumab-[5PEG-MMAD]), or NHS (Z13, generating trastuzumab-[MMAD]$_n$), which resulted in a wider conjugation pattern across the antibody, and dosed to rats to compare the tolerability of the antibody drug conjugates. Both conjugates were given as 10, 30 and 100 mg/kg single bolus doses. All animals dosed at 10, and 30 mg/kg doses of both conjugates during the one week study period survived without significant body weight loss. However, the 100 mg/kg dose group showed a clear difference between random conjugation (Z13) and site selective conjugation to CLκ-K$^{80}$ (Z1). Greater than 50% of the animals in 100 mg/kg dose of the random conjugate (NHS conjugation) died within the one week study period while all animals in the 100 mg/kg dose of the site selective conjugate (PFP conjugation) survived without significant body weight loss (Table 59). This may suggest that preferential conjugation at CLκ-K$^{80}$ may provide a more reliable mechanism for conjugation of Effector Moieties then traditional 'random' approaches, as conjugation on multiple surface lysine residues may give rise to Effector Moieties that have less reliable cleavage and degradation patterns.

TABLE 59

Site selective conjugation of toxin improves the tolerability of the antibody drug conjugates. Comparison of tolerability of trastuzumab -[PEG$_5$-MMAD] in rats after conjugation using Z1 and Z13 as Z* groups.

| Conjugate | Conjugation type | Dose (mg/Kg) | % Survival |
|---|---|---|---|
| Trastuzumab-[PEG$_5$-MMAD] | PFP | 10 | 100 |
|  |  | 30 | 100 |
|  |  | 100 | 100 |
| Trastuzumab-[MMAD]$_n$ | NHS | 10 | 100 |
|  |  | 30 | 100 |
|  |  | 100 | 50 |

Example 34 h38C2 Conjugated with Toxin and Cleavable Linker

A targeting peptide was conjugated to the combining site of a CLκ-D$^{77}$A mutated version of catalytic antibody h38C2 (HC=SEQ ID NO:65 and LC=SEQ ID NOs:37 and 67) using a linker of the formula P-Q-W as herein described, with a β-lactam group as the W group to form a covalent attachment with the side chain of K$^{99}$ of SEQ ID NO:65. This conjugated antibody was then further conjugated with the PFP-activated ester of an exemplary Auristatin-based toxin attached to a valine-citrulline p-aminobenzyl carbamate cleavable linker ([PFP-PEG$_2$-ValCitABC-TOXIN]).

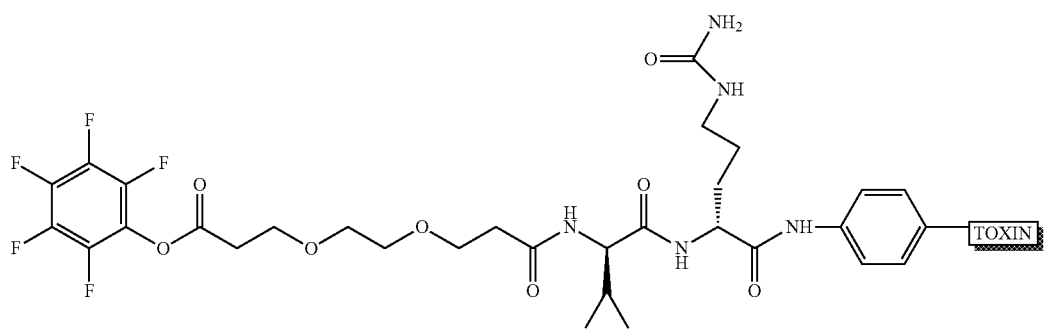 [SMILES: Cc1ccc(NC(=O)[C@@H](CCCNC(N)=O)NC(=O)[C@H](NC(=O)CCOCCOCCC(=O)Oc2c(F)c(F)c(F)c(F)c2F)C(C)C)cc1]

A distribution of conjugates was observed with primarily 2-3 toxins per antibody scaffold (Table 60). In vitro cytotoxicity assays of this conjugate demonstrated potent antiproliferative effects in AU565 cell lines ($IC_{50}$=0.4 nM) and OVCAR5 cell lines ($IC_{50}$=0.2 nM).

TABLE 60

Conjugation profile of h38C2 conjugated to [PFP-PEG$_2$-ValCitABC-TOXIN].

| | Conjugation Additions (CA) (%) | | | | | | |
|---|---|---|---|---|---|---|---|
| | 0 | 1 | 2 | 3 | 4 | 5 | Avg CA |
| PFP-PEG$_2$-ValCitABC-TOXIN | 4 | 8 | 31 | 29 | 18 | 10 | 2.8 |

Example 35

A structural analog of PFP, with a trifluoromethyl group replacing the para-fluorine atom, was used to make a derivative Z* group; 2,3,5,6-tetrafluoro-4-(trifluoromethyl)phenyl (Z16):

2,3,5,6-tetrafluoro-4-(trifluoromethyl)phenyl

This was used to generate a Z16-PEG$_5$ linker, which was conjugated to the test peptide SEQ ID NO:27, and tested in conjugation with the test antibody 2.12.1.fx. In contrast to other Z* groups tested, this derivative gave a conjugate with a slightly higher level of conjugation for the native 2.12.1.fx compared to 2.12.1.fx-[CLκ-$D^{77}$A], but both levels of intact conjugation were higher for the conjugate using the Z16 group than the corresponding PFP (Z1) analogs (around 10% increase in overall average CA compared to Z1). Using Z16, both native 2.12.1.fx and 2.12.1.fx-[CLκ-$D^{77}$A] conjugations showed an equivalent level of 1CA, and this was lower than that observed for native 2.12.1.fx conjugated with [PFP-PEG$_5$-$K^{11}$-SEQ:27]: for other conjugations, the level of 1CA is typically reduced in the $D^{77}$A compared to the corresponding native antibody. Overall, the results suggest that the leaving group D16 is more reactive than Z1 (PFP) (Table 61).

The Z16 leaving group shows roughly equivalent derivatization for both the native 2.12.1.fx and 2.12.1.fx-[CLκ-$D^{77}$A] antibodies and the amount of underivatized LC is small in both cases. Again the overall level of LC and HC derivatization is increased using Z*16 compared to Z1. The leaving group Z16 appears a more reactive ester than PFP, but it is possible that the $CF_3$ group is providing an additional interaction near the CLκ-$K^{80}$ region that is also driving reactivity and preferential derivatization of the LC

TABLE 61

Analysis of 2.12.1.fx and 2.12.1.fx.-[CLκ-$D^{77}$A] conjugation to [PEG$_5$-$K^{11}$-SEQ: 27] using different reactive Z* groups Z1 and Z16. Ab % CA shows the overall % of conjugation additions per antibody, with reduced light chain and heavy chain analysis also shown (LC % CA, HC % CA). Δ indicates the difference between the WT and $D^{185}$A mutant results for Ab % CA. The % of 1-LC % relative to the respective WT run is shown in the right column, as described in Table 53.

| | | Ab % CA | | | | | Avg CA | Δ | LC % CA | | | Avg CA-LC | HC % CA | | Avg CA-HC | 1LC WT % |
|---|---|---|---|---|---|---|---|---|---|---|---|---|---|---|---|---|
| Z* | 2.12.1.fx | 0 | 1 | 2 | 3 | 4 | CA | Δ | 0 | 1 | 2 | LC | 0 | 1 | HC | WT % |
| 1 | WT | 1 | 17 | 51 | 25 | 5 | 2.16 | | 14 | 77 | 9 | 0.96 | 84 | 16 | 0.16 | |
| 1 | $D^{77}$A | 4 | 6 | 60 | 23 | 7 | 2.23 | 0.07 | 0 | 86 | 13 | 1.13 | 92 | 8 | 0.08 | 112 |
| 16 | WT | 4 | 4 | 44 | 36 | 12 | 2.48 | | 5 | 83 | 12 | 1.07 | 81 | 19 | 0.19 | |
| 16 | $D^{77}$A | 9 | 9 | 31 | 33 | 18 | 2.43 | 0.05 | 1 | 79 | 20 | 1.2 | 89 | 11 | 0.11 | 95 |

Example 36 Synthesis of Toxin 0101

Experimental for Toxin 0101 (#54 in the Schematic)
Preparation of 2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

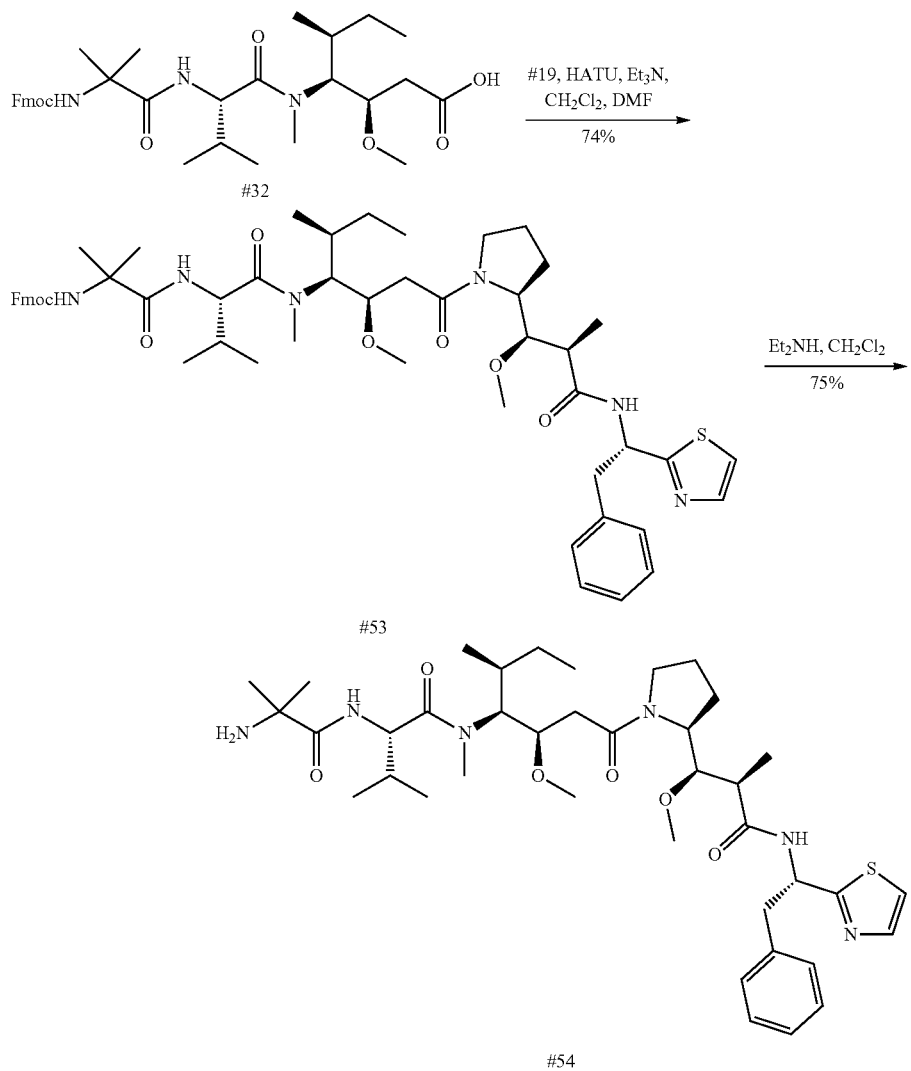

LC-MS: m/z 965.7 [M+H$^+$], 987.6 [M+Na$^+$], retention time=1.04 mins; HPLC (Protocol A): m/z 965.4 [M+H$^+$], retention time=11.344 mins (purity >97%), $^1$H NMR (400 MHz, DMSO-d$_6$), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24 (4 s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H]. Step 2. Synthesis of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54)

According to general procedure A (below), from #53 (701 mg, 0.726 mmol) in dichloromethane (10 mL, 0.07 M) was synthesized the crude desired material, which was purified Step 1. Synthesis of N-[(9H-fluoren-9-ylmethoxy)carbonyl]-2-methylalanyl-N-R3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53). According to general procedure D (below), from #32 (2.05 g, 2.83 mmol, 1 eq.) in dichloromethane (20 mL, 0.1 M) and N,N-dimethylformamide (3 mL), the amine #19 ((2R,3R)-3-methoxy-2-methyl-N-[(1S)-2-phenyl-1-(1,3-thiazol-2-yl)ethyl]-3-[(2S)-pyrrolidin-2-yl]propanamide, trifluoroacetic acid salt) (2.5 g, 3.4 mmol, 1.2 eq.), HATU (1.29 g, 3.38 mmol, 1.2 eq.) and triethylamine (1.57 mL, 11.3 mmol, 4 eq.) was synthesized the crude desired material, which was purified by silica gel chromatography (Gradient: 0% to 55% acetone in heptane), producing #53 (2.42 g, 74%) as a solid.

by silica gel chromatography (Gradient: 0% to 10% methanol in dichloromethane). The residue was diluted with diethyl ether and heptane and was concentrated in vacuo to afford #54 (406 mg, 75%) as a white solid. LC-MS: m/z 743.6 [M+H+], retention time=0.70 minutes; HPLC (Protocol A): m/z 743.4 [M+H+], retention time=6.903 minutes, (purity >97%); $^1$H NMR (400 MHz, DMSO-d$_6$), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3 Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 1H], [4.49 (dd, J=9, 8 Hz) and 4.60 (dd, J=9, 7 Hz), total 1H], 3.16, 3.20, 3.21 and 3.25 (4 s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

General Procedure A: Fmoc removal using diethylamine. To a solution of the Fmoc-containing compound in dichloromethane was added an equal volume of diethylamine. Reaction progress was monitored by LC-MS (or HPLC or TLC); the reaction was usually completed within three hours. Solvents were removed in vacuo, and the residue was then azeotroped three times with heptane. The residue was then diluted with dichloromethane and a small amount of methanol before being reduced down onto silica and purified by chromatography on silica gel, eluting with methanol in dichloromethane to afford the desired material.

General Procedure D: coupling with O-(7-azabenzotriazol-1-yl)-N,N,N',N'-tetramethyluronium hexafluorophosphate (HATU). To a stirring solution of the amine (1 eq.) and acid (1.1 eq.) in dichloromethane: N,N-dimethylformamide (4:1, 0.3 M in amine) was added HATU (1.2 eq.) followed by Et$_3$N (3 eq.). Reaction progress was monitored by LC-MS (or HPLC or TLC), the reaction was usually completed within three hours. Solvents were removed in vacuo. The residue was azeotroped three times with heptane and was diluted with a small amount of ethyl acetate before being reduced down onto silica and purified by silica gel or reverse phase chromatography.

Example 37 Preparation of MAC Comprising mAb Hu08 and Toxin 0101

Hu08 is a human anti-IL-13Rα2 antibody, and is described fully in U.S. 61/723,545, whose contents are herein incorporated by reference.
A mutant version of hu08, comprising the CLκ-D$^{77}$A mutation was generated according to standard protocols (hu08-[CLκ-D77A]). Toxin-0101 (#54: Example 36) was conjugated with a cleavable linker to form the structure:

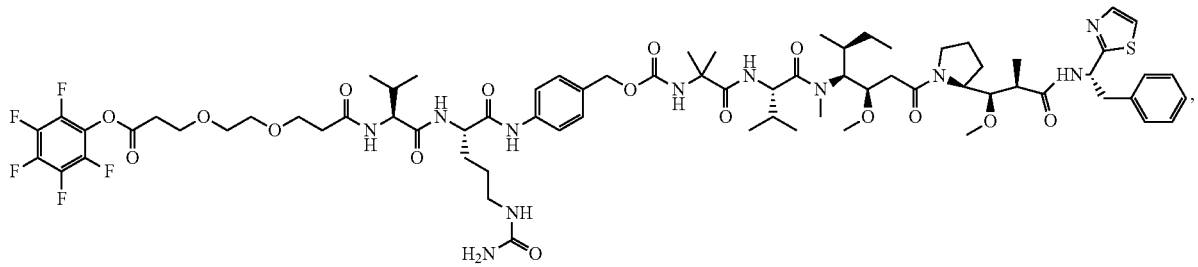 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCOCCOCCC(=O)Oc2c(F)c(F)c(F)c(F)c2F)C(C)C)cc1)C(C)C]

and then the toxin-linker was conjugated to hu08-[CLκ-D77A] according to the techniques described herein. The compound hu08-vc-0101 was generated, resulting in non-specific conjugation of multiples of Toxin-0101 on the antibody hu08 via the linker-Toxin-0101 species:

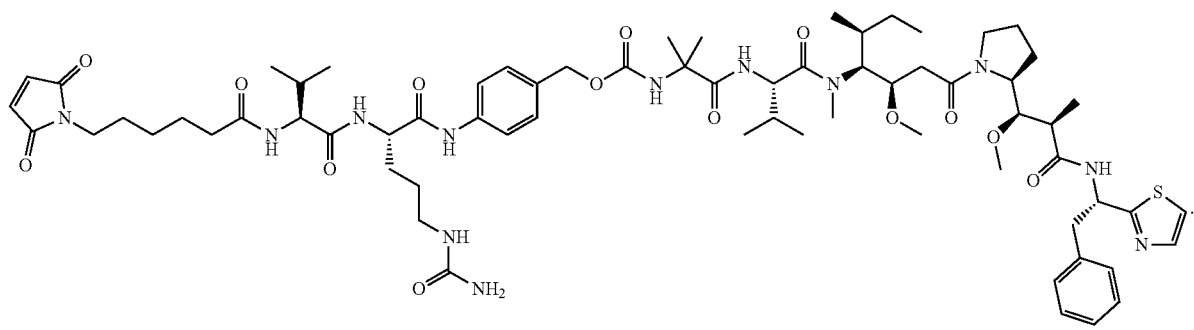 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

In Vitro Cytotoxicity Assay

Cell lines expressing the IL-13Rα2 antigen and a negative control cell line were cultured with increasing concentrations of hu08-[CLκ-D$^{77}$A]. After four days, viability of cultures were assessed. IC$_{50}$ values were calculated by logistic non-linear regression and are presented as ng Ab/mL.

The data demonstrate that hu08-vc0101 and hu08-[CLκ40, -D$^{77}$A] were both effective against both of the IL-13Rα2 positive cell lines tested (PC3MM2 and A375), having an IC$_{50}$ ranging from 2.5 to 7.9 ng Ab/mL (Table 62). Neither hu08-vc0101 nor hu08-[CLκ-D$^{77}$A] were active against the IL-13Rα2 negative cell line, H460, and the non-IL-13Rα2 binding control, hIgG8.84-vc0101, was not active against any of the cell lines tested.

TABLE 62

In vitro cytotoxicity assay of hu08-[CLκ-D$^{77}$A] -0101.

| ADC | Toxin: Ab | IC$_{50}$ (ng Ab/mL) | | |
|---|---|---|---|---|
| | | PC3MM2 | A375 | H460 |
| hu08-vc-0101 | 3.2 | 2.5 | 3.8 | >400000 |
| hu08-[CLκ-D$^{77}$A] -0101 | 1.9 | 4.9 | 7.9 | >400000 |
| hIgG8.8-vc-0101 | 3.7 | >400000 | >400000 | >400000 |

Subcutaneous Xenograft Models of Cys Mutant ADCs

Female, athymic (nude) mice were injected s.c. with PC3MM2 tumor cells. Mice with staged tumors, approximately 0.1 to 0.3 g (n=8 to 10 mice/treatment group) were administered intravenously q4d×4 with normal saline (vehicle) or MAC-0001. Compounds were dosed based on Ab content. Tumors were measured at least once a week and their size (mm2+/-☐SEM) is calculated as mm$^3$=0.5×(tumor width$^2$)×(tumor length). The data in Table 63 indicate that hu08-[CLκ-D$^{77}$A]-0101 inhibits the growth of PC3MM2 xenografts.

TABLE 63

| ADC | Dose single dose | PC3MM2 xenograft, tumor volume (mm$^3$ ± SEM) | | | | | | | | | |
|---|---|---|---|---|---|---|---|---|---|---|---|
| | | Day 0 | Day 5 | Day 8 | Day 12 | Day 15 | Day 20 | Day 30 | Day 41 | Day 55 | Day 77 |
| Vehicle | 0 | 325 ± 9 | 590 ± 41 | 782 ± 79 | 1140 ± 142 | GT | GT | GT | GT | GT | GT |
| hu08-[CLκ-D$^{77}$A]-0101 | 1.5 | 328 ± 49 | 393 ± 96 | 352 ± 106 | 432 ± 124 | 556 ± 236 | 732 ± 305 | GT | GT | GT | GT |
| hu08-vc-0101 | 1.5 | 333 ± 12 | 431 ± 40 | 281 ± 25 | 299 ± 32 | 362 ± 47 | 450 ± 58 | 956 ± 166 | GT | GT | GT |

GT = group terminated due to large tumor size

Example 38 Trastuzumab MMAD Conjugate Activities

Three trastuzumab conjugates were made: trastuzumab-[5PEG-MMAD], hTrast-[CLκ-D$^{77}$A]-[5PEG-MMAD], and trastuzumab-(MMAD)$_n$, where MMAD was connected to a 5PEG linker with Z13 (NHS) as leaving group, and conjugated to trastuzumab without directional conjugation techniques, resulting in non-specific conjugation of MMAD to trastuzumab surface lysines (see Examples 30-33)

[PFP-5PEG-MMAD]

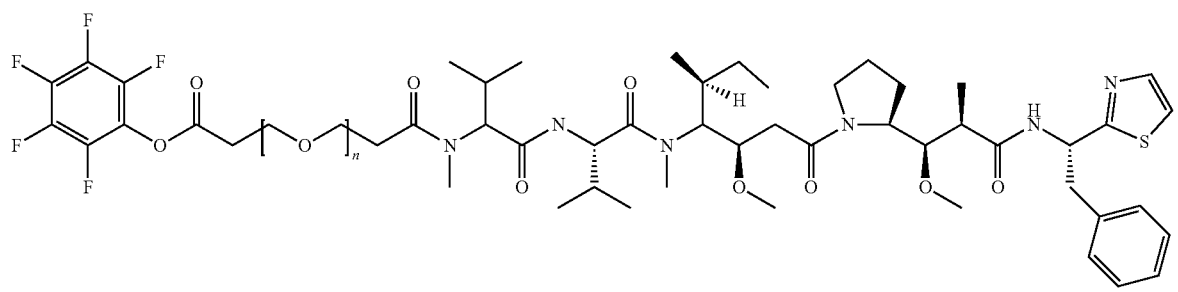

n = 5

-continued

[NHS-5PEG-MMAD]

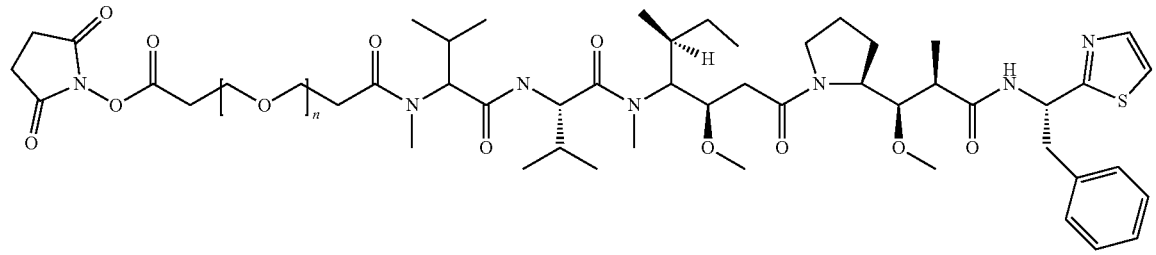

n = 5

-[5PEG-MMAD]

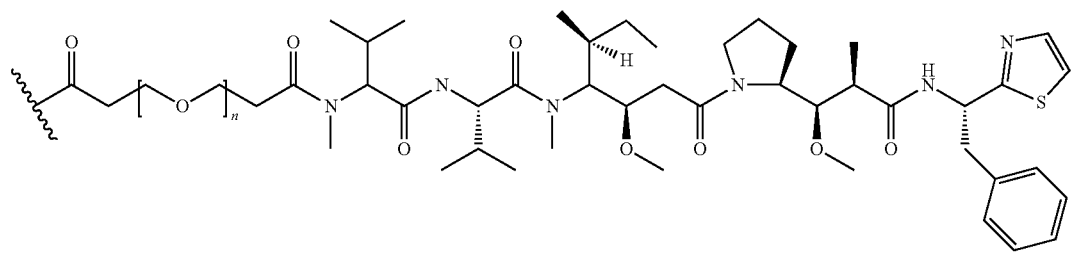

n = 5

The three mAb conjugates were evaluated in an exploratory toxicity study in rats in which animals received single intravenous bolus doses of each ADC at 0 (vehicle), 10, 30, and 100 mg/kg (5 male rats/group) and were then observed for 14 days. Toxicology evaluation included daily clinical observations, weekly body weight measurements and clinical pathology evaluation on the day of necropsy. Animals were euthanized on day 15 and selected tissues were collected for microscopic examination. In addition, blood samples were collected from all animals at approximately 0.0833 (5 min), 6, 24 (day 2), 48 (day 3), 72 (day 4), 96 (day 5), 168 (day 8), and 312 (day 14) hrs post-dose and analyzed for antibody-conjugate and trastuzumab antibody concentrations.

Results

The plasma exposures (based on AUC) were overall similar for all 3 conjugates at any given dose. The AUC(0-312) of hTrast-[CLκ-D$^{77}$A]-[5PEG-MMAD], trastuzumab-[5PEG-MMAD] and trastuzumab-(MMAD)$_n$ at 100 mg/kg were 177000, 174000 and 139000 ng·h/mL, respectively. hTrast-[CLκ-D$^{77}$A]-[5PEG-MMAD] and trastuzumab-[5PEG-MMAD] were clinically well tolerated at all doses. However, trastuzumab-(MMAD)$_n$ administration at 100 mg/kg was associated with marked clinical signs and premature euthanasia of ⅕ rats on Day 8. Other rats from this group had decreased skin turgor and decreased body weight gain.

Clinical pathology changes were overall similar with hTrast-[CLκ-D$^{77}$A]-[5PEG-MMAD] and trastuzumab-[5PEG-MMAD] and included in particular mild decreases in red blood cell (RBC) mass (RBC count, hemoglobin and/or hematocrit) at ≥10 or ≥30 mg/kg and minimal increases in aspartate aminotransferase (AST) at 100 mg/kg. The RBC mass changes were more pronounced with trastuzumab-(MMAD)$_n$ and were associated with decreased erythroid cellularity in the bone marrow. Other noteworthy trastuzumab-(MMAD)$_n$-related clinical pathology changes at 100 mg/kg included moderate decreases in platelet counts and mild increases in ALT, AST, ALP and total bilirubin.

Microscopic findings were overall similar for hTrast-[CLκ-D$^{77}$A]-[5PEG-MMAD] and trastuzumab-[5PEG-MMAD] and included alveolar histiocytosis/inflammation in the lung, degeneration of small bile ducts in the liver and increased tingible body macrophages (containing cell debris) in the bone marrow. Increased mitoses in several tissues and single cell necrosis in the cornea were considered pharmacologically mediated effects of tubulin inhibition resulting in mitotic arrest and apoptosis. By contrast, trastuzumab-(MMAD)$_n$ administration was associated with more pronounced microscopic tissue alterations, which included tubular degeneration/necrosis and glomerulopathy in the kidney; single cell necrosis, bile duct degeneration and hyperplasia and centrilobular necrosis/fibrosis in the liver; alveolar histiocytosis/inflammation in the lung; increased tangible body macrophages, degeneration/decreased numbers of hematopoietic cells and osteolysis in the bone marrow; decreased marginal zone cellularity in the spleen. Of special note, centrilobular fibrosis in the liver in association with disruption of the normal lobular architecture was consistent with a reparative change suggesting earlier, more extensive treatment-related hepatocellular damage. In addition, pharmacologically mediated increased mitoses and/or single cell necrosis were observed in several tissues.

In summary, hTrast-[CLκ-D$^{77}$A]-[5PEG-MMAD] and trastuzumab-[5PEG-MMAD] were well tolerated at all doses (10, 30, and 100 mg/kg) and demonstrated overall similar toxicity profiles. Trastuzumab-(MMAD)$_n$ administration led to premature mortality at 100 mg/kg and was associated with significant target organ toxicities in the liver, kidney, lung and bone marrow in particular.

Example 39 Modeling of CLκ and CLλ

FIG. 10A depicts an Ig fold of a constant light domain containing a 3-stranded β-sheet packed against a 4-stranded β-sheet. The fold is stabilized by hydrogen bonding between the β-strands of each β-sheet, by hydrophobic bonding between residues of opposite β-sheets in the interior, and by a disulfide bond between the β-sheets. The 3-stranded β-sheet comprises β-strands C, F, and G, and the 4-stranded β-sheet has β-strands A, B, E, and D. The letters A through G denote the sequential positions of the β-strands along the amino acid sequence of the Ig fold. Linking each β-strand with the subsequent β-strand is an amino acid connecting chain that may or may not comprise a turn (A/B) or α-helix (E/F) (FIG. 10B).

FIG. 8B plots the secondary structures along the primary sequence of the mouse and human CLκ, and the human CLλ. The EF connecting chain between β-strands E and F of the CLκ and CLλ have identical secondary structure and consist of a 5-6 residue α-helical region (CLκ-$K^{75}$-$K^{80}$, and CLλ-$P^{78}$-$S^{81}$), followed by a 2-3 amino-acid turn (CLκ-$H^{81}$-$K^{82}$ and CLλ-$H^{82}$-$S^{84}$) (FIGS. 8B and 10). The CD connecting chain brings the side chain of structurally equivalent aspartic acids (CLκ-$D^{53}$, CLλ-$D^{45}$) to the vicinity of the EF chain (approximately 3.5 Å), and allows CLκ-$D^{53}$ interact with the imidazole ring of CLκ-$H^{81}$.

Modeling of the CLλ and comparison with the CLκ suggests that CLλ-$D^{45}$ cooperates with the imidazole ring of CLλ-$H^{82}$ in the same manner, and that mutating CLλ-$S^{81}$ to CLλ-$K^{81}$ recreates a similar local environment as found on the CLκ, and so allows directional conjugation to the CLλ.

Accordingly, the present invention also provides for CLλ domains comprising one of the following mutations: CLλ-$S^{81}$K, and CLλ-$K^{80}$x/$S^{81}$K, wherein x is any amino acid except P, K, R or H, wherein the numbering is according to SEQ ID NO:93. In some aspects, the invention provides for novel CLλ domains comprising $K^{81}$, or $x^{80}/K^{81}$, wherein x is one of G, A, I, L, V, S, T, M, N, Q, F, Y, W, D, or E. In some aspects, the invention also provides for a CLλ domain comprising a sequence selected from the group consisting of SEQ ID NO:94, and SEQ ID NO:95.

Modeling also suggests that CLλ-$E^{77}$ would be available to form a salt bridge with either of CLλ-$K^{80}$ or CLλ-$K^{81}$ in the same manner as CLκ-$D^{77}$ appears to form a salt bridge to CLκ-$K^{80}$. Thus, mutating CLλ-$E^{77}$ to any of R, L, S, G, Q, P, N, V, I, T, and M is likely to facilitate directional conjugation at either of CLλ-$K^{80}$CLλ when $S^{81}$Δ (i.e. deletion of $S^{81}$), or CLλ-$K^{81}$. Accordingly, the present invention also provides for a CLλ domain comprising a sequence selected from the group consisting of SEQ ID NO:96 and SEQ ID NO:97.

Example 40 Modeling of CLκ-$K^{80}$ Conjugation Mechanism

Structure and Sequence Description

Crystal structures of the Fab domain of 2.12.1.fx and h38C2-[CLκ-$D^{77}$A] were used to model the specificity of CLκ-$K^{80}$ reactivity towards a halo-phenol (such as PFP)/ester-mediated conjugation. Experience with conjugations across multiple and varied antibodies, as well as early modeling analysis, indicated that modeling only needed be focused on the CLκ, as the remainder of the antibody appeared to exert very little, if any, influence on the mechanism of conjugation.

Computational Approach

The goal of the computational calculations was to clarify the critical attributes of CLκ-$K^{80}$ and interacting residues that preferentially bias this site towards the PFP-ester conjugation reaction. After the 3-D coordinates of CLκ and CLκ-$D^{77}$A were selected from the crystal structure (based on those coordinates that contained those residues already identified as being relevant to directional conjugation), the coordinates were subjected to standard computational protocols, such as protein preparation, attachment of hydrogen atoms, and force field parameters assignment.

Hydrogen atoms were assigned to all amino acid atoms on the respective 3D CLκ domain according to the calculated pKa values and pI (protein ionization potential). pKa is the value of a protonation state of a given titratable amino acid at the neutral pH (negative logarithm of hydrogen concentration) taking in to account the influence of amino acids in the protein chain (*Spassov; A fast and accurate computational approach to protein ionization. Protein Science* 2008, 17, 1955-1970). The results of these calculations are shown in Table 64.

TABLE 64 pKa values of amino acid residues in CLκ

| Titratable residues | Calculated pKa | Standard pKa |
|---|---|---|
| CLκ-$D^{14}$ | 3.315 | 3.65 |
| CLκ-$D^{43}$ | 3.324 | 3.65 |
| CLκ-$D^{59}$ | 3.667 | 3.65 |
| CLκ-$D^{62}$ | 4.411 | 3.65 |
| CLκ-$D^{77}$ | 3.307 | 3.65 |
| CLκ-$E^{15}$ | 3.93 | 4.25 |
| CLκ-$E^{35}$ | 3.906 | 4.25 |
| CLκ-$E^{53}$ | 4.604 | 4.25 |
| CLκ-$E^{57}$ | 4.284 | 4.25 |
| CLκ-$E^{79}$ | 3.636 | 4.25 |
| CLκ-$E^{89}$ | 4.244 | 4.25 |
| CLκ-$Y^{32}$ | 10.276 | 10.07 |
| CLκ-$Y^{65}$ | 11.847 | 10.07 |
| CLκ-$Y^{78}$ | 11.844 | 10.07 |
| CLκ-$Y^{84}$ | 14 | 10.07 |
| CLκ-$H^{81}$ | 7.22 | 6.0 |
| CLκ-$H^{90}$ | 6.126 | 6.0 |
| CLκ-$K^{18}$ | 11.057 | 10.53 |
| CLκ-$K^{37}$ | 10.761 | 10.53 |
| CLκ-$K^{40}$ | 10.505 | 10.53 |
| CLκ-$K^{61}$ | 10.852 | 10.53 |
| CLκ-$K^{75}$ | 10.952 | 10.53 |
| CLκ-$K^{80}$ | 11.119 | 10.53 |
| CLκ-$K^{82}$ | 10.451 | 10.53 |
| CLκ-$K^{99}$ | 10.706 | 10.53 |
| CLκ-$R^{34}$ | 13.428 | 12.48 |
| CLκ-$R^{103}$ | 14 | 12.48 |

Hydrogen atoms are added accordingly to the pKa value for all titratable amino acids and for the remaining amino acids, according to the atomic valence number. The calculations indicated that CLκ-$H^{81}$ is unprotonated at pH 7.0-7.4 (physiological pH). This observation is consistent with proposed mechanism for catalytic reaction, where CLκ-$H^{81}$ acts as a nucleophilic catalyst. In general, conjugation would be expected to decrease with as the pH goes below about pH 6.5-7.0, as CLκ-$H^{81}$ would be protonated. As the pH increases above about 7.4, a greater overall level of conjugation would be predicted, as other residues (especially lysines) become more reactive and contribute to the overall conjugation reaction, consequently we would expect that the directional effect would be increasingly lost as the pH rises.

This correlates with what was observed in the pH study shown in Example 4, Table 4.

Minimization

CHARMm [Chemistry at HARvard Macromolecular Mechanics] is an energy minimization technique, and was used to bring the 3-D structures to the equilibrium position and find the best geometrical position for its atomic structure. CHARMm was used at the first step with the SMART Minimizer with 1000 steps of Steepest Descent minimization with a RMS gradient tolerance of 3[Kcal/(mol*Å)], followed by Conjugate Gradient minimization with a RMS gradient of 0.01. For the energy change, a tolerance of 3[Kcal/(mol*Å)] was applied to the average gradient during a cycle of minimization. The Steepest Descent method takes the molecule to the nearest minimum and the Conjugated Gradient improves the final conformation obtained. Momany Rone charges were used, (as described in Momany & Rone; Validation of the general purpose QUANTA 3.2/ CHARMm force field. Comp. Chem. 1992, 13, 888-900.) The minimized structure of CLκ differed by 1 Å when compared to the un-minimized structure.

Complex Between CLκ Domains and PFP-PEG$_2$

The respective complexes between a PFP ester and the CLκ and CLκ-D$^{77}$A domains was built in silico to better understand each interaction. Structural analysis of the 3D CLκ domains by the Accelrys protocol Define and Edit Binding Site (Discovery Studio software version DS3.5) revealed a region that could be termed a 'binding pocket', located between the CD and EF connecting chains, and underneath CLκ-K$^{80}$, as shown in FIG. 11. This pocket is facilitated by the amino acids located at CLκ-K$^{75}$-E$^{79}$ (EF α-helix on the EF connecting chain), CLκ-K$^{80}$-K$^{82}$ (EF loop on the EF connecting chain) and CLκ-V$^{42}$ (CD loop on the CD connecting chain) giving the shape and the electrostatic properties required by the catalytic reaction.

To measure the pocket size, the Define and Edit Binding Site protocol was used on the previously minimized CLκ structure. This protocol requires defining the CLκ domain as a receptor to use on it the space filling method to calculate the cavity size and assess its suitability for binding of a molecule with a particular size, such as PFP. The binding site of a receptor can be represented in many ways, for example a sphere or a list of residues surrounding this sphere. To define a binding site, the receptor is first mapped to a grid. Grid points within a given distance of the receptor atoms are marked as occupied by the receptor, and thus undesirable as locations for ligand atoms. Two methods exist to identify a binding site. The first uses an "eraser" algorithm to identify sites based on the shape of the receptor. The second uses the volume occupied by a known ligand already positioned in an active site (Venkatachalam et al *Flt: a novel method for the shape-directed rapid docking of ligands to protein active sites. J. Mol. Graph. Model* 2003, 21, 289-307).

As a result of protocol execution, binding sites are identified as a set of points located on a grid that encompasses the molecule under consideration. This definition permits measurement of the size and shape of the binding site, which allows for its qualification as a binding site. PFP-PEG2 was docked manually to the site surrounded by amino acids experimentally identified as important for the catalytic reaction. These amino acids were CLκ-K$^{80}$, CLκ-H$^{81}$, CLκ-D$^{43}$ and other amino acids within 10 Å distance from CLκ-K$^{80}$ (shown in Table 54).

The initial complex between each CLκ domain and a PFP ester was minimized using the QM/MM hybrid method, applying the CHARMm force field for the CLκ domain and QM calculations for the PFP ester. The PFP ester was minimized prior to the placement using first CHARMm then the QM/MM approach in which the PFP ester is treated as a QM system. The structure was minimized using the CHARMm minimization protocol described above.

For the minimizations of the complex, a QM/MM hybrid protocol was used in which quantum mechanical (QM) calculations gave information about the electron densities change upon interaction with WT or mutated protein allowing us to capture the influence of the surrounding environment on the PFP ester electron densities and its susceptibility to the conjugation reaction. The QM/MM protocol is a hybrid method where the molecular system is divided into two regions: first, the central region PFP ester, to be treated by a QM calculation and second, the outer region CLκ domain, treated by molecular mechanics (MM) methods.

QM treatment brings a higher level of theory, enabling the modeling of additional phenomena compared to traditional forcefield techniques, for example, where a chemical reaction occurs or polarization effects play an important role. The remaining bulk of the structure is described using a forcefield CLκ. The way in which the two regions are allowed to interact and how the total QM/MM energy is evaluated define the specific QM/MM protocol employed. Energy calculated in this method is composed from three basic parts: the QM energy of the PFP ester ($E_{QM}$), CD-kappa ($E_{MM}$), and the interaction energy between these two systems ($EQ_{MMM}$). The formula $E_{tot}=E_{QM}+E_{MM}+E_{QM/MM}$ is used.

As far as the coulomb interaction between the electronic density of the QM region and the forcefield point charges is concerned, QM/MM methods in this application always employ electronic embedding. This means that the forcefield atom's partial charges enter the QM calculation as an external potential, thereby polarizing the QM electronic density relative to a QM calculation in vacuo, and giving rise to an electrostatic interaction energy between the QM density and the point charges. Contrary to the handling of the electrostatic interactions in QM/MM methods, the van der Waals interactions are treated entirely at the classical level. This means that appropriate forcefield parameters must be determined for all atoms in the simulation. The van der Waals QM/MM interaction energy (and forces) is a part of the CHARMm simulation server energy and is listed as a separate term in the output file.

Calculations

The total effects observed from in vitro experiments during and after the conjugation can be modeled by computational techniques using stepwise approximations to describe such phenomenon as:

1. PFP binding pocket size—binding of the PFP ester and direction.
2. Protein stability—especially, the stability of a PFP binding pocket.

3. Tautomerization of the imidazole ring of CLκ-H[81].
4. Directional PFP placement.
5. Initial interaction between the PFP ester and CLκ.
6. Reactivity of each of the catalytic amino acids.

Modeling Results

Identification of the binding pocket in the CLκ domain permitted modeling and docking-placement of the PFP ester. After the PFP ester was modeled as docked into the respective CLκ binding site, the 3-D structure of the complex was minimized using a hybrid method QM/MM. In this approach, the PFP ester was defined as a QM system and the CLκ domain was treated by a MM method. After minimization of the complex, a network of intermolecular interactions between the CLκ and the PFP ester was revealed. This network was formed by intermolecular hydrogen bonds, hydrophobic interactions, and 7-electron stacking. All of these forces together appear to be involved in formation of a network responsible for the directional placement and conjugation of the PFP ester to CLκ-K[80]. The minimized structure of the complex indicates that CLκ-H[81] is an important catalytic amino acid.

It is known that the imidazole moiety in histidine sidechains can serve as a catalytic amino acid in enzymatic reactions, with the imidazole acting as a nucleophile and forming an acyl imidazole during the catalytic transition state [*J Phys Chem B*. 2011 Oct. 20; 115(41):11895-901. Epub 2011 Sep. 23]. It is also known that the imidazole ring of histidine can undergo tautomerization, depending on whether the Nδ or Nε atom bonds with H:

Scheme I

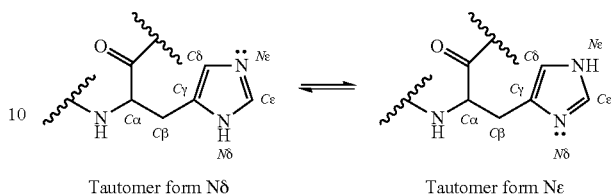

Tautomer form Nδ        Tautomer form Nε

Spatial positioning of CLκ-H[81] in the PFP binding pocket points to the requirement of Nδ tautomeric form of imidazole ring CLκ-H[81] for nucleophilic attack on carbonyl carbon of the PFP ester. It also indicates a requirement for the electron lone pair at Nε to be in the same plane as the carbonyl carbon of PFP ester group. This is possible when the imidazole ring of CLκ-H[81] is in the Nδ tautomeric form (see Scheme II). The tautomeric equilibrium can be controlled by the hydrogen bond interactions with the neighboring hydrogen acceptor amino acids. There are two aspartic acid residues, CLκ-D[77] and CLκ-D[43], in the vicinity of CLκ-H[81] and both of them appear to control the tautomerization state of the CLκ-H[81] imidazole ring.

Scheme II A: Initial intermolecular complex is formed between CLk-K[80], PFP-ester and CLk-H[81].
B-C: Transition state with acyl imidazole and the PFP alcohol. C: Producdt of conjugation reaction.

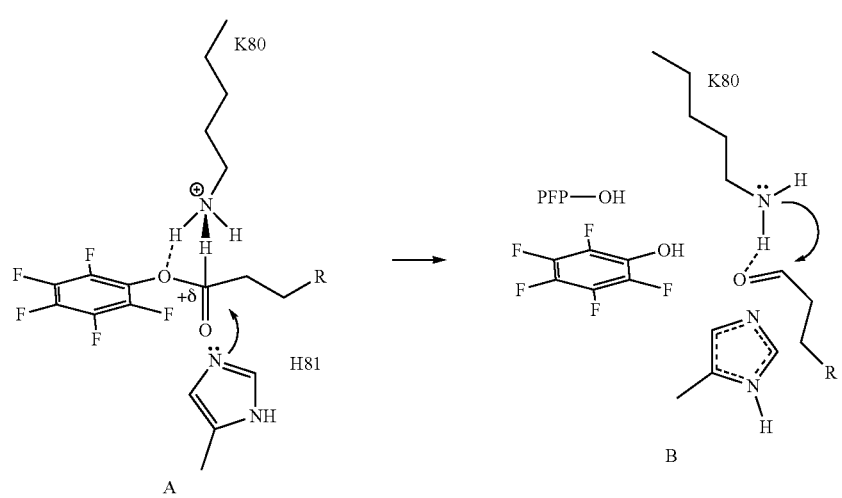

FIG. 12 depicts the 3-D arrangement of CLκ-H$^{81}$, CLκ-D$^{43}$ and CLκ-D$^{77}$, accompanied by the distances between the oxygen atoms of the aspartic acids and nitrogen atoms of the imidazole ring. Hydrogen bonding between CLκ-D$^{43}$ and CLκ-H$^{81}$ promote and stabilize the catalytically-active tautomeric form NO, while the hydrogen bond with CLκ-D$^{77}$ will promote the catalytically-inactive form of CLκ-H$^{81}$ NE. In addition to the hydrogen bonds formed between CLκ-H$^{81}$ Nδ and CLκ-D$^{77}$ Oδ (negatively charged), CLκ-H$^{81}$ Nε and CLκ-D$^{77}$ Oδ, CLκ-H$^{81}$ Nδ can form a hydrogen bond with the carbonyl oxygen of the CLκ-D$^{77}$ backbone. This last interaction stabilizes the catalytically-active conformation of CLκ-K$^{81}$ NO, rendering it capable of catalysis. It is known from the mutational analysis and computational work discussed herein that the optimal conformation for CLκ-K$^{81}$ reactivity involves hydrogen bonding with CLκ-D$^{43}$ via Nδ, as this stabilizes an active conformation capable of the hydrogen Hε transfer from CLκ-K$^{80}$ Nε. The two other CLκ-K$^{81}$ tautomeric forms will therefore most likely be less active or inactive in the catalytic reaction.

Modeling the Effect of CLκ-D$^{77}$A Mutation

As predicted from the WT model, in the [CLκ-D$^{77}$A] domain, CLκ-H$^{81}$ forms a hydrogen bond with CLκ-D$^{43}$ via the imidazole Nδ atom, exposing electron pair at NE for the nucleophilic attack on carbonyl carbon of the ester group in the PFP-PEG2 molecule (Scheme III). FIGS. 13A, 13B and 13C depict a comparison of crystal structure modeled CLκ and CLκ-D$^{77}$A domains, and illustrate the shift in spatial position of CLκ-H$^{81}$ in the CLκ-D$^{77}$A mutant.

Scheme III Schematic showing effect of CLκ-D77A mutation on ability of CLκ-H$^{81}$ to provide Nε lone pair.

-continued

H81  
D43

Mutations to CLκ-$D^{77}$

Modeling suggests that CLκ-$D^{77}$ mutations would have a significant impact on the conjugation rate of CLκ-$K^{80}$. A series of QM/MM calculations were conducted on the CLκ domain complexed with PFP, where CLκ-$D^{77}$ was mutated to all other natural amino acids (CLκ-$D^{77}$C was excluded).

Modeling and experimental analysis suggests that CLκ-$D^{77}$ may bind to PFP and change the unfavorable electron density on the ester atoms of PFP moiety involved in the catalytic reaction. The CLκ-$D^{77}$A mutation would then improve the conjugation rate by allowing better distribution of the electron densities on the reacting atoms of PFP ester.

Analysis of the calculation results performed on the mutants of CLκ-$D^{77}$ indicate that the best performing mutants (in terms of conjugation efficiency) are likely to be those small hydrophobic amino acids unable to form hydrogen bonds to the PFP moiety. Modeling data therefore suggests the mutations CLκ-$D^{77}$G, CLκ-$D^{77}$P, CLκ-$D^{77}$M, CLκ-$D^{77}$L, CLκ-$D^{77}$I, CLκ-$D^{77}$A, and CLκ-$D^{77}$V would improve directional conjugation. As seen in Example 26, this is borne out by experimental testing. All CLκ $^{77}$ mutants with hydrophobic amino acids have no impact on the tautomeric equilibrium of CLκ-$H^{81}$, thus CLκ-$H^{81}$ remains in the Nδ tautomeric form and consequently conjugation rates improve.

Modeling also suggest that most hydrophilic amino acids are likely to result in higher protein stability than CLκ-$D^{77}$ according to by QM/MM calculations; and points to the mutations CLκ-$D^{77}$S and CLκ-$D^{77}$T in particular, and also CLκ-$D^{77}$Q, CLκ-$D^{77}$N, CLκ-$D^{77}$H and CLκ-$D^{77}$R as potentially improving directional conjugation. As seen in Example 26, this is also borne out by experimental testing.

In addition to the interaction energies and the modifications of the charge distribution, the strongest interaction and the lower conjugation rates were observed for CLκ-$D^{77}$F and CLκ-$D^{77}$Y mutants. The model indicates that the side chains of these aromatic amino acids include directly into the binding pocket, and are likely to be involved in 7-electron stacking interactions with the PFP group and therefore change the directional placement of PFP moiety. In addition, aromatic amino acids can sterically hinder PFP, preventing a similar binding mode to that possible in the WT protein thus adversely impacting the directional placement of the PFP moiety and resulting in a decreased conjugation rate. Interestingly, the model suggests that the side chain of CLκ-$D^{77}$W occupies a slightly different spatial position to the aromatic side chains of CLκ-$D^{77}$F and CLκ-$D^{77}$Y, with the CLκ-$D^{77}$W indole group sitting outside the binding pocket and not predicted to interfere with the spatial access of a halo-phenyl ester to the binding pocket. The model also predicts that a conservative mutation, such as CLκ-$D^{77}$E is likely to have a similar effect on the tautomeric form of CLκ-$H^{81}$, but due to the larger side-chain, create additional steric interference in the binding pocket. Mutations to CLκ-$D^{77}$C or CLκ-$D^{77}$K are also predicted to interfere with the reactivity of the site.

CLκ-$D^{77}$ favors the presence of the hydrogen atom on Nε of the imidazole ring, while CLκ-$D^{77}$A favors maintaining the hydrogen at the position Nδ. Spatial distribution of amino acids in the site indicates the important function Nδ tautomeric form of CLκ-$H^{81}$ in the catalytic reaction enabling nucleophilic attack by Nε at the carbonyl carbon of the ester group, further facilitating directional conjugation.

Example 41 Predictive Modeling Based on Model of CLκ and CLκ-$D^{77}$A

The impact of mutations on protein stability and interaction strength with the PFP ester were analyzed to identify the most relevant and reactive mutants of CLκ. For this computational experiment, key amino acids within a 10A distance from Cα carbon of CLκ-$K^{80}$ were selected and analysed for (except CLκ-$K^{80}$ and CLκ-$H^{81}$, given the unique requirement for each of the residues).

For many or most of the mutations modeled for PFP conjugation with the CLκ or CLκ-$D^{77}$A, it will be understood that in certain applications, it may appropriate to substitute or retain a residue that would reduce PFP conjugation in the CLκ or CLκ-$D^{77}$A, as it may be desirable to reduce or increase the pocket size; such as where larger or smaller halo-phenols are used as Z1 groups, or where the precise geometry of a specific immunoglobulin domain appears to merit such a feature.

CLκ-$K^{75}$

This residue does not appear to have any direct impact on the conjugation reactivity of CLκ-$K^{80}$ in the native or CLκ-$D^{77}$A mutant by QM/MM calculations.

CLκ-$A^{76}$

CLκ-$A^{76}$ is located at the beginning of the α-helix, and lies and above the plane that contains the hydrogen-bonded carboxyl group of CLκ-$D^{77}$ and the hydroxyl group of CLκ-$S^{74}$. This location allows amino acids with a large sidechain to interact with CLκ-$D^{77}$ and they may have a positive impact of the conjugation reaction, especially those with hydrophilic groups capable of hydrogen bond formation. Most amino acid substitutions at this residue would be expected to have little effect on conjugation, specifically CLκ-$S^{74}$A, CLκ-$S^{74}$D, CLκ-$S^{74}$E, CLκ-$S^{74}$I, CLκ-$S^{74}$L, CLκ-CLκ-$S^{74}$F, CLκ-$S^{74}$W and CLκ-$S^{74}$V. Other residues that could provide hydrogen bonding opportunities would be expected to enhance conjugation, namely CLκ-$S^{74}$R, CLκ-$S^{74}$N, CLκ-$S^{74}$Q, CLκ-$S^{74}$H, and CLκ-$S^{74}$K, and to a lesser degree CLκ-$S^{74}$S, CLκ-$S^{74}$T and CLκ-$S^{74}$Y. While residues that disrupt the α-helix may have a somewhat negative effect on directional conjugation to CLκ-$K^{80}$, such as CLκ-$S^{74}$G and CLκ-$S^{74}$P, directional conjugation is unlikely to be abrogated, merely reduced. Introduction of a cysteine would present a risk of the potential to form aggregates in expression.

CLκ-$Y^{78}$

CLκ-$Y^{78}$ is located on the α-helix, facing the opposite direction to the binding pocket. CLκ-$Y^{78}$ makes a number of hydrophobic interactions with surrounding amino acids and supports the CLκ structure. Accordingly, smaller sidechains (Ala, Ser, Thr and Val) or those that affect the stability or formation of the α-helix (Gly, Pro) will be more likely to adversely affect the conjugation reaction to CLκ-$K^{80}$, although as these mutations are not predicted to directly interfere with the CLκ-$K^{80}$ reactivity, such mutations may not necessarily abrogate directional conjugation. Additionally, CLκ-$Y^{78}$ appear to interact with the sidechain of CLκ-$R^{103}$, thus hydrophobic or negatively-charged sidechains would be expected to favor conjugation to facilitate this interaction (Asn, Asp, Gln, Glu, Phe and Trp). Other sidechains would not be expected to effect the conjugation reaction (Arg, His, Ile, Leu, Lys and Met).

CLκ-E$^{79}$

Modeling suggests that the side chain of CLκ-E$^{79}$ is pointing in the opposite direction from the binding site. In addition, CLκ-E$^{79}$ appears to form a salt bridge with sidechain of CLκ-K$^{75}$. Based on the modelling, it is postulated that most amino acid substitutions in this position would have little effect on the conjugation reaction (Asn, Asp, Gln, His, Met, Phe, Ser, Thr, Tyr and Trp). Small hydrophilic or charged residues would likely favour the conjugation reaction (Ala, Arg, Ile, Leu, Lys and Val), while those that affect the stability or formation of the α-helix (Gly, Pro) may adversely affect the conjugation reaction to CLκ-K$^{80}$, without necessarily abrogating directional conjugation.

CLκ-V$^{83}$

This residue does not appear to have a direct impact on the conjugation reaction with CLκ-K$^{80}$ by experimental data and QM/MM calculations.

TABLE 65

Summary of effect of mutations on certain CLκ residues on directional conjugation to CLκ-K$^{80}$.

| | A$^{76}$ | D$^{77}$ | Y$^{78}$ | E$^{79}$ |
|---|---|---|---|---|
| G | 0 | +++ | -- | - |
| P | 0 | +++ | -- | - |
| A | WT | ++ | - | + |
| V | 0 | + | - | + |
| L | 0 | ++ | 0 | + |
| I | 0 | ++ | 0 | + |
| M | 0 | +++ | 0 | 0 |
| F | 0 | --- | + | 0 |
| W | 0 | + | + | 0 |
| Y | + | --- | WT | 0 |
| T | + | +++ | - | 0 |
| S | + | +++ | - | 0 |
| N | ++ | ++ | + | 0 |
| Q | ++ | ++ | + | 0 |
| D | 0 | WT | + | 0 |
| E | 0 | -- | + | WT |
| H | ++ | ++ | 0 | 0 |
| R | ++ | ++ | 0 | + |
| K | ++ | -- | 0 | + |

Additional Modeling

CLκ-V$^{42}$

CLκ-V$^{42}$ is positioned at the end of β-strand C and the beginning of the CD loop. From a careful examination of the structure, it was observed that CLκ-V$^{42}$ is located underneath the imidazole ring of CLκ-H$^{81}$ (FIGS. 14 and 15). To help determine the nature of the interactions between CLκ-H$^{81}$ and CLκ-V$^{42}$, the x,y,z coordinates of the centroid for the imidazole ring were calculated, followed by measurement of the distance between the calculated centroid and the hydrogen atom Hδ of the CLκ-V$^{42}$. This distance of 2.9 Å indicates direct interactions between the π-electrons on the imidazole ring and the hydrogen Hδ of CLκ-V$^{42}$. This interaction therefore appears to strongly influence the optimal positioning of CLκ-H$^{81}$ in the pocket and for the tautomeric equilibrium shift to the Nδ tautomer. Thus, while not essential, the presence of CLκ-V$^{42}$ exerts a positive influence on directional conjugation. These analyses are borne out by experimental data, where it was found that CLκ-V$^{42}$A mutation caused a decrease in the conjugation rate (Table 54). Modeling suggests that CLκ-V$^{42}$I is likely to be able to assist in positioning the CLκ-H$^{81}$ imidazole ring to favour directional conjugation, although the slightly larger side chain will reduce the overall binding pocket size. In many circumstances, this reduction of pocket size may not have an appreciable effect on the directional conjugation mechanics. CLκ-V$^{42}$L may also be able to assist with positioning the CLκ-H$^{81}$ imidazole ring.

CLκ-D$^{43}$

CLκ-D$^{43}$ is located on the CD loop. In native CLκ, CLκ-D$^{43}$ appears to interact with the backbone of CLκ-H$^{81}$ and CLκ-K$^{82}$, contributing to protein stability. No hydrogen bonds between Hδ of CLκ-H$^{81}$ and the carboxylic group of CLκ-D$^{43}$ were identified on the crystal structure of CLκ. This may suggest that CLκ-D$^{43}$ exerts only a minimal influence on the tautomeric equilibrium of the Nδ catalytically active form of CLκ-H$^{81}$. However, experimental analysis with 2.12.1.fx-[CLκ-D$^{43}$A] mutants showed that mutating this residue had a significant inhibitory effect on directional conjugation. Taken together with the overall model, it is likely that CLκ-H$^{81}$ alternates between the catalytically active and inactive form, forming H-bonds between CLκ-D$^{43}$ and CLκ-D$^{77}$ as it does so, and that removing the CLκ-D$^{43}$ residue eliminates one of the forces pushing CLκ-H$^{81}$ towards the active Nδ tautomer.

Analyses of the CLκ-D$^{77}$A crystal structure revealed a well-defined hydrogen bond between hydrogen Nδ and the CLκ-D$^{43}$ carboxylic group. This suggests that one of the most significant effects of the CLκ-D$^{77}$A mutant is in stabilization of CLκ-H$^{81}$ catalytically favorable tautomeric form NO, as shown in FIGS. 13 and 14. Finally, proximity of CLκ-D$^{43}$ to CLκ-H$^{81}$ would allow CLκ-D$^{43}$ to participate in the catalytic reaction as a hydrogen atom recipient in the last step of the putative reaction mechanism (Scheme III). Thus the role of CLκ-D$^{43}$ in the native CLκ and CLκ-D$^{77}$A mutant, appears to be in stabilization of catalytically active Nδ tautomeric form of CLκ-H$^{81}$ and participation in the catalytic reaction as the hydrogen atom recipient.

The modeling analyses strongly suggests that binding of the PFP molecule in native CLκ is controlled by the tautomeric forms of CLκ-H$^{81}$, and the affinity of this binding is in turn controlled by the state of the tautomeric equilibrium constant. The presence of Nδ tautomeric form allows the lone pair on Nε to nucleophilic attack the PFP carbonyl (Scheme III).

CLκ-D$^{43}$ is involved in the catalytic reaction by being a hydrogen ion acceptor (Scheme III). CLκ-D$^{43}$ was mutated in silico to all 19 amino acids and in the final series of calculated mutants, the WT protein (comprising CLκ-D$^{43}$) creates the highest interaction energy with the CLκ-PFP ester complex, with CLκ-D$^{43}$N also predicted to be of similar chain length and be able to form a hydrogen bond to the CLκ-H$^{81}$ NO, thus aiding the catalytically-active tautomeric form Nδ of CLκ-H$^{81}$. Other residues likely to be acceptable substitutions are CLκ-D$^{43}$E, CLκ-D$^{43}$Q and CLκ-D$^{43}$S, these being able to form the desired H-bond with CLκ-H$^{81}$, but likely to have chain lengths either slightly too large or small to be of optimal size for CLκ conjugation with PFP, but may be better suited to either optimizing a non-CLκ immunoglobulin domain for directional conjugation with PFP, or optimizing an Ig domain for conjugation with a different halo-phenyl ester.

CLκ-N$^{44}$

CLκ-N$^{44}$ is located on the CD loop. Its sidechain is pointing outwards, away from the PFP binding pocket, and appears not to have any role in, nor influence on, the conjugation reaction. QM/MM calculations predicted that polar amino acids and those with a negatively-charged sidechain may enhance protein stability due to the putative interactions with CLκ-K$^{41}$, also located outside of the pocket.

CLκ-L$^{46}$

A CLκ-L$^{46}$A mutation had a relatively neutral impact on the conjugation rate, based on experimental data, as well as from our QM/MM calculations. CLκ-L$^{46}$A is located outside of the PFP binding pocket, but it may facilitate the pocket shape due to the size of its sidechain. Being located outside of the pocket, it can interact with amino acids located outside of the pocket as well. Mutations to large and hydrophilic sidechains may increase protein stability due to the interaction with CLκ-Q$^{39}$ and support the shape of the PFP pocket according to QM/MM calculations.

CLκ-Q$^{47}$

A CLκ-Q$^{47}$A mutation improved the conjugation rate. This mutation is likely exerting an effect by increasing the size of the PFP binding site, thus impacting complex formation and protein stability in a positive way according to modeling calculations. Amino acids with larger sidechains will likely impact conjugation in a slightly negative way, according to QM/MM calculations. Thus, mutations to CLκ-Q$^{47}$A, CLκ-Q$^{47}$G, CLκ-Q$^{47}$V, CLκ-Q$^{47}$I, CLκ-Q$^{47}$L, CLκ-Q$^{47}$T, CLκ-Q$^{47}$S, CLκ-Q$^{47}$N, CLκ-Q$^{47}$D, CLκ-Q$^{47}$H, CLκ-Q$^{47}$P, or CLκ-Q$^{47}$E will likely be beneficial or neutral; whereas mutations to CLκ-Q$^{47}$W, CLκ-Q$^{47}$F, CLκ-Q$^{47}$Y, or CLκ-Q$^{47}$K may have a somewhat negative impact on PFP conjugation to a CLκ domain. As before, it will be understood that in certain applications, it may be desirable to reduce the pocket size; such as where smaller halo-phenols are used as Z1 groups, or where the precise geometry of a specific immunoglobulin domain appears to merit such a feature.

CLκ-S[48]

Mutation of CLκ-S[48]A improved the conjugation rates according to experimental data: modeling suggest that the reason for this is most likely due to the change of electrostatic properties of the pocket. Hydrophobic amino acids at this position will therefore likely have a positive impact on the directional conjugation. Consequently, the following mutations may be especially favoured: CLκ-S[48]A, CLκ-S[48]G, CLκ-S[48]V, CLκ-S[48]I, CLκ-S[48]L, CLκ-S[48]P, and CLκ-S[48]M. Other mutations are likely to be tolerated.

Example 42 Double and Triple Mutations of CLκ-D[77]A

Antibody 2.12.1.fx was used to test the effect of further mutations to the CLκ region. As before, numbering of residues is according to their location within the CLκ (SEQ ID NO:6, for example). CLκ-D[43] and CLκ-H[81] were each mutated to Ala in on 2.12.1.fx-[CLκ-D[77]A] antibody to understand the conjugation mechanisms. Mutations were generated on 2.12.1.fx light chain following protocols described in QuickChange site-directed mutagenesis kit (Stratagene). The antibodies 2.12.1.fx, 2.12.1.fx-[CLκ-D[77]A] (CLκ comprising SEQ ID NO:37), 2.12.1.fx-[CLκ-D[43]A] (CLκ comprising SEQ ID NO:15), 2.12.1.fx, 2.12.1.fx-[CLκ-D[43]A/D[77]A] (CLκ comprising SEQ ID NO:127), 2.12.1.fx-[CLκ-D[77]A/H[81]A] (CLκ comprising SEQ ID NO:128), and 2.12.1.fx-[CLκ-D[43]A/D[77]A/H[81]A] (CLκ comprising SEQ ID NO:129), were transiently expressed in HEK 293 cells, and purified using protein A affinity column. The purified mAbs were characterized using MS.

The expressed antibodies were buffer exchanged to 20 mM sodium acetate, 200 mM trehalose pH 5.5 at 20 mg/ml. The antibody solutions were then spiked with 60 mM sodium phosphate pH 7.7. [$PEG_5$-$K^{11}$-SEQ:27] (ABP) was resuspended with 50% propylene glycol and mixed with the protein at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple ABP conjugation sites are observed as distinct signals separated by the mass difference of an ABP. Relative quantitation of multiple ABP conjugation species is performed by measuring the signal magnitude. Results of % CA are shown in Table 66.

TABLE 66

Intact conjugation analysis of 2.12.1.fx-[CLκ-mutants] with ABP.

| | CLκ SEQ ID | % CA 0 | 1 | 2 | 3 | 4 | Avg CA |
|---|---|---|---|---|---|---|---|
| 2.12.1.fx | 6 | 1 | 15 | 53 | 26 | 5 | 2.2 |
| D[77]A | 37 | 2 | 3 | 56 | 32 | 7 | 2.39 |
| D[43]A | 15 | 17 | 38 | 31 | 14 | 0 | 1.41 |
| D[43]A/D[77]A | 127 | 4 | 21 | 46 | 21 | 7 | 2.06 |
| D[77]A/H[81]A | 128 | 33 | 38 | 20 | 10 | 0 | 1.07 |
| D[43]A/D[77]A/H[81]A | 129 | 25 | 40 | 28 | 7 | 0 | 1.18 |

The extent of ABP conjugation was examined separately on the light and heavy chains of 2.12.1.fx and 2.12.1.fx-[CLκ mutants]. MACs were denatured and disulfide bonds were reduced using guanidine hydrochloride and dithiothreitol. The resulting free light and heavy chains were analyzed using LCMS to determine the conjugation profile on each (Table 67).

TABLE 67

Reduced heavy, light chain conjugation analysis of 2.12 1.fx-[CLκ-mutants] with ABP. The % of 1-LC % relative to the respective WT run is shown in the right column, as described in Table 67.

| | CLκ SEQ ID | LC % CA 0 | 1 | 2 | Avg CA-LC | HC % CA 0 | 1 | Avg CA-HC | 1LC WT % |
|---|---|---|---|---|---|---|---|---|---|
| 2.12.1.fx | 6 | 23 | 69 | 8 | 0.85 | 86 | 14 | 0.14 | |
| D[77]A | 37 | 1 | 92 | 7 | 1.06 | 97 | 3 | 0.03 | 133 |
| D[43]A | 15 | 68 | 30 | 1 | 0.33 | 79 | 21 | 0.21 | 43 |
| D[43]A/D[77]A | 127 | 24 | 64 | 12 | 0.88 | 90 | 10 | 0.1 | 93 |
| D[77]A/H[81]A | 128 | 72 | 28 | 0 | 0.28 | 85 | 15 | 0.15 | 41 |
| D[43]A/D[77]A/H[81]A | 129 | 76 | 20 | 4 | 0.28 | 87 | 13 | 0.13 | 29 |

These results are consistent with the His tautomer hypothesis. In the CLκ-$D^{77}$A mutant, CLκ-$D^{43}$ stabilizes the catalytically active tautomer of CLκ-$H^{81}$, which in turn allows CLκ-$K^{80}$ to be more receptive and reactive to a PFP-ester. Conversely, in the CLκ-$D^{43}$A mutant, CLκ-$D^{77}$ stabilizes the inactive tautomer of CLκ-$H^{81}$, therefore leading to a reduction in the directional conjugation observed at CLκ-$K^{80}$. In the double mutant CLκ-$D^{43}$A/$D^{77}$A, there are no interactions between CLκ-$H^{81}$ and either of CLκ-$D^{43}$ or CLκ-$D^{77}$, and accordingly, the double mutant acts more like the WT CLκ.

Example 43 Rabbit CLκ Analysis

Rabbit antibody light chain kappa region (rCLκ) has the same 3D structure as that of other immunoglobulins. rCLκ has Asp at position 151 (kabat number), Ser at position 188, and His at 189, (rCLκ-$D^{43}$, rCLκ-$S^{80}$, rCLκ-$H^{81}$). It was postulated that a rCLκ-$S^{80}$K mutant may create the reaction site for PFP directional conjugation. To validate this hypothesis, two trastuzumab rabbit chimera antibodies were constructed. mAb "rTrast" (rabbit trastuzumab) comprises the VL and VH domains of trastuzumab (SEQ ID NOs:75 and 72 respectively) fused to the rCLκ and rabbit constant heavy chain (rCH) (SEQ ID NOs:130 and 131 respectively), to generate the full length rTrast-LC (SEQ ID NO:132) and rTrast-HC (SEQ ID NO:133).

rTrast-[rCLκ-$S^{80}$K] comprises the VL and VH domains of trastuzumab (SEQ ID NOs:75 and 72 respectively) fused to the rCLκ-$S^{80}$K (SEQ ID NO:134) and rabbit constant heavy chain (rCH) (SEQ ID NO:131), to generate the full length rTrast-LC-[rCLκ-$S^{80}$K] (SEQ ID NO:135) and rTrast-HC (SEQ ID NO:133).

Rabbit IgG heavy chain and kappa1 light chain were PCRed from plasmids pFUSE-CHIg-rG and pFUSE2ss-CLIg-rk1 (Invivogen) respectively with ends overlapping with trastuzumab variable domains and vector. Trastuzumab VH and VL were PCRed from synthetic genes with ends overlapping with vector and rabbit constant domains. PCRs were mixed with a modified pCEP4 vector (Invitrogen) cut with BglII and NheI following protocols described in Quick PCR Cloning Kit (BPS Bioscience). Insert DNA were confirmed by DNA sequencing. rCLκ-$S^{80}$K mutation was generated following protocols described in Quick PCR Cloning Kit (BPS Bioscience). Mutation was introduced by oligonucleotide primers and cloned to a modified pCEP4 vector (Invitrogen) cut with BglII and NheI. Insert DNA were confirmed by DNA sequencing.

The chimeric mAbs were transiently expressed in HEK 293 cells, and purified using protein A affinity column. Each of the purified mAbs were characterized using MS. Each of the antibodies was buffer exchanged to 20 mM sodium acetate, 200 mM trehalose pH 5.5 at 20 mg/ml, and then spiked with 60 mM sodium phosphate pH 7.7. [$PEG_5$-$K^{11}$-SEQ:27] (ABP) was resuspended with 50% propylene glycol and mixed with the protein at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple ABP conjugation sites are observed as distinct signals separated by the mass difference of an ABP. Relative quantitation of multiple ABP conjugation species is performed by measuring the signal magnitude.

The extent of ABP conjugation was examined on the light of antibodies. MACs were denatured and disulfide bonds were reduced using guanidine hydrochloride and dithiothreitol. The resulting free light and heavy chains were analyzed using LCMS to determine the conjugation profile on each (Table 68).

TABLE 68

Intact conjugation and reduced light chain analysis of rabbit chimera conjugated with ABP.

| | % CA | | | | Avg | LC % CA | | | Avg | 1LC |
|---|---|---|---|---|---|---|---|---|---|---|
| | 0 | 1 | 2 | 3 | CA | 0 | 1 | 2 | CA-LC | WT % |
| rTrast | 58 | 24 | 19 | 0 | 0.61 | 56 | 38 | 6 | 0.5 | |
| rTrast-[rCLκ-$S^{80}$K] | 10 | 25 | 54 | 11 | 1.657 | 18 | 73 | 8 | 0.89 | 192 |

The rCLκ-$S^{80}$K mutation significantly increased total conjugation (0.61 to 1.657) and 1CA on the light chain (38% to 73%). This result suggests that a directional conjugation site can be created on CLκ chains from species other than human, as long as the critical residues, CLκ-$K^{80}H^{81}$, are present on the immunoglobulin. The % of 1-LC % relative to the respective WT run is shown in the right column, as described in Table 68.

Example 44 Lambda Chain

As demonstrated in Example 10 above, hCLλ does not demonstrate directional conjugation with PFP esters. hCLλ shares sequence identity with hCLκ at hCLκ-$D^{43}$ (CLλ-$D^{48}$) and hCLκ-$H^{81}$ (CLλ-$H^{82}$), and has serine in place of hCLκ-$K^{80}$ (CLλ-$S^{81}$). It was postulated that a CLλ-$S^{81}$K mutant may enable PFP conjugation to at the CLλ-$S^{81}$K residue.

Comparing the crystal structures of CLκ and CLλ (FIGS. 17 & 18), CLκ-$V^{42}$ is located at the bottom of the putative PFP binding pocket, whereas the corresponding residue in CLλ is CLλ-$A^{44}$. As discussed above, CLκ-$V^{42}$A mutations have a negative impact on the directional conjugation, likely owing to the ability of CLκ-$V^{42}$ to stabilize the orientation of the imidazole ring of CLκ-$H^{81}$. Modeling suggested that a CLλ-$A^{44}$V mutation should exert a similar effect on CLλ-$H^{82}$.

As in Example 10, and Examples 15-17, a monoclonal anti-human IL22 antibody (hIL22) was used as an exemplary CLλ comprising antibody. hIL22 comprised SEQ ID NOs:136 and 137 (hIL22-LC and hIL22-HC respectively), and variable light chain comprising SEQ ID NO:138 (hIL22-CLλ-VL).

A number of mutant versions of hIL22 were generated, to assess the effects of various CLλ mutations on directional conjugation. All hIL22 mutant antibodies comprised SEQ ID NO:137 (hIL22-HC), and SEQ ID NO:138 (hIL22-CLλ-VL).

hIL22-[LKJ] comprised the A/K swap as described in Example 15, and comprised a CL of SEQ ID NO:61.

hIL22-[CLλ-S$^{81}$K] comprised the single residue swap of CLλ-S$^{81}$K, and comprised SEQ ID NO:140. hIL22-[CLλ-Q$^{78}$A/S$^{81}$K] comprised a double mutation in the loop, and comprised SEQ ID NO:141. hIL22-[CLλ-A$^{44}$V/S$^{81}$K] comprised the CLλ-S$^{81}$K residue swap, and also a CLλ-A44V mutation at the bottom of the "binding pocket", and comprised SEQ ID NO:142. hIL22-[CLλ-A$^{44}$V/Q$^{78}$A/S$^{81}$K] comprised both loop mutations CLλ-Q$^{78}$A and CLλ-S$^{81}$K, as well as the "binding pocket" CLλ-A$^{44}$V mutation, and comprised SEQ ID NO:143. All the point mutations were generated on hIL22-LC following protocols described in QuickChange site-directed mutagenesis kit (Stratagene). Mutations were introduced by oligonucleotide primers and confirmed by DNA sequencing.

hIL22-[CLλ-λ$^{76-84}$/145] comprised inserting SEQ ID NO:145 in place of the CLλ E-F loop, located from CLλ-P$^{76}$ inclusive through to CLλ-S$^{83}$ inclusive. SEQ ID NO:145 comprises the sequence KAAYEKHKV, which corresponds to the [CLκ-D$^{77}$A] E-F loop (i.e. between β-strands E and F) from [CLκ-D$^{77}$A]K$^{75}$ inclusive through to [CLκ-D$^{77}$A]K$^{82}$ inclusive.

hIL22-[CLλ-λ$^{76-84}$/145] was generated by overlap PCR. Mutations were introduced by oligonucleotide primers. Primer specific to the 5' end of hIL22-LC paired with a reverse primer encoding SEQ ID NO:145, and a forward primer encoding SEQ ID NO:145, paired with the reverse primer specific to the 3' end of 1L22-LC were used to PCR amplify DNA fragments carrying CLκ E-F loop using 1L22-LC as template. These two PCR products were mixed as templates; 1L22-LC forward primer and reverse primer were used in overlap PCR reaction to amplify the full length 1L22-LC DNA with SEQ ID NO:145. The PCR was then digested with restriction enzyme BglII and NheI. The digested PCR was ligated with a modified pCEP4 plasmid (Invitrogen) cut with BglII and NheI.

The mutated mAbs were transiently expressed in HEK 293 cells, and purified using protein A affinity column. The purified mAbs were characterized using MS.

Each of the antibodies was buffer exchanged to 20 mM sodium acetate, 200 mM trehalose pH 5.5 at 20 mg/ml, and then spiked with 60 mM sodium phosphate pH 7.7. [PEG$_5$-K$^{11}$-SEQ:27] (ABP) was resuspended with 50% propylene glycol and mixed with the protein at a 4.3:1 molar ratio and allowed to react overnight at room temperature. All samples were diluted to 2 mg/ml and the extent of ABP conjugation was examined separately on the light and heavy chains of antibodies. The MACs were denatured and disulfide bonds were reduced using guanidine hydrochloride and dithiothreitol. The resulting free light and heavy chains were analyzed using LCMS to determine the conjugation profile on each (Table 69).

TABLE 69

Reduced heavy, light chain conjugation analysis of lambda antibody and mutants.

| Ab conjugated with ABP | CL SEQ ID | LC % CA | | | | HC % CA | | | |
|---|---|---|---|---|---|---|---|---|---|
| | | 0 | 1 | 2 | Ave LC | 0 | 1 | 2 | Ave HC |
| 2.12.1.fx | 6 | 15 | 79 | 6 | 0.91 | 93 | 7 | 0 | 0.07 |
| 2.12.1.fx-CLκ-D$^{77}$A | 37 | 0 | 92 | 8 | 1.08 | 98 | 2 | 0 | 0.02 |
| Trastuzumab-WT | 76 | 32 | 66 | 2 | 0.7 | 83 | 17 | 0 | 0.17 |
| Trastuzumab-CLκ-D$^{77}$A | 77 | 0 | 95 | 5 | 1.05 | 90 | 10 | 0 | 0.1 |
| hIL22 | 136 | 100 | 0 | 0 | 0 | 76 | 22 | 2 | 0.26 |
| hIL22-[LKJ] | 61 | 55 | 45 | 0 | 0.45 | 79 | 21 | 0 | 0.21 |
| hIL22-[CLλ-S$^{81}$K] | 140 | 69 | 31 | 0 | 0.31 | 80 | 20 | 0 | 0.2 |
| hIL22-[CLλ-Q$^{78}$A/S$^{81}$K] | 141 | 89 | 11 | 0 | 0.11 | 85 | 15 | 0 | 0.15 |
| hIL22-[CLλ-A$^{44}$V/S$^{81}$K] | 142 | 48 | 52 | 0 | 0.52 | 87 | 13 | 0 | 0.13 |
| hIL22-[CLλ-A$^{44}$V/Q$^{78}$A/S$^{81}$K] | 143 | 30 | 70 | 0 | 0.7 | 82 | 18 | 0 | 0.18 |
| hIL22-[CLλ-A$^{76-84}$/145] | 144 | 83 | 17 | 0 | 0.34 | 82 | 18 | 0 | 0.2 |

A single point mutation CLλ-S$^{81}$K enabled PFP conjugation to the CLλ. The LC % 1CA increased from 0% to 31% on the CLλ-S$^{81}$K mutant compared against the unmutated hIL22, with more conjugation additions seemingly occurring at the newly created conjugation site than at any other single site on the antibody. Peptide mapping studies confirmed that the conjugation events were occurring on CLλ-S$^{81}$K (Table 70).

TABLE 70

Overview of peptide mapping studies on hIL22-[CLλ-S$^{81}$K]-CL.

| Protein Chain | Peptide | Average Δ (% conjugation, n = 3) |
|---|---|---|
| hIL22-[CLλ-S$^{81}$K]-CL | SEQ ID NO: 140, residues 80-85 | 54 ± 10 |
| hIL22-[CLλ-S$^{81}$K]-HC | SEQ ID NO: 137, residues 96-103 | 21 ± 10 |
| hIL22-[CLλ-S$^{81}$K]-HC | SEQ ID NO: 137, residues 95-103 | 19 ± 10 |

Referring back to Table 69, combining mutations at CLλ-S$^{81}$K and CLλ-A$^{44}$V (hIL22-[CLλ-A$^{44}$V/S$^{81}$K]) further increased light chain 1CA to 52%.

Interestingly, while the CLλ-Q$^{78}$A/CLλ-S$^{81}$K double mutation did improve conjugation of the CLλ-S$^{81}$K compared to WT CLλ (1CA from 0% to 11%), the improvement was less pronounced than that seen in the single CLλ-S$^{81}$K mutant. This correlates well with the model: the effect of mutating CLκ-D$^{77}$ is to remove the hydrogen bond between CLκ-D$^{77}$ and CLκ-H$^{81}$, enabling CLκ-H$^{81}$ to revert to the catalytically tautomeric Nδ form. The corresponding position to CLκ-D$^{77}$ is CLλ-Q$^{78}$, which both modeling and mutational analysis suggest would not have a limiting effect on CLλ-H$^{82}$. Taken together, this suggests that the diminishing effect of CLλ-Q$^{78}$A on the directional conjugation is likely caused by an alteration to the size and shape of the binding pocket.

Most surprising, however, was the result of the triple mutation CLλ-A$^{44}$V/Q78A/S$^{81}$K. Directional conjugation as measured by the 1CA % increased to 70%; reaching levels typically seen in native CLκ domains.

These results and analysis were borne out by the similar level of directional conjugation seen in the loop swap (hIL22-[CLλ-λ$^{76-84}$/145]).

Overall, these data suggested that the CLλ-Q$^{78}$A mutation does improve directionality of CLλ-S$^{81}$K conjugation, provided the size and shape of the binding pocket is adapted for the specific Z group used. Moreover, the results of CLλ mutants suggested that directional conjugation sites can be created on immunoglobulins other than CLκ, provided that the motif KH is present in the correct 3D location. Naturally, the binding pocket must be of suitable size and shape to accommodate the specific halo-phenyl ester employed, and, as demonstrated herein, additional features, such as the presence or absence of residues corresponding to CLκ-V$^{42}$, CLκ-D$^{43}$, and CLκ-D$^{77}$ can have significant effects on the rate and optimization of directional conjugation of the KH motif relative to the specific immunoglobulin domain and halo-phenyl ester. While PFP was used in these examples, it will be apparent that other Z groups with acceptable levels of directional conjugation may be selected, and using rational modeling techniques, a balance may be obtained between the desired Z group, size of the binding pocket and the specific mutations required to maintain an active binding pocket.

Example 45 Recreating PFP Conjugation Sites on CH Domains

The CH domains of antibodies also comprise immunoglobulin structures. Prior to modeling the domains as described in Examples 40 and 41, it was postulated that moving the conjugation motif to the EF loop portion of the EF connecting chain of other CH domains may permit directional conjugation. A sequence alignment of the CHγ1 (SEQ ID NO:147), CHγ2 (SEQ ID NO:155), CHγ3 (SEQ ID NO:158), CLκ (SEQ ID NO:6) and CLλ (SEQ ID NO:57) domains is shown in FIG. 16.

Two mutant versions were made on the CH1 domain.

In hCHγ1-m1, the sequence LGTQT (SEQ ID NO:152), which corresponds to residues L$^{76}$-T$^{80}$ of SEQ ID NO:147, was removed, and replaced by EKHKV (SEQ ID NO:153), which corresponds to E$^{79}$-V$^{83}$ of CLκ. The resultant mutant, hCHγ1-m1, comprised SEQ ID NO:148.

In CHγ1-m2, the sequence LGTQT (SEQ ID NO:152), which corresponds to residues L$^{76}$-T$^{80}$ of SEQ ID NO:147, was removed, and replaced by YEKHKV (SEQ ID NO:154), which corresponds to Y$^{78}$-V$^{83}$ of CLκ-. The resultant mutant, hCHγ1-m2, comprised SEQ ID NO:150. The additional Y residue was incorporated to allow the hCHγ1-m2 sequence to better align with CLκ sequence.

Sequence alignment indicated that hCHγ1 lacks an Asp residue corresponding to CLκ-D$^{43}$. Accordingly, two additional mutants were generated; where each of hCHγ1-m1 and hCHγ1-m2 were subjected to an additional insertional mutation of an Asp residue between CHγ1-S$^{43}$ and CHγ1-G$^{44}$, creating the two new mutants of hCHγ1-m1-D$^{44}$ (SEQ ID NO:149) and hCHγ1-m2-D$^{44}$ (SEQ ID NO:151).

A mutant version of hCHγ2 (SEQ ID NO:155) was generated, where residues N$^{85}$G$^{86}$ of SEQ ID NO:155 were substituted with KH to generate hCHγ2-m (SEQ ID NO:156). Sequence alignment suggested that hCHγ2 (SEQ ID NO:155) comprised an Asp residue (D$^{50}$) at a location that may correspond to CLκ-D$^{43}$.

A mutant version of hCHγ3 (SEQ ID NO:157) was generated, where residues Q$^{79}$G$^{80}$ of SEQ ID NO:157 were substituted with KH to generate hCHγ3-m (SEQ ID NO:158). Sequence alignment suggested that hCHγ3 (SEQ ID NO:155) comprised an Asn residue (N$^{44}$) at a location corresponding to CLκ-D$^{43}$.

Trastuzumab was used as a model Ab in the study. All the hTrast-CHγ mutants were expressed with a [CLκ-K$^{80}$A] mutation, so that conjugation events would preferentially occur on the test CHγ domain. The hTrast-LC-[CLκ-K$^{80}$A] (SEQ ID NO:146) mutation was generated following protocols described in QuickChange site-directed mutagenesis kit (Stratagene).

The mutations on CHγ domains were generated using overlap PCR. Mutations were introduced by oligonucleotide primers. Primer specific to the 5' end of trastuzumab HC paired with a reverse primer carrying the desired mutation, and a forward primer carrying the desired mutation paired with the reverse primer specific to the 3' end of trastuzumab HC were used to PCR amplify DNA fragments using trastuzumab HC as template. These two PCR products were mixed as templates; trastuzumab heavy chain forward primer and reverse primer were used in overlap PCR reaction to amplify the full length trastuzumab HC DNA with desired mutations. The PCR was then digested with restriction enzyme BglII and NheI. The digested PCR was ligated with a modified pCEP4 plasmid (Invitrogen) cut with BglII and NheI.

The trastuzumab antibody carrying mutations were transiently expressed in HEK 293 cells, and purified using protein A affinity column. The purified mAbs were characterized using MS.

The expressed antibody was buffer exchanged to 20 mM sodium acetate, 200 mM trehalose pH 5.5 at 20 mg/ml. The proteins were then spiked with 60 mM sodium phosphate pH 7.7. ABP was resuspended with 50% propylene glycol and mixed with the protein at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple ABP conjugation sites are observed as distinct signals separated by the mass difference of an ABP. Relative quantitation of multiple ABP conjugation species is performed by measuring the signal magnitude.

TABLE 71

Intact conjugation analysis of hTrast antibody and CHγ domain mutants.

| | % CA | | | | |
|---|---|---|---|---|---|
| Ab + ABP | 0 | 1 | 2 | 3 | Avg CA |
| hTrast | 1 | 16 | 56 | 24 | 2.112 |
| hTrast-[CLκ-D77A] | 0 | 1 | 62 | 34 | 2.338 |
| hTrast-[CLκ-K80A] | 48 | 41 | 10 | 2 | 0.665 |
| hTrast-[CLκ-K$^{80}$A]/CHγ1-m1 | 23 | 48 | 24 | 5 | 1.107 |
| hTrast-[CLκ-K$^{80}$A]/CHγ1-m2 | 24 | 48 | 24 | 4 | 1.087 |
| hTrast-[CLκ-K$^{80}$A]/CHγ1-m1-D$^{44}$ | 33 | 49 | 17 | 1 | 0.854 |
| hTrast-[CLκ-K$^{80}$A]/CHγ1-m2-D$^{44}$ | 41 | 45 | 12 | 2 | 0.746 |
| hTrast-[CLκ-K$^{80}$A]/CHγ2m | 45 | 44 | 9 | 3 | 0.694 |
| hTrast-[CLκ-K$^{80}$A]/CHγ3m | 40 | 44 | 13 | 3 | 0.78 |

The extent of ABP conjugation was examined separately on the light and heavy chains of trastuzumab and trastuzumab mutants. MAC product was denatured and disulfide bonds were reduced using guanidine hydrochloride and dithiothreitol. The resulting free light and heavy chains were analyzed using LCMS to determine the conjugation profile on each chain (Table 72).

TABLE 72

Reduced heavy, light chain conjugation analysis of hTrast antibody and CHγ domain mutants. The % of 1-HC % relative to the respective WT run is shown in the right column, as described in Table 53, although in this example, hTrast-[CLκ-K$^{80}$A] HC 1CA was taken as the WT FIGURE.

|  | LC % CA | | | | HC % CA | | | | |
| --- | --- | --- | --- | --- | --- | --- | --- | --- | --- |
|  | 0 | 1 | 2 | Avg CA-LC | 0 | 1 | 2 | Avg CA-HC | 1HC WT % |
| hTrast | 32 | 66 | 2 | 0.7 | 83 | 17 | 0 | 0.17 | N/A |
| hTrast-[CLκ-D$^{77}$A] | 0 | 95 | 5 | 1.05 | 90 | 10 | 0 | 0.1 | N/A |
| hTrast-[CLκ-K$^{80}$A] | 98 | 2 | 0 | 0.02 | 79 | 21 | 0 | 0.21 |  |
| hTrast-[CLκ-K$^{80}$A]/CHγ1-m1 | 99 | 1 | 0 | 0.01 | 64 | 31 | 5 | 0.41 | 148 |
| hTrast-[CLκ-K$^{80}$A]/CHγ1-m2 | 98 | 2 | 0 | 0.02 | 62 | 32 | 6 | 0.44 | 152 |
| hTrast-[CLκ-K$^{80}$A]/CHγ1-m1-D$^{44}$ | 97 | 3 | 0 | 0.03 | 74 | 24 | 2 | 0.28 | 114 |
| hTrast-[CLκ-K$^{80}$A]/CHγ1-m2-D$^{44}$ | 97 | 3 | 0 | 0.03 | 73 | 24 | 3 | 0.3 | 114 |
| hTrast-[CLκ-K$^{80}$A]/CHγ2m | 99 | 1 | 0 | 0.01 | 75 | 23 | 2 | 0.27 | 110 |
| hTrast-[CLκ-K$^{80}$A]/CHγ3m | 100 | 0 | 0 | 0 | 70 | 27 | 3 | 0.33 | 129 |

The total conjugation on hTrast-[CLκ-K$^{80}$A]/CHγ1-m1 and hTrast-[CLκ-K$^{80}$A]/CHγ1-m2 were increased compared to hTrast-[CLκ-K$^{80}$A], from 0.66 CA to ~1CA; and the HC 1CA of these two mutants increased from 21% to 31%, and improvement of about 150% This supports the hypothesis that directional conjugation can be introduced to immunoglobulin domains other than CLκ and CLλ by the introduction of the KH motif.

The total conjugation on hTrast-[CLκ-K$^{80}$A]/CHγ2m also increased, but to a lesser extent than that of the CHγ1 mutants. A comparison of the sequences of the CHγ1 and CHγ2 sequences shows that at the residue corresponding to CLκ-D$^{77}$, CHγ1 comprises Ser, and CHγ2 comprises Asp. This could suggest that a mutation similar to the CLκ-D$^{77}$ mutations in CHγ2 domains could improve the extent of conjugation.

In addition, the improvement in conjugation on the CHγ3 HC, while evident, was also modest in comparison to the CHγ1 domain mutants. The CHγ3 domain sequence appeared to comprise Arg at a position corresponding to CLκ-D77, and Ser at a position corresponding to CLκ-D$^{43}$.

Furthermore, the conjugation of the CA % HC for both hTrast-[CLκ-K$^{80}$A]/CHγ1-m1-D$^{44}$ and hTrast-[CLκ-K$^{80}$A]/CHγ1-m2-D$^{44}$ showed a very surprising result, in that the apparent increase in conjugation seen in both hTrast-[CLκ-K$^{80}$A]/CHγ1-m1 and hTrast-[CLκ-K$^{80}$A]/CHγ1-m2 went from approximately 150% of WT to only about 114% of WT.

An explanatory hypothesis suggested that the sequence alignment of FIG. 17 may not accurately align the respective residues according to where they are found on a 3D immunoglobulin structure.

Example 46 Modeling the Immunoglobulin Fold

Consequently, crystal structure coordinates for the hCHγ1, hCHγ2 and hCHγ3 domains were obtained from the "Protein Data Bank", maintained by Rutgers, the State University of New Jersey, Center for Integrative Proteomics Research, the San Diego Supercomputer Center (SDSC) and Skaggs School of Pharmacy and Pharmaceutical Sciences, San Diego. The structure of hCHλ1 is based on X-ray structure of 3dv, available through the "Protein Data Bank". The structure of hCHλ2 is based on the X-ray structure of 2dts available through the "Protein Data Bank". The structure of hCHλ3 is based on the X-ray structure of 2dts available through the "Protein Data Bank". The structure of hCLλ is based on the X-ray structure of 4fqh available through the "Protein Data Bank".

An homology alignment was generated, which aligned the sequences according to structure (FIG. 17). Crystal structure comparisons of CLκ and hCHγ1-m1 (FIG. 19) showed that the hCHγ-CD connecting chain comprised a short α-helix. Modeling suggested that this CD α-helix presents the native S$^{43}$ and the hTrast-[CLκ-K$^{80}$A]/CHγ1-m1-D44 Asp insertion with side chains extending away from the binding pocket (FIGS. 20 & 21), and that the addition of CHγ1-D$^{44}$ increases the size of and extends the CD α-helix. In addition, the model suggests that the CHγ1-Q$^{79}$H residue is not in the optimal planar orientation, reducing its ability to participate in the reaction between PFP and the adjacent CHγ1-T$^{78}$K (FIG. 21).

A comparison of the CLκ and CHγ1-m1-D44 domains of FIG. 22 suggests that the pocket shape may be optimized by removing the CD α-helix on the CD connecting chain, and replacing with a loop structure. Accordingly, a mutant CHγ1 domain, SEQ ID NO:165, was modelled and minimized. SEQ ID NO:165 comprises the CHγ1-T$^{84}$K/Q$^{79}$H double mutation of the CHγ1-m1 mutant, as well as substituting the CHγ1 CD connecting chain from CHγ1-N$^{42}$ inclusive through to CHγ1-L$^{46}$ inclusive with KVDNALA (SEQ ID NO:166); SEQ ID NO:166 corresponds to residues of the CLκ domain (SEQ ID NO:6), with an additional Ala residue added. Modeling results shown in FIG. 22 suggest that CHγ1-Q$^{79}$H occupies a more planar orientation, assisted by the introduced Val residue on the CD connecting chain. Mutating this residue to Leu or Ile may provide further stabilization to the imidazole ring, owing to the longer side chains being able to close the increased gap to the H residue, relative to the distance in native CLκ. Significantly, the model places the adjacent Asp residue in a suitable orientation and distance from CHγ1-Q$^{79}$H to favour the δ-tautomeric form, and promote increased reactivity of CHγ1-T$^{78}$K.

Similar modeling was performed on the CHγ2 and CHγ3 domains. FIG. 24 compares key WT residues of CLκ and CHγ2. While CHγ2-D$^{49}$ and CHγ2-D$^{50}$ appear to be in the correct position and orientation to assist with directional conjugation, CHγ2-D$^{82}$ occupies a position even closer to CHγ2-G$^{86}$H in the 3D model, thereby favouring the ε-tautomeric form, and reducing the reactivity of CHγ2-N$^{85}$K. This model suggests that the CHγ2-D$^{82}$ residue may explain the relatively low increase in directional conjugation seen in the CHγ2m mutant. FIG. 26 illustrates a minimized model of a proposed mutant for CHγ2: comprising the mutations CHγ2-D$^{82}$A/N$^{85}$K/G$^{86}$H (SEQ ID NO:167). An immediate difference is seen: the imidazole ring appears in a more planar orientation, and within a suitable distance to CHγ2-D$^{50}$ to bias formation of the δ-tautomer, and the CHγ2-D$^{82}$A mutation has opened up the binding pocket, likely leading to a reduction in steric inhibition of PFP access.

FIGS. 27-29 show the corresponding comparisons of CLκ with CHγ3 WT, and CHγ3m mutant. The model suggests that despite there being no residue biasing CHγ3-G$^{80}$H towards the ε-tautomer form, the availability of CHγ3-Q$^{79}$K to conjugate is likely sterically hindered by the long CHγ3-R$^{76}$ side-chain. FIG. 30 illustrates a minimized model of a first proposed mutant for CHγ3: hCH3γm-CD1/EF, comprising the mutations CHγ3-S$^{43}$V/N$^{44}$D/R$^{76}$A/Q$^{79}$K/G$^{80}$H (SEQ ID NO:168). The modeled difference can be easily observed in FIG. 30B: the availability of the binding pocket has opened up, and reduced steric interference on the reactive Lys.

From the sidechain distances in the modeled structure of FIG. 30B, it is unlikely that CHγ3-S$^{43}$V or CHγ3-N$^{44}$D interact with CHγ3-G$^{80}$H to the same extent as the corresponding residues in CLκ. Accordingly, a second proposed mutant for CHγ3 was also minimized and modeled: hCH3γm-CD2/EF, comprising the mutations CHγ3S$^{43}$L/N$^{44}$E/R$^{76}$A/Q$^{79}$K/G$^{80}$H (SEQ ID NO:169). The introduction of suitable residues on the CD connecting chain with longer side chains (CHγ3-S$^{43}$L instead of CHγ3-S$^{43}$V, and CHγ3-N$^{44}$E instead of CHγ3-E$^{44}$D) is modeled to have a binding pocket with greater structure similarities to that of CLκ (FIG. 31), and a greater likelihood of hydrogen bonding between CHγ3-N$^{44}$E and CHγ3-G$^{86}$H than between CHγ3-N$^{44}$D and CHγ3-G$^{80}$H.

Sequences of the CHγ domains and mutants were aligned with the CLκ and CLλ (FIG. 32).

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings In so far as specific examples found herein do not fall within the scope of an invention, said specific example may be explicitly disclaimed.

The use of the term "or" in the claims is used to mean "and/or" unless explicitly indicated to refer to alternatives only or the alternative are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

TABLE 73

| Toxin # | IUPAC name | STRUCTURE |
|---|---|---|
| #54 | 2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54 | 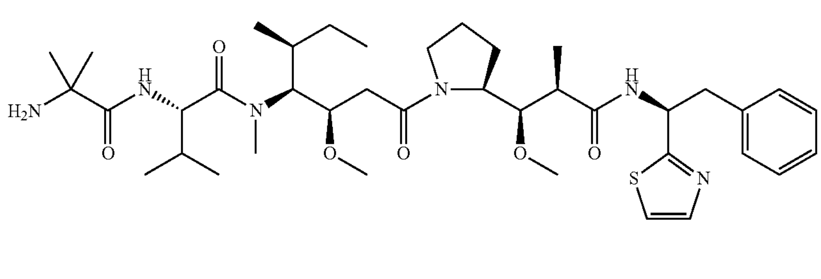 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C] |

TABLE 73-continued

| Toxin # | IUPAC name | STRUCTURE |
|---|---|---|
| #226 | N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#226) | 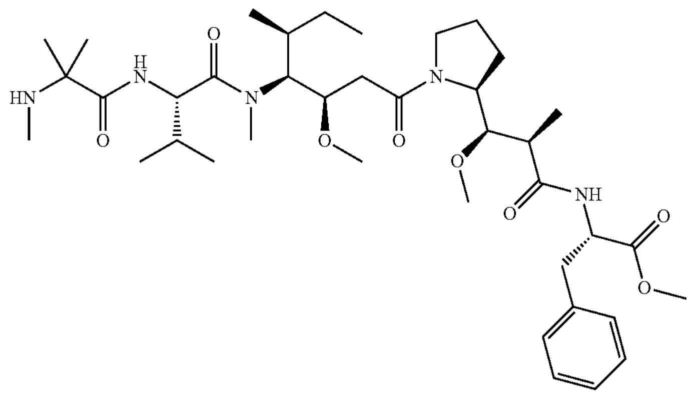 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)C(C)(C)NC)C(C)C] |
| #194 | N,2-{[(3S)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide trifluoroacetic acid salt (#194) | 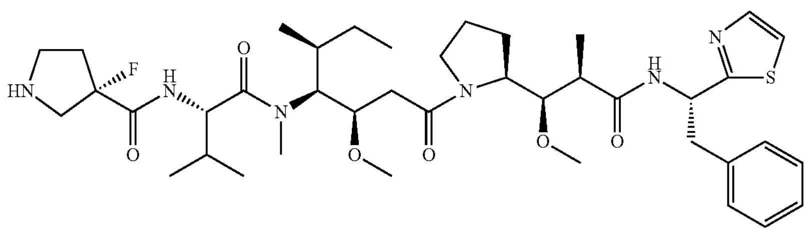 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@]1(F)CCNC1)C(C)C] |
| #192 | N,2-{[(3R)-3-fluoropyrrolidin-3-yl]carbonyl}-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide trifluoroacetic acid salt (#192) | 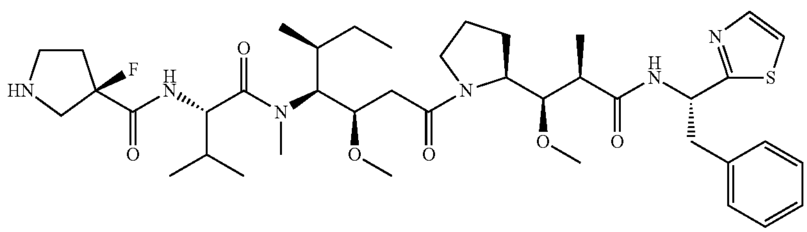 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@@]1(F)CCNC1)C(C)C] |
| #201 | 1,2-dimethyl-D-prolyl-N-[(3R,4S,5S)-1-{(2S)-2-[(1R,2R)-3-{[(2S)-3-(4-aminophenyl)-1-methoxy-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide, formate salt (#201) | 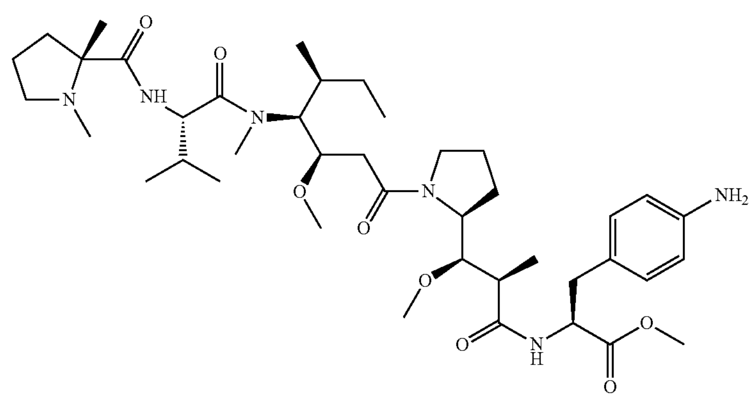 [SMILES: CC[C@H](C)[C@@H]([C@@H](CC(=O)N1CCC[C@H]1[C@H](OC)[C@@H](C)C(=O)N[C@@H](Cc1ccc(N)cc1)C(=O)OC)OC)N(C)C(=O)[C@@H](NC(=O)[C@@]1(C)CCCN1C)C(C)C] |
| #158 | N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L-valyl)amino]heptanoyl}pyrrolidin-2-yl]-2-methylpropanoyl}-L-phenylalaninate, trifluoroacetic acid salt (#158) | 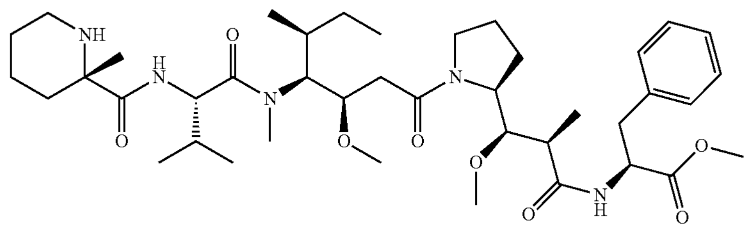 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCCN1)C(C)C] |

TABLE 73-continued

| Toxin # | IUPAC name | STRUCTURE |
|---|---|---|
| #70 | 2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#70) | 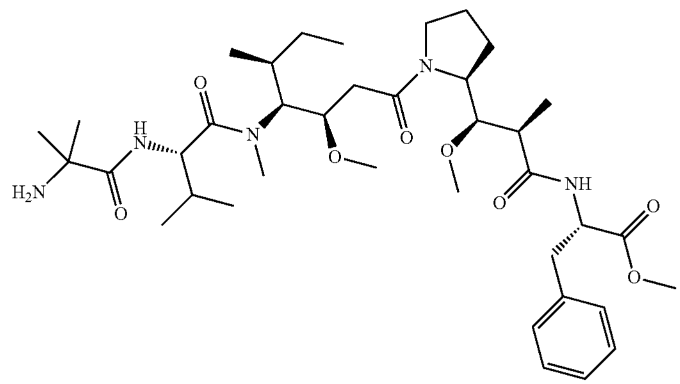 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)C(C)(C)N)C(C)C] |
| #47 | N²-[(1-Aminocyclopentyl)carbonyl]-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#47) | 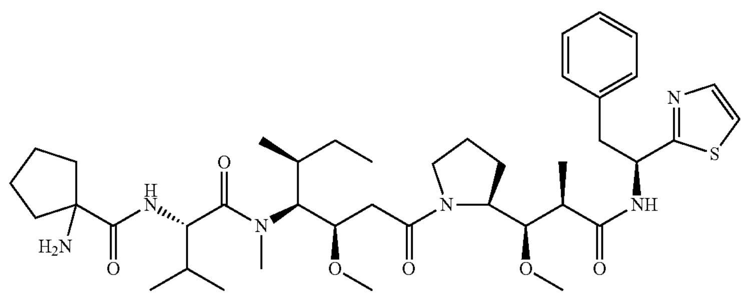 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C1(N)CCCC1)C(C)C] |
| #130 | N,2-dimethylalanyl-N-[(3R,4S,5S)-1-{(2S)-2-[(1R,2R)-3-{[(2S)-1-tert-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#130) | 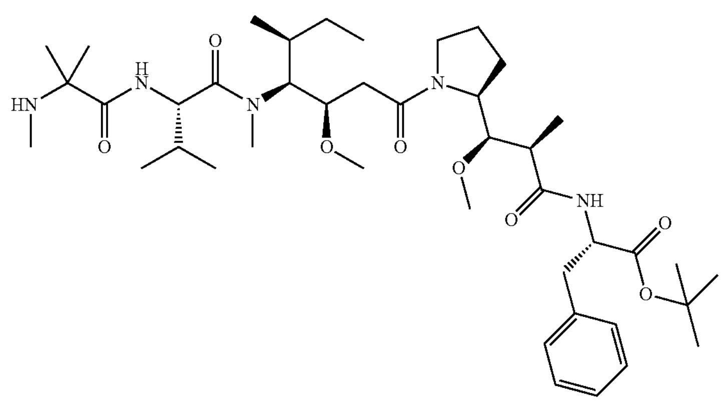 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)C(C)(C)NC)C(C)C] |
| #159 | methyl N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalaninate, trifluoroacetic acid salt (#159) | 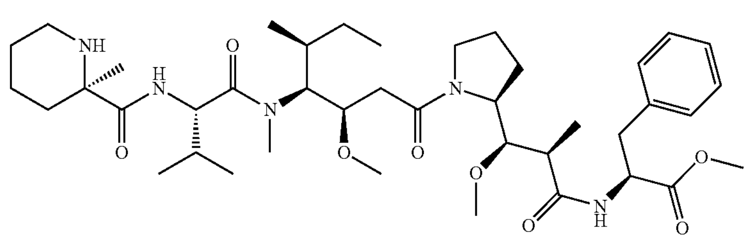 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@@]1(C)CCCCN1)C(C)C] |
| #209 | 1,2-dimethyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide, trifluoroacetic acid salt (#209) | 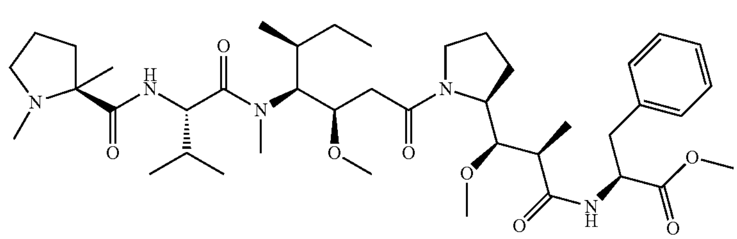 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1C)C(C)C] |

TABLE 73-continued

| Toxin # | IUPAC name | STRUCTURE |
|---|---|---|
| #131 | 2-methyl-D-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide, trifluoroacetic acid salt (#131) | 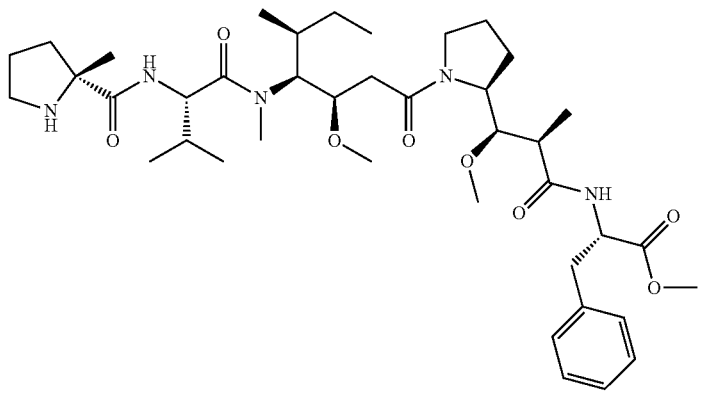 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@@]1(C)CCCN1)C(C)C] |
| #117 | 2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3 oxopropyl]pyrrolidin-1-yl}-5-methyl-1-oxoheptan-4-yl]-N-methyl-L-valinamide, trifluoroacetic acid salt (#117) | 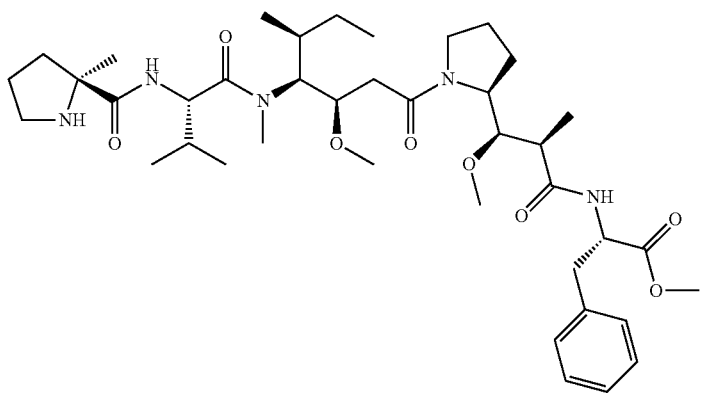 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C] |
| #115 | N,2-dimethylalanyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide, trifluoroacetic acid salt (115) | 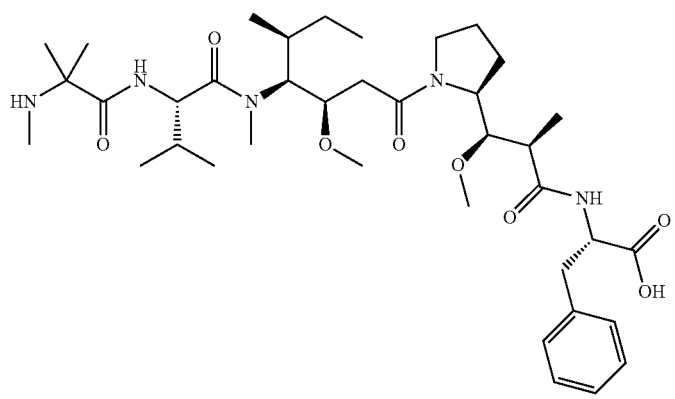 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C] |
| #69 | 2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (#69) | 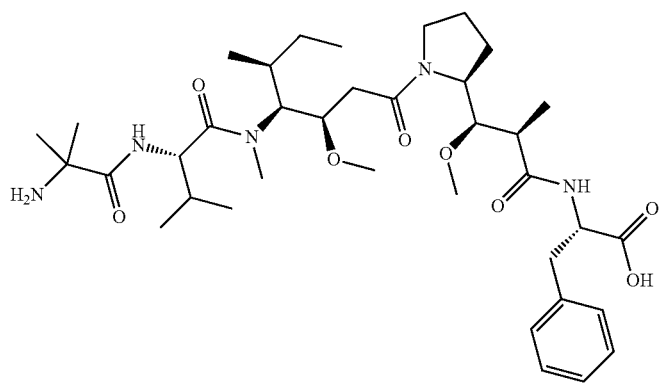 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)N)C(C)C] |

US 11,780,935 B2

251 252

TABLE 73-continued

| Toxin # | IUPAC name | STRUCTURE |
|---|---|---|
| #151 | 1,2-dimethyl-L-prolyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#151) | 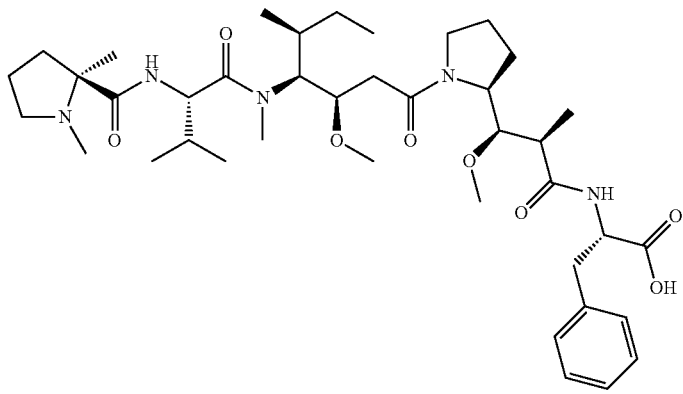 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1C)C(C)C] |
| #162 | N-{(2R,3R)-3-methoxy-3-[(2S)-1-{(3R,4S,5S)-3-methoxy-5-methyl-4-[methyl(N-{[(2S)-2-methylpiperidin-2-yl]carbonyl}-L-valyl)amino]heptanoyl}pyrrolidin-2-yl]-2-methylpropanoyl}-L-phenylalanine, trifluoroacetic acid salt (#162) | 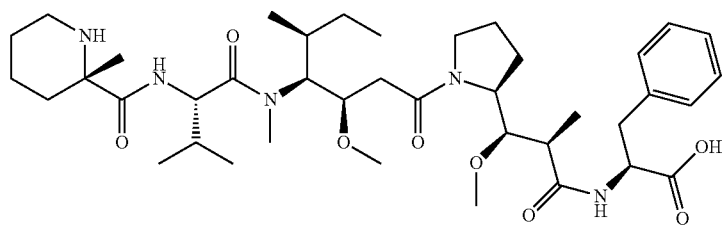 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCCN1)C(C)C] |
| #153 | 1,2-dimethyl-D-prolyl-N-{(1S,2R)-4-{(2S)-2-[(1R,2R)-3-{[(1S)-1-carboxy-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide (#153) | 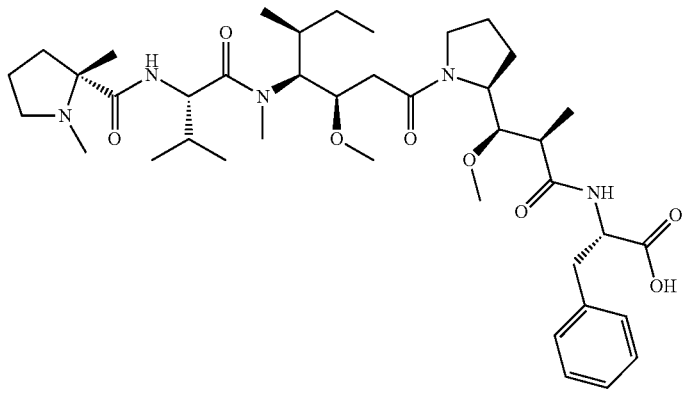 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@]1(C)CCCN1C)C(C)C] |
| #118 | 2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#118) | 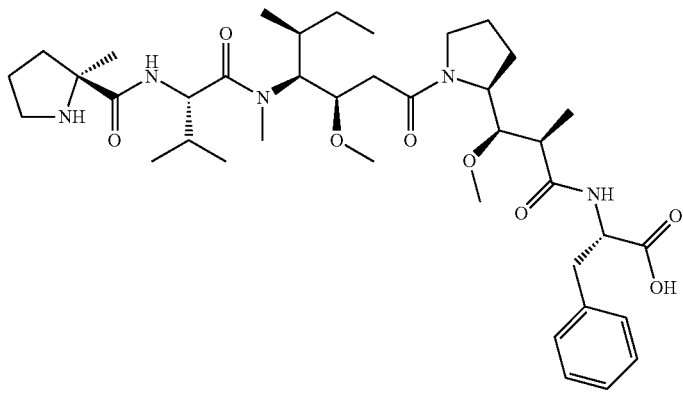 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C] |

TABLE 73-continued

| Toxin # | IUPAC name | STRUCTURE |
|---|---|---|
| #163 | N-{(2R,3R)-3-methoxy-3-[(2S)-1-{(3R,4S,5S)-3-methoxy-5-methyl-4-[methyl(N-{[(2R)-2-methylpiperidin-2-yl]carbonyl}-L-valyl)amino]heptanoyl}pyrrolidin-2-yl]-2-methylpropanoyl}-L-phenylalanine, trifluoroacetic acid salt. (#163) | 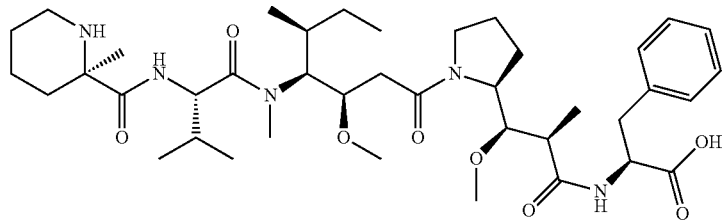 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@]1(C)CCCCN1)C(C)C] |
| #217 | N-{(2R,3R)-3-[(2S)-1-{(3R,4S,5S)-4-[(N-{[(3R)-3-fluoropyrrolidin-3-yl]carbonyl}-L-valyl)(methyl)amino]-3-methoxy-5-methylheptanoyl}pyrrolidin-2-yl]-3-methoxy-2-methylpropanoyl}-L-phenylalanine, trifluoroacetic acid salt (#217) | 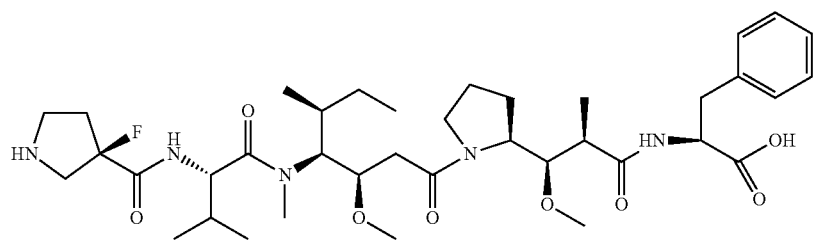 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@]1(F)CCNC1)C(C)C] |
| #112 | 2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide (#112) | 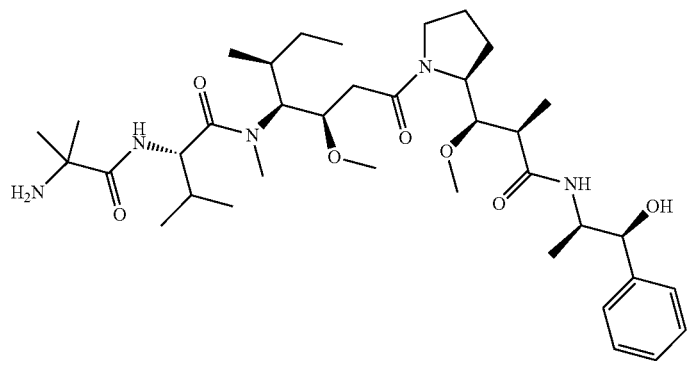 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)C(C)(C)N)C(C)C] |
| MMAD | The wavy line indicates a typical location for linker attachment. In non-conjugated form, the wavy line is typically conneted to a H atom. | 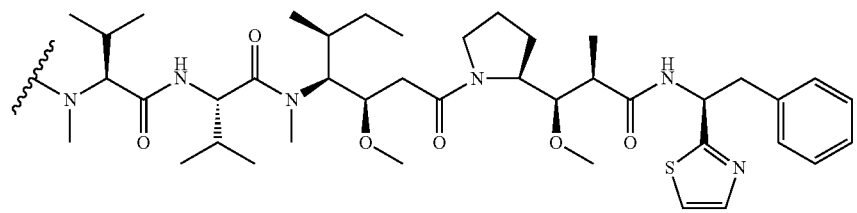 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)c1nccs1)OC)C(C)C)C(C)C] |
| MMAE | The wavy line indicates a typical location for linker attachment. In non-conjugated form, the wavy line is typically conneted to a H atom. | 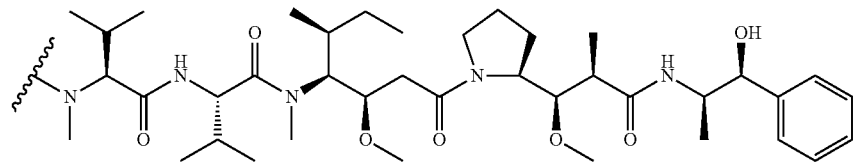 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C] |
| MMAF | The wavy line indicates a typical location for linker attachment. In non-conjugated form, the wavy line is typically conneted to a H atom. | 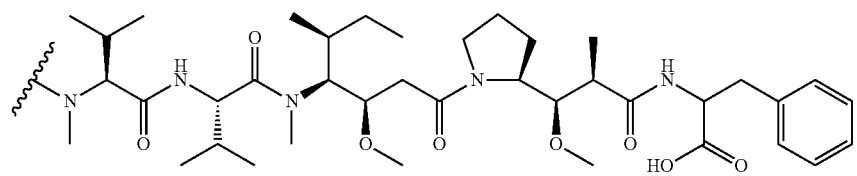 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)NC(Cc1ccccc1)C(=O)O)OC)C(C)C)C(C)C] |

The invention claimed is:

1. An antibody or antigen binding portion thereof comprising a mammalian constant light domain;
    wherein said mammalian constant light domain comprises a sequence selected from the group consisting of: SEQ ID NO: 37; SEQ ID NO: 38; SEQ ID NO: 41; SEQ ID NO: 40; SEQ ID NO: 54; SEQ ID NO: 49; SEQ ID NO: 50; and SEQ ID NO: 42;
    wherein a K located at a position corresponding to residue 80 comprises a side chain with an ε-amino group covalently attached to a linker,
    and pharmaceutically acceptable salts, stereoisomers, tautomers, and solvates, thereof.

2. The antibody or antigen binding portion thereof as claimed in claim 1, further comprising a residue selected from the group consisting of V, I and L at a position corresponding to residue 42 of.

3. The antibody or antigen binding portion thereof as claimed in claim 1, wherein the residues at positions corresponding to residues 42 and 43 of are not in α-helical formation.

4. The antibody or antigen binding portion thereof as claimed in claim 1, wherein the mammalian antibody constant domain is a humanized or human domain.

5. The antibody or antigen binding portion thereof as claimed in claim 1, wherein the constant domain is connected to an antibody variable domain.

6. The antibody or antigen binding portion thereof as claimed in claim 1, wherein the linker comprises a formula selected from the group consisting of $X^1$-$Y^1$-$Z^1$, $X^1$-$\Phi$-$Y^1$-$Z^1$, and $X^1$-$Y^1$-$\Phi$-Z, wherein $\Phi$ is a cleavable group, $X^1$ is a group covalently connectable to at least one Effector Moiety, $Y^1$ is a linear or branched connecting chain, and Z is a group covalently connected to the ε-amino group of the side chain of K that is located at a position corresponding to residue 80 of.

7. The antibody or antigen binding portion thereof as claimed in claim 6, wherein the cleavable group $\Phi$ is present, and is of the formula

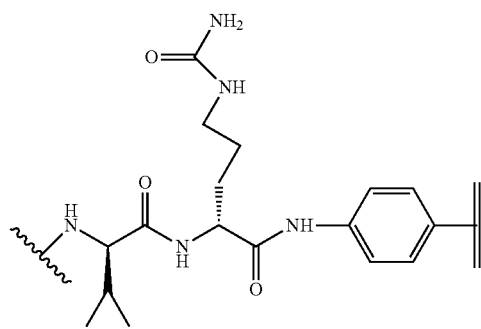

wherein the wavy line and parallel line each indicate a point of attachment to either the $X^1$, $Y^1$ or $Z^1$ group as appropriate.

8. The antibody or antigen binding portion thereof as claimed in claim 6, wherein the linker is selected from the group consisting of:

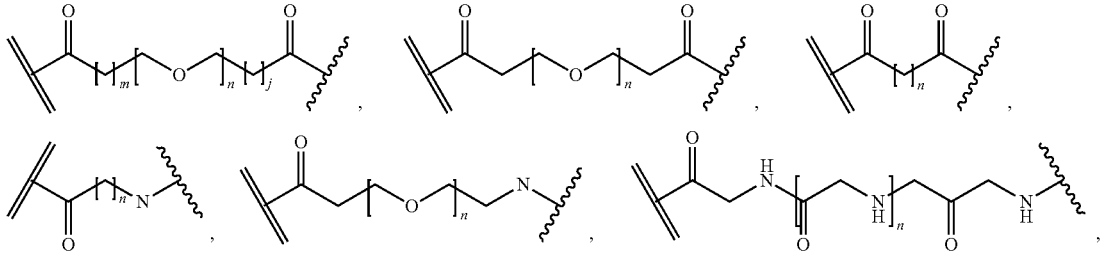

-continued
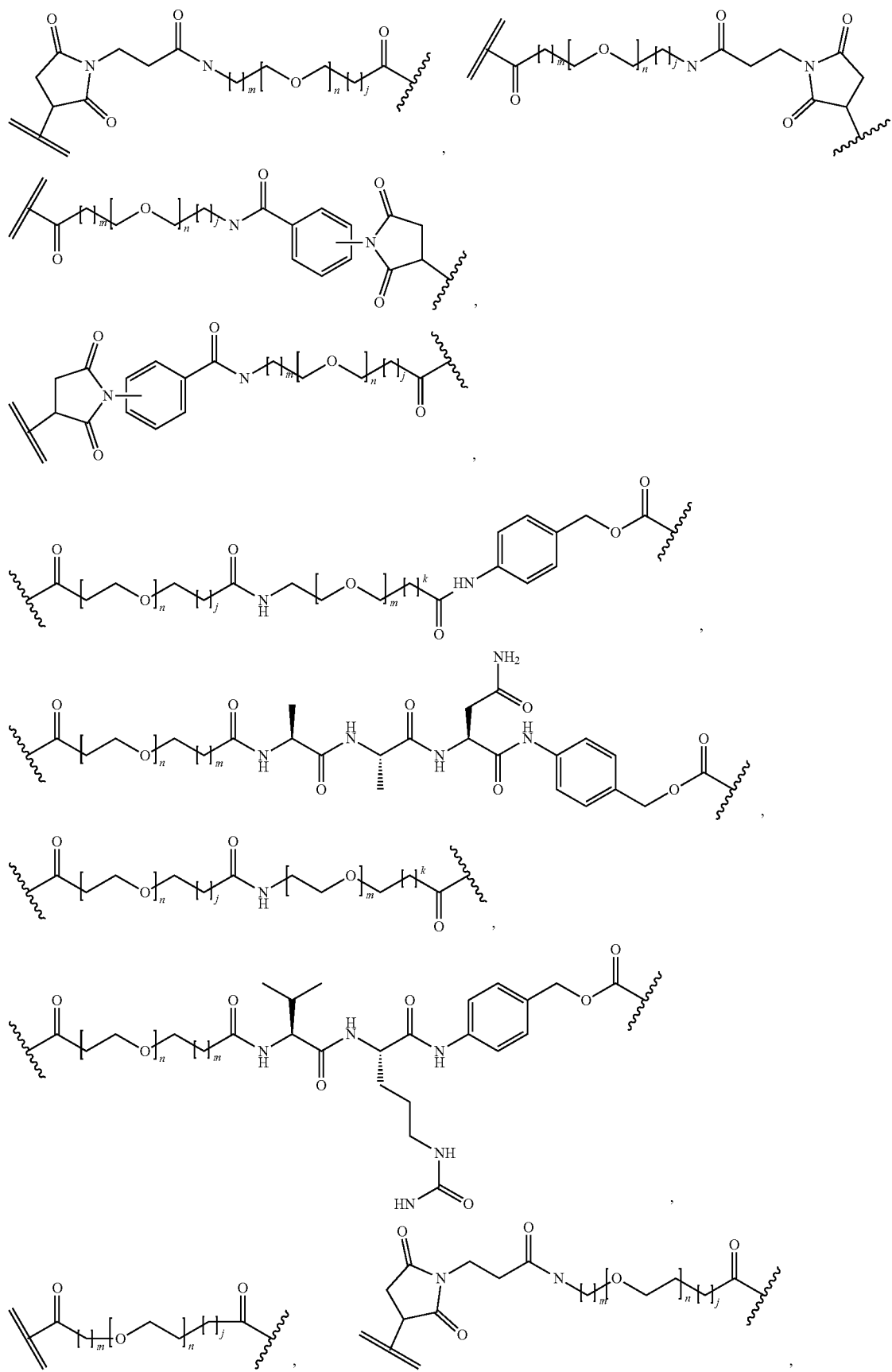

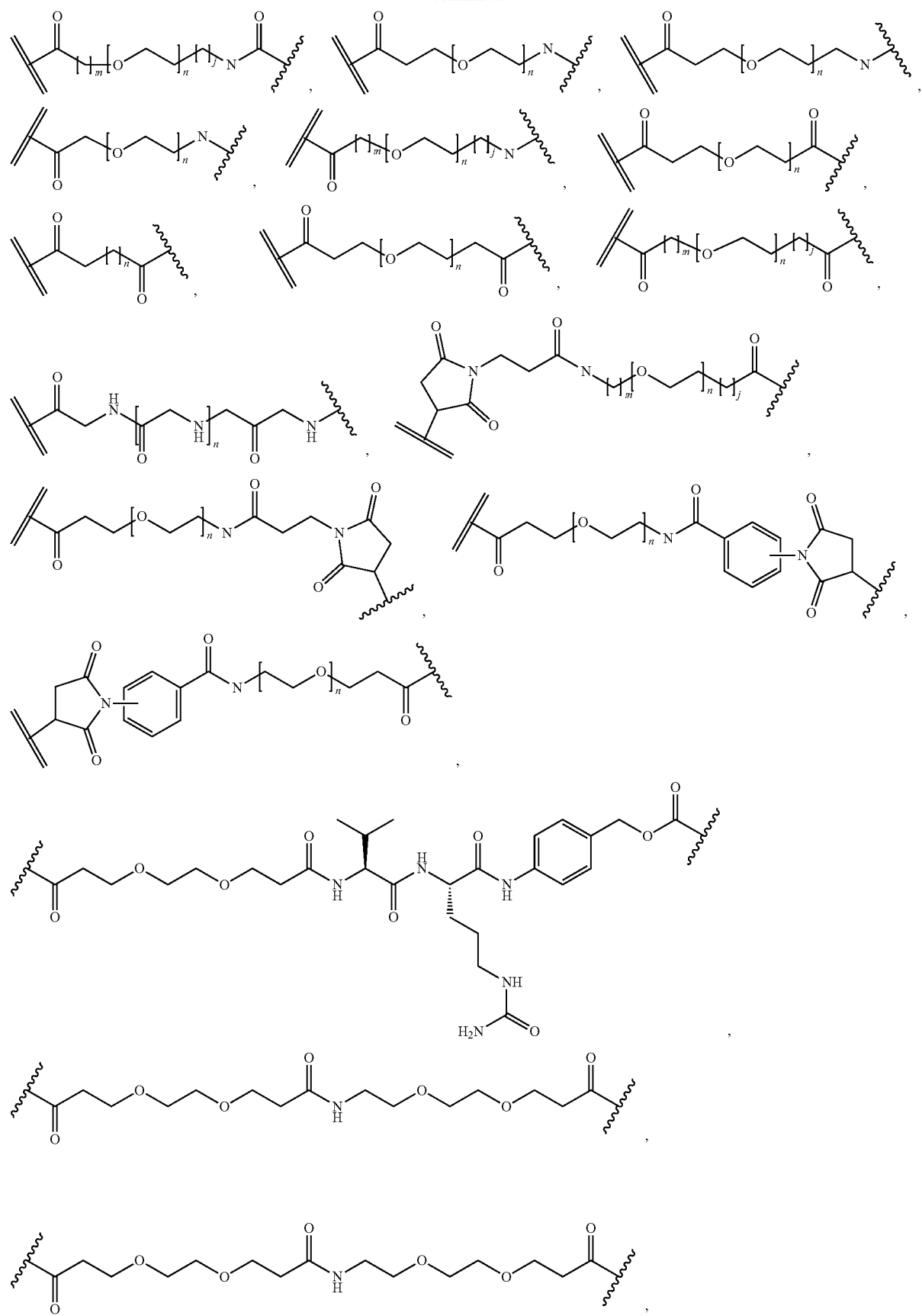

-continued

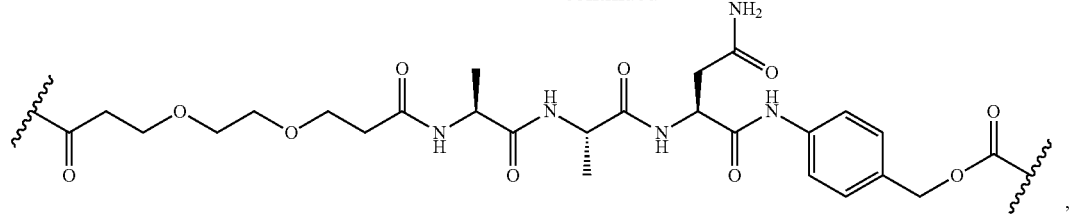

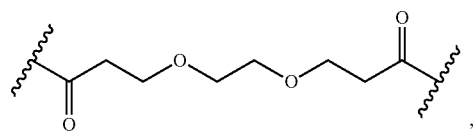

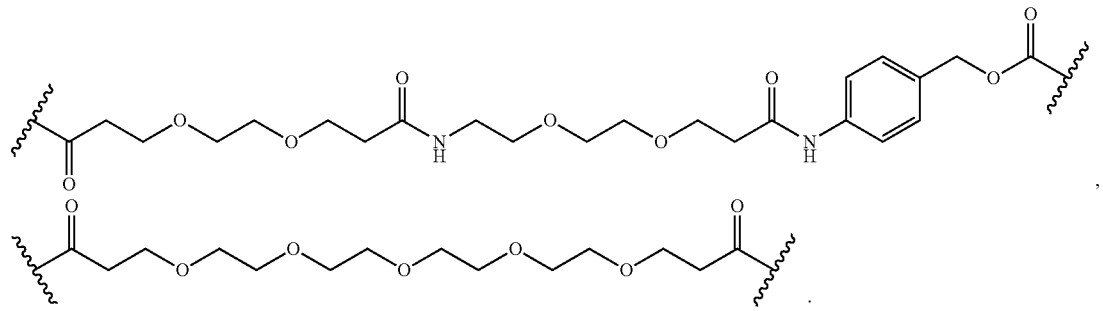

, and

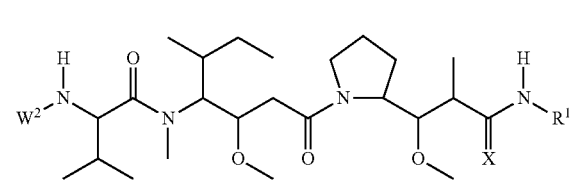

.

wherein m, n, j and k are each independently a range whose lower limits are selected from the group consisting of 0, 1, 2, 3, 4, 5, 6, 7, 8, 9, 10, 11, 12, 13, 14, 15, 16, 17, 18, 19, and 20, and whose upper limit is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30, and wherein the overall length of the linker does not exceed 200 atoms.

9. The antibody or antigen binding portion thereof as claimed in claim 6, wherein the Effector Moiety is a therapeutic agent, protein, peptide, nucleic acid, aptamer, small molecule, protein agonist, protein antagonist, metabolic regulator, hormone, toxin, growth factor, or diagnostic agent.

10. The antibody or antigen binding portion thereof as claimed in claim 9, wherein the Effector Moiety is a toxin, and comprises the formula:

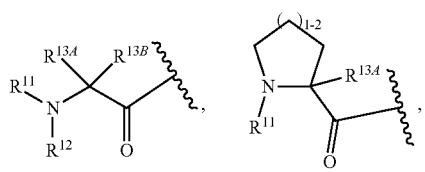

or a pharmaceutically acceptable salt or solvate thereof, wherein, independently for each occurrence,
W² is

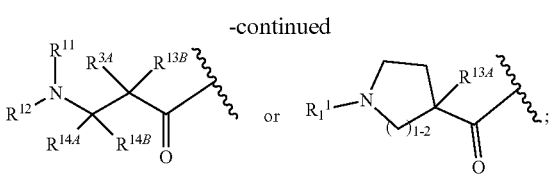

-continued

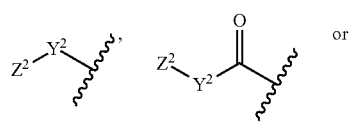

R¹¹ is

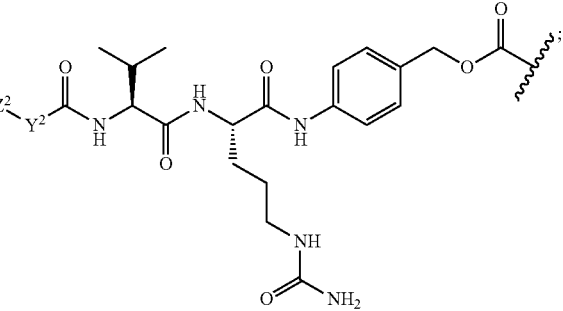

$Y^2$ is $-C_2-C_{20}$ alkylene-, $-C_2-C_{20}$ heteroalkylene-; $-C_3-C_8$ carbocyclo-, -arylene-, $-C_3-C_8$heterocyclo-, $-C_1-C_{10}$alkylene-arylene-, -arylene-$C_1-C_{10}$alkylene-, $-C_1-C_{10}$alkylene-($C_3-C_8$carbocyclo)-, $-(C_3-C_8$carbocyclo)-$C_1-C_{10}$alkylene-, $-C_1-C_{10}$alkylene-($C_3-C_8$heterocyclo)- or $-(C_3-C_8$ heterocyclo)-$C_1-C_{10}$alkylene-;

$Z^2$ is

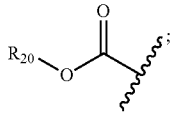

$R^{12}$ is hydrogen, $C_1$-$C_8$ alkyl or $C_1$-$C_8$ haloalkyl;
$R^{13A}$ and $R^{13B}$ are either of the following:
(i) $R^{13A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, aralkyl or halogen; and
$R^{13B}$ is $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl or halogen; or
(ii) $R^{13A}$ and $R^{13B}$ taken together are $C_2$-$C_8$ alkylene or $C_1$-$C_8$ heteroalkylene;
$R^{14A}$ and $R^{14B}$ are either of the following:
(i) $R^{14A}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; and
$R^{14B}$ is hydrogen, $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl or aralkyl; or
(ii) $R^{14A}$ and $R^{14B}$ taken together are $C_2$-$C_8$ alkylene or $C_1$-$C_8$ heteroalkylene;
$R^{15}$ is

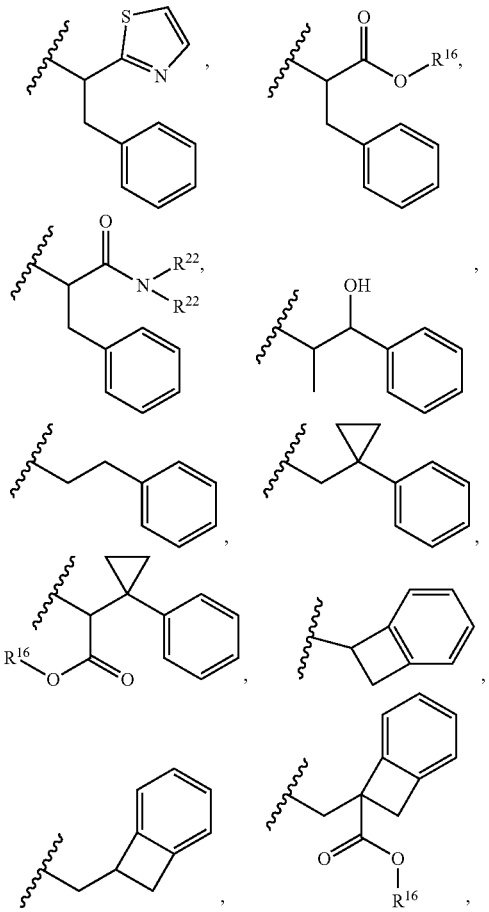

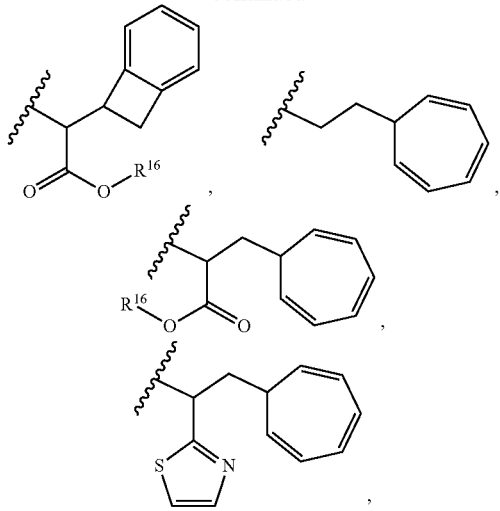

$C_1$-$C_{10}$ heterocyclyl, $C_3$-$C_8$ carbocycly and $C_6$-$C_{14}$ aryl optionally substituted with 1, 2, 3, 4 or 5 groups independently selected from the group consisting of —$C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR'—O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R' and —SR', wherein each R' is independently selected from the group consisting of hydrogen, $C_1$-$C_8$ alkyl and unsubstituted aryl, or two R' can, together with the nitrogen to which they are attached, form a $C_1$-$C_{10}$ heterocyclyl;
or $R^{15}$ is

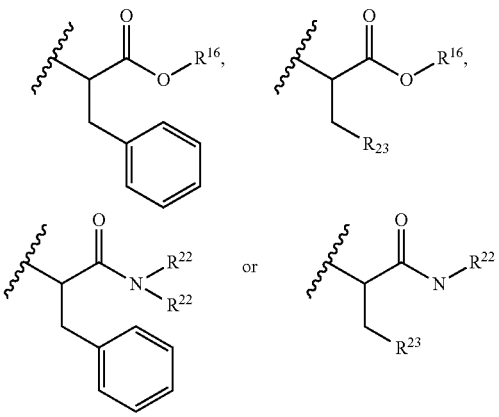

optionally substituted with 1, 2, 3, 4 or 5 groups independently selected from the group consisting of $C_1$-$C_8$ alkyl, —$C_1$-$C_8$ alkyl-N(R')$_2$, —$C_1$-$C_8$ alkyl-C(O)R', —$C_1$-$C_8$ alkyl-C(O)OR', —O—($C_1$-$C_8$ alkyl), —C(O)R', —OC(O)R', —C(O)OR', —C(O)N(R')$_2$, —NHC(O)R', —S(O)$_2$R', —S(O)R', —OH, halogen, —N$_3$, —N(R')$_2$, —CN, —NHC(=NH)NH$_2$, —NHCONH$_2$, —S(=O)$_2$R', —SR and arylene-R', wherein each R' is independently selected from the group consisting of hydrogen, $C_1$-$C_8$ alkyl, $C_1$-$C_8$heterocyclyl, $C_1$-$C_{10}$alkylene-$C_3$-$C_8$heterocyclyl and aryl, or two R' can, together with the nitrogen to which they are attached, form a $C_1$-$C_{10}$ heterocyclyl;

$R^{16}$ is hydrogen, —$C_1$-$C_8$ alkyl, —$C_2$-$C_8$ alkenyl, —$C_2$-$C_8$ alkynyl or -$C_1$-$C_8$ haloalkyl;

$R^{22}$ is hydrogen, $C_1$-$C_4$ alkyl, $C_1$-$C_{10}$ heterocyclyl or $C_6$-$C_{14}$ aryl;

$R^{23}$ is $C_1$-$C_{10}$ heterocyclyl; and $R^{17}$ is independently selected for each occurrence from the group consisting of F, Cl, I and Br;

$R^{20}$ is -aryl, —$C_1$-$C_{10}$alkylene-aryl, where aryl on $R^{10}$ comprising aryl is substituted with $[R^{17}]_h$;

h is 5; and

X is O or S;

provided that when $R^{13A}$ is hydrogen X is S.

11. The antibody or antigen binding portion thereof as claimed in claim 9, wherein the Effector Moiety is a toxin, and is selected from the group consisting of

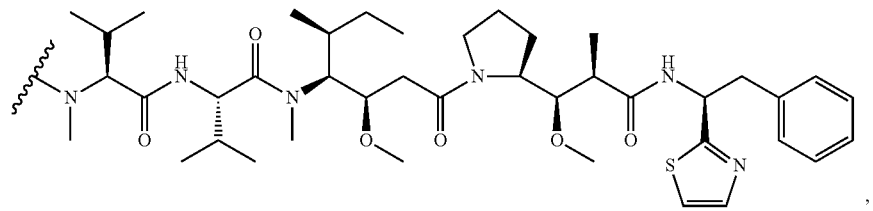
,
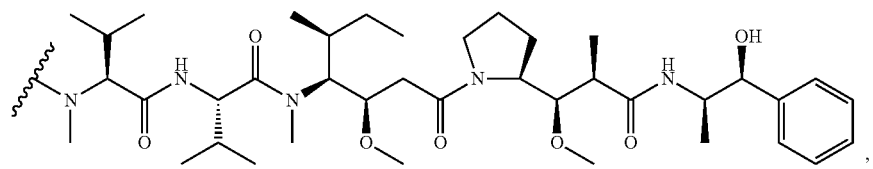
,
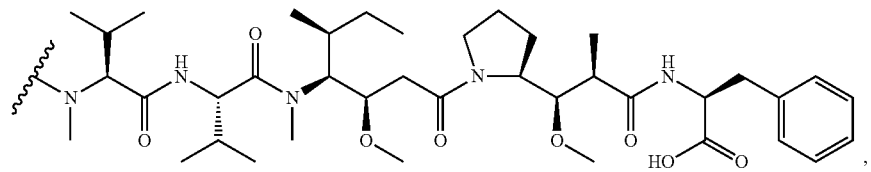
,
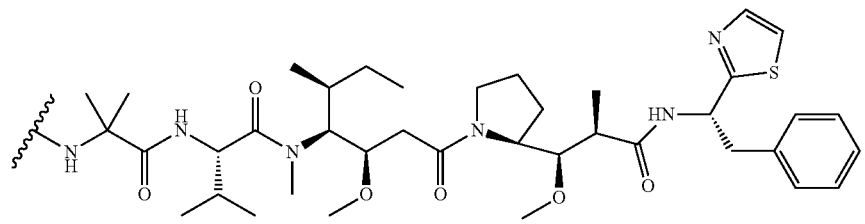
,
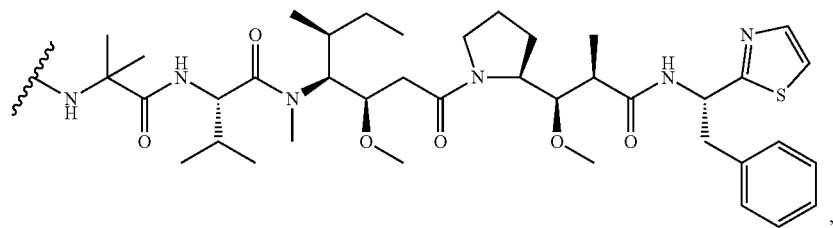
,
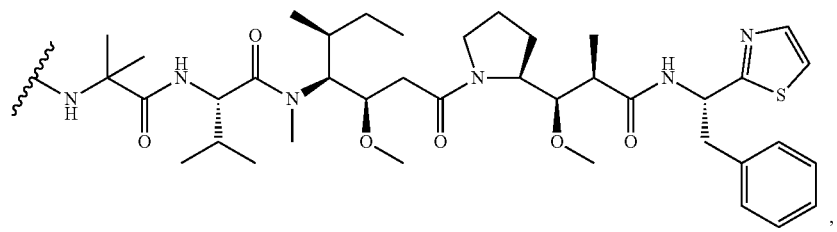
, -continued

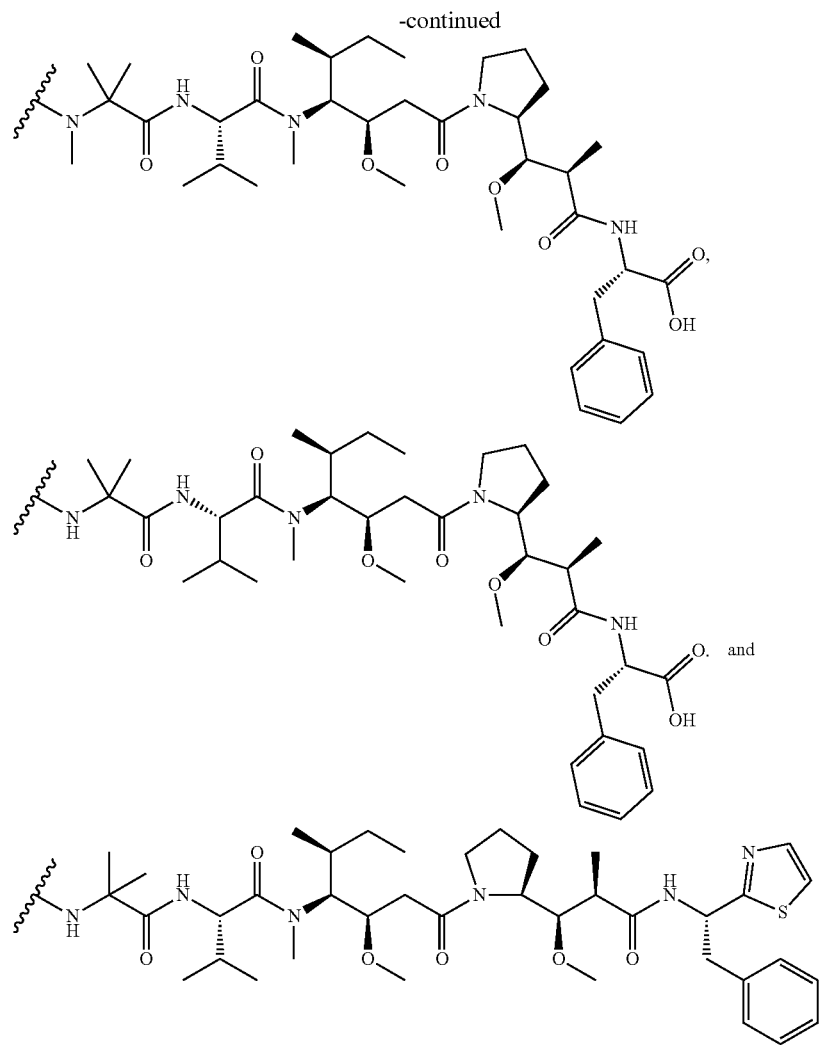

12. The antibody as claimed in claim 1, wherein the constant light domain is a kappa domain (CLk).

13. The antibody as claimed in claim 1, wherein the constant light domain is a lambda domain (CLA).

14. A composition comprising multiples of the antibody or antigen binding portion thereof as claimed in claim 1, wherein at least about 70% of the antibodies or antigen binding portions thereof comprises the linker covalently attached to the ε-amine group of the side chain of K that is located at a position corresponding to residue 80.

15. The antibody or antigen binding portion thereof as claimed in claim 1, wherein the antibody is a full length antibody, Fab, Fab', F(ab')$_2$, V$_H$, diabody, or minibody.

16. The antibody or antigen binding portion thereof as claimed in claim 1, wherein the antibody comprises VH and VL domains from an antibody selected from the group consisting of h38C2, rituximab, cetuximab, infliximab, adalimumab, natalizumab, omalizumab, ranibizumab, trastuzumab and palivizumab.

* * * * *